(12) United States Patent
Matsumoto et al.

(10) Patent No.: US 6,911,468 B2
(45) Date of Patent: Jun. 28, 2005

(54) TYROSINE PHOSPHATASE INHIBITORS

(75) Inventors: Takahiro Matsumoto, Hyogo (JP); Nozomi Katayama, Tsukuba (JP); Hiroshi Mabuchi, Ikoma-gun (JP)

(73) Assignee: Takeda Chemical Industries, Ltd., Osaka (JP)

( * ) Notice: Subject to any disclaimer, the term of this patent is extended or adjusted under 35 U.S.C. 154(b) by 114 days.

(21) Appl. No.: 10/276,674

(22) PCT Filed: May 21, 2001

(86) PCT No.: PCT/JP01/04201
§ 371 (c)(1), (2), (4) Date: Nov. 15, 2002

(87) PCT Pub. No.: WO01/90067
PCT Pub. Date: Nov. 29, 2001

(65) Prior Publication Data
US 2003/0144338 A1 Jul. 31, 2003

(30) Foreign Application Priority Data

May 22, 2000 (JP) ........................................ 2000-154441
Aug. 10, 2000 (JP) ........................................ 2000-247954

(51) Int. Cl.$^7$ ........................ A61K 31/40; C07D 207/30
(52) U.S. Cl. ........................ 514/427; 548/560; 548/562; 548/563; 514/428
(58) Field of Search ................................. 548/562, 563, 548/560; 514/427, 428

(56) References Cited

U.S. PATENT DOCUMENTS

| | | | |
|---|---|---|---|
| 3,168,529 A | * | 2/1965 | Short .......................... 548/562 |
| 4,113,871 A | | 9/1978 | Stach et al. |
| 5,096,919 A | | 3/1992 | Wasley et al. .............. 514/427 |
| 5,385,929 A | | 1/1995 | Bjorge et al. ............... 514/422 |

FOREIGN PATENT DOCUMENTS

| | | |
|---|---|---|
| EP | 0378991 | 7/1990 |
| EP | 1386913 | 2/2004 |
| WO | WO98/05637 | 2/1998 |
| WO | WO 99/46244 | 9/1999 |
| WO | WO99/58518 | 11/1999 |
| WO | WO 99/58520 | 11/1999 |
| WO | WO99/61410 | 12/1999 |
| WO | WO00/27792 | 5/2000 |

OTHER PUBLICATIONS

Fuji, et al. "Preparation of Alkyl–Substituted Indoles in the Benzene Portion. Part 6. Synthetic Procedure for 4–,5–,6–, or 7–Alkoxy– and Hydroxyindole Derivatives" CHEM. PHARM. BULL. 40(9):2344–2352 (1992).

Thiault, et al. "N–Arylpymole derivatives with analgesic and antiinflammatory activity" Farmaco, ED. SCI. 39(9):765–780(1984) Abstract.(Caplus File Search Results Attached).

Yoshida, et al. "Synthesis of Anti–inflammatory Compounds. I. Studies on the Synthesis and Anti–inflammatory Activity of Phenyl Substituted" Yakugaku Zasshi 93(5): 584–598(1973) Abstract (Caplus File Search Results Attached).

* cited by examiner

Primary Examiner—Golam M M Shameem
(74) Attorney, Agent, or Firm—Elaine M. Ramesh; Mark Chao

(57) ABSTRACT

A compound of the formula (I):

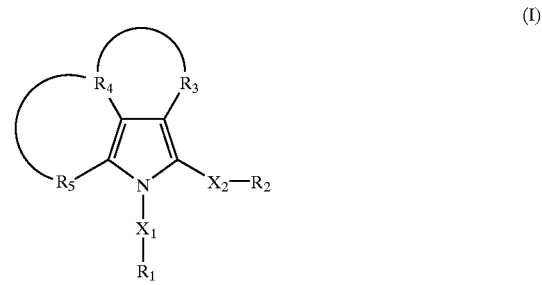

(I)

wherein $X_1$ and $X_2$ are the same or different and each is a bond or a spacer having 1 to 20 atom(s) in the main chain;

one of $R_1$ and $R_2$ is a cycle group having substituent(s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group or a hydrogen atom; and $R_3$, $R_4$ and $R_5$ are the same or different and each is a hydrogen atom or a substituent, or $R_4$ may link together with $R_3$ or $R_5$ to form an optionally substituted ring;

provided that when $R_3$ is a hydrogen atom, $R_4$ is a hydrogen atom and $R_5$ is methyl, $X_2$—$R_2$ is not 4-cyclohexylphenyl; when $R_3$ is 4-methoxyphenyl, $R_4$ is a hydrogen atom and $R_5$ is methyl, $X_2$—$R_2$ is not 4-methoxyphenyl; and when $R_1$ or $R_2$ is a hydrogen atom, the adjacent $X_1$ or $X_2$ is not a $C_{1-7}$ alkylene;

or a salt thereof exhibits a protein tyrosine phosphatase inhibitory action and is useful as a prophylactic or therapeutic agent for diabetes or the like.

10 Claims, No Drawings

US 6,911,468 B2

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Designed oligonucleotide primer to amplify
      PTP1B cDNA

<400> SEQUENCE: 1
ccgtcatgga gatggaaaag                                                    20

<210> SEQ ID NO 2
<211> LENGTH: 20
<212> TYPE: DNA
<213> ORGANISM: Artificial Sequence
<220> FEATURE:
<223> OTHER INFORMATION: Designed oligonucleotide primer to amplify
      PTP1B cDNA

<400> SEQUENCE: 2
agggtcaggc tatgtgttgc                                                    20

<210> SEQ ID NO 3
<211> LENGTH: 1322
<212> TYPE: DNA
<213> ORGANISM: Homo sapiens

<400> SEQUENCE: 3
ccgtcatgga gatggaaaag gagttcgagc agatcgacaa gtccgggagc tgggcggcca        60
tttaccagga tatccgacat gaagccagtg acttcccatg tagagtggcc aagcttccta       120
agaacaaaaa ccgaaatagg tacagagacg tcagtccctt tgaccatagt cggattaaac       180
tacatcaaga agataatgac tatatcaacg ctagtttgat aaaaatggaa gaagcccaaa       240
ggagttacat tcttacccag ggcccttttgc ctaacacatg cggtcacttt tgggagatgg       300
tgtgggagca gaaaagcagg ggtgtcgtca tgctcaacag agtgatggag aaaggttcgt       360
taaaatgcgc acaatactgg ccacaaaaag aagaaaaaga gatgatcttt gaagacacaa       420
atttgaaatt aacattgatc tctgaagata tcaagtcata ttatacagtg cgacagctag       480
aattggaaaa ccttacaacc caagaaactc gagagatctt acatttccac tataccacat       540
ggcctgactt tggagtccct gaatcaccag cctcattctt gaactttctt ttcaaagtcc       600
gagagtcagg gtcactcagc ccggagcacg ggcccgttgt ggtgcactgc agtgcaggca       660
tcggcaggtc tggaaccttc tgtctggctg atacctgcct cttgctgatg gacaagagga       720
aagacccttc ttccgttgat atcaagaaag tgctgttaga aatgaggaag tttcggatgg       780
ggctgatcca gacagccgac cagctgcgct tctcctacct ggctgtgatc gaaggtgcca       840
aattcatcat gggggactct tccgtgcagg atcagtggaa ggagctttcc cacgaggacc       900
tggagccccc acccgagcat atccccccac ctcccggcc acccaaacga atcctggagc       960
cacacaatgg gaaatgcagg gagttcttcc caaatcacca gtgggtgaag aagagaccc      1020 aggaggataa agactgcccc atcaaggaag aaaaggaag ccccttaaat gccgcacccct      1080 acggcatcga aagcatgagt caagacactg aagttagaag tcgggtcgtg ggggaagtc      1140 ttcgaggtgc ccaggctgcc tccccagcca aggggagcc gtcactgccc gagaaggacg      1200
aggaccatgc actgagttac tggaagccct tcctggtcaa catgtgcgtg gctacggtcc      1260

-continued

| tcacggccgg cgcttacctc tgctacaggt tcctgttcaa cagcaacaca tagcctgacc | 1320 |
| ct | 1322 |

<210> SEQ ID NO 4
<211> LENGTH: 21
<212> TYPE: DNA
<213> ORGANISM: Artificial Sequence
<220> FEATURE:
<223> OTHER INFORMATION: Designed oligonucleotide primer to amplify
      PTP1B cDNA

<400> SEQUENCE: 4

| tacatatgga gatggaaaag g | 21 |

<210> SEQ ID NO 5
<211> LENGTH: 24
<212> TYPE: DNA
<213> ORGANISM: Artificial Sequence
<220> FEATURE:
<223> OTHER INFORMATION: Designed oligonucleotide primer to amplify
      PTP1B cDNA

<400> SEQUENCE: 5

| tagtcgacat tgtgtggctc cagg | 24 |

<210> SEQ ID NO 6
<211> LENGTH: 976
<212> TYPE: DNA
<213> ORGANISM: Homo sapiens

<400> SEQUENCE: 6

| tacatatgga gatggaaaag gagttcgagc agatcgacaa gtccgggagc tgggcggcca | 60 |
| tttaccagga tatccgacat gaagccagtg acttcccatg tagagtggcc aagcttccta | 120 |
| agaacaaaaa ccgaaatagg tacagagacg tcagtccctt tgaccatagt cggattaaac | 180 |
| tacatcaaga agataatgac tatatcaacg ctagtttgat aaaaatggaa gaagcccaaa | 240 |
| ggagttacat tcttacccag ggccctttgc ctaacacatg cggtcacttt gggagatgg | 300 |
| tgtgggagca gaaaagcagg ggtgtcgtca tgctcaacag agtgatggag aaaggttcgt | 360 |
| taaaatgcgc acaatactgg ccacaaaaag aagaaaaga gatgatcttt gaagacacaa | 420 |
| atttgaaatt aacattgatc tctgaagata tcaagtcata ttatacagtg cgacagctag | 480 |
| aattggaaaa ccttacaacc caagaaactc gagagatctt acatttccac tataccacat | 540 |
| ggcctgactt tggagtccct gaatcaccag cctcattctt gaactttctt ttcaaagtcc | 600 |
| gagagtcagg gtcactcagc ccggagcacg ggcccgttgt ggtgcactgc agtgcaggca | 660 |
| tcggcaggtc tggaaccttc tgtctggctg atacctgcct cttgctgatg gacaagagga | 720 |
| aagacccttc ttccgttgat atcaagaaag tgctgttaga aatgaggaag tttcggatgg | 780 |
| ggctgatcca gacagccgac cagctgcgct ctcctacct ggctgtgatc gaaggtgcca | 840 |
| aattcatcat gggggactct tccgtgcagg atcagtggaa ggagctttcc cacgaggacc | 900 |
| tggagccccc acccgagcat atcccccac ctccccggcc acccaaacga atcctggagc | 960 |
| cacacaatgt cgacta | 976 |

<210> SEQ ID NO 7
<211> LENGTH: 321
<212> TYPE: PRT
<213> ORGANISM: Homo sapiens

<400> SEQUENCE: 7

| | | | | | | | | | | | | | | | |
|---|---|---|---|---|---|---|---|---|---|---|---|---|---|---|---|
| Met | Glu | Met | Glu | Lys | Glu | Phe | Glu | Gln | Ile | Asp | Lys | Ser | Gly | Ser | Trp |
| 1 | | | | 5 | | | | | 10 | | | | | 15 | |
| Ala | Ala | Ile | Tyr | Gln | Asp | Ile | Arg | His | Glu | Ala | Ser | Asp | Phe | Pro | Cys |
| | | | 20 | | | | | 25 | | | | | 30 | | |
| Arg | Val | Ala | Lys | Leu | Pro | Lys | Asn | Lys | Asn | Arg | Asn | Arg | Tyr | Arg | Asp |
| | | | 35 | | | | | 40 | | | | | 45 | | |
| Val | Ser | Pro | Phe | Asp | His | Ser | Arg | Ile | Lys | Leu | His | Gln | Glu | Asp | Asn |
| | | 50 | | | | | 55 | | | | | 60 | | | |
| Asp | Tyr | Ile | Asn | Ala | Ser | Leu | Ile | Lys | Met | Glu | Glu | Ala | Gln | Arg | Ser |
| 65 | | | | | 70 | | | | | 75 | | | | | 80 |
| Tyr | Ile | Leu | Thr | Gln | Gly | Pro | Leu | Pro | Asn | Thr | Cys | Gly | His | Phe | Trp |
| | | | | 85 | | | | | 90 | | | | | 95 | |
| Glu | Met | Val | Trp | Glu | Gln | Lys | Ser | Arg | Gly | Val | Val | Met | Leu | Asn | Arg |
| | | | 100 | | | | | 105 | | | | | 110 | | |
| Val | Met | Glu | Lys | Gly | Ser | Leu | Lys | Cys | Ala | Gln | Tyr | Trp | Pro | Gln | Lys |
| | | | 115 | | | | | 120 | | | | | 125 | | |
| Glu | Glu | Lys | Glu | Met | Ile | Phe | Glu | Asp | Thr | Asn | Leu | Lys | Leu | Thr | Leu |
| | | 130 | | | | | 135 | | | | | 140 | | | |
| Ile | Ser | Glu | Asp | Ile | Lys | Ser | Tyr | Tyr | Thr | Val | Arg | Gln | Leu | Glu | Leu |
| 145 | | | | | 150 | | | | | 155 | | | | | 160 |
| Glu | Asn | Leu | Thr | Thr | Gln | Glu | Thr | Arg | Glu | Ile | Leu | His | Phe | His | Tyr |
| | | | | 165 | | | | | 170 | | | | | 175 | |
| Thr | Thr | Trp | Pro | Asp | Phe | Gly | Val | Pro | Glu | Ser | Pro | Ala | Ser | Phe | Leu |
| | | | 180 | | | | | 185 | | | | | 190 | | |
| Asn | Phe | Leu | Phe | Lys | Val | Arg | Glu | Ser | Gly | Ser | Leu | Ser | Pro | Glu | His |
| | | | 195 | | | | | 200 | | | | | 205 | | |
| Gly | Pro | Val | Val | His | Cys | Ser | Ala | Gly | Ile | Gly | Arg | Ser | Gly | Thr | |
| | | 210 | | | | | 215 | | | | | 220 | | | |
| Phe | Cys | Leu | Ala | Asp | Thr | Cys | Leu | Leu | Leu | Met | Asp | Lys | Arg | Lys | Asp |
| 225 | | | | | 230 | | | | | 235 | | | | | 240 |
| Pro | Ser | Ser | Val | Asp | Ile | Lys | Lys | Val | Leu | Leu | Glu | Met | Arg | Lys | Phe |
| | | | | 245 | | | | | 250 | | | | | 255 | |
| Arg | Met | Gly | Leu | Ile | Gln | Thr | Ala | Asp | Gln | Leu | Arg | Phe | Ser | Tyr | Leu |
| | | | 260 | | | | | 265 | | | | | 270 | | |
| Ala | Val | Ile | Glu | Gly | Ala | Lys | Phe | Ile | Met | Gly | Asp | Ser | Ser | Val | Gln |
| | | 275 | | | | | 280 | | | | | 285 | | | |
| Asp | Gln | Trp | Lys | Glu | Leu | Ser | His | Glu | Asp | Leu | Glu | Pro | Pro | Pro | Glu |
| | | 290 | | | | | 295 | | | | | 300 | | | |
| His | Ile | Pro | Pro | Pro | Arg | Pro | Pro | Lys | Arg | Ile | Leu | Glu | Pro | His | |
| 305 | | | | 310 | | | | | 315 | | | | | 320 | |
| Asn | | | | | | | | | | | | | | | |
| 321 | | | | | | | | | | | | | | | |

<210> SEQ ID NO 8
<211> LENGTH: 969
<212> TYPE: DNA
<213> ORGANISM: Homo sapiens

<400> SEQUENCE: 8

```
tatggagatg gaaaaggagt tcgagcagat cgacaagtcc gggagctggg cggccattta    60
ccaggatatc cgacatgaag ccagtgactt cccatgtaga gtggccaagc ttcctaagaa   120
caaaaaccga ataggtaca gagacgtcag tccctttgac catagtcgga ttaaactaca   180
```

-continued

```
tcaagaagat aatgactata tcaacgctag tttgataaaa atggaagaag cccaaaggag    240
ttacattctt acccagggcc ctttgcctaa cacatgcggt cacttttggg agatggtgtg    300
ggagcagaaa agcagggtg tcgtcatgct caacagagtg atggagaaag gttcgttaaa     360
atgcgcacaa tactggccac aaaaagaaga aaaagagatg atctttgaag acacaaattt    420
gaaattaaca ttgatctctg aagatatcaa gtcatattat acagtgcgac agctagaatt    480
ggaaaacctt acaacccaag aaactcgaga gatcttacat ttccactata ccacatggcc    540
tgactttgga gtccctgaat caccagcctc attcttgaac tttcttttca aagtccgaga    600
gtcagggtca ctcagcccgg agcacgggcc cgttgtggtg cactgcagtg caggcatcgg    660
caggtctgga accttctgtc tggctgatac ctgcctcttg ctgatggaca agaggaaaga    720 ccttcttcc gttgatatca agaaagtgct gttagaaatg aggaagtttc ggatggggct     780
gatccagaca gccgaccagc tgcgcttctc ctacctggct gtgatcgaag gtgccaaatt    840
catcatgggg gactcttccg tgcaggatca gtggaaggag cttccacg aggacctgga      900 gcccccaccc gagcatatcc ccccacctcc ccggccaccc aaacgaatcc tggagccaca    960
caatgtcga                                                             969
```

TYROSINE PHOSPHATASE INHIBITORS

This application is the National Phase filing of International Patent Application No. PCT/JP01/04201, filed 21 May 2001.

TECHNICAL FIELD

The present invention relates to a pyrrole compound having a protein tyrosine phosphatase (hereinafter sometimes to be abbreviated as PTP) inhibitory action, which is useful as a drug such as a prophylactic or therapeutic agent of diabetes and the like.

The present invention also relates to a protein tyrosine phosphatase inhibitor containing a pyrrole compound.

The present invention further relates to a prophylactic or therapeutic agent of diabetes containing a pyrrole compound.

BACKGROUND ART

As compounds having a protein tyrosine phosphatase inhibitory action, the following compounds are known.
1) WO99/46244 discloses a compound of the formula:

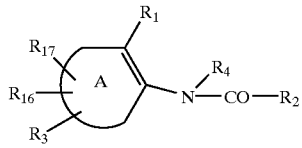

wherein
A is together with a double bond to represent furanyl, thiophenyl, pyrrolyl, oxazolyl, thiazolyl, imidazolyl, pyrazolyl, isoxazolyl, isothiazolyl, 1,2,3-oxadiazolyl, furazanyl or 1,2,3-triazolyl;
$R_1$ is hydrogen, $COR_5$ and the like;
$R_2$ is $COR_5$ and the like;
$R_3$, $R_{16}$ and $R_{17}$ are each independently hydrogen and the like;
$R_4$ is hydrogen, hydroxy and the like;
$R_5$ is hydroxy and the like.
2) WO99/58520 discloses a compound of the formula:

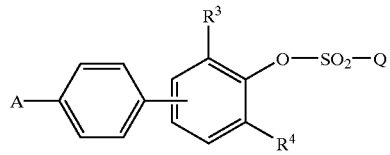

wherein

A is 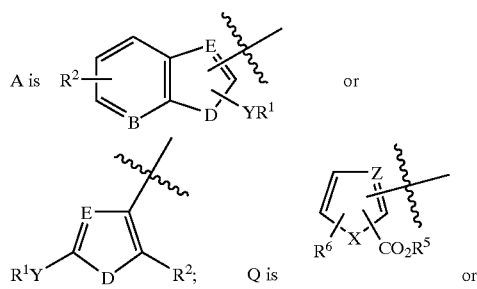  Q is

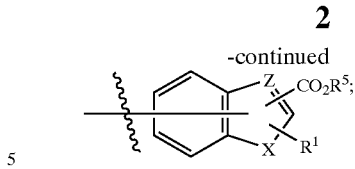

B is a carbon atom or a nitrogen atom;
D is an oxygen atom, a sulfur atom or a nitrogen atom;
E is a carbon atom or a nitrogen atom;
X is a carbon atom, a nitrogen atom, an oxygen atom or a sulfur atom;
Y is a bond, methylene, C(O) or CH(OH);
Z is CH=CH, a nitrogen atom, an oxygen atom or a sulfur atom;
$R^1$ is a $C_{1-12}$ alkyl; a $C_{6-10}$ aryl; a $C_{7-15}$ aralkyl; a halogen; trifluoromethyl; a $C_{1-6}$ alkoxy; Het-alkyl (wherein the alkyl group includes 1 to 6 carbon atom(s)); a $C_{6-10}$ aryl mono-, di- or tri-substituted with trifluoromethyl, a $C_{1-6}$ alkyl or a $C_{1-6}$ alkoxy;
Het is

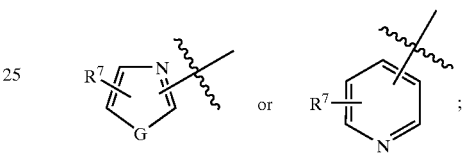

$R^7$ is $C_{1-3}$ alkylene;
G is an oxygen atom, a sulfur atom or a nitrogen atom;
$R^2$ is a hydrogen atom, a $C_{1-6}$ alkyl, a $C_{1-6}$ alkoxy, a halogen or trifluoromethyl;
$R^3$ and $R^4$ are each independently a hydrogen atom; halogen; a $C_{1-6}$ alkyl; a $C_{6-10}$ aryl; a halogen; trifluoromethyl; a $C_{1-6}$ alkoxy; a $C_{6-10}$ aryl which is mono-, di- or tri-substituted with trifluoromethyl, a $C_{1-6}$ alkyl or a $C_{1-6}$ alkoxy; nitro; alkylsulfamide; arylsulfamide; a $C_{3-8}$ cycloalkyl; or 5 to 7 membered heterocycle having 1 to 3 heteroatom(s) selected from an oxygen atom, a nitrogen atom and a sulfur atom;
$R^5$ is a hydrogen atom; a $C_{1-6}$alkyl; a $C_{6-10}$ aryl mono-, di- or tri-substituted with trifluoromethyl, a halogen, a $C_{1-6}$ alkyl, a $C_{7-15}$ aralkyl or a heteroaryl; and
$R^6$ is a hydrogen atom, $-OR^5$ or $-OCOR^5$;
provided that when $R^1$ is a halogen, Y is a bond.
Moreover, pyrrole compounds of the following formula are known.
3) Farmaco, Ed. Sci (1984), 39 (9), p765 discloses a compound of the formula:

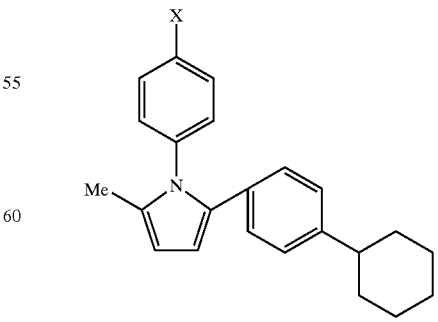

4) Yakugaku Zasshi (1973), 93 (5), p584 discloses a compound of the formula:

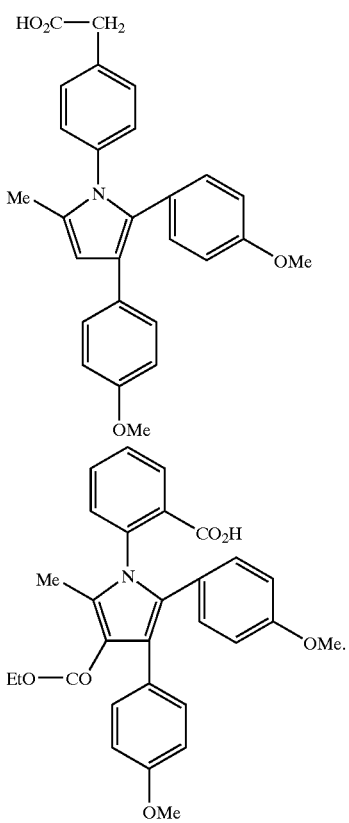

However, none of the above-mentioned pyrrole compounds is reported to be a protein tyrosine phosphatase inhibitor or a prophylactic or therapeutic agent of diabetes.

Therefore, there is a strong demand for development of a pyrrole compound which has protein tyrosine phosphatase inhibitory action and useful as a medicament such as a prophylactic or therapeutic agent for diabetes and the like.

DISCLOSURE OF THE INVENTION

The present invention relates to (1) a novel compound characterized by the chemical structure wherein at least one of the substituent on the nitrogen atom of pyrrole ring and the substituent on the carbon atom constituting the pyrrole ring and adjacents to the nitrogen atom, has a cycle group substituted with a carboxy-$C_{1-6}$ alkoxy group and/or a carboxy-$C_{1-6}$ aliphatic hydrocarbon group; which is the compound of the formula:

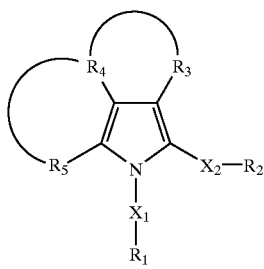

(I)

wherein $X_1$ and $X_2$ are the same or different and each is a bond or a spacer having 1 to 20 atom(s) in the main chain;

one of $R_1$ and $R_2$ is a cycle group having substituent(s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group or a hydrogen atom; and $R_3$, $R_4$ and $R_5$ are the same or different and each is a hydrogen atom or a substituent, or $R_4$ may link together with $R_3$ or $R_5$ to form an optionally substituted ring;

provided that when $R_3$ is a hydrogen atom, $R_4$ is a hydrogen atom and $R_5$ is methyl, $X_2$—$R_2$ is not 4-cyclohexylphenyl; when $R_3$ is 4-methoxyphenyl, $R_4$ is a hydrogen atom and $R_5$ is methyl, $X_2$—$R_2$ is not 4-methoxyphenyl; and when $R_1$ or $R_2$ is a hydrogen atom, the adjacent $X_1$ or $X_2$ is not a $C_{1-7}$ alkylene, or a salt thereof;

(2) the compound according to the above-mentioned (1), wherein $X_1$ and $X_2$ are the same or different and each is a bond or a spacer having 1 to 8 atom(s) in the main chain; and one of $R_1$ and $R_2$ is a cycle group having substituent(s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group;

(3) the compound according to the above-mentioned (1), wherein $R_1$ or $R_2$ is a $C_{6-14}$ aryl substituted with a carboxy-($C_{6-14}$ aryl-substituted)$C_{1-6}$ alkoxy group or a $C_{1-6}$ alkoxy-carbonyl-($C_{6-14}$ aryl-substituted)$C_{1-6}$ alkoxy group;

(4) the compound according to the above-mentioned (1), wherein one of $R_1$ and $R_2$ is a $C_{6-14}$ aryl substituted with a carboxy-($C_{6-14}$ aryl-substituted) $C_{1-6}$ alkoxy group or a $C_{1-6}$ alkoxy-carbonyl-($C_{6-14}$ aryl-substituted)$C_{1-6}$ alkoxy group, and the other is an optionally substituted $C_{6-14}$ aryl;

(5) the compound according to the above-mentioned (1), wherein $X_1$ and $X_2$ are the same or different and each is a bond or a $C_{1-8}$ alkylene;

(6) the compound according to the above-mentioned (1), wherein $R_3$, $R_4$ and $R_5$ are the same or different and each is a hydrogen atom or a hydrocarbon group;

(7) the compound according to the above-mentioned (1), wherein each $R_3$ and $R_4$ is a hydrogen atom;

(8) the compound according to the above-mentioned (1), wherein $R_5$ is a $C_{1-6}$ alkyl;

(9) a prodrug of the compound according to the above-mentioned (1);

(10) a pharmaceutical composition comprising the compound according to the above-mentioned (1) or a prodrug thereof;

(11) the pharmaceutical composition according to the above-mentioned (10), which is a protein tyrosine phosphatase inhibitor;

(12) the pharmaceutical composition according to the above-mentioned (10), which is a prophylactic or therapeutic agent of diabetes;

(13) a protein tyrosine phosphatase inhibitor comprising a compound of the formula:

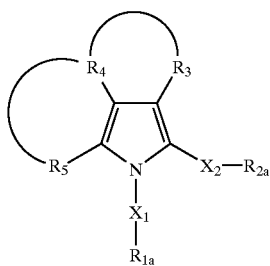

(II)

wherein $X_1$ and $X_2$ are the same or different and each is a bond or a spacer having 1 to 20 atom(s) in the main chain;

one of $R_{1a}$ and $R_{2a}$ is a cycle group having substituent(s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group or a hydrogen atom; and $R_3$, $R_4$ and $R_5$ are the same or different and each is a hydrogen atom or a substituent, or $R_4$ may link together with $R_3$ or $R_5$ to form an optionally substituted ring, or a salt thereof;

(14) the inhibitor according to the above-mentioned (13), wherein $X_1$ and $X_2$ are the same or different and each is a bond or a spacer having 1 to 8 atom(s) in the main chain; and one of $R_{1a}$ and $R_{2a}$ is a cycle group having substituent (s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group;

(15) a prophylactic or therapeutic agent of diabetes comprising a compound of the formula:

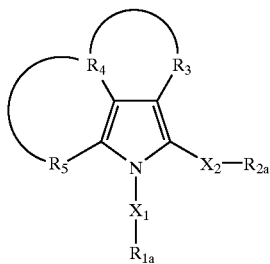

(II)

wherein $X_1$ and $X_2$ are the same or different and each is a bond or a spacer having 1 to 20 atom(s) in the main chain;

one of $R_{1a}$ and $R_{2a}$ is a cycle group having substituent(s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group or a hydrogen atom; and $R_3$, $R_4$ and $R_5$ are the same or different and each is a hydrogen atom or a substituent, or $R_4$ may link together with $R_3$ or $R_5$ to form an optionally substituted ring, or a salt thereof;

(16) the agent according to the above-mentioned (15), wherein $X_1$ and $X_2$ are the same or different and each is a bond or a spacer having 1 to 8 atom(s) in the main chain; and one of $R_{1a}$ and $R_{2a}$ is a cycle group having substituent (s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s), and the other is an optionally substituted cycle group;

(17) a method for preventing or treating diabetes in a mammal in need thereof, which comprises administering to said mammal an effective amount of a compound of the formula (II) or a salt thereof;

(18) Use of a compound of the formula (II) or a salt thereof, for manufacturing a prophylactic or therapeutic agent for diabetes; and

(19) a method for preparing a compound of the formula:

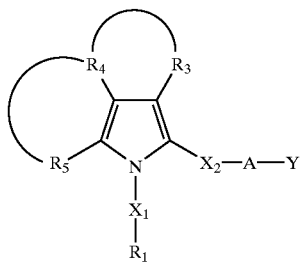

wherein A is a cycle group and the other symbols in the formula have the same meanings as the above-mentioned (1) or a salt thereof, which comprises reacting a compound of the formula:

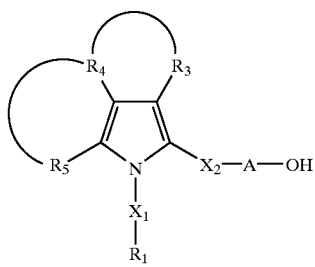

wherein the symbols in the formula have the same meanings as above
or a salt thereof
with a compound of the formula:

H—Y wherein Y is an optionally substituted carboxy-$C_{1-6}$ alkoxy group.

The "spacer having 1 to 20 atom(s) in the main chain" which is represented by $X_1$ or $X_2$, means a divalent group in which 1 to 20 atom(s) is(are) ranged in the main chain. The number of the "atom(s) in the main chain" is counted so as to be the least number.

The "spacer having 1 to 20 atom(s) in the main chain" includes, for example, a divalent group consisting of 1 to 5 (preferably 1 to 3) groups selected from —O—; —S—; —CO—; —SO—; —SO$_2$—; —NR$^6$— (R$^6$ is a hydrogen atom, an optionally substituted (e.g., halogenated) $C_{1-6}$ alkyl, an optionally substituted (e.g., halogenated) $C_{1-6}$ alkyl-carbonyl or an optionally substituted (e.g., halogenated) $C_{1-6}$ alkylsulfonyl); and an optionally substituted divalent $C_{1-6}$ aliphatic hydrocarbon group and the like.

The "optionally halogenated $C_{1-6}$ alkyl" represented by R$^6$ includes, for example, $C_{1-6}$ alkyl optionally having 1 to 5, preferably 1 to 3 halogen atom(s) (e.g., fluorine, chlorine, bromine, iodine and the like) at the substitutable position(s), and the examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

The "optionally halogenated $C_{1-6}$ alkyl-carbonyl" represented by $R^6$ includes, $C_{1-6}$ alkyl-carbonyl optionally having 1 to 5, preferably 1 to 3 halogen atom(s) (e.g., fluorine, chlorine, bromine, iodine and the like) at the substitutable position(s), and the examples include, for example, acetyl, monochloroacetyl, trifluoroacetyl, trichloroacetyl, propanoyl, butanoyl, pentanoyl, hexanoyl and the like.

The "optionally halogenated $C_{1-6}$ alkylsulfonyl" represented by $R^6$ includes, $C_{1-6}$ alkylsulfonyl optionally having 1 to 5, preferably 1 to 3 halogen atom(s) (e.g., fluorine, chlorine, bromine, iodine and the like) at the substitutable position(s), and the examples include, for example, methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, sec-butylsulfonyl, tert-butylsulfonyl, pentylsulfonyl, hexylsulfonyl and the like.

The "divalent $C_{1-6}$ aliphatic hydrocarbon group" of the "optionally substituted divalent $C_{1-6}$ aliphatic hydrocarbon group" includes, for example,
(1) $C_{1-6}$ alkylene (e.g., $—CH_2—$, $—(CH_2)_2—$, $—(CH_2)_3—$, $—(CH_2)_4—$, $—(CH_2)_5—$, $—(CH_2)_6—$, $—CH(CH_3)—$, $—C(CH_3)_2—$, $—(CH(CH_3))_2—$, $—(CH_2)_2C(CH_3)_2—$, $—(CH_2)_3C(CH_3)_2—$ and the like);
(2) $C_{2-6}$ alkenylene (e.g., $—CH=CH—$, $—CH_2—CH=CH—$, $—CH=CH—CH_2—$, $—CH=CH—CH_2—CH_2—$, $—C(CH_3)_2—CH=CH—$, $—CH_2—CH=CH—CH_2—$, $—CH_2—CH_2—CH=CH—$, $—CH=CH—CH=CH—$, $—CH=CH—CH_2—CH_2—CH_2—$ and the like);
(3) $C_{2-6}$ alkynylene (e.g., $—C≡C—$, $—CH_2—C≡C—$, $—CH_2—C≡C—CH_2—CH_2—$ and the like) and the like.

The "substituent" of the "optionally substituted divalent $C_{1-6}$ aliphatic hydrocarbon group" includes, for example, halogen atom (e.g., fluorine, chlorine, bromine, iodine and the like), hydroxy group and the like. The number of the "substituent" is, for example, 1 to 5, preferably 1 to 3.

Preferable examples of the "spacer having 1 to 20 atom(s) in the main chain" include,
(1) $C_{1-20}$ alkylene optionally having 1 to 3 substituent(s) (preferably, halogen atom, hydroxy group and the like) (e.g., $—CH_2—$, $—(CH_2)_2—$, $—(CH_2)_3—$, $—CH(OH)(CH_2)_2—$, $—(CH_2)_4—$, $—(CH_2)_5—$, $—(CH_2)_6—$, $—CHCH_3—$, $—C(CH_3)_2—$, $—CH(CF_3)—$, $—(CH(CH_3))_2—$, $—(CF_2)_2—$, $—(CH_2)_2C(CH_3)_2—$, $—(CH_2)_3C(CH_3)_2—$, $—(CH_2)_7—$, $—(CH_2)_8—$, $—(CH_2)_9—$, $—(CH_2)_{10}—$, $—(CH_2)_{11}—$, $—(CH_2)_{12}—$, $—(CH_2)_{13}—$, $—(CH_2)_{14}—$, $—(CH_2)_{15}—$, $—(CH_2)_{16}—$, $—(CH_2)_{17}—$, $—(CH_2)_{18}—$, $—(CH_2)_{19}—$, $—(CH_2)_{20}—$ and the like);
(2) $C_{2-20}$ alkenylene optionally having 1 to 3 substituent(s) (preferably, halogen atom, hydroxy group and the like) (e.g., $—CH=CH—$, $—CH_2—CH=CH—$, $—CH=CH—CH_2—$, $—CH=CH—CH_2—CH_2—$, $—CH_2—CF=CH—$, $—C(CH_3)_2—CH=CH—$, $—CH_2—CH=CH—CH_2—$, $—CH_2—CH_2—CH=CH—$, $—CH=CH—CH=CH—$, $—CH=CH—CH_2—CH_2—CH_2—$ and the like);
(3) $C_{2-20}$ alkynylene optionally having 1 to 3 substituent(s) (preferably, halogen atom, hydroxy group and the like)

(e.g., $—C≡C—$, $—CH_2—C≡C—$, $—CH_2—C≡C—CH_2—CH_2—$ and the like);
(4) $—(CH_2)_{w1a}O(CH_2)_{w2a}—$, $—(CH_2)_{w1a}S(CH_2)_{w2a}—$, $—(CH_2)_{w1a}CO(CH_2)_{w2a}—$, $—(CH_2)_{w1a}SO(CH_2)_{w2a}—$, $—(CH_2)_{w1a}SO_2(CH_2)_{w2a}—$, $—(CH_2)_{w1a}NR^6(CH_2)_{w2a}—$;
(5) $—(CH_2)_{w3a}CO—$, $—(CH_2)_{w3a}CONR^6(CH_2)_{w4a}—$, $—(CH_2)_{w3a}NR^6CO(CH_2)_{w4a}—$, $—(CH_2)_{w3a}SO_2NR^6(CH_2)_{w4a}—$, $—(CH_2)_{w3a}NR^6SO_2(CH_2)_{w4a}—$, $—(CH_2)_{w3a}COO(CH_2)_{w4a}—$;
(6) $—(CH_2)_{w5a}NR^6CONR^{6b}(CH_2)_{w6a}—$;
(wherein $R^6$ has the same meaning as above; $R^{6b}$ has the same meaning as $R^6$; w1a and w2a are each an integer of 0 to 19 and w1a+w2a is 0 to 19; w3a and w4a are each an integer of 0 to 18 and w3a+w4a is 0 to 18; w5a and w6a are each an integer of 0 to 17 and w5a+w6a is 0 to 17) and the like.

Among the above-mentioned "spacer having 1 to 20 atom(s) in the main chain", the following "spacer having 1 to 8 atom(s) in the main chain" are preferred.
(1) $C_{1-8}$ alkylene optionally having 1 to 3 substituent(s) (preferably, halogen atom, hydroxy group and the like) (e.g., $—CH_2—$, $—(CH_2)_2—$, $—(CH_2)_3—$, $—CH(OH)(CH_2)_2—$, $—(CH_2)_4—$, $—(CH_2)_5—$, $—(CH_2)_6—$, $—CHCH_3—$, $—C(CH_3)_2—$, $—CH(CF_3)—$, $—(CH(CH_3))_2—$, $—(CF_2)_2—$, $—(CH_2)_2C(CH_3)_2—$, $—(CH_2)_3C(CH_3)_2—$ and the like);
(2) $C_{2-8}$ alkenylene optionally having 1 to 3 substituent(s) (preferably, halogen atom, hydroxy group and the like) (e.g., $—CH=CH—$, $—CH_2—CH=CH—$, $—CH=CH—CH_2—$, $—CH=CH—CH_2—CH_2—$, $—CH_2—CF=CH—$, $—C(CH_3)_2—CH=CH—$, $—CH_2—CH=CH—CH_2—$, $—CH_2—CH_2—CH=CH—$, $—CH=CH—CH=CH—$, $—CH=CH—CH_2—CH_2—CH_2—$ and the like);
(3) $C_{2-8}$ alkynylene optionally having 1 to 3 substituent(s) (preferably, halogen atom, hydroxy group and the like) (e.g., $—C≡C—$, $—CH_2—C≡C—$, $—CH_2—C≡C—CH_2—CH_2—$ and the like);
(4) $—(CH_2)_{w1}O(CH_2)_{w2}—$, $—(CH_2)_{w1}S(CH_2)_{w2}—$, $—(CH_2)_{w1}CO(CH_2)_{w2}—$, $—(CH_2)_{w1}SO(CH_2)_{w2}—$, $—(CH_2)_{w1}SO_2(CH_2)_{w2}—$, $—(CH_2)_{w1}NR^6(CH_2)_{w2}—$;
(5) $—(CH_2)_{w3}CO—$, $—(CH_2)_{w3}CONR^6(CH_2)_{w4}—$, $—(CH_2)_{w3}NR^6CO(CH_2)_{w4}—$, $—(CH_2)_{w3}SO_2NR^6(CH_2)_{w4}—$, $—(CH_2)_{w3}NR^6SO_2(CH_2)_{w4}—$, $—(CH_2)_{w3}COO(CH_2)_{w4}—$;
(6) $—(CH_2)_{w5}NR^6CONR^{6b}(CH_2)_{w6}—$;
($R^6$ has the same meaning as above; $R^{6b}$ has the same meaning as $R^6$; w1 and w2 are each an integer of 0 to 5 and w1+w2 is 0 to 7; w3 and w4 are each an integer of 0 to 4 and w3+w4 is 0 to 6; w5 and w6 are each an integer of 0 to 3 and w5+w6 is 0 to 5) and the like.

The "spacer having 1 to 20 atom(s) in the main chain" is preferably $C_{1-20}$ alkylene (preferably $C_{1-8}$ alkylene) or $C_{2-20}$ alkenylene (preferably $C_{2-8}$ alkenylene) and the like, each of which optionally has 1 to 3 substituent(s) (preferably, halogen atom, hydroxy group and the like).

Preferably, $X_1$ or $X_2$ is a bond or $C_{1-20}$ alkylene (preferably $C_{1-8}$ alkylene) optionally having 1 to 3 substituent(s) (preferably, halogen atom, hydroxy group and the like). More preferably, $X_1$ or $X_2$ is a bond or $C_{1-8}$ alkylene.

Preferably, in the formula (I) or (II), $X_1$ and $X_2$ are the same or different and each is a bond or a $C_{1-8}$ alkylene.

The "cycle group" of the "cycle group having substituent (s) selected from 1) an optionally substituted carboxy-$C_{1-6}$ alkoxy group and 2) an optionally substituted carboxy-$C_{1-6}$ aliphatic hydrocarbon group, wherein the cycle group optionally has additional substituent(s)" and the "optionally substituted cycle group" represented by $R_1$, $R_2$, $R_{1a}$ or $R_{2a}$ includes an aromatic hydrocarbon group, an aromatic heterocycle group, a non-aromatic cyclic hydrocarbon group, a non-aromatic heterocycle group and the like.

The preferred aromatic hydrocarbon group is, for example, $C_{6-14}$ aryl and the like. The $C_{6-14}$ aryl includes, for example, phenyl, naphthyl, anthryl, phenanthryl, acenaphthylenyl, biphenylyl and the like.

The aromatic heterocycle group includes, for example, a 5- to 7-membered aromatic monocyclic heterocycle or aromatic fused heterocycle group containing 1 to 4 heteroatom(s) selected from an oxygen atom, a sulfur atom and a nitrogen atom as a ring-constituting atom, besides carbon atoms. The aromatic fused heterocycle group includes, for example, a group formed by fusion of the 5- to 7-membered aromatic monocyclic heterocycle group with a 6-membered ring containing 1 or 2 nitrogen atom(s), benzene ring or a 5-membered ring containing one sulfur atom and the like.

The aromatic heterocycle group includes, for example, 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,3,4-oxadiazol-2-yl, 1,3,4-thiadiazol-2-yl, 1,2,4-triazol-1-yl, 1,2,4-triazol-3-yl, 1,2,3-triazol-1-yl, 1,2,3-triazol-2-yl, 1,2,3-triazol-4-yl, tetrazol-1-yl, tetrazol-5-yl, 2-quinolyl, 3-quinolyl, 4-quinolyl, 2-quinazolyl, 4-quinazolyl, 2-quinoxalyl, 2-benzoxazolyl, 2-benzothiazolyl, benzimidazol-1-yl, benzimidazol-2-yl, indol-1-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and the like.

Preferable non-aromatic cyclic hydrocarbon group is non-aromatic cyclic hydrocarbon group having 3 to 10 carbon atoms. The non-aromatic cyclic hydrocarbon group includes, for example, $C_{3-10}$ cycloalkyl, $C_{3-10}$ cycloalkenyl, $C_{4-10}$ cycloalkadienyl and the like.

The $C_{3-10}$ cycloalkyl includes, cyclopropyl, cyclobutyl, cyclopentyl, cyclohexyl, cycloheptyl, cyclooctyl, bicyclo[3.2.1]heptyl, bicyclo[2.2.2]octyl, bicyclo[3.2.1]octyl, bicyclo[3.2.2]nonyl, bicyclo[4.2.1]nonyl, bicyclo[4.3.1]decyl, tricyclo[3.3.1.1$^{3,7}$]decyl and the like.

The $C_{3-10}$ cycloalkenyl includes, cyclopropenyl, cyclobutenyl, cyclopentenyl (e.g., 2-cyclopenten-1-yl, 3-cyclopenten-1-yl), cyclohexenyl (e.g., 2-cyclohexen-1-yl, 3-cyclohexen-1-yl), cycloheptenyl, cyclooctenyl and the like.

The $C_{4-10}$ cycloalkadienyl includes cycloheptadienyl, cyclopentadienyl (e.g., 2,4-cyclopentadien-1-yl), cyclohexadienyl (e.g., 2,4-cyclohexadien-1-yl, 2,5-cyclohexadien-1-yl) and the like.

The non-aromatic cyclic hydrocarbon group includes 2,3-dihydro-1H-inden-2-yl and the like, in addition to the groups as mentioned above.

The non-aromatic heterocycle group includes, for example, a 5- to 7-membered non-aromatic monocyclic heterocycle group or non-aromatic fused heterocycle group containing 1 to 4 heteroatom(s) selected from an oxygen atom, a sulfur atom and a nitrogen atom as a ring-constituting atom, besides carbon atoms. The non-aromatic fused heterocycle group includes, for example, a group formed by fusing the 5- to 7-membered non-aromatic monocyclic heterocycle group together with a 6-membered ring containing 1 or 2 nitrogen atom(s), benzene ring or a 5-membered ring containing one sulfur atom and the like.

The non-aromatic heterocycle group includes, for example, 1-pyrrolidinyl, piperidino, morpholino, thiomorpholino, 1-piperazinyl, hexamethyleneimin-1-yl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxooxazolidin-3-yl, 2,4-dioxothiazolidin-3-yl and the like.

The "cycle group" is preferably an aromatic hydrocarbon group, and more preferably $C_{6-14}$ aryl such as phenyl, naphthyl, biphenylyl and the like. Among these groups, phenyl is preferable.

The "substituent" which may be possessed by the "cycle group" represented by $R_1$, $R_2$, $R_{1a}$ or $R_{2a}$ includes, for example, halogen atom (e.g., fluorine, chlorine, bromine, iodine and the like), nitro, cyano, optionally substituted $C_{1-8}$ (preferably $C_{1-6}$) aliphatic hydrocarbon group, optionally substituted $C_{6-14}$ aryl, optionally substituted $C_{7-19}$ aralkyl, optionally substituted $C_{3-10}$ cycloalkyl, hydroxy, optionally substituted $C_{1-12}$ (preferably $C_{1-6}$) alkoxy, optionally substituted $C_{6-14}$ aryloxy, optionally substituted $C_{7-19}$ aralkyloxy, optionally substituted $C_{3-10}$ cycloalkyloxy, mercapto, optionally substituted $C_{1-6}$ alkylthio, optionally substituted $C_{6-14}$ arylthio, optionally substituted $C_{7-19}$ aralkylthio, optionally substituted $C_{3-10}$ cycloalkylthio, amino, mono-$C_{1-6}$ alkylamino, di-$C_{1-6}$ alkylamino, optionally substituted heterocycle group, acyl, acylamino, acyloxy and the like.

The number of the above-mentioned substituents is, for example, 1 to 5, preferably 1 to 3. When the number of the substituents is not less than 2, the substituents may be the same or different.

The "$C_{1-8}$ aliphatic hydrocarbon group" of the "optionally substituted $C_{1-8}$ aliphatic hydrocarbon group" includes, for example, $C_{1-8}$ (preferably $C_{1-6}$) alkyl (e.g., methyl, ethyl, propyl, isopropyl, butyl, isobutyl, sec-butyl, tert-butyl, pentyl, hexyl, heptyl, octyl and the like), $C_{2-6}$ alkenyl (e.g., vinyl, allyl, isopropenyl, 2-butenyl and the like), $C_{2-6}$ alkynyl (e.g., ethynyl, propargyl, 2-butynyl and the like) and the like.

The "$C_{6-14}$ aryl" of the "optionally substituted $C_{6-14}$ aryl" includes one exemplified as the "cycle group".

The "$C_{7-19}$ aralkyl" of the "optionally substituted $C_{7-19}$ aralkyl" includes, for example, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl and the like.

The "$C_{3-10}$ cycloalkyl" of the "optionally substituted $C_{3-10}$ cycloalkyl" includes one exemplified as the "cycle group".

The "$C_{1-12}$ alkoxy" of the "optionally substituted $C_{1-12}$ (preferably $C_{1-6}$) alkoxy" includes, for example, methoxy, ethoxy, propoxy, isopropoxy, butoxy, isobutoxy, sec-butoxy, pentyloxy, hexyloxy, heptyloxy, octyloxy, nonyloxy, decyloxy, undecyloxy, dodecyloxy and the like.

The "$C_{6-14}$ aryloxy" of the "optionally substituted $C_{6-14}$ aryloxy" includes, for example, phenyloxy, 1-naphthyloxy, 2-naphthyloxy and the like.

The "$C_{7-19}$ aralkyloxy" of the "optionally substituted $C_{7-19}$ aralkyloxy" includes, for example, benzyloxy, phenethyloxy, diphenylmethyloxy, triphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy, 6-phenylhexyloxy and the like.

The "$C_{3-10}$cycloalkyloxy" of the "optionally substituted $C_{3-10}$ cycloalkyloxy" includes, for example, cyclopropyloxy, cyclobutyloxy, cyclopentyloxy, cyclohexyloxy and the like.

The "$C_{1-6}$ alkylthio" of the "optionally substituted $C_{1-6}$ alkylthio" includes, for example, methylthio, ethylthio, propylthio, isopropylthio, butylthio, sec-butylthio, tert-butylthio, pentylthio, hexylthio and the like.

The "$C_{6-14}$ arylthio" of the "optionally substituted $C_{6-14}$ arylthio" includes, for example, phenylthio, 1-naphthylthio, 2-naphthylthio and the like.

The "$C_{7-19}$ aralkylthio" of the "optionally substituted $C_{7-19}$ aralkylthio" includes, for example, benzylthio, phenethylthio, diphenylmethylthio, triphenylmethylthio, 1-naphthylmethylthio, 2-naphthylmethylthio, 2,2-diphenylethylthio, 3-phenylpropylthio, 4-phenylbutylthio, 5-phenylpentylthio and the like.

The "$C_{3-10}$ cycloalkylthio" of the "optionally substituted $C_{3-10}$ cycloalkylthio" includes, for example, cyclopropylthio, cyclobutylthio, cyclopentylthio, cyclohexylthio and the like.

The "mono-$C_{1-6}$ alkylamino" includes, for example, methylamino, ethylamino, propylamino, isopropylamino, butylamino and the like.

The "di-$C_{1-6}$ alkylamino" includes, for example, dimethylamino, diethylamino, dipropylamino, dibutylamino, ethylmethylamino and the like.

The "heterocycle group" of the "optionally substituted heterocycle group" includes "aromatic heterocycle group" and "non-aromatic heterocycle group" exemplified as the "cycle group".

The "substituent" of the "optionally substituted $C_{1-8}$ aliphatic hydrocarbon group", "optionally substituted $C_{6-14}$ aryl", "optionally substituted $C_{7-19}$ aralkyl", "optionally substituted $C_{3-10}$ cycloalkyl", "optionally substituted $C_{1-12}$ alkoxy", "optionally substituted $C_{6-14}$ aryloxy", "optionally substituted $C_{7-19}$ aralkyloxy", "optionally substituted $C_{3-10}$ cycloalkyloxy", "optionally substituted $C_{1-6}$ alkylthio", "optionally substituted $C_{6-14}$ arylthio", "optionally substituted $C_{7-19}$ aralkylthio", "optionally substituted $C_{3-10}$ cycloalkylthio" and "optionally substituted heterocycle group" include, for example, halogen atom (e.g., fluorine, chlorine, bromine, iodine and the like), nitro, cyano, optionally halogenated $C_{1-6}$ alkyl, $C_{6-14}$ aryl, hydroxy, optionally halogenated $C_{1-6}$ alkoxy, mercapto, optionally halogenated $C_{1-6}$ alkylthio, amino, mono-$C_{1-6}$ alkylamino, di-$C_{1-6}$ alkylamino, formyl, carboxy, carbamoyl, thiocarbamoyl, optionally halogenated $C_{1-6}$alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy, heterocycle group, $C_{3-10}$ cycloalkyl optionally substituted with $C_{1-6}$alkyl and the like.

The number of the above-mentioned substituents is, for example, 1 to 5, preferably 1 to 3. When the number of the substituents is not less than 2, the substituents may be the same or different.

The "optionally halogenated $C_{1-6}$ alkyl", "optionally halogenated $C_{1-6}$ alkyl-carbonyl" and "optionally halogenated $C_{1-6}$alkylsulfonyl" include those exemplified as $R^6$.

The "$C_{6-14}$ aryl" includes one exemplified as the "cycle group".

The "optionally halogenated $C_{1-6}$ alkoxy" includes, for example, $C_{1-6}$ alkoxy optionally having 1 to 5, preferably 1 to 3 halogen atom(s) (e.g., fluorine, chlorine, bromine, iodine and the like) and the like. The examples thereof include, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

The "optionally halogenated $C_{1-6}$ alkylthio" includes, for example, $C_{1-6}$ alkylthio optionally having 1 to 5, preferably 1 to 3 halogen atom(s) (e.g., fluorine, chlorine, bromine, iodine and the like) and the like. The examples threof include, for example, methylthio, difluoromethylthio, trifluoromethylthio, ethylthio, propylthio, isopropylthio, butylthio, 4,4,4-trifluorobutylthio, sec-butylthio, tert-butylthio, pentylthio, hexylthio and the like.

The "mono-$C_{1-6}$ alkylamino" and "di-$C_{1-6}$ alkylamino" include those exemplified as the "substituent" for $R_1$ and the like.

The "$C_{1-6}$ alkoxy-carbonyl" includes, for example, methoxycarbonyl, ethoxycarbonyl, propoxycarbonyl, tert-butoxycarbonyl and the like.

The "mono-$C_{1-6}$ alkyl-carbamoyl" includes, for example, methylcarbamoyl, ethylcarbamoyl and the like.

The "di-$C_{1-6}$alkyl-carbamoyl" includes, for example, dimethylcarbamoyl, diethylcarbamoyl, ethylmethylcarbamoyl and the like.

The "optionally halogenated $C_{1-6}$ alkyl-carboxamide" include, for example, $C_{1-6}$ alkyl-carboxamide optionally having 1 to 5, preferably 1 to 3 halogen atom(s) (e.g., fluorine, chlorine, bromine, iodine and the like) and the like. The examples thereof include, for example, acetamide, trifluoroacetamide, propanamide, butanamide and the like.

The "$C_{1-6}$ alkoxy-carboxamide" includes, for example, methoxycarboxamide, ethoxycarboxamide, propoxycarboxamide, butoxycarboxamide and the like.

The "$C_{1-6}$ alkylsulfonylamino" includes, for example, methylsulfonylamino, ethylsulfonylamino and the like.

The "$C_{1-6}$ alkyl-carbonyloxy" includes, for example, acetoxy, propanoyloxy and the like.

The "$C_{1-6}$ alkoxycarbonyloxy" includes, for example, methoxycarbonyloxy, ethoxycarbonyloxy, propoxycarbonyloxy, butoxycarbonyloxy and the like.

The "mono-$C_{1-6}$ alkyl-carbamoyloxy" includes, for example, methylcarbamoyloxy, ethylcarbamoyloxy and the like.

The "di-$C_{1-6}$ alkyl-carbamoyloxy" includes, for example, dimethylcarbamoyloxy, diethylcarbamoyloxy and the like.

The "heterocycle group" includes, the "aromatic heterocycle group" and "non-aromatic heterocycle group" exemplified as the "cycle group".

The "$C_{3-10}$ cycloalkyl" of "$C_{3-10}$ cycloalkyl optionally substituted with $C_{1-6}$ alkyl" includes one exemplified as the "cycle group". The "$C_{1-6}$ alkyl" of the "$C_{3-10}$ cycloalkyl optionally substituted with $C_{1-6}$ alkyl" includes, for example, methyl, ethyl, propyl, isopropyl, butyl, isobutyl, sec-butyl, tert-butyl, pentyl, hexyl and the like.

The "acyl" includes, for example, an acyl of the formula: —CO—$R^7$, —CO—$OR^7$, —CO—$NR^7R^8$, —CS—$NR^7R^8$, —$SO_2$—$R^{7a}$, —SO—$R^{7a}$ [wherein $R^7$ is (i) a hydrogen atom, (ii) an optionally substituted hydrocarbon group, or (iii) an optionally substituted heterocycle group; $R^{7a}$ is (i) an optionally substituted hydrocarbon group, or (ii) an optionally substituted heterocycle group; $R^8$ is a hydrogen atom or a $C_{1-6}$ alkyl; $R^7$ and $R^8$ may form an optionally substituted nitrogen-containing heterocycle together with the adjacent nitrogen atom] and the like.

The "hydrocarbon group" of the "optionally substituted hydrocarbon group" represented by $R^7$ or $R^{7a}$ includes, for example, hydrocarbon group having 1 to 19 carbon atom(s) (e.g., alkyl, alkenyl, alkynyl, cycloalkyl, aryl, aralkyl and the like) and the like. Among these, the following a) to f) are preferred.

a) $C_{1-6}$alkyl (e.g., methyl, ethyl, propyl, isopropyl, butyl, isobutyl, sec-butyl, tert-butyl, pentyl, hexyl and the like);

b) $C_{2-6}$ alkenyl (e.g., vinyl, allyl, isopropenyl, 2-butenyl and the like);

c) $C_{2-6}$alkynyl (e.g., ethynyl, propargyl, 2-butynyl and the like);

d) $C_{3-10}$ cycloalkyl (e.g., cyclopropyl, cyclobutyl, cyclopentyl, cyclohexyl and the like);

e) $C_{6-14}$ aryl (e.g., phenyl, 1-naphthyl, 2-naphthyl, 2-indenyl, 2-anthryl and the like); and f) $C_{7-19}$ aralkyl (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl and the like).

The "hydrocarbon group" is preferably $C_{1-6}$ alkyl, $C_{6-14}$ aryl, $C_{7-19}$aralkyl and the like.

The "substituent" of the "optionally substituted hydrocarbon group" includes one exemplified as the "substituent" of the "optionally substituted $C_{1-8}$ aliphatic hydrocarbon group" and the like.

The number of the above-mentioned substituents is, for example, 1 to 5, preferably 1 to 3. When the number of the substituents is not less than 2, the substituents may be the same or different.

The "optionally substituted heterocycle group" represented by $R^7$ or $R^{7a}$ includes the "optionally substituted heterocycle group" exemplified as the "substituent" of $R_1$ or $R_2$.

The "$C_{1-6}$ alkyl" represented by $R^8$ includes one exemplified as the "$C_{1-8}$ aliphatic hydrocarbon group".

The "nitrogen-containing heterocycle" of the "optionally substituted nitrogen-containing heterocycle" formed by $R^7$, $R^8$ and the adjacent nitrogen atom include, for example, a 5- to 7-membered nitrogen-containing heterocycle containing at least one nitrogen atom(s) besides carbon atoms and optionally containing 1 to 3 heteroatom(s) selected from a nitrogen atom, a sulfur atom and an oxygen atom, and the like. The "nitrogen-containing heterocycle" is preferably piperidine, morpholine, thiomorpholine, piperazine, pyrrolidine and the like.

The "substituent" of the "optionally substituted nitrogen-containing heterocycle" includes one exemplified as the "substituent" of the "optionally substituted $C_{1-8}$ aliphatic hydrocarbon group" and the like.

The number of the above-mentioned substituents is, for example, 1 to 5, preferably 1 to 3. When the number of the substituents is not less than 2, the substituents may be the same or different.

The "acyl" is preferably formyl, carboxy, carbamoyl, optionally halogenated $C_{1-6}$alkyl-carbonyl (e.g., acetyl and the like), $C_{1-6}$ alkoxycarbonyl (e.g., methoxycarbonyl, ethoxycarbonyl, propoxycarbonyl, tert-butoxycarbonyl and the like), $C_{6-14}$ aryl-carbonyl (e.g., benzoyl, 1-naphthoyl, 2-naphthoyl and the like), $C_{6-14}$ aryloxy-carbonyl (e.g., phenyloxycarbonyl, 1-naphthyloxycarbonyl, 2-naphthyloxycarbonyl and the like), $C_{7-19}$ aralkyloxy-carbonyl (e.g., benzyloxycarbonyl, phenethyloxycarbonyl and the like), heterocyclic carbonyl (e.g., nicotinoyl and the like), mono-$C_{1-6}$ alkyl-carbamoyl (e.g., methylcarbamoyl, ethylcarbamoyl and the like), di-$C_{1-6}$ alkyl-carbamoyl (e.g., dimethylcarbamoyl, diethylcarbamoyl, ethylmethylcarbamoyl and the like), $C_{6-14}$ arylcarbamoyl (e.g., phenylcarbamoyl, naphthylcarbamoyl and the like), hetero- cyclic carbamoyl (e.g., 2-pyridinylcarbamoyl, 2-quinolylcarbamoyl and the like), optionally halogenated $C_{1-6}$alkylsulfonyl (e.g., methylsulfonyl and the like), $C_{6-14}$ arylsulfonyl (e.g., phenylsulfonyl and the like) and the like.

The "acylamino" includes, for example, an amino mono- or di-substituted with the "acyl", and preferably includes, an acylamino of the formula: —$NR^9$—$COR^{10}$, —$NR^9$—$COOR^{10a}$, —$NR^9$—$SO_2R^{10a}$, —$NR^9$—$CONR^{10a}R^{10b}$ [wherein $R^9$ is a hydrogen atom or a $C_{1-6}$ alkyl; $R^{10}$ has the same meaning as $R^7$; $R^{10a}$ has the same meaning as $R^{7a}$; $R^{10b}$ has the same meaning as $R^8$] and the like.

The "$C_{1-6}$ alkyl" represented by $R^9$ includes one exemplified as the "$C_{1-8}$ aliphatic hydrocarbon group".

The "acylamino" is preferably formylamino, optionally halogenated $C_{1-6}$ alkyl-carboxamide (e.g., methylcarboxamide, trifluoromethylcarboxamide, pentylcarboxamide and the like), $C_{6-14}$aryl-carboxamide (e.g., phenylcarboxamide and the like), $C_{7-19}$ aralkyl-carboxamide (e.g., benzylcarboxamide and the like), heterocyclic carboxamide (e.g., benzothiophen-2-ylcarboxamide and the like), optionally halogenated $C_{1-6}$ alkoxy-carboxamide (e.g., methoxycarboxamide, ethoxycarboxamide, propoxycarboxamide, butoxycarboxamide and the like), $C_{6-14}$ arylaminocarbonylamino (e.g., phenylaminocarbonylamino and the like), optionally halogenated $C_{1-6}$ alkylsulfonylamino (e.g., methylsulfonylamino, trifluoromethylsulfonylamino, ethylsulfonylamino and the like), $C_{6-14}$ arylsulfonylamino (e.g., phenylsulfonylamino and the like) and the like.

The "acyloxy" includes, for example, an oxy substituted with one "acyl", preferably, an acyloxy of the formula: —O—$COR^{11}$, —O—$COOR^{11}$, —O—$CONHR^{11}$ [wherein $R^{11}$ has the same meaning as $R^7$] and the like.

The "acyloxy" is preferably optionally halogenated $C_{1-6}$ alkyl-carbonyloxy (e.g., acetoxy, propanoyloxy and the like), $C_{6-14}$aryl-carbonyloxy (e.g., benzoyloxy and the like), optionally halogenated $C_{1-6}$ alkoxy-carbonyloxy (e.g., methoxycarbonyloxy, trifluoromethoxycarbonyloxy, ethoxycarbonyloxy, propoxycarbonyloxy, butoxycarbonyloxy and the like), mono-$C_{1-6}$ alkyl-carbamoyloxy (e.g., methylcarbamoyloxy, ethylcarbamoyloxy and the like), di-$C_{1-6}$ alkyl-carbamoyloxy (e.g., dimethylcarbamoyloxy, diethylcarbamoyloxy and the like), $C_{6-14}$ aryl-carbamoyloxy (e.g., phenylcarbamoyloxy, naphthylcarbamoyloxy and the like), heterocyclic carbonyloxy (e.g., nicotinoyloxy and the like) and the like.

The "substituent" possessed by the "cycle group" represented by $R_1$, $R_2$, $R_{1a}$ or $R_{2a}$ is, preferably, 1) halogen atom (preferably fluorine, chlorine, bromine and the like);

2) optionally substituted $C_{1-8}$ aliphatic hydrocarbon group (preferably, $C_{1-8}$ alkyl or $C_{2-6}$ alkenyl each optionally having 1 to 3 substituent(s) selected from $C_{3-10}$ cycloalkyl optionally substituted with $C_{1-6}$ alkyl, halogen atom, carboxy and $C_{1-6}$ alkoxy-carbonyl, and the like);

3) optionally substituted $C_{1-12}$ alkoxy (preferably $C_{1-12}$ alkoxy optionally having 1 to 4 substituent(s) selected from $C_{3-10}$ cycloalkyl optionally substituted with $C_{1-6}$ alkyl, carboxy, $C_{6-14}$ aryl and halogen atom, and the like);

4) optionally substituted $C_{6-14}$ aryloxy (preferably phenoxy and the like);

5) optionally substituted $C_{3-10}$ cycloalkyl (preferably $C_{3-10}$ cycloalkyl optionally substituted with $C_{1-6}$ alkyl and the like);

6) $C_{7-19}$ aralkyl (preferably benzyl and the like);

7) heterocycle group (preferably 2-benzoxazolyl and the like); and the like.

The "substituent" possessed by the "cycle group" represented by $R_1$, $R_2$, $R_{1a}$ or $R_{2a}$ is, more preferably,
1) halogen atom (preferably, fluorine, chlorine, bromine and the like);
2) optionally substituted $C_{1-6}$ aliphatic hydrocarbon group (preferably $C_{1-6}$ alkyl or $C_{2-6}$ alkenyl each optionally having 1 to 3 substituent(s) selected from a halogen atom, carboxy and $C_{1-6}$ alkoxy-carbonyl, and the like);
3) optionally substituted $C_{1-6}$ alkoxy (preferably $C_{1-6}$ alkoxy optionally having 1 to 3 substituent(s) selected from carboxy and $C_{6-14}$ aryl, and the like);
4) optionally substituted $C_{6-14}$ aryloxy (preferably phenoxy and the like); and the like.

With regard to the "cycle group" represented by $R_1$, $R_2$, $R_{1a}$ or $R_{2a}$, "$R_1$ or $R_2$" and "$R_{1a}$ or $R_{2a}$" have "the substituent selected from 1) optionally substituted carboxy-$C_{1-6}$ alkoxy group and 2) optionally substituted carboxy $C_{1-6}$ aliphatic hydrocarbon group".

The "optionally substituted carboxy-$C_{1-6}$ alkoxy group" includes the group in which the "optionally substituted $C_{1-6}$ alkoxy group" exemplified as the "substituent" of the "cycle group" represented by $R_1$, etc. is further substituted with the "optionally substituted carboxy".

The "substituent" of the "optionally substituted carboxy" includes an optionally substituted hydrocarbon group, an optionally substituted heterocycle group and the like.

The "optionally substituted hydrocarbon group" and "optionally substituted heterocycle group" include those exemplified as $R^7$.

The "optionally substituted carboxy-$C_{1-6}$ alkoxy group" is preferably carboxy-$C_{1-6}$ alkoxy group (e.g., carboxy-methoxy, carboxy-ethoxy and the like); $C_{1-6}$ alkoxy-carbonyl-$C_{1-6}$ alkoxy group (e.g., methoxy-carbonyl-methoxy, ethoxy-carbonyl-methoxy, tert-butoxy-carbonyl-methoxy, methoxy-carbonyl-ethoxy, ethoxy-carbonyl-ethoxy, tert-butoxy-carbonyl-ethoxy and the like); carboxy-($C_{6-14}$ aryl substituted) $C_{1-6}$ alkoxy group (e.g., carboxy-(phenyl)methoxy, carboxy-(phenyl)ethoxy and the like); $C_{1-6}$ alkoxy-carbonyl-($C_{6-14}$ aryl substituted)$C_{1-6}$ alkoxy group (e.g., methoxy-carbonyl-(phenyl)methoxy, ethoxycarbonyl-(phenyl)methoxy, tert-butoxycarbonyl-(phenyl)methoxy, methoxy-carbonyl(phenyl)ethoxy, ethoxycarbonyl(phenyl)ethoxy, tert-butoxycarbonyl (phenyl)ethoxy and the like); carboxy(heterocycle substituted)$C_{1-6}$ alkoxy group (e.g., carboxy-(indol-3-yl)methoxy, carboxy-(indol-3-yl)ethoxy and the like); $C_{1-6}$ alkoxy-carbonyl-(heterocycle substituted) $C_{1-6}$ alkoxy group (e.g., methoxycarbonyl-(indol-3-yl)methoxy, ethoxycarbonyl-(indol-3-yl)methoxy, tert-butoxycarbonyl-(indol-3-yl)methoxy, methoxycarbonyl-(indol-3-yl)ethoxy, ethoxycarbonyl-(indol-3-yl)ethoxy, tert-butoxycarbonyl-(indol-3-yl)ethoxy and the like) and the like. Among these, carboxy-($C_{6-14}$ aryl substituted) $C_{1-6}$ alkoxy group, $C_{1-6}$ alkoxy-carbonyl-($C_{6-14}$ aryl substituted)$C_{1-6}$ alkoxy group are preferable, specifically, carboxy-(phenyl)ethoxy, methoxy-carbonyl-(phenyl)ethoxy, ethoxycarbonyl-(phenyl)ethoxy and the like are preferable.

The "optionally substituted carboxy-$C_{1-6}$ aliphatic hydrocarbon group" includes the group in which the "optionally substituted $C_{1-6}$ aliphatic hydrocarbon group" exemplified as the "substituent" which may be possessed by the "cycle group" represented by $R_1$, etc., is further substituted with the "optionally substituted carboxy".

The "substituent" of the "optionally substituted carboxy" includes optionally substituted hydrocarbon group, optionally substituted heterocycle group and the like.

The "optionally substituted hydrocarbon group" and "optionally substituted heterocycle group" include those exemplified as $R^7$.

The "optionally substituted carboxy-$C_{1-6}$ aliphatic hydrocarbon group" is preferably carboxy-$C_{1-6}$ alkyl group (e.g., carboxymethyl, carboxyethyl and the like); $C_{1-6}$ alkoxy-carbonyl-$C_{1-6}$ alkyl group (e.g., methoxy-carbonyl-methyl, ethoxy-carbonyl-methyl, tert-butoxy-carbonyl-methyl, methoxy-carbonyl-ethyl, ethoxy-carbonyl-ethyl, tert-butoxy-carbonyl-ethyl and the like); carboxy-$C_{2-6}$ alkenyl group (e.g., carboxy-vinyl and the like); $C_{1-6}$ alkoxy-carbonyl-$C_{2-6}$ alkenyl group (e.g., methoxy-carbonyl-vinyl, ethoxy-carbonyl-vinyl, tert-butoxy-carbonyl-vinyl and the like) and the like.

In the formula (I), $R_1$ or $R_2$ is preferably a $C_{6-14}$ aryl substituted with a carboxy-($C_{6-14}$ aryl-substituted)$C_{1-6}$ alkoxy group or a $C_{1-6}$ alkoxy-carbonyl-($C_{6-14}$ aryl-substituted)$C_{1-6}$ alkoxy group.

Further, in the formula (I), it is preferred that one of $R_1$ and $R_2$ is a $C_{6-14}$ aryl substituted with a carboxy-($C_{6-14}$ aryl-substituted)$C_{1-6}$ alkoxy group or a $C_{1-6}$ alkoxy-carbonyl-($C_{6-14}$ aryl-substituted)$C_{1-6}$alkoxy group and the other is an optionally substituted $C_{6-14}$aryl.

Moreover, in the formula (I), it is preferred that $R_2$ is a $C_{6-14}$ aryl substituted with a carboxy-($C_{6-14}$ aryl-substituted) $C_{1-6}$ alkoxy group or a $C_{1-6}$ alkoxy-carbonyl-($C_{6-14}$aryl-substituted)$C_{1-6}$alkoxy group and $R_1$ is an optionally substituted $C_{6-14}$ aryl.

The "substituent" represented by $R_3$, $R_4$ or $R_5$ includes, optionally substituted hydrocarbon group, optionally substituted heterocycle group, halogen atom (e.g., fluorine, chlorine, bromine, iodine and the like), nitro, cyano, hydroxy, optionally halogenated $C_{1-6}$ alkoxy, mercapto, optionally halogenated $C_{1-6}$ alkylthio, amino, mono-$C_{1-6}$ alkylamino, di-$C_{1-6}$ alkylamino, formyl, carboxy, carbamoyl, thiocarbamoyl, optionally halogenated $C_{1-6}$ alkyl-carbonyl, $C_{1-6}$ alkoxy-carbonyl, mono-$C_{1-10}$ alkyl (preferably $C_{1-6}$ alkyl)-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and the like.

The number of the above-mentioned substituents is, for example, 1 to 5, preferably 1 to 3. When the number of the substituents is not less than 2, the substituents may be the same or different.

The "optionally substituted hydrocarbon group" and "optionally substituted heterocycle group" include those exemplified as $R^7$.

The "optionally halogenated $C_{1-6}$ alkoxy", "optionally halogenated $C_{1-6}$ alkylthio", "$C_{1-6}$ alkoxy-carbonyl", "mono-$C_{1-6}$ alkyl-carbamoyl", "di-$C_{1-6}$ alkyl-carbamoyl", "optionally halogenated $C_{1-6}$ alkyl-carboxamide", "$C_{1-6}$ alkoxy-carboxamide", "$C_{1-6}$ alkylsulfonylamino", "$C_{1-6}$ alkyl-carbonyloxy", "$C_{1-6}$ alkoxy-carbonyloxy", "mono-$C_{1-6}$ alkyl-carbamoyloxy", "di-$C_{1-6}$ alkyl-carbamoyloxy" include those exemplified as the "substituent" of the "optionally substituted $C_{1-8}$ aliphatic hydrocarbon group".

The "optionally halogenated $C_{1-6}$ alkyl-carbonyl" and "an optionally halogenated $C_{1-6}$ alkylsulfonyl" include those exemplified as $R^6$.

The "mono-$C_{1-6}$ alkylamino" and "di-$C_{1-6}$alkylamino" include those exemplified as the "substituent" of $R_1$, etc.

$R_3$, $R_4$ and $R_5$ are preferably hydrogen atom or hydrocarbon group, and more preferably, hydrogen atom, $C_{1-6}$ alkyl (preferably methyl, ethyl, propyl and the like), $C_{6-14}$ aryl (preferably phenyl and the like) and the like.

Especially, $R_3$ and $R_4$ are preferably hydrogen atom. $R_5$ is especially preferably $C_{1-6}$ alkyl (preferably methyl and the like).

$R_4$ may link together with $R_3$ or $R_5$ to form a "optionally substituted ring".

The "ring" of the "optionally substituted ring" includes benzene ring, $C_{3-8}$ cycloalkene, $C_{4-8}$ cycloalkadiene, 5- to 8-membered aromatic heterocycle, 5- to 8-membered non-aromatic heterocycle and the like.

The $C_{3-8}$ cycloalkene includes, for example, cyclopropene, cyclobutene, cyclopentene, cyclohexene, cycloheptene, cyclooctene and the like.

The $C_{4-10}$ cycloalkadiene includes, for example, cycloheptadiene, cyclopentadiene, cyclohexadiene and the like.

The 5- to 8-membered aromatic heterocycle includes a 5- to 8-membered aromatic monocyclic heterocycle containing 1 to 3 heteroatom(s) selected from an oxygen atom, a sulfur atom and a nitrogen atom as a ring-constituting atom, besides carbon atoms.

The 5- to 8-membered aromatic heterocycle includes, for example, thiophene, furan, pyrrole, imidazole, pyrazole, thiazole, isothiazole, oxazole, isoxazole, pyridine, pyrazine, pyrimidine, pyridazine and the like.

The 5- to 8-membered non-aromatic heterocycle includes a 5- to 8-membered non-aromatic monocyclic heterocycle containing 1 to 3 heteroatom(s) selected from an oxygen atom, a sulfur atom and a nitrogen atom as a ring-constituting atom, besides carbon atoms.

The 5- to 8-membered non-aromatic heterocycle includes, for example, pyrroline, pyrazoline and the like.

Among the above-mentioned "ring", benzene ring is preferred.

The "substituent" of the "optionally substituted ring" includes one exemplified as the "substituent" of the "optionally substituted $C_1$ aliphatic hydrocarbon group". The "optionally substituted ring" is preferably benzene ring.

The preferred example of the compound of formula (I) (hereinafter sometimes abbreviated as compound (I)) includes, for example, the following compounds.

A compound wherein $X_1$ and $X_2$ are same or different and each is a bond or a $C_{1-8}$ alkylene;

one of $R_1$ and $R_2$ (preferably $R_2$) is a $C_{6-14}$ aryl (preferably phenyl) substituted with a carboxy-($C_{6-14}$ aryl-substituted)$C_{1-6}$ alkoxy group or a $C_{1-6}$ alkoxy-carbonyl-($C_{6-14}$ aryl-substituted)$C_{1-6}$ alkoxy group [preferably, carboxy-(phenyl)ethoxy, methoxycarbonyl-(phenyl)ethoxy, ethoxycarbonyl-(phenyl)ethoxy], and the other (preferably $R_1$) is a $C_{6-14}$ aryl (preferably phenyl) optionally having 1 or 2 substituent(s) selected from the following:

1) a halogen atom (preferably, fluorine, chlorine, bromine and the like);
2) a $C_{1-8}$ alkyl or a $C_{2-6}$ alkenyl each optionally having 1 to 3 substituent(s) selected from a $C_{3-10}$ cycloalkyl optionally substituted with a $C_{1-6}$ alkyl, a halogen atom, carboxy and a $C_{1-6}$ alkoxy-carbonyl;
3) a $C_{1-12}$ alkoxy optionally having 1 to 4 substituent(s) selected from a $C_{3-10}$ cycloalkyl optionally substituted with a $C_{1-6}$ alkyl, carboxy, a $C_{6-14}$ aryl and a halogen atom;
4) a $C_{6-14}$ aryloxy (preferably, phenoxy and the like);
5) a $C_{3-10}$ cycloalkyl optionally substituted with a $C_{1-6}$ alkyl;
6) a $C_{7-19}$ aralkyl (preferably, benzyl and the like); and
7) a heterocycle group (preferably 2-benzoxazolyl and the like);

$R_3$ and $R_4$ are each a hydrogen atom; and $R_5$ is a $C_{1-6}$ alkyl (preferably methyl and the like)

The salts of the compound (I) or (II) include, for example, a salt with inorganic base, organic base, inorganic acid, organic acid or the like.

The preferred example of the salt with inorganic base includes, for example, an alkaline metal salt such as sodium salt, potassium salt and the like; an alkaline earth metal salt such as calcium salt, magnesium salt, barium salt and the like; alminium salt; ammonium salt and the like.

The preferred example of the salt with organic base includes, for example, a salt with trimethylamine, triethylamine, pyridine, picoline, ethanolamine, diethanolamine, triethanolamine, dicyclohexylamine, N,N-dibenzylethylenediamine or the like.

The preferred example of the salt with inorganic acid includes, for example, a salt with hydrochloric acid, hydrobromic acid, nitric acid, sulfuric acid, phosphoric acid or the like.

The preferred example of the salt with organic acid, for example, a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like; and a salt with basic or acidic amino acid.

The preferred example of the salt with basic amino acid includes, for example, a salt with arginine, lysine, ornithine or the like. The preferred example of the salt with acidic amino acid includes, for example, a salt with aspartic acid, glutamic acid or the like.

Among these salts, a pharmaceutically acceptable salt is preferable, and an alkaline metal salt such as sodium salt is more preferable.

The compound (I), (II) and salts thereof (hereinafter sometimes abbreviated as the present compound) may be an anhydrate or a hydrate. The hydrate may have 0.5 to 3 water molecule(s).

The present compound may be labeled with isotope (e.g., $^3H$, $^{14}C$, $^{35}S$, $^{125}I$ and the like).

When the present compound contains an optical isomer, a stereoisomer, a position isomer or a rotational isomer thereof, they are encompassed in the present compound and each may be isolated by a synthesis and separation procedure known per se. For example, when the present compound contains an optical isomer thereof, the optical isomer resolved from the compound is also encompassed in the present compound.

The optical isomer is produced by a method known per se. Specifically, the optical isomer is obtained by using an optically active intermediate, or by optical resolution of the mixture of a final racemate product by a conventional method.

The present compound is preferably optically active.

As the optical resolution method, a method known per se, for example, the following fractional recrystallization method, chiral column method, diastereomer method and the like are used.

1) Fractional Recrystallization Method

A salt of racemate with an optically acytive compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine and the like) is formed, which is separated by fractional recrystallization method, and a free optical isomer is obtained by neutralization step where desired.

2) Chiral Column Method

A racemate or a salt thereof is applied to a column for separation of an optical isomer (chiral column) to allow separation. In the case of liquid chromatography, for example, a mixture of a optical isomer was added to a chiral column such as ENANTIO-OVM (manufactured by TOSOH Corporation) or CHIRAL series (manufactured by Daicel) and the like, and developed with water, various buffers (e.g., phosphate buffer), an organic solvent (e.g., ethanol, methanol, isopropanol, acetonitrile, trifluoroacetic acid, diethylamine and the like) or a mixture thereof to separate the optical isomers. In the case of gas chromatography, for example, the separation was performed using a chiral column such as CP-Chirasil-DeX CB (GL SCIENCES, Inc.) and the like.

3) Diastereomer Method

A racemate mixture is converted to a diastereomer mixture by chemical reaction with an optically active reagent, which is prepared into a homogenous substance by a conventional separation method (e.g., fraction recrystallization, chromatography method and the like), and subjected to a chemical treatment such as hydrolysis reaction and the like to cut off the optically active reagent moiety, whereby an optical isomer is obtained. For example, when the present compound has hydroxy or primary or secondary amino in the molecule, the compound and an optically active organic acid (e.g., MTPA [α-methoxy α-(trifluoromethyl)-phenylacetic acid], (-)-menthoxy acetic acid and the like) may be subjected to a condensation reaction to give an ester form or amide form diastereomer, respectively. When the present compound has a carboxylic acid group, the compound and an optically active amine or alcohol reagent are subjected to a condensation reaction to give an amide form or ester form diastereomer. The diastereomer thus separated is converted to an optical isomer of the original compound by acid hydrolysis or base hydrolysis reaction.

The present compound may be used as a prodrug.

A prodrug of the present compound is a compound that converts to the present compound due to the reaction of enzyme, gastric acid and the like under the physiological condition in vivo, i.e. a compound that converts to the present compound by enzymatic oxidation, reduction, hydrolysis and the like, and a compound that converts to the present compound by hydrolysis and the like due to gastric acid. The prodrug of the present compound includes a compound wherein an amino group of the present compound is acylated, alkylated or phosphorylated [e.g., a compound wherein an amino group of the present compound is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like]; a compound wherein a hydroxy group of the present compound is acylated, alkylated, phosphorylated or borated (e.g., a compound wherein a hydroxy group of the present compound is acetylated, palmitoylated, propanoylated, pivaloylated, succinylated, fumalylated, alanylated, dimethylaminomethylcarbonylated or the like); a compound wherein a carboxyl group of the present compound is esterified or amidated [e.g., a compound wherein a carboxyl group of the present compound is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl) methyl esterified, cyclohexyloxycarbonylethyl esterified, methylamidated and the like] and the like. These compounds may be produced from the present compound according to a method known per se.

A prodrug the present compound may be a compound that converts to the present compound under the physiological condition described in Pharmaceutical research and development, vol. 7, Molecule Design, 163–198, Hirokawa Shoten (1990).

The present compound may be prepared by the following [Production method 1], [Production method 2] or a similar method thereto.

The compound (IIIa), (IVa), (V), (IIIb), (IVb), (IIIc), (VI) used as a starting compound, may be used as a salt. Such salt includes one exemplified as the salt of the compound (I) or (II).

[Production Method 1]

The compound (Ia) which is a compound of the formula (I) wherein $R_1$ is "a cycle group having an optionally substituted carboxy-$C_{1-6}$ alkoxy group, and wherein the cycle group optionally has additional substituent(s)" may be prepared by, for example, the following [Method A].

[Method A]

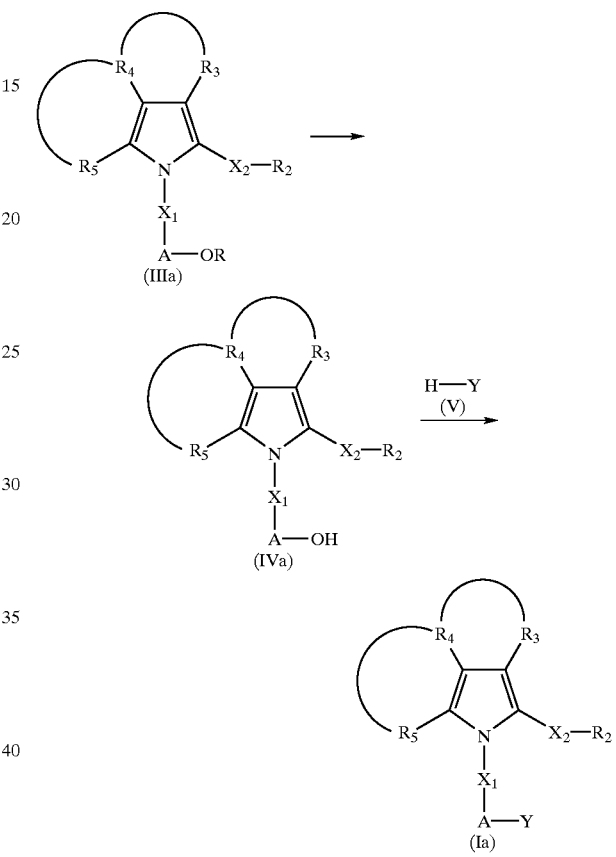

wherein A is a cycle group, R is a $C_{1-6}$ alkyl, Y is an optionally substituted carboxy-$C_{1-6}$ alkoxy group and the other symbols have the same meanings as above.

The "cycle group" represented by A includes the "cycle group" exemplified in $R_1$ or $R_2$.

The "$C_{1-6}$ alkyl" represented by R includes methyl, ethyl, propyl, isopropyl, butyl, isobutyl, sec-butyl, tert-butyl, pentyl, hexyl and the like. Among these, methyl is preferred.

The "optionally substituted carboxy $C_{1-6}$ alkoxy group" represented by Y includes the "optionally substituted carboxy-$C_{1-6}$ alkoxy group" exemplified in $R_1$ or $R_2$.

In this method, compound (IIIa) is firstly subjected to alkyl elimination reaction to give compound (IVa).

The alkyl elimination reaction is carried out by contacting with an acid in a solvent that does not adversely influence the reaction, according to a typical method.

The solvent that does not adversely influence the reaction includes, for example, halogenated hydrocarbons such as chloroform, methylene chloride and the like. The amount of the solvent to be used is 1 to 100 fold-volume of compound (IIIa).

The acid includes, for example, boron tribromide, hydrogen bromide and the like.

The amount of the acid to be used is preferably from 1 to 10 molar equivalent per compound (IIIa).

The reaction temperature is generally from about −50 to about 150° C.

The reaction time is generally from about 0.5 to about 20 hours.

The thus-obtained compound (IVa) may be isolated and purified by a known separation and purification means, such as concentration, concentration under reduced pressure, solvent extraction, crystallization, recrystallization, phase transfer, chromatography and the like. Alternatively, the compound (IVa) may be used in the next reaction without isolation.

The compound (IVa) is then reacted with compound (V) to give compound (Ia).

This reaction may be carried out according to a method known per se, for example, the method described in Synthesis, page 1 (1981) and the like or a similar method thereto.

That is, this reaction is carried out in a solvent that does not adversely influence the reaction, in the presence of organic phosphorous compound and an electrophilic agent.

The organic phosphorous compound includes, for example, triphenylphosphine, tributylphosphine and the like.

The electrophilic agent includes, for example, diethyl azodicarboxylate, diisopropyl azodicarboxylate, azodicarbonyldipiperazine and the like.

Each of the amounts of the organic phosphorous compound and the electrophilic agent is preferably from about 1 to about 5 molar equivalent per compound (IVa).

The solvent that does not adversely influence the reaction includes, for example, ethers such as diethylether, tetrahydrofuran, dioxane and the like; halogenated hydrocarbons such as chloroform, methylene chloride and the like; aromatic hydrocarbons such as benzene, toluene, xylene and the like; amides such as N,N-dimethylformamide; sulfoxides such as dimethylsulfoxide and the like, and the like. Two or more of these solvents may be used upon mixing at a suitable ratio. The amount of the solvent to be used is, for example, from 1 to 100 fold-volume per compound (IVa).

The reaction temperature is generally from about −50 to about 150° C., preferably from about −10 to about 100° C.

The reaction time is generally from about 0.5 to about 20 hours.

The thus-obtained compound (Ia) may be isolated and purified by a known separation and purification method, such as concentration, concentration under reduced pressure, solvent extraction, crystallization, recrystallization, phase transfer, chromatography and the like.

The compound (Ia) obtained by the [Method A] is subjected to hydrolysis reaction where desired, to give compound (Iaa) wherein a carboxy of the "optionally substituted carboxy-$C_{1-6}$ alkoxy group" represented by Y is free.

The hydrolysis reaction is carried out in a water-containing solvent in the presence of an acid or a base, according to a typical method.

The acid includes, for example, hydrochloric acid, sulfuric acid, acetic acid, hydrobromic acid and the like.

The base includes, for example, an alkaline metal carbonate salt such as potassium carbonate, sodium carbonate and the like; an alkaline metal alkoxide such as sodium methoxide and the like; an alkaline metal hydroxide such as potassium hydroxide, sodium hydroxide, lithium hydroxide, and the like.

The amount of the acid or base to be used is generally excess to compound (Ia). The amount of the acid to be used is preferably from about 2 to about 50 equivalents per compound (Ia). The amount of the base to be used is preferably from about 1.2 to about 5 equivalents per compound (Ia).

The water-containing solvent includes, for example, a mixture of water with one or more solvents selected from alcohols such as methanol, ethanol; ethers such as tetrahydrofuran, dioxane, diethylether; dimethylsulfoxide, acetone and the like. The amount of the solvent to be used is, for example, 1 to 100 fold-volume per compound (Ia).

The reaction temperature is generally from about −20 to about 150° C., preferably about −10 to about 100° C.

The reaction time is generally from about 0.1 to about 20 hours.

The thus-obtained compound (Iaa) may be isolated and purified by a known separation and purification method, such as concentration, concentration under reduced pressure, solvent extraction, crystallization, recrystallization, phase transfer, chromatography and the like.

The compound (IIIa) used as a starting compound in the [Method A] may be prepared according to a method known per se, for example, the method described in Chemistry of Heterocyclic Compounds, vol. 48, Part 1, pp. 105–294 (1990); Journal of Medicinal Chemistry, vol. 40, pp. 1619–1633 (1997) and the like or a similar method thereto.

Also, the compound (V) used as a starting compound in the [Method A] may be prepared according to a method known per se.

The compound (Ib) which is a compound of the formula (I) wherein $R_2$ is "a cycle group having an optionally substituted carboxy-$C_{1-6}$ alkoxy group wherein the cycle group optionally has additional substituent(s)" may be prepared by the following [Method B].

[Method B]

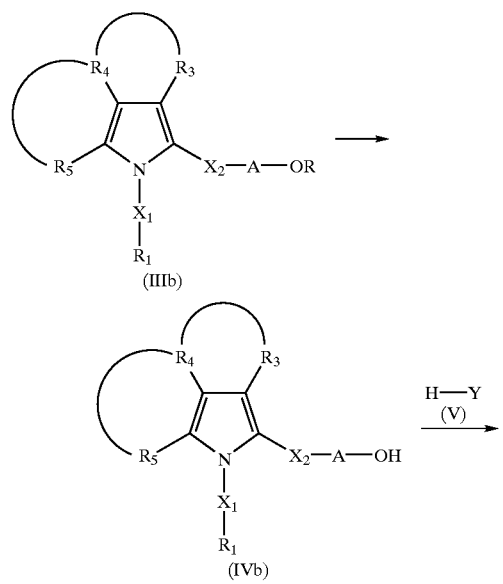

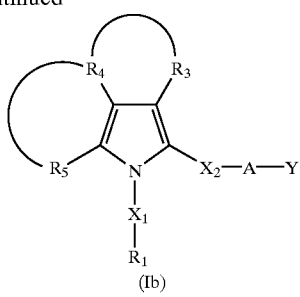
(Ib)

wherein the symbols have the same meanings as above.

This method is carried out similarly to the [Method A].

The compound (Ib) obtained by [Method B] may be subjected to a hydrolysis reaction where desired, to give compound (Ibb) wherein a carboxy of the "optionally substituted carboxy-$C_{1-6}$ alkoxy group" represented by Y is free.

The hydrolysis reaction is carried out in a similar manner in the case of the compound (Iaa).

The thus-obtained compound (Ibb) may be isolated and purified by a known separation and purification method, such as concentration, concentration under reduced pressure, solvent extraction, crystallization, recrystallization, phase transfer, chromatography and the like.

The compound (IIIb) used as a starting compound of the [Method B] may be produced by a method known per se, for example, the method described in Chemistry of Heterocyclic Compounds, vol. 48, Part 1, pp. 105–294 (1990); Journal of Medicinal Chemistry, vol. 40, pp. 1619–1633 (1997) and the like or a similar method thereto.

[Production Method 2]

The compound (Ic) which is a compound of the formula (I) wherein one of $R_1$ and $R_2$ is "a cycle group having an optionally substituted carboxy-$C_{1-6}$ aliphatic hydrocarbon group wherein the cycle group optionally has additional substituent(s)" may be prepared by, for example, the following method.

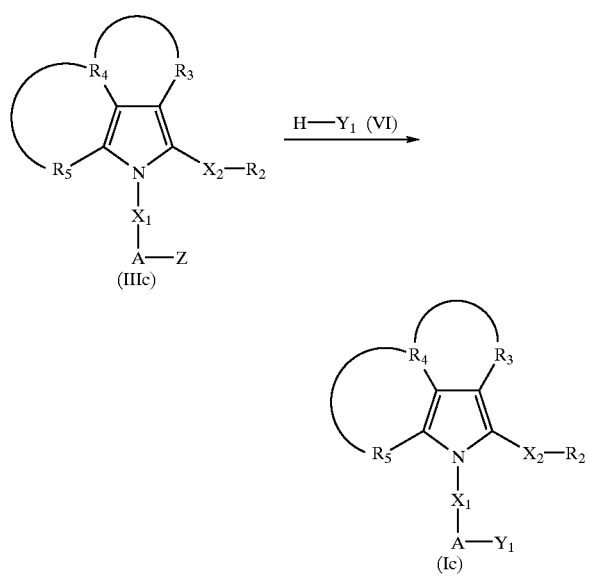

wherein Z is a halogen atom or trifluoromethanesulfonyloxy, $Y_1$ is an optionally substituted carboxy-$C_{1-6}$ aliphatic hydrocarbon group, and the other simbols have the same meanings as above.

The halogen atom represented by Z includes fluorine, chlorine, bromine and the like. Z is preferably bromine and the like.

The "optionally substituted carboxy-$C_{1-6}$ aliphatic hydrocarbon group" represented by $Y_1$ includes the "optionally substituted carboxy-$C_{1-6}$ aliphatic hydrocarbon group" exemplified in $R_1$ or $R_2$.

In this method, compound (IIIc) is reacted with compound (VI) to give compound (Ic).

This reaction is carried out in a solvent that does not adversely influence the reaction, in the presence of a base, a phosphine compound and a palladium compound.

The base includes, for example, an alkaline metal carbonate salt such as potassium carbonate, sodium carbonate and the like; an alkaline metal acetic acid salt such as sodium acetate and the like; an organic base such as triethylamine, tributylamine and the like, and the like.

The amount of the base to be used is preferably from about 1 to about 5 molar equivalent per compound (IIIc).

The phosphine compound includes, for example, tris(2-methylphenyl)phosphine, triphenylphosphine and the like.

The palladium compound includes, for example, palladium(II) acetate, palladium(II) chloride, palladium carbon, tetrakis(triphenylphosphine)palladium, bis(triphenylphosphine)dichloropalladium(II), bis(benzylideneacetone)palladium and the like.

Each of the amounts of the phosphine compound and palladium compound to be used is preferably about 0.02 to about 5 molar equivalent per compound (IIIc).

The solvent that does not adversely influence the reaction includes, for example, ethers such as diethylether, tetrahydrofuran, dioxane and the like; halogenated hydrocarbons such as chloroform, methylene chloride and the like; aromatic hydrocarbons such as benzene, toluene, xylene and the like; amides such as N,N-dimethylformamide and the like; sulfoxides such as dimethylsulfoxide and the like, acetonitrile and the like. Two or more of these solvents may be used upon mixing at a suitable ratio. The amount of the solvent to be used is, for example, from 1 to 100 fold-volume per compound (IIIc).

The reaction temperature is generally from about −50 to about 250° C., preferably from about −10 to about 200° C.

The reaction time is generally from about 0.5 to about 100 hours.

The thus-obtained compound (Ic) may be isolated and purified by a known separation and purification method, such as concentration, concentration under reduced pressure, solvent extraction, crystallization, recrystallization, phase transfer, chromatography and the like.

The compound (Ic) obtained by the [Production method 2] may be subjected to a hydrolysis reaction where desired, to give compound (Icc) wherein a carboxy of the "optionally substituted carboxy-$C_{1-6}$ aliphatic hydrocarbon group" represented by $Y_1$ is free.

The hydrolysis reaction is carried out in a similar manner in the case of the compound (Iaa).

The thus-obtained compound (Icc) may be isolated and purified by a known separation and purification method, such as concentration, concentration under reduced pressure, solvent extraction, crystallization, recrystallization, phase transfer, chromatography and the like.

The compound (IIIc) used as a starting compound in the [Production method 2] may be prepared according to a method known per se, for example, the method described in Chemistry of Heterocyclic Compounds, vol. 48, Part 1, pp.

105–294 (1990); Journal of Medicinal Chemistry, vol. 40, pp. 1619–1633 (1997) and the like or a similar method thereto.

Also, the compound (VI) used as a starting compound in the [Production method 2] may be prepared according to a method known per se.

In each of the above-mentioned reactions, when the starting compound has amino, carboxy, hydroxy or carbonyl as a substituent, a protective group generally used in peptide chemistry may be introduced in the substituent. In this case, the protective group is removed after reaction where desired, to give the object compound.

The protective group of amino includes, for example, formyl, $C_{1-6}$alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-10}$aralkyl-carbonyl (e.g., benzylcarbonyl and the like), $C_{7-14}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$alkenyl (e.g., 1-allyl and the like) and the like. These groups are optionally substituted with 1 to 3 of a halogen atom (e.g., fluorine, chlorine, bromine, iodine and the like), $C_{1-6}$ alkoxy (e.g., methoxy, ethoxy, propoxy and the like), nitro and the like.

The protective group of carboxy includes, for example, $C_{1-6}$ alkyl (e.g., methyl, ethyl, propyl, isopropyl, butyl, tert-butyl and the like), $C_{7-11}$aralkyl (e.g., benzyl and the like), phenyl, trityl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted with 1 to 3 halogen atom(s) (e.g., fluorine, chlorine, bromine, iodine and the like), $C_{1-6}$ alkoxy (e.g., methoxy, ethoxy, propoxy and the like) and nitro and the like.

The protective group of hydroxy includes, for example, $C_{1-6}$ alkyl (e.g., methyl, ethyl, propyl, isopropyl, butyl, tert-butyl and the like), phenyl, trityl, $C_{7-10}$aralkyl (e.g., benzyl and the like), formyl, $C_{1-6}$ alkyl-carbonyl (e.g., acetyl, propionyl and the like), benzoyl, $C_{7-10}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted with 1 to 3 of a halogen atom (e.g., fluorine, chlorine, bromine, iodine and the like), $C_{1-6}$alkyl (e.g., methyl, ethyl, n-propyl and the like), $C_{1-6}$ alkoxy (e.g., methoxy, ethoxy, propoxy and the like), nitro and the like.

The protective group of carbonyl includes, for example, cyclic acetal (e.g., 1,3-dioxane and the like), an acyclic acetal (e.g., di-$C_{1-6}$alkylacetal and the like) and the like.

The removing of the above-mentioned protective groups may be carried out according to a method known per se, for example the method described in Protective Groups in Organic Synthesis, John Wiley and Sons (1980) and the like. For example, a method using an acid, a base, ultraviolet ray, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction method and the like are used.

The present compound shows low toxicity and can be used as an agent for preventing or treating various diseases mentioned below in mammals (e.g., human, mouse, rat, rabbit, dog, cat, cattle, horse, swine, simian and the like), as such or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder, disintegrant for solid preparations; and solvent, dissolution aids, suspending agent, isotonicity agent, buffer, soothing agent and the like for liquid preparations. Where necessary, additive for pharmaceutical preparations such as preservative, antioxidant, coloring agent, sweetening agent and the like can be used.

Preferable examples of the excipient include lactose, saccharose, D-mannitol, D-sorbitol, starch, pregelatinized starch, dextrin, crystalline cellulose, low-substituted hydroxypropylcellulose, sodium carboxymethylcellulose, gum arabic, dextrin, pullulan, light silicic anhydride, synthetic aluminum silicate, magnesium aluminate metasilicate and the like.

Preferable examples of the lubricant include magnesium stearate, calcium stearate, talc, colloidal silica and the like.

Preferable examples of the binder include pregelatinized starch, sucrose, gelatin, gum arabic, methylcellulose, carboxymethylcellulose, sodium carboxymethylcellulose, crystalline cellulose, saccharose, D-mannitol, trehalose, dextrin, pullulan, hydroxypropyl cellulose, hydroxypropylmethylcellulose, polyvinylpyrrolidone and the like.

Preferable examples of the disintegrant include lactose, saccharose, starch, carboxymethylcellulose, calcium carboxymethylcellulose, sodium croscarmellose, sodium carboxymethyl starch, light silicic anhydride, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferable examples of the dissolution aids include polyethylene glycol, propylene glycol, D-mannitol, trehalose, benzyl benzoate, ethanol, Tris aminomethane, cholesterol, triethanolamine, sodium carbonate, sodium citrate, sodium salicylate, sodium acetate and the like.

Preferable examples of the suspending agent include surfactants such as stearyltriethanolamine, sodium lauryl sulfate, lauryl aminopropionate, lecithin, benzalkonium chloride, benzethonium chloride, monostearic glyceride and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferable examples of the isotonicity agent include sodium chloride, glycerol, D-mannitol, D-sorbitol, glucose and the like.

Preferable examples of the buffer include phosphate buffer, acetate buffer, carbonate buffer, citrate buffer, and the like.

Preferable examples of the soothing agent include benzyl alcohol and the like.

Preferable examples of the preservative include p-oxybenzoic acid esters, chlorobutanol, benzyl alcohol, phenethyl alcohol, dehydroacetic acid, sorbic acid and the like.

Preferable examples of the antioxidant include sulfite, ascorbate and the like.

Preferable examples of the coloring agent include water-soluble edible tar pigment (e.g., foodcolors such as Food Color Red Nos. 2 and 3, Food Color Yellow Nos. 4 and 5, Food Color Blue Nos. 1 and 2 and the like, water insoluble lake pigment (e.g., aluminum salt of the aforementioned water-soluble edible tar pigment and the like), natural pigments (e.g., beta carotene, chlorophyll, red iron oxide etc.) and the like.

Preferable examples of the sweetening agent include saccharin sodium, dipotassium glycyrrhetinate, aspartame, stevia and the like.

The dosage form of the pharmaceutical composition may be, for example, oral agents such as tablets, capsules (including soft capsules and micro capsules), granules, powders, syrups, emulsions, suspensions and the like; or parenteral agents such as injections (e.g., subcutaneous injections, intravenous injections, intramuscular injections, intraperitoneal injections and the like), external agents (e.g., nasal preparations, transdermal preparations, ointments and the like), suppositories (e.g., rectal suppositories, vaginal suppositories and the like), pellets, infusion and the like. These may be administered safely via oral or parenteral route. The pharmaceutical composition may be sustained-release preparations.

The pharmaceutical composition can be produced according to a method conventionally used in the field of pharmaceutical preparation, such as the method described in Japan Pharmacopoeia and the like. The specific production methods of the pharmaceutical preparation are described in detail in the following.

For example, an oral agent is produced by adding, to the active ingredient, excipient (e.g., lactose, sucrose, starch, D-mannitol and the like), disintegrant (e.g., calcium carboxymethylcellulose and the like), binder (e.g., pregelatinated starch, gum arabic, carboxymethylcellulose, hydroxypropylcellulose, polyvinylpyrrolidone and the like), lubricant (e.g., talc, magnesium stearate, polyethylene glycol 6000 and the like) and the like, compression-molding the mixture, and where necessary, coating the same using a coating base for masking of taste, enteric property or sustained release according to a method known per se.

Examples of the coating base include a sugar-coating base, a water-soluble film coating base, an enteric film coating base, a sustained release film coating base and the like.

As a sugar-coating base, sucrose may be used, along with one or two species selected from talc, precipitated calcium carbonate, gelatin, gum arabic, pullulan, carnauba wax and the like.

As a water-soluble film coating base, for example, cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkyl methacrylate copolymer E [Eudragit E, tradename, Rohm Pharma], polyvinylpyrrolidone and the like; polysaccharides such as pullulan and the like; and the like are used.

As a enteric film coating base, for example, cellulose polymers such as hydroxypropylmethylcellulose phthalate, hydroxypropylmethylcellulose acetate succinate, carboxymethylethylcellulose, acetic phthalic cellulose and the like; acrylic acid polymers such as methacrylic acid copolymer L [Eudragit L, tradename, Rohm Pharma], methacrylic acid copolymer LD [Eudragit L-30D55, trademark, Rohm Pharma], methacrylic acid copolymer S [Eudragit S, trademark, Rohm Pharma] and the like; naturally occurring substance such as shellac and the like; and the like are used.

As a sustained release film coating base, for example, cellulose polymers such as ethylcellulose and the like; acrylic acid polymers such as aminoalkyl methacrylate copolymer RS [Eudragit RS, trademark, Rohm Pharma], ethyl acrylate-methyl methacrylate copolymer suspension [Eudragit NE, tradename, Rohm Pharma] and the like, and the like are used.

Two or more kinds of the above-mentioned coating bases may be mixed in an appropriate ratio for use. In addition, a light shielding agent such as titanium oxide, iron sesquioxide and the like may be used during coating.

An injection is produced by dissolving, suspending or emulsifying an active ingredient in an aqueous solvent (e.g., distilled water, physiological saline, Ringer's solution and the like) or an oily solvent (e.g., plant oil such as olive oil, sesame oil, cottonseed oil, corn oil and the like, propylene glycol and the like) and the like, together with a dipersing agent (e.g., polysorbate 80, polyoxyethylene hydrogenated castor oil 60 and the like), polyethylene glycol, carboxymethylcellulose, sodium alginate and the like), preservative (e.g., methylparaben, propylparaben, benzyl alcohol, chlorobutanol, phenol and the like), isotonicity agent (e.g., sodium chloride, glycerol, D-mannitol, D-sorbitol, glucose and the like) and the like. In this step, dissolution aids (e.g., sodium salicylate, sodium acetate and the like), stabilizers (e.g., human serum albumin and the like), soothing agents (e.g., benzyl alcohol and the like) and the like may be used on demand.

The present compound has superior PTP inhibitory action and is useful as a prophylactic or therapeutic agent of diseases caused by PTP.

The PTP includes, cytoplasmic-type PTP, receptor-type PTP, dual specificity phosphatase of which substrate includes phosphorylated serine/threonine in addition to phosphorylated tyrosine, low molecular weight (LWN)-PTP and the like.

The cytoplasmic-type PTP includes, for example, PTP-1B, T-cell PTP (TC-PTP), rat brain PTP, STEP, PTPMEG1, PTPH1, PTPD1, PTPD2, FAP-1/BAS, PTP1C, SH-PTP2, SHP-2, PTP1D, SHP-1 and the like.

The receptor-type PTP includes, for example, CD45, CD45/LCA, LAR, PTP α, PTP β, PTP δ, PTP ε, PTP ζ, PTP μ, PTP κ, PTPσ, SAP-1, PTP-U2/GLEPP1, DEP-1, OST-PTP and the like.

The dual specificity phosphatase includes, for example, MAPK phosphatase, PAC-1, rVH6, KAP, VH-1, VHR, cdc25 and the like.

The present compound has a superior inhibitory action, especially to PTP-1B, among these PTPs.

The "diseases caused by PTP" includes, for example, diabetes (e.g., insulin-dependent diabetes (type I diabetes), insulin-independent diabetes (type II diabetes), gestational diabetes and the like), impaired glucose tolerance (IGT), tumor (e.g., pulmonary cancer, kidney cancer, pancreatic cancer, breast cancer, ovary cancer, leukemia, prostate cancer, skin cancer and the like), autoimmune disease, immunodeficiency, allergic disease (e.g., asthma and the like), born disease (e.g., osteoporosis and the like), infectious disease (e.g., respiratory infection, urinary tract infection, digestive infection, skin soft tissue infection, lower limb infection and the like), arthritic disease (e.g., chronic rheumatoid arthritis, osteoarthritis and the like) and the like.

Among these diseases, the present compound is useful as a prophylactic and therapeutic agent of diabetes such as insulin-dependent diabetes (type I diabetes), insulin-independent diabetes (type II diabetes), gestational diabetes, impaired glucose tolerance (IGT) and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, a non-fasting blood glucose level (glucose concentration of intravenous plasma) of not less than 200 mg/dl. A condition not falling under the above-mentioned diabetes, and which is not, "a condition showing a fasting blood glucose level (glucose concentration of intravenous plasma) of less than 110 mg/dl and a 75 g oral glucose tolerance test (75 g OGTT) 2 h level (glucose concentration of intravenous plasma) of less than 140 mg/dl" (normal type), is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl or a 75 g oral glucose tolerance test 2 h level (glucose concentration of intravenous plasma) of not less than 200 mg/dl.

According to the above-mentioned reports, impaired glucose tolerance is a condition showing a 75 g oral glucose tolerance test 2 h level (glucose concentration of intravenous plasma) of not less than 140 mg/dl and less than 200 mg/dl. Furthermore, according to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), only a condition showing a 75 g oral glucose tolerance test 2 h level (glucose concentration of intravenous plasma) of less than 140 mg/dl is called IFG (Impaired Fasting Glycemia).

The present compound can be also used as a prophylactic and therapeutical agent of diabetes, borderline type, impaired glucose tolerance, IFG (Impaired Fasting Glucose) and IFG (Impaired Fasting Glycemia), as determined according to the above-mentioned new diagnostic criteria. Moreover, the present compound can prevent progress of borderline type, impaired glucose tolerance, IFG (Impaired Fasting Glucose) or IFG (Impaired Fasting Glycemia) into diabetes.

The present compound can be also used as a prophylactic or therapeutic agent of, for example, hyperlipidemia (e.g., hypertriglyceridemia, hypercholesterolemia, low HDL lipemia and the like); diabetic complications [e.g, neuropathy, nephropathy, retinopathy, cataract, macroangiopathy, osteopenia, hyperosmolar diabetic coma, diabetic gangrene, xerostomia, acoustic hypesthesia, cerebrovascular disorder, peripheral blood circulation disorder and the like]; obesity; cachexia (e.g., cancerous cachexia, tuberculous cachexia, diabetic cachexia, blood disease cachexia, endocrine disease cachexia, infectious disease cachexia or cachexia due to aquired immunodeficiency syndrome); fatty liver; hypertension; polycystic ovary syndrome; kidney disease (e.g., diabetic nephropathy, glomerular nephritis, glomerulosclerosis, nephritic syndrome, hypertensive nephrosclerosis, end stage kidney disease and the like); muscular dystrophy; myocardial infarction; angina pectoris; cerebral infarction; Syndrome X; hyperinsulinemia-induced sensory disorder; irritable bowel syndrome; acute or chronic diarrhea; inflammatory diseases (e.g., chronic rheumatoid arthritis, spondylitis deformans, arthritis deformans, lumber pain, gout, postoperative traumatic inflammation, remission of tumentia, neuralgia, pharyngolaryngitis, cystitis, hepatitis, pneumonia, pancreatitis and the like); arterial sclerosis (e.g., atherosclerosis and the like) and the like.

The present compound may also used as an insulin sensitizer; an insulin sensitivity enhancer; an antithrombotic agent; an agent for suppressing progress of impaired glucose tolerance into diabetes and the like.

The present compound may also used for amelioration of symptom such as abdominal pain, nausea, vomition, epigastric discomfort and the like accompanied with peptic ulcer, acute or chronic gastritis, biliary tract dyskinesia, cholecystitis and the like.

The present compound may also used, based on its ability of controlling (stimulating or suppressing) appetite, as for example, a therapeutic agent for leanness and cibophobia (increasing body weight of the subject suffering from leanness or cibophobia) or a therapeutic agent for obesity.

Although the dose of the present compound varies depending on the administration subject, administration route, target disease, condition and the like, for example, it is desirable that the present compound as an active ingredient is generally administered in a single dose of about 0.01–100 mg/kg body weight, preferably about 5–100 mg/kg body weight 1 to 3 times a day, for oral administration to an adult diabetic patients.

The present compound can be used in combination with therapeutic agents such as a therapeutic agent of diabetes, a therapeutic agent of diabetic complications, an antihyperlipemia agent, an antihypertensive agent, an antiobestic agent, a diuretic, a chemotherapeutic agent, immunotherapeutic agent and the like (hereinafter to be referred to as a combination drug) for the purpose of enhancing the effect.

The timing of administration of the present compound and a combination drug is not limited. These may be simultaneously administered or administered in a staggered times to an administration subject. The dose of the combination drug can be appropriately determined based on the dose clinically employed. The proportion of the present compound and combination drug can be appropriately determined depending on the administration subject, administration route, target disease, condition, combination and the like. When, for example, the administration subject is human, a combination drug is used in an amount of 0.01–100 parts by weight per 1 part by weight of the present compound.

Examples of the therapeutic agent of diabetes include insulin preparations (e.g., animal insulin preparations extracted from pancreas of cattle, swine; human insulin preparations synthesized by genetic engineering techniques using Escherichia coli or yeast); insulin sensitizers other than the present compound (e.g., pioglitazone or hydrochloride thereof, troglitazone, rosiglitazone or maleate thereof, GI-262570, JTT-501, MCC-555, YM-440, KRP-297, CS-011 and the like), (α-glucosidase inhibitors (e.g., voglibose, acarbose, miglitol, emiglitate and the like), biguanides (e.g., phenformin, metformin, buformin and the like), insulin secretagogues (e.g., sulfonylureas such as tolbutamide, glibenclamide, gliclazide, chlorpropamide, tolazamide, acetohexamide, glyclopyramide, glimepiride and the like; repaglinide, senaglinide, nateglinide, mitiglinide, GLP-1 and the like), amyrin agonists (e.g., pramlintide and the like), protein tyrosine phosphatase inhibitors other than the present compound (e.g., vanadic acid and the like), β3 agonists (e.g., CL-316243, SR-58611-A, UL-TG-307, SB-226552, AJ-9677, BMS-196085, AZ40140 and the like) and the like.

Examples of the therapeutic agent of diabetic complications include aldose reductase inhibitors (e.g., Tolrestat, Epalrestat, Zenarestat, Zopolrestat, Minalrestat, Fidarestat, SK-860, CT-112 and the like), neurotrophic factors (e.g., NGF, NT-3, BDNF and the like), PKC inhibitors (e.g., LY-333531 and the like), AGE inhibitors (e.g., ALT946, pimagedine, pyratoxanthine, N-phenacylthiazolium bromide (ALT766) and the like), active oxygen scavengers (e.g., thioctic acid and the like), cerebral vasodilators (e.g., tiapride, mexiletine and the like), and the like.

Examples of the antihyperlipemia agent include HMG-CoA reductase inhibitors (e.g., cerivastatin, pravastatin, simvastatin, lovastatin, atorvastatin, fluvastatin, itavastatin and sodium salts thereof and the like), squalene synthase inhibitors or fibrate compounds having a triglyceride lowering action (e.g., bezafibrate, clofibrate, simfibrate, clinofibrate and the like) and the like.

Examples of the antihypertensive agent include angiotensin converting enzyme inhibitors (e.g., captopril, enalapril, alacepril, delapril, llsinopril, imidapril, benazepril, cilazapril, temocapril, trandolapril and the like), angiotensin II antagonists (e.g., candesartan cilexetil, losartan, eprosartan, valsartan, termisartan, irbesartan, tasosartan and the like), calcium antagonists (e.g., nicardipine hydrochloride, manidipine hydrochloride, nisoldipine, nitrendipine, nilvadipine and the like) and the like.

Examples of the antiobestic agent include central antiobestic agents (e.g., Dexfenfluramine, fenfluramine, phentermine, Sibutramine, amfepramone, dexamphetamine, Mazindol, phenylpropanolamine, clobenzorex and the like), pancreatic lipase inhibitors (e.g., orlistat and the like), β3 agonists (e.g., CL-316243, SR-58611-A, UL-TG-307, SB-226552, AJ-9677, BMS-196085, AZ40140 and the like), peptide anorexiants (e.g., leptin, CNTF (Ciliary Neurotropic Factor) and the like), cholecystokinin agonists (e.g., lintitript, FPL-15849 and the like) and the like.

Examples of the diuretic include xanthine derivatives (e.g., sodium salicylate theobromine, calcium salicylate theobromine and the like), thiazide preparations (e.g., ethiazide, cyclopenthiazide, trichloromethiazide, hydrochiorothiazide, hydroflumethiazide, benzylhydrochlorothiazide, penflutizide, polythiazide, methyclothiazide and the like), antialdosterone agents (e.g., spironolactone, triamterene and the like), carbonate dehydrating enzyme inhibitors (e.g., acetazolamide and the like), chlorobenzenesulfonamide agents (e.g., chlortalidone, mefruside, indapamide and the like), azosemide, isosorbide, etacrynic acid, piretanide, bumetanide, furosemide and the like.

Examples of the chemotherapeutic agent include alkylation agents (e.g., cyclophosphamide, ifosfamide and the like), metabolic antagonists (e.g., methotrexate, 5-fluorouracil and the like), anti-cancer antibiotics (e.g., mitomycin, adriamycin and the like), plant-derived anti-cancer agents (e.g., vincristin, vindesine, taxol and the like), cisplatin, carboplatin, etopoxide and the like. Of these, furtulon and neofurtulon which are 5-fluorouracil derivatives and the like are preferable.

Examples of the immunotherapeutic agent include microorganism or bacterial components (e.g., muramyl dipeptide derivative, picibanil and the like), polysaccharides having immunity potentiating activity (e.g., lentinan, sizofiran, krestin and the like), cytokines obtained by genetic engineering techniques (e.g., interferon, interleukin (IL) and the like), colony stimulating factors (e.g., granulocyte colony stimulating factor, erythropoietin and the like) and the like, with preference given to IL-1, IL-2, IL-12 and the like.

Furthermore, drugs having a cachexia-improving action established in animal models and clinical situations, such as cyclooxygenase inhibitors (e.g., Indometacin and the like) [Cancer Research, vol. 49, 5935–5939, 1989], progesterone derivatives (e.g., Megesterol acetate) [Journal of Clinical Oncology, vol. 12, 213–225, 1994], glucosteroid (e.g., dexamethasone and the like), metoclopramide agents, tetrahydrocannabinol agents (ibid.), fat metabolism improving agents (e.g., eicosapentaenoic acid and the like) [British Journal of Cancer, vol. 68, 314–318, 1993], growth hormones, IGF-1, or antibodies to a cachexia-induced factor such as TNF-α, LIF, IL-6, Oncostatin M and the like, can be used in combination with the present compound.

The combination drug is preferably an insulin preparation, an insulin sensitizer, an α-glucosidase inhibitor, a biguanide, an insulin secretagogue (preferably a sulfonylurea) or the like.

Two or more of the above-mentioned combination drugs can be used in combination in an appropriate ratio. Preferable combinations in the case of using two or more combination drugs are, for example, as shown in the following.

1) an insulin sensitizer and an insulin preparation;
2) an insulin sensitizer and an insulin secretagogue (preferably sulfonylurea);
3) an insulin sensitizer and α-glucosidase inhibitor;
4) an insulin sensitizer and a biguanide;
5) an insulin sensitizer, an insulin preparation and a biguanide;
6) an insulin sensitizer, an insulin preparation and an insulin secretagogue (preferably sulfonylurea);
7) an insulin sensitizer, an insulin preparation and α-glucosidase inhibitor;
8) an insulin sensitizer, an insulin secretagogue (preferably sulfonylurea) and a biguanide;
9) an insulin sensitizer, an insulin secretagogue (preferably sulfonylurea) and α-glucosidase inhibitor; and
10) an insulin sensitizer, a biguanide and α-glucosidase inhibitor.

When the present compound is used in combination with a combination drug, the amount thereof can be reduced within a safe range in consideration of counteraction of these agents. Particularly, the doses of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent of diabetic complications, antihyperlipemia agent and antihypertensive agent can be reduced whereby an adverse effect which may be caused by these agents can be prevented effectively.

BEST MODE FOR CARRYING OUT OF THE INVENTION

The present invention is explained in more detail by the following Examples, Formulation Examples and Experimental Examples. These do not limit the present invention and the present invention can be modified within the range that does not deviate from the scope of the invention.

In the following Examples, the "room temperature" is 0 to 30° C. Unless otherwise mentioned, the "%" means percent by weight.

The infrared spectrum was measured by diffuse reflection method using Fourier transform type infrared spectrometer.

The abbreviations used in this specification mean the following.

S: singlet
d: doublet
t: triplet q: quartet
m: multiplet
br: broad
J: coupling constant
Hz: Hertz
CDCl₃: deuterated chloroform
DMSO-d₆: deuterated dimethylsulfoxide
DMSO: dimethylsulfoxide
THF: tetrahydrofuran
DMF: N,N-dimethylformamide
¹H-NMR: proton nuclear magnetic resonance (generally, free form was measured in CDCl₃.)
IR: infrared absoption spectrum In the present specification, when a base, an amino acid and the like are represented by abbreviations, these abbreviations are based on the abbreviations by IUPAC-IUB Commision on Biochemical Nomenclature or conventional abbreviations in the art. With regard to amino acids, when an optical isomer exists, it represents L form unless otherwise mentioned.

In the following Test Examples, gene engineering methods such as cloning method, base sequencing method and the like, are carried out according to a known method (e.g., the method described in Molecular Cloning, Sambrook et al., Cold Spring Harbor Lab. Press (1989) and the like).

The sequence numbers of the sequence listing of the present specification mean the following sequences.

[SEQ ID NO: 1]
The base sequence of primer 1 used in Test Example 1.
[SEQ ID NO: 2]
The base sequence of primer 2 used in Test Example 1.
[SEQ ID NO: 3]
The base sequence of PTP-1B cDNA (1322 bp) described in Test Example 1.
[SEQ ID NO: 4]
The base sequence of primer 3 used in Test Example 1.
[SEQ ID NO: 5]
The base sequence of primer 4 used in Test Example 1.
[SEQ ID NO: 6]
The base sequence of PCR reaction product (976 bp) described in Test Example 1.
[SEQ ID NO: 7]
The amino acid sequence of PTP-1B enzyme active domain described in Test Example 1.
[SEQ ID NO: 8]
The base sequence of PTP-1B cDNA fragment inserted to pET32a(+) described in Test Example 1.

EXAMPLES

Example 1

Ethyl (2R)-2-{4-[1-(4-bromophenyl)-1H-pyrrol-2-yl]phenoxy}-3-phenylpropanoate (1) 3-(5,5-Dimethyl-1,3-dioxan-2-yl)-1-propanol To an aqueous solution of 2,2-dimethyl-1,3-propanediol (100 g, 960 mmol) (200 ml) was added concentrated hydrochloric acid (20 ml) and 2,3-dihydrofuran (66.1 ml, 874 mmol) and the mixture was stirred at room temperature for 12 hours. The reaction solution was adjusted to pH 9 with aqueous 5 N sodium hydroxide and extracted with chloroform. The extract was dried over magnesium sulfate anhydride and the solvent was removed under reduced pressure. The residue was distilled under reduced pressure to give the object compound as an oily substance. 126 g (yield: 82.9%)

¹H-NMR (CDCl₃) δ; 0.73 (3H, s), 1.19 (3H, s), 1.67–1.81 (4H, m), 2.49 (1H, bs), 3.41–3.65 (6H, m), 4.48 (1H, t, J=4.4 Hz).

IR (KBr) cm⁻¹; 2932, 2853, 1471, 1394, 1142, 1041, 980, 926.

(2) 3-(5,5-Dimethyl-1,3-dioxan-2-yl)-1-propanal

To a solution of oxalyl chloride (16.6 ml, 190 mmol) in methylene chloride (75 ml) was added dropwise dimethylsulfoxide (29.8 ml, 420 mmol) at −78° C. over 15 minutes. The mixture was stirred for 15 minutes and added dropwise a solution of 3-(5,5-dimethyl-1,3-dioxane-2-yl)-1-propanol (30.0 g, 172 mmol) in methylene chloride (300 ml) over 35 minutes, and the mixture was stirred at −78° C. for 1 hour. Then, to the obtained mixture was added triethylamine (83.5 ml, 600 mmol) and the mixture was stirred at −70° C. for 1 hour, then the temperature of the mixture was raised to room temperature, and the mixture was stirred at room temperature for 2 hours. The reaction solution was poured into water and extracted with methylene chloride. The extracts were collected and washed with saturated aqueous sodium bicarbonate and dried over magnesium sulfate anhydride, and the solvent was removed under reduced pressure. The residue was purified by silica gel column chromatography (hexane:ethyl acetate=9:1) to give the object compound as an oily substance. 17.0 g (yield: 52.0%)

¹H-NMR (CDCl₃) δ; 0.72 (3H, s), 1.17 (3H, s), 1.94–2.01 (2H, m), 2.55–2.63 (2H, m), 3.41 (2H, d, J=11.0 Hz), 3.59 (2H, d, J=11.0 Hz), 4.51 (1H, t, J=4.0 Hz), 9.77 (1H, s).

IR (KBr) cm⁻¹; 2957, 2847, 1725, 1472, 1395, 1140, 1105, 1041, 1017, 972, 928.

(3) 3-(5,5-Dimethyl-1,3-dioxan-2-yl)-1-(4-methoxyphenyl)-1-propanol

To a suspension of magnesium (440 mg, 18.1 mmol) in THF (10 ml) was added a drop of 1,2-dibromoethane, and a solution of 4-bromoaniline (2.17 ml, 17.4 mmol) in THF (10 ml) was added dropwise to the mixture. The reaction solution was stirred at 70° C. for 1 hour and cooled to −70° C. Then, 3-(5,5-dimethyl-1,3-dioxan-2-yl)-1-propanal (2 g, 11.6 mmol) was added to the solution. The obtained mixture was stirred at −70° C. for 2 hours and at room temperature for 1 hour. The mixture was poured into 10% aqueous ammonium chloride and extracted with ethyl acetate. The extracts were collected, washed with water and dried over magnesium sulfate anhydride, and the solvent was removed under reduced pressure. The residue was purified by silica gel column chromatography (hexane:ethyl acetate=3:1) to give the object compound as an oily substance. 1.36 g (yield: 41.8%)

¹H-NMR (CDCl₃) δ; 0.72 (3H, s), 1.19 (3H, s), 1.71–1.95 (4H, m), 2.58 (1H, d, J=3.6 Hz), 3.42 (2H, d, J=11.0 Hz), 3.61 (2H, d, J=11.0 Hz), 3.80 (3H, s), 4.47 (1H, t, J=4.0 Hz), 4.63–4.71 (1H, m), 6.86 (2H, d, J=8.4 Hz), 7.27 (2H, d, J=8.4 Hz).

IR (KBr) cm⁻¹; 3399, 2955, 2851, 1613, 1514, 1470, 1395, 1248, 1177, 1134, 1036, 980, 833.

(4) 3-(5,5-Dimethyl-1,3-dioxan-2-yl)-1-(4-methoxyphenyl)-1-propanone

To a solution of 3-(5,5-dimethyl-1,3-dioxan-2-yl)-1-(4-methoxyphenyl)-1-propanol (1.18 g, 4.21 mmol) in methylene chloride (50 ml) was added pyridinium chlorochromate (1.36 g, 6.32 mmol) and the mixture was stirred at room temperature for 3 hours, and the solvent was removed under reduced pressure. The residue was purified by silica gel column chromatography (ether) to give the object compound as a solid. 1.10 g (yield: 94.0%)

¹H-NMR (CDCl₃) δ; 0.72 (3H, s), 1.19 (3H, s), 2.03–2.13 (2H, m), 3.10 (2H, t, J=7.8 Hz), 3.43 (2H, d, J=10.2 Hz), 3.60 (2H, d, J=10.2 Hz), 3,87 (3H, s), 4.56 (1H, t, J=4.8 Hz), 6.93 (2H, d, J=8.8 Hz), 7.96 (2H, d, J=8.8 Hz).

IR (KBr) cm⁻¹; 2955, 1678, 1601, 1510, 1258, 1171, 1132, 1030, 995, 837.

(5) 1-(4-Bromophenyl)-2-(4-methoxyphenyl)-1H-pyrrole

A solution of 3-(5,5-dimethyl-1,3-dioxane-2-yl)-1-(4-methoxyphenyl)-1-propanone (1.00 g, 3.59 mol), 4-bromoaniline (679 mg, 3.95 mmol) and p-toluenesulfonic acid monohydrate (51.5 mg, 0.271 mmol) in toluene (50 ml) was refluxed for 20 hours under heating. The solvent was removed under reduced pressure, and the residue was purified by silica gel column chromatography (hexane:ethyl acetate=20:1) to give the object compound as a solid. 960 mg (yield: 81.4%)

$^1$H-NMR (CDCl$_3$) δ; 3.78 (3H, s), 6.34–6.35 (2H, m), 6.77 (2H, d, J=8.8 Hz), 6.86–7.07 (5H, m), 7.43 (2H, d, J=8.8 Hz).

IR (KBr) cm$^{-1}$; 1507, 1491, 1246, 1030, 831, 714.

Elementary analysis for C$_{17}$H$_{14}$NBrO; Calculated: C, 62.21; H, 4.30; N, 4.27. Found: C, 62.14; H, 4.22; N, 4.28.

(6) 4-[1-(4-Bromophenyl)-1H-pyrrol-2-yl]phenol

To a solution of 1-(4-bromophenyl)-2-(4-methoxyphenyl)-1H-pyrrole (960 mg, 2.93 mmol) in methylene chloride (30 ml) was added boron tribromide (1.11 ml, 11.7 mmol) at 0° C. The mixture was stirred at 0° C. for 30 minutes and at room temperature for 2 hours, and the reaction solution was poured into ice water. The organic layer was separated, washed with saturated aqueous sodium bicarbonate and dried over magnesium sulfate anhydride, and the solvent was removed under reduced pressure. The residue was purified by silica gel column chromatography (hexane:ethyl acetate=3:1) to give the object compound as a solid. 512 mg (yield: 55.6%)

$^1$H-NMR (CDCl$_3$) δ; 4.91 (1H s), 6.34–6.35 (2H, m), 6.70 (2H, d, J=8.8 Hz), 6.86–7.06 (5H, m), 7.43 (2H, d, J=8.8 Hz)

IR (KBr) cm$^{-1}$; 3200, 1491, 1240, 833, 826,721.

Elementary analysis for C$_{16}$H$_{12}$NBrO; Calculated: C, 61.17; H, 3.85; N, 4.46. Found: C, 61.16; H, 3.81; N, 4.16.

(7) Ethyl (S)-2-hydroxy-3-phenylpropanoate (S)-Phenylalanine (25.0 g, 151 mmol) was suspended in chloroform (100 ml). Concentrated hydrochloric acid (15 ml) was added to the suspension, stirred at room temperature for 30 minutes, and the produced crystals were filtered out. The crystals were dissolved into 5% sulfuric acid (450 ml). To the obtained mixture, an aqueous solution of sodium nitrite (20.6 g, 298 mmol) (120 ml) was added dropwise at 0° C. over 3 hours. The reaction solution was extracted with ether and the extract was dried over magnesium sulfate anhydride, and the solvent was removed under reduced pressure. To the residue were added p-toluenesulfonic acid monohydrate (243 mg, 12.8 mmol) and ethanol (250 ml) and the mixture was refluxed for 12 hours under heating, and the solvent was removed under reduced pressure. The residue was purified by silica gel column chromatography (hexane:ethyl acetate=10:1) to give the object compound as a solid. 4.86 g (yield: 13.6%)

$^1$H-NMR (CDCl$_3$) δ; 1.28 (3H, t, J=7.4 Hz), 2.77 (1H, d, J=6.2 Hz), 2.97 (1H, dd, J=14, 6.6 Hz), 3.14 (1H, dd, J=14, 4.4 Hz), 4.22 (2H, q, J=7.4 Hz), 4.39–4.48 (1H, m), 7.20–7.35 (5H, m).

IR (KBr) cm$^{-1}$; 3445, 2982, 1732, 1496, 1454, 1271, 1202, 1096, 1030, 747, 700.

$[α]_D^{25.5}$ −21.2° (c4.37, benzene), lit $[α]_D^{24}$ −22.6 (c4.33, benzene)

(8) Ethyl (2R)-2-{4-[1-(4-bromophenyl)-1H-pyrrol-2-yl]phenoxy}-3-phenylpropanoate To a solution of 4-[1-(4-bromophenyl)-1H-pyrrol-2-yl]phenol (1.20 g, 3.82 mmol), ethyl (S)-2-hydroxy-3-phenylpropanoate (888 mg, 4.58 mmol) and triphenylphosphine (1.20 g, 4.58 mmol) in toluene (10 ml) was added diethyl azodicarboxylate (40%, 2.00 g, 4.58 mmol) and the mixture was stirred at 80° C. for 1.5 hours, and the solvent was removed under reduced pressure. The residue was purified by silica gel column chromatography (hexane:ethyl acetate=20:1) to give the object compound as a solid. 860 mg (yield: 46.0%)

$^1$H-NMR (CDCl$_3$) δ; 1.66 (3H, t, J=7.0 Hz), 3.21–3.24 (2H, m), 4.16 (2H, q, J=7.0 Hz), 4.75 (1H, t, J=5.8 Hz), 6.32 (2H, t, J=2.6 Hz), 6.70 (2H, d, J=8.8 Hz), 6.86 (1H, t, J=2.6 Hz), 6.85–7.01 (4H, m), 7.26–7.29 (5H, m), 7.41 (2H, d, J=8.8 Hz).

IR (KBr) cm$^{-1}$; 1750, 1505, 1493, 1238, 1184, 1071, 1032, 833, 702.

$[α]_D^{24}$+16.0° (c 0.54, chloroform)

Example 2

(2R)-2-{4-[1-(4-Bromophenyl)-1H-pyrrol-2-yl]phenoxy}-3-phenylpropanoic acid

To a mixed solution of ethyl (2R)-2-{4-[1-(4-bromophenyl)-1H-pyrrol-2-yl]phenoxy}-3-phenylpropanoate (280 mg, 0.571 mmol) obtained in Example 1 in THF (2 ml)-methanol (1 ml) was added an aqueous 5 N sodium hydroxide (0.685 ml, 3.43 mmol) and the mixture was stirred at room temperature for 1 hour. The reaction solution was diluted with ethyl acetate and neutralized with 1 N hydrochloric acid. The organic layer was separated and washed with water. The organic layer was dried over magnesium sulfate anhydride and the solvent was removed under reduced pressure to give the object compound as an oily substance. 240 mg (yield: 90.9%)

$^1$H-NMR (CDCl$_3$) δ; 3.26 (2H, d, J=7.0 Hz), 4.81 (1H, t, J=7.0 Hz), 6.33 (2H, d, J=2.4 Hz), 6.70 (2H, d, J=8.8 Hz), 6.86 (1H, t, J=2.4 Hz), 6.99 (4H, d, J=8.8 Hz), 7.26–7.29 (5H, m), 7.41 (2H, d, J=8.8 Hz).

IR (KBr) cm$^{-1}$; 3031, 1725, 1491, 1234, 831.

$[α]_D^{27}$+4.10 (c 0.42, chloroform)

Example 3

Ethyl (2E)-3-[4-(1-{4-[(1E)-3-ethoxy-3-oxo-1-propenyl]phenyl}-5-methyl-1H-pyrrol-2-yl)phenyl]-2-propenoate (1) 1-(4-Bromophenyl)-1,4-pentanedione A suspension of 4-bromobenzaldehyde (25.0 g, 135 mmol), triethylamine (29.3 ml, 210 mmol), methyl vinyl ketone (8.74 ml, 105 mmol) and 3-ethyl-5-(2-hydroxyethyl)-4-methyl thiazolium bromide (5.30 g, 21.0 mmol) in ethanol (50 ml) was stirred at 77° C. for 20 hours and the solvent was removed under reduced pressure. 2 N hydrochloric acid was added to the residue and the mixture was extracted with ethyl acetate. The extracts were collected and washed with saturated aqueous sodium bicarbonate, dried over magnesium sulfate anhydride, and the solvent was removed under reduced pressure. To the residue was added diisopropylether to give the object compound as crystals. 10.8 g (yield: 31.4%)

Melting point: 76–77° C. (hexane-ethyl acetate).

$^1$H-NMR (CDCl$_3$) δ; 2.26 (3H, s), 2.89 (2H, t, J=6.0 Hz), 3.23 (2H, t, J=6.0 Hz), 7.60 (2H, d, J=8.8 Hz), 7.85 (2H, d, J=8.8 Hz).

IR (KBr) cm$^{-1}$; 1707, 1676, 1586, 1410, 1318, 1071, 995, 847, 828, 750.

Elementary analysis for C$_{11}$H$_{11}$OBr; Calculated: C, 51.79; H, 4.35. Found: C, 51.82; H, 4.44.

(2) 1,2-Bis(4-bromophenyl)-5-methyl-1H-pyrrole

A solution of 1-(4-bromophenyl)-1,4-pentanedione (2.55 g, 10.0 mol), 4-bromoaniline (1.72 g, 10.0 mmol) and p-toluenesulfonic acid monohydrate (144 mg, 0.755 mmol) in toluene (50 ml) was refluxed for 20 hours under heating.

The solvent was removed under reduced pressure, and the residue was purified by silica gel column chromatography (hexane) to give the object compound as a solid. 3.43 g (yield: 87.7%)

$^1$H-NMR (CDCl$_3$) δ; 2.12 (3H, s), 6.08 (1H, d, J=3.4 Hz), 6.34 (1H, d, J=3.4 Hz), 6.90 (2H, d, J=8.8 Hz), 7.10 (2H, d, J=8.8 Hz), 7.27 (2H, d, J=8.8 Hz), 7.50 (2H, d, J=8.8 Hz).

IR (KBr) cm$^{-1}$; 1508, 1489, 1410, 1319, 1071, 1009, 833, 766, 733, 559.

Elementary analysis for C$_{17}$H$_{13}$NBr$_2$ Calculated: C, 52.21; H, 3.35; N, 3.58. Found: C, 52.20; H, 3.33; N, 3.53.

(3) Ethyl (2E)-3-[4-(1-{4-[(1E)-3-ethoxy-3-oxo-1-propenyl]phenyl}-5-methyl-1H-pyrrol-2-yl)phenyl]-2-propenoate A solution of 1,2-bis(4-bromophenyl)-5-methyl-1H-pyrrole (2.00 g, 5.115 mmol), ethyl acrylate (1.39 ml, 12.8 mmol), tris(2-methylphenyl)phosphine (125 mg, 0.410 mmol), palladium acetate (23.0 mg, 0.102 mmol) and triethylamine (1.78 ml, 12.8 mmol) in DMF (4 ml) was stirred at 100° C. for 18 hours under nitrogen atmospheric current. The obtained mixture was poured into water and extracted with ethyl acetate. The extract was colleted and washed with water and dried over magnesium sulfate anhydride, and the solvent was removed under reduced pressure. The residue was purified by silica gel column chromatography (ethyl acetate:hexane=85:15) to give the object compound as a solid. 2.00 g (yield: 91.3%)

$^1$H-NMR (CDCl$_3$) δ; 1.27–1.38 (6H, m), 2.16 (3H, s), 4.21–4.33 (4H, m), 6.12 (1H, d, J=3.4 Hz), 6.28–6.48 (3H, m), 7.04 (2H, d, J=8.4 Hz), 7.17 (2H, d, J=8.4 Hz), 7.30 (2H, d, J=8.4 Hz), 7.52–7.73 (4H, m).

IR (KBr) cm$^{-1}$; 2980, 1713, 1636, 1603, 1514, 1310, 1267, 1204, 1179, 1040, 982, 839, 768, 731.

Elementary analysis for C$_{27}$H$_{27}$NO$_4$ 0.1 H$_2$O; Calculated: C, 75.19; H, 6.36; N, 3.24. Found: C, 74.99; H, 6.27; N, 3.19.

Example 4

(2E)-3-[4-(1-{4-[(1E)-2-Carboxyethenyl]phenyl}-5-methyl-1H-pyrrol-2-yl)phenyl]-2-propenoic acid To a mixed solution of ethyl (2E)-3-[4-(1-{4-[(1E)-3-ethoxy-3-oxo-1-propenyl]phenyl}-5-methyl-1H-pyrrol-2-yl)phenyl]-2-propenoate (429 mg, 1.00 mmol) obtained in Example 3 in THF (4 ml)-methanol (2 ml) was added an aqueous 5 N sodium hydroxide(1.20 ml, 6 mmol), and the mixture was stirred at room temperature for 12 hours and diluted with ethyl acetate. The solution was neutralized with 1 N hydrochloric acid and the the organic layer was separated. The organic layer was washed with water, dried over magnesium sulfate anhydride and the solvent was removed under reduced pressure to give the object compound as a solid. 300 mg (yield: 80.4%)

$^1$H-NMR (CDCl$_3$) δ; 2.16 (3H, s), 6.11 (1H, s), 6.27–6.48 (3H, m), 7.04 (2H, d, J=8.4 Hz), 7.17 (2H, d, J=8.0 Hz), 7.30 (2H, d, J=8.4 Hz), 7.53–7.72 (4H, m).

IR (KBr) cm$^{-1}$; 2982, 1688, 1628, 1601, 1520, 1426, 1310, 1279, 1209, 1186, 990, 839, 738.

Elementary analysis for C$_{23}$H$_{19}$NO$_4$ 0.5 H$_2$O; Calculated: C, 72.24; H, 5.27; N, 3.66. Found: C, 72.48; H, 4.99; N, 3.25.

Example 5

Ethyl (2R)-2-{4-[1-(4-Bromophenyl)-5-methyl-1H-pyrrol-2-yl]phenoxy}-3-phenylpropanoate (1) 1-(4-Methoxyphenyl)-1,4-pentanedione A solution of p-anisaldehyde (18.4 g, 135 mmol), triethylamine (29.3 ml, 210 mmol), methyl vinyl ketone (8.74 ml, 105 mmol) and 3-ethyl-5-(2-hydroxyethyl)-4-methylthiazolium bromide (5.30 g, 21.0 mmol) in ethanol (50 ml) was stirred at 77° C. for 20 hours and the solvent was removed under reduced pressure. To the residue was added 2 N hydrochloric acid and extracted with ethyl acetate. The extracts were collected, washed with saturated aqueous sodium bicarbonate and dried over magnesium sulfate anhydride, and the solvent was removed under reduced pressure. The residue was purified by silica gel column chromatography (hexane:ethyl acetate=1:1) to give the object compound as an oily substance. 10.8 g (yield: 49.8%)

$^1$H-NMR (CDCl$_3$) δ; 2.26 (3H, s), 2.87 (2H, t, J=6.4 Hz), 3.24 (2H, t, J=6.4 Hz), 3.88 (3H, s), 6.92 (2H, d, J=8.8 Hz), 7.96 (2H, d, J=8.8 Hz).

IR (KBr) cm$^{-1}$; 1717, 1676, 1599, 1508, 1250, 1173, 1030, 835.

(2) 1-(4-Bromophenyl)-2-(4-methoxyphenyl)-5-methyl-1H-pyrrole

A solution of 1-(4-methoxyphenyl)-1,4-pentanedione (3.00 g, 14.5 mol), 4-bromoaniline (2.50 g, 14.5 mmol) and p-toluenesulfonic acid monohydrate (208 mg, 1.09 mmol) in toluene (100 ml) was refluxed for 12 hours under heating. The solvent was removed under reduced pressure and the residue was purified by silica gel column chromatography (hexane:ethyl acetate=20:1) to give the object compound as an oily substance. 3.21 g (yield: 64.7%)

$^1$H-NMR (CDCl$_3$) δ; 2.12 (3H, s), 3.75 (3H, s), 6.06 (1H, d, J=3.2 Hz), 6.25 (1H, d, J=3.2 Hz), 6.72 (2H, d, J=8.8 Hz), 6.93–7.05 (4H, m), 7.47 (2H, d, J=8.8 Hz).

IR (KBr) cm$^{-1}$; 1528, 1489, 1391, 1246, 1034, 766.

(3) 4-[1-(4-Bromophenyl)-5-methyl-1H-pyrrol-2-yl]phenol

To a solution of 1-(4-bromophenyl)-2-(4-methoxyphenyl)-5-methyl-1H-pyrrole (2.10 g, 6.14 mmol) in methylene chloride (45 ml) was added boron tribromide (2.33 ml, 24.6 mmol) at 0° C. The mixture was stirred at 0° C. for 15 minutes and at room temperature for 0.5 hour, and the reaction solution was poured into ice water. The organic layer was separated, washed with saturated aqueous sodium bicarbonate, dried over magnesium sulfate anhydride and solvent was removed under reduced pressure. The residue was purified by silica gel column chromatography (hexane:ethyl acetate=9:1) to give the object compound as a solid. 1.82 g (yield: 90.0%)

$^1$H-NMR (DMSO-d$_6$) δ; 2.12 (3H, s), 4.73 (1H, s), 6.06 (1H, d, J=3.6 Hz), 6.24 (1H, d J=3.6 Hz), 6.63 (1H, d, J=8.8 Hz), 6.92 (2H, d, J=8.8 Hz), 7.00 (2H, d, J=8.8 Hz), 7.47 (2H, d, J=8.8 Hz).

IR (KBr) cm$^{-1}$; 3378, 1524, 1489, 1393, 1262, 1211, 1173, 833, 768, 737.

Elementary analysis for C$_{17}$H$_{14}$NOBr; Calculated: C, 62.21; H, 4.30; N, 4.27. Found: C, 62.05; H, 4.31; N, 4.19.

(4) Ethyl (2R)-2-{4-[1-(4-bromophenyl)-5-methyl-1H-pyrrol-2-yl]phenoxy}-3-phenylpropanoate To a solution of 4-[1-(4-bromophenyl)-5-methyl-1H-pyrrol-2-yl]phenol (1.00 g, 3.04 mmol), ethyl (S)-2-hydroxy-3-phenylpropanoate (886 mg, 4.56 mmol) and triphenylphosphine (1.20 g, 4.56 mmol) in toluene (50 ml) was added diethyl azodicarboxylate (40%, 1.99 g, 4.56 mmol), and the mixture was stirred at 80° C. for 3.5 hours and the solvent was removed under reduced pressure. The residue was purified by silica gel column chromatography (hexane:ethyl acetate=20:1) to give the object compound as a solid. 440 mg (yield: 28.8%)

$^1$H-NMR (CDCl$_3$) δ; 1.15 (3H, t, J=7.4 Hz), 2.11 (3H, s), 3.18–3.22 (2H, m), 4.14 (2H, q, J=7.4 Hz), 4.68–4.74 (1H, m), 6.04 (1H, d, J=3.8 Hz), 6.22 (1H, d, J=3.8 Hz), 6.63 (2H, d, J=8.8 Hz), 6.90 (2H, d, J=8.8 Hz), 6.97 (2H, d, J=8.4 Hz), 7.15–7.28 (5H, m), 7.45 (2H, d, J=8.4 Hz).

IR (KBr) cm$^{-1}$; 1753, 1736, 1524, 1489, 1238, 1184, 1071, 833, 739, 700.

[α]$_D^{25}$+13.6° (c 0.770, chloroform)

Elementary analysis for C$_{28}$H$_{26}$NO$_3$Br; Calculated: C, 66.67; H, 5.20; N, 2.78. Found: C, 66.63; H, 5.23; N, 2.75.

Example 6

(2R)-2-{4-[1-(4-Bromophenyl)-5-methyl-1H-pyrrol-2-yl]phenoxy}-3-phenylpropanoic acid To a mixed solution of ethyl (2R)-2-{4-[1-(4-bromophenyl)-5-methyl-1H-pyrrol-2-yl]phenoxy}-3-phenylpropanoate (340 mg, 0.674 mmol) obtained in Example 5 in THF (4 ml)-methanol (2 ml) was added 5 N aqueous sodium hydroxide (0.404 ml, 2.02 mmol), and the mixture was stirred at room temperature for 1 hour. The reaction solution was diluted with ethyl acetate and water, and neutralized with 1 N hydrochloric acid. The organic layer was separated and washed with water. The organic layer was dried over magnesium sulfate anhydride and the solvent was removed under reduced pressure to give the object as an oily substance. 282 mg (yield: 87.9%)

$^1$H-NMR (CDCl$_3$) δ; 2.10 (3H, s), 3.23 (2H, d, J=6.6 Hz), 4.76 (1H, t, J=6.6 Hz), 6.05 (1H, d, J=3.2 Hz), 6.22 (1H, d, J=3.2 Hz), 6.63 (2H, d, J=8.8 Hz), 6.90 (2H, d, J=8.8 Hz), 6.97 (2H, d, J=8.8 Hz), 7.27 (5H, bs), 7.45 (2H, d, J=8.8 Hz).

IR (KBr) cm$^{-1}$; 3063, 1730, 1522, 1489, 1236, 1181, 1071, 833, 735, 700.

[α]$_D^{25}$-1.97° (c 1.70, chloroform)

Example 7

Ethyl (2R)-2-{2,6-dibromo-4-[1-(4-bromophenyl)-5-methyl-1H-pyrrol-2-yl]phenoxy}-3-phenylpropanoate (1) 3,5-Dibromo-4-hydroxybenzaldehyde To a solution of 4-hydroxybenzaldehyde (11.0 g, 90.0 mmol) and sodium acetate (22.9 g, 279 mmol) in acetic acid (150 ml) was added dropwise a solution of bromine (30.2 g, 190 mmol) in acetic acid (50 ml) at room temperature, and the reaction solution was stirred at room temperature for 1 hour and the solvent was removed under reduced pressure. To the residue was added hexane and the obtained crystals were filtered out, washed with water and subjected to air drying to give the object compound as crystals. 24.5 g (yield: 97.2%)

$^1$H-NMR (CDCl$_3$) δ; 6.42 (1H, bs), 8.00 (2H, s), 9.80 (1H, s).

IR (KBr) cm$^{-1}$; 3148, 1674, 1580, 1549, 1476, 1381, 1304, 1201, 1121, 874, 741, 658.

(2) 3,5-Dibromo-4-methoxybenzaldehyde

To a solution of 3,5-dibromo-4-hydroxybenzaldehyde (5.00 g, 17.9 mmol) in DMF (100 ml) were added potassium carbonate (3.22 g, 23.3 mmol) and iodomethane (1.45 ml, 23.3 mmol), and the mixture was stirred at room temperature for 10 hours. The obtained mixture was poured into water and extracted with ethyl acetate. The extracts were collected, washed with water and dried over magnesium sulfate anhydride, and the solvent was removed under reduced pressure to give the object compound as a solid. 5.10 g (yield: 97.0%)

$^1$H-NMR (CDCl$_3$) δ; 3.97 (3H, s), 8.03 (2H, s), 9.80 (1H, s).

IR (KBr) cm$^{-1}$; 1707, 1694, 1547, 1470, 1368, 1264, 1190, 987, 747, 731.

Elementary analysis for C$_8$H$_6$O$_2$Br$_3$; Calculated: C, 32.69; H, 2.06. Found: C, 32.69; H, 2.02.

(3) 1-(3,5-Dibromo-4-methoxyphenyl)-1,4-pentanedione

A mixed solution of 3,5-dibromo-4-methoxybenzaldehyde (5.00 g, 17.0 mmol), methyl vinyl ketone (1.10 ml, 13.2 mmol), triethylamine (3.69 ml, 26.4 mmol) and 3-ethyl-5-(2-hydroxyethyl)-4-methyl thiazolium bromide (667 mg, 2.64 mmol) in ethanol (20 ml) was stirred at 77° C. for 8 hours, and the solvent was removed under reduced pressure. The residue was purified by silica gel column chromatography (hexane:ethyl acetate=4:1) to isolate the object compound as a solid. 3.31 g (yield: 68.8%)

$^1$H-NMR (CDCl$_3$) δ; 2.25 (3H, s), 2.89 (2H, t, J=6.0 Hz), 3.18 (2H, t, J=6.0 Hz), 3.94 (3H, s), 8.12 (2H, s).

IR (KBr) cm$^{-1}$; 1717, 1690, 1381, 1260, 1163, 995, 737.

(4) 1-(4-Bromophenyl)-2-(3,5-dibromo-4-methoxyphenyl)-5-methyl-1H-pyrrole

A solution of 1-(3,5-dibromo-4-methoxyphenyl)-1,4-pentanedione (3.00 g, 8.24 mmol), 4-bromoaniline (1.42 g, 8.24 mmol) and p-toluenesulfonic acid monohydrate (118 mg, 0.619 mmol) in toluene (100 ml) was refluxed for 20 hours under heating and the solvent was removed under reduced pressure. The residue was purified by silica gel column chromatography (hexane:ethyl acetate=30:1) to isolate the object compound as an oily substance. 2.86 g (yield: 69.4%)

$^1$H-NMR (CDCl$_3$) δ; 2.11 (3H, s), 3.83 (3H, s), 6.07 (1H, d, J=3.4 Hz), 6.32 (1H, d, J=3.4 Hz), 7.02 (2H, d, J=8.4 Hz), 7.14 (2H, s), 7.55 (2H, d, J=8.4 Hz).

IR (KBr) cm$^{-1}$; 1591, 1491, 1462, 1408, 1250, 1069, 1001, 835, 747, 733.

(5) 2,6-Dibromo-4-[1-(4-bromophenyl)-5-methyl-1H-pyrrol-2-yl]phenol

To a solution of 1-(4-bromophenyl)-2-(3,5-dibromo-4-methoxyphenyl)-5-methyl-1H-pyrrole (2.60 g, 5.20 mmol) in methylene chloride (50 ml) was added boron tribromide (1.97 ml, 20.8 mmol) at 0° C., and the mixture was stirred at 0° C. for 1 hour. The obtained mixture was poured into ice water and extracted with ethyl acetate. The extracts were collected and washed with saturated aqueous sodium bicarbonate and dried over magnesium sulfate anhydride, and the solvent was removed under reduced pressure. The residue was purified by silica gel column chromatography (hexane:ethyl acetate=10:1) to isolate the object compound as a solid. 2.40 g (yield: 95.2%)

$^1$H-NMR (CDCl$_3$) δ; 2.11 (3H, s), 5.73 (1H, s), 6.06 (1H, d, J=3.8 Hz), 6.27 (1H, d, J=3.8 Hz), 7.01 (2H, d, J=8.8 Hz), 7.11 (2H, s), 7.54 (2H, d, J=8.8 Hz).

IR (KBr) cm$^{-1}$; 3490, 1508, 1491, 1458, 1412, 1318, 1159, 1069, 833, 747, 733.

Elementary analysis for C$_{17}$H$_{12}$NOBr$_3$; Calculated: C, 42.01; H, 2.49; N, 2.88. Found: C, 42.05; H, 2.54; N, 2.83.

(6) Ethyl (2R)-2-{2,6-dibromo-4-[1-(4-bromophenyl)-5-methyl-1H-pyrrol-2-yl]phenoxyl}-3-phenylpropanoate To a solution of 2,6-dibromo-4-[1-(4-bromophenyl)-5-methyl-1H-pyrrol-2-yl]phenol (500 mg, 1.03 mmol), ethyl (S)-2-hydroxy-3-phenylpropanoate (300 mg, 1.55 mmol) and triphenylphosphine (405 mg, 1.55 mmol) in toluene (5 ml) was added diisopropyl azodicarboxylate (0.305 ml, 1.55 mmol) at room temperature. The obtained mixture was stirred at room temperature for 1 hour and at 80° C. for 1 hour, and the solvent was removed under reduced pressure. The residue was purified by silica gel column chromatography (hexane:ethyl acetate=30:1) to isolate the object compound as a solid. 670 mg (yield: 98.2%)

$^1$H-NMR (CDCl$_3$) δ; 1.06 (3H, t, J=7.2 Hz), 2.11 (3H, s), 3.37–3.42 (2H, m), 3.98–4.09 (2H, m), 4.84–4.91 (1H, m), 6.07 (1H, d, J=3.6 Hz), 6.33 (1H, d, J=3.6 Hz), 7.01 (2H, d, J=8.8 Hz), 7.14 (2H, s), 7.23–7.29 (5H, m), 7.54 (2H, d, J=8.8 Hz).

IR (KBr) cm$^{-1}$; 1746, 1491, 1445, 1408, 1242, 1069, 1015, 835, 747, 731, 700.

[α]$_D^{20}$ 28.8° (c 0.550, chloroform)

Example 8

(2R)-2-{2,6-Dibromo-4-[1-(4-bromophenyl)-5-methyl-1H-pyrrol-2-yl]phenoxy}-3-phenylpropanoic acid To a mixed solution of ethyl (2R)-2-{2,6-dibromo-4-[1-(4-bromophenyl)-5-methyl-1H-pyrrol-2-yl]phenoxy}-3-phenylpropanoate (400 mg, 0.604 mmol) obtained in Example 7 in THF (4 ml)-methanol (2 ml) was added 1N aqueous sodium hydroxide (1.21 ml, 1.21 mmol) and the mixture was stirred at room temperature for 3 hours. The obtained mixture was neutralized with 1 N hydrochloric acid and extracted with ethyl acetate. The extracts were collected, washed with water and dried over magnesium sulfate anhydride, and the solvent was removed under reduced pressure to give the object compound as an oily substance. 269 mg (yield: 70.4%)

$^1$H-NMR (CDCl$_3$) δ; 2.11 (3H, s), 3.37 (2H, d, J=7.0 Hz), 5.08 (1H, t, J=7.0 Hz), 6.07 (1H, d, J=3.4 Hz), 6.33 (1H, d, J=3.4 Hz), 7.00 (2H, d, J=8.8 Hz), 7.11 (2H, s), 7.22–7.26 (5H, m), 7.55 (2H, d, J=8.8 Hz).

IR (KBr) cm$^{-1}$; 3065, 1725, 1493, 1445, 1410, 1240, 1069, 835, 733, 700.

[α]$_D^{21}$ 17.9° (c 1.48, chloroform)

Elementary analysis for C$_{26}$H$_{20}$NO$_3$Br$_3$ 0.5 H$_2$O; Calculated: C, 48.55; H, 3.29; N, 2.18. Found: C, 48.66; H, 3.51; N, 1.97.

Example 9

Ethyl (2R)-2-({4'-[1-(4-bromophenyl)-5-methyl-1H-pyrrol-2-yl][1,1'-biphenyl]-4-yl}oxy)-3-phenylpropanoate (1) Methyl 4-(4'-methoxyphenyl)benzoate A mixed solution of 4-(4'-hydroxyphenyl)benzoic acid (10.0 g, 4.67 mmol), iodomethane (19.9 g, 14.0 mmol) and N,N-dimethylformamide (80 ml) was stirred at 60° C. for 3 hours. To the obtained mixture was added ethyl acetate (200 ml) and water (150 ml), the mixture was stirred and the organic layer was separated. The organic layer was washed with 5% aqueous potassium hydrogen sulfate and water, and dried over sodium sulfate anhydride. The solvent was concentrated under reduced pressure and the object compound (10.5 g) was obtained from the residue as colorless crystals. Melting point: 177–178° C.

$^1$H-NMR (CDCl$_3$) δ; 3.86 (3H, s), 3.94 (3H, s), 7.00 (2H, d, J=8.8 Hz), 7.58 (2H, d, J=8.8 Hz), 7.62 (2H, d, J=8.4 Hz), 8.08 (2H, d, J=8.4 Hz).

(2) 4-(4'-methoxyphenyl)benzylalcohol

Methyl 4-(4'-methoxyphenyl)benzoate (3.0 g, 12.3 mmol) was added in portions to a suspension of lithium aluminum hydride (0.94 g, 25.0 mmol) in tetrahydrofuran (40 ml) at room temperature for 20 minutes with stirring. The reaction solution was refluxed for 2 hours under heating and cooled to 0° C. To the residue was added water (1 ml) and 1 N aqueous sodium hydroxide (3 ml), the insoluble matter was filtered out and the filtrate was concentrated under reduced pressure. The object compound (1.2 g) was obtained from the residue as colorless crystals.

Melting point: 163–164° C.

$^1$H-NMR (CDCl$_3$) δ; 3.86 (3H, s), 4.73 (2H, s), 7.48 (2H, d, J=8.8 Hz), 7.37–7.58 (6H, m).

(3) 4'-Methoxy[1,1'-biphenyl]-4-carbaldehyde

A mixed solution of 4-(4'-methoxyphenyl)benzylalcohol (1.20 g, 5.60 mmol), manganese dioxide (2.0 g) and tetrahydrofuran (25 ml) was stirred at room temperature for 72 hours. The reaction solution was filtered and the filtrate was concentrated under reduced pressure. The residue was purified by silica gel column chromatography (hexane:ethyl acetate:tetrahydrofuran=5:1:1) to give the object compound (1.1 g) as colorless crystals. Melting point: 99–100° C.

$^1$H-NMR (CDCl$_3$) δ; 3.87 (3H, s), 7.01 (2H, d, J=8.8 Hz), 7.60 (2H, d, J=8.8 Hz), 7.72 (2H, d, J=8.2 Hz), 7.93 (2H, d, J=8.2 Hz), 10.04 (1H, s).

(4) 1-(4'-Methoxy[1,1'-biphenyl]-4-yl)-1,4-pentanedione

A mixed solution of 4'-methoxy[1,1'-biphenyl]-4-carbaldehyde (1.08 g, 5.09 mmol), methyl vinyl ketone (277 mg, 3.96 mmol), triethylamine (1.10 ml, 7.91 mmol) and 3-ethyl-5-(2-hydroxyethyl)-4-methyl thiazolium bromide (200 mg, 0.791 mmol) in ethanol (6 ml) was stirred at 77° C. for 4 days, and the solvent was removed under reduced pressure. The residue was purified by silica gel column chromatography (hexane:ethyl acetate=5:1) to isolate the object compound as a solid. 510 mg (yield: 45.9%)

$^1$H-NMR (CDCl$_3$) δ; 2.27 (3H, s), 2.91 (2H, t, J=6.2 Hz), 3.30 (2H, t, J=6.2 Hz), 3.86 (3H, s), 7.00 (2H, d, J=9.2 Hz), 7.56–7.67 (4H, m), 8.02 (2H, d, J=8.6 Hz).

IR (KBr) cm$^{-1}$; 1709, 1674, 1601, 1260, 818, 743.

(5) 1-(4-Bromophenyl)-2-(4'-methoxy[1,1'-biphenyl]-4-yl)-5-methyl-1H-pyrrole

A solution of 1-(4'-methoxy[1,1'-biphenyl]-4-yl)-1,4-pentanedione (500 mg, 1.77 mmol), 4-bromoaniline (306 mg, 1.77 mmol) and p-toluenesulfonic acid monohydrate (25.3 mg, 0.133 mmol) in toluene (30 ml) was refluxed for 12 hours under heating and the solvent was removed under reduced pressure. The residue was purified by silica gel column chromatography (hexane:ethyl acetate=30:1) to isolate the object compound as a solid. 430 mg (yield: 58.1%)

$^1$H-NMR (CDCl$_3$) δ; 2.14 (3H, s), 3.83 (3H, s), 6.10 (1H, d, J=3.2 Hz), 6.37 (1H, d, J=3.2 Hz), 6.93 (2H, d, J=8.8 Hz), 7.04–7.10 (4H, m), 7.36 (2H, d, J=8.4 Hz), 7.46–7.53 (4H, m).

IR (KBr) cm$^{-1}$; 1609, 1507, 1489, 1248, 1040, 822, 766, 733.

(6) 4'-[1-(4-Bromophenyl)-5-methyl-1H-pyrrol-2-yl][1,1'-biphenyl]-4-ol

To a solution of 1-(4-bromophenyl)-2-(4'-methoxy[1,1'-biphenyl]-4-yl)-5-methyl-1H-pyrrole (418 mg, 1.00 mmol) in methylene chloride (30 ml) was added boron tribromide (0.378 ml, 4.00 mmol) at 0° C., and the mixture was stirred at 0° C. for 1 hour. The obtained mixture was poured into ice water and extracted with ethyl acetate. The extracts were collected, washed with saturated aqueous sodium bicarbonate and dried over magnesium sulfate anhydride, and the solvent was removed under reduced pressure. To the residue was added hexane and the mixture was filtrated to give the object compound as a solid. 400 mg (yield: 99.0%)

$^1$H-NMR (CDCl$_3$) δ; 2.14 (3H, s), 4.92 (1H, bs), 6.11 (1H, d, J=3.2 Hz), 6.38 (1H, d, J=3.2 Hz), 6.86 (2H, d, J=8.4 Hz), 7.04–7.53 (10H, m).

IR (KBr) cm$^{-1}$; 3406, 1508, 1489, 1258, 1175, 908, 824, 768, 733.

(7) Ethyl (2R)-2-({4'-[1-(4-bromophenyl)-5-methyl-1H-pyrrol-2-yl][1,1'-biphenyl]-4-yl}oxy)-3-phenylpropanoate To a solution of 4'-[1-(4-bromophenyl)-5-methyl-1H-pyrrol-2-yl][1,1'-biphenyl]-4-ol (380 mg, 0.941 mmol), ethyl (S)-2-hydroxy-3-phenylpropanoate (274 mg, 1.41 mmol) and triphenylphosphine (370 mg, 1.41 mmol) in toluene (7 ml) was added 1,1'-(azodicarbonyl)dipiperidine (356 mg, 1.41 mmol) at room temperature. The obtained mixture was stirred at room temperature for 30 minutes and at 80° C. for 2 hours, diluted with ethyl acetate and washed with water. The organic layer was separated and dried over magnesium sulfate anhydride, and the solvent was removed under reduced pressure. The residue was purified by silica gel column chromatography (hexane:ethyl acetate 30:1) to isolate the object compound as an oily substance. 184 mg (yield: 33.7%)

$^1$H-NMR (CDCl$_3$) δ; 1.19 (3H, t, J=7.4 Hz), 2.14 (3H, s), 3.24–3.28 (2H, m), 4.18 (2H, q, J=7.4 Hz), 4.78–4.84 (1H, m), 6.10 (1H, d, J=3.2 Hz), 6.37 (1H, d, J=3.2 Hz), 6.86 (2H, d, J=8.8 Hz), 7.03–7.52 (15H, m).

IR (KBr) cm$^{-1}$; 1752, 1732, 1609, 1507, 1489, 1238, 1181, 822, 733.

$[α]_D^{21}$ 11.0° (c 0.600, chloroform)

Example 10

(2R)-2-({4'-[1-(4-Bromophenyl)-5-methyl-1H-pyrrol-2-yl][1,1'-biphenyl]-4-yl}oxy)-3-phenylpropanoic acid To a mixed solution of ethyl (2R)-2-({4'-[1-(4-bromophenyl)-5-methyl-1H-pyrrol-2-yl][1,1'-biphenyl]-4-yl}oxy)-3-phenylpropanoate obtained in Example 9 (184 mg, 0.317 mmol) in THF (2 ml) and methanol (1 ml) was added an aqueous solution of 1N potassium hydroxide (0.951 ml, 0.951 mmol) and the mixture was stirred at room temperature for 3 hours. The obtained mixture was neutralized with 1 N hydrochloric acid and extracted with ethyl acetate. The extracts were collected, washed with water and dried over magnesium sulfate anhydride, and the solvent was removed under reduced pressure. To the residue was added hexane and the mixture was filtrated to give the object compound as a solid. 150 mg (yield: 85.7%)

$^1$H-NMR (CDCl$_3$) δ; 2.14 (3H, s), 3.30 (2H, d, J=6.0 Hz), 4.89 (1H, t, J=6.0 Hz), 6.10 (1H, d, J=3.2 Hz), 6.37 (1H, d, J=3.2 Hz), 6.87 (2H, d, J=8.8 Hz), 7.03–7.52 (15H, m).

IR (KBr) cm$^{-1}$; 3430, 1728, 1607, 1505, 1487, 1240, 1179, 1071, 824, 735.

$[α]_D^{21}$ -4.12° (c 1.06, chloroform)

Elementary analysis for $C_{32}H_{26}NO_3Br·H_2O$; Calculated: C, 67.37; H, 4.95; N, 2.46. Found: C, 67.56; H, 5.02; N, 2.42.

Example 11 tert-Butyl (E)-3-[4-(1-{4-[(E)-3-(tert-butoxy)-3-oxo-1-propenyl]phenyl}-1H-pyrrol-2-yl)phenyl]-2-propenoate (1) 1-(4-Bromophenyl)-3-(1,3-dioxolan-2-yl)-1-propanone To a suspension of magnesium (4.10 g, 165 mmol) in THF (100 ml) was added dropwise a solution of 2-(2-bromoethyl)-1,3-dioxane (27.2 g, 150 mmol) in THF (100 ml) at room temperature over 15 minutes. The obtained solution was stirred at room temperature for 30 minutes and to the mixture was added dropwise a solution of 4-bromobenzaldehyde (18.5 g, 100 mmol) in THF (100 ml) at −70° C. The obtained solution was stirred at −70 to −20° C. for 1.5 hours and added a solution of 10% ammonium chloride (300 ml). The temperature of the mixture was raised to room temperature and the mixture was extracted with ethyl acetate. The extract was washed with water, dried over magnesium sulfate anhydride and concentrated under reduced pressure. The residue was purified by silica gel column chromatography (hexane:ethyl acetate=5:1) to give the object compound as crystals. 2.46 g (yield: 8.6%)

Melting point: 71–72° C. (hexane-ethyl acetate).

$^1$H-NMR (CDCl$_3$) δ; 2.10–2.17 (2H, m), 3.08 (2H, t, J=7.4 Hz), 3.84–4.01 (4H, m), 5.00 (1H, t, J=4.4 Hz), 7.60 (2H, d, J=8.4 Hz), 7.83 (2H, d, J=8.4 Hz).

IR (KBr) cm$^{-1}$; 2877, 1684, 1585, 1396, 1138, 1070, 1032, 812, 799.

Elementary analysis for $C_{12}H_{13}O_3Br$; Calculated: C, 50.55; H,4.60. Found: C, 50.57; H, 4.52.

(2) 1,2-Bis(4-bromophenyl)-1H-pyrrole

A solution of 1-(4-bromophenyl)-3-(1,3-dioxolan-2-yl)-1-propanone (500 mg, 1.75 mol), 4-bromoaniline (332 mg, 1.93 mmol) and p-toluenesulfonic acid monohydrate (25.0 mg, 0.132 mmol) in toluene (50 ml) was refluxed for 20 hours under heating and the mixture was concentrated under reduced pressure. The residue was purified by silica gel column chromatography (hexane:ethyl acetate=9:1) to give the object compound as a solid. 450 mg (yield: 68.2%).

$^1$H-NMR (CDCl$_3$) δ; 6.34–6.44 (2H, m), 6.90–7.05 (5H, m), 7.35 (2H, d, J=8.8 Hz), 7.46 (2H, d, J=8.8 Hz).

IR (KBr) cm$^{-1}$; 1489, 1071, 1009, 829, 725, 714.

Elementary analysis for $C_{16}H_{11}NBr$; Calculated: C, 50.96; H, 2.94; N, 3.71. Found: C, 50.73; H, 2.75; N, 3.52.

(3) tert-Butyl (E)-3-[4-(1-{4-[(E)-3-(tert-butoxy)-3-oxo-1-propenyl]phenyl}-1H-pyrrol-2-yl)phenyl]-2-propenoate A solution of 1,2-bis(4-bromophenyl)-1H-pyrrole (1.82 g, 4.83 mmol), t-butyl ester acrylate (1.77 ml, 12.1 mmol), tris(2-methoxyphenyl)phosphine (118 mg, 0.387 mmol), palladium acetate (21.7 mg, 0.0967 mmol) and triethylamine (1.69 ml, 12.1 mmol) in DMF (4 ml) was stirred at 100° C. for 21 hours under nitrogen atmosphere. The obtained mixture was poured into water and extracted with ethyl acetate. The ethyl acetate layer was washed with water and dried over magnesium sulfate anhydride, and the solvent was removed under reduced pressure. The residue was purified by silica gel column chromatography (hexane:ethyl acetate=2:1) to give the object compound as a solid. 1.76 g (yield: 77.2%).

$^1$H-NMR (CDCl$_3$) δ; 1.52 (9H, s), 1.53 (9H, s), 6.30 (1H, d, J=16.2 Hz), 6.34 (1H, d, J=16.2 Hz), 6.37–6.40 (1H, m), 6.49–6.52 (1H, m), 6.96–6.98 (1H, m), 7.10–7.61 (10H, m).

IR (KBr) cm$^{-1}$; 2978, 1705, 1634, 1605, 1516, 1456, 1368, 1325, 1209, 1154, 982, 835,731, 720.

Example 12

(E)-3-[4-(1-{4-[(E)-3-Hydroxy-3-oxo-1-propenyl]phenyl}-1H-pyrrol-2-yl)phenyl]-2-propenoic acid To a solution of tert-butyl (E)-3-[4-(1-{4-[(E)-3-(tert-butoxy)-3-oxo-1-propenyl]phenyl}-1H-pyrrol-2-yl)phenyl]-2-propenoate obtained in Example 11 (800 mg, 1.70 mmol) in dichloromethane (10 ml) was added trifluoroacetic acid (10 ml), the mixture was stirred at room temperature for 1 hour and the solvent was removed under reduced pressure. To the residue was added water, neutralized with 1N aqueous sodium hydroxide and the mixture was filtrated to give crude crystals. The crystals were recrystallized from THF and ethyl acetate. 193 mg (yield: 31.6%)

Melting point:>300° C.

$^1$H-NMR (DMSO-d$_6$) δ; 6.35–6.59 (4H, m), 7.12–7.25 (5H, m), 7.50–7.76 (6H, m).

IR (KBr) cm$^{-1}$; 2976, 1682, 1630, 1603, 1514, 1427, 1318, 1282, 1221, 1186, 992, 945, 839, 723.

Elementary analysis for $C_{22}H_{17}NO_4 \cdot 0.5H_2O$; Calculated: C, 71.73; H, 4.93; N, 3.80. Found: C, 71.95; H, 4.88; N, 3.55.

Example 13 tert-Butyl 3-(4-{1-[4-(3-tert-butoxy-3-oxopropyl) phenyl]-1H-pyrrol-2-yl}phenylpropanoate To a solution of tert-butyl (E)-3-[4-(1-{4-[(E)-3-(tert-butoxy)-3-oxo-1-propenyl]phenyl}-1H-pyrrol-2-yl) phenyl]-2-propenoate obtained in Example 11 (471 mg, 1.00 mmol) in methanol (40 ml) was added 10% palladium carbon (50 mg), and the mixture was stirred at room temperature for 12 hours under hydrogen atmosphere. The obtained solution was filtered and the solvent was removed under reduced pressure. The residue was purified by silica gel column chromatography (hexane:ethyl acetate=10:1) to give the object compound as an oily substance. 249 mg (yield: 52.4%)

$^1$H-NMR (CDCl$_3$) δ; 1.40 (9H, s), 1.41 (9H, s), 2.43–2.58 (4H, m), 2.72–2.94 (4H, m), 6.31–6.42 (2H, m), 6.87–7.16 (9H, m).

IR (KBr) cm$^{-1}$; 2976, 1732, 1520, 1368, 1148, 847, 716.

Example 14

3-(4-{1-[4-(2-Carboxyethyl)phenyl]-1H-pyrrol-2-yl}phenyl)propanoic acid

To a solution of tert-butyl 3-(4-{1-[4-(3-tert-butoxy-3-oxopropyl)phenyl]-1H-pyrrol-2-yl}phenylpropanoate (249 mg, 0.524 mmol) obtained in Example 13 in methylene chloride (4 ml) was added trifluoroacetic acid (2 ml) at 0° C., and the mixture was stirred at room temperature for 1 hour and the solvent was removed under reduced pressure. To the residue was added water, and the mixture was neutralized with 1N aqueous sodium hydroxide and extracted with ethyl acetate. The extracts were collected, washed with water and dried over magnesium sulfate anhydride, and the solvent was removed under reduced pressure to give the object compound as an oily substance. 170 mg (yield: 98.3%)

$^1$H-NMR (CDCl$_3$) δ; 2.57–2.69 (4H, m), 2.80–2.96 (4H, m), 6.34–6.41 (2H, m), 6.92–7.11 (9H, m).

IR (KBr) cm$^{-1}$; 3031, 1709, 1518, 1418, 1287, 1209, 1184, 910, 839, 731.

Example 15

Ethyl (2R)-2-{4-[1-(4-{[(1R)-1-benzyl-2-ethoxy-2-oxoethyl]oxy}phenyl)-1H-pyrrol-2-yl]phenoxy}-3-phenylpropanoate (1) 3-(1,3-Dioxane-2-yl)-1-(4-methoxyphenyl)-1-propanone To a suspension of magnesium (4.10 g, 165 mmol) in THF (100 ml) was added dropwise a solution of 2-(2-bromoethyl)-1,3-dioxane (27.2 g, 150 mmol) in THF (100 ml) at room temperature over 15 minutes. The obtained solution was stirred at room temperature for 30 minutes. To this solution was added dropwise a solution of 4-anisaldehyde (13.6 g, 100 mmol) in THF (100 ml) at −70° C. The obtained solution was stirred at −70 to −20° C. for 4 hours and at room temperature for 1 hour, and a solution of 10% ammonium chloride was added and extracted with ethyl acetate. The extract was washed with water, dried over magnesium sulfate anhydride and concentrated under reduced pressure. The residue was purified by silica gel column chromatography (hexane:ethyl acetate=4:1) to give the object compound as an oily substance. 2.86 g (yield: 12.1%)

$^1$H-NMR (CDCl$_3$) δ; 2.08–2.18 (2H, m), 3.07 (2H, t, J=7.6 Hz), 3.83–4.00 (7H, m), 5.00 (1H, t, J=4.4 Hz), 6.93 (2H, d, J=8.8 Hz), 7.96 (2H, d, J=8.8 Hz).

IR (KBr) cm$^{-1}$; 2944, 2880, 1682, 1601, 1510, 1260, 1510, 1260, 1171, 1030, 835.

(2) 1,2-Bis (4-methoxyphenyl)-1H-pyrrole

A solution of 3-(1,3-dioxane-2-yl)-1-(4-methoxyphenyl)-1-propanone (700 mg, 3.26 mol), 4-anisidine (402 mg, 3.26 mmol) and p-toluenesulfonic acid monohydrate (42.5 mg, 0.223 mmol) in toluene (70 ml) was refluxed for 20 hours under heating and the solution was concentrated under reduced pressure. The residue was purified by silica gel column chromatography (hexane:ethyl acetate=9:1) to give the object compound as a solid. 481 mg (yield: 58.2%)

$^1$H-NMR (CDCl$_3$) δ; 3.77 (3H, s), 3.81 (3H, s), 6.32–6.34 (2H, m), 6.73–6.86 (5H, m), 7.04–7.11 (4H, m).

IR (KBr) cm$^{-1}$; 2930, 1514, 1464, 1248, 1177, 1036, 833, 714.

Elementary analysis for $C_{18}H_{17}NO_2$; Calculated: C, 77.40; H, 6.13; N, 5.01. Found: C, 77.21; H, 6.05; N, 4.92.

(3) 4-[2-(4-Hydroxyphenyl)-1H-pyrrol-1-yl]phenol

To a solution of 1,2-bis(4-methoxyphenyl)-1H-pyrrole (1.40 g, 5.02 mmol) in methylene chloride (40 ml) was added boron tribromide (3.80 ml, 40.2 mmol) at 0° C. The obtained solution was stirred at 0° C. for 30 minutes and poured into ice water. The organic layer was separated, washed with saturated aqueous sodium bicarbonate and dried over magnesium sulfate anhydride. The solvent was removed under reduced pressure. The residue was purified by silica gel column chromatography (hexane:ethyl acetate=3:1) to give the object compound as a solid. 1.20 g (yield: 95.2%)

$^1$H-NMR (DMSO-d$_6$) δ; 6.18–6.19 (2H, m), 6.61 (2H, d, J=8.8 Hz), 6.72 (2H, d, J=8.8 Hz), 6.85–6.96 (5H, m), 9.35 (1H, s), 9.57 (1H, s).

IR (KBr) cm$^{-1}$; 3274, 1516, 1254, 1227, 1196, 835, 820, 718, 557.

Elementary analysis for $C_{16}H_{13}NO_2 \cdot 0.4 H_2O$; Calculated: C, 74.35; H, 5.38; N, 5.42. Found: C, 74.66; H, 5.32; N, 5.19.

(4) Ethyl (2R)-2-{4-[1-(4-{[(1R)-1-benzyl-2-ethoxy-2-oxoethyl]oxy}phenyl)-1H-pyrrol-2-yl]phenoxyl-3-phenylpropanoate To a solution of 4-[2-(4-hydroxyphenyl)-1H-pyrrol-1-yl]phenol (1.00 g, 3.98 mmol), (S)-2-hydroxy-3-phenylpropanoic acid ethyl ester (2.32 g, 11.9 mol) and triphenylphosphine (3.12 g, 11.9 mol) in toluene (10 ml) was added dropwise diethyl azodicarboxylate (40%, 5.18 g, 11.9 mmol) at room temperature. The reaction solution was stirred at room temperature for 10 minutes and 80° C. for 5 hours, and the solvent was removed under reduced pressure. The residue was purified by silica gel column chromatography (hexane:ethyl acetate=9:1) to give the object compound as an oily substance. 233 mg (yield: 9.7%)

$^1$H-NMR (CDCl$_3$) δ; 1.10–1.22 (6H, m), 3.20–3.25 (4H, m), 4.09–4.21 (4H, m), 4.69–4.79 (2H, m), 6.28 (1H, d, J=2.6 Hz), 6.65 (2H, d, J=8.8 Hz), 6.74 (2H, d, J=8.8 Hz), 6.80 (1H, t, J=2.6 Hz), 6.94–7.02 (4H, m), 7.26–7.30 (10H, m).

IR (KBr) cm$^{-1}$; 1751, 1726, 1512, 1240, 1184, 1084, 1032, 835, 735, 700.

Example 16

(2R)-2-{4-[1-(4-{[(1R)-1-Carboxy-2-phenylethyl]oxy}phenyl)-1H-pyrrol-2-yl]phenoxy}-3-phenylpropanoic acid To a mixed solution of ethyl (2R)-2-{4-[1-(4-{[(1R)-1-benzyl-2-ethoxy-2-oxoethyl]oxy}phenyl)-1H-pyrrol-2-yl]

phenoxy}-3-phenylpropanoate obtained in Example 15 (233 mg, 0.386 mmol) in THF (2 ml)-methanol (1 ml) was added 5 N aqueous sodium hydroxide (0.463 ml, 2.32 mmol). The obtained solution was stirred at room temperature for 12 hours, neutralized with 1 N hydrochloric acid and extracted with ethyl acetate. the ethyl acetate layer was washed with water, dried over magnesium sulfate anhydride and the solvent was removed under reduced pressure to give the object compound as an oily substance. 187 mg (yield: 88.6%)

$^1$H-NMR (CDCl$_3$) δ; 3.24–3.28 (4H, m), 4.73–4.82 (2H, m), 6.30 (2H, s), 6.66 (2H, d, J=8.8 Hz), 6.73 (2H, d, J=9.2 Hz), 6.83–6.94 (5H, m), 7.24–7.30 (10H, m).

IR (KBr) cm$^{-1}$; 3063, 1730, 1508, 1238, 1181, 1084, 910, 835, 733, 700.

$[α]_D^{25}$ 26.0° (c 0.625, chloroform)

Elementary analysis for C$_{34}$H$_{29}$NO$_6$ 1.5.H$_2$O; Calculated: C, 71.07; H, 5.61; N, 2.44. Found: C, 71.02; H, 5.89; N, 2.24.

Example 17

Ethyl (2R)-2-{4-[2-(4-bromophenyl)-1H-pyrrol-1-yl]phenoxy}-3-phenylpropanoate (1) 2-(4-bromophenyl)-1-(4-methoxyphenyl)-1H-pyrrole A solution of 1-(4-bromophenyl)-3-(1,3-dioxolan-2-yl)-1-propanone (500 mg, 1.75 mol), 4-anisidine (238 mg, 1.93 mmol) and p-toluenesulfonic acid monohydrate (25.0 mg, 0.132 mmol) in toluene (50 ml) was refluxed for 20 hours with heating and the solution was concentrated under reduced pressure. The residue was purified by silica gel column chromatography (hexane:ethyl acetate=20:1) to give the object compound as a solid. 412 mg (yield: 71.8%)

$^1$H-NMR (CDCl$_3$) δ; 3.82 (3H, s), 6.31–6.43 (2H, m), 6.83–6.89 (3H, m), 6.98 (2H, d, J=8.4 Hz), 7.08 (2H, d, J=8.8 Hz), 7.31 (2H, d, J=8.4 Hz).

IR (KBr) cm$^{-1}$; 1514, 1250, 833, 729.

Elementary analysis for C$_{17}$H$_{14}$NBrO; Calculated: C, 62.21; H, 4.30; N, 4.27. Found: C, 62.10; H, 4.28; N, 4.26.

(2) 4-[2-(4-Bromophenyl)-1H-pyrrol-1-yl]phenol

To a solution of 2-(4-bromophenyl)-1-(4-methoxyphenyl)-1H-pyrrole (3.00 g, 9.14 mmol) in methylene chloride (100 ml) was added boron tribromide (3.46 ml, 36.6 mmol) at 0° C., and the mixture was stirred at 0° C. for 10 minutes and at room temperature for 0.5 hour. The obtained solution was poured into ice water and extracted with ethyl acetate. The extracts were collected and washed with saturated aqueous sodium bicarbonate, dried over magnesium sulfate anhydride, solvent was removed under reduced pressure. The residue was purified by silica gel column chromatography (hexane:ethyl acetate=3:1) to isolate the object compound as a solid. 2.80 g (yield: 97.6%)

$^1$H-NMR (CDCl$_3$) δ; 4.89 (1H, bs), 6.31–6.43 (2H, m), 6.78 (2H, d, J=8.8 Hz), 6.87–7.07 (5H, m), 7.32 (2H, d, J=8.4 Hz).

IR (KBr) cm$^{-1}$; 3191, 1514, 1487, 1458, 1236, 837, 826, 729.

(3) Ethyl (2R)-2-{4-[2-(4-bromophenyl)-1H-pyrrol-1-yl]phenoxy}-3-phenylpropanoate To a solution of 4-[2-(4-bromophenyl)-1H-pyrrol-1-yl]phenol (2.10 g, 6.68 mmol), ethyl (S)-2-hydroxy-3-phenylpropanoate (1.56 g, 8.02 mmol) and triphenylphosphine (2.10 g, 8.02 mmol) in toluene (10 ml) was added diethyl azodicarboxylate (40%, 3.79 g, 8.02 mmol), and the mixture was stirred at 80° C. for 4 hours and the solvent was removed under reduced pressure. The residue was purified by silica gel column chromatography (hexane:ethyl acetate=20:1) to give the object compound as a solid. 1.10 g (yield: 33.5%)

$^1$H-NMR (CDCl$_3$) δ; 1.18 (3H, t, J=7.0 Hz), 3.25 (2H, d, J=6.8 Hz), 4.18 (2H, q, J=7.0 Hz), 4.78 (1H, t, J=6.8 Hz), 6.30–6.41 (2H, m), 6.78 (2H, d, J=8.8 Hz), 6.84–6.86 (1H, m), 6.94 (2H, d, J=8.4 Hz), 7.02 (2H, d, J=8.8 Hz), 7.26–7.32 (7H, m).

IR (KBr) cm$^{-1}$; 1750, 1512, 1487, 1240, 1190, 1074, 831, 721, 700.

$[α]_D^{24}$ +18.5° (c 0.425, chloroform)

Elementary analysis for C$_{27}$H$_{24}$NO$_3$Br; Calculated: C, 66.13; H, 4.93; N, 2.86. Found: C, 66.20; H, 5.06; N, 2.72.

Example 18

(2R)-2-{4-[2-(4-bromophenyl)-1H-pyrrol-1-yl]phenoxy}-3-phenylpropanoic acid

To a mixed solution of ethyl (2R)-2-{4-[2-(4-bromophenyl)-1H-pyrrol-1-yl]phenoxy}-3-phenylpropanoate (200 mg, 0.408 mmol) obtained in Example 17 in THF (2 ml)-methanol (1 ml) was added an aqueous solution of 1 N potassium hydroxide (0.245 ml, 1.22 mmol), and the mixture was stirred at room temperature for 1 hour. The reaction solution was diluted with ethyl acetate and neutralized with 1 N hydrochloric acid, and the organic layer was separated. The organic layer was washed with water and dried over magnesium sulfate anhydride, and the solvent was removed under reduced pressure to give the object compound as an oily substance. 178 mg (yield: 94.2%)

$^1$H-NMR (CDCl$_3$) δ; 3.28–3.31 (2H, m), 4.82–4.88 (1H, m), 6.29–6.42 (2H, m), 6.79 (2H, d, J=8.8 Hz), 6.84–6.86 (1H, m), 6.94 (2H, d, J=8.4 Hz), 7.03 (2H, d, J=8.8 Hz), 7.26–7.32 (7H, m).

IR (KBr) cm$^{-1}$; 3032, 1730, 1510, 1238, 1073, 831, 731.

$[α]_D^{27}$ +8.76° (c 0.515, chloroform)

Example 19

Ethyl (2R)-2-{4-[1-(4-bromophenyl)-5-ethyl-1H-pyrrol-2-yl]phenoxy}-3-phenylpropanoate (1) 1-(4-Methoxyphenyl)-1,4-hexanedione A mixed solution of p-anisaldehyde (10.0 g, 73.4 mmol), ethylvinylketone (5.68 ml, 57.0 mmol), 3-ethyl-5-(2-hydroxyethyl)-4-methyl thiazolium bromide (2.88 g, 11.4 mmol) and triethylamine (15.9 ml, 114 mmol) in ethanol (100 ml) was stirred at 77° C. for 20 hours, and the solvent was removed under reduced pressure. The residue was purified by silica gel column chromatography (hexane:ethyl acetate=9:1) to isolate the object compound as a solid. 4.40 g (yield: 35.2%)

$^1$H-NMR (CDCl$_3$) δ; 1.10 (3H, t, J=7.4 Hz), 2.56 (2H, q, J=7.4 Hz), 2.84 (2H, t, J=6.2 Hz), 3.25 (2H, t, J=6.2 Hz), 3.87 (3H, s), 6.93 (2H, d, J=9.2 Hz), 7.97 (2H, d, J=9.2 Hz).

IR (KBr) cm$^{-1}$; 1715, 1676, 1601, 1510, 1262, 1240, 1171, 1115, 1026, 839.

Elementary analysis for C$_{13}$H$_{16}$O$_3$; Calculated: C, 70.89; H, 7.32. Found: C, 70.96; H, 7.21.

(2) 1-(4-Bromophenyl)-2-ethyl-5-(4-methoxyphenyl)-1H-pyrrole

A solution of 1-(4-methoxyphenyl)-1,4-hexanedione (4.00 g, 18.2 mmol), 4-bromoaniline (3.12 g, 18.2 mmol) and p-toluenesulfonic acid monohydrate (260 mg, 1.37 mmol) in toluene (150 ml) was refluxed for 20 hours under heating and the solvent was removed under reduced pressure. The residue was purified by silica gel column chromatography (hexane:ethyl acetate=30:1) to isolate the object compound as a solid. 6.25 g (yield: 96.5%)

$^1$H-NMR (CDCl$_3$) δ; 1.14 (3H, t, J=7.8 Hz), 2.44 (2H, q, J=7.8 Hz), 3.75 (3H, s), 6.09 (1H, d, J=3.6 Hz), 6.28 (1H, d,

J=3.6 Hz), 6.71 (2H, d, J=8.8 Hz), 6.97 (2H, d, J=8.8 Hz), 7.02 (2H, d, J=8.8 Hz), 7.47 (2H, d, J=8.8 Hz).

IR (KBr) cm$^{-1}$; 1524, 1489, 1248, 1034, 833.

Elementary analysis for $C_{19}H_{18}NOBr$; Calculated: C, 64.06; H, 5.09; N, 3.93. Found: C, 64.11; H, 5.16; N, 3.94.

(3) 4-[1-(4-Bromophenyl)-5-ethyl-1H-pyrrol-2-yl]phenol

To a solution of 1-(4-bromophenyl)-2-ethyl-5-(4-methoxyphenyl)-1H-pyrrole (5.50 g, 15.4 mmol) in methylene chloride (200 ml) was added boron tribromide (5.84 ml, 61.8 mmol) at 0° C. The obtained solution was stirred at 0° C. for 1 hour, poured into ice water and extracted with ethyl acetate. The extracts were collected and washed with saturated aqueous sodium bicarbonate and dried over magnesium sulfate anhydride, and the solvent was removed under reduced pressure. The residue was purified by silica gel column chromatography (hexane:ethyl acetate=5:1) to isolate the object compound as an oily substance. 5.01 g (yield: 94.9%)

$^1$H-NMR (CDCl$_3$) δ; 1.14 (3H, t, J=7.6 Hz), 2.44 (2H, q, J=7.6 Hz), 5.03 (1H, s), 6.09 (1H, d, J=3.2 Hz), 6.27 (1H, d, J=3.2 Hz), 6.63 (2H, d, J=8.4 Hz), 6.91 (2H, d, J=8.4 Hz), 7.01 (2H, d, J=8.4 Hz), 7.47 (2H, d, J=8.4 Hz).

IR (KBr) cm$^{-1}$; 2969, 1526, 1489, 1223, 831.

(4) Ethyl (2R)-2-{4-[1-(4-bromophenyl)-5-ethyl-1H-pyrrol-2-yl]phenoxy}-3-phenylpropanoate To a solution of 4-[1-(4-bromophenyl)-5-ethyl-1H-pyrrol-2-yl]phenol (738 mg, 2.16 mmol), ethyl (S)-2-hydroxy-3-phenylpropanoate (628 mg, 3.24 mmol) and triphenylphosphine (850 mg, 3.24 mmol) in toluene (8 ml) was added 1,1'-(azodicarbonyl)dipiperidine (817 mg, 3.24 mmol) at room temperature. The obtained solution was stirred at room temperature for 1 hour and at 80° C. for 2 hours, diluted with ethyl acetate and washed with water. The organic layer was separated and dried over magnesium sulfate anhydride, and the solvent was removed under reduced pressure. The residue was purified by silica gel column chromatography (hexane:ethyl acetate=30:1) to isolate the object compound as an oily substance. 535 mg (yield: 47.8%)

$^1$H-NMR (CDCl$_3$) δ; 1.09–1.18 (6H, m), 2.42 (2H, q, J=7.6 Hz), 3.18–3.22 (2H, m), 4.15 (2H, q, J=6.6 Hz), 4.71 (1H, t, J=6.8 Hz), 6.07 (1H, d, J=3.6 Hz), 6.25 (1H, d, J=3.6 Hz), 6.62 (2H, d, J=8.4 Hz), 6.89 (2H, d, J=8.4 Hz), 6.99 (2H, d, J=8.8 Hz), 7.22–7.30 (5H, m), 7.45 (2H, d, J=8.8 Hz).

IR (KBr) cm$^{-1}$; 1753, 1736, 1520, 1489, 1240, 1182, 1069, 835.

$[α]_D^{21}$ 14.4° (c 1.06, chloroform)

Example 20

(2R)-2-{4-[1-(4-bromophenyl)-5-ethyl-1H-pyrrol-2-yl]phenoxy}-3-phenylpropanoic acid To a mixed solution of ethyl (2R)-2-{4-[1-(4-bromophenyl)-5-ethyl-1H-pyrrol-2-yl]phenoxy}-3-phenylpropanoate obtained in Example 19 (425 mg, 0.820 mmol) in THF (6 ml)-methanol (3 ml) was added an aqueous solution of 1N potassium hydroxide (2.46 ml, 2.46 mmol) and the mixture was stirred at room temperature for 1 hour. The obtained solution was neutralized with 1 N hydrochloric acid and extracted with ethyl acetate. The extracts were collected, washed with water and dried over magnesium sulfate anhydride, and the solvent was removed under reduced pressure to give the object compound as an oily substance. 360 mg (yield: 89.6%)

$^1$H-NMR (CDCl$_3$) δ; 1.12 (3H, t, J=7.6 Hz), 2.42 (2H, q, J=7.6 Hz), 3.24 (2H, d, J=6.6 Hz), 4.78 (1H, t, J=6.6 Hz), 6.08 (1H, d, J=3.6 Hz), 6.27 (1H, d, J=3.6 Hz), 6.64 (2H, d, J=8.8 Hz), 6.92 (2H, d, J=8.8 Hz), 6.99 (2H, d, J=8.8 Hz), 7.25–7.28 (5H, m), 7.46 (2H, d, J=8.8 Hz).

IR (KBr) cm$^{-1}$; 3031, 1725, 1518, 1489, 1238, 1069, 835.

Example 21

Ethyl (2R)-2-{4-[1-(4-bromophenyl)-5-phenyl-1H-pyrrol-2-yl]phenoxy}-3-phenylpropanoate (1) 1-Phenyl-2-propen-1-ol To a solution of 1 N vinylmagnesium bromide in THF (100 ml) was added dropwise benzaldehyde (9.15 ml, 90.0 mmol) at 0° C. The obtained solution was stirred at 0° C. for 2 hours, and an aqueous solution of 1 N ammonium chloride (200 ml) was added to the mixture. The reaction solution was stirred at room temperature for 1 hour and extracted with ethyl acetate. The extracts were collected, washed with water and dried over magnesium sulfate anhydride, and the solvent was removed under reduced pressure to give the object compound as an oily substance. 11.8 g (yield: 97.5%)

$^1$H-NMR (CDCl$_3$) δ; 1.97 (1H, d, J=3.6 Hz), 5.17–5.23 (2H, m), 5.36 (1H, d, J=15.8 Hz), 5.98–6.14 (1H, m), 7.24–7.41 (5H, m).

IR (KBr) cm$^{-1}$; 3291, 1493, 1454, 1024, 990, 928, 762, 700.

(2) 1-Phenyl-2-propen-1-one

To a solution of oxalyl chloride (9.11 ml, 104 mmol) in methylene chloride (114 ml) was added dimethylsulfoxide (15.0 ml, 211 mmol) at −60° C., then to the mixture was added 1-phenyl-2-propen-1-ol (11.8 g, 87.9 mmol). The obtained solution was stirred at −60° C. for 30 minutes, and to the mixture was added dropwise triethylamine (47.8 ml, 343 mmol) at −60° C. The temperature of the reaction solution was raised to room temperature and the solution was poured into water. The organic layer was separated and dried over magnesium sulfate anhydride, and the solvent was removed under reduced pressure. The residue was purified by silica gel column chromatography (hexane:ethyl acetate=30:1) to isolate the object compound as an oily substance. 2.10 g (yield: 18.1%)

$^1$H-NMR (CDCl$_3$) δ; 5.94 (1H, dd, J=1.8, 8.6 Hz), 6.44 (1H, dd, J=1.8, 17.2 Hz), 7.17 (1H, dd, J=8.6, 17.2 Hz), 7.39–7.52 (3H, m), 7.91–7.98 (2H, m).

IR (KBr) cm$^{-1}$; 1672, 1597, 1449, 1404, 1233, 968, 910, 745, 729, 698.

(3) 1-(4-Methoxyphenyl)-4-phenyl-1,4-butanedione 1-(4-Methoxyphenyl)-4-phenyl-1,4-butanedione was synthesized from 1-phenyl-2-propen-1-one as a solid, according to the similar manner to that of Example 19(1). yield: 16.4%

$^1$H-NMR (CDCl$_3$) δ; 3.43–3.45 (4H, m), 3.88 (3H, s), 6.96 (2H, d, J=7.2 Hz), 7.44–7.59 (3H, m), 8.01–8.07 (4H, m).

IR (KBr) cm$^{-1}$; 1678, 1601, 1510, 1262, 1231, 1171, 1030, 993, 835, 766, 691.

(4) 1-(4-Bromophenyl)-2-(4-methoxyphenyl)-5-phenyl-1H-pyrrole 1-(4-Bromophenyl)-2-(4-methoxyphenyl)-5-phenyl-1H-pyrrole was isolated from 1-(4-methoxyphenyl)-4-phenyl-1,4-butanedione as a solid, according to the similar manner to that of Example 19(2). yield: 63.2%.

$^1$H-NMR (CDCl$_3$) δ; 3.78 (3H, s), 6.39 (1H, d, J=3.6 Hz), 6.45 (1H, d, J=3.6 Hz), 6.75 (2H, d, J=9.2 Hz), 6.87 (2H, d, J=8.8 Hz), 6.94–7.26 (7H, m), 7.35 (2H, d, J=8.8 Hz).

IR (KBr) cm$^{-1}$; 1491, 1248, 831, 756.

(5) 4-[1-(4-bromophenyl)-5-phenyl-1H-pyrrol-2-yl]phenol

4-[1-(4-bromophenyl)-5-phenyl-1H-pyrrol-2-yl]phenol was synthesized from 1-(4-bromophenyl)-2-(4- methoxyphenyl)-5-phenyl-1H-pyrrole as a solid, according to the similar manner to that of Example 19(3). yield: 18.2%

$^1$H-NMR (CDCl$_3$) δ; 4.71 (1H, s), 6.38 (1H, d, J=3.6 Hz), 6.44 (1H, d, J=3.6 Hz), 6.68 (2H, d, J=8.8 Hz), 6.84–7.26 (9H, m), 7.35 (2H, d, J=8.8 Hz).

IR (KBr) cm$^{-1}$; 3395, 1599, 1491, 1262, 1173, 831, 758.

(6) Ethyl (2R)-2-{4-[1-(4-bromophenyl)-5-phenyl-1H-pyrrol-2-yl]phenoxy}-3-phenylpropanoate Ethyl (2R)-2-{4-[1-(4-bromophenyl)-5-phenyl-1H-pyrrol-2-yl]phenoxy}-3-phenylpropanoate was synthesized from 4-[1-(4-bromophenyl)-5-phenyl-1H-pyrrol-2-yl] phenol as a solid, according to the similar manner to that of Example 19(4). yield: 62.7%

$^1$H-NMR (CDCl$_3$) δ; 1.16 (3H, t, J=7.4 Hz), 3.20–3.26 (2H, m), 4.15 (2H, q, J=7.4 Hz), 4.71–4.78 (1H, m), 6.36 (1H, d, J=3.6 Hz), 6.43 (1H, d, J=3.6 Hz), 6.67 (2H, d, J=8.8 Hz), 6.72–7.35 (16H, m).

IR (KBr) cm$^{-1}$; 1732, 1491, 1236, 833, 758, 698.

Example 22

(2R)-2-{4-[1-(4-Bromophenyl)-5-phenyl-1H-pyrrol-2-yl] phenoxy}-3-phenylpropanoic acid (2R)-2-{4-[1-(4-Bromophenyl)-5-phenyl-1H-pyrrol-2-yl] phenoxy}-3-phenylpropanoic acid was synthesized as a solid, from ethyl (2R)-2-{4-[1-(4-bromophenyl)-5-phenyl-1H-pyrrol-2-yl]phenoxy}-3-phenylpropanoate obtained in Example 21, according to the similar manner to that of Example 20. yield: 72.5%

$^1$H-NMR (CDCl$_3$) δ; 3.25–3.28 (2H, m), 4.80–4.86 (1H, m), 6.37 (1H, d, J=3.6 Hz), 6.43 (1H, d, J=3.6 Hz), 6.69 (2H, d, J=9.2 Hz), 6.82–7.36 (16H, m).

IR (KBr) cm$^{-1}$; 3393, 1725, 1491, 1238, 1225, 833, 756, 698.

$[α]_D^{23}$ –1.86° (c 1.06, chloroform)

Elementary analysis for C$_{31}$H$_{24}$NBrO$_3$0.7H$_2$O; Calculated: C, 67.40; H, 4.75; N, 2.27. Found: C, 67.57; H, 4.658; N, 2.54.

Example 23

Ethyl (2R)-2-{4-[1-(4-bromophenyl)-4,5-dimethyl-1H-pyrrol-2-yl]phenoxy}-3-phenylpropanoate (1) 1-(4-Methoxyphenyl)-3-methyl 1,4-pentanedione A mixed solution of p-anisaldehyde (10.0 g, 73.4 mmol), 3-methyl-3-buten-2-one (4.79 g, 57.0 mmol), 3-ethyl-5-(2-hydroxyethyl)-4-methyl thiazolium bromide (2.88 g, 11.4 mmol) and triethylamine (15.9 ml, 114 mmol) in ethanol (8 ml) was stirred at 77° C. for 12 hours and the solvent was removed under reduced pressure. The residue was purified by silica gel column chromatography (hexane:ethyl acetate= 7:1) to isolate the object compound as an oily substance. 1.61 g (yield: 12.9%)

$^1$H-NMR (CDCl$_3$) δ; 1.19 (3H, d, J=7.0 Hz), 2.30 (3H, s), 2.90 (2H, dd, J=17.6, 4.4 Hz), 3.15–3.34 (1H, m), 3.48 (1H, dd, J=17.6, 8.8 Hz), 3.86 (3H, s), 6.92 (2H, d, J=8.8 Hz), 7.93 (2H, d, J=8.8 Hz).

IR (KBr) cm$^{-1}$; 1713, 1674, 1601, 1510, 1262, 1169, 1030, 835.

(2) 1-(4-Bromophenyl)-5-(4-methoxyphenyl)-2,3-dimethyl-1H-pyrrole

A solution of 1-(4-methoxyphenyl)-3-methyl-1,4-pentanedione (1.60 g, 7.26 mmol), 4-bromoaniline (1.25 g, 7.26 mmol) and p-toluenesulfonic acid monohydrate (104 mg, 0.545 mmol) in toluene (50 ml) was refluxed for 48 hours under heating and the solvent was removed under reduced pressure. The residue was purified by silica gel column chromatography (hexane:ethyl acetate=30:1) to isolate the object compound as an oily substance. 630 mg (yield: 24.3%)

$^1$H-NMR (CDCl$_3$) δ; 2.04 (3H, s), 2.11 (3H, s), 3.75 (3H, s), 6.15 (1H, s), 6.70 (2H, d, J=8.8 Hz), 6.93–7.01 (4H, m), 7.46 (2H, d, J=8.8 Hz).

IR (KBr) cm$^{-1}$; 1528, 1489, 1246, 1034, 833, 804.

(3) 4-[1-(4-Bromophenyl)-4,5-dimethyl-1H-pyrrol-2-yl] phenol

To a solution of 1-(4-bromophenyl)-5-(4-methoxyphenyl)-2,3-dimethyl-1H-pyrrole (610 mg, 1.71 mmol) in methylene chloride (30 ml) was added boron tribromide (0.647 ml, 6.84 mmol) at 0° C. The obtained solution was stirred at 0° C. for 1 hour, poured into ice water and extracted with ethyl acetate. The extracts were collected and washed with saturated aqueous sodium bicarbonate and dried over magnesium sulfate anhydride, and the solvent was removed under reduced pressure. The residue was purified by silica gel column chromatography (hexane:ethyl acetate=6:1) to isolate the object compound as an oily substance. 358 mg (yield: 61.2%)

$^1$H-NMR (CDCl$_3$) δ; 2.10 (3H, s), 2.11 (3H, s), 4.94 (1H, bs), 6.15 (1H, s), 6.63 (2H, d, J=8.8 Hz), 6.90 (2H, d, J=8.8 Hz), 6.98 (2H, d, J=8.8 Hz), 7.46 (2H, d, J=8.8 Hz).

IR (KBr) cm$^{-1}$; 3338, 1530, 1489, 1262, 1171, 835.

(4) Ethyl (2R)-2-{4-[1-(4-Bromophenyl)-4,5-dimethyl-1H-pyrrol-2-yl]phenoxy}-3-phenylpropanoate To a solution of 4-[1-(4-bromophenyl)-4,5-dimethyl-1H-pyrrol-2-yl]phenol (342 mg, 1.00 mmol), ethyl (S)-2-hydroxy-3-phenylpropanoate (291 mg, 1.50 mmol) and triphenylphosphine (393 mg, 1.50 mmol) in toluene (5 ml) was added 1,1'-(azodicarbonyl)dipiperidine (378 mg, 1.50 mmol) at room temperature. The obtained solution was stirred at room temperature for 1 hour and at 80° C. for 4 hours, diluted with ethyl acetate and washed with water. The organic layer was separated and dried over magnesium sulfate anhydride, and the solvent was removed under reduced pressure. The residue was purified by silica gel column chromatography (hexane:ethyl acetate=30:1) to isolate the object compound as an oily substance. 299 mg (yield: 57.7%)

$^1$H-NMR (CDCl$_3$) δ; 1.14 (3H, t, J=7.0 Hz), 2.05 (3H, s), 2.09 (3H, s), 3.18–3.22 (2H, m), 4.12 (2H, q, J=7.0 Hz), 4.67–4.74 (1H, m), 6.13 (1H, s), 6.62 (2H, d, J=8.8 Hz), 6.88 (2H, d, J=8.8 Hz), 6.95 (2H, d, J=8.8 Hz), 7.26–7.29 (5H, m), 7.44 (2H, d, J=8.8 Hz).

IR (KBr) cm$^{-1}$; 1755, 1732, 1526, 1489, 1238, 1182, 1069, 835.

$[α]_D^{24}$ 9.9553° (c 0.510, chloroform)

Example 24

(2R)-2-{4-[1-(4-Bromophenyl)-4,5-dimethyl-1H-pyrrol-2-yl]phenoxy}-3-phenylpropanoic acid To the mixed solution of ethyl (2R)-2-{4-[1-(4-bromophenyl)-4,5-dimethyl-1H-pyrrol-2-yl]phenoxy}-3-phenylpropanoate obtained in Example 23 (280 mg, 0.540 mmol) in THF (6 ml)-methanol (3 ml) was added 1N aqueous potassium hydroxide (1.62 ml, 1.62 mmol). The obtained solution was stirred at room temperature for 1 hour, neutralized with 1 N hydrochloric acid and extracted with ethyl acetate. The extracts were collected, washed with water and dried over magnesium sulfate anhydride, and the solvent was removed under reduced pressure to give the object compound as an oily substance. 237 mg (yield: 89.5%)

$^1$H-NMR (CDCl$_3$) δ; 2.02 (3H, s), 2.09 (3H, s), 3.24 (2H, d, J=5.6 Hz), 4.77 (1H, t, J=5.6 Hz), 6.14 (1H, s), 6.63 (2H, d, J=8.8 Hz), 6.90 (2H, d, J=8.8 Hz), 6.96 (2H, d, J=8.8 Hz), 7.26–7.29 (5H, m), 7.45 (2H, d, J=8.8 Hz).

IR (KBr) cm$^{-1}$; 3450, 1728, 1526, 1489, 1236, 1068, 835, 735, 700.

$[\alpha]_D^{24}$ −4.93° (c 1.06, chloroform)

Example 25

Ethyl (2R)-2-{4-[1-(4-Bromophenyl)-3,5-dimethyl-1H-pyrrol-2-yl]phenoxy}-3-phenylpropanoate (1) 1-(4-Methoxyphenyl)-2-methyl-1,4-pentanedione 1-(4-Methoxyphenyl)-2-methyl-1,4-pentanedione was synthesized from 3-penten-2-one as an oily substance, according to the similar manner to that of Example 23(1). yield: 16.0%

$^1$H-NMR (CDCl$_3$) δ; 1.29 (3H, d, J=6.6 Hz), 2.17 (3H, s), 2.49–2.71 (2H, m), 3.09–3.22 (1H, m), 3.87 (3H, s), 6.94 (2H, d, J=8.8 Hz), 7.97 (2H, d, J=8.8 Hz).

IR (KBr) cm$^{-1}$; 1715, 1672, 1599, 1512, 1252, 1175, 1032, 837.

(2) 1-(4-Bromophenyl)-2-(4-methoxyphenyl)-3,5-dimethyl-1H-pyrrole 1-(4-Bromophenyl)-2-(4-methoxyphenyl)-3,5-dimethyl-1H-pyrrole was synthesized from 1-(4-methoxyphenyl)-2-methyl-1,4-pentanedione as an oily substance, according to the similar manner to that of Example 23 (2). yield: 13.0%

$^1$H-NMR (CDCl$_3$) δ; 2.11 (6H, s), 3.76 (3H, s), 5.97 (3H, s), 6.74 (2H, d, J=8.6 Hz), 6.90–6.96 (4H, m), 7.40 (2H, d, J=8.6 Hz).

IR (KBr) cm$^{-1}$; 1528, 1491, 1246, 1177, 833, 810.

(3) 4-[1-(4-Bromophenyl)-3,5-dimethyl-1H-pyrrol-2-yl]phenol

4-[1-(4-Bromophenyl)-3,5-dimethyl-1H-pyrrol-2-yl]phenol was synthesized from 1-(4-methoxyphenyl)-2-methyl-1,4-pentanedione as an oily substance, according to the similar manner to that of Example 23 (3). yield: 66.6%

$^1$H-NMR (CDCl$_3$) δ; 2.10 (6H, s), 4.83 (1H, bs), 5.96 (1H, s), 6.66 (2H, d, J=8.8 Hz), 6.85–6.94 (4H, m), 7.40 (2H, d, J=8.8 Hz).

IR (KBr) cm$^{-1}$; 3389, 1530, 1491, 1387, 1262, 1171, 835, 819, 800, 733.

(4) Ethyl (2R)-2-{4-[1-(4-bromophenyl)-3,5-dimethyl-1H-pyrrol-2-yl]phenoxy}-3-phenylpropanoate Ethyl (2R)-2-{4-[1-(4-bromophenyl)-3,5-dimethyl-1H-pyrrol-2-yl]phenoxy}-3-phenylpropanoate was synthesized from 4-[1-(4-bromophenyl)-3,5-dimethyl-1H-pyrrol-2-yl]phenol as an oily substance, according to the similar manner to that of Example 23 (4). yield: 74.2%

$^1$H-NMR (CDCl$_3$) δ; 1.13 (3H, t, J=7.2 Hz), 2.08 (3H, s), 2.09 (3H, s), 3.19–3.23 (2H, m), 4.14 (2H, q, J=7.2 Hz), 4.70–4.76 (1H, m), 5.95 (1H, s), 6.66 (2H, d, J=8.8 Hz), 6.83–7.30 (9H, m), 7.38 (2H, d, J=8.8 Hz).

IR (KBr) cm$^{-1}$; 1753, 1734, 1526, 1493, 1236, 1182, 1071, 737, 700.

$[\alpha]_D^{25}$ 10.3° (c 0.640, chloroform)

Example 26

(2R)-2-{4-[1-(4-Bromophenyl)-3,5-dimethyl-1H-pyrrol-2-yl]phenoxy}-3-phenylpropanoic acid (2R)-2-{4-[1-(4-Bromophenyl)-3,5-dimethyl-1H-pyrrol-2-yl]phenoxy}-3-phenylpropanoic acid was synthesized from ethyl (2R)-2-{4-[1-(4-bromophenyl)-3,5-dimethyl-1H-pyrrol-2-yl]phenoxy}-3-phenylpropanoate obtained in Example 25, as an oily substance, according to the similar manner to that of Example 24. yield: 84.9%

$^1$H-NMR (CDCl$_3$) δ; 2.08 (3H, s), 2.09 (3H, s), 3.25 (2H, d, J=6.6 Hz), 4.08 (1H, t, J=6.6 Hz), 5.96 (1H, s), 6.67 (2H, d, J=8.4 Hz), 6.87 (2H, d, J=8.4 Hz), 7.26–7.28 (5H, m), 7.39 (2H, d, J=8.4 Hz).

IR (KBr) cm$^{-1}$; 3061, 1728, 1526, 1493, 1238, 1071, 909, 833, 731, 700.

$[\alpha]_D^{26}$ −8.50° (c 1.01, chloroform)

Example 27

Ethyl (2R)-2-{4-[1-(4-bromophenyl)-5-methyl-3-propyl-1H-pyrrol-2-yl]phenoxy}-3-phenylpropanoate (1) 1-(4-Methoxyphenyl)-2-propyl-1,4-pentanedione 1-(4-Methoxyphenyl)-2-propyl-1,4-pentanedione was synthesized from 3-hepten-2-one as an oily substance, according to the similar manner to that of Example 23(1). yield: 12.8%

$^1$H-NMR (CDCl$_3$) δ; 0.91 (3H, t, J=7.0 Hz), 1.22–1.49 (4H, m), 2.17 (3H, s), 2.54–2.72 (2H, m), 3.07–3.21 (1H, m), 3.87 (3H, s), 6.95 (2H, d, J=8.8 Hz), 7.98 (2H, d, J=8.8 Hz).

IR (KBr) cm$^{-1}$; 1713, 1669, 1601, 1510, 1254, 1169, 1032, 835.

(2) 1-(4-Bromophenyl)-2-(4-methoxyphenyl)-5-methyl-3-propyl-1H-pyrrole 1-(4-Bromophenyl)-2-(4-methoxyphenyl)-5-methyl-3-propyl-1H-pyrrole was synthesized from 1-(4-methoxyphenyl)-2-propyl-1,4-pentanedione as an oily substance, according to the similar manner to that of Example 23(2). yield: 12.2%

$^1$H-NMR (CDCl$_3$) δ; 0.93 (3H, t, J=7.4 Hz), 1.53–1.64 (2H, m), 2.12 (3H, s), 2.41 (2H, t, J=7.4 Hz), 3.76 (3H, s), 6.74 (2H, d, J=8.8 Hz), 6.90–6.96 (4H, m), 7.39 (2H, d, J=8.4 Hz).

IR (KBr) cm$^{-1}$; 1528, 1491, 1246, 1177, 1071, 1036, 1007, 833, 814.

(3) 4-[1-(4-Bromophenyl)-5-methyl-3-propyl-1H-pyrrol-2-yl]phenol

4-[1-(4-Bromophenyl)-5-methyl-3-propyl-1H-pyrrol-2-yl]phenol was synthesized from 1-(4-bromophenyl)-2-(4-methoxyphenyl)-5-methyl-3-propyl-1H-pyrrole as an oily substance, according to the similar manner to that of Example 23(3). yield: 71.7%

$^1$H-NMR (CDCl$_3$) δ; 0.92 (3H, t, J=7.2 Hz), 1.52–1.64 (2H, m), 2.12 (3H, s), 2.40 (2H, t, J=7.4 Hz), 4.79 (1H, s), 6.00 (1H, s), 6.66 (2H, d, J=8.4 Hz), 6.87–6.94 (4H, m), 7.39 (2H, d, J=8.8 Hz).

IR (KBr) cm$^{-1}$; 3420, 1530, 1491, 1262, 835, 822.

(4) Ethyl (2R)-2-{4-[1-(4-bromophenyl)-5-methyl-3-propyl-1H-pyrrol-2-yl]phenoxy}-3-phenylpropanoate Ethyl (2R)-2-{4-[1-(4-bromophenyl)-5-methyl-3-propyl-1H-pyrrol-2-yl]phenoxy}-3-phenylpropanoate was synthesized from 4-[1-(4-bromophenyl)-5-methyl-3-propyl-1H-pyrrol-2-yl]phenol as an oily substance, according to the similar manner to that of Example 23(4). yield: 64.1%

$^1$H-NMR (CDCl$_3$) δ; 0.91 (3H, t, J=7.4 Hz), 1.12 (3H, t, J=7.0 Hz), 1.47–1.62 (2H, m), 2.10 (3H, s), 2.38 (3H, t, J=7.4 Hz), 3.19–3.23 (2H, m), 4.14 (2H, q, J=7.0 Hz), 4.70–4.77 (1H, m), 5.98 (1H, s), 6.66 (2H, d, J=8.8 Hz), 6.85–6.91 (4H, m), 7.26–7.31 (5H, m), 7.36 (2H, d, J=8.6 Hz).

IR (KBr) cm$^{-1}$; 1755, 1732, 1526, 1493, 1236, 1181, 1071, 833, 700.

$[\alpha]_D^{24}$ 7.64° (c 0.845, chloroform)

Example 28

(2R)-2-{4-[1-(4-Bromophenyl)-5-methyl-3-propyl-1H-pyrrol-2-yl]phenoxy}-3-phenylpropanoic acid (2R)-2-{4-[1-(4-Bromophenyl)-5-methyl-3-propyl-1H-pyrrol-2-yl]phenoxy}-3-phenylpropanoic acid was synthesized from ethyl (2R)-2-{4-[1-(4-bromophenyl)-5-methyl-3-propyl-1H-pyrrol-2-yl]phenoxy}-3-phenylpropanoate obtained in Example 27, as an oily substance, according to the similar manner to that of Example 24. yield: 93.1%

$^1$H-NMR (CDCl$_3$) δ; 0.91 (3H, t, J=7.0 Hz), 1.51–1.63 (2H, m), 2.10 (3H, s), 2.38 (3H, t, J=7.4 Hz), 3.25 (2H, d, J=6.6 Hz), 4.80 (1H, t, J=6.6 Hz), 5.98 (1H, s), 6.67 (2H, d, J=8.8 Hz), 6.88 (4H, d, J=8.8 Hz), 7.26–7.28 (5H, m), 7.37 (2H, d, J=8.8 Hz).

IR (KBr) cm$^{-1}$; 3065, 1728, 1526, 1491, 1236, 1179, 1071, 833, 735, 700.

$[α]_D^{21}$ -8.44° (c 1.25, chloroform)

Example 29

Ethyl (2R)-2-{4-[1-(4-bromophenyl)-5-methyl-3-phenyl-1H-pyrrol-2-yl]phenoxy}-3-phenylpropanoate (1) 1-(4-Methoxyphenyl)-2-phenyl-1,4-pentanedione 1-(4-Methoxyphenyl)-2-phenyl-1,4-pentanedione was synthesized from benzalacetone as an oily substance, according to the similar manner to that of Example 23(1). yield: 16.6%

$^1$H-NMR (CDCl$_3$) δ; 2.19 (3H, s ), 2.73 (1H, dd, J=4.4, 17.4 Hz), 3.59 (1H, dd, J=10.2, 17.4 Hz), 3.81 (3H, s), 5.07 (1H, dd, J=4.4, 10.2 Hz), 6.86 (2H, d, J=8.8 Hz), 7.16–7.28 (5H, m), 7.95 (2H, d, J=8.8 Hz).

IR (KBr) cm$^{-1}$; 1715, 1672, 1601, 1574, 1510, 1248, 1169, 1028, 842, 702.

(2) 1-(4-Bromophenyl)-2-(4-methoxyphenyl)-5-methyl-3-phenyl-1H-pyrrole 1-(4-Bromophenyl)-2-(4-methoxyphenyl)-5-methyl-3-phenyl-1H-pyrrole was synthesized from 1-(4-methoxyphenyl)-2-phenyl-1,4-pentanedione as a solid, according to the similar manner to that of Example 23(2). yield: 56.6%

$^1$H-NMR (CDCl$_3$) δ; 2.15 (3H, s), 3.75 (3H, s), 6.29 (1H, s), 6.97 (2H, d, J=8.6 Hz), 6.89–6.99 (4H, m), 7.08–7.26 (5H, m), 7.42 (2H, d, J=8.8 Hz).

IR (KBr) cm$^{-1}$; 1508, 1491, 1298, 1177, 1034, 833, 762.

Elementary analysis for C$_{24}$H$_{20}$NOBr; Calculated: C, 82.91; H, 4.82; N, 3.35. Found: C, 69.15; H, 4.97; N, 3.20.

(3) 4-[1-(4-Bromophenyl)-5-methyl-3-phenyl-1H-pyrrol-2-yl]phenol

4-[1-(4-Bromophenyl)-5-methyl-3-phenyl-1H-pyrrol-2-yl]phenol was synthesized from 1-(4-bromophenyl)-2-(4-methoxyphenyl)-5-methyl-3-phenyl-1H-pyrrole as a solid, according to the similar manner to that of Example 23(3). yield: 83.1%

$^1$H-NMR (CDCl$_3$) δ; 2.15 (3H, s), 4.76 (1H, bs), 6.28 (1H, s), 6.60 (2H, d, J=8.8 Hz), 6.87 (2H, d, J=8.8 Hz), 6.96 (2H, d, J=8.8 Hz), 7.10–7.26 (5H, m), 7.42 (2H, d, J=8.8 Hz).

IR (KBr) cm$^{-1}$; 3281, 1534, 1508, 1491, 1370, 1260, 1171, 1005, 835, 762, 698.

Elementary analysis for C$_{23}$H$_{18}$NOBr·0.6H$_2$O; Calculated: C, 66.55; H, 4.66; N, 3.37. Found: C, 66.43; H, 4.37; N, 3.17.

(4) Ethyl (2R)-2-{4-[1-(4-bromophenyl)-5-methyl-3-phenyl-1H-pyrrol-2-yl]phenoxy}-3-phenylpropanoate Ethyl (2R)-2-{4-[1-(4-bromophenyl)-5-methyl-3-phenyl-1H-pyrrol-2-yl]phenoxy}-3-phenylpropanoate was synthesized from 4-[1-(4-bromophenyl)-5-methyl-3-phenyl-1H-pyrrol-2-yl]phenol as an oily substance, according to the similar manner to that of Example 23(4). yield: 37.1%

$^1$H-NMR (CDCl$_3$) δ; 1.11 (3H, t, J=7.4 Hz), 2.13 (3H, s), 3.18–3.22 (2H, m), 4.13 (2H, q, J=7.4 Hz), 4.69–4.75 (1H, m), 6.26 (1H, s), 6.60 (2H, d, J=8.8 Hz), 6.85 (2H, d, J=8.8 Hz), 6.93 (2H, d, J=8.8 Hz), 7.09–7.30 (10H, m), 7.40 (2H, d, J=8.8 Hz).

IR (KBr) cm$^{-1}$; 1755, 1732, 1532, 1508, 1491, 1281, 1236, 1181, 1071, 1030, 1007, 843, 762, 700.

$[α]_D^{25}$ 8.30° (c 0.615, chloroform)

Example 30

(2R)-2-{4-[1-(4-Bromophenyl)-5-methyl-3-phenyl-1H-pyrrol-2-yl]phenoxy}-3-phenylpropanoic acid (2R)-2-{4-[1-(4-Bromophenyl)-5-methyl-3-phenyl-1H-pyrrol-2-yl]phenoxy}-3-phenylpropanoic acid was synthesized from ethyl (2R)-2-{4-[1-(4-bromophenyl)-5-methyl-3-phenyl-1H-pyrrol-2-yl]phenoxy}-3-phenylpropanoate obtained in Example 29, as an oily substance, according to the similar manner to that of Example 24. yield: 88.8%

$^1$H-NMR (CDCl$_3$) δ; 2.13 (3H, s), 3.25 (2H, d, J=6.8 Hz), 4.79 (1H, t, J=6.8 Hz), 6.26 (1H, s), 6.60 (2H, d, J=8.4 Hz), 6.86 (2H, d, J=8.4 Hz), 6.92 (2H, d, J=8.4 Hz), 7.06–7.27 (10H, m), 7.40 (2H, d, J=8.4 Hz).

IR (KBr) cm$^{-1}$; 3063, 1728, 1508, 1491, 1236, 909, 841, 762, 733, 698.

$[α]_D^{25}$ -17.2° (c 1.08, chloroform)

Example 31

Ethyl (2R)-2-{4-[1-(4-bromophenyl)-5-methyl-1H-pyrrol-2-yl]phenoxy}-3-(1H-indol-3-yl)propanoate (1) Ethyl 2-hydroxy-3-(1H-indol-3-yl)propanoate A solution of 2-hydroxy-3-(1H-indol-3-yl)propanoic acid (1.00 g, 4.87 mmol) and p-toluenesulfonic acid monohydrate (180 mg, 0.944 mmol) in ethanol (50 ml) was refluxed for 12 hours under heating and the solvent was removed under reduced pressure. The residue was purified by silica gel column chromatography (hexane:ethyl acetate=3:1) to isolate the object compound as a solid. 1.00 g (yield: 87.7%)

$^1$H-NMR (CDCl$_3$) δ; 1.23 (3H, t, J=7.2 Hz), 2.80 (1H, d, J=6.4 Hz), 3.13–3.35 (2H, m), 4.07–4.24 (2H, m), 4.46–4.55 (1H, m), 7.07–7.26 (4H, m), 7.34 (2H, d, J=7.0 Hz), 7.62 (2H, d, J=7.8 Hz), 8.08 (1H, bs).

IR (KBr) cm$^{-1}$; 3341, 1726, 1281, 1215, 1096, 1026, 741.

(2) Ethyl (2R)-2-{4-[1-(4-bromophenyl)-5-methyl-1H-pyrrol-2-yl]phenoxy}-3-(1H-indol-3-yl)propanoate To a solution of 4-[1-(4-bromophenyl)-5-methyl-1H-pyrrol-2-yl]phenol (400 mg, 1.22 mmol), ethyl 2-hydroxy-3-(1H-indol-3-yl)propanoate (424 mg, 1.82 mmol) and triphenylphosphine (477 mg, 1.82 mmol) in toluene (4 ml) was added 1,1'-(azodicarbonyl)dipiperidine (459 mg, 1.82 mmol) at room temperature. The obtained solution was stirred at room temperature for 1 hour and at 80° C. for 4 hours, diluted with ethyl acetate and with water. The organic layer was separated and dried over magnesium sulfate anhydride, and the solvent was removed under reduced pressure. The residue was purified by silica gel column chromatography (hexane:ethyl acetate=30:1) to isolate the object compound as an oily substance. 124 mg (yield: 18.7%)

$^1$H-NMR (CDCl$_3$) δ; 1.12 (3H, t, J=7.2 Hz), 2.10 (3H, s), 3.38 (2H, d, J=6.2 Hz), 4.13 (2H, q, J=7.2 Hz), 4.79 (1H, t, J=6.2 Hz), 6.04 (1H, d, J=3.2 Hz), 6.22 (1H, d, J=3.2 Hz), 6.65 (2H, d, J=8.8 Hz), 6.89 (2H, d, J=8.8 Hz), 6.97 (2H, d, J=8.4 Hz), 7.10–7.42 (4H, m), 7.45 (2H, d, J=8.4 Hz), 7.67 (1H, d, J=7.0 Hz), 8.03 (1H, bs).

IR (KBr) cm$^{-1}$; 3411, 1738, 1524, 1489, 1233, 1184, 1071, 835, 743.

Example 32

(2R)-2-{4-[1-(4-Bromophenyl)-5-methyl-1H-pyrrol-2-yl]phenoxy}-3-(1H-indol-3-yl)propanoic acid To a mixed solution of ethyl (2R)-2-{4-[1-(4-bromophenyl)-5-methyl-1H-pyrrol-2-yl]phenoxy}-3-(1H- indol-3-yl)propanoate obtained in Example 31 (124 mg, 0.228 mmol) in THF (2 ml)-methanol (1 ml) was added 1N aqueous potassium hydroxide (0.685 ml, 0.685 mmol). The obtained solution was stirred at room temperature for 1 hour, neutralized with 1 N hydrochloric acid and extracted with ethyl acetate. The extracts were collected, washed with water and dried over magnesium sulfate-anhydride, and the solvent was removed under reduced pressure to give the object compound as a solid. 80.6 mg (68.6%)

$^1$H-NMR (CDCl$_3$) δ; 2.10 (3H, s), 3.41 (2H, d, J=6.2 Hz), 4.85 (1H, t, J=6.2 Hz), 6.05 (1H, d, J=3.4 Hz), 6.24 (1H, d, J=3.4 Hz), 6.66 (2H, d, J=8.8 Hz), 6.90–7.35 (8H, m), 7.45 (2H, d, J=8.4 Hz), 7.64 (1H, d, J=7.0 Hz), 7.97 (1H, bs).

IR (KBr) cm$^{-1}$; 3416, 3056, 1725, 1522, 1489, 1231, 1071, 909, 833, 737.

Example 33

Ethyl (2R)-2-{4-[1-(4-bromophenyl)-5-propyl-1H-pyrrol-2-yl]phenoxy}-3-phenylpropanoate (1) 1-(4-Methoxyphenyl)-1,4-heptanedione 1-(4-Methoxyphenyl)-1,4-heptanedione was synthesized from 1-hexen-3-one as an oily substance, according to the similar manner to that of Example 19(1). yield: 20.2%

$^1$H-NMR (CDCl$_3$) δ; 0.94 (3H, t, J=7.6 Hz), 1.59–1.71 (2H, m), 2.52 (2H, t, J=7.2 Hz), 2.84 (2H, t, J=6.2 Hz), 3.24 (2H, t, J=6.2 Hz), 3.87 (3H, s), 6.93 (2H, d, J=8.8 Hz), 7.97 (2H, d, J=8.8 Hz).

IR (KBr) cm$^{-1}$; 1713, 1678, 1601, 1510, 1260, 1171, 1026, 833.

(2) 1-(4-Bromophenyl)-2-(4-methoxyphenyl)-5-propyl-1H-pyrrole 1-(4-Bromophenyl)-2-(4-methoxyphenyl)-5-propyl-1H-pyrrole was synthesized from 1-(4-methoxyphenyl)-1,4-heptanedione as a solid, according to the similar manner to that of Example 19(2). yield: 74.1%

$^1$H-NMR (CDCl$_3$) δ; 0.89 (3H, t, J=7.2 Hz), 1.46–1.58 (2H, m), 2.40 (2H, t, J=7.0 Hz), 3.75 (3H, s), 6.08 (1H, d, J=3.2 Hz), 6.27 (1H, d, J=3.2 Hz), 6.71 (2H, d, J=8.8 Hz), 6.92–7.06 (4H, m), 7.48 (2H, d, J=8.8 Hz).

IR (KBr) cm$^{-1}$; 1522, 1489, 1248, 1034, 833, 766.

(3) 4-[1-(4-Bromophenyl)-5-propyl-1H-pyrrol-2-yl]phenol

4-[1-(4-Bromophenyl)-5-propyl-1H-pyrrol-2-yl]phenol was synthesized from 1-(4-bromophenyl)-2-(4-methoxyphenyl)-5-propyl-1H-pyrrole as a solid, according to the similar manner to that of Example 19(3). yield: 88.0%

$^1$H-NMR (CDCl$_3$) δ; 0.88 (3H, t, J=7.2 Hz), 1.43–1.59 (2H, m), 2.40 (2H, t, J=8.0 Hz), 4.60 (1H, s), 6.08 (1H, d, J=3.4 Hz), 6.26 (1H, d, J=3.4 Hz), 6.63 (2H, d, J=8.8 Hz), 6.91 (2H, d, J=8.8 Hz), 7.01 (2H, d, J=8.4 Hz), 7.47 (2H, d, J=8.4 Hz)

IR (KBr) cm$^{-1}$; 3376, 1522, 1489, 1260, 1173, 833, 770, 733.

(4) Ethyl (2R)-2-{4-[1-(4-bromophenyl)-5-propyl-1H-pyrrol-2-yl]phenoxy}-3-phenylpropanoate Ethyl (2R)-2-{4-[1-(4-bromophenyl)-5-propyl-1H-pyrrol-2-yl]phenoxy}-3-phenylpropanoate was synthesized from 4-[1-(4-bromophenyl)-5-propyl-1H-pyrrol-2-yl]phenol as a solid according to the similar manner to that of Example 19 (4). yield: 23.4%

$^1$H-NMR (CDCl$_3$) δ; 0.88 (3H, t, J=7.2 Hz), 1.14 (3H, t, J=7.4 Hz), 1.45–1.55 (2H, m), 2.38 (2H, t, J=7.6 Hz), 3.18–3.22 (2H, m), 4.14 (2H, q, J=7.4 Hz), 4.68–4.74 (1H, m), 6.06 (1H, d, J=3.8 Hz), 6.25 (1H, d, J=3.8 Hz),6.63 (2H, d, J=8.8Hz), 6.89 (2H, d, J=8.8 Hz), 6.99 (2H, d, J=8.8 Hz), 7.26–7.28 (5H, m), 7.46 (2H, d, J=8.8 Hz).

IR (KBr) cm$^{-1}$; 1753, 1732, 1520, 1489, 1238, 1182, 1071, 835, 766, 735.

$[\alpha]_D^{22}$ 17.0° (c 0.645, chloroform)

Example 34

(2R)-2-{4-[1-(4-Bromophenyl)-5-propyl-1H-pyrrol-2-yl]phenoxy}-3-phenylpropanoic acid (2R)-2-{4-[1-(4-Bromophenyl)-5-propyl-1H-pyrrol-2-yl]phenoxy}-3-phenylpropanoic acid was synthesized from ethyl (2R)-2-{4-[1-(4-bromophenyl)-5-propyl-1H-pyrrol-2-yl]phenoxy}-3-phenylpropanoate obtained in Example 33, as a solid, according to the similar manner to that of Example 20. yield: 93.2%

$^1$H-NMR (CDCl$_3$) δ; 0.88 (3H, t, J=6.2 Hz), 1.45–1.56 (2H, m), 2.38 (2H, t, J=8.0 Hz), 3.24 (2H, d, J=6.8 Hz), 4.79 (1H, t, J=6.8 Hz), 6.07 (1H, d, J=3.8 Hz), 6.26 (1H, d, J=3.8 Hz), 6.64 (2H, d, J=8.8 Hz), 6.91 (2H, d, J=8.8 Hz), 6.99 (2H, d, J=8.8 Hz), 7.26–7.28 (5H, m), 7.47 (2H, d, J=8.8 Hz).

IR (KBr) cm$^{-1}$; 2957, 1726, 1520, 1489, 1236, 1071, 833, 768.

$[\alpha]_D^{22}$ –2.76° (c 1.07, chloroform)

Example 35

Ethyl (2R)-2-[4-(1-phenyl-1H-pyrrol-2-yl)phenoxy]-3-phenylpropanoate (1) 2-(4-Methoxyphenyl)-1-phenyl-1H-pyrrole A solution of 3-(5,5-dimethyl-1,3-dioxane-2-yl)-1-(4-methoxyphenyl)-1-propanone (2.00 g, 7.19 mmol), aniline (0.655 ml, 7.19 mmol) and p-toluenesulfonic acid monohydrate (103 mg, 0.543 mmol) in toluene (100 ml) was refluxed for 48 hours under heating and the solvent was removed under reduced pressure. The residue was purified by silica gel column chromatography (hexane:ethyl acetate= 20:1) to isolate the object compound as a solid. 1.17 g (yield: 65.4%)

$^1$H-NMR (CDCl$_3$) δ; 3.76 (3H, s), 6.34–6.36 (2H, m), 6.75 (2H, d, J=8.8 Hz), 6.91 (1H, t, J=2.2 Hz), 7.05 (2H, d, J=8.8 Hz), 7.13–7.32 (5H, m)

IR (KBr) cm$^{-1}$; 1613, 1597, 1498, 1464, 1246, 1177, 1034, 833, 764, 714, 698.

(2) 4-(1-Phenyl-1H-pyrrol-2-yl)phenol

To a solution of 2-(4-methoxyphenyl)-1-phenyl-1H-pyrrole (1.00 g, 4.02 mmol) in methylene chloride (30 ml) was added boron tribromide (1.52 ml, 16.1 mmol) at 0° C. The obtained solution was stirred at 0° C. for 0.5 hours and at room temperature for 0.5 hours, poured into ice water and extracted with ethyl acetate. The extracts were collected and washed with saturated aqueous sodium bicarbonate and dried over magnesium sulfate anhydride, and the solvent was removed under reduced pressure. The residue was purified by silica gel column chromatography (hexane:ethyl acetate=9:1) to isolate the object compound as a solid. 880 mg (yield: 93.0%)

$^1$H-NMR (DMSO-d$_6$) δ; 4.89 (1H, s), 6.34 (2H, d, J=2.2 Hz), 6.67 (2H, d, J=8.4 Hz), 6.91 (1H, d, J=2.2 Hz), 7.00 (2H, d, J=8.8 Hz), 7.15 (2H, d, J=8.4 Hz), 7.25–7.36 (3H, m)

IR (KBr) cm$^{-1}$; 3364, 1597, 1500, 1464, 1258, 1219, 1171, 835, 764, 716, 698.

(3) Ethyl (2R)-2-[4-(1-Phenyl-1H-pyrrol-2-yl)phenoxy]-3-phenylpropanoate

To a solution of 4-(1-phenyl-1H-pyrrol-2-yl)phenol (750 mg, 3.19 mmol), ethyl (S)-2-hydroxy-3-phenylpropanoate (930 mg, 4.79 mmol) and triphenylphosphine (1.26 g, 4.79 mmol) in toluene (5 ml) was added diethyl azodicarboxylate (40%, 2.08 g, 4.79 mmol). The obtained solution was stirred at 80° C. for 12 hours and the solvent was removed under reduced pressure. The residue was purified by silica gel column chromatography (hexane:ethyl acetate=20:1) to give the object compound as a solid. 590 mg (yield: 45.0%)

$^1$H-NMR (CDCl$_3$) δ; 1.11 (3H, t, J=7.2 Hz), 3.18–3.22 (2H, m), 4.11 (2H, q, J=7.2 Hz), 4.69–4.76 (1H, m), 6.29–6.33 (2H, m), 6.67 (2H, d, J=8.8 Hz), 6.87 (1H, t, J=2.6 Hz), 6.98 (2H, d, J=8.8 Hz), 7.08–7.31 (10H, m).

IR (KBr) cm$^{-1}$; 1755, 1732, 1597, 1549, 1504, 1464, 1454, 1285, 1238, 1181, 1084, 1034, 833, 766, 700.

$[α]_D^{25}$ 15.7° (c 0.810, chloroform)

Example 36

(2R)-2-[4-(1-Phenyl-1H-pyrrol-2-yl)phenoxy]-3-phenylpropanoic acid

To a mixed solution of ethyl (2R)-2-[4-(1-phenyl-1H-pyrrol-2-yl)phenoxy]-3-phenylpropanoate obtained in Example 35 (400 mg, 0.973 mmol) in THF (4 ml)-methanol (2 ml) was added 5 N aqueous sodium hydroxide (0.584 ml, 2.92 mmol) and the mixture was stirred at room temperature for 1 hour. The reaction solution was diluted with ethyl acetate and water, and neutralized with 1 N hydrochloric acid, and the organic layer was separated. The organic layer was washed with water and dried over magnesium sulfate anhydride, and the solvent was removed under reduced pressure to give the object compound as an oily substance. 299 mg (yield: 80.2%)

$^1$H-NMR (CDCl$_3$) δ; 3.25 (2H, d, J=6.6 Hz), 4.79 (1H, t, J=6.6 Hz), 6.33 (2H, d, J=2.2 Hz), 6.68 (2H, d, J=8.8 Hz), 6.90 (1H, t, J=2.2 Hz), 7.00 (2H, d, J=8.8 Hz), 7.10–7.30 (10H, m).

IR (KBr) cm$^{-1}$; 3063, 1726, 1499, 1236, 1179, 1084, 833, 700.

$[α]_D^{25}$ –0.982° (c 0.855, chloroform)

Example 37

Ethyl (2R)-2-{4-[1-(4-methylphenyl)-1H-pyrrol-2-yl]phenoxy}-3-phenylpropanoate (1) 2-(4-Methoxyphenyl)-1-(4-methylphenyl)-1H-pyrrole 2-(4-Methoxyphenyl)-1-(4-methylphenyl)-1H-pyrrole was synthesized from p-toluidine as a solid, according to the similar manner to that of Example 35(1). 860 mg (yield: 60.6%)

$^1$H-NMR (CDCl$_3$) δ; 2.35 (3H, s), 3.77 (3H, s), 6.33–6.34 (2H, m), 6.75 (2H, d, J=8.6 Hz), 6.87–6.90 (1H, m), 7.02–7.14 (6H, m).

IR (KBr) cm$^{-1}$; 1516, 1506, 1462, 1246, 1175, 1032, 824, 712, 559.

Elementary analysis for C$_{18}$H$_{17}$NO; Calculated: C, 82.85; H, 6.51; N, 5.32. Found: C, 81.98; H, 6.30; N, 5.25.

(2) 4-[1-(4-Methylphenyl)-1H-pyrrol-2-yl]phenol

4-[1-(4-Methylphenyl)-1H-pyrrol-2-yl]phenol was synthesized from 2-(4-methoxyphenyl)-1-(4-methylphenyl)-1H-pyrrole as a solid, according to the similar manner to that of Example 35(2). 525 mg (yield: 72.8%)

$^1$H-NMR (CDCl$_3$) δ; 2.35 (3H, s), 4.64 (1H, s), 6.33 (2H, d, J=1.8 Hz), 6.67 (2H, d, J=8.8 Hz), 6.88 (1H, t, J=1.8 Hz), 6.99–7.13 (6H, m).

IR (KBr) cm$^{-1}$; 3377, 1516, 1507, 1464, 1339, 1258, 1173, 835, 825, 715.

(3) Ethyl (2R)-2-{4-[1-(4-methylphenyl)-1H-pyrrol-2-yl]phenoxy}-3-phenylpropanoate Ethyl (2R)-2-{4-[1-(4-methylphenyl)-1H-pyrrol-2-yl]phenoxy}-3-phenylpropanoate was synthesized from 4-[1-(4-methylphenyl)-1H-pyrrol-2-yl]phenol as a solid, according to the similar manner to that of Example 35(3). yield: 21.0%

$^1$H-NMR (CDCl$_3$) δ; 1.15 (3H, t, J=7.4 Hz), 2.34 (3H, s), 3.20–3.23 (2H, m), 4.15 (2H, q, J=7.4 Hz), 4.71–4.77 (1H, m), 6.31 (2H, t, J=2.2 Hz), 6.68 (2H, d, J=8.8 Hz), 6.86 (1H, t, J=2.2 Hz), 6.97–7.11 (6H, m), 7.11–7.28 (5H, m).

IR (KBr) cm$^{-1}$; 1755, 1732, 1516, 1505, 1238, 1184, 1086, 1032, 826, 714, 700.

$[α]_D^{23}$ 16.8° (c 0.545, chloroform)

Example 38

(2R)-2-{4-[1-(4-Methylphenyl)-1H-pyrrol-2-yl]phenoxy}-3-phenylpropanoic acid (2R)-2-{4-[1-(4-Methylphenyl)-1H-pyrrol-2-yl]phenoxy}-3-phenylpropanoic acid was synthesized from ethyl (2R)-2-{4-[1-(4-methylphenyl)-1H-pyrrol-2-yl]phenoxy}-3-phenylpropanoate obtained in Example 37, as an oily substance, according to the similar manner to that of Example 36. yield: 97.7%

$^1$H-NMR (CDCl$_3$) δ; 2.34 (2H, s), 3.25 (2H, d, J=5.8 Hz), 4.79 (1H, t, J=5.8 Hz), 6.33 (2H, t, J=2.6 Hz), 6.78 (2H, d, J=9.2 Hz), 6.87 (1H, t, J=2.6 Hz), 6.99–7.12 (6H, m), 7.22–7.31 (5H, m).

IR (KBr) cm$^{-1}$; 3032, 1726, 1516, 1504, 1235, 1179, 1084, 824, 716, 700.

$[α]_D^{23}$ 0.742° (c 2.32, chloroform)

Example 39

Ethyl (2R)-2-{4-[1-(4-chlorophenyl)-1H-pyrrol-2-yl]phenoxy}-3-phenylpropanoate (1) 1-(4-Chlorophenyl)-2-(4-methoxyphenyl)-1H-pyrrole 1-(4-Chlorophenyl)-2-(4-methoxyphenyl)-1H-pyrrole was synthesized from p-chloroaniline as a solid, according to the similar manner to that of Example 35(1). yield: 50.9%

$^1$H-NMR (CDCl$_3$) δ; 3.78 (3H, s), 6.35 (2H, d, J=2.4 Hz), 6.78 (2H, d, J=9.0 Hz), 6.88 (1H, t, J=2.4 Hz), 7.03–7.11 (4H, m), 7.28 (2H, d, J=9.4 Hz).

IR (KBr) cm$^{-1}$; 1495, 1248, 1032, 833, 712.

Elementary analysis for C$_{17}$H$_{14}$NOCl; Calculated: C, 71.96; H, 4.97; N, 4.94. Found: C, 71.96; H, 5.07; N, 4.87.

(2) 4-[1-(4-Chlorophenyl)-1H-pyrrol-2-yl]phenol

4-[1-(4-Chlorophenyl)-1H-pyrrol-2-yl]phenol was synthesized from 1-(4-chlorophenyl)-2-(4-methoxyphenyl)-1H-pyrrole as a solid, according to the similar manner to that of Example 35(2). yield: 69.9%

$^1$H-NMR (CDCl$_3$) δ; 4.68 (1H, s), 6.33 (2H, d, J=2.2 Hz), 6.70 (2H, d, J=8.8 Hz), 6.87 (1H, t, J=2.2 Hz), 7.00 (2H, d, J=8.8 Hz), 7.08 (2H, d, J=9.2 Hz), 7.28 (2H, d, J=9.2 Hz).

IR (KBr) cm$^{-1}$; 3179, 1495, 1240, 826, 729.

(3) Ethyl (2R)-2-{4-[1-(4-chlorophenyl)-1H-pyrrol-2-yl]phenoxy}-3-phenylpropanoate Ethyl (2R)-2-{4-[1-(4-chlorophenyl)-1H-pyrrol-2-yl]phenoxy}-3-phenylpropanoate was synthesized from 4-[1-(4-chlorophenyl)-1H-pyrrol-2-yl]phenol as a solid, according to the similar manner to that of Example 35(3). yield: 37.6%

$^1$H-NMR (CDCl$_3$) δ; 1.16 (3H, t, J=7.4 Hz), 3.20–3.24 (2H, m), 4.16 (2H, q, J=7.4 Hz), 4.71–4.78 (1H, m), 6.33 (2H, t, J=2.6 Hz), 6.70 (2H, d, J=9.2 Hz), 6.86 (1H, t, J=2.6 Hz), 6.96–7.09 (4H, m), 7.24–7.29 (7H, m).

IR (KBr) cm$^{-1}$; 1753, 1732, 1495, 1238, 1184, 1092, 833, 700.

$[α]_D^{24}$ 18.8° (c 0.675, chloroform)

Example 40

(2R)-2-{4-[1-(4-Chlorophenyl)-1H-pyrrol-2-yl]phenoxy}-3-phenylpropanoic acid (2R)-2-{4-[1-(4-Chlorophenyl)-1H-pyrrol-2-yl]phenoxy}-3-phenylpropanoic acid was synthesized from ethyl (2R)-2-{4-[1-(4-chlorophenyl)-1H-pyrrol-2-yl]phenoxy}-3-phenylpropanoate obtained in Example 39, as an oily substance, according to the similar manner to that of Example 36. yield: 92.6%

¹H-NMR (CDCl₃) δ; 3.26 (2H, d, J=5.4 Hz), 4.81 (1H, t, J=5.4 Hz), 6.33 (2H, t, J=2.2 Hz), 6.70 (2H, d, J=8.8 Hz), 6.86 (1H, t, J=2.2 Hz), 6.96–7.09-(4H, m), 7.23–7.31 (7H, m).

IR (KBr) cm⁻¹; 3029, 1732, 1495, 1236, 1092, 833, 715.

$[\alpha]_D^{23}$ 6.97° (c 3.92, chloroform)

Example 41

Ethyl (2R)-2-{4-[1-(4-trifluoromethylphenyl)-1H-pyrrol-2-yl]phenoxy}-3-phenylpropanoate (1) 1-(4-Methoxyphenyl)-2-(4-trifluoromethylphenyl)-1H-pyrrole 1-(4-Methoxyphenyl)-2-(4-trifluoromethylphenyl)-1H-pyrrole was synthesized from 4-trifluoromethyl aniline as a solid, according to the similar manner to that of Example 35(1). yield: 61.4%

¹H-NMR (CDCl₃) δ; 3.77 (3H, s), 6.38 (2H, d, J=2.2 Hz), 6.79 (2H, d, J=8.8 Hz), 6.93 (1H, t, J=2.2 Hz), 7.05 (2H, d, J=8.8 Hz), 7.25 (2H, d, J=8.4 Hz), 7.57 (2H, d, J=8.4 Hz).

IR (KBr) cm⁻¹; 1615, 1508, 1325, 1248, 1171, 1127, 1109, 1069, 847, 835, 714.

Elementary analysis for C₁₈H₁₄NOF₃; Calculated: C, 68.13; H, 4.45; N, 4.41. Found: C, 68.26; H, 4.50; N, 4.27.

(2) 4-[1-(4-Trifluorophenylphenyl)-1H-pyrrol-2-yl]phenol

4-[1-(4-Trifluorophenylphenyl)-1H-pyrrol-2-yl]phenol was synthesized from 1-(4-methoxyphenyl)-2-(4-trifluoromethylphenyl)-1H-pyrrole as a solid, according to the similar manner to that of Example 35(2). yield: 90.4%

¹H-NMR (CDCl₃) δ; 4.77 (1H, s), 6.37 (2H, d, J=2.6 Hz), 6.71 (2H, d, J=8.8 Hz), 6.92–7.02 (3H, m), 7.24 (2H, d, J=8.4 Hz), 7.57 (2H, d, J=8.4 Hz).

IR (KBr) cm⁻¹; 3300, 1617, 1508, 1325, 1252, 1165, 1128, 1107, 1069, 849, 835, 718.

(3) Ethyl (2R)-2-{4-[1-(4-trifluoromethylphenyl)-1H-pyrrol-2-yl]phenoxy}-3-phenylpropanoate Ethyl (2R)-2-{4-[1-(4-trifluoromethylphenyl)-1H-pyrrol-2-yl]phenoxy}-3-phenylpropanoate was synthesized from 4-[1-(4-trifluorophenylphenyl)-1H-pyrrol-2-yl]phenol as a solid, according to the similar manner to that of Example 35(3). yield: 36.0%

¹H-NMR (CDCl₃) δ; 1.16 (3H, t, J=7.0 Hz), 3.21–3.24 (2H, m), 4.15 (2H, q, J=7.0 Hz), 4.17–4.78 (1H, m), 6.35 (2H, s), 6.71 (2H, d, J=8.8 Hz), 6.92–7.00 (3H, m), 7.20–7.29 (7H, m), 7.55 (2H, d, J=8.0 Hz).

IR (KBr) cm⁻¹; 1755, 1732, 1615, 1506, 1325, 1167, 1127, 1069, 847, 700.

$[\alpha]_D^{23}$ 16.5° (c 0.705, chloroform)

Example 42

(2R)-2-{4-[1-(4-Trifluoromethylphenyl)-1H-pyrrol-2-yl]phenoxy}-3-phenylpropanoic acid (2R)-2-{4-[1-(4-Trifluoromethylphenyl)-1H-pyrrol-2-yl]phenoxy}-3-phenylpropanoic acid was synthesized from ethyl (2R)-2-{4-[1-(4-trifluoromethylphenyl)-1H-pyrrol-2-yl]phenoxy}-3-phenylpropanoate obtained in Example 41, as an oily substance, according to a similar manner to that of Example 36. yield: 90.9%

¹H-NMR (CDCl₃) δ; 3.25–3.28 (2H, m), 4.79–4.85 (1H, m), 6.35 (2H, d, J=2.6 Hz), 6.72 (2H, d, J=8.8 Hz), 6.93 (1H, t, J=2.6 Hz), 7.00 (2H, d, J=8.8 Hz), 7.20–7.32 (7H, m), 7.56 (2H, d, J=8.8 Hz).

IR (KBr) cm⁻¹; 3029, 1728, 1507, 1325, 1238, 1169, 1127, 1069, 847, 700.

$[\alpha]_D^{21}$ 4.97° (c 4.67, chloroform)

Example 43

Ethyl (2R)-2-{4-[1-(4-chlorophenyl)-5-methyl-1H-pyrrol-2-yl]phenoxy}-3-phenylpropanoate (1) 1-(4-Chlorophenyl)-1-(4-methoxyphenyl)-5-methyl-1H-pyrrole 1-(4-Chlorophenyl)-1-(4-methoxyphenyl)-5-methyl-1H-pyrrole was synthesized from p-chloroaniline as a solid, according to the similar manner to that of Example 5(2). yield: 45.0%

¹H-NMR (CDCl₃) δ; 2.12 (3H, s), 3.75 (3H, s), 6.07 (1H, d, J=3.2 Hz), 6.25 (1H, d, J=3.2 Hz), 6.71 (2H, d, J=8.8 Hz), 6.97 (2H, d, J=8.8 Hz), 7.07 (2H, d, J=8.8 Hz), 7.32 (2H, d, J=8.8 Hz).

IR (KBr) cm⁻¹; 1526, 1493, 1246, 1179, 1092, 1034, 835, 766.

(2) 4-[1-(4-Chlorophenyl)-5-methyl-1H-pyrrol-2-yl]phenol

4-[1-(4-Chlorophenyl)-5-methyl-1H-pyrrol-2-yl]phenol was synthesized from 1-(4-chlorophenyl)-1-(4-methoxyphenyl)-5-methyl-1H-pyrrole as a solid, according to the similar manner to that of Example 5(3). yield: 93.5%

¹H-NMR (CDCl₃) δ; 2.12 (3H, s), 4.78 (1H, s), 6.06 (1H, d, J=3.4 Hz), 6.24 (1H, d, J=3.4 Hz), 6.63 (2H, d, J=8.8 Hz), 6.92 (1H, d, J=8.8 Hz), 7.06 (2H, d, J=8.4 Hz), 7.32 (2H, d, J=8.4 Hz).

IR (KBr) cm⁻¹; 3335, 1526, 1493, 1393, 1264, 1092, 835, 768.

(3) Ethyl (2R)-2-{4-[1-(4-chlorophenyl)-5-methyl-1H-pyrrol-2-yl]phenoxy}-3-phenylpropanoate Ethyl (2R)-2-{4-[1-(4-chlorophenyl)-5-methyl-1H-pyrrol-2-yl]phenoxy}-3-phenylpropanoate was synthesized from 4-[1-(4-chlorophenyl)-5-methyl-1H-pyrrol-2-yl]phenol as a solid, according to the similar manner to that of Example 5(4). yield: 14.8%

¹H-NMR (CDCl₃) δ; 1.15 (3H, t, J=7.2 Hz), 2.11 (3H, s), 3.18–3.22 (2H, m), 4.15 (2H, q, J=7.2 Hz), 4.68–4.74 (1H, m), 6.05 (1H, d, J=3.2 Hz), 6.22 (1H, d, J=3.2 Hz), 6.63 (2H, d, J=9.0 Hz), 6.90 (2H, d, J=9.0 Hz), 7.03 (2H, d, J=8.4 Hz), 7.22–7.33 (7H, m).

IR (KBr) cm⁻¹; 1755, 1732, 1524, 1495, 1238, 1184, 1092, 837, 764, 700.

$[\alpha]_D^{23}$ 18.1° (c 0.525, chloroform)

Example 44

(2R)-2-{4-[1-(4-chlorophenyl)-5-methyl-1H-pyrrol-2-yl]phenoxy}-3-phenylpropanoic acid (2R)-2-{4-[1-(4-chlorophenyl)-5-methyl-1H-pyrrol-2-yl]phenoxy}-3-phenylpropanoic acid was synthesized from ethyl (2R)-2-{4-[1-(4-chlorophenyl)-5-methyl-1H-pyrrol-2-yl]phenoxy}-3-phenylpropanoate obtained in Example 43, as an oily substance, according to the similar manner to that of Example 6. yield: 89.7%

¹H-NMR (CDCl₃) δ; 2.11 (3H, s), 3.24 (2H, d, J=5.4 Hz), 4.78 (1H, t, J=5.4 Hz), 6.05 (1H, d, J=3.6 Hz), 6.23 (1H, d, J=3.6 Hz), 6.64 (2H, d, J=8.8 Hz), 6.92 (2H, d, J=8.8 Hz), 7.04 (2H, d, J=8.8 Hz), 7.26–7.33 (7H, m).

IR (KBr) cm⁻¹; 3130, 1719, 1522, 1493, 1238, 1092, 910, 837, 735, 700.

Example 45

Ethyl (2R)-2-{4-[5-methyl-1-(4-trifluoromethylphenyl)-1H-pyrrol-2-yl]phenoxy}-3-phenylpropanoate (1) 2-(4-Methoxyphenyl)-5-methyl-1-(4-trifluoromethylphenyl)-1H-pyrrole 2-(4-Methoxyphenyl)-5-methyl-1-(4-trifluoromethylphenyl)-1H-pyrrole was synthesized from 4-trifluoromethylaniline as a solid, according to the similar manner to that of Example 5(2). yield: 38.6%

$^1$H-NMR (CDCl$_3$) δ; 2.15 (3H, s), 3.75 (3H, s), 6.10 (1H, d, J=3.6 Hz), 6.27 (1H, d, J=3.6 Hz), 6.71 (2H, d, J=8.8 Hz), 6.95 (2H, d, J=8.8 Hz), 7.25 (2H, d, J=8.8 Hz), 7.62 (2H, d, J=8.8 Hz).

IR (KBr) cm$^{-1}$; 1615, 1526, 1327, 1248, 1169, 1128, 1069, 1034, 851, 835, 768.

(2) 4-[5-Methyl-1-(4-trifluoromethylphenyl)-1H-pyrrol-2-yl]phenol

4-[5-Methyl-1-(4-trifluoromethylphenyl)-1H-pyrrol-2-yl]phenol was synthesized from 2-(4-methoxyphenyl)-5-methyl-1-(4-trifluoromethylphenyl)-1H-pyrrole as a solid, according to the similar manner to that of Example 5(3). yield: 90.8%

$^1$H-NMR (CDCl$_3$) δ; 2.15 (3H, s), 4.81 (1H, s), 6.09 (1H, d, J=3.2 Hz), 6.26 (1H, d, J=3.2 Hz), 6.63 (2H, d, J=8.8 Hz), 6.90 (2H, d, J=8.8 Hz), 7.24 (2H, d, J=8.4 Hz), 7.61 (2H, d, J=8.4 Hz).

IR (KBr) cm$^{-1}$; 3306, 1615, 1526, 1327, 1169, 1128, 1069, 851, 839, 770.

(3) Ethyl (2R)-2-{4-[5-methyl-1-(4-trifluoromethylphenyl)-1H-pyrrol-2-yl]phenoxy}-3-phenylpropanoate Ethyl (2R)-2-{4-[5-methyl-1-(4-trifluoromethylphenyl)-1H-pyrrol-2-yl]phenoxy}-3-phenylpropanoate was synthesized from 4-[5-methyl-1-(4-trifluoromethylphenyl)-1H-pyrrol-2-yl]phenol as a solid, according to the similar manner to that of Example 5(4). yield: 27.0%

$^1$H-NMR (CDCl$_3$) δ; 1.13 (3H, t, J=7.0 Hz), 2.13 (3H, s), 3.18–3.22 (2H, m), 4.13 (2H, q, J=7.0 Hz), 4.67–4.74 (1H, m), 6.08 (1H, d, J=3.2 Hz), 6.24 (1H, d, J=3.2 Hz), 6.63 (2H, d, J=8.8 Hz), 6.87 (2H, d, J=8.8 Hz), 7.20–7.27 (7H, m), 7.60 (2H, d, J=8.0 Hz).

IR (KBr) cm$^{-1}$; 1753, 1738, 1524, 1327, 1238, 1169, 1127, 1069, 851.

$[\alpha]_D^{22}$ 14.6° (c 0.620, chloroform)

Example 46

(2R)-2-{4-[5-Methyl-1-(4-trifluoromethylphenyl)-1H-pyrrol-2-yl]phenoxy}-3-phenylpropanoic acid (2R)-2-{4-[5-methyl-1-(4-trifluoromethylphenyl)-1H-pyrrol-2-yl]phenoxy}-3-phenylpropanoic acid was synthesized from ethyl (2R)-2-{4-[5-methyl-1-(4-trifluoromethylphenyl)-1H-pyrrol-2-yl]phenoxy}-3-phenylpropanoate obtained in Example 45, as an oily substance, according to the similar manner to that of Example 6. yield: 94.9%

$^1$H-NMR (CDCl$_3$) δ; 2.13 (3H, s), 3.22–3.25 (2H, m), 4.74–4.80 (1H, m), 6.08 (1H, d, J=3.4 Hz), 6.25 (1H, d, J=3.4 Hz), 6.64 (2H, d, J=8.8 Hz), 6.89 (2H, d, J=8.8 Hz), 7.20–7.30 (7H, m), 7.60 (2H, d, J=8.0 Hz).

IR (KBr) cm$^{-1}$; 3030, 1726, 1524, 1327, 1238, 1169, 1128, 1069, 851, 768, 700.

Example 47

Ethyl (2R)-2-[4-(1-benzyl-5-methyl-1H-pyrrol-2-yl)phenoxy]-3-phenylpropanoate (1) 1-Benzyl-2-(4-methoxyphenyl)-5-methyl-1H-pyrrole 1-Benzyl-2-(4-methoxyphenyl)-5-methyl-1H-pyrrole was synthesized from benzylamine as an oily substance, according to the similar manner to that of Example 5(2). yield: 64.6%

$^1$H-NMR (CDCl$_3$) δ; 2.13 (3H, s), 3.78 (3H, s), 5.08 (2H, s), 6.02 (1H, d, J=3.0 Hz), 6.15 (1H, d, J=3.0 Hz), 6.82 (2H, d, J=8.4 Hz), 6.91 (2H, d, J=7.0 Hz), 7.16–7.34 (5H, m).

IR (KBr) cm$^{-1}$; 1526, 1287, 1246, 1177, 1032, 837, 760, 731, 696.

(2) 4-(1-Benzyl-5-methyl-1H-pyrrol-2-yl)phenol 4-(1-Benzyl-5-methyl-1H-pyrrol-2-yl)phenol was synthesized from 1-benzyl-2-(4-methoxyphenyl)-5-methyl-1H-pyrrole as an oily substance, according to the similar manner to that of Example 5(3). yield: 87.5%

$^1$H-NMR (CDCl$_3$) δ; 2.13 (3H, s), 4.95 (1H, s), 5.07 (2H, s), 6.01 (1H, d, J=3.2 Hz), 6.14 (1H, d, J=3.2 Hz), 6.73 (2H, d, J=8.4 Hz), 6.90 (1H, d, J=8.0 Hz), 7.13 (2H, d, J=8.4 Hz), 7.17–7.34 (3H, m).

IR (KBr) cm$^{-1}$; 3367, 1526, 1481, 1400, 1262, 1229, 1173, 839, 760, 729, 696.

(3) Ethyl (2R)-2-[4-(1-benzyl-5-methyl-1H-pyrrol-2-yl)phenoxy]-3-phenylpropanoate To a solution of 4-(1-benzyl-5-methyl-1H-pyrrol-2-yl)phenol (500 mg, 1.90 mmol), ethyl (S)-2-hydroxy-3-phenylpropanoate (553 mg, 2.85 mmol) and triphenylphosphine (748 mg, 2.85 mmol) in toluene (5 ml) was added 1,1'-(azodicarbonyl)dipiperidine (719 mg, 2.85 mmol). The obtained solution was stirred at room temperature for 0.5 hours and at 80° C. for 3 hours and the solvent was removed under reduced pressure. The residue was purified by silica gel column chromatography (hexane:ethyl acetate=20:1) to give the object compound as an oily substance. 487 mg (yield: 58.3%)

$^1$H-NMR (CDCl$_3$) δ; 1.17 (3H, t, J=7.4 Hz), 2.11 (3H, s), 3.20–3.24 (2H, m), 4.15 (2H, q, J=7.4 Hz), 4.71–4.77 (1H, m), 5.05 (2H, s), 6.00 (1H, d, J=3.4 Hz), 6.12 (1H, d, J=3.4 Hz), 6.74 (2H, d, J=8.8 Hz), 6.89 (2H, d, J=8.0 Hz), 7.12 (2H, d, J=8.8 Hz), 7.19–7.33 (8H, m).

IR (KBr) cm$^{-1}$; 1750, 1730, 1530, 1240, 1180, 1020, 840, 760, 740, 700.

$[\alpha]_D^{24}$ 15.1° (c 0.690, chloroform)

Example 48

(2R)-2-[4-(1-Benzyl-5-methyl-1H-pyrrol-2-yl)phenoxy]-3-phenylpropanoic acid (2R)-2-[4-(1-Benzyl-5-methyl-1H-pyrrol-2-yl)phenoxy]-3-phenylpropanoic acid was synthesized from ethyl (2R)-2-[4-(1-benzyl-5-methyl-1H-pyrrol-2-yl)phenoxy]-3-phenylpropanoate obtained in Example 47, as an oily substance, according to the similar manner to that of Example 6. yield: 92.5%

$^1$H-NMR (CDCl$_3$) δ; 2.11 (3H, s), 3.25 (2H, d, J=7.0 Hz), 4.79 (1H, t, J=7.0 Hz), 5.05 (2H, s), 6.00 (1H, d, J=3.2 Hz), 6.12 (1H, d, J=3.2 Hz), 6.75 (2H, d, J=8.8 Hz), 6.88 (2H, d, J=8.0 Hz), 7.13 (2H, d, J=8.8 Hz), 7.24–7.33 (8H, m).

IR (KBr) cm$^{-1}$; 3031, 1728, 1524, 1238, 1181, 1082, 837, 758, 731, 698.

$[\alpha]_D^{26}$ 1.03° (c 1.04, chloroform)

Example 49

Ethyl (2S)-2-{4-[1-(4-bromophenyl)-5-methyl-1H-pyrrol-2-yl]phenoxy}-3-phenylpropanoate (1) Ethyl (R)-2-hydroxy-3-phenylpropanoate The object compound was obtained from (R)-phenylalanine as a solid, according to the similar manner to that of Example 1(7). yield: 63.5%

$^1$H-NMR (CDCl$_3$) δ; 1.28 (3H, t, J=7.4 Hz), 2.77 (1H, d, J=6.2 Hz), 2.97 (1H, dd, J=14, 6.6 Hz), 3.14 (1H, dd, J=14, 4.4 Hz), 4.22 (2H, q, J=7.4 Hz), 4.39–4.48 (1H, m), 7.20–7.35 (5H, m).

IR (KBr) cm$^{-1}$; 3445, 2982, 1732, 1496, 1454, 1271, 1202, 1096, 1030, 747, 700.

$[α]_D^{25}$+21.2° (c4.00, benzene)

(2) Ethyl (2S)-2-{4-[1-(4-bromophenyl)-5-methyl-1H-pyrrol-2-yl]phenoxy}-3-phenylpropanoate To a solution of 4-[1-(4-bromophenyl)-5-methyl-1H-pyrrol-2-yl]phenol (400 mg, 1.22 mmol), ethyl (R)-2-hydroxy-3-phenylpropanoate (353 mg, 1.82 mmol) and triphenylphosphine (477 g, 1.82 mmol) in toluene (4 ml) was added 1,1'-(azodicarbonyl)dipiperidine (459 mg, 1.82 mmol). The obtained solution was stirred at 80° C. for 3 hours and diluted with ethyl acetate. The obtained solution was washed with water, dried over magnesium sulfate anhydride, solvent was removed under reduced pressure. The residue was purified by silica gel column chromatography (hexane:ethyl acetate=30:1) to give the object compound as a solid. 286 mg (yield: 46.5%)

$^1$H-NMR (CDCl$_3$) δ; 1.15 (3H, t, J=7.4 Hz), 2.11 (3H, s), 3.18–3.22 (2H, m), 4.14 (2H, q, J=7.4 Hz), 4.68–4.74 (1H, m), 6.04 (1H, d, J=3.8 Hz), 6.22 (1H, d, J=3.8 Hz), 6.63 (2H, d, J=8.8 Hz), 6.90 (2H, d, J=8.8 Hz), 6.97 (2H, d, J=8.4 Hz), 7.15–7.28 (5H, m), 7.54 (2H, d, J=8.4 Hz).

IR (KBr) cm$^{-1}$; 1753, 1736, 1524, 1489, 1238, 1184, 1071, 833, 700.

$[α]_D^{24}$-14.5° (c 0.770, chloroform)

Example 50

(2S)-2-{4-[1-(4-Bromophenyl)-5-methyl-1H-pyrrol-2-yl]phenoxy}-3-phenylpropanoic acid To a mixed solution of ethyl (2S)-2-{4-[1-(4-bromophenyl)-5-methyl-1H-pyrrol-2-yl]phenoxy}-3-phenylpropanoate obtained in Example 49 (256 mg, 0.508 mmol) in THF (4 ml)-methanol (2 ml) was added 1 N aqueous potassium hydroxide (1.52 ml) and stirred at room temperature for 1 hour. The reaction solution was diluted with ethyl acetate and water and neutralized with 1 N hydrochloric acid, and the organic layer was separated. The organic layer was washed with water, dried over magnesium sulfate anhydride, solvent was removed under reduced pressure to give the object compound as an oily substance. 230 mg (yield: 95.4%)

$^1$H-NMR (CDCl$_3$) δ; 2.10 (3H, s), 3.23 (2H, d, J=6.6 Hz), 4.76 (1H, t, J=6.6 Hz), 6.05 (1H, d, J=3.2 Hz), 6.22 (1H, d, J=3.2 Hz), 6.63 (2H, d, J=8.8 Hz), 6.90 (2H, d, J=8.8 Hz), 6.97 (2H, d, J=8.8 Hz), 7.27 (5H, bs), 7.45 (2H, d, J=8.8 Hz).

IR (KBr) cm$^{-1}$; 1730, 1522, 1489, 1236, 1181, 1071, 833, 735, 700.

$[α]_D^{24}$ 1.61° (c 1.70, chloroform)

Example 51

Ethyl (2R)-2-(4-{1-[2-(4-bromophenyl)ethan-1-yl]-5-methyl-1H-pyrrol-2-yl}phenoxy)-3-phenylpropanoate (1) 1-[2-(4-Bromophenyl)ethyl]-2-(4-methoxyphenyl)-5-methyl-1H-pyrrole A solution of 1-(4-methoxyphenyl)-1,4-pentanedione (3.20 g, 15.5 mol), 2-(4-bromophenyl)ethylamine (3.74 g, 18.7 mmol) and p-toluenesulfonic acid monohydrate (150 mg, 0.871 mmol) in toluene (100 ml) was refluxed for 20 hours with heating. The insoluble matter was filtered out and the filtrate was concentrated under reduced pressure. The residue was purified by silica gel column chromatography (hexane:ethyl acetate=8:1) to give the object compound as an oily substance. 3.93 g (yield: 68.0%)

$^1$H-NMR (CDCl$_3$) δ; 2.21 (3H, s), 2.67 (2H, t, J=7.6 Hz), 3.85 (3H, s), 4.04 (2H, t, J=7.6 Hz), 5.91 (1H, d, J=3.4 Hz), 6.02 (1H, d, J=3.4 Hz), 6.72 (2H, d, J=8.2 Hz), 6.91 (2H, d, J=9.0 Hz), 7.21 (2H, d, J=9.0 Hz), 7.30 (2H, d, J=8.2 Hz).

IR (KBr) cm$^{-1}$; 1613, 1526, 1487, 1285, 1246, 1175, 1036, 1011, 837, 760.

(2) 4-[1-[2-(4-Bromophenyl)ethan-1-yl]-5-methyl-1H-pyrrol-2-yl]phenol

To a solution of 1-[2-(4-bromophenyl)ethyl]-2-(4-methoxyphenyl)-5-methyl-1H-pyrrole (3.46 g, 9.34 mmol) in methylene chloride (40 ml) was added boron tribromide (9.35 g, 37.3 mmol) at 0° C. The mixture was stirred at 0° C. for 1 hour, and the reaction solution was poured into ice water and extracted with methylene chloride. The organic layers were collected, washed with saturated aqueous sodium bicarbonate and dried over magnesium sulfate anhydride, and the solvent was removed under reduced pressure. The residue was purified by silica gel column chromatography (hexane:ethyl acetate=3:1) to give the object compound as a solid. 3.33 g (yield: 100%)

$^1$H-NMR (CDCl$_3$) δ; 2.21 (3H, s), 2.67 (2H, t, J=7.6 Hz), 4.03 (2H, t, J=7.6 Hz), 4.95 (1H, s), 5.91 (1H, d, J=3.8 Hz), 6.01 (1H, d, J=3.8 Hz), 6.72 (2H, d, J=8.8 Hz), 6.84 (2H, d, J=8.8 Hz), 7.15 (2H, d, J=8.4 Hz), 7.30 (2H, d, J=8.4 Hz).

IR (KBr) cm$^{-1}$; 3378, 2922, 1524, 1487, 1399, 1308, 1264, 1171, 1073, 1011, 912, 837.

(3) Ethyl (2R)-2-(4-{1-[2-(4-bromophenyl)ethan-1-yl]-5-methyl-1H-pyrrol-2-yl}phenoxy)-3-phenylpropanoate To a solution of 4-[1-[2-(4-bromophenyl)ethan-1-yl]-5-methyl-1H-pyrrol-2-yl]phenol (3.00 g, 8.42 mmol), ethyl (S)-2-hydroxy-3-phenylpropanoate (1.96 g, 10.1 mmol) and triphenylphosphine (2.65 g, 10.1 mmol) in toluene (30 ml) was added diethyl azodicarboxylate (1.76 g, 10.1 mmol) and refluxed for 20 hours under heating. The insoluble matter was filtered out and the filtrate was diluted with ethyl acetate. The obtained solution was washed with water and dried over magnesium sulfate anhydride, and the solvent was removed under reduced pressure. The residue was purified by silica gel column chromatography (hexane:ethyl acetate=8:1) to give the object compound as an oily substance. 2.40 g (yield: 54.0%)

$^1$H-NMR (CDCl$_3$) δ; 1.21 (3H, t, J=7.4Hz), 2.20 (3H, s), 2.64 (2H, t, J=6.8 Hz), 3.27 (2H, d, J=7.0 Hz), 4.00 (2H, t, J=6.8 Hz), 4.14 (2H, q, J=7.4Hz), 4.82 (1H, t, J=7.0 Hz), 5.89 (1H, d, J=3.2 Hz), 5.98 (1H, d, J=3.2 Hz), 6.66 (2H, d, J=8.4 Hz), 6.83 (2H, d, J=8.6 Hz), 7.13 (2H, d, J=8.6 Hz), 7.20–7.40 (7H, m).

Example 52

(2R)-2-(4-{1-[2-(4-bromophenyl)ethan-1-yl]-5-methyl-1H-pyrrol-2-yl}phenoxy)-3-phenylpropanoic acid To a mixed solution of ethyl (2R)-2-(4-{1-[2-(4-bromophenyl)ethan-1-yl]-5-methyl-1H-pyrrol-2- yl}phenoxy)-3-phenylpropanoate obtained in Example 51 (2.40 g, 4.51 mmol) in THF (10 ml)-ethanol (40 ml) was added 5 N aqueous sodium hydroxide (6.00 ml, 30.0 mmol) and stirred at 50° C. for 2 hours. The reaction solution was neutralized with 1 N hydrochloric acid and extracted with ethyl acetate. The extracts were collected, washed with water and dried over magnesium sulfate anhydride. The solvent was removed under reduced pressure. The residue was purified by silica gel column chromatography (ethyl acetate) to give the object compound as an oily substance. 2.01 g (yield: 89.0%)

$^1$H-NMR (CDCl$_3$) δ; 2.20 (3H, s), 2.63 (2H, t, J=7.2 Hz), 3.32 (2H, d, J=7.0 Hz), 4.01 (2H, t, J=7.2 Hz), 4.89 (1H, t, J=7.0 Hz), 5.90 (1H, d, J=3.6 Hz), 5.97 (1H, d, J=3.6 Hz), 6.64 (2H, d, J=8.4 Hz), 6.84 (2H, d, J=8.4 Hz), 7.12 (2H, d, J=8.8 Hz), 7.20–7.40 (7H, m).

IR (KBr) cm$^{-1}$; 3031, 2932, 1725, 1524, 1487, 1402, 1233, 1073, 1013, 910, 735.

Example 53

Ethyl (2R)-2-{4-[1-(3-phenoxybenzyl)-5-methyl-1H-pyrrol-2-yl]phenoxy}-3-phenylpropanoate (1) 2-(4-Methoxyphenyl)-5-methyl-1-(3-phenoxybenzyl)-1H-pyrrole A solution of 1-(4-methoxyphenyl)-1,4-pentanedione (2.62 g, 12.7 mol), 3-phenoxybenzylamine hydrochloric acid salt (3.59 g, 15.2 mmol) and p-toluenesulfonic acid monohydrate (120 mg, 0.697 mmol) in toluene (100 ml) was refluxed for 20 hours under heating. The insoluble matter was filtered out and the filtrate was concentrated under reduced pressure. The residue was purified by silica gel column chromatography (hexane:ethyl acetate=8:1) to give the object compound as crystals. 2.57 g (yield: 55.0%)

Melting point: 100–101° C.

$^1$H-NMR (CDCl$_3$) δ; 2.15 (3H, s), 3.79 (3H, s), 5.04 (2H, s), 5.99 (1H, d, J=3.4 Hz), 6.11 (1H, d, J=3.4 Hz), 6.55–6.65 (2H, m), 6.75–6.90 (3H, m), 6.90–7.00 (2H, m), 7.05–7.40 (6H, m).

IR (KBr) cm$^{-1}$; 1613, 1584, 1526, 1487, 1443, 1287, 1248, 1211, 1179, 1034.

Elementary analysis for $C_{25}H_{23}NO_2$; Calculated: C, 81.27; H, 6.27; N, 3.79. Found: C, 81.28; H, 6.46; N, 3.71.

(2) 4-[1-(3-Phenoxybenzyl)-5-methyl-1H-pyrrol-2-yl]phenol

4-[1-(3-Phenoxybenzyl)-5-methyl-1H-pyrrol-2-yl]phenol was obtained from 2-(4-methoxyphenyl)-5-methyl-1-(3-phenoxybenzyl)-1H-pyrrole as an oily substance, according to the similar manner to that of Example 51(2). yield: 100%

$^1$H-NMR (CDCl$_3$) δ; 2.15 (3H, s), 5.03 (2H, s), 4.95 (1H, s), 5.99 (1H, d, J=3.2 Hz), 6.10 (1H, d, J=3.2 Hz), 6.61 (2H, d, J=8.8 Hz), 6.76 (2H, d, J=8.8 Hz), 6.80–6.90 (1H, m), 6.90–7.00 (2H, m), 7.0–7.20 (3H, m), 7.20–7.40 (3H, m).

IR (KBr) cm$^{-1}$; 3412, 1613, 1584, 1526, 1487, 1445, 1250, 1211, 839, 760.

(3) Ethyl (2R)-2-{4-[1-(3-phenoxybenzyl)-5-methyl-1H-pyrrol-2-yl]phenoxy}-3-phenylpropanoate Ethyl (2R)-2-{4-[1-(3-phenoxybenzyl)-5-methyl-1H-pyrrole-2-yl]phenoxy}-3-phenylpropanoate was obtained from 4-[1-(3-phenoxybenzyl)-5-methyl-1H-pyrrol-2-yl]phenol as an oily substance, according to the similar manner to that of Example 51(3). yield: 66.0%

$^1$H-NMR (CDCl$_3$) δ; 1.17 (3H, t, J=7.0 Hz), 2.13 (3H, s), 3.21–3.25 (2H, m), 4.17 (2H, q,J=7.0 Hz), 4.72–4.79 (1H, m), 5.00 (2H, s), 5.97 (1H, d,J=3.4 Hz), 6.08 (1H, d, J=3.4 Hz), 6.57–7.36 (18H, m).

Example 54

(2R)-2-{4-[1-(3-phenoxybenzyl)-5-methyl-1H-pyrrol-2-yl]phenoxy}-3-phenylpropanoic acid (2R)-2-{4-[1-(3-Phenoxybenzyl)-5-methyl-1H-pyrrol-2-yl]phenoxy}-3-phenylpropanoic acid was obtained from ethyl (2R)-2-{4-[1-(3-phenoxybenzyl)-5-methyl-1H-pyrrol-2-yl]phenoxy}-3-phenylpropanoate obtained in Example 53, as an oily substance, according to the similar manner to that of Example 52. yield: 80.0%

$^1$H-NMR (CDCl$_3$) δ; 2.12 (3H, s), 3.20–3.30 (2H, m), 4.70–4.90 (1H, m), 4.97 (2H, s), 5.90–6.00 (1H, m), 6.00–6.10 (1H, m), 6.50–6.65 (2H, m), 6.70–6.90 (3H, m), 6.90–7.00 (2H, m), 7.00–7.20 (3H, m), 7.20–7.40 (8H, m).

IR (KBr) cm$^{-1}$; 3034, 2932, 1726, 1584, 1524, 1487, 1445, 1244, 1084, 909, 758.

Example 55

Ethyl (2R)-2-[4-(1-dodecyl-5-methyl-1H-pyrrol-2-yl)phenoxy]-3-phenylpropanoate (1) 1-Dodecyl-2-(4-methoxyphenyl)-5-methyl-1H-pyrrole A solution of 1-(4-methoxyphenyl)-1,4-pentanedione (3.00 g, 14.5 mol), dodecylamine (3.24 g, 17.5 mmol) and p-toluenesulfonic acid (150 mg, 0.871 mmol) in toluene (100 ml) was refluxed for 10 hours under heating using Dean-Stark's apparatus. The insoluble matter was filtered out and the filtrate was concentrated under reduced pressure. The residue was purified by silica gel column chromatography (hexane:ethyl acetate=8:1) to give the object compound as an oily substance. 4.01 g (yield: 78%)

$^1$H-NMR (200 MHz, CDCl$_3$) δ; 0.88 (3H, t, J=6.4 Hz), 1.05–1.40 (18H, m), 1.40–1.60 (2H, m), 2.30 (3H, s), 3.80 (2H, t, J=8.0 Hz), 3.84 (3H, s), 5.92 (1H, d, J=3.2 Hz), 6.02 (1H, d, J=3.2 Hz), 6.92 (2H, d, J=8.4 Hz), 7.28 (2H, d, J=8.4 Hz).

IR (KBr) cm$^{-1}$; 2926, 2853, 1613, 1526, 1466, 1246, 1175, 1036, 835, 754.

(2) 4-(1-Dodecyl-5-methyl-1H-pyrrol-2-yl)phenol

To a solution of 1-dodecyl-2-(4-methoxyphenyl)-5-methyl-1H-pyrrole (4.01 g, 11.3 mmol) in methylene chloride (100 ml) was added boron tribromide (11.3 g, 45.0 mmol) at 0° C. The mixture was stirred at 0° C. for 1 hour, poured into ice water and extracted with methylene chloride. The organic layers were collected, washed with saturated aqueous sodium bicarbonate and dried over magnesium sulfate anhydride, and the solvent was removed under reduced pressure. The residue was purified by silica gel column chromatography (hexane:ethyl acetate=4:1) to give the object compound as an oily substance. 2.97 g (yield: 77%)

$^1$H-NMR (CDCl$_3$) δ; 0.88 (3H, t, J=6.4 Hz), 1.10–1.40 (18H, m), 1.40–1.65 (2H, m), 2.30 (3H, s), 3.79 (2H, t, J=8.0 Hz), 4.87 (1H, s), 5.91 (1H, d, J=3.6 Hz), 6.01 (1H, d, J=3.6 Hz), 6.84 (2H, d, J=8.8 Hz), 7.23 (2H, d, J=8.8 Hz).

IR (KBr) cm$^{-1}$; 3397, 2924, 2853, 1615, 1526, 1468, 1262, 1171, 837, 756.

(3) Ethyl (2R)-2-[4-(1-dodecyl-5-methyl-1H-pyrrol-2-yl)phenoxy]-3-phenylpropanoate To a solution of 4-(1-dodecyl-5-methyl-1H-pyrrol-2-yl)phenol (2.97 g, 8.70 mmol), ethyl (S)-2-hydroxy-3-phenylpropanoate (1.86 g, 9.58 mmol) and triphenylphosphine (2.51 g, 9.57 mmol) in toluene (120 ml) was added diethyl azodicarboxylate (1.67 g, 9.57 mmol) and the mixture was refluxed for 20 hours under heating. The insoluble matter was filtered out and the filtrate was diluted with ethyl acetate. The obtained solution was washed with water and dried over magnesium sulfate anhydride, and the solvent was removed under reduced pressure. The residue was purified by silica gel column chromatography (hexane:ethyl acetate=8:1) to give the object compound as an oily substance. 1.49 g (yield: 33%)

$^1$H-NMR (CDCl$_3$) δ); 0.88 (3H, t, J=6.4 Hz), 1.10–1.30 (21H, m), 1.40–1.60 (2H, m), 2.28 (3H, s), 3.26 (2H, d,

J=7.2 Hz), 3.76 (2H, t, J=7.6 Hz), 4.19 (2H, q, J=7.0 Hz), 4.81 (1H, t, J=7.2 Hz), 5.90 (1H, d, J=3.0 Hz), 5.98 (1H, d, J=3.0 Hz), 6.84 (2H, d, J=8.8 Hz), 7.15–7.40 (7H, m).

Example 56

(2R)-2-[4-(1-Dodecyl-5-methyl-1H-pyrrol-2-yl) phenoxy]-3-phenylpropanoic acid

To a solution of ethyl (2R)-2-[4-(1-dodecyl-5-methyl-1H-pyrrol-2-yl)phenoxy]-3-phenylpropanoate obtained in Example 55 (1.49 g, 2.88 mmol) in ethanol (30 ml) was added 5 N aqueous sodium hydroxide (3.00 ml, 15.0 mmol) and the mixture was stirred at room temperature for 1 hour. The reaction solution was neutralized with 1 N hydrochloric acid and extracted with ethyl acetate. The extracts were collected, washed with water and dried over magnesium sulfate anhydride. The solvent was removed under reduced pressure, and the residue was purified by silica gel column chromatography (ethyl acetate) to give the object compound as an oily substance. 1.15 g (yield: 82%)

$^1$H-NMR (CDCl$_3$) δ; 0.88 (3H, t, J=6.6 Hz), 1.00–1.40 (18H, m), 1.40–1.65 (2H, m), 2.28 (3H, s), 3.31 (2H, d, J=5.8 Hz), 3.76 (2H, t, J=8.0 Hz), 4.89 (1H, t, J=5.8 Hz), 5.90 (1H, d, J=3.6 Hz), 5.98 (1H, d, J=3.6 Hz), 6.86 (2H, d, J=8.8 Hz), 7.20–7.40 (7H, m).

IR (KBr) cm$^{-1}$; 2924, 2853, 1728, 1524, 1238, 1179, 1084, 835, 754.

Example 57

Ethyl (2R)-2-[4-(5-methyl-1-octyl-1H-pyrrol-2-yl) phenoxy]-3-phenylpropanoate

The object compound was obtained according to the similar manner to that of Example 55.
(1) 2-(4-Methoxyphenyl)-5-methyl-1-octyl-1H-pyrrole
   Oily substance (yield: 78%)
   $^1$H-NMR (CDCl$_3$) δ; 0.86 (3H, t, J=6.6 Hz), 1.05–1.30 (10H, m), 1.40–1.65 (2H, m), 2.30 (3H, s), 3.80 (2H, t, J=8.0 Hz), 3.84 (3H, s), 5.92 (1H, d, J=3.6 Hz), 6.02 (1H, d, J=3.6 Hz), 6.92 (2H, d, J=8.8 Hz), 7.28 (2H, d, J=8.8 Hz).
   IR (KBr) cm$^{-1}$; 2928, 2855, 1613, 1526, 1481, 1285, 1246, 1175, 1034, 835, 754.
(2) 4-(5-Methyl-1-octyl-1H-pyrrol-2-yl)phenol
   Oily substance (yield: 95%)
   $^1$H-NMR (CDCl$_3$) δ; 0.86 (3H, t, J=6.6 Hz), 1.05–1.35 (10H, m), 1.40–1.60 (2H, m), 2.30 (3H, s), 3.79 (2H, t, J=7.8 Hz), 4.94 (1H, s), 5.92 (1H, d, J=3.6 Hz), 6.01 (1H, d, J=3.6 Hz), 6.85 (2H, d, J=8.8 Hz), 7.23 (2H, d, J=8.8 Hz).
   IR (KBr) cm$^{-1}$; 3366, 2928, 1615, 1526, 1481, 1468, 1262, 1171, 837, 758.
(3) Ethyl (2R)-2-[4-(5-methyl-1-octyl-1H-pyrrol-2-yl)phenoxy]-3-phenylpropanoate
   Oily substance (yield: 34%)
   $^1$H-NMR (CDCl$_3$) δ; 0.86 (3H, t, J=6.6 Hz), 1.19 (3H, t, J=7.6 Hz), 1.10–1.40 (10H, m), 1.40–1.60 (2H, m), 2.28 (3H, s), 3.26 (2H, d, J=6.6 Hz), 3.76 (2H, t, J=7.6 Hz), 4.19 (2H, q, J=6.6 Hz), 4.80 (1H, t, J=6.6 Hz), 5.90 (1H, d, J=3.2 Hz), 5.98 (1H, d, J=3.2 Hz), 6.84 (2H, d, J=8.4 Hz), 7.21 (2H, d, J=8.4 Hz), 7.20–7.40 (5H, m).

Example 58

(2R)-2-[4-(5-Methyl-1-octyl-1H-pyrrol-2-yl)phenoxy]-3-phenylpropanoic acid

The object compound was obtained from the compound obtained in Example 57, according to the similar manner to that of Example 56.

Oily substance (yield: 88%)
$^1$H-NMR (CDCl$_3$) δ; 0.85 (3H, t, J=6.4 Hz), 1.00–1.40 (10H, m), 1.40–1.60 (2H, m), 2.28 (3H, s), 3.30 (2H, d, J=6.0 Hz), 3.76 (2H, t, J=7.8 Hz), 4.88 (1H, t, J=6.0 Hz), 5.90 (1H, d, J=3.6 Hz), 5.99 (1H, d, J=3.6 Hz), 6.86 (2H, d, J=8.8 Hz), 7.20–7.40 (7H, m).

IR (KBr) cm$^{-1}$; 2924, 2855, 1728, 1524, 1236, 1179, 1084, 835, 756, 700.

Example 59

Ethyl (2R)-2-[4-(5-methyl-1-nonyl-1H-pyrrol-2-yl) phenoxy]-3-phenylpropanoate

The object compound was obtained according to the similar manner to that of Example 55.
(1) 2-(4-Methoxyphenyl)-5-methyl-1-nonyl-1H-pyrrole
   Oily substance (yield: 74%)
   $^1$H-NMR (CDCl$_3$) δ; 0.87 (3H, t, J=6.6 Hz), 1.05–1.35 (12H, m), 1.45–1.65 (2H, m), 2.30 (3H, s), 3.79 (2H, t, J=8.0 Hz), 3.84 (3H, s), 5.92 (1H, d, J=3.2 Hz), 6.01 (1H, d, J=3.2 Hz), 6.92 (2H, d, J=8.4 Hz), 7.28 (2H, d, J=8.4 Hz).
   IR (KBr) cm$^{-1}$; 2928, 2855, 1613, 1526, 1466, 1285, 1246, 1175, 1034, 835, 754.
(2) 4-(5-Methyl-1-nonyl-1H-pyrrol-2-yl)phenol
   Oily substance (yield: 100%)
   $^1$H-NMR (CDCl$_3$) δ; 0.87 (3H, t, J=6.6 Hz), 1.10–1.40 (12H, m), 1.45–1.65 (2H, m), 2.30 (3H, s), 3.79 (2H, t, J=7.8 Hz), 4.92 (1H, s), 5.92 (1H, d, J=3.4 Hz), 6.01 (1H, d, J=3.4 Hz), 6.84 (2H, d, J=8.8 Hz), 7.23 (2H, d, J=8.8 Hz).
   IR (KBr) cm$^{-1}$; 3345, 2926, 2855, 1615, 1526, 1481, 1262, 1171, 837, 758.
(3) Ethyl (2R)-2-[4-(5-methyl-1-nonyl-1H-pyrrol-2-yl)phenoxy]-3-phenylpropanoate
   Oily substance (yield: 33%)
   $^1$H-NMR (CDCl$_3$) δ; 0.87 (3H, t, J=6.4 Hz), 1.05–1.40 (15H, m), 1.40–1.65 (2H, m), 2.28 (3H, s), 3.26 (2H, d, J=6.6 Hz), 3.76 (2H, t, J=7.8 Hz), 4.19 (2H, q, J=7.2 Hz), 4.81 (1H, t, J=6.6 Hz), 5.90 (1H, d, J=3.6 Hz), 5.98 (1H, d, J=3.6 Hz), 6.84 (2H, d, J=8.8 Hz), 7.15–7.40 (7H, m).

Example 60

(2R)-2-[4-(5-Methyl-1-nonyl-1H-pyrrol-2-yl) phenoxy]-3-phenylpropanoic acid

The object compound was obtained from the compound obtained in Example 59, according to the similar manner to that of Example 56.

Oily substance (yield: 91%)
$^1$H-NMR (CDCl$_3$) δ; 0.87 (3H, t, J=6.6 Hz), 1.00–1.40 (12H, m), 1.40–1.60 (2H, m), 2.28 (3H, s), 3.31 (2H, d, J=6.0 Hz), 3.76 (2H, t, J=7.4 Hz), 4.89 (1H, t, J=6.0 Hz), 5.91 (1H, d, J=3.4 Hz), 5.99 (1H, d, J=3.4 Hz), 6.86 (2H, d, J=8.8 Hz), 7.20–7.40 (7H, m).

IR (KBr) cm$^{-1}$; 3031, 2926, 2855, 1728, 1524, 1238, 1179, 1086, 835, 756, 700.

Example 61

Ethyl (2R)-2-[4-(1-decyl-5-methyl-1H-pyrrol-2-yl) phenoxy]-3-phenylpropanoate

The object compound was obtained according to the similar manner to that of Example 55.
(1) 1-Decyl-2-(4-methoxyphenyl)-5-methyl-1H-pyrrole
   Oily substance (yield: 79%)
   $^1$H-NMR (CDCl$_3$) δ; 0.88 (3H, t, J=6.6 Hz), 1.10–1.35 (16H, m), 2.30 (3H, s), 3.80 (2H, t, J=8.0 Hz), 3.84 (3H, s), 5.92 (1H, d, J=3.4 Hz), 6.01 (1H, d, J=3.4 Hz), 6.92 (2H, d, J=8.8 Hz), 7.28 (2H, d, J=8.8 Hz).

IR (KBr) cm$^{-1}$; 2926, 2855, 1613, 1526, 1481, 1466, 1285, 1246, 1175, 1034, 835, 756.

(2) 4-(1-Decyl-5-methyl-1H-pyrrol-2-yl)phenol

Oily substance (yield: 81%)

$^1$H-NMR (CDCl$_3$) δ; 0.88 (3H, t, J=6.4 Hz), 1.05–1.40 (16H, m), 2.30 (3H, s), 3.79 (2H, t, J=8.0 Hz), 4.78 (1H, s), 5.92 (1H, d, J=3.6 Hz), 6.01 (1H, d, J=3.6 Hz), 6.84 (2H, d, J=8.8 Hz), 7.23 (2H, d, J=8.8 Hz).

IR (KBr) cm$^{-1}$; 3331, 2926, 2855, 1615, 1526, 1481, 1262, 1171, 837, 758.

(3) Ethyl (2R)-2-[4-(1-decyl-5-methyl-1H-pyrrol-2-yl)phenoxy]-3-phenylpropanoate Oily substance (yield: 38%)

$^1$H-NMR (CDCl$_3$) δ; 0.88 (3H, t, J=6.6 Hz), 1.00–1.40 (17H, m), 1.40–1.60 (2H, m), 2.28 (3H, s), 3.26 (2H, d, J=6.6 Hz), 3.76 (2H, t, J=8.0 Hz), 4.19 (2H, q, J=7.0 Hz), 4.81 (1H, t, J=6.6 Hz), 5.90 (1H, d, J=3.4 Hz), 5.98 (1H, d, J=3.4 Hz), 6.84 (2H, d, J=8.4 Hz), 7.21 (2H, d, J=8.4 Hz), 7.20–7.40 (5H, m).

Example 62

(2R)-2-[4-(1-Decyl-5-methyl-1H-pyrrol-2-yl)phenoxy]-3-phenylpropanoic acid

The object compound was obtained from the compound obtained in Example 61, according to the similar manner to that of Example 56.

Oily substance (yield: 68%)

$^1$H-NMR (CDCl$_3$) δ; 0.87 (3H, t, J=6.4 Hz), 1.05–1.60 (16H, m), 2.28 (3H, s), 3.31 (2H, d, J=6.2 Hz), 3.76 (2H, t, J=7.8 Hz), 4.88 (1H, t, J=6.2 Hz), 5.90 (1H, d, J=3.2 Hz), 5.99 (1H, d, J=3.2 Hz), 6.86 (2H, d, J=8.4 Hz), 7.20–7.40 (7H, m).

IR (KBr) cm$^{-1}$; 3031, 2926, 2855, 1728, 1524, 1481, 1238, 1179, 1084, 835, 756.

Example 63

Ethyl (2R)-2-[4-(1-undecyl-5-methyl-1H-pyrrol-2-yl)phenoxy]-3-phenylpropanoate

The object compound was obtained according to the similar manner to that of Example 55.

(1) 2-(4-Methoxyphenyl)-5-methyl-1-undecyl-1H-pyrrole

Oily substance (yield: 79%)

$^1$H-NMR (CDCl$_3$) δ; 0.88 (3H, t, J=6.4 Hz), 1.10–1.35 (16H, m), 1.40–1.65 (2H, m), 2.30 (3H, s), 3.79 (2H, t, J=7.8 Hz), 3.84 (3H, s), 5.92 (1H, d, J=3.4 Hz), 6.01 (1H, d, J=3.4 Hz), 6.92 (2H, d, J=8.8 Hz), 7.28 (2H, d, J=8.8 Hz).

IR (KBr) cm$^{-1}$; 2924, 2853, 1615, 1526, 1464, 1285, 1246, 1175, 1036, 835, 756.

(2) 4-(5-Methyl-1-undecyl-1H-pyrrol-2-yl)phenol

Oily substance (yield: 94%)

$^1$H-NMR (CDCl$_3$) δ; 0.88 (3H, t, J=6.4 Hz), 1.10–1.40 (16H, m), 1.40–1.60 (2H, m), 2.30 (3H, s), 3.79 (2H, t, J=7.8 Hz), 4.89 (1H, s), 5.92 (1H, d, J=3.2 Hz), 6.09 (1H, d, J=3.2 Hz), 6.85 (2H, d, J=8.8 Hz), 7.23 (2H, d, J=8.8 Hz).

IR (KBr) cm$^{-1}$; 2922, 2855, 1526, 1466, 1262, 1171, 837, 758.

(3) Ethyl (2R)-2-[4-(5-methyl-1-undecyl-1H-pyrrol-2-yl)phenoxy]-3-phenylpropanoate Oily substance (yield: 37%)

$^1$H-NMR (CDCl$_3$) δ; 0.88 (3H, t, J=6.4 Hz), 1.10–1.35 (19H, m), 1.40–1.60 (2H, m), 2.28 (3H, s), 3.26 (2H, d, J=6.6 Hz), 3.76 (2H, t, J=7.8 Hz), 4.19 (2H, q, J=7.2 Hz), 4.81 (1H, t, J=6.6 Hz), 5.90 (1H, d, J=3.2 Hz), 5.98 (1H, d, J=3.2 Hz), 6.84 (2H, d, J=8.8 Hz), 7.21 (2H, d, J=8.8 Hz), 7.20–7.40 (5H, m).

Example 64

(2R)-2-[4-(5-Methyl-1-undecyl-1H-pyrrol-2-yl)phenoxy]-3-phenylpropanoic acid

The object compound was obtained from the compound obtained in Example 63, according to the similar manner to that of Example 56.

Oily substance (yield: 89%)

$^1$H-NMR (CDCl$_3$) δ; 0.87 (3H, t, J=6.6 Hz), 1.05–1.40 (16H, m), 1.40–1.60 (2H, m), 2.28 (3H, s), 3.29 (2H, d, J=5.8 Hz), 3.75 (2H, t, J=8.0 Hz), 4.87 (1H, t, J=5.8 Hz), 5.90 (1H, d, J=3.2 Hz), 5.97 (1H, d, J=3.2 Hz), 6.85 (2H, d, J=8.4 Hz), 7.22 (2H, d, J=8.4 Hz), 7.25–7.40 (5H, m).

IR (KBr) cm$^{-1}$; 2924, 2853, 1728, 1524, 1481, 1238, 1179, 1084, 835, 756, 700.

Example 65

Ethyl (2R)-2-[4-(5-methyl-1-tridecyl-1H-pyrrol-2-yl)phenoxy]-3-phenylpropanoate

The object compound was obtained according to the similar manner to that of Example 55.

(1) 2-(4-Methoxyphenyl)-5-methyl-1-tridecyl-1H-pyrrole

Oily substance (yield: 92%)

$^1$H-NMR (CDCl$_3$) δ; 0.88 (3H, t, J=6.6 Hz), 1.10–1.40 (20H, m), 1.40–1.60 (2H, m), 2.30 (3H, s), 3.80 (2H, t, J=8.0 Hz), 3.84 (3H, s), 5.92 (1H, d, J=3.2 Hz), 6.02 (1H, d, J=3.2 Hz), 6.92 (2H, d, J=8.8 Hz), 7.28 (2H, d, J=8.8 Hz).

IR (KBr) cm$^{-1}$; 2924, 2853, 1603, 1526, 1466, 1246, 1173, 1036, 835, 754.

(2) 4-(5-Methyl-1-tridecyl-1H-pyrrol-2-yl)phenol

Oily substance (yield: 94%)

$^1$H-NMR (CDCl$_3$) δ; 0.88 (3H, t, J=6.4 Hz), 1.10–1.40 (20H, m), 1.40–1.65 (2H, m), 2.29 (3H, s), 3.78 (2H, t, J=7.8 Hz), 5.91 (1H, d, J=4.2 Hz), 6.01 (1H, d, J=4.2 Hz), 6.84 (2H, d, J=8.8 Hz), 7.21 (2H, d, J=8.8 Hz).

IR (KBr) cm$^{-1}$; 3391, 2924, 2853, 1613, 1526, 1466, 1260, 1171, 837, 756.

(3) Ethyl (2R)-2-[4-(5-methyl-1-tridecyl-1H-pyrrol-2-yl)phenoxy]-3-phenylpropanoate Oily substance (yield: 34%)

$^1$H-NMR (CDCl$_3$) δ; 0.88 (3H, t, J=6.4 Hz), 1.10–1.40 (23H, m), 1.40–1.60 (2H, m), 2.28 (3H, s), 3.26 (2H, d, J=6.6 Hz), 3.76 (2H, t, J=7.8 Hz), 4.19 (2H, q, J=7.2 Hz), 4.81 (1H, t, J=6.6 Hz), 5.90 (1H, d, J=3.2 Hz), 5.98 (1H, d, J=3.2 Hz), 6.84 (2H, d, J=8.6 Hz), 7.21 (2H, d, J=8.6 Hz), 7.20–7.40 (5H, m).

Example 66

(2R)-2-[4-(5-Methyl-1-tridecyl-1H-pyrrol-2-yl)phenoxy]-3-phenylpropanoic acid

The object compound was obtained from the compound obtained in Example 65, according to the similar manner to that of Example 56.

Oily substance (yield: 52%)

$^1$H-NMR (CDCl$_3$) δ; 0.88 (3H, t, J=6.6 Hz), 1.10–1.40 (20H, m), 1.40–1.60 (2H, m), 2.28 (3H, s), 3.30 (2H, d, J=5.2 Hz), 3.76 (2H, t, J=8.0 Hz), 4.88 (1H, t, J=5.2 Hz), 5.90 (1H, d, J=3.0 Hz), 5.98 (1H, d, J=3.0 Hz), 6.86 (2H, d, J=8.8 Hz), 7.20–7.40 (7H, m).

IR (KBr) cm$^{-1}$; 2926, 2853, 1725, 1597, 1524, 1236, 1179, 1084, 909, 837, 754.

Example 67

Ethyl (2R)-2-(4-{1-[3-(4-butylphenyl)propan-1-yl]-5-methyl-1H-pyrrol-2-yl}phenoxy)-3-phenylpropanoate

(1) Ethyl (E)-3-(4-butylphenyl)acrylate

To a solution of 4-butylbenzaldehyde (9.91 g, 61.1 mmol) and triethyl phosphonoacetate (13.8 g, 61.5 mmol) in N,N-dimethylformamide (120 ml) was added sodium hydride (60% oily, 2.46 g, 61.5 mmol) at 0° C. and the mixture was stirred at 0° C. for 1 hour. The reaction solution was poured into ice water and extracted with ethyl acetate. The extract was washed with water and saturated brine, dried over magnesium sulfate anhydride and concentrated under reduced pressure to give the object compound as an oily substance. 14.2 g (yield: 100%)

$^1$H-NMR (200 MHz, CDCl$_3$) δ; 0.93 (3H, t, J=7.2 Hz), 1.20–1.70 (7H, m), 2.63 (2H, t, J=8.0 Hz), 4.26 (2H, q, J=7.2 Hz), 6.40 (1H, d, J=16.2 Hz), 7.20 (2H, d, J=8.0 Hz), 7.45 (2H, d, J=8.0 Hz), 7.67 (1H, d, J=16.2 Hz).

IR (KBr) cm$^{-1}$; 2932, 1713, 1636, 1310, 1267, 1208, 1173, 1038, 984, 826.

(2) Ethyl 3-(4-butylphenyl)propanoate

To a solution of ethyl (E)-3-(4-butylphenyl)acrylate (14.2 g, 61.1 mmol) in tetrahydrofuran (120 ml) was added 10% palladium carbon (4.00 g) and the mixture was hydrogenated. The reaction solution was filtrated and the filtrate was concentrated under reduced pressure to give the object compound as an oily substance. 14.3 g (yield: 100%)

$^1$H-NMR (200 MHz, CDCl$_3$) δ; 0.92 (3H, t, J=7.4 Hz), 1.23 (3H, t, J=7.0 Hz), 1.20–1.65 (4H, m), 2.56 (2H, t, J=6.0 Hz), 2.60 (2H, t, J=8.0 Hz), 2.92 (2H, t, J=8.0 Hz), 4.13 (2H, q, J=7.0 Hz), 7.10 (4H, s).

IR (KBr) cm$^{-1}$; 2957, 2930, 1738, 1514, 1466, 1372, 1252, 1179, 1159, 1040, 820, 735.

(3) 3-(4-Butylphenyl)propanol

To a solution of ethyl 3-(4-butylphenyl)propanoate (3.48 g, 14.9 mmol) in tetrahydrofuran (30 ml) was added lithium aluminum hydride (394 mg, 10.4 mmol) at 0° C. and the mixture was stirred for 1 hour. To the reaction mixture was added 1N hydrochloric acid and the mixture was extracted with ethyl acetate. The extract was washed with water and saturated brine, dried over magnesium sulfate anhydride and concentrated under reduced pressure to give the object compound as an oily substance. 2.86 g (yield: 100%)

$^1$H-NMR (200 MHz, CDCl$_3$) δ; 0.92 (3H, t, J=7.2 Hz), 1.20–1.65 (4H, m), 1.80–2.00 (2H, m), 2.58 (2H, t, J=7.8 Hz), 2.68 (2H, t, J=7.8 Hz), 3.68 (2H, t, J=6.6 Hz), 7.10 (4H, s).

IR (KBr) cm$^{-1}$; 3299, 2955, 2857, 1738, 1514, 1454, 1377, 910, 777.

(4) 3-(4-Butylphenyl)propyl methanesulfonate

To a solution of 3-(4-butylphenyl)propanol (2.86 g, 14.9 mmol) and triethylamine (1.51 g, 14.9 mmol) in ethyl acetate (30 ml) was added methanesulfonyl chloride (1.70 g, 14.9 mmol) and the mixture was stirred at room temperature for 2 hours. The reaction solution was washed with water and saturated brine, dried over magnesium sulfate anhydride and concentrated under reduced pressure to give the object compound as an oily substance. 4.02 g (yield: 100%)

$^1$H-NMR (200 MHz, CDCl$_3$) δ; 0.92 (3H, t, J=7.2 Hz), 1.20–1.70 (4H, m), 1.95–2.15 (2H, m), 2.58 (2H, t, J=7.8 Hz), 2.72 (2H, t, J=7.8 Hz), 2.99 (3H, s), 4.23 (2H, t, J=6.4 Hz), 7.10 (4H, s).

IR (KBr) cm$^{-1}$; 2957, 2928, 1732, 1514, 1354, 1175, 974, 930, 829.

(5) N-[3-(4-Butylphenyl)propan-1-yl]phthalimide

To a solution of 3-(4-butylphenyl)propyl methanesulfonate (4.02 g, 14.9 mmol) in N,N-dimethylformamide (40 ml) was added potassium phthalimide (2.76 g, 14.9 mmol) and the mixture was stirred at 80° C. for 3 hours. The reaction solution was poured into ice water and extracted with ethyl acetate. The extract was washed with water and saturated brine, dried over magnesium sulfate anhydride and concentrated under reduced pressure. The residue was purified by silica gel column chromatography (hexane:ethyl acetate=3:1) to give the object compound as an oily substance. 4.48 g (yield: 94%)

$^1$H-NMR (200 MHz, CDCl$_3$) δ; 0.91 (3H, t, J=7.2 Hz), 1.20–1.45 (2H, m), 1.45–1.60 (2H, m), 1.95–2.10 (2H, m), 2.53 (2H, t, J=7.6 Hz), 2.66 (2H, t, J=7.6 Hz), 3.74 (2H, t, J=7.2 Hz), 7.00–7.15 (4H, m), 7.70 (2H, dd, J=5.8 and 2.8 Hz), 7.83 (2H, dd, J=5.8 and 2.8 Hz).

IR (KBr) cm$^{-1}$; 2955, 2932, 1773, 1715, 1466, 1397, 1370, 1022, 720.

(6) 3-(4-Butylphenyl)propylamine hydrochloric acid salt

To a solution of N-[3-(4-butylphenyl)propan-1-yl]phthalimide (4.48 g, 13.9 mmol) in ethanol (40 ml) was added hydrazine monohydrate (1.03 g, 20.6 mmol) and refluxed for 2 hours under heating. The reaction solution was filtrated and the filtrate was concentrated under reduced pressure. To the residue was added 5N aqueous sodium hydroxide and the mixture was extracted with ethyl acetate. The extract was washed with saturated brine, dried over magnesium sulfate anhydride and concentrated under reduced pressure. The residue was dissolved in ethanol (50 ml) and concentrated hydrochloric acid (3.0 ml) was added to the mixture, and the mixture was stirred at room temperature for 1 hour. The reaction solution was concentrated under reduced pressure to give the object compound as a colorless crystal. The compound was then washed with diethylether. 1.89 g (yield: 60%)

$^1$H-NMR (200 MHz, DMSO-d$_6$) δ; 0.89 (3H, t, J=7.6 Hz), 1.31 (2H, tq, J=7.6 and 7.6 Hz), 1.53 (2H, tt, J=7.6 and 7.6 Hz), 1.83 (2H, tt, J=7.6 and 7.6 Hz), 2.50–2.65 (4H, m), 2.65–2.85 (2H, m), 7.11 (4H, s), 7.80–8.10 (2H, m).

IR (KBr) cm$^{-1}$; 2934, 2066, 1597, 1472, 1152, 974, 826, 754.

(7) 1-[3-(4-Butylphenyl)propan-1-yl]-2-(4-methoxyphenyl)-5-methyl-1H-pyrrole

A solution of 3-(4-butylphenyl)propylamine hydrochloric acid salt (1.70 g, 7.46 mmol), 1-(4-methoxyphenyl)-1,4-pentanedione (1.53 g, 7.42 mmol) and p-toluenesulfonic acid monohydrate (70.0 mg, 0.407 mmol) in toluene (20 ml) was refluxed for 20 hours under heating and the solvent was removed under reduced pressure. The residue was silica gel chromatography (hexane:ethyl acetate=8:1) to give the object compound as an oily substance. 1.28 g (yield: 48%)

$^1$H-NMR (CDCl$_3$) δ; 0.91 (3H, t, J=7.2 Hz), 1.20–1.45 (2H, m), 1.45–1.65 (2H, m), 1.75–1.95 (2H, m), 2.24 (3H, s), 2.44 (2H, t, J=7.6 Hz), 2.56 (2H, t, J=7.6 Hz), 3.83 (2H, t, J=7.6 Hz), 3.84 (3H, s), 5.91 (1H, d, J=4.0 Hz), 6.02 (1H, d, J=4.0 Hz), 6.88 (2H, d, J=8.8 Hz), 6.94 (2H, d, J=8.2 Hz), 7.04 (2H, d, J=8.2 Hz), 7.24 (2H, d, J=8.8 Hz).

IR (KBr) cm$^{-1}$; 2955, 2930, 1613, 1526, 1464, 1285, 1246, 1175, 1034, 835.

(8) 4-{1-[3-(4-Butylphenyl)propan-1-yl]-5-methyl-1H-pyrrol-2-yl}phenol

To a solution of 1-[3-(4-butylphenyl)propan-1-yl]-2-(4-methoxyphenyl)-5-methyl-1H-pyrrole (1.28 g, 3.54 mmol) in methylene chloride (20 ml) was added boron tribromide (3.55 g, 14.2 mmol) at 0° C. The mixture was stirred at 0° C. for 2 hours, and the reaction solution was poured into ice water and extracted with dichloromethane. The extract was washed with saturated aqueous sodium bicarbonate, dried over magnesium sulfate anhydride and the solvent was removed under reduced pressure. The residue was purified by silica gel column chromatography (hexane:ethyl acetate=3:1) to give the object compound as an oily substance. 880 mg (yield: 72%)

$^1$H-NMR (CDCl$_3$) δ; 0.92 (3H, t, J=7.2 Hz), 1.25–1.45 (2H, m), 1.45–1.65 (2H, m), 1.75–1.95 (2H, m), 2.24 (3H, s), 2.44 (2H, t, J=7.6 Hz), 2.56 (2H, t, J=7.6 Hz), 3.82 (2H, t, J=7.6 Hz), 4.90 (1H, s), 5.91 (1H, d, J=3.2 Hz), 6.01 (1H, d, J=3.2 Hz), 6.81 (2H, d, J=8.8 Hz), 6.94 (2H, d, J=8.0 Hz), 7.05 (2H, d, J=8.0 Hz), 7.19 (2H, d, J=8.8 Hz).

IR (KBr) cm$^{-1}$; 3411, 2955, 2930, 1615, 1526, 1400, 1260, 1171, 837, 818, 758.

(9) Ethyl (2R)-2-(4-{1-[3-(4-butylphenyl)propan-1-yl]-5-methyl-1H-pyrrol-2-yl}phenoxy)-3-phenylpropanoate A solution of 4-{1-[3-(4-butylphenyl)propan-1-yl]-5-methyl-1H-pyrrol-2-yl}phenol (880 mg, 2.53 mmol), ethyl (S)-2-hydroxy-3-phenylpropanoate (492 mg, 2.53 mmol), triphenylphosphine (665 mg, 2.54 mmol) and diethyl azodicarboxylate (442 mg, 2.54 mmol) in toluene (30 ml) was refluxed for 20 hours under heating. The residue was poured into water, extracted with ethyl acetate, washed with saturated brine and dried over magnesium sulfate anhydride. The solvent was removed under reduced pressure and the residue was purified by silica gel column chromatography (hexane:ethyl acetate=8:1) to give the object compound as an oily substance. 440 mg (yield: 33%)

$^1$H-NMR (CDCl$_3$) δ; 0.91 (3H, t, J=7.2 Hz), 1.19 (3H, t, J=7.0 Hz), 1.25–1.40 (2H, m), 1.50–1.65 (2H, m), 1.70–1.90 (2H, m), 2.22 (3H, s), 2.41 (2H, t, J=7.2 Hz), 2.55 (2H, t, J=7.2 Hz), 3.26 (2H, d, J=6.4 Hz), 3.80 (2H, t, J=7.8 Hz), 4.19 (2H, q, J=7.0 Hz), 4.81 (1H, t, J=6.4 Hz), 5.89 (1H, d, J=3.2 Hz), 5.98 (1H, d, J=3.2 Hz), 6.82 (2H, d, J=8.4 Hz), 6.93 (2H, d, J=8.0 Hz), 7.04 (2H, d, J=8.0 Hz), 7.19 (2H, d, J=8.4 Hz), 7.20–7.40 (5H, m).

Example 68

Sodium (2R)-2-(4-{1-[3-(4-Butylphenyl)propan-1-yl]-5-methyl-1H-pyrrol-2-yl}phenoxy)-3-phenylpropanoate (1) (2R)-2-(4-{1-[3-(4-butylphenyl)propan-1-yl]-5-methyl-1H-pyrrol-2-yl}phenoxy)-3-phenylpropanoic acid To a solution of ethyl (2R)-2-(4-{1-[3-(4-butylphenyl)propan-1-yl]-5-methyl-1H-pyrrol-2-yl}phenoxy)-3-phenylpropanoate (440 mg, 0.840 mmol) in ethanol (10 ml) was added 5 N aqueous potassium hydroxide (0.80 ml, 4.00 mmol) and the mixture was stirred at room temperature for 1 hour. The reaction solution was neutralized with 1N aqueous hydrochloric acid, extracted with ethyl acetate, washed with saturated aqueous NaCl and dried over magnesium sulfate anhydride. The solvent was removed under reduced pressure and the residue was purified by silica gel column chromatography (ethyl acetate) to give the object compound as an oily substance. 336 mg, (81%)

$^1$H-NMR (CDCl$_3$) δ; 0.91 (3H, t, J=7.2 Hz), 1.20–1.40 (2H, m), 1.45–1.65 (2H, m), 1.70–1.95 (2H, m), 2.21 (3H, s), 2.41 (2H, t, J=7.8 Hz), 2.55 (2H, t, J=7.6 Hz), 3.30 (2H, d, J=6.2 Hz), 3.80 (2H, t, J=7.6 Hz), 4.89 (1H, t, J=6.2 Hz), 5.89 (1H, d, J=3.2 Hz), 5.98 (1H, d, J=3.2 Hz), 6.83 (2H, d, J=8.4 Hz), 6.94 (2H, d, J=8.0 Hz), 7.04 (2H, d, J=8.0 Hz), 7.20 (2H, d, J=8.4 Hz), 7.25–7.40 (5H, m).

IR (KBr) cm$^{-1}$; 3031, 2928, 1728, 1522, 1481, 1236, 1177, 1084, 837, 758, 700.

(2) Sodium (2R)-2-(4-{1-[3-(4-butylphenyl)propan-1-yl]-5-methyl-1H-pyrrol-2-yl}phenoxy)-3-phenylpropanoate Ethanol (30 ml) and a solution of 1N sodium hydroxide in ethanol (2.74 ml) were added to (2R)-2-(4-{1-[3-(4-butylphenyl)propan-1-yl]-5-methyl-1H-pyrrol-2-yl}phenoxy)-3-phenylpropanoic acid (1.51 g, 3.05 mmol) and the mixture was concentrated. To the residue was added diisopropylether to give the object compound as a solid. 1.06 g (yield 67.0%)

$^1$H-NMR (DMSO-d$_6$) δ; 0.88 (3H, t, J=7.0 Hz), 1.18–1.86 (6H, m), 2.14 (3H, s), 2.32–2.51 (4H, m), 2.91–3.16 (2H, m), 3.76 (2H, t, J=7.2 Hz), 4.29–4.33 (1H, m), 5.75 (1H, d, J=3.8 Hz), 5.79 (1H, d, J=3.8 Hz), 6.73 (2H, d, J=8.8 Hz), 6.93–7.33 (11H, m).

IR (KBr) cm$^{-1}$; 2930, 1615, 1520, 1399, 1238, 1059, 1030, 829, 760, 700.

Example 69

Ethyl (2R)-2-{4-[5-methyl-1-(4-pentylphenylpropyl)-1H-pyrrol-2-yl]phenoxy}-3-phenylpropanoate (1) Ethyl (2E)-3-(4-pentylphenyl)propenoate To a solution of 4-pentylbenzaldehyde (25 g, 142 mmol) and ethyl diethylphosphonoacetate (30 ml, 150 mmol) in THF was added sodium hydride (60%, 6 g, 150 mmol), and the mixture was stirred at room temperature for 12 hours and poured into ice water. The reaction mixture was extracted with ethyl acetate. The organic layer was washed with saturated brine and dried over magnesium sulfate anhydride, and the solvent was removed under reduced pressure to give the object compound as an oily substance. 39.6 g, (yield 100%)

$^1$H-NMR (CDCl$_3$) δ; 0.88 (3H, m), 1.26 (7H, m), 1.58 (2H, m), 2.61 (2H, t, J=7.8 Hz), 4.27 (2H, q, J=7.0 Hz), 6.38 (1H, d, J=15.8 Hz), 7.18 (2H, d, J=8.0 Hz), 7.43 (2H, d, J=8.0 Hz), 7.66 (1H, d, J=15.8 Hz).

(2) Ethyl (2E)-3-(4-pentylphenyl)propanoate

To a solution of ethyl (2E)-3-(4-pentylphenyl) propenoate (39.6 g, 142 mmol) in ethanol (300 ml) was added 10% palladium carbon (4 g) and the mixture was stirred under hydrogen atmosphere. The insoluble matter was filtered out and the filtrate was concentrated to give the object compound as an oily substance. 30.7 g (yield 100%)

$^1$H-NMR (CDCl$_3$) δ; 0.88 (3H, m), 1.26 (7H, m), 1.58 (2H, m), 2.60 (4H, q, J=7.8 Hz), 2.90 (2H, t, J=7.8 Hz), 4.14 (2H, q, J=7.0 Hz), 7.10 (4H, s), (3) 3-(4-Pentylphenyl)propanol To a solution of ethyl (2E)-3-(4-pentylphenyl)propanoate (37.3 g, 142 mmol) in THF (300 ml) was added lithium aluminum hydride (5.3 g, 142 mmol) at 0° C. and the mixture was stirred at room temperature for 30 minutes. The reaction mixture was poured into ice and the insoluble matter was filtered out. The filtrate was concentrated to give the object compound as an oily substance. 37.6 g (yield 100%)

$^1$H-NMR (CDCl$_3$) δ; 0.88 (3H, m), 1.26 (5H, m), 1.60 (2H, m), 1.88 (2H, m), 2.66 (4H, m), 3.66 (2H, t, J=6.6Hz), 7.10 (4H, s).

(4) 3-(4-Pentylphenyl)propyl mesylate

To a solution of 3-(4-pentylphenyl)propanol (30.8 g, 149 mmol) and triethylamine (22 ml, 155 mmol) in THF (300 ml) was added mesyl chloride (11.6 ml, 150 mmol) at 0° C., and the mixture was stirred at room temperature for 30 minutes. The reaction mixture was poured into ice and extracted with ethyl acetate. The organic layer was washed with saturated brine and dried over magnesium sulfate anhydride, and the organic layer was concentrated to give the object compound as an oily substance. 42.4 g, (yield 100%)

$^1$H-NMR (CDCl$_3$) δ; 0.88 (3H, m), 1.26 (5H, m), 1.60 (2H, m), 2.05 (2H, m), 2.57 (2H, t, J=7.2 Hz), 2.71 (2H, t, J=7.2 Hz), 2.93 (3H, s), 4.21 (2H, t, J=6.6 Hz),7.10 (4H, s).

(5) N-3-(4-Pentylphenyl)propyl phthalimide

A solution of 3-(4-pentylphenyl)propyl mesylate (42.4 g, 149 mmol) and potassium phthalimide (27.6 g, 149 mmol)

in DMF (200 ml) was stirred at 80° C. for 3 hours. The reaction solution was poured into ice water and extracted with ethyl acetate. The organic layer was washed with saturated brine and dried over magnesium sulfate anhydride, and the organic layer was concentrated. The residue was purified by silica gel column chromatography (hexane:ethyl acetate=5:1) to give the object compound as an oily substance. 41.1 g, (yield 82%)

$^1$H-NMR (CDCl$_3$) δ; 0.88 (3H, m), 1.26 (5H, m), 1.61 (2H, m), 2.05 (2H, m), 2.52 (2H, t, J=7.2 Hz), 2.66 (2H, t, J=7.2 Hz), 3.74 (2H, t, J=7.0. Hz), 7.13 (4H, m), 7.64–7.85 (4H, m).

(6) 3-(4-Pentylphenyl)propylamine

A solution of N-3-(4-pentylphenyl)propylphthalimide (41.1 g, 123 mmol) and hydrazinemonohydrate (9.0 ml, 185 mmol) in ethanol (300 ml) was refluxed for 3 hours. The reaction mixture was dissolved in 5N aqueous sodium hydroxide and extracted with ethyl acetate. The organic layer was washed with saturated brine and dried over magnesium sulfate anhydride, and the organic layer was concentrated to give the object compound as an oily substance. 13.5 g, (yield 53%)

$^1$H-NMR (CDCl$_3$) δ; 0.88 (3H, m), 1.26 (5H, m),1.60 (2H, m), 1.78 (2H, m), 1.99 (2H, s), 2.76–2.52 (5H, m), 7.09 (4H, s)

(7) 2-(4-Benzyloxyphenyl)-5-methyl-1-(4-pentylphenylpropyl)-1H-pyrrole

A solution of 3-(4-pentylphenyl)propylamine (1.8 g, 8.8 mmol) and 1-(4-benzyloxyphenyl)-1,4-pentanedione (2.43 g, 8.7 mmol) and p-toluenesulfonic acid monohydrate (200 mg) in toluene (30 ml) was refluxed for 12 hours under heating and the solvent was removed under reduced pressure. The residue was silica gel chromatography (hexane:ethyl acetate=9:1) to give the object compound as an oily substance. 2.99 g, (yield 75%)

$^1$H-NMR (CDCl$_3$) δ; 0.88 (3H, m), 1.26 (4H, m), 1.60 (2H, m), 1.87 (2H, s), 2.22 (3H, s), 2.47 (2H, t, J=3.2 Hz), 2.56 (2H, t, J=3.2 Hz), 3.82 (2H, t, J=7.8 Hz), 5.06 (2H, s), 5.91 (1H, d, J=3.4 Hz), 6.03 (1H, d, J=3.4 Hz), 7.56–6.89 (13H, m).

(8) 4-[5-Methyl-1-(4-pentylphenylpropyl)-1H-pyrrol-2-yl]phenol

To a solution of 2-(4-benzyloxyphenyl)-5-methyl-1-(4-pentylphenylpropyl)-1H-pyrrole (2.99 g, 6.6 mmol) in ethanol (60 ml) was added 10% palladium carbon (300 mg) and the mixture was stirred under hydrogen atmosphere. The insoluble matter was filtered out and the filtrate was concentrated to give the object compound as an oily substance. 1.28 g, (yield 54% )

$^1$H-NMR (CDCl$_3$) δ; 0.88 (3H, m), 1.26 (4H, m), 1.60 (2H, m), 1.87 (2H, s), 2.22 (3H, s), 2.47 (2H, t, J=3.2 Hz), 2.56 (2H, t, J=3.2 Hz), 3.82 (2H, t, J=7.8 Hz),5.91 (1H, d, J=3.4 Hz), 6.03 (1H, d, J=3.4 Hz), 6.78–7.00 (4H, m), 7.05 (2H, d, J=8.0 Hz), 7.20 (2H, d, J=8.6 Hz).

(9) Ethyl (2R)-2-{4-[5-methyl-1-(4-pentylphenylpropyl)-1H-pyrrol-2-yl]phenoxy}-3-phenylpropanoate A solution of 4-[5-methyl-1-(4-pentylphenylpropyl)-1H-pyrrol-2-yl]phenol (1.3 g, 3.6 mmol), ethyl (S)-2-hydroxy-3-phenylpropanoate (1.05 g, 5.4 mmol), 1,1'-(azodicarbonyl)dipiperidine (1.36 g, 5.4 mmol) and triphenylphosphine (1.42 g, 5.4 mmol) in toluene (40 ml) was stirred at 80° C. for 12 hours. The reaction solution was poured into water and extracted with ethyl acetate, and the extract was washed with saturated brine and dried over magnesium sulfate anhydride. The solvent was removed under reduced pressure and the residue was purified by silica gel column chromatography (hexane:ethyl acetate=15:1) to give the object compound as an oily substance. 250 mg, (yield 13%)

$^1$H-NMR (CDCl$_3$) δ; 0.88 (3H, m), 1.26 (7H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 4.00–3.86 (4H, m), 4.20 (2H, q, J=7.2 Hz), 4.81 (1H, t, J=7.2 Hz), 5.91 (1H, d, J=3.4 Hz), 6.03 (1H, d, J=3.4 Hz), 6.87–6.70 (6H, m), 7.19–7.34 (7H, m).

Example 70

Sodium (2R)-2-{4-[5-methyl-1-(4-pentylphenylpropyl)-1H-pyrrol-2-yl]phenoxy}-3-phenylpropanoate (1) (2R)-2-{4-[5-Methyl-1-(4-pentylphenylpropyl)-1H-pyrrol-2-yl]phenoxy}-3-phenylpropanoic acid To a mixed solution of ethyl (2R)-2-{4-[5-methyl-1-(4-pentylphenylpropyl)-1H-pyrrol-2-yl]phenoxy}-3-phenylpropanoate (230 mg, 0.43 mmol) in THF (5 ml) and methanol (2.5 ml) was added 1N aqueous potassium hydroxide (1.3 ml, 1.3 mmol) and the mixture was stirred at room temperature for 1 hour. The reaction solution was neutralized with 1N hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 145 mg, (yield 66%)

$^1$H-NMR (CDCl$_3$) δ; 0.88 (3H, m), 1.26 (4H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 3.86–4.00 (4H, m), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).

(2) Sodium (2R)-2-{4-[5-methyl-1-(4-pentylphenylpropyl)-1H-pyrrol-2-yl]phenoxy}-3-phenylpropanoate To a solution of (2R)-2-{4-[5-methyl-1-(4-pentylphenylpropyl)-1H-pyrrol-2-yl]phenoxy}-3-phenylpropanoic acid (135 mg, 0.27 mmol) in ethanol (5 ml) was added 1N sodium hydroxide-ethanol (245 ml, 0.25 mmol) and the mixture was concentrated. To the residue was added hexane to give the object compound as a solid. 25 mg, (18%)

$^1$H-NMR (DMSO) δ; 0.88 (3H, m), 1.26 (4H, m), 1.60 (2H, m), 1.87 (2H, s), 2.13 (3H, s), 2.37 (2H, m), 2.56 (2H, m), 3.27 (2H, m), 3.76 (2H, m), 4.31 (1H, m), 5.78 (2H, m), 6.70–7.34 (13H, m).

Elementary analysis for $C_{34}H_{38}NO_{3-2.0}H_2O$; Calculated: C, 71.93; H, 7.46; N, 2.47. Found: C, 72.12; H, 7.03; N, 2.31.

Example 71

Ethyl (2R)-2-{4-[5-methyl-1-(4-heptylphenylpropyl)-1H-pyrrol-2-yl]phenoxy}-3-phenylpropanoate (1) Ethyl (2E)-3-(4-heptylphenyl)propenoate The object compound was obtained from 4-heptylbenzaldehyde as an oily substance, according to the similar manner to that of Example 69 (1). yield: 29%

$^1$H-NMR (CDCl$_3$) δ; 0.88 (3H, m), 1.26 (11H, m), 1.58 (2H, m), 2.61 (2H, t, J=7.8 Hz), 4.27 (2H, q, J=7.0 Hz), 6.38 (1H, d, J=15.8 Hz), 7.18 (2H, d, J=8.0 Hz), 7.43 (2H, d, J=8.4 Hz), 7.66 (1H, d, J=16.2 Hz).

(2) Ethyl (2E)-3-(4-heptylphenyl)propanoate

The object compound was obtained from ethyl (2E)-3-(4-heptylphenyl)propenoate as an oily substance, according to the similar manner to that of Example 69 (2). yield: 100%

$^1$H-NMR (CDCl$_3$) δ; 0.88 (3H, m), 1.26 (11H, m), 1.58 (2H, m), 2.60 (4H, q, J=7.8 Hz), 2.90 (2H, t, J=7.8 Hz), 4.14 (2H, q, J=7.0 Hz), 7.10 (4H, s).

(3) 3-(4-Heptylphenyl)propanol

The object compound was obtained from ethyl (2E)-3-(4-heptylphenyl)propanoate as an oily substance, according to the similar manner to that of Example 69 (3). yield: 96%

¹H-NMR (CDCl₃) δ; 0.88 (3H, m), 1.26 (9H, m), 1.60 (2H, m), 1.88 (2H, m), 2.66 (4H, m), 3.66 (2H, t, J=6.6Hz), 7.10 (4H, s).
(4) 3-(4-Heptylphenyl)propyl mesylate The object compound was obtained from 3-(4-heptylphenyl)propanol as an oily substance, according to the similar manner to that of Example 69 (4). yield: 100%

¹H-NMR (CDCl₃) δ; 0.88 (3H, m), 1.26 (9H, m), 1.60 (2H, m), 2.05 (2H, m), 2.57 (2H, t, J=7.2 Hz), 2.71 (2H, t, J=7.2 Hz), 2.93 (3H, s), 4.21 (2H, t, J=6.6 Hz), 7.10 (4H, s).
(5) N-3-(4-Pentylphenyl)propylphthalimide The object compound was obtained from 3-(4-heptylphenyl)propyl mesylate as an oily substance, according to the similar manner to that of Example 69(5). yield: 85%

¹H-NMR (CDCl₃) δ; 0.88 (3H, m), 1.26 (9H, m), 1.61 (2H, m), 2.05 (2H, m), 2.52 (2H, t, J=7.2 Hz), 2.66 (2H, t, J=7.2 Hz), 3.74 (2H, t, J=7.0. Hz), 7.13 (4H, m), 7.64–7.85 (4H, m).
(6) 3-(4-Heptylphenyl)propylamine The object compound was obtained from N-3-(4-pentylphenyl)propylphthalimide as an oily substance, according to the similar manner to that of Example 69(6). yield: 94%

¹H-NMR (CDCl₃) δ; 0.88 (3H, m), 1.26 (9H, m), 1.60 (2H, m), 1.78 (2H, m), 1.99 (2H, s), 2.52–2.76 (5H, m) 7.09 (4H, s).
(7) 2-(4-Benzyloxyphenyl)-5-methyl-1-(4-heptylphenylpropyl)-1H-pyrrole The object compound was obtained from 3-(4-heptylphenyl)propylamine as an oily substance, according to the similar manner to that of Example 69(7). yield: 63%

¹H-NMR (CDCl₃) δ; 0.88 (3H, m), 1.26 (8H, m), 1.60 (2H, m), 1.87 (2H, s), 2.22 (3H, s), 2.47 (2H, t, J=3.2 Hz), 2.56 (2H, t, J=3.2 Hz), 3.82 (2H, t, J=7.8 Hz), 5.06 (2H, s), 5.91 (1H, d, J=3.4 Hz), 6.03 (1H, d, J=3.4 Hz), 6.89–7.56 (13H, m).
(8) 4-[5-Methyl-1-(4-heptylphenylpropyl)-1H-pyrrol-2-yl]phenol The object compound was obtained from 2-(4-benzyloxyphenyl)-5-methyl-1-(4-heptylphenylpropyl)-1H-pyrrole as an oily substance, according to the similar manner to that of Example 69(8). yield: 100%

¹H-NMR (CDCl₃) δ; 0.88 (3H, m), 1.26 (8H, m), 1.60 (2H, m), 1.87 (2H, s), 2.22 (3H, s), 2.47 (2H, t, J=3.2 Hz), 2.56 (2H, t, J=3.2 Hz), 3.82 (2H, t, J=7.8 Hz), 5.91 (1H, d, J=3.4 Hz), 6.03 (1H, d, J=3.4 Hz), 6.78–7.00 (4H, m), 7.05 (2H, d, J=8.0 Hz), 7.20 (2H, d, J=8.6 Hz).
(9) Ethyl (2R)-2-{4-[5-methyl-1-(4-heptylphenylpropyl)-1H-pyrrol-2-yl]phenoxy}-3-phenylpropanoate The object compound was obtained from 4-[5-methyl-1-(4-heptylphenylpropyl)-1H-pyrrol-2-yl]phenol as an oily substance, according to the similar manner to that of Example 69(8). yield: 47%

¹H-NMR (CDCl₃) δ; 0.88 (3H, m), 1.26 (11H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 4.00–3.86 (4H, m), 4.20 (2H, q, J=7.2 Hz), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).

Example 72

Sodium (2R)-2-{4-[5-methyl-1-(4-heptylphenylpropyl)-1H-pyrrol-2-yl]phenoxy}-3-phenylpropanoate (1) (2R)-2-{4-[5-Methyl-1-(4-heptylphenylpropyl)-1H-pyrrol-2-yl]phenoxy}-3-phenylpropanoic acid The object compound was obtained from ethyl (2R)-2-{4-[5-methyl-1-(4-heptylphenylpropyl)-1H-pyrrol-2-yl]phenoxy}-3-phenylpropanoate as an oily substance, according to the similar manner to that of Example 70(1). yield: 92%

¹H-NMR (CDCl₃) v; 0.88 (3H, m), 1.26 (8H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 3.86–4.00 (4H, m), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).
(2) Sodium (2R)-2-{4-[5-methyl-1-(4-heptylphenylpropyl)-1H-pyrrol-2-yl]phenoxy}-3-phenylpropanoate The object compound was obtained from (2R)-2-{4-[5-methyl-1-(4-heptylphenylpropyl)-1H-pyrrol-2-yl]phenoxy}-3-phenylpropanoic acid as a solid, according to the similar manner to that of Example 70 (2). yield: 23%

¹H-NMR (DMSO) δ; 0.84 (3H, m), 1.24 (6H, m), 1.51 (2H, m), 1.72 (2H, s), 2.14 (3H, s), 2.34 (2H, m), 3.05 (4H, m), 3.77 (2H, m), 4.34 (2H, m), 5.03 (1H, m), 5.80 (2H, m), 6.74–7.30 (13H, m).

Elementary analysis for $C_{36}H_{42}NO_3$; Calculated: C, 77.25; H, 7.56; N, 2.50. Found: C, 76.91; H, 7.43; N, 2.34.

Example 73

Ethyl (2R)-2-([4-[1-(4-hexylphenylpropyl)-5-methyl-1H-pyrrol-2-yl]phenyl]oxy)-3-phenylpropanoate (1) Ethyl (2E)-3-(4-hexylphenyl)propenoate The object compound was obtained from 4-hexylbenzaldehyde as an oily substance, according to the similar manner to that of Example 69(1). yield: 100%

¹H-NMR (CDCl₃) 67 ; 0.88 (3H, m), 1.26 (9H, m), 1.58 (2H, m), 2.61 (2H, t, J=7.8 Hz), 4.27 (2H, q, J=7.0 Hz), 6.38 (1H, d, J=15.8 Hz), 7.18 (2H, d, J=8.4 Hz), 7.43 (2H, d, J=8.4 Hz), 7.66 (1H, d, J=15.8 Hz).

IR (KBr) cm⁻¹; 2955, 2930, 2857, 1714, 1637, 1466, 1271, 1172, 1034, 981, 825.
(2) Ethyl (2E)-3-(4-hexylphenyl)propanoate The object compound was obtained from ethyl (2E)-3-(4-hexylphenyl)propenoate as an oily substance, according to the similar manner to that of Example 69(2). yield: 100%

¹H-NMR (CDCl₃) δ; 0.88 (3H, m), 1.26 (9H, m), 1.58 (2H, m), 2.60 (4H, q, J=7.8 Hz), 2.90 (2H, t, J=7.8 Hz), 4.14 (2H, q, J=7.0 Hz), 7.10 (4H, s).

IR (KBr) cm⁻¹; 2957, 2930, 2856, 1738, 1456, 1273, 1176, 1028, 970, 823.
(3) 3-(4-Hexylphenyl)propanol The object compound was obtained from ethyl (2E)-3-(4-hexylphenyl)propanoate as an oily substance, according to the similar manner to that of Example 69(3). yield: 100%

¹H-NMR (CDCl₃) δ; 0.88 (3H, m), 1.26 (6H, m), 1.60 (2H, m), 1.88 (2H, m), 2.66 (4H, m), 3.66 (2H, t, J=6.6 Hz), 7.10 (4H, s),

IR (KBr) cm⁻¹; 2955, 2872, 1514, 1456, 1338, 1045, 914, 806.
(4) 3-(4-Hexylphenyl)propyl mesylate The object compound was obtained from 3-(4-hexylphenyl)propanol as an oily substance, according to the similar manner to that of Example 69(4). yield: 84%

¹H-NMR (CDCl₃) δ; 0.88 (3H, m), 1.26 (6H, m), 1.60 (2H, m), 2.05 (2H, m), 2.57 (2H, t, J=7.2 Hz), 2.71 (2H, t, J=7.2 Hz), 2.99 (3H, s), 4.21 (2H, t, J=6.6 Hz), 7.10 (4H, s).

IR (KBr) cm⁻¹; 2955, 2857, 1514, 1466, 1354, 1175, 927, 828.
(5) 2-(4-Hexylphenylpropyl)-1H-isoindol-1,3-(2H)-dione The object compound was obtained from 3-(4-hexylphenyl)propyl mesylate as an oily substance, according to the similar manner to that of Example 69(5). yield: 94%

¹H-NMR (CDCl₃) δ; 0.88 (3H, m), 1.26 (6H, m), 1.61 (2H, m), 2.05 (2H, m), 2.52 (2H, t, J=7.2 Hz), 2.66 (2H, t, J=7.2 Hz), 3.74 (2H, t, J=7.0. Hz), 7.13 (4H, m), 7.64–7.85 (4H, m).

IR (KBr) cm⁻¹; 2928, 2855, 1714, 1468, 1397, 1022, 719.

(6) 3-(4-Hexylphenyl)propylamine

The object compound was obtained from 2-(4-hexylphenylpropyl)-1H-isoindol-1,3-(2H)-dione as an oily substance, according to the similar manner to that of Example 69(6). yield: 81%

¹H-NMR (CDCl₃) δ; 0.88 (3H, m), 1.26 (6H, m), 1.60 (2H, m), 1.78 (2H, m), 1.99 (2H, s), 2.52–2.76 (5H, m), 7.09 (4H, s).

IR (KBr) cm⁻¹; 2928, 2854, 1514, 1466, 1379, 1315, 912, 742.

(7) 1-(4-Hexylphenylpropyl)-2-methyl-5-[4-[(phenylmethyl)oxy]phenyl]-1H-pyrrole

The object compound was obtained from 3-(4-hexylphenyl)propylamine as an oily substance, according to the similar manner to that of Example 69 (7). yield: 55%

¹H-NMR (CDCl₃) δ; 0.88 (3H, m), 1.26 (6H, m), 1.60 (2H, m), 1.87 (2H, s), 2.22 (3H, s), 2.47 (2H, t, J=3.2 Hz), 2.56 (2H, t, J=3.2 Hz), 3.82 (2H, t, J=7.8 Hz), 5.06 (2H, s), 5.91 (1H, d, J=3.4 Hz), 6.03 (1H, d, J=3.4 Hz), 6.89–7.56 (13H, m).

IR (KBr) cm⁻¹; 2928, 2857, 1524, 1466, 1242, 912, 742.

(8) 4-[1-(4-Hexylphenylpropyl)-5-methyl-1H-pyrrol-2-yl]phenol

The object compound was obtained from 1-(4-hexylphenylpropyl)-2-methyl-S-[4-[(phenylmethyl)oxy]phenyl]-1H-pyrrole as an oily substance, according to the similar manner to that of Example 69(8). yield: 100%

¹H-NMR (CDCl₃) δ; 0.88 (3H, m), 1.26 (6H, m), 1.60 (2H, m), 1.87 (2H, s), 2.22 (3H, s), 2.47 (2H, t, J=3.2 Hz), 2.56 (2H, t, J=3.2 Hz), 3.82 (2H, t, J=7.8 Hz), 5.91 (1H, d, J=3.4 Hz), 6.03 (1H, d, J=3.4 Hz), 6.78–7.00 (4H, m), 7.20 (2H, d, J=8.6 Hz), 7.05 (2H, d, J=8.6 Hz).

IR (KBr) cm⁻¹; 2928, 2855, 1526, 1466, 1261, 1170, 837, 762.

(9) Ethyl (2R)-2-([4-[1-(4-hexylphenylpropyl)-5-methyl-1H-pyrrol-2-yl]phenyl]oxy)-3-phenylpropanoate The object compound was obtained from 4-[1-(4-hexylphenylpropyl)-5-methyl-1H-pyrrol-2-yl]phenol as an oily substance, according to the similar manner to that of Example 69 (9). yield: 57%

¹H-NMR (CDCl₃) δ; 0.88 (3H, m), 1.26 (9H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 3.86–4.00 (4H, m), 4.20 (2H, q, J=7.2 Hz), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).

IR (KBr) cm⁻¹; 2930, 2855, 1755, 1522, 1481, 1238, 1180, 1084, 835, 756.

Example 74

Sodium (2R)-2-([4-[1-(4-hexylphenylpropyl)-5-methyl-1H-pyrrol-2-yl]phenyl]oxy)-3-phenylpropanoate (1) (2R)-2-([4-[1-(4-Hexylphenylpropyl)-5-methyl-1H-pyrrol-2-yl]phenyl]oxy)-3-phenylpropanoic acid The object compound was obtained from ethyl (2R)-2-([4-[1-(4-hexylphenylpropyl)-5-methyl-1H-pyrrol-2-yl]phenyl]oxy)-3-phenylpropanoate as an oily substance, according to the similar manner to that of Example 70(1). yield: 99%

¹H-NMR (CDCl₃) δ; 0.88 (3H, m), 1.26 (6H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 3.86–4.00 (4H, m), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).

IR (KBr) cm⁻¹; 2928, 2855, 1726, 1521, 1481, 1236, 1179, 1084, 835, 756.

(2) Sodium (2R)-2-([4-[1-(4-hexylphenylpropyl)-5-methyl-1H-pyrrol-2-yl]phenyl]oxy)-3-phenylpropanoate The object compound was obtained from (2R)-2-([4-[1-(4-hexylphenylpropyl)-5-methyl-1H-pyrrol-2-yl]phenyl]oxy)-3-phenylpropanoic acid as a solid, according to the similar manner to that of Example 70 (2). yield: 53%

¹H-NMR (DMSO) δ; 0.88 (3H, m), 1.26 (4H. m), 1.60 (2H, m), 1.87 (2H, s), 2.13 (3H, s), 2.37 (2H, m), 2.56 (2H, m), 3.27 (2H, m), 3.76 (2H, m), 4.31 (1H, m), 5.78 (2H, m), 6.70–7.34 (13H, m).

Elementary analysis for C₃₅H₄₀NO₃Na-0.5H₂O; Calculated: C, 75.78; H, 7.45; N, 2.53. Found: C, 75.53; H, 7.22; N, 2.57.

Example 75

Ethyl (2R)-2-([4-[1-(4-pentylphenylethyl)-5-methyl-1H-pyrrol-2-yl]phenyl]oxy)-3-phenylpropanoate (1) 3-(4-Pentylphenyl)propanoic acid To a solution of ethyl 3-(4-pentylphenyl)propanoate (26.6 g, 107 mmol) in THF (100 ml) and methanol (50 ml) was added 5N aqueous sodium hydroxide (50 ml) and the mixture was stirred at room temperature for 2 hours. The reaction solution was neutralized with IN hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as a solid. 13.9 g, (yield 83%)

¹H-NMR (CDCl₃) δ; 0.88 (3H, t, J=2.6 Hz), 1.26 (4H, m), 1.64 (2H, m), 2.53–2.71 (4H, m), 2.94 (2H, t, J=7.0 Hz), 7.11 (4H, s).

IR (KBr) cm⁻¹; 2928, 2857, 1699, 1441, 1288, 1224, 1020, 943, 820.

(2) 1,1-Dimethylethyl-2-(4-pentylphenyl)ethylcarbamate

A solution of 3-(4-pentylphenyl)propanoic acid (19.6 g, 89 mmol), triethylamine (12.4 ml, 89 mmol) and diphenylphosphorylazide (19.1 ml, 89 m mmol) in t-BuOH (175 ml) was stirred at 80° C. for 12 hours. To the reaction mixture was poured saturated aqueous sodium bicarbonate and the mixture was extracted with ethyl acetate. The organic layer was washed with saturated brine and dried over magnesium sulfate anhydride. The solvent was removed under reduced pressure and the residue was purified by silica gel column chromatography (hexane:ethyl acetate=20:1) to give the object compound as an oily substance. 5.8 g, (yield 22%)

¹H-NMR (CDCl₃) δ; 0.88 (3H, m), 1.22–1.58 (15H, m), 2.57 (2H, m), 2.75 (2H, t, J=7.2 Hz), 3.34 (2H, m), 7.11 (4H, s).

IR (KBr) cm⁻¹; 2928, 2857, 1709, 1514, 1366, 1171.

(3) 3-(4-Pentylphenyl)ethylamine hydrochloride

A solution of 1,1-dimethylethyl-2-(4-pentylphenyl)ethylcarbamate (5.75 g, 19.7 mmol) and a solution of 4N hydrogen chloride in ethyl acetate (20 ml, 80 mmol) in ethyl acetate (200 ml) was stirred for 3 hours. The reaction mixture was concentrated to give the object compound as a solid. 1.4 g, (yield 31%)

¹H-NMR (DMSO) δ; 0.86 (3H, m), 1.29 (4H, m), 1.55 (2H, m), 2.51 (2H, m), 2.94 (4H, m), 7.16 (4H, m), 8.23 (1H, s).

(4) 1-(4-Pentylphenylethyl)-2-methyl-5-[4-[(phenylmethyl)oxy]phenyl]-1H-pyrrole

A solution of 3-(4-pentylphenyl)ethylamine hydrochloride (1.4 g, 6.20 mmol), 1-(4-benzyloxyphenyl)-1,4-pentanedione (1.7 g, 6.02 mmol) and p-toluenesulfonic acid monohydrate (100 mg) in toluene (40 ml) was refluxed for 12 hours under heating and the solvent was removed under reduced pressure. The residue was purified by silica gel chromatography (hexane:ethyl acetate=20:1) to give the object compound as an oily substance. 2.29 g (yield 87%)

$^1$H-NMR (CDCl$_3$) δ; 0.88 (3H, m), 1.26 (4H, m), 1.60 (2H, m), 2.12 (3H, s), 2.55–2.66 (4H, m), 2.92 (2H, t, J=8.4 Hz), 4.97 (2H, s), 6.06 (1H, d, J=3.4 Hz), 6.25 (1H, d, J=3.4 Hz), 6.76–7.41 (13H, m).

IR (KBr) cm$^{-1}$; 3034, 2928, 2856, 1734, 1524, 1454, 1240, 912, 742.

(5) 4-[1-(4-Pentylphenylethyl)-5-methyl-1H-pyrrol-2-yl]phenol

To a solution of 1-(4-pentylphenylethyl)-2-methyl-5-[4-[(phenylmethyl)oxy]phenyl]-1H-pyrrole (2.29 g, 5.54 mmol) in ethanol (150 ml) was added 10% palladium carbon (200 mg) and the mixture was stirred under hydrogen atmosphere. The insoluble matter was filtered out and the filtrate was concentrated to give the object compound as an oily substance. 1.82 g, (yield 100%)

$^1$H-NMR (CDCl$_3$) δ; 0.88 (3H, m), 1.26 (4H, m), 1.62 (2H, m), 2.12 (3H, s), 2.65 (4H, m), 2.92 (2H, t, J=8.4 Hz), 6.04 (1H, d, J=3.4 Hz), 6.24 (1H, d, J=3.4 Hz), 6.50 (2H, d, J=6.6 Hz), 6.93–7.30 (6H, m).

IR (KBr) cm$^{-1}$; 2930, 2857, 1713, 1516, 1437, 1264, 1173, 835, 760.

(6) Ethyl (2R)-2-([4-[1-(4-pentylphenylethyl)-5-methyl-1H-pyrrol-2-yl]phenyl]oxy)-3-phenylpropanoate A solution of 4-[1-(4-pentylphenylethyl)-5-methyl-1H-pyrrol-2-yl]phenol (1.82 g, 5.2 mmol), ethyl (S)-2-hydroxy-3-phenylpropanoate (1.0 g, 5.1 mmol), 1,1'-(azodicarbonyl)dipiperidine (1.29 g, 5.1 mmol) and triphenylphosphine (1.34 g, 5.1 mmol) in toluene (5 ml) was stirred at 80° C. for 12 hours. The reaction solution was poured into water and extracted with ethyl acetate. The extract was washed with saturated brine and dried over magnesium sulfate anhydride. The solvent was removed under reduced pressure and the residue was purified by silica gel column chromatography (hexane:ethyl acetate=20:1) to give the object compound as an oily substance. 660 mg, (yield 23%)

$^1$H-NMR (CDCl$_3$) δ; 0.88 (3H, m), 1.26 (9H, m), 1.66 (2H, m), 2.10 (3H, s), 2.65 (4H, m), 3.20 (2H, m), 4.15 (2H, q, J=7.2 Hz), 4.69 (1H, t, J=7.2 Hz), 6.02 (1H, d, J=3.4 Hz), 6.22 (1H, d, J=3.4 Hz), 6.59 (2H, d, J=6.6 Hz), 6.87–7.28 (11H, m).

IR (KBr) cm$^{-1}$; 2930, 2857, 1736, 1522, 1483, 1236, 1182, 1084, 835, 760.

Example 76

Sodium (2R)-2-([4-[1-(4-pentylphenylethyl)-5-methyl-1H-pyrrol-2-yl]phenyl]oxy)-3-phenylpropanoate (1) (2R)-2-([4-[1-(4-Pentylphenylethyl)-5-methyl-1H-pyrrol-2-yl]phenyl]oxy)-3-phenylpropanoic acid To a mixed solution of ethyl (2R)-2-([4-[1-(4-pentylphenylethyl)-5-methyl-1H-pyrrol-2-yl]phenyl]oxy)-3-phenylpropanoate (660 mg, 1.26 mmol) in THF (15 ml) and methanol (7 ml) was added 1N aqueous potassium hydroxide (4.0 ml, 4.0 mmol) and the mixture was stirred for 1 hour at room temperature. The reaction solution was neutralized with 1N hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 615 mg, (yield 98%)

$^1$H-NMR (CDCl$_3$) δ; 0.88 (3H, m), 1.26 (6H, m), 1.66 (2H, m), 2.10 (3H, s), 2.65 (4H, m), 3.20 (2H, m), 4.69 (1H, t, J=7.2 Hz), 6.02 (1H, d, J=3.4 Hz), 6.22 (1H, d, J=3.4 Hz), 6.59 (2H, d, J=6.6 Hz), 6.87–7.28 (11H, m).

IR (KBr) cm$^{-1}$; 2930, 2859, 1717, 1520, 1392, 1238, 1181, 1084, 835, 760.

(2) Sodium (2R)-2-([4-[1-(4-pentylphenylethyl)-5-methyl-1H-pyrrol-2-yl]phenyl]oxy)-3-phenylpropanoate To a solution of (2R)-2-([4-[1-(4-pentylphenylethyl)-5-methyl-1H-pyrrol-2-yl]phenyl]oxy)-3-phenylpropanoic acid (615 mg, 1.24 mmol) in ethanol (10 ml) was added 1N sodium hydroxide-ethanol (1.21 ml, 1.21 mmol) and the mixture was concentrated. To the residue was added hexane to give the object compound as a solid. 500 mg, (yield 62%)

$^1$H-NMR (DMSO) δ; 0.85 (3H, m), 1.25 (4H, m), 1.51 (2H, m), 2.09 (3H, s), 2.49 (2H, m), 2.65 (2H, m), 2.92–3.18 (2H, m), 3.93 (2H, m), 4.35 (1H, m), 5.73, (1H, d, J=3.2 Hz), 5.83 (1H, d, J=3.6 Hz), 6.76–7.34 (13H, m).

Elementary analysis for $C_{33}H_{36}NO_3Na \cdot 1.0H_2O$; Calculated: C, 73.39; H, 7.15; N. 2.61. Found: C, 73.77; H, 6.89; N, 2.56.

Example 77

Ethyl (2R)-2-([4-[1-(4-hexylphenylethyl)-5-methyl-1H-pyrrol-2-yl]phenyl]oxy)-3-phenylpropanoate (1) 3-(4-Hexylphenyl)propanoic acid The object compound was obtained from ethyl 3-(4-pentylphenyl)propanoate as an oily substance, according to the similar manner to that of Example 75(1). yield: 96%

$^1$H-NMR (CDCl$_3$) δ; 0.88 (3H, t, J=2.6 Hz), 1.26 (6H, m), 1.64 (2H, m), 2.53–2.71 (4H, m), 2.94 (2H, t, J=7.0 Hz), 7.11 (4H, s).

IR (KBr) cm$^{-1}$; 2928, 2857, 1699, 1441, 1288, 1224, 1020, 943, 820.

(2) 1,1-Dimethylethyl 2-(4-hexylphenyl)ethylcarbamate

The object compound was obtained from 3-(4-hexylphenyl)propanoic acid as an oily substance, according to the similar manner to that of Example 75(2). yield: 30%

$^1$H-NMR (CDCl$_3$) δ; 0.88 (3H, m), 1.58–1.22 (17H, m), 2.57 (2H, m), 2.75 (2H, t, J=7.2 Hz), 3.34 (2H, m), 7.11 (4H, s).

IR (KBr) cm$^{-1}$; 2928, 2857, 1709, 1514, 1366, 1171.

(3) 3-(4-Hexylphenyl)ethylamine hydrochloride

The object compound was obtained from 1,1-dimethylethyl 2-(4-hexylphenyl)ethylcarbamate as a solid, according to the similar manner to that of Example 75(3). yield: 36%

$^1$H-NMR (DMSO) δ; 0.86 (3H, m), 1.29 (6H, m), 1.55 (2H, m), 2.51 (2H, m), 2.94 (4H, m), 7.16 (4H, m), 8.23 (1H, s).

(4) 1-(4-Hexylphenylethyl)-2-methyl-5-[4-[(phenylmethyl)oxy]phenyl]-1H-pyrrole

The object compound was obtained from 3-(4-hexylphenyl)ethylamine hydrochloride as an oily substance, according to the similar manner to that of Example 75(4). yield: 65%

$^1$H-NMR (CDCl$_3$) δ; 0.88 (3H, m), 1.26 (6H, m), 1.60 (2H, m), 2.12 (3H, s), 2.55–2.66 (4H, m), 2.92 (2H, t, J=8.4 Hz), 4.97 (2H, s), 6.06 (1H, d, J=3.4 Hz), 6.25 (1H, d, J=3.4 Hz), 6.76–7.41 (13H, m).

IR (KBr) cm$^{-1}$; 3034, 2928, 2856, 1734, 1524, 1454, 1240, 912, 742.

(5) 4-[1-(4-Hexylphenylethyl)-5-methyl-1H-pyrrol-2-yl]phenol

The object compound was obtained from 1-(4-hexylphenylethyl)-2-methyl-5-[4-[(phenylmethyl)oxy]phenyl]-1H-pyrrole as an oily substance, according to the similar manner to that of Example 75(5). yield: 100%

$^1$H-NMR (CDCl$_3$) δ; 0.88 (3H, m), 1.26 (6H, m), 1.62 (2H, m), 2.12 (3H, s), 2.65 (4H, m), 2.92 (2H, t, J=8.4 Hz), 6.04 (1H, d, J=3.4 Hz), 6.24 (1H, d, J=3.4 Hz), 6.50 (2H, d, J=6.6 Hz), 6.93–7.30 (6H, m).

IR (KBr) cm$^{-1}$; 2930, 2857, 1713, 1516, .1437, 1264, 1173, 835, 760.

(6) Ethyl (2R)-2-([4-[1-(4-hexylphenylethyl)-5-methyl-1H-pyrrol-2-yl]phenyl]oxy)-3-phenylpropanoate The object compound was obtained from 4-[1-(4-hexylphenylethyl)-5-methyl-1H-pyrrol-2-yl]phenol as an oily substance, according to the similar manner to that of Example 75 (5). yield: 47%

$^1$H-NMR (CDCl$_3$) δ; 0.88 (3H, m), 1.26 (11H, m), 1.66 (2H, m), 2.10 (3H, s), 2.65 (4H, m), 3.20 (2H, m), 4.15 (2H, q, J=7.2 Hz), 4.69 (1H, t, J=7.2 Hz), 6.02 (1H, d, J=3.4 Hz), 6.22 (1H, d, J=3.4 Hz), 6.59 (2H, d, J=6.6 Hz), 6.87–7.28 (11H, m).

IR (KBr) cm$^{-1}$; 2930, 2857, 1736, 1522, 1483, 1236, 1182, 1084, 835, 760.

Example 78

Sodium (2R)-2-([4-[1-(4-hexylphenylethyl)-5-methyl-1H-pyrrol-2-yl]phenyl]oxy)-3-phenylpropanoate (1) (2R)-2-([4-[1-(4-Hexylphenylethyl)-5-methyl-1H-pyrrol-2-yl]phenyl]oxy)-3-phenylpropanoic acid The object compound was obtained from ethyl (2R)-2-([4-[1-(4-hexylphenylethyl)-5-methyl-1H-pyrrol-2-yl]phenyl]oxy)-3-phenylpropanoate as an oily substance, according to the similar manner to that of Example 76(1). yield: 99%

$^1$H-NMR (CDCl$_3$) δ; 0.88 (3H, m), 1.26 (8H, m), 1.66 (2H, m), 2.10 (3H, s), 2.65 (4H, m), 3.20 (2H, m), 4.69 (1H, t, J=7.2 Hz), 6.02 (1H, d, J=3.4 Hz), 6.22 (1H, d, J=3.4 Hz), 6.59 (2H, d, J=6.6 Hz), 6.87–7.28 (1H, m).

IR (KBr) cm$^{-1}$; 2930, 2859, 1717, 1520, 1392, 1238, 1181, 1084, 835, 760.

(2) Sodium (2R)-2-([4-[1-(4-hexylphenylethyl)-5-methyl-1H-pyrrol-2-yl]phenyl]oxy)-3-phenylpropanoate The object compound was obtained from (2R)-2-([4-[1-(4-hexylphenylethyl)-5-methyl-1H-pyrrol-2-yl]phenyl]oxy)-3-phenylpropanoic acid as a solid, according to the similar manner to that of Example 76(2). yield: 94%

$^1$H-NMR (DMSO) δ; 0.85 (3H, m), 1.25 (6H, m), 1.51 (2H, m), 2.09 (3H, s), 2.49 (2H, m), 2.65 (2H, m), 3.18–2.92 (2H, m), 3.93 (2H, m), 4.35 (1H, m), 5.73 (1H, d, J=3.2 Hz), 5.83 (1H, d, J=3.6 Hz), 6.76–7.34 (13H, m).

Elementary analysis for C$_{34}$H$_{38}$NO$_3$Na; Calculated: C, 76.81; H, 7.20; N, 2.63. Found: C, 76.73; H, 7.35; N, 2.50.

Example 79

Ethyl (2R)-2-{4-[5-methyl-1-(4-heptylphenylmethyl)-1H-pyrrol-2-yl]phenoxy}-3-phenylpropanoate (1) 4-Heptylphenylbenzylalcohol To a solution of lithium aluminium hydride (3.5 g, 91 mmol) in THF (50 ml) was added a solution of 4-heptylbenzoic acid (10.0 g, 45.4 mmol) in THF (200 ml) at 0° C. and refluxed for 3 hours. The reaction mixture was cooled to 0° C., water (10 ml) was added carefully to the reaction mixture, then 1N aqueous sodium hydroxide (30 ml) was added to the mixture. The insoluble matter was filtered out and the filtrate was concentrated to give the object compound as an oily substance. 8.38 g, (yield 89%)

$^1$H-NMR (CDCl$_3$) δ; 0.88 (3H, t, J=6.2 Hz), 1.35 (8H, m), 1.56 (2H, m), 2.60 (2H, t, J=7.4 Hz), 4.64 (2H, s), 7.27 (2H, d, J=8.0 Hz), 7.16 (2H, d, J=8.0 Hz).

IR (KBr) cm$^{-1}$; 2930, 1458, 1202, 1016, 742.

(2) 4-Heptylphenylmethyl mesylate

To a solution of 4-heptylphenylbenzylalcohol (8.38 g, 40.6 mmol) and triethylamine (7.7 ml, 55 mmol) in THF (100 ml) was added mesylchloride (3.8 ml, 49 mmol) at 0° C. and the mixture was stirred at room temperature for 30 minutes. The reaction mixture was poured into ice and extracted with ethyl acetate. The organic layer was washed with saturated brine and dried over magnesium sulfate anhydride. The organic layer was concentrated to give the object compound as an oily substance. 12.8 g, (yield 100%)

$^1$H-NMR (CDCl$_3$) δ; 0.88 (3H, m), 1.35 (8H, m), 1.56 (2H, m), 2.86 (3H, s), 5.21 (2H, s), 7.26 (4H, m).

IR (KBr) cm$^{-1}$; 2932, 1354, 1175, 925, 820.

(3) 2-(4-Heptylphenylmethyl)-1H-isoindol-1,3-(2H)-dione

A solution of 4-heptylphenylmethyl mesylate (11.5 g, 40.6 mmol) and potassium phthalimide (7.6 g, 40.6 mmol) in DMF (60 ml) was stirred at 80° C. for 3 hours. The reaction mixture was poured into ice-water and extracted with ethyl acetate. The organic layer was washed with saturated brine and dried over magnesium sulfate anhydride, and the organic layer was concentrated. The residue was purified by silica gel column chromatography (hexane:ethyl acetate=5:1) to give the object compoundas crystals. 12.7 g, (yield 93%)

$^1$H-NMR (CDCl$_3$) δ; 0.88 (3H, m), 1.26 (8H, m), 1.61 (2H, m), 2.55 (2H, t, J=7.2 Hz), 4.81 (2H, s), 7.11–7.36 (4H, m), 7.64–7.85 (4H, m).

IR (KBr) cm$^{-1}$; 2928, 1712, 1392, 1348, 1101, 937, 715.

(4) 4-Heptylphenylmethylamine

A solution of 2-(4-heptylphenylmethyl)-1H-isoindole-1,3-(2H)-dione (12.7 g, 38 mmol) and hydrazinemonohydrate (3.7 ml, 76 mmol) in ethanol (200 ml) was refluxed for 3 hours. The reaction mixture was dissolved in 5N aqueous sodium hydroxide and extracted with ethyl acetate. The organic layer was washed with saturated brine and dried over magnesium sulfate anhydride. The organic layer was concentrated to give the object compound as an oily substance. 7.44 g, (yield 96%)

$^1$H-NMR (CDCl$_3$) δ; 0.88 (3H, m), 1.26 (8H, m), 1.56 (2H, m), 2.17 (2H, s), 2.58 (2H, d, J=7.2 Hz), 3.02 (2H, s), 7.15 (4H, s).

IR (KBr) cm$^{-1}$; 2928, 1485, 1310, 1019, 818, 744.

(5) 2-(4-Benzyloxyphenyl)-5-methyl-1-(4-heptylphenylpropyl)-1H-pyrrole

A solution of 4-heptylphenylmethyl amine (2.05 g, 10.0 mmol), 1-(4-benzyloxyphenyl)-1,4-pentanedione (2.8 g, 9.9 mmol) and p-toluenesulfonic acid monohydrate (100 mg) in toluene (40 ml) was refluxed for 12 hours under heating and the solvent was removed under reduced pressure. The residue was silica gel chromatography (hexane:ethyl acetate=20:1) to give the object compound as an oily substance. 2.47 g, (yield 55%)

$^1$H-NMR (CDCl$_3$) δ; 0.88 (3H, m), 1.29 (8H, m), 1.57 (2H, m), 2.13 (3H, s), 2.56 (2H, t, J=3.2 Hz), 5.04 (2H, s), 5.06 (2H, s), 6.01 (1H, d, J=3.3 Hz), 6.14 (1H, d, J=3.3 Hz), 6.81–7.56 (13H, m).

IR (KBr) cm$^{-1}$; 2928, 2857, 1528, 1454, 1240, 1020, 835, 750.

(6) 4-[5-Methyl-1-(4-heptylphenylmethyl)-1H-pyrrol-2-yl]phenol

To a solution of 2-(4-benzyloxyphenyl)-5-methyl-1-(4-heptylphenylpropyl)-1H-pyrrole (2.47 g, 5.47 mmol) in ethanol (200 ml) was added 10% palladium carbon (300 mg) and the mixture was stirred under hydrogen atmosphere. The insoluble matter was filtered out and the filtrate was concentrated to give the object compound as an oily substance. 1.98 g, (yield 100%)

$^1$H-NMR (CDCl$_3$) δ; 0.89 (3H, m), 1.28 (8H, m), 1.58 (2H, m), 2.13 (3H, s), 2.56 (2H, t, J=3.2 Hz), 3.89 (1H, s), 5.04 (2H, s), 6.00 (1H, d, J=3.4 Hz), 6.15 (1H, d, J=3.4 Hz), 6.72–6.84 (4H, m), 7.07–7.26 (4H, m).

IR (KBr) cm$^{-1}$; 2930, 2857, 1526, 1400, 1259, 1020, 839, 760.

(7) Ethyl (2R)-2-{4-[5-methyl-1-(4-heptylphenylmethyl)-1H-pyrrol-2-yl]phenoxy}-3-phenylpropanoate A solution of 4-[5-methyl-1-(4-heptylphenylmethyl)-1H-pyrrol-2-yl]phenol (1.98 g, 5.5 mmol), ethyl (S)-2-hydroxy-3-phenylpropanoate (1.2 g, 6.2 mmol), 1,1'-(azodicarbonyl) dipiperidine (1.56 g, 6.2 mmol) and triphenylphosphine (1.63 g, 6.2 mmol) in toluene (5 ml) was stirred at 80° C. for 12 hours. The reaction solution was poured into water and extracted with ethyl acetate. The extract was washed with saturated brine and dried over magnesium sulfate anhydride. The solvent was removed under reduced pressure and the residue was purified by silica gel column chromatography (hexane:ethyl acetate=20:1) to give the object compound as an oily substance. 1.03 g, (yield 32%)

$^1$H-NMR (CDCl$_3$) δ; 0.88 (3H, m), 7.30–7.07 (9H, m), 1.26 (11H, m), 1.58 (2H, m), 2.11 (3H, s), 2.56 (2H, t, J=3.2 Hz), 3.22 (2H, m), 4.15 (2H, q, J=7.2 Hz), 4.75 (1H, t, J=7.2 Hz), 5.01 (2H, s), 5.99 (1H, d, J=3.4 Hz), 6.11 (1H, d, J=3.4 Hz), 6.74–6.81 (4H, m).

IR (KBr) cm$^{-1}$; 2930, 2857, 1755, 1523, 1238, 1182, 1030, 837, 760.

Example 80

Sodium (2R)-2-{4-[5-methyl-1-(4-heptylphenylpropyl)-1H-pyrrol-2-yl]phenoxy}-3-phenylpropanoate (1) (2R)-2-{4-[5-Methyl-1-(4-heptylphenylpropyl)-1H-pyrrol-2-yl]phenoxy}-3-phenylpropanoic acid To a mixed solution of ethyl (2R)-2-{4-[5-methyl-1-(4-heptylphenylpropyl)-1H-pyrrol-2-yl]phenoxy}-3-phenylpropanoate (1.03 g, 1.76 mmol) in THF (15 ml) and methanol (7 ml) was added 1N aqueous potassium hydroxide (5.3 ml, 5.3 mmol) and the mixture was stirred for 1 hour at room temperature. The reaction solution was neutralized with 1N aqueous hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 969 mg, (yield 99%)

$^1$H-NMR (CDCl$_3$) δ; 0.88 (3H, m), 1.26 (8H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 3.86–4.00 (4H, m), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).

(2) Sodium (2R)-2-{4-[5-methyl-1-(4-heptylphenylpropyl)-1H-pyrrol-2-yl]phenoxy}-3-phenylpropanoate To a solution of (2R)-2-{4-[5-methyl-1-(4-heptylphenylpropyl)-1H-pyrrol-2-yl]phenoxy}-3-phenylpropanoic acid (969 mg, 1.74 mmol) in ethanol (10 ml) was added 1N sodium hydroxide-ethanol solution (1.71 ml, 1.71 mmol) and the mixture was concentrated. To the residue was added hexane to give the object compound as a solid. 740 mg, (yield 80%)

$^1$H-NMR (DMSO) δ; 0.84 (3H, m), 1.25 (8H, m), 1.52 (2H, m), 2.03 (3H, s), 2.50 (2H, m), 3.14–2.86 (2H, m), 4.25 (1H, dd, J=9.2 Hz J=2.8 Hz), 5.03 (2H, s), 5.87 (1H, d, J=3.0 Hz), 5.94 (1H, d, J=3.0 Hz), 6.70 (4H, t, J=9.2 Hz), 7.00–7.29 (9H, m)

Example 81

Ethyl (2R)-2-{4-[1-(4'-ethyl-1,1'-biphenyl-4-ylmethyl)-5-methyl-1H-pyrrol-2-yl]phenoxy}-3-phenylpropanoate (1) 4'-Ethyl-1,1'-biphenyl-4-methylalcohol The object compound was obtained from 4'-ethyl-4-biphenylcarboxylic acid as a solid, according to the similar manner to that of Example 79(1). yield: 100%

$^1$H-NMR (CDCl$_3$) δ; 1.28 (3H, t, J=7.8 Hz), 1.71 (1H, m), 2.68 (2H, q, J=7.8 Hz), 4.73 (2H, d, J=5.4 Hz), 7.26–7.62 (8H, m).

IR (KBr) cm$^{-1}$; 3270, 2926, 2851, 1449, 1001, 800.

(2) 4'-Ethyl-1,1'-biphenyl-4-methyl mesylate

The object compound was obtained from 4'-ethyl-1,1'-biphenyl-4-methylalcohol as a solid, according to the similar manner to that of Example 79(2). yield: 100%

$^1$H-NMR (CDCl$_3$) δ; 1.28 (3H, t, J=7.8 Hz), 1.71 (1H, m), 2.68 (2H, q, J=7.8 Hz), 3.00 (3H, s), 5.28 (2H, s), 7.23–7.60 (8H, m).

IR (KBr) cm$^{-1}$; 3025, 2924, 2851, 1449, 1354, 1175, 929, 816.

(3) 2-(4'-Ethyl-1,1'-biphenyl-4-methyl)-1H-isoindole-1,3(2H)-dione

The object compound was obtained from 4'-ethyl-1,1'-biphenyl-4-methyl mesylate as a solid, according to the similar manner to that of Example 79(3). yield: 61%

$^1$H-NMR (CDCl$_3$) δ; 1.26 (3H, t, J=7.5 Hz), 2.68 (2H, q, J=7.5 Hz), 4.88 (2H, s), 7.24–7.87 (12H, m).

IR (KBr) cm$^{-1}$; 3029, 2968, 2880, 1717, 1500, 1397, 1346, 1091, 943, 715.

(4) 3-(4'-Ethyl-1,1'-biphenyl-4-methyl)methylamine

The object compound was obtained from 2-(4'-ethyl-1,1'-biphenyl-4-methyl)-1H-isoindol-1,3(2H)-dione as a solid, according to the similar manner to that of Example 79(4). yield: 100%

$^1$H-NMR (CDCl$_3$) δ; 1.28 (3H, t, J=7.4 Hz), 1.63 (2H, s), 2.68 (2H, q, J=7.8 Hz), 3.91 (2H, s), 7.25–7.58 (8H, m).

IR (KBr) cm$^{-1}$; 2961, 2870, 1498, 1456, 1400, 1327, 931, 806.

(5) 2-(4-Benzyloxyphenyl)-1-(4'-ethyl-1,1'-biphenyl-4-methyl)-5-methyl-1H-pyrrole The object compound was obtained from 3-(4'-ethyl-1,1'-biphenyl-4-methyl)methylamine as a solid, according to the similar manner to that of Example 79 (5). yield: 58%

$^1$H-NMR (CDCl$_3$) δ; 1.26 (3H, t, J=6.9 Hz), 2.17 (3H, s), 2.68 (2H, q, J=7.8 Hz), 5.04 (2H, s), 5.13 (2H, s), 6.04 (1H, d, J=3.4 Hz), 6.15 (1H, d, J=3.4 Hz), 6.93, (4H, m), 7.26–7.52 (13H, m).

IR (KBr) cm$^{-1}$; 3030, 2964, 2864, 1609, 1523, 1242, 1175, 1020, 812.

(6) 4-[1-(4'-Ethyl-1,1'-biphenyl-4-ylmethyl)-5-methyl-1H-pyrrol-2-yl]phenol

The object compound was obtained from 2-(4-benzyloxyphenyl)-1-(4'-ethyl-1,1'-biphenyl-4-methyl)-5-methyl-1H-pyrrole as a solid, according to the similar manner to that of Example 79(6). yield: 100%

$^1$H-NMR (CDCl$_3$) δ; 1.27 (3H, t, J=7.8 Hz), 2.17 (3H, s), 2.70 (2H, q, J=7.8 Hz), 5.11 (2H, s), 6.04 (1H, d, J=3.6 Hz), 6.16 (1H, d, J=3.3 Hz), 6.75 (2H, d, J=8.7 Hz), 6.96 (2H, d, J=8.1 Hz), 7.17 (2H, d, J=8.4 Hz), 7.26 (2H, d, J=6.3 Hz), 7.49 (4H, m).

IR (KBr) cm$^{-1}$; 3023, 2968, 2930, 2870, 1525, 1400, 1260, 1171, 840, 760.

(7) Ethyl (2R)-2-{4-[1-(4'-ethyl-1,1'-biphenyl-4-ylmethyl)-5-methyl-1H-pyrrol-2-yl]phenoxy}-3-phenylpropanoate The object compound was obtained from 4-[1-(4'-ethyl-1,1'-biphenyl-4-ylmethyl)-5-methyl-1H-pyrrol-2-yl]phenol as a solid, according to the similar manner to that of Example 79(7). yield: 37%

$^{1}$H-NMR (CDCl$_3$) δ; 1.33–1.12 (6H, m), 2.15 (3H, s), 2.70 (2H, q, J=7.6 Hz), 3.23 (2H, m), 4.16 (2H, q, J=7.2 Hz), 4.74 (1H, t, J=7.2 Hz), 5.09 (2H, s), 6.00 (1H, d, J=3.8 Hz), 6.13 (1H, d, J=3.6 Hz), 6.74 (2H, d, J=8.8 Hz), 6.92 (2H, d, J=8.6 Hz), 7.14–7.52 (13H, m).

IR (KBr) cm$^{-1}$; 3030, 2967, 2899, 1751, 1522, 1280, 1240, 1084, 1030, 837, 760.

Example 82

Sodium (2R)-2-{4-[1-(4'-ethyl-1,1'-biphenyl-4-ylmethyl)-5-methyl-1H-pyrrol-2-yl]phenoxy}-3-phenylpropanoate (1) (2R)-2-{4-[1-(4'-Ethyl-1,1'-biphenyl-4-ylmethyl)-5-methyl-1H-prrol-2-yl]phenoxy}-3-phenylpropanoic acid The object compound was obtained from ethyl (2R)-2-{4-[1-(4'-ethyl-1,1'-biphenyl-4-ylmethyl)-5-methyl-1H-pyrrol-2-yl]phenoxy}-3-phenylpropanoate as an oily substance, according to the similar manner to that of Example 80(1). yield: 96%

$^{1}$H-NMR (CDCl$_3$) δ; 1.27 (3H, t, J=7.8 Hz), 2.15 (3H, s), 2.70 (2H, q, J=7.6 Hz), 3.23 (2H, m), 4.74 (1H, t, J=7.2 Hz), 5.09 (2H, s), 6.00 (1H, d, J=3.8 Hz), 6.13 (1H, d, J=3.6 Hz), 6.74 (2H, d, J=8.8 Hz), 6.92 (2H, d, J=8.6 Hz), 7.14–7.52 (13H, m).

IR (KBr) cm$^{-1}$; 3028, 2964, 2855, 1725, 1524, 1238, 1084, 812, 733.

(2) Sodium (2R)-2-{4-[1-(4'-ethyl-1,1'-biphenyl-4-ylmethyl)-5-methyl-1H-pyrrol-2-yl]phenoxy}-3-phenylpropanoate The object compound was obtained from (2R)-2-{4-[1-(4'-ethyl-1,1'-biphenyl-4-ylmethyl)-5-methyl-1H-pyrrol-2-yl]phenoxy}-3-phenylpropanoic acid as a solid, according to the similar manner to that of Example 80(1). yield: 99%

$^{1}$H-NMR (DMSO) δ; 1.20 (3H, t, J=7.6 Hz), 2.07 (3H, s), 2.65, (2H, q, J=7.6 Hz), 3.14–2.93 (2H, m), 4.34 (1H, dd, J=9.2 Hz J=3.0 Hz), 5.11 (2H, s), 5.91 (1H, d, J=3.2 Hz), 5.98 (1H, d, J=3.6 Hz), 6.70 (2H, d, J=8.8 Hz), 6.88 (2H, d, J=8.0 Hz), 7.05–7.28 (9H, m), 7.56 (4H, m).

Elementary analysis for C$_{35}$H$_{32}$NO$_3$Na·1.5H$_2$O; Calculated: C, 74.45; H, 6.25; N, 2.48. Found: C, 74.03; H, 5.90; N, 2.09.

Example 83

Ethyl (2R)-2-[(4-[5-methyl-1-[(4'-propyl-1,1'-biphenyl-4-yl)methyl]-1H-pyrrol-2-yl]phenyl)oxy]-3-phenylpropanoate (1) 4'-Propyl-1,1'-biphenyl-4-methylalcohol The object compound was obtained from 4'-propyl-4-biphenyl carboxylic acid as a solid, according to the similar manner to that of Example 79(1). yield: 100%

$^{1}$H-NMR (CDCl$_3$) δ; 0.98 (3H, t, J=7.2 Hz), 1.67 (2H, m), 2.63 (2H, t, J=8.1 Hz), 3.49 (1H, s), 4.73 (2H, s), 7.19 (2H, d, J=8.0 Hz), 7.24–7.60 (8H, m).

IR (KBr) cm$^{-1}$; 3248, 2953, 2870, 1491, 1400, 1049, 1013, 800.

(2) 4'-Propyl-1,1'-biphenyl-4-methyl mesylate

The object compound was obtained from 4'-propyl-1,1'-biphenyl-4-methylalcohol as a solid, according to the similar manner to that of Example 79(2). yield: 100%

$^{1}$H-NMR (CDCl$_3$) δ; 0.97 (3H, t, J=7.2 Hz), 1.67 (2H, t, J=7.6 Hz), 2.63 (2H, t, J=7.4 Hz), 3.00 (3H, s), 5.28 (2H, s), 7.23–7.60 (8H, m).

IR (KBr) cm$^{-1}$; 2955, 2930, 2870, 1498, 1352, 1173, 1005, 914, 804.

(3) 2-(4'-Propyl-1,1'-biphenyl-4-methyl)-1H-isoindol-1,3-(2H)-dione

The object compound was obtained from 4'-propyl-1,1'-biphenyl-4-methyl mesylate as a solid, according to the similar manner to that of Example 79(3). yield: 24%

$^{1}$H-NMR (CDCl$_3$) δ; 0.96 (3H, t, J=7.2 Hz), 1.65 (2H, m), 2.61 (2H, t, J=7.2 Hz), 4.89 (2H, s), 7.22–7.89 (12H, m).

IR (KBr) cm$^{-1}$; 3209, 2959, 2870, 1720, 1397, 1308, 1089, 939, 714.

(4) 3-(4'-Propyl-1,1'-biphenyl-4-methyl)methylamine

The object compound was obtained from 2-(4'-propyl-1,1'-biphenyl-4-methyl)-1H-isoindol-1,3 (2H)-dione as a solid, according to the similar manner to that of Example 79(4). yield: 71%

$^{1}$H-NMR (CDCl$_3$) δ; 0.97 (3H, t, J=7.4 Hz), 1.70 (2H, m), 2.63 (2H, t, J=7.4 Hz), 3.91 (2H, s), 7.23–7.61 (8H, m).

IR (KBr) cm$^{-1}$; 2959, 2870, 1558, 1498, 1398, 1305, 801.

(5) 2-(4-Benzyloxyphenyl)-1-(4'-propyl-1,1'-biphenyl-4-methyl)-5-methyl-1H-pyrrole The object compound was obtained from 3-(4'-propyl-1,1'-biphenyl-4-methyl)methylamine as a solid, according to the similar manner to that of Example 79(5). yield: 56%

$^{1}$H-NMR (CDCl$_3$) δ; 0.97 (3H, t, J=6.9 Hz), 1.63 (2H, m), 2.17 (3H, s), 2.62 (2H, t, J=6.9 Hz), 5.04 (2H, s), 5.12 (2H, s), 6.03 (1H, d, J=4.2 Hz), 6.17 (1H, d, J=3.3 Hz), 6.89–7.52 (17H, m).

IR (KBr) cm$^{-1}$; 3037, 2959, 2870, 1524, 1240, 1024, 835, 758.

(6) 4-[5-Methyl-1-[(4'-propyl1,1'-biphenyl-4-yl)methyl]-5-methyl-1H-pyrrol-2-yl]phenol The object compound was obtained from 2-(4-benzyloxyphenyl)-1-(4'-propyl-1,1'-biphenyl-4-methyl)-5-methyl-1H-pyrrole as a solid, according to the similar manner to that of Example 79 (6). yield: 100%

$^{1}$H-NMR (CDCl$_3$) δ; 0.96 (3H, t, J=7.4 Hz), 1.67 (2H, q, J=7.4 Hz), 2.17 (3H, s), 2.62 (2H, t, J=7.4 Hz), 5.11 (2H, s), 6.03 (1H, d, J=3.4 Hz), 6.16 (1H, d, J=3.2 Hz), 6.75 (2H, d, J=8.8 Hz), 6.96 (2H, d, J=8.2 Hz), 7.15–7.53 (8H, m).

IR (KBr) cm$^{-1}$; 3024, 2959, 2870, 1526, 1400, 1260, 1170, 839, 796.

(7) Ethyl (2R)-2-[(4-[5-methyl-1-[(4'-propyl-1,1'-biphenyl-4-yl)methyl]-1H-pyrrol-2-yl]phenyl)oxy]-3-phenylpropanoate The object compound was obtained from 4-[5-methyl-1-[(4'-propyl-1,1'-biphenyl-4-yl) methyl]-5-methyl-1H-pyrrol-2-yl]phenol as a solid, according to the similar manner to that of Example 79(7). yield: 52%

$^{1}$H-NMR (CDCl$_3$) δ; 0.96 (3H, t, J=7.4 Hz), 1.16 (3H, t, J=7.2 Hz), 1.69 (2H, q, J=7.4 Hz), 2.15 (3H, s), 2.65 (2H, t, J=7.4 Hz), 3.24 (2H, m), 4.17 (2H, q, J=7.2 Hz), 4.74 (1H, t, J=7.2 Hz), 5.08 (2H, s), 6.01 (1H, d, J=3.4 Hz), 6.14 (1H, d, J=3.4 Hz), 6.75 (2H, d, J=8.8 Hz), 6.97 (2H, d, J=8.2 Hz), 7.14–7.52 (13H, m).

IR (KBr) cm$^{-1}$; 3088, 2959, 2870, 1752, 1524, 1240, 1186, 1082, 912, 742.

Example 84

Sodium (2R)-2-[(4-[5-methyl-1-[(4'-propyl-1,1'-biphenyl-4-yl) methyl]-1H-pyrrol-2-yl]phenyl)oxy]-3-phenylpropanoate (1) (2R)-2-[(4-[5-Methyl-1-[(4'-propyl-1,1'-biphenyl-4-yl) methyl]-1H-pyrrol-2-yl]phenyl)oxy]-3-phenylpropanoic acid The object compound was obtained from ethyl (2R)-2-[(4-[5-methyl-1-[(4'-propyl-1,1'-biphenyl-4-yl)methyl]-1H-pyrrol-2-yl]phenyl)oxy]-3-phenylpropanoate as an oily substance, according to the similar manner to that of Example 80(1). yield: 94%

¹H-NMR (CDCl₃) δ; 0.96 (3H, t, J=7.4 Hz), 1.69 (2H, q, J=7.4 Hz), 2.15 (3H, s), 2.65 (2H, t, J=7.4 Hz), 3.24 (2H, m), 4.74 (1H, t, J=7.2 Hz), 5.08 (2H, s), 6.01 (1H, d, J=3.4 Hz), 6.14 (1H, d, J=3.4 Hz), 6.75 (2H, d, J=8.8 Hz), 6.97 (2H, d, J=8.2 Hz), 7.14–7.52 (13H, m).

IR (KBr) cm⁻¹; 3028, 2961, 2870, 1723, 1524, 1238, 912, 743.

(2) Sodium (2R)-2-[(4-[5-methyl-1-[(4'-propyl-1,1'-biphenyl-4-yl)methyl]-1H-pyrrol-2-yl]phenyl)oxy]-3-phenylpropanoate The object compound was obtained from (2R)-2-[(4-[5-methyl-1-[(4'-propyl-1,1'-biphenyl-4-yl)methyl]-1H-pyrrol-2-yl]phenyl)oxy]-3-phenylpropanoic acid as a solid, according to the similar manner to that of Example 80(2). yield: 87%

¹H-NMR (DMSO) δ; 0.90 (3H, t, J=7.4 Hz), 1.60 (2H, m), 2.07 (3H, s), 2.65 (2H, m), 2.93–3.14 (2H, m), 4.30 (1H, dd, J=9.2 Hz J=3.0 Hz), 5.12 (2H, s), 5.91 (1H, d, J=3.2 Hz), 5.98 (1H, d, J=3.6 Hz), 6.70 (2H, d, J=8.8 Hz), 6.89 (2H, d, J=8.0 Hz), 7.04–7.58 (13H, m).

Elementary analysis for $C_{36}H_{34}NO_3Na \cdot 1.5H_2O$ ; Calculated: C, 74.72; H, 6.44; N, 2.42. Found: C, 74.23; H, 6.06; N, 1.92.

Example 85

Ethyl (2R)-2-([4-[1-(4'-propyl-1,1'-phenylpropyl)-5-methyl-1H-pyrrol-2-yl]phenyl]oxy)-3-phenylpropanoate (1) Ethyl (2E)-3-(4'-propyl-1,1'-phenyl)propenoate The object compound was obtained from 4'-propylphenylbenzaldehyde as an oily substance, according to the similar manner to that of Example 69 (1). yield: 100%

¹H-NMR (CDCl₃) δ; 0.88 (3H, t, J=7.4 Hz), 1.32 (5H, m), 1.58 (2H, m), 1.70 (2H, q, J=7.6 Hz), 2.63 (2H, t, J=7.8 Hz), 4.29 (2H, q, J=7.0 Hz), 6.41 (1H, m), 7.26 (2H, m), 7.60 (6H, m), 7.74 (1H, s).

IR (KBr) cm⁻¹; 2961, 2932, 2872, 1738, 1633, 1269, 1175, 1030, 912, 743.

(2) Ethyl (2E)-3-(4'-propyl-1,1'-phenyl)propanoate

The object compound was obtained from ethyl (2E)-3-(4'-propyl-1,1'-phenyl)propenoate as an oily substance, according to the similar manner to that of Example 69(2). yield: 100%

¹H-NMR (CDCl₃) δ; 0.88 (3H, m), 1.26 (3H, m), 1.58 (2H, m), 2.60 (4H, q, J=7.8 Hz), 2.99 (2H, t, J=7.8 Hz), 4.15 (4H, m), 7.25 (4H, m), 7.48 (4H, m).

IR (KBr) cm⁻¹; 2959, 2930, 2870, 1736, 1499, 1271, 1179, 1028, 970, 804.

(3) 3-(4'-Propyl-1,1'-phenyl)propanol

The object compound was obtained from ethyl (2E)-3-(4'-propyl-1,1'-phenyl)propanoate as an oily substance, according to the similar manner to that of Example 69(3). yield: 100%

¹H-NMR (CDCl₃) δ; 0.97 (3H, t, J=7.4 Hz), 1.66 (2H, m), 1.92 (2H, m), 2.62 (2H, t, J=7.4 Hz), 2.75 (2H, t, J=7.4 Hz), 3.71 (2H, t, J=6.6 Hz), 7.25 (4H, m), 7.48 (4H, m)

IR (KBr) cm⁻¹; 2928, 2870, 1499, 1454, 1377, 1059, 794.

(4) 3-(4'-Propyl-1,1'-phenyl)propyl mesylate

The object compound was obtained from 3-(4'-propyl-1,1'-phenyl)propanol as an oily substance, according to the similar manner to that of Example 69(4). yield: 69%

¹H-NMR (CDCl₃) δ; 7.50 (4H, s), 0.97 (3H, t, J=7.4 Hz), 1.66 (2H, m), 2.04 (2H, m), 2.62 (2H, t, J=7.2 Hz), 2.78 (2H, t, J=7.2 Hz), 2.99 (3H, s), 4.25 (2H, t, J=6.6 Hz), 7.22 (4H, m).

IR (KBr) cm⁻¹; 2955, 2870, 1498, 1466, 1348, 1172, 956, 804.

(5) 2-(4'-Propyl-1,1'-phenylpropyl)-1H-isoindol-1,3-(2H)-dione

The object compound was obtained from 3-(4'-propyl-1,1'-phenyl)propyl mesylate as an oily substance, according to the similar manner to that of Example 69(5). yield: 86%

¹H-NMR (CDCl₃) δ; 0.97 (3H, t, J=7.4 Hz), 1.65 (2H, m), 2.07 (2H, m), 2.65 (2H, t, J=7.2 Hz), 2.76 (2H, t, J=7.2 Hz), 3.76 (2H, t, J=7.0. Hz), 7.20–7.85 (12H, m).

IR (KBr) cm⁻¹; 2955, 2870, 1713, 1498, 1397, 1055, 912, 742.

(6) 3-(4'-Propyl-1,1'-phenyl)propylamine

The object compound was obtained from 2-(4'-propyl-1,1'-phenylpropyl)-1H-isoindol-1,3-(2H)-dione as an oily substance, according to the similar manner to that of Example 69(6). yield: 94%

¹H-NMR (CDCl₃) δ; 0.93 (3H, t, J=7.4 Hz), 1.62 (2H, m), 1.73 (2H, m), 1.95 (2H, s), 2.81–2.57 (4H, m), 3.49 (1H, s), 3.69 (2H, t, J=7.0. Hz), 7.24 (4H, m), 7.50 (4H, m).

IR (KBr) cm⁻¹; 2930, 2870, 1572, 1499, 1377, 1338, 1057, 802.

(7) 1-(4'-propyl-1,1'-phenylpropyl)-2-methyl-5-[4-[(phenylmethyl)oxy]phenyl]-1H-pyrrole The object compound was obtained from 3-(4'-propyl-1,1'-phenyl)propylamine as an oily substance, according to the similar manner to that of Example 69(7). yield: 31%

¹H-NMR (CDCl₃) δ; 0.96 (3H, t, J=7.4 Hz), 1.67 (2H, m), 2.27 (3H, s), 2.52 (2H, t, J=3.2 Hz), 2.62 (2H, t, J=3.2 Hz), 5.01 (2H, s), 5.92 (1H, d, J=3.4 Hz), 6.02 (1H, d, J=3.4 Hz), 6.92–7.51 (17H, m).

IR (KBr) cm⁻¹; 2955, 2930, 2868, 1522, 1423, 1252, 1026, 833, 734.

(8) 4-[1-(4'-Propyl-1,1'-phenylpropyl)-5-methyl-1H-pyrrol-2-yl]phenol

The object compound was obtained from 1-(4'-propyl-1,1'-phenylpropyl)-2-methyl-5-[4-[(phenylmethyl)oxy]phenyl]-1H-pyrrole as an oily substance, according to the similar manner to that of Example 69(8). yield: 100%

¹H-NMR (CDCl₃) δ; 0.97 (3H, t, J=7.4 Hz), 1.66 (2H, m), 2.36 (3H, s), 2.51 (2H, t, J=3.2 Hz), 2.63 (2H, t, J=3.2 Hz), 3.76 (2H, t, J=7.8 Hz), 5.91 (1H, d, J=3.4 Hz), 6.01 (1H, d, J=3.4 Hz), 6.77 (2H, d, J=8.0 Hz), 7.28 (6H, m), 7.51 (4H, m).

IR (KBr) cm⁻¹; 2959, 2930, 2868, 1526, 1499, 1400, 1264, 1169, 837, 760.

(9) Ethyl (2R)-2-([4-[1-(4'-propyl-1,1'-phenylpropyl)-5-methyl-1H-pyrrol-2-yl]phenyl]oxy)-3-phenylpropanoate The object compound was obtained from 4-[1-(4'-propyl-1,1'-phenylpropyl)-5-methyl-1H-pyrrol-2-yl]phenol as an oily substance, according to the similar manner to that of Example 69(9). yield: 30%

¹H-NMR (CDCl₃) δ; 0.97 (3H, m), 1.20 (3H, m), 1.60 (2H, m), 2.22 (3H, s), 2.47 (2H, t, J=3.2 Hz), 2.56 (2H, t, J=3.2 Hz), 3.27 (2H, m), 4.20 (2H, q, J=7.2 Hz), 5.91 (1H, d, J=3.4 Hz), 6.03 (1H, d, J=3.4 Hz), 6.87–6.70 (6H, m), 7.19–7.34 (7H, m).

IR (KBr) cm⁻¹; 2959, 2870, 1752, 1522, 1466, 1240, 1182, 1084, 912, 743.

Example 86

Sodium (2R)-2-([4-[1-(4'-propyl-1,1'-phenylpropyl)-5-methyl-1H-pyrrol-2-yl]phenyl]oxy)-3-phenylpropanoate (1) (2R)-2-([4-[1-(4'-Propyl-1,1'-phenylpropyl)-5-methyl-1H-pyrrol-2-yl]phenyl]oxy)-3-phenylpropanoic acid The object compound was obtained from ethyl (2R)-2-([4-[1-(4'-propyl-1,1'-phenylpropyl)-5-methyl-1H-pyrrol-2- yl]phenyl]oxy)-3-phenylpropanoate as an oily substance, according to the similar manner to that of Example 70(1). yield: 98%

$^1$H-NMR (CDCl$_3$) δ; 0.97 (3H, m), 1.60 (2H, m), 2.22 (3H, s), 2.47 (2H, t, J=3.2 Hz), 2.56 (2H, t, J=3.2 Hz), 3.27 (2H, m), 5.91 (1H, d, J=3.4 Hz), 6.03 (1H, d, J=3.4 Hz), 6.70–6.87 (6H, m), 7.19–7.34 (7H, m).

IR (KBr) cm$^{-1}$; 3030, 2930, 2868, 1726, 1522, 1496, 1240, 1182, 833, 756.

(2) Sodium (2R)-2-([4-[1-(4'-propyl-1,1'-phenylpropyl)-5-methyl-1H-pyrrol-2-yl]phenyl]oxy)-3-phenylpropanoate The object compound was obtained from (2R)-2-([4-[1-(4'-propyl-1,1'-phenylpropyl)-5-methyl-1H-pyrrol-2-yl]phenyl]oxy)-3-phenylpropanoic acid as a solid, according to the similar manner to that of Example 70(2). yield: 60%

$^1$H-NMR (DMSO) δ; 0.91 (3H, m), 1.60 (2H, m), 1.78 (2H, m), 2.19 (3H, s), 2.58 (2H, m), 3.04 (2H, m), 3.46 (2H, m), 3.80 (2H, m), 4.43 (1H, m), 5.78 (2H, m), 6.74–7.58 (17H, m)

Example 87

Ethyl (2R)-2-([4-[1-(4-pentylphenyl)-5-methyl-1H-pyrrol-2-yl]phenyl]oxy)-3-phenylpropanoate (1) 1-(4-Pentylphenyl)-2-methyl-5-[4-[(phenylmethyl)oxy]phenyl]-1H-pyrrole A solution of 4-pentylphenylamine (1.0 g, 6.2 mmol), 1-(4-benzyloxyphenyl)-1,4-pentanedione (1.7 g, 6.02 mmol) and p-toluenesulfonic acid monohydrate (100 mg) in toluene (40 ml) was refluxed for 12 hours under heating and the solvent was removed under reduced pressure. The residue was purified by silica gel chromatography (hexane:ethyl acetate=20:1) to give the object compound as an oily substance. 1.76 g, (yield: 69%)

$^1$H-NMR (CDCl$_3$) δ; 0.88 (3H, t, J=7.0 Hz), 1.32 (4H, m), 1.63 (2H, m), 2.13 (3H, s), 2.62 (2H, t, J=7.4 Hz), 4.79 (2H, s), 6.05 (1H, d, J=3.3 Hz), 6.26 (1H, d, J=3.3 Hz), 6.73–7.56 (13H, m).

IR (KBr) cm$^{-1}$; 2928, 2858, 1522, 1392, 1240, 1026, 833, 760.

(2) 4-[1-(4-Pentylphenyl)-5-methyl-1H-pyrrol-2-yl]phenol

To a solution of 1-(4-pentylphenyl)-2-methyl-5-[4-[(phenylmethyl)oxy]phenyl]-1H-pyrrole (1.76 g, 4.3 mmol) in ethanol (150 ml) was added 10% palladium carbon (200 mg) and the mixture was stirred under hydrogen atmosphere. The insoluble matter was filtered out and the filtrate was concentrated to give the object compound as an oily substance. 1.38 g, (yield: 100%)

$^1$H-NMR (CDCl$_3$) δ; 0.88 (3H, t, J=7.0 Hz), 1.30 (4H, m), 1.58 (2H, m), 2.12 (3H, s), 2.61 (2H, t, J=7.2 Hz), 6.05 (1H, d, J=3.4 Hz), 6.25 (1H, d, J=3.4 Hz), 6.60 (2H, m), 6.90–7.25 (6H, m).

IR (KBr) cm$^{-1}$; 2928, 2857, 1514, 1395, 1261, 1172, 835, 762.

(3) Ethyl (2R)-2-([4-[1-(4-pentylphenyl)-5-methyl-1H-pyrrol-2-yl]phenyl]oxy)-3-phenylpropanoate A solution of 4-[1-(4-pentylphenyl)-5-methyl-1H-pyrrol-2-yl]phenol (1.37 g, 4.3 mmol), ethyl (S)-2-hydroxy-3-phenylpropanoate (1.0 g, 5.1 mmol), 1,1'-(azodicarbonyl)dipiperidine (1.29 g, 5.1 mmol) and triphenylphosphine (1.34 g, 5.1 mmol) in toluene (5 ml) was stirred at 80° C. for 12 hours. The mixrture was poured into water, extracted with ethyl acetate, washed with saturated brine and dried over magnesium sulfate anhydride. The solvent was removed under reduced pressure and the residue was purified by silica gel column chromatography (hexane:ethyl acetate=20:1) to give the object compound as an oily substance. 670 mg, (yield: 31%)

$^1$H-NMR (CDCl$_3$) δ; 0.88 (3H, t, J=7.0 Hz), 1.13 (3H, t, J=7.4 Hz), 1.26 (4H, m), 1.58 (2H, m), 2.10 (3H, s), 2.61 (2H, t, J=7.2 Hz), 3.19 (2H, m), 4.12 (2H, q, J=7.0 Hz), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm$^{-1}$; 2928, 2857, 1755, 1520, 1236, 1182, 1036, 833, 760.

Example 88

Sodium (2R)-2-([4-[1-(4-pentylphenyl)-5-methyl-1H-pyrrol-2-yl]phenyl]oxy)-3-phenylpropanoate (1) (2R)-2-([4-[1-(4-pentylphenyl)-5-methyl-1H-pyrrol-2-yl]phenyl]oxy)-3-phenylpropanoic acid To a mixed solution of ethyl (2R)-2-([4-[1-(4-pentylphenyl)-5-methyl-1H-pyrrol-2-yl]phenyl]oxy)-3-phenylpropanoate (670 mg, 1.35 mmol) in THF (15 ml) and methanol (7 ml) was added 1N aqueous potassium hydroxide (4.0 ml, 4.0 mmol) and the mixture was stirred for 1 hour at room temperature. The mixture was neutralized with 1N hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 621 mg, (yield: 99%)

$^1$H-NMR (CDCl$_3$) δ; 0.88 (3H, t, J=7.0 Hz), 1.26 (4H, m), 1.58 (2H, m), 2.10 (3H, s), 2.61 (2H, t, J=7.2 Hz), 3.19 (2H, m), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm$^{-1}$; 2928, 2857, 1726, 1518, 1238, 1181, 1084, 833, 760.

(2) Sodium (2R)-2-([4-[1-(4-pentylphenyl)-5-methyl-1H-pyrrol-2-yl]phenyl]oxy)-3-phenylpropanoate To a solution of (2R)-2-([4-[1-(4-pentylphenyl)-5-methyl-1H-pyrrol-2-yl]phenyl]oxy)-3-phenylpropanoic acid (621 mg, 1.33 mmol) in ethanol (10 ml) was added 1N sodium hydroxide-ethanol solution (1.3 ml, 1.3 mmol) and the mixture was concentrated. To the residue was added hexane to give the object compound as a solid. 460 mg, (yield: 71%)

$^1$H-NMR (DMSO) δ; 0.85 (3H, m), 1.26 (4H, m), 1.56 (2H, m), 2.00 (3H, s), 2.59 (2H, m), 2.86–3.14 (2H, m), 4.25 (1H, dd, J=9.2 Hz J=2.8 Hz), 5.94 (1H, d, J=3.0 Hz), 6.09 (1H, d, J=3.2 Hz), 6.50 (4H, d, J=8.8 Hz), 6.80 (4H, d, J=8.8 Hz), 7.00–7.29 (9H, m).

Elementary analysis for C$_{31}$H$_{32}$NO$_3$Na; Calculated: C, 74.98; H, 6.88; N, 2.73. Found: C, 75.61; H, 6.77; N, 2.69.

Example 89

Ethyl (2R)-2-([4-[1-(4-hexylphenyl)-5-methyl-1H-pyrrol-2-yl]phenyl]oxy)-3-phenylpropanoate (1) 1-(4-Hexylphenyl)-2-methyl-5-[4-[(phenylmethyl)oxy]phenyl]-1H-pyrrole The object compound was obtained from 4-hexylphenylamine as an oily substance, according to the similar manner to that of Example 87(1). yield: 71%

$^1$H-NMR (CDCl$_3$) δ; 0.88 (3H, t, J=7.0 Hz), 1.32 (6H, m), 1.63 (2H, m), 2.13 (3H, s), 2.62 (2H, t, J=7.4 Hz), 4.79 (2H, s), 6.05 (1H, d, J=3.3 Hz), 6.26 (1H, d, J=3.3 Hz), 6.73–7.56 (13H, m).

IR (KBr) cm$^{-1}$; 2928, 2858, 1522, 1392, 1240, 1026, 833, 760.

(2) 4-[1-(4-Hexylphenyl)-5-methyl-1H-pyrrol-2-yl]phenol

The object compound was obtained from 1-(4-hexylphenyl)-2-methyl-5-[4-[(phenylmethyl)oxy]phenyl]-1H-pyrrole as an oily substance, according to the similar manner to that of Example 87(2). yield:.100%

¹H-NMR (CDCl₃) δ; 0.88 (3H, t, J=7.0 Hz), 1.30 (6H, m), 1.58 (2H, m), 2.12 (3H, s), 2.61 (2H, t, J=7.2 Hz), 6.05 (1H, d, J=3.4 Hz), 6.25 (1H, d, J=3.4 Hz), 6.60 (2H, m), 6.90–7.25 (6H, m).

IR (KBr) cm⁻¹; 2928, 2857, 1514, 1395, 1261, 1172, 835, 762.

(3) Ethyl (2R)-2-([4-[1-(4-hexylphenyl)-5-methyl-1H-pyrrol-2-yl]phenyl]oxy)-3-phenylpropanoate The object compound was obtained from 4-[1-(4-hexylphenyl)-5-methyl-1H-pyrrol-2-yl]phenol as an oily substance, according to the similar manner to that of Example 87(3). yield: 46%

¹H-NMR (CDCl₃) δ; 0.88 (3H, t, J=7.0 Hz), 1.13 (3H, t, J=7.4 Hz), 1.26 (6H, m), 1.58 (2H, m), 2.10 (3H, s), 2.61 (2H, t, J=7.2 Hz), 3.19 (2H, m), 4.12 (2H, q, J=7.0 Hz), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm⁻¹; 2928, 2857, 1755, 1520, 1236, 1182, 1036, 833, 760.

Example 90

Sodium (2R)-2-([4-[1-(4-hexylphenyl)-5-methyl-1H-pyrrol-2-yl]phenyl]oxy)-3-phenylpropanoate (1) (2R)-2-([4-[1-(4-Hexylphenyl)-5-methyl-1H-pyrrol-2-yl]phenyl]oxy)-3-phenylpropanoic acid The object compound was obtained from ethyl (2R)-2-([4-[1-(4-hexylphenyl)-5-methyl-1H-pyrrol-2-yl]phenyl]oxy)-3-phenylpropanoate as an oily substance, according to the similar manner to that of Example 88(1). yield: 99%

¹H-NMR (CDCl₃) δ; 0.88 (3H, t, J=7.0 Hz), 1.26 (6H, m), 1.58 (2H, m), 2.10 (3H, s), 2.61 (2H, t, J=7.2 Hz), 3.19 (2H, m), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm⁻¹; 2928, 2857, 1726, 1518, 1238, 1181, 1084, 833, 760.

(2) Sodium (2R)-2-([4-[1-(4-hexylphenyl)-5-methyl-1H-pyrrol-2-yl]phenyl]oxy)-3-phenylpropanoate The object compound was obtained from (2R)-2-([4-[1-(4-hexylphenyl)-5-methyl-1H-pyrrol-2-yl]phenyl]oxy)-3-phenylpropanoic acid as an oily substance, according to the similar manner to that of Example 88(2). yield: 87%

¹H-NMR (DMSO) δ; 0.85 (3H, m), 1.26 (6H, m), 1.56 (2H, m), 2.00 (3H, s), 2.59 (2H, m), 3.14–2.86 (2H, m), 4.25 (1H, dd, J=9.2 Hz J=2.8 Hz), 5.94 (1H, d, J=3.0 Hz), 6.09 (1H, d, J=3.2 Hz), 6.50 (4H, d, J=8.8 Hz), 6.80 (4H, d, J=8.8 Hz), 7.00–7.29 (9H, m).

Elementary analysis for C₃₂H₃₄NO₃Na·0.5H₂O; Calculated: C, 74.98; H, 6.88; N, 2.73. Found: C, 75.61; H, 6.77; N, 2.69.

Example 91

Ethyl (2R)-2-([4-[1-(4-heptylphenyl)-5-methyl-1H-pyrrol-2-yl]phenyl]oxy)-3-phenylpropanoate (1) 1-(4-Heptylphenyl)-2-methyl-5-[4-[(phenylmethyl)oxy]phenyl]-1H-pyrrole The object compound was obtained from 4-heptylphenylamine as an oily substance, according to the similar manner to that of Example 87(1). yield: 66%

¹H-NMR (CDCl₃) δ; 0.88 (3H, t, J=7.0 Hz), 1.32 (8H, m), 1.63 (2H, m), 2.13 (3H, s), 2.62 (2H, t, J=7.4 Hz), 4.79 (2H, s), 6.05 (1H, d, J=3.3 Hz), 6.26 (1H, d, J=3.3 Hz), 6.73–7.56 (13H, m).

IR (KBr) cm⁻¹; 2928, 2858, 1522, 1392, 1240, 1026, 833, 760.

(2) 4-[1-(4-Heptylphenyl)-5-methyl-1H-pyrrol-2-yl]phenol

The object compound was obtained from 1-(4-heptylphenyl)-2-methyl-5-[4-[(phenylmethyl)oxy]phenyl]-1H-pyrrole as an oily substance, according to the similar manner to that of Example 87 (2). yield: 100%

¹H-NMR (CDCl₃) δ; 0.88 (3H, t, J=7.0 Hz), 1.30 (8H, m), 1.58 (2H, m), 2.12 (3H, s), 2.61 (2H, t, J=7.2 Hz), 6.05 (1H, d, J=3.4 Hz), 6.25 (1H, d, J=3.4 Hz), 6.60 (2H, m), 6.90–7.25 (6H, m).

IR (KBr) cm⁻¹; 2928, 2857, 1514, 1395, 1261, 1172, 835, 762.

(3) Ethyl (2R)-2-([4-[1-(4-heptylphenyl)-5-methyl-1H-pyrrol-2-yl]phenyl]oxy)-3-phenylpropanoate The object compound was obtained from 4-[1-(4-heptylphenyl)-5-methyl-1H-pyrrol-2-yl]phenol as an oily substance, according to the similar manner to that of Example 87(3). yield: 41%

¹H-NMR (CDCl₃) δ; 0.88 (3H, t, J=7.0 Hz), 1.13 (3H, t, J=7.4 Hz), 1.26 (8H, m), 1.58 (2H, m), 2.10 (3H, s), 2.61 (2H, t, J=7.2 Hz), 3.19 (2H, m), 4.12 (2H, q, J=7.0 Hz), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm⁻¹; 2928, 2857, 1755, 1520, 1236, 1182, 1036, 833, 760.

Example 92

Sodium (2R)-2-([4-[1-(4-heptylphenyl)-5-methyl-1H-pyrrol-2-yl]phenyl]oxy)-3-phenylpropanoate (1) (2R)-2-([4-[1-(4-Heptylphenyl)-5-methyl-1H-pyrrol-2-yl]phenyl]oxy)-3-phenylpropanoic acid The object compound was obtained from ethyl (2R)-2-([4-[1-(4-heptylphenyl)-5-methyl-1H-pyrrol-2-yl]phenyl]oxy)-3-phenylpropanoate as an oily substance, according to the similar manner to that of Example 88(1). yield: 98%

¹H-NMR (CDCl₃) δ; 0.88 (3H, t, J=7.0 Hz), 1.26 (8H, m), 1.58 (2H, m), 2.10 (3H, s), 2.61 (2H, t, J=7.2 Hz), 3.19 (2H, m), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm⁻¹; 2928, 2857, 1726, 1518, 1238, 1181, 1084, 833, 760.

(2) Sodium (2R)-2-([4-[1-(4-heptylphenyl)-5-methyl-1H-pyrrol-2-yl]phenyl]oxy)-3-phenylpropanoate The object compound was obtained from (2R)-2-([4-[1-(4-heptylphenyl)-5-methyl-1H-pyrrol-2-yl]phenyl]oxy)-3-phenylpropanoic acid as a solid, according to the similar manner to that of Example 88(2). yield: 73%

¹H-NMR (DMSO) δ; 0.85 (3H, m), 1.26 (8H, m), 1.56 (2H, m), 2.00 (3H, s), 2.59 (2H, m), 3.14–2.86 (2H, m), 4.25 (1H, dd, J=9.2 Hz J=2.8 Hz), 5.94 (1H, d, J=3.0 Hz), 6.09 (1H, d, J=3.2 Hz), 6.50 (4H, d, J=8.8 Hz), 6.80 (4H, d, J=8.8 Hz), 7.00–7.29 (9H, m).

Example 93

Ethyl (2R)-2-([4-[1-(4-octylphenyl)-5-methyl-1H-pyrrol-2-yl]phenyl]oxy)-3-phenylpropanoate (1) 1-(4-Octylphenyl)-2-methyl-5-[4-[(phenylmethyl)oxy]phenyl]-1H-pyrrole The object compound was obtained from 4-octylphenylamine as an oily substance, according to the similar manner to that of Example 87 (1). yield: 71%

¹H-NMR (CDCl₃) δ; 0.88 (3H, t, J=7.0 Hz), 1.32 (10H, m), 1.63 (2H, m), 2.13 (3H, s), 2.62 (2H, t, J=7.4 Hz), 4.79 (2H, s), 6.05 (1H, d, J=3.3 Hz), 6.26 (1H, d, J=3.3 Hz), 6.73–7.56 (13H, m).

IR (KBr) cm⁻¹; 2928, 2858, 1522, 1392, 1240, 1026, 833, 760.

(2) 4-[1-(4-Octylphenyl)-5-methyl-1H-pyrrol-2-yl]phenol

The object compound was obtained from 1-(4-octylphenyl)-2-methyl-5-[4-[(phenylmethyl)oxy]phenyl]-

1H-pyrrole as an oily substance, according to the similar manner to that of Example 87 (2). yield: 100%

$^1$H-NMR (CDCl$_3$) δ; 0.88 (3H, t, J=7.0 Hz), 1.30 (10H, m), 1.58 (2H, m), 2.12 (3H, s), 2.61 (2H, t, J=7.2 Hz), 6.05 (1H, d, J=3.4 Hz), 6.25 (1H, d, J=3.4 Hz), 6.60 (2H, m), 6.90–7.25 (6H, m).

IR (KBr) cm$^{-1}$; 2928, 2857, 1514, 1395, 1261, 1172, 835, 762.

(3) Ethyl (2R)-2-([4-[1-(4-octylphenyl)-5-methyl-1H-pyrrol-2-yl]phenyl]oxy)-3-phenylpropanoate The object compound was obtained from 4-[1-(4-octylphenyl)-5-methyl-1H-pyrrol-2-yl]phenol as an oily substance, according to the similar manner to that of Example 87(3). yield: 40%

$^1$H-NMR (CDCl$_3$) δ; 0.88 (3H, t, J=7.0 Hz), 1.13 (3H, t, J=7.4 Hz), 1.58 (2H, m), 1.26 (10H, m), 2.10 (3H, s), 2.61 (2H, t, J=7.2 Hz), 3.19 (2H, m), 4.12 (2H, q, J=7.0 Hz), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm$^{-1}$; 2928, 2857, 1755, 1520, 1236, 1182, 1036, 833, 760.

Example 94

Sodium (2R)-2-([4-[1-(4-octylphenyl)-5-methyl-1H-pyrrol-2-yl]phenyl]oxy)-3-phenylpropanoate (1) (2R)-2-([4-[1-(4-Octylphenyl)-5-methyl-1H-pyrrol-2-yl]phenyl]oxy)-3-phenylpropanoic acid The object compound was obtained from ethyl (2R)-2-([4-[1-(4-octylphenyl)-5-methyl-1H-pyrrol-2-yl]phenyl]oxy)-3-phenylpropanoate as an oily substance, according to the similar manner to that of Example 88(1). yield: 99%

$^1$H-NMR (CDCl$_3$) δ; 0.88 (3H, t, J=7.0 Hz), 1.26 (10H, m), 1.58 (2H, m), 2.10 (3H, s), 2.61 (2H, t, J=7.2 Hz), 3.19 (2H, m), 4.69 (1H, t, J=6.5 Hz), 6.03 (1H, d, J=3.4 Hz), 6.22 (1H, d, J=3.4 Hz), 6.58 (2H, m), 6.89–7.29 (11H, m).

IR (KBr) cm$^{-1}$; 2928, 2857, 1726, 1518, 1238, 1181, 1084, 833, 760.

(2) Sodium (2R)-2-([4-[1-(4-octylphenyl)-5-methyl-1H-pyrrol-2-yl]phenyl]oxy)-3-phenylpropanoate The object compound was obtained from (2R)-2-([4-[1-(4-octylphenyl)-5-methyl-1H-pyrrol-2-yl]phenyl]oxy)-3-phenylpropanoic acid as a solid, according to the similar manner to that of Example 88(2). yield: 87%

$^1$H-NMR (DMSO) δ; 0.85 (3H, m), 1.26 (10H, m), 1.56 (2H, m), 2.00 (3H, s), 2.59 (2H, m), 2.86–3.14 (2H, m), 4.25 (1H, dd, J=9.2 Hz J=2.8 Hz), 5.94 (1H, d, J=3.2 Hz), 6.09 (1H, d, J=3.2 Hz), 6.50 (4H, d, J=8.8 Hz), 6.80 (4H, d, J=8.8 Hz), 7.00–7.29 (9H, m).

Example 95

Ethyl (2R)-2-(4-[5-methyl-1-(tricyclo[3.3.1.1$^{3,7}$]dec-1-ylmethyl)-1H-pyrrol-2-yl]phenyl)oxy)-3-phenylpropanoate (1) 2-Methyl-5-[4-[(phenylmethyl)oxy]phenyl]-1-(tricyclo[3.3.1.1$^{3,7}$]dec-1-ylmethyl)-1H-pyrrole The object compound was obtained from adamantylmethylamine as an oily substance, according to the similar manner to that of Example 87 (1). yield: 44%

$^1$H-NMR (CDCl$_3$) δ; 1.00–1.82 (15H, m), 2.07 (2H, s), 2.34 (3H, s), 5.12 (2H, s), 5.96 (1H, d, J=3.2 Hz), 6.04 (1H, d, J=3.2 Hz), 7.00 (2H, d, J=7.0 Hz), 7.27 (2H, d, J=6.6 Hz), 7.34–7.47 (5H, m).

IR (KBr) cm$^{-1}$; 2901, 2845, 1524, 1452, 1244, 1024, 912, 835, 735.

(2) 4-[5-Methyl-1-(tricyclo[3.3.1.1$^{3,7}$]dec-1-ylmethyl)-1H-pyrrole-1H-pyrrol-2-yl]phenol The object compound was obtained from 2-methyl-5-[4-[(phenylmethyl)oxy]phenyl]-1-(tricyclo[3.3.1.1$^{3,7}$]dec-1-ylmethyl)-1H-pyrrole as an oily substance, according to the similar manner to that of Example 87(2). yield: 100%

$^1$H-NMR (CDCl$_3$) δ; 1.00–1.82 (15H, m), 1.80 (2H, s), 2.31 (3H, s), 2.61 (2H, t, J=7.2 Hz), 5.93 (1H, d, J=3.4 Hz), 6.01 (1H, d, J=3.4 Hz), 6.80 (2H, d, J=7.0 Hz), 7.16–7.22 (2H, m).

IR (KBr) cm$^{-1}$; 2905, 2849, 1524, 1450, 1223, 1101, 912, 742.

(3) Ethyl (2R)-2-(4-[5-methyl-1-(tricyclo[3.3.1.1$^{3,7}$]dec-1-ylmethyl)-1H-pyrrol-2-yl]phenyl)oxy)-3-phenylpropanoate The object compound was obtained from 4-[5-methyl-1-(tricyclo[3.3.1.1$^{3,7}$]dec-1-ylmethyl)-1H-pyrrole-1H-pyrrol-2-yl]phenol as an oily substance, according to the similar manner to that of Example 87(3). yield: 49%

$^1$H-NMR (CDCl$_3$) δ; 1.82–1.00 (18H, m), 1.78 (2H, s), 2.30 (3H, s), 3.27 (2H, m), 4.17 (2H, q, J=7.0 Hz), 4.82 (1H, t, J=6.5 Hz), 5.91 (1H, d, J=3.4 Hz), 5.97 (1H, d, J=3.4 Hz), 6.80 (2H, d, J=7.0 Hz), 7.17–7.33 (7H, m).

IR (KBr) cm$^{-1}$; 2903, 2849, 1755, 1734, 1524, 1481, 1226, 1180, 1032, 837, 760.

Example 96

Sodium (2R)-2-(4-[5-methyl-1-(tricyclo[3.3.1.1$^{3,7}$]dec-1-ylmethyl)-1H-pyrrol-2-yl]phenyl)oxy)-3-phenylpropanoate (1) (2R)-2-(4-[5-Methyl-1-(tricyclo[3.3.1.1$^{3,7}$]dec-1-ylmethyl)-1H-pyrrol-2-yl]phenyl)oxy)-3-phenylpropanoic acid The object compound was obtained from ethyl (2R)-2-(4-[5-methyl-1-(tricyclo[3.3.1.1$^{3,7}$]dec-1-ylmethyl)-1H-pyrrol-2-yl]phenyl)oxy)-3-phenylpropanoate as an oily substance, according to the similar manner to that of Example 88(1). yield: 98%

$^1$H-NMR (CDCl$_3$) δ; 1.00–1.82 (15H, m), 1.78 (2H, s), 2.30 (3H, s), 3.27 (2H, m), 4.82 (1H, t, J=6.5 Hz), 5.91 (1H, d, J=3.4 Hz), 5.97 (1H, d, J=3.4 Hz), 6.80 (2H, d, J=7.0 Hz), 7.17–7.33 (7H, m).

IR (KBr) cm$^{-1}$; 2905, 2850, 1728, 1522, 1236, 1178, 1080, 837, 760.

(2) Sodium (2R)-2-(4-[5-methyl-1-(tricyclo[3.3.1.1$^{3,7}$]dec-1-ylmethyl)-1H-pyrrol-2-yl]phenyl)oxy)-3-phenylpropanoate The object compound was obtained from (2R)-2-(4-[5-methyl-1-(tricyclo[3.3.1.1$^{3,7}$]dec-1-ylmethyl)-1H-pyrrol-2-yl]phenyl)oxy)-3-phenylpropanoic acid as a solid, according to the similar manner to that of Example 88 (2). yield: 95%

$^1$H-NMR (DMSO) δ; 1.00–1.78 (15H, m), 2.00 (3H, s), 2.86–3.14 (2H, m), 4.31 (1H, dd, J=9.2 Hz J=2.8 Hz), 5.78 (2H, s), 6.74 (2H, d, J=7.6 Hz), 7.05–7.31 (7H, m)

Elementary analysis for C$_{31}$H$_{34}$NO$_3$Na·1.5H$_2$O; Calculated: C, 71.79; H, 7.19; N, 2.70. Found: C, 71.94; H, 7.16; N, 2.55.

Example 97

Ethyl (2R)-2-([4-[1-(2,3-dihydro-1H-inden-2-yl)-5-methyl-1H-pyrrol-2-yl]phenyl]oxy)-3-phenylpropanoate (1) 1-(2,3-Dihydro-1H-inden-2-yl)-2-methyl-5-[4-[(phenylmethyl)oxy]phenyl]-1H-pyrrole The object compound was obtained from 2,3-dihydro-1H-inden-2-ylamine as an oily substance, according to the similar manner to that of Example 87(1). yield: 44%

¹H-NMR (CDCl₃) δ; 2.34 (3H, s), 3.39 (4H, m), 5.12 (2H, s), 5.96 (1H, d, J=3.4 Hz), 6.04 (1H, d, J=3.4 Hz), 7.00 (2H, d, J=7.0 Hz), 7.27 (2H, d, J=7.0 Hz), 7.34–7.47 (5H, m).

IR (KBr) cm⁻¹; 2901, 2845, 1524, 1452, 1244, 1024, 912, 835, 735.

(2) 4-[1-(2,3-Dihydro-1H-inden-2-yl)-5-methyl-1H-pyrrole-1H-pyrrol-2-yl]phenol

The object compound was obtained from 1-(2,3-dihydro-1H-inden-2-yl)-2-methyl-5-[4-[(phenylmethyl)oxy]phenyl]-1H-pyrrole as an oily substance, according to the similar manner to that of Example 87(2). yield: 100%

¹H-NMR (CDCl₃) δ; 2.24 (3H, s), 3.39 (4H, m), 5.21 (1H, m), 5.98 (1H, d, J=3.6 Hz), 6.02 (1H, d, J=3.6 Hz), 6.83 (2H, d, J=8.7 Hz), 7.19–7.29 (6H, m).

IR (KBr) cm⁻¹; 2928, 1526, 1485, 1388, 1261, 1170, 839, 745.

(3) Ethyl (2R)-2-([4-[1-(2,3-dihydro-1H-inden-2-yl)-5-methyl-1H-pyrrol-2-yl]phenyl]oxy)-3-phenylpropanoate The object compound was obtained from 4-[1-(2,3-dihydro-1H-inden-2-yl)-5-methyl-1H-pyrrole-1H-pyrrol-2-yl]phenol as an oily substance, according to the similar manner to that of Example 87(3). yield: 40%

¹H-NMR (CDCl₃) δ; 1.20 (3H, m), 2.22 (3H, s), 3.23–3.39 (4H, m), 4.19 (2H, q, J=7.0 Hz), 4.77 (1H, t, J=6.5 Hz), 5.18 (1H, m), 5.98 (1H, d, J=3.6 Hz), 6.02 (1H, d, J=3.6 Hz), 6.83 (2H, d, J=8.7 Hz), 7.19–7.34 (11H, m).

IR (KBr) cm⁻¹; 2978, 1753, 1522, 1483, 1389, 1238, 1030, 837, 747.

Example 98

Sodium (2R)-2-([4-[1-(2,3-dihydro-1H-inden-2-yl)-5-methyl-1H-pyrrol-2-yl]phenyl]oxy)-3-phenylpropanoate (1) (2R)-2-([4-[1-(2,3-Dihydro-1H-inden-2-yl)-5-methyl-1H-pyrrol-2-yl]phenyl]oxy)-3-phenylpropanoic acid The object compound was obtained from ethyl (2R)-2-([4-[1-(2,3-dihydro-1H-inden-2-yl)-5-methyl-1H-pyrrol-2-yl]phenyl]oxy)-3-phenylpropanoate as an oily substance, according to the similar manner to that of Example 88 (1). yield: 97%

¹H-NMR (CDCl₃) δ; 2.22 (3H, s), 3.23–3.39 (4H, m), 4.77 (1H, t, J=6.9 Hz), 5.18 (1H, m), 5.98 (1H, d, J=3.6 Hz), 6.02 (1H, d, J=3.6 Hz), 6.83 (2H, d, J=8.4 Hz), 7.19–7.34 (11H, m).

IR (KBr) cm⁻¹; 3030, 2928, 1725, 1521, 1238, 912, 745.

(2) Sodium (2R)-2-([4-[1-(2,3-dihydro-1H-inden-2-yl)-5-methyl-1H-pyrrol-2-yl]phenyl]oxy)-3-phenylpropanoate The object compound was obtained from (2R)-2-([4-[1-(2,3-dihydro-1H-inden-2-yl)-5-methyl-1H-pyrrol-2-yl]phenyl]oxy)-3-phenylpropanoic acid as a solid, according to the similar manner to that of Example 88(1). yield: 92%

¹H-NMR (DMSO) δ; 2.00 (3H, s), 3.14–2.86 (2H, m), 4.31 (1H, dd, J=9.2 Hz J=2.8 Hz), 5.78 (2H, s), 6.74 (2H, d, J=7.6 Hz), 7.05–7.31 (7H, m).

Example 99

Ethyl (2R)-2-{4-[5-methyl-1-(4-pentylphenylmethyl)-1H-pyrrol-2-yl]phenoxy}-3-phenylpropanoate (1) 4-Pentylphenylbenzylalcohol To a solution of lithium aluminium hydride (3.95 g, 104 mmol) in THF (50 ml) was added a solution of 4-pentylbenzoic acid (10.0 g, 52 mmol) in THF (200 ml) and the mixture was refluxed at 0° C. for 3 hours. The reaction mixture was cooled to 0° C., water (10 ml) was added carefully to the reaction mixture, then 1N aqueous sodium hydroxide (30 ml) was added to the mixture. The insoluble matter was filtered out and the filtrate was concentrated to give the object compound as an oily substance. 8.76 g, (yield 94%)

¹H-NMR (CDCl₃) δ; 0.88 (3H, t, J=6.2 Hz), 1.35 (4H, m), 1.56 (2H, m), 2.60 (2H, t, J=7.4 Hz), 4.64 (2H, s), 7.16 (2H, d, J=8.0 Hz), 7.27 (2H, d, J=8.0 Hz).

IR (KBr) cm⁻¹; 2930, 1458, 1202, 1016, 742.

(2) 4-Pentylphenylmethyl mesylate

To a solution of 4-pentylphenylbenzylalcohol (8.76 g, 49.0 mmol) and triethylamine (7.7 ml, 55 mmol) in THF (100 ml) was added mesyl chloride (3.95 ml, 51 mmol) at 0° C. and the mixture was stirred at room temperature for 30 minutes. The reaction mixture was poured into ice, extracted with ethyl acetate, the organic layer was washed with saturated brine and dried over magnesium sulfate anhydride. The organic layer was concentrated to give the object compound as an oily substance. 13.8 g, (yield 100%)

¹H-NMR (CDCl₃) δ; 0.88 (3H, m), 1.35 (4H, m), 1.56 (2H, m), 2.86 (3H, s), 5.21 (2H, s), 7.26 (4H, m).

IR (KBr) cm⁻¹; 2932, 1354, 1175, 925, 820.

(3) 2-(4-Pentylphenylmethyl)-1H-isoindol-1,3-(2H)-dione

A solution of 4-pentylphenylmethyl mesylate (6.97 g, 27.2 mmol) and potassium phthalimide (5.03 g, 27.2 mmol) in DMF (40 ml) was stirred at 80° C. for 3 hours. The reaction mixture was poured into ice water and extracted with ethyl acetate. The organic layer was washed with saturated brine and dried over magnesium sulfate anhydride, and the organic layer was concentrated. The residue was purified by silica gel column chromatography (hexane:ethyl acetate=5:1) to give the object compound as crystals. 7.03 g, (yield 84%)

¹H-NMR (CDCl₃) δ; 0.88 (3H, m), 1.26 (4H, m), 1.61 (2H, m), 2.55 (2H, t, J=7.2 Hz), 4.81 (2H, s), 7.11–7.36 (4H, m), 7.64–7.85 (4H, m).

IR (KBr) cm⁻¹; 2928, 1712, 1392, 1348, 1101, 937, 715.

(4) 4-Pentylphenylmethyl amine

A solution of 2-(4-pentylphenylmethyl)-1H-isoindol-1,3-(2H)-dione (7.03 g, 23 mmol) and hydrazinemonohydrate (1.7 ml, 35 mmol) in ethanol (100 ml) was refluxed for 3 hours. The reaction mixture was dissolved into 5N aqueous sodium hydroxide and extracted with ethyl acetate. The organic layer was washed with saturated brine and dried over magnesium sulfate anhydride. The organic layer was concentrated to give the object compound as an oily substance. 4.02 g, (yield 99%)

¹H-NMR (CDCl₃) δ; 0.88 (3H, m), 1.26 (4H, m), 1.56 (2H, m), 2.17 (2H, s), 2.58 (2H, d, J=7.2 Hz), 3.02 (2H, s), 7.15 (4H, s).

IR (KBr) cm⁻¹; 2928, 1485, 1310, 1019, 818, 744.

(5) 2-(4-Benzyloxyphenyl)-5-methyl-1-(4-pentylphenylpropyl)-1H-pyrrole

A solution of 4-pentylphenylmethylamine (2.0 g, 11.3 mmol), 1-(4-benzyloxyphenyl)-1,4-pentanedione (3.2 g, 11.2 mmol) and p-toluenesulfonic acid monohydrate (100 mg) in toluene (30 ml) was refluxed for 12 hours under heating and the solvent was removed under reduced pressure. The residue was purified by silica gel chromatography (hexane:ethyl acetate=20:1) to give the object compound as an oily substance. 3.09 g, (yield 65%)

¹H-NMR (CDCl₃) δ; 0.88 (3H, m), 1.29 (4H, m), 1.57 (2H, m), 2.13 (3H, s), 2.56 (2H, t, J=3.2 Hz), 5.04 (2H, s), 5.06 (2H, s), 6.01 (1H, d, J=3.3 Hz), 6.14 (1H, d, J=3.3 Hz), 6.81–7.56 (13H, m).

IR (KBr) cm⁻¹; 2928, 2857, 1528, 1454, 1240, 1020, 835, 750.

(6) 4-[5-Methyl-1-(4-pentylphenylmethyl)-1H-pyrrol-2-yl]phenol

To a solution of 2-(4-benzyloxyphenyl)-5-methyl-1-(4-pentylphenylpropyl)-1H-pyrrole (3.09 g, 7.3 mmol) in ethanol (200 ml) was added 10% palladium carbon (400 mg) and the mixture was stirred under hydrogen atmosphere. The insoluble matter was filtered out and the filtrate was concentrated to give the object compound as an oily substance. 2.45 g, (yield 100%)

$^1$H-NMR (CDCl$_3$) δ; 0.89 (3H, m), 1.28 (4H, m), 1.58 (2H, m), 2.13 (3H, s), 2.56 (2H, t, J=3.2 Hz), 3.89 (1H, s), 5.04 (2H, s), 6.00 (1H, d, J=3.4 Hz), 6.15 (1H, d, J=3.4 Hz), 6.72–6.84 (4H, m), 7.07–7.26 (4H, m).

IR (KBr) cm$^{-1}$; 2930, 2857, 1526, 1400, 1259, 1020, 839, 760.

(7) Ethyl (2R)-2-{4-[5-methyl-1-(4-pentylphenylmethyl)-1H-pyrrol-2-yl]phenoxy}-3-phenylpropanoate A solution of 4-[5-methyl-1-(4-pentylphenylmethyl)-1H-pyrrol-2-yl]phenol (1.5 g, 4.5 mmol), ethyl (S)-2-hydroxy-3-phenylpropanoate (1.3 g, 6.75 mmol), 1,1'-(azodicarbonyl)dipiperidine (1.7 g, 6.75 mmol) and triphenylphosphine (1.8 g, 6.75 mmol) in toluene (7 ml) was stirred at 80° C. for 12 hours. The reaction solution was poured into water and extracted with ethyl acetate. The extract was washed with saturated brine and dried over magnesium sulfate anhydride. The solvent was removed under reduced pressure and the residue was purified by silica gel column chromatography (hexane:ethyl acetate=15:1) to give the object compound as an oily substance. 1.12 g, (yield 49%)

$^1$H-NMR (CDCl$_3$) δ; 0.88 (3H, m), 1.26 (7H, m), 1.58 (2H, m), 2.11 (3H, s), 2.56 (2H, t, J=3.2 Hz), 3.22 (2H, m), 4.15 (2H, q, J=7.2 Hz), 4.75 (1H, t, J=7.2 Hz), 5.01 (2H, s), 5.99 (1H, d, J=3.4 Hz), 6.11 (1H, d, J=3.4 Hz), 6.74–6.81 (4H, m), 7.07–7.30 (9H, m).

IR (KBr) cm$^{-1}$; 2930, 2857, 1755, 1523, 1238, 1182, 1030, 837, 760.

Example 100

Sodium (2R)-2-{4-[5-methyl-1-(4-pentylphenylpropyl)-1H-pyrrol-2-yl]phenoxy}-3-phenylpropanoate (1) (2R)-2-{4-[5-methyl-1-(4-pentylphenylpropyl)-1H-pyrrol-2-yl]phenoxy}-3-phenylpropanoic acid To a mixed solution of ethyl (2R)-2-{4-[5-methyl-1-(4-pentylphenylpropyl)-1H-pyrrol-2-yl]phenoxy}-3-phenylpropanoate (1.12 g, 2.20 mmol) in THF (20 ml) and methanol (10 ml) was added 1N aqueous potassium hydroxide (6.6 ml, 6.6 mmol) and the mixture was stirred for 1 hour at room temperature. The reaction solution was neutralized with 1N aqueous hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 1.00 g, (yield 94%)

$^1$H-NMR (CDCl$_3$) δ; 0.88 (3H, m), 1.26 (4H, m), 1.60 (2H, m), 1.87 (2H, s), 2.22 (3H, s), 2.47 (2H, t, J=3.2 Hz), 2.56 (2H, t, J=3.2 Hz), 3.27 (2H, m), 3.86–4.00 (4H, m), 4.81 (1H, t, J=7.2 Hz), 5.91 (1H, d, J=3.4 Hz), 6.03 (1H, d, J=3.4 Hz), 6.70–6.87 (6H, m), 7.19–7.34 (7H, m).

(2) Sodium (2R)-2-{4-[5-methyl-1-(4-pentylphenylpropyl)-1H-pyrrol-2-yl]phenoxy}-3-phenylpropanoate To a solution of (2R)-2-{4-[5-methyl-1-(4-pentylphenylpropyl)-1H-pyrrol-2-yl]phenoxy}-3-phenylpropanoic acid (1.00 g, 2.08 mmol) in ethanol (20 ml) was added 1N sodium hydroxide-ethanol solution (2.04 ml, 2.04 mmol) and the mixture was concentrated. To the residue was added hexane to give the object compound as a solid. 730 mg, (yield 70%)

$^1$H-NMR (DMSO) δ; 0.84 (3H, m), 1.25 (4H, m), 1.52 (2H, m), 2.03 (3H, s), 2.50 (2H, m), 3.14–2.86 (2H, m), 4.25 (1H, dd, J=9.2 Hz J=2.8 Hz), 5.03 (2H, s), 5.87 (1H, d, J=3.0 Hz), 5.94 (1H, d, J=3.2 Hz), 6.70 (4H, t, J=9.2 Hz), 7.00–7.29 (9H, m).

Elementary analysis for C$_{32}$H$_{34}$NO$_3$Na-0.5H$_2$O; Calculated: C, 74.98; H, 6.88; N, 2.73. Found: C, 75.27; H, 6.54; N, 2.56.

Example 101

Ethyl (2R)-2-{4-[1-(4-hexylphenylmethyl)-5-methyl-1H-pyrrol-2-yl]phenoxy}-3-phenylpropanoate (1) 4-Hexylphenylmethylalcohol The object compound was obtained from 4-hexylbenzoic acid as an oily substance, according to the similar manner to that of Example 99 (1). yield: 100%

$^1$H-NMR (CDCl$_3$) δ; 0.88 (3H, t, J=6.2 Hz), 1.35 (6H, m), 1.60 (2H, m), 2.60 (2H, t, J=7.4 Hz), 4.64 (2H, s), 7.16 (2H, d, J=8.0 Hz), 7.27 (2H, d, J=8.0 Hz).

IR (KBr) cm$^{-1}$; 2928, 1458, 1201, 1012, 810.

(2) 3-(4-Hexylphenyl)propyl mesylate

The object compound was obtained from 4-hexylphenylmethyl alcohol as an oily substance, according to the similar manner to that of Example 99(2). yield: 100%

$^1$H-NMR (CDCl$_3$) δ; 0.88 (3H, m), 1.26 (6H, m), 1.60 (2H, m), 2.93 (3H, s), 5.21 (2H, s), 7.20–7.35 (4H, m).

IR (KBr) cm$^{-1}$; 2928, 2857, 1466, 1354, 1174, 928, 824.

(3) 2-(4-Hexylphenylmethyl)-1H-isoindol-1,3-(2H)-dione

The object compound was obtained from 3-(4-hexylphenyl)propyl mesylate as an oily substance, according to the similar manner to that of Example 99(3). yield: 98%

$^1$H-NMR (CDCl$_3$) δ; 0.88 (3H, m), 1.26 (6H, m), 1.56 (2H, m), 2.55 (2H, t, J=7.2 Hz), 4.00 (2H, s), 7.10–7.34 (4H, m), 7.66–7.85 (4H, m).

IR (KBr) cm$^{-1}$; 2928, 2855, 1717, 1458, 1392, 1346, 1082, 937, 715.

(4) 3-(4-Hexylphenyl)methylamine

The object compound was obtained from 2-(4-hexylphenylmethyl)-1H-isoindol-1,3-(2H)-dione as an oily substance, according to the similar manner to that of Example 99(4). yield: 100%

$^1$H-NMR (CDCl$_3$) δ; 0.88 (3H, m), 1.28 (6H, m), 1.55 (2H, m), 1.99 (2H, s), 2.58 (2H, t, J=7.2 Hz), 3.81 (2H, s), 7.12 (4H, m).

IR (KBr) cm$^{-1}$; 2926, 2854, 1483, 1371, 1309, 1019, 818.

(5) 2-(4-Benzyloxyphenyl)-1-(4-hexylphenylmethyl)-5-methyl-1H-pyrrole

The object compound was obtained from 3-(4-hexylphenyl)methylamine as an oily substance, according to the similar manner to that of Example 99(5). yield: 66%

$^1$H-NMR (CDCl$_3$) δ; 0.88 (3H, m), 1.26 (6H, m), 1.58 (2H, m), 2.13 (3H, s), 2.56 (2H, t, J=3.2 Hz), 5.04 (2H, s), 5.05 (2H, s), 6.00 (1H, d, J=3.4 Hz), 6.14 (1H, d, J=3.4 Hz), 6.80–7.44 (13H, m).

IR (KBr) cm$^{-1}$; 2928, 2854, 1523, 1242, 912, 743.

(6) 4-[1-(4-Hexylphenylmethyl)-5-methyl-1H-pyrrol-2-yl]phenol

The object compound was obtained from 2-(4-benzyloxyphenyl)-1-(4-hexylphenylmethyl)-5-methyl-1H-pyrrole as an oily substance, according to the similar manner to that of Example 99(6). yield: 100%

¹H-NMR (CDCl₃) δ; 0.88 (3H, m), 1.26 (6H, m), 1.58 (2H, m), 2.12 (3H, s), 2.56 (2H, t, J=3.2 Hz), 3.75 (1H, s), 5.04 (2H, s), 6.01 (1H, d, J=3.4 Hz), 6.13 (1H, d, J=3.4 Hz), 6.70–6.83 (4H, m), 7.07–7.26 (4H, m).
IR (KBr) cm⁻¹; 2928, 2857, 1525, 1261, 840, 760.
(7) Ethyl (2R)-2-{4-[1-(4-hexylphenylmethyl)-5-methyl-1H-pyrrol-2-yl]phenoxy}-3-phenylpropanoate The object compound was obtained from 4-[1-(4-hexylphenylmethyl)-5-methyl-1H-pyrrol-2-yl]phenol as an oily substance, according to the similar manner to that of Example 99(7). yield: 41%
¹H-NMR (CDCl₃) δ; 0.88 (3H, m), 1.26 (9H, m), 1.57 (2H, m), 2.11 (3H, s), 2.56 (2H, t, J=3.2 Hz), 3.23 (2H, m), 4.15 (2H, q, J=7.2 Hz), 4.74 (1H, t, J=7.2 Hz), 5.01 (2H, s), 5.99 (1H, d, J=3.4 Hz), 6.11 (1H, d, J=3.4 Hz), 6.73–7.06 (4H, m), 7.10–7.30 (9H, m).
IR (KBr) cm⁻¹; 2928, 2855, 1753, 1523, 1238, 1182, 1028, 837, 758.

Example 102

Sodium (2R)-2-{4-[1-(4-hexylphenylmethyl)-5-methyl-1H-pyrrol-2-yl]phenoxy}-3-phenylpropanoate (1) (2R)-2-{4-[1-(4-Hexylphenylmethyl)-5-methyl-1H-pyrrol-2-yl]phenoxy}-3-phenylpropanoic acid The object compound was obtained from ethyl (2R)-2-{4-[1-(4-hexylphenylmethyl)-5-methyl-1H-pyrrol-2-yl]phenoxy}-3-phenylpropanoate as an oily substance, according to the similar manner to that of Example 100(1). yield: 99%
¹H-NMR (CDCl₃) δ; 0.88 (3H, m), 1.26 (6H, m), 1.58 (2H, m), 2.11 (3H, s), 2.56 (2H, t, J=3.2 Hz), 3.25 (2H, m), 4.80 (1H, t, J=7.2 Hz), 5.02 (2H, s), 5.99 (1H, d, J=3.4 Hz), 6.11 (1H, d, J=3.4 Hz), 6.75–6.81 (4H, m), 7.07–7.30 (9H, m).
IR (KBr) cm⁻¹; 2930, 2856, 1728, 1524, 1238, 912, 748.
(2) Sodium (2R)-2-{4-[1-(4-hexylphenylmethyl)-5-methyl-1H-pyrrol-2-yl]phenoxy}-3-phenylpropanoate The object compound was obtained from (2R)-2-{4-[1-(4-hexylphenylmethyl)-5-methyl-1H-pyrrol-2-yl]phenoxy}-3-phenylpropanoic acid as a solid, according to the similar manner to that of Example 100(2). yield: 77%
¹H-NMR (DMSO) δ; 0.84 (3H, m), 1.25 (6H, m), 1.51 (2H, m), 2.03 (3H, s), 2.50 (2H, m), 2.87–3.15 (2H, m), 4.25 (1H, dd, J=9.6 Hz J=3.2 Hz), 5.03 (2H, s), 5.87 (1H, d, J=3.4 Hz), 5.94 (1H, d, J=3.2 Hz), 6.75 (4H, t, J=8.0 Hz), 7.04–7.29 (9H, m).
Elementary analysis for C₃₃H₃₆NO₃Na·0.5H₂O; Calculated: C, 75.26; H, 7.08; N, 2.66. Found: C, 75.01; H, 6.74; N, 2.44.

Example 103

Ethyl (2R)-2-{4-[1-(4-cyclohexylphenylmethyl)-5-methyl-1H-pyrrol-2-yl]phenoxy}-3-phenylpropanoate (1) 4-Cyclohexylphenylmethyl alcohol The object compound was obtained from 4-cyclohexyl benzoic acid as an oily substance, according to the similar manner to that of Example 99(1). yield: 100%
¹H-NMR (CDCl₃) δ; 1.22–1.89 (10H, m), 2.54 (1H, m), 4.65 (2H, s), 7.19 (2H, d, J=8.0 Hz), 7.29 (2H, d, J=8.0 Hz).
IR (KBr) cm⁻¹; 3270, 2926, 2851, 1449, 1001, 800.
(2) 3-(4-Cyclohexylphenyl)methyl mesylate The object compound was obtained from 4-cyclohexylphenylmethyl alcohol as an oily substance, according to the similar manner to that of Example 99(2). yield: 100%
¹H-NMR (CDCl3) δ; 1.22–1.89 (10H, m), 2.54 (1H, m), 2.93 (3H, s), 5.21 (2H, s), 7.20–7.35 (4H, m).
IR (KBr) cm⁻¹; 3025, 2924, 2851, 1449, 1354, 1175, 929, 816.
(3) 2-(4-Cyclohexylphenylmethyl)-1H-isoindol-1,3-(2H)-dione The object compound was obtained from 3-(4-cyclohexylphenyl)methyl mesylate as an oily substance, according to the similar manner to that of Example 99(3). yield: 96%
¹H-NMR (CDCl₃) δ; 1.22–1.83 (10H, m), 2.45 (1H, m), 4.01 (2H, s), 7.13–7.65 (4H, m), 7.67–7.88 (4H, m).
IR (KBr) cm⁻¹; 3057, 2926, 2851, 1717, 1392, 1346, 1084 939, 716.
(4) 3-(4-Cyclohexylphenyl)methylamine The object compound was obtained from 2-(4-cyclohexylphenylmethyl)-1H-isoindol-1,3-(2H)-dione as an oily substance, according to the similar manner to that of Example 99(4). yield: 88%
¹H-NMR (CDCl₃) δ; 1.48 (5H, m), 1.77 (5H, m), 2.13 (2H, s), 2.48 (1H, m), 3.81 (2H, s), 7.21 (4H, m)
IR (KBr) cm⁻¹; 2922, 2851, 1448, 1383, 1319, 912, 825, 743.
(5) 2-(4-Benzyloxyphenyl)-1-(4-cyclohexylphenylmethyl)-5-methyl-1H-pyrrole The object compound was obtained from 3-(4-cyclohexylphenyl)methylamine as an oily substance, according to the similar manner to that of Example 99(5). yield: 60%
¹H-NMR (CDCl₃) δ; 1.21–1.83 (10H, m), 2.13 (3H, s), 2.46 (1H, m), 5.04 (2H, s), 5.05 (2H, s), 6.00 (1H, d, J=3.4 Hz), 6.14 (1H, d, J=3.4 Hz), 6.81–7.44 (13H, m).
IR (KBr) cm⁻¹; 2924, 2851, 1522, 1242, 1020, 835, 733.
(6) 4-[1-(4-Cyclohexylphenylmethyl)-5-methyl-1H-pyrrol-2-yl]phenol The object compound was obtained from 2-(4-benzyloxyphenyl)-1-(4-cyclohexylphenylmethyl)-5-methyl-1H-pyrrole as an oily substance, according to the similar manner to that of Example 99(6). yield: 100%
¹H-NMR (CDCl₃) δ; 1.33–1.49 (5H, m), 1.71–1.86 (5H, m), 2.12 (3H, s), 2.45 (1H, m), 5.04 (2H, s), 6.01 (1H, d, J=3.4 Hz), 6.13 (1H, d, J=3.4 Hz), 6.73–6.84 (4H, m), 7.10–7.18 (4H, m).
IR (KBr) cm⁻¹; 2926, 2851, 1524, 1446, 1260, 1171, 840, 762.
(7) Ethyl (2R)-2-{4-[1-(4-cyclohexylphenylmethyl)-5-methyl-1H-pyrrol-2-yl]phenoxy}-3-phenylpropanoate The object compound was obtained from 4-[1-(4-cyclohexylphenylmethyl)-5-methyl-1H-pyrrol-2-yl]phenol as an oily substance, according to the similar manner to that of Example 99(7). yield: 40%
¹H-NMR (CDCl₃) δ; 1.61–1.85 (13H, m), 2.11 (3H, s), 2.45 (1H, m), 3.23 (2H, m), 4.15 (2H, q, J=7.2 Hz), 4.74 (1H, t, J=7.2 Hz), 5.01 (2H, s), 5.99 (1H, d, J=3.4 Hz), 6.11 (1H, d, J=3.4 Hz), 6.73–7.08 (4H, m), 7.12–7.30 (9H, m).
IR (KBr) cm⁻¹; 2928, 2851, 1755, 1521, 1280, 1181, 1030, 837, 760.

Example 104

Sodium (2R)-2-{4-[1-(4-hexylphenylmethyl)-5-methyl-1H-pyrrol-2-yl]phenoxy}-3-phenylpropanoate (1) (2R)-2-{4-[1-(4-Cyclohexylphenylmethyl)-5-methyl-1H-pyrrol-2-yl]phenoxy}-3-phenylpropanoic acid The object compound was obtained from ethyl (2R)-2-{4-[1-(4-cyclohexylphenylmethyl)-5-methyl-1H-pyrrol-2-yl]phenoxy}-3-phenylpropanoate as an oily substance, according to the similar manner to that of Example 100(1). yield: 95%

¹H-NMR (CDCl₃) δ; 1.24–1.88 (10H, m), 2.11 (3H, s), 2.46 (1H, m), 3.25 (2H, m), 4.80 (1H, t, J=7.2 Hz), 5.01 (2H, s), 5.99 (1H, d, J=3.4 Hz), 6.11 (1H, d, J=3.4 Hz), 6.75–6.82 (4H, m), 7.09–7.29 (9H, m).

IR (KBr) cm⁻¹; 2926, 2851, 1726, 1522, 1236, 912, 743.

(2) Sodium (2R)-2-{4-[1-(4-hexylphenylmethyl)-5-methyl-1H-pyrrol-2-yl]phenoxy}-3-phenylpropanoate The object compound was obtained from (2R)-2-{4-[1-(4-cyclohexylphenylmethyl)-5-methyl-1H-pyrrol-2-yl]phenoxy}-3-phenylpropanoic acid as a solid, according to the similar manner to that of Example 100(2). yield: 96%

¹H-NMR (DMSO) δ; 1.33 (5H, m), 1.73 (5H, m), 2.03 (3H, s), 2.42 (1H, m), 2.87–3.15 (2H, m), 4.25 (1H, dd, J=9.2 Hz J=3.0 Hz), 5.03 (2H, s), 5.87 (1H, d, J=3.4 Hz), 5.94 (1H, d, J=3.4 Hz), 6.75 (4H, t, J=8.6 Hz), 7.01–7.29 (9H, m)

Elementary analysis for $C_{33}H_{34}NO_3Na\cdot H_2O$; Calculated: C, 74.27; H, 6.80; N, 2.62. Found: C, 74.02; H, 6.74; N, 2.42.

Example 105

Ethyl (2R)-2-{4-[1-(1,1'-biphenyl-4-ylmethyl)-5-methyl-1H-pyrrol-2-yl]phenoxy}-3-phenylpropanoate (1) 1,1'-Biphenyl-4-methylalcohol The object compound was obtained from 4-phenylbenzoic acid as an oily substance, according to the similar manner to that of Example 99(1). yield: 100%

¹H-NMR (CDCl₃) δ; 1.22–1.89 (10H, m), 2.54 (1H, m), 4.65 (2H, s), 7.19 (2H, d, J=8.0 Hz), 7.29 (2H, d, J=8.0 Hz).

IR (KBr) cm⁻¹; 3270, 2926, 2851, 1449, 1001, 800.

(2) 1,1'-Biphenyl-4-methyl mesylate

The object compound was obtained from 1,1'-biphenyl-4-methyl alcohol as an oily substance, according to the similar manner to that of Example 99(2). yield: 100%

¹H-NMR (CDCl₃) δ; 1.22–1.89 (10H, m), 2.54 (1H, m), 2.93 (3H, s), 5.21 (2H, s), 7.20–7.35 (4H, m).

IR (KBr) cm⁻¹; 3025, 2924, 2851, 1449, 1354, 1175, 929, 816.

(3) 2-(1,1'-Biphenyl-4-methyl)-1H-isoindol-1,3-(2H)-dione

The object compound was obtained from 1,1'-biphenyl-4-methyl mesylate as an oily substance, according to the similar manner to that of Example 99(3). yield: 96%

¹H-NMR (CDCl₃) δ; 1.22–1.83 (10H, m), 2.45 (1H, m), 4.01 (2H, s), 7.13–7.65 (4H, m), 7.67–7.88 (4H, m).

IR (KBr) cm⁻¹; 3057, 2926, 2851, 1717, 1392, 1346, 1084 939, 716.

(4) 3-(1,1'-Biphenyl-4-methyl)methylamine

The object compound was obtained from 2-(1,1'-biphenyl-4-methyl)-1H-isoindol-1,3-(2H)-dione as an oily substance, according to the similar manner to that of Example 99(4). yield: 88%

¹H-NMR (CDCl₃) δ; 1.48 (5H, m), 1.77 (5H, m), 2.13 (2H, s), 2.48 (1H, m), 3.81 (2H, s), 7.21 (4H, m).

IR (KBr) cm⁻¹; 2922, 2851, 1448, 1383, 1319, 912, 825, 743.

(5) 2-(4-Benzyloxyphenyl)-1-(1,1'-biphenyl-4-methyl)-5-methyl-1H-pyrrole

The object compound was obtained from 3-(1,1'-biphenyl-4-methyl)methylamine as an oily substance, according to the similar manner to that of Example 99 (5). yield: 60%

¹H-NMR (CDCl₃) δ; 1.21–1.83 (10H, m), 2.13 (3H, s), 2.46 (1H, m), 5.04 (2H, s), 5.05 (2H, s), 6.00 (1H, d, J=3.4 Hz), 6.14 (1H, d, J=3.4 Hz), 6.81–7.44 (13H, m).

IR (KBr) cm⁻¹; 2924, 2851, 1522, 1242, 1020, 835, 733.

(6) 4-[1-(1,1'-Biphenyl-4-ylmethyl)-5-methyl-1H-pyrrol-2-yl]phenol

The object compound was obtained from 2-(4-benzyloxyphenyl)-1-(1,1'-biphenyl-4-methyl)-5-methyl-1H-pyrrole as an oily substance, according to the similar manner to that of Example 99(6). yield: 100%

¹H-NMR (CDCl₃) δ; 1.33–1.49 (5H, m), 1.86–1.71 (5H, m), 2.12 (3H, s), 2.45 (1H, m), 5.04 (2H, s), 6.01 (1H, d, J=3.4 Hz), 6.13 (1H, d, J=3.4 Hz), 6.73–6.84 (4H, m), 7.10–7.18 (4H, m).

IR (KBr) cm⁻¹; 2926, 2851, 1524, 1446, 1260, 1171, 840, 762.

(7) Ethyl (2R)-2-{4-[1-(1,1'-biphenyl-4-ylmethyl)-5-methyl-1H-pyrrol-2-yl]phenoxy}-3-phenylpropanoate The object compound was obtained from 4-[1-(1,1'-biphenyl-4-ylmethyl)-5-methyl-1H-pyrrol-2-yl]phenol as an oily substance, according to the similar manner to that of Example 99(7). yield: 40%

¹H-NMR (CDCl₃) δ; 1.61–1.85 (13H, m), 2.11 (3H, s), 2.45 (1H, m), 3.23 (2H, m), 4.15 (2H, q, J=7.2 Hz), 4.74 (1H, t, J=7.2 Hz), 5.01 (2H, s), 5.99 (1H, d, J=3.4 Hz), 6.11 (1H, d, J=3.4 Hz), 6.73–7.08 (4H, m), 7.12–7.30 (9H, m).

IR (KBr) cm⁻¹; 2928, 2851, 1755, 1521, 1280, 1181, 1030, 837, 760.

Example 106

Sodium (2R)-2-{4-[1-(1,1'-biphenyl-4-ylmethyl)-5-methyl-1H-pyrrol-2-yl]phenoxy}-3-phenylpropanoate (1) (2R)-2-{4-[1-(1,1'-Biphenyl-4-ylmethyl)-5-methyl-1H-pyrrol-2-yl]phenoxy}-3-phenylpropanoic acid The object compound was obtained from ethyl (2R)-2-{4-[1-(1,1'-biphenyl-4-ylmethyl)-5-methyl-1H-pyrrol-2-yl]phenoxy}-3-phenylpropanoate as an oily substance, according to the similar manner to that of Example 100(1). yield: 95%

¹H-NMR (CDCl₃) δ; 1.24–1.88 (10H, m), 2.11 (3H, s), 2.46 (1H, m), 3.25 (2H, m), 4.80 (1H, t, J=7.2 Hz), 5.01 (2H, s), 5.99 (1H, d, J=3.4 Hz), 6.11 (1H, d, J=3.4 Hz), 6.75–6.82 (4H, m), 7.09–7.29 (9H, m).

IR (KBr) cm⁻¹; 2926, 2851, 1726, 1522, 1236, 912, 743.

(2) Sodium (2R)-2-{4-[1-(1,1'-biphenyl-4-ylmethyl)-5-methyl-1H-pyrrol-2-yl]phenoxy}-3-phenylpropanoate The object compound was obtained from (2R)-2-{4-[1-(1,1'-biphenyl-4-ylmethyl)-5-methyl-1H-pyrrol-2-yl]phenoxy}-3-phenylpropanoic acid as a solid, according to the similar manner to that of Example 100(2). yield: 96%

¹H-NMR (DMSO) δ; 2.07 (3H, s), 2.87–3.15 (2H, m), 4.30 (1H, dd, J=9.2 Hz J=3.0 Hz), 5.12 (2H, s), 5.91 (1H, d, J=3.2 Hz), 5.98 (1H, d, J=3.6 Hz), 6.70 (2H, d, J=8.8 Hz), 6.90 (2H, d, J=8.0 Hz), 7.04–7.44 (10H, m), 7.61 (4H, t, J=7.8 Hz).

Elementary analysis for $C_{33}H_{28}NO_3Na\cdot 1.5H_2O$; Calculated: C, 73.86; H, 5.82; N, 2.61. Found: C, 74.15; H, 6.06; N, 2.39.

Example 107

Ethyl (2R)-2-{4-[5-methyl-1-(4-[heptylyl(cyclohexyl)aminophenylmethyl]-1H-pyrrol-2-yl}phenoxy]-3-phenylpropanoate (1) 4-Aminobenzylamino-t-butylcarbamate Di t-butylcarbonate (113 ml, 495 mmol) was added dropwise to a solution of 4-aminobenzylamine (60.4 g, 495 mmol) in THF (300 ml) at 0° C. The mixture was stirred at room temperature for 1 hour, and the mixture was poured into water and extracted with ethyl acetate. The organic layer was washed with saturated aqueous sodium chloride, dried over magnesium sulfate anhydride, and the solvent was removed under reduced pressure to give the object compound. This compound was recrystallized from ethanol-ether. solid 110 g, (yield 99%)

$^1$H-NMR (CDCl$_3$) δ; 1.35 (9H, s), 3.90 (2H, s), 4.91 (2H, s), 6.50 (2H, d, J=8.4 Hz), 6.87 (2H, d, J=8.4 Hz), 7.16 (1H, s).

(2) 4-[Heptylylamino]benzylamino-t-butylcarbamate

Heptanoyl chloride (25 g, 168 mmol) was added dropwise to a solution of 4-aminobenzylamino-t-butylcarbamate (35.5 g, 160 mmol) in THF (500 ml) at 0° C. The mixture was stirred at room temperature for 1 hour, and the mixture was poured into water and extracted with ethyl acetate. The organic layer was washed with saturated aqueous sodium chloride and dried over magnesium sulfate anhydride, and the solvent was removed under reduced pressure to give the object compound. This compound was recrystallized from ethanol-ether. solid 41.8 g, (yield 78%)

$^1$H-NMR (CDCl$_3$) δ; 0.89 (3H, m), 1.35 (17H, m), 2.32 (2H, t, J=7.6 Hz), 4.25 (2H, d, J=6.0 Hz), 7.2 (1H, s), 7.22 (2H, d, J=8.4 Hz), 7.46 (2H, d, J=8.4 Hz).

(3) 4-[Heptylyl(cyclohexyl)amino]benzylamino-t-butylcarbamate

To a solution of 4-[heptylylamino]benzyiamino-t-butylcarbamate (5.0 g, 15 mmol) in THF (60 ml) and DMF (60 ml) was added sodium hydride (600 mg, 15 mmol) and the mixture was stirred at room temperature for 1 hour. To a solution was added cyclohexylmethyl bromide (2.1 ml, 15 mmol) and the mixture was stirred at 80° C. for 24 hours. To the reaction solution was added water and the mixture was extracted with ethyl acetate. The organic layer was washed with saturated aqueous sodium chloride and dried over magnesium sulfate anhydride, and the solvent was removed under reduced pressure. The residue was purified by silica gel chromatography (hexane:ethyl acetate=7:1) to give the object compound as an oily substance. 580 mg, (yield 9%)

$^1$H-NMR (CDCl$_3$) δ; 1.01–2.00 (33H, m), 2.03 (2H, t, J=7.6 Hz), 3.54 (2H, d, J=4.8 Hz), 4.37–4.15 (2H, dd, J=33.6 Hz, J=6.0 Hz), 7.24 (2H, d, J=8.4 Hz), 7.32 (2H, d, J=8.4 Hz).

(4) 4-[Heptylyl(cyclohexyl)amino]benzylamine

To a solution of 4-[heptylyl(cyclohexyl)amino]-benzylamino-t-butylcarbamate (580 mg, 1.36 mmol) in ethyl acetate (20 ml) was added 4N hydrogen chloride-ethyl acetate solution (10 ml, 40 mmol) and the mixture was stirred at room temperature for 1 hour. The solvent was removed under reduced pressure to give the object compound as a solid. 540 mg, (yield 100%)

$^1$H-NMR (DMSO) δ; 0.78–1.60 (21H, m), 1.96 (1H, m), 2.56 (2H, m), 3.52 (2H, d, J=7.0 Hz), 4.04 (2H, d, J=5.2 Hz), 7.30–7.64 (4H, m), 8.57 (2H, s).

(5) 2-(4-Benzyloxyphenyl)-5-methyl-1-[4-[heptylyl (cyclohexyl)aminophenylmethyl]]-1H-pyrrole A solution of 4-[heptylyl(cyclohexyl)amino]benzylamine (540 mg, 1.47 mmol), 1-(4-benzyloxyphenyl)-1,4-pentanedione (410 mg, 1.45 mmol) and p-toluenesulfonic acid monohydrate (50 mg) in toluene (10 ml) was refluxed for 12 hours under heating and the solvent was removed under reduced pressure. The residue was purified by silica gel chromatography (hexane:ethyl acetate=9:1) to give the object compound as an oily substance. 370 mg, (yield 44%)

$^1$H-NMR (CDCl$_3$) δ; 0.79–1.67 (22H, m), 1.96 (2H, t, J=7.4 Hz), 2.16 (3H, s), 3.52 (2H, d, J=7.4 Hz), 5.05 (2H, s), 5.10 (2H, s), 6.03 (1H, d, J=3.2 Hz), 6.15 (1H, d, J=3.2 Hz), 6.89–7.44 (13H, m).

IR (KBr) cm$^{-1}$; 2924, 2853, 1659, 1524, 1396, 1242, 1020, 835, 758.

(6) 4-[5-Methyl-1-[4-[heptylyl(cyclohexyl) aminophenylmethyl]-1H-pyrrol-2-yl]]phenol To a solution of 2-(4-benzyloxyphenyl)-5-methyl-1-[4-[heptylyl(cyclohexyl)aminophenylmethyl]]-1H-pyrrole (370 mg, 0.64 mmol) in ethanol (20 ml) was added 10% palladium carbon (40 mg) and the mixture was stirred under hydrogen atmosphere. The insoluble matter was filtered out and the filtrate was concentrated to give the object compound as an oily substance. 310 mg, (yield 100%)

$^1$H-NMR (CDCl$_3$) δ; 0.98–1.66 (22H, m), 1.97 (2H, t, J=8.0 Hz), 2.17 (3H, s), 3.53 (2H, t, J=7.8 Hz), 5.10 (2H, s), 6.02 (1H, d, J=3.4 Hz), 6.14 (1H, d, J=3.4 Hz), 6.78–7.28 (8H, m).

IR (KBr) cm$^{-1}$; 2926, 2853, 1634, 1512, 1448, 1402, 1269, 839, 758.

(7) Ethyl (2R)-2-{4-[5-methyl-1-(4-[heptylyl(cyclohexyl) aminophenylmethyl]-1H-pyrrol-2-yl)phenoxy]-3-phenylpropanoate A solution of 4-[5-methyl-1-[4-[heptylyl(cyclohexyl)-aminophenylmethyl]-1H-pyrrol-2-yl]]phenol (300 mg, 0.62 mmol), ethyl (S)-2-hydroxy-3-phenylpropanoate (180 mg, 0.925 mmol), 1,1'-(azodicarbonyl)dipiperidine (234 mg, 0.925 mmol) and triphenylphosphine (243 mg, 0.925 mmol) in toluene (1 ml) was stirred at 80° C. for 12 hours. The mixture was poured into water, extracted with ethyl acetate, washed with saturated brine and dried over magnesium sulfate anhydride. The solvent was removed under reduced pressure and the residue was purified by silica gel column chromatography (hexane:ethyl acetate=9:1) to give the object compound as an oily substance. 117 mg, (yield 28%)

$^1$H-NMR (CDCl$_3$) δ; 0.83–1.66 (25H, m), 1.96 (2H, t, J=8.0 Hz), 2.14 (3H, s), 3.22 (2H, m), 3.53 (2H, d, J=7.5 Hz), 4.20 (2H, q, J=7.2 Hz), 4.76 (1H, t, J=7.2 Hz), 5.07 (2H, s), 6.00 (1H, d, J=3.4 Hz), 6.13 (1H, d, J=3.4 Hz), 6.75–7.30 (13H, m).

IR (KBr) cm$^{-1}$; 2926, 1753, 1657, 1523, 1398, 1240, 1182, 1030, 912, 837, 743.

Example 108

Sodium (2R)-2-{4-[5-methyl-1-(4-[heptylyl (cyclohexyl)aminophenylmethyl]-1H-pyrrol-2-yl) phenoxy]-3-phenylpropanoate (1) (2R)-2-{4-[5-Methyl-1-(4-[heptylyl(cyclohexyl)-aminophenylmethyl]-1H-pyrrol-2-yl)phenoxy]-3-phenylpropanoic acid To a solution of ethyl (2R)-2-{4-[5-methyl-1-(4-[heptylyl (cyclohexyl)aminophenylmethyl]-1H-pyrrol-2-yl) phenoxy]-3-phenylpropanoate (117 mg, 0.18 mmol) in THF (2 ml) and methanol (1 ml) was added 1N aqueous potassium hydroxide (0.6 ml, 0.6 mmol) and the mixture was stirred for 1 hour at room temperature. The reaction solution was neutralized with 1N aqueous hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 111 mg, (yield 97%)

$^1$H-NMR (CDCl$_3$) δ; 0.83–1.66 (22H, m), 1.96 (2H, t, J=8.0 Hz), 2.14 (3H, s), 3.22 (2H, m), 3.53 (2H, d, J=7.5 Hz), 4.76 (1H, t, J=7.2 Hz), 5.07 (2H, s), 6.00 (1H, d, J=3.4 Hz), 6.13 (1H, d, J=3.4 Hz), 6.75–7.30 (13H, m).

IR (KBr) cm$^{-1}$; 2926, 2853, 1743, 1615, 1523, 1450, 1242, 1180, 1082, 835, 758.

(2) Sodium (2R)-2-{4-[5-methyl-1-(4-[heptylyl (cyclohexyl)-aminophenylmethyl]-1H-pyrrol-2-yl) phenoxy]-3-phenylpropanoate To a solution of (2R)-2-{4-[5-methyl-1-(4-[heptylyl (cyclohexyl)aminophenylmethyl]-1H-pyrrol-2-yl)

phenoxy]-3-phenylpropanoic acid (111 mg, 0.17 mmol) in ethanol (1 ml) was added 1N sodium hydroxide-ethanol solution (0.165 ml, 0.165 mmol) and the mixture was concentrated. To the residue was added isopropylether to give the object compound as a solid. 79 mg, (yield 71%)

$^1$H-NMR (DMSO) δ; 0.75–1.36 (18H, m), 1.58 (4H, m), 1.88 (2H, m), 2.05 (3H, s), 3.15–2.88 (2H, m), 3.45 (2H, d, J=7.0 Hz), 4.35 (1H, m), 5.09 (2H, s), 5.89 (1H, d, J=3.2 Hz), 5.95 (1H, d, J=3.2 Hz), 6.69 (2H, d, J=8.8 Hz), 6.85 (2H, d, J=8.0 Hz), 7.03 (2H, d, J=8.4 Hz), 7.14–7.29 (7H, m).

Elementary analysis for $C_{41}H_{49}N_2O_4Na \cdot 1.5H_2O$; Calculated: C, 72.01; H, 7.66; N. 4.10. Found: C, 72.22; H, 7.39; N, 3.86.

Example 109

Ethyl (2R)-2-{4-[5-methyl-1-(4-[heptylyl(propyl)-aminophenylmethyl]-1H-pyrrol-2-yl)phenoxy]-3-phenylpropanoate (1) 4-Aminobenzylamino-t-butylcarbamate Di t-butyl carbonate (113 ml, 495 mmol) was added dropwise to a solution of 4-aminobenzylamine (60.4 g, 495 mmol) in THF (300 ml) at 0° C. The mixture was stirred at room temperature for 1 hour, poured into water and extracted with ethyl acetate. The organic layer was washed with saturated aqueous sodium chloride, dried over magnesium sulfate anhydride, and the solvent was removed under reduced pressure to give the object compound. This compound was recrystallized from ethanol-ether. Solid 110 g, (yield 99%)

$^1$H-NMR (CDCl$_3$) δ; 1.35 (9H, s), 3.90 (2H, s), 4.91 (2H, s), 6.50 (2H, d, J=8.4 Hz), 6.87 (2H, d, J=8.4 Hz), 7.16 (1H, s).

(2) 4-[Heptylylamino]benzylamino-t-butylcarbamate

Heptanoyl chloride (25 g, 168 mmol) was added dropwise to a solution of 4-aminobenzylamino-t-butylcarbamate (35.5 g, 160 mmol) in THF (500 ml) at 0° C. The mixture was stirred at room temperature for 1 hour, poured into water and extracted with ethyl acetate. The organic layer was washed with saturated aqueous sodium chloride and dried over magnesium sulfate anhydride, and the solvent was removed under reduced pressure to give the object compound. This compound was recrystallized from ethanol-ether. Solid 41.8 g, (yield 78%)

$^1$H-NMR (CDCl$_3$) δ; 0.89 (3H, m), 1.35 (17H, m), 2.32 (2H, t, J=7.6 Hz), 4.25 (2H, d, J=6.0 Hz), 7.2 (1H, s), 7.22 (2H, d, J=8.4 Hz), 7.46 (2H, d, J=8.4 Hz).

(3) 4-[Heptylyl(propyl)amino]benzylamino-t-butylcarbamate

To a solution of 4-[heptylylamino]benzylamino-t-butylcarbamate (5.0 g, 15 mmol) in THF (60 ml) and DMF (60 ml) was added sodium hydride (532 mg, 13.3 mmol) and the mixture was stirred at room temperature for 1 hour. To the mixture was added iodopropane (1.3 ml, 13.2 mmol) and the mixture was stirred at 80° C. for 24 hours. To the reaction solution was added water and the mixture was extracted with ethyl acetate. The organic layer was washed with saturated aqueous sodium chloride, dried over magnesium sulfate anhydride, and the solvent was removed under reduced pressure. The residue was purified by silica gel chromatography (hexane:ethyl acetate=7:1) to give the object compound as an oily substance. 2.68 g, (yield 54%)

$^1$H-NMR (CDCl$_3$) δ; 0.89 (6H, m), 1.19 (6H, m), 1.50 (13H, m), 2.03 (2H, t, J=7.6 Hz), 3.61 (2H, m), 4.38 (2H, d, J=5.8 Hz), 4.92 (1H, s), 7.22 (2H, d, J=8.4 Hz), 7.46 (2H, d, J=8.4 Hz).

(4) 4-[Heptylyl(propyl)amino]benzylamine

To a solution of 4-[heptylyl(propyl)amino]benzylamino-t-butylcarbamate (2.68 g, 7.1 mmol) in ethyl acetate (100 ml) was added 4N hydrogen chloride-ethyl acetate solution (40 ml, 160 mmol)and the mixture was stirred at room temperature for 1 hour. An aqueous 8N NaOH was poured into the mixture to adjust the pH to 14 and the mixture was extracted with ethyl acetate. The organic layer was washed with saturated aqueous sodium chloride, dried over magnesium sulfate anhydride, and the solvent was removed under reduced pressure to give the object compound as an oily substance. 2.2 g, (yield 100%)

$^1$H-NMR (CDCl$_3$) δ; 0.89 (6H, m), 1.23–1.49 (8H, m), 1.73 (2H, s), 2.05 (2H, t, J=8.6 Hz), 3.63 (2H, m), 3.92 (2H, s), 7.10 (2H, d, J=8.4 Hz), 7.34 (2H, d, J=8.4 Hz).

(5) 2-(4-Benzyloxyphenyl)-5-methyl-1-[4-[heptylyl(propyl)aminophenylmethyl]]-1H-pyrrole A solution of 4-[heptylyl(propyl)amino]phenylmethyl amine (1.96 g, 7.1 mmol), 1-(4-benzyloxyphenyl)-1,4-pentanedione (1.98 g, 7.02 mmol), p-toluenesulfonic acid monohydrate (200 mg) in toluene (40 ml) was refluxed for 12 hours under heating and the solvent was removed under reduced pressure. The residue was purified by silica gel chromatography (hexane:ethyl acetate=9:1) to give the object compound as an oily substance. 2.55 g, (yield 69%)

$^1$H-NMR (CDCl$_3$) δ; 0.89 (6H, m), 1.23–1.49 (6H, m), 1.73 (4H, s), 2.00 (2H, t, J=7.4 Hz), 2.16 (3H, s), 3.61 (2H, m), 5.05 (2H, s), 5.12 (2H, s), 6.03 (1H, d, J=3.2 Hz), 6.15 (1H, d, J=3.2 Hz), 6.89–7.40 (13H, m).

(6) 4-[5-Methyl-1-[4-[heptylyl(propyl)aminophenylmethyl]-1H-pyrrol-2-yl]]phenol

To a solution of 2-(4-benzyloxyphenyl)-5-methyl-1-(4-[heptylyl(propyl)amino])-1H-pyrrole (2.55 g, 4.9 mmol) in ethanol (50 ml) was added 10% palladium carbon (250 mg) and the mixture was stirred under hydrogen atmosphere. The insoluble matter was filtered out and the filtrate was concentrated to give the object compound as an oily substance. 2.2 g, (yield 100%)

$^1$H-NMR (CDCl$_3$) δ; 0.88 (6H, m), 1.26 (6H, m), 1.50 (4H, m), 1.98 (2H, t, J=8.0 Hz), 2.15 (3H, s), 3.61 (2H, t, J=7.8 Hz), 5.10 (2H, s), 6.02 (1H, d, J=3.4 Hz), 6.14 (1H, d, J=3.4 Hz), 6.78–7.00 (4H, m), 7.05 (2H, d, J=8.0 Hz), 7.20 (2H, d, J=8.6 Hz).

(7) Ethyl (2R)-2-{4-[5-methyl-1-(4-[heptylyl(propyl)-aminophenylmethyl]-1H-pyrrol-2-yl)phenoxy]-3-phenylpropanoate A solution of 4-[5-methyl-1-(4-[heptylyl(propyl)-aminophenylmethyl]-1H-pyrrol-2-yl)phenol (2.1 g, 4.9 mmol), ethyl (S)-2-hydroxy-3-phenylpropanoate (1.43 g, 7.35 mmol), 1,1'-(azodicarbonyl)dipiperidine (1.86 g, 7.35 mmol) and triphenyiphosphine (1.93 g, 7.35 mmol) in toluene (10 ml) was stirred at 80° C. for 12 hours. The mixture was poured into water, extracted with ethyl acetate, washed with saturated brine and dried over magnesium sulfate anhydride. The solvent was removed under reduced pressure and the residue was purified by silica gel column chromatography (hexane:ethyl acetate=5:1) to give the object compound as an oily substance. 1.44 g, (yield 48%)

$^1$H-NMR (CDCl$_3$) δ; 0.88 (6H, m), 1.26 (7H, m), 1.60 (2H, m), 1.87 (4H, m), 2.14 (3H, s), 3.21 (2H, m), 3.57–3.78 (4H, m), 4.20 (2H, q, J=7.2 Hz), 4.76 (1H, t, J=7.2 Hz), 5.07 (2H, s), 6.00 (1H, d, J=3.4 Hz), 6.13 (1H, d, J=3.4 Hz), 6.75–7.28 (13H, m).

IR (KBr) cm$^{-1}$; 2928, 1775, 1658, 1523, 1398, 1238, 1082, 835, 758.

Example 110

Sodium (2R)-2-{4-[5-methyl-1-(4-[heptylyl(propyl)-aminophenylmethyl]-1H-pyrrol-2-yl)phenoxy]-3-phenylpropanoate (1) (2R)-2-{4-[5-Methyl-1-(4-[heptylyl(propyl) aminophenylmethyl]-1H-pyrrol-2-yl)phenoxy]-3-phenylpropanoic acid To a mixed solution of ethyl (2R)-2-{4-[5-methyl-1-(4-[heptylyl(propyl)aminophenylmethyl]-1H-pyrrol-2-yl) phenoxy]-3-phenylpropanoate (2.15 g, 3.38 mmol) in THF (30 ml) and methanol (15 ml) was added 1N aqueous potassium hydroxide (10.1 ml, 10.1 mmol) and the mixture was stirred for 1 hour at room temperature. The reaction solution was neutralized with 1N aqueous hydrochloric acid, extracted with ethyl acetate, washed with saturated brine and dried over magnesium sulfate anhydride. The solvent was removed under reduced pressure and the residue was purified by silica gel column chromatography (ethyl acetate) to give the object compound as an oily substance. 2.03 g, (yield 98%)

$^1$H-NMR (CDCl$_3$) δ; 0.88 (6H, m), 1.26 (4H, m), 1.60 (2H, m), 1.87 (4H, m), 2.14 (3H, s), 3.21 (2H, m), 3.57–3.78 (4H, m), 4.76 (1H, t, J=7.2 Hz), 5.07 (2H, s), 6.00 (1H, d, J=3.4 Hz), 6.13 (1H, d, J=3.4 Hz), 6.75–7.28 (13H, m).

IR (KBr) cm$^{-1}$; 2930, 1732, 1616, 1523, 1240, 1082, 835, 700.

(2) Sodium (2R)-2-{4-[5-methyl-1-(4-[heptylyl(propyl)-aminophenylmethyl]-1H-pyrrol-2-yl)phenoxy]-3-phenylpropanoate To a solution of (2R)-2-{4-[5-methyl-1-(4-[heptylyl (propyl)aminophenylmethyl]-1H-pyrrol-2-yl)phenoxy]-3-phenylpropanoic acid (2.0 g, 3.29 mmol) in ethanol (20 ml) was added 1N sodium hydroxide-ethanol solution (3 ml, 3.0 mmol) and the mixture was concentrated. To the residue was added isopropylether to give the object compound as a solid. 977 mg, (yield 75%)

$^1$H-NMR (DMSO) δ; 0.78 (6H, m), 1.08 (6H, m), 1.33 (2H, m), 1.88 (2H, m), 2.04 (3H, s), 2.85–3.14 (4H, m), 3.51 (2H, t, J=6.6 Hz), 4.24 (1H, t, J=7.2 Hz), 5.10 (2H, s), 5.89 (1H, d, J=3.4 Hz), 5.97 (1H, d, J=3.4 Hz), 6.67 (2H, d, J=8.8 Hz), 6.86 (2H, d, J=8.8 Hz), 7.02 (2H, d, J=8.8 Hz), 7.14–7.23 (7H, m).

Example 111

Ethyl (2R)-2-{4-[5-methyl-1-(4-[heptylyl(pentyl)-aminophenylmethyl]-1H-pyrrol-2-yl)phenoxy]-3-phenylpropanoate (1) 4-[Heptylyl(pentyl)amino]benzylamino-t-butylcarbamate The object compound was obtained from iodopentane as an oily substance, according to the similar manner to that of Example 109 (3). yield: 94%

$^1$H-NMR (CDCl$_3$) δ; 0.89 (6H, m), 1.19 (10H, m), 1.50 (13H, m), 2.03 (2H, t, J=7.6 Hz), 3.61 (2H, m), 4.38 (2H, d, J=5.8 Hz), 4.92 (1H, s), 7.22 (2H, d, J=8.4 Hz), 7.46 (2H, d, J=8.4 Hz).

(2) 4-[Heptylyl(pentyl)amino]benzylamine

The object compound was obtained from 4-[heptylyl (pentyl)amino]benzylamino-t-butylcarbamate as an oily substance, according to the similar-manner to that of Example 109 (4). yield: 100%

$^1$H-NMR (CDCl$_3$) δ; 0.89 (6H, m), 1.23–1.49 (12H, m), 1.73 (2H, s), 2.05 (2H, t, J=8.6 Hz), 3.63 (2H, m), 3.92 (2H, s), 7.10 (2H, d, J=8.4 Hz), 7.34 (2H, d, J=8.4 Hz)

IR (KBr) cm$^{-1}$; 2926, 1651, 1404, 1263, 1140, 845, 727.

(3) 2-(4-Benzyloxyphenyl)-5-methyl-1-(4-[heptylyl(pentyl) aminophenylmethyl]-1H-pyrrole The object compound was obtained from 4-[heptylyl (pentyl)amino]benzylamine as an oily substance, according to the similar manner to that of Example 109(5). yield: 72%

$^1$H-NMR (CDCl$_3$) δ; 0.89 (6H, m), 1.23–1.49 (10H, m), 1.73 (4H, s), 2.00 (2H, t, J=7.4 Hz), 2.16 (3H, s), 3.61 (2H, m), 5.05 (2H, s), 5.12 (2H, s), 6.03 (1H, d, J=3.2 Hz) 6.15 (1H, d, J=3.2 Hz), 6.89–7.40 (13H, m).

IR (KBr) cm$^{-1}$; 2930, 1655, 1523, 1242, 1020, 835, 758.

(4) 4-[5-Methyl-1-(4-[heptylyl(pentyl) aminophenylmethyl]-1H-pyrrol-2-yl)phenol

The object compound was obtained from 2-(4-benzyloxyphenyl)-5-methyl-1-(4-[heptylyl(pentyl) aminophenylmethyl]-1H-pyrrole as an oily substance, according to the similar manner to that of Example 109(6). yield: 100%

$^1$H-NMR (CDCl$_3$) δ; 0.88 (6H, m), 1.26 (10H, m), 1.50 (4H, m), 1.98 (2H, t, J=8.0 Hz), 2.15 (3H, s), 3.61 (2H, t, J=7.8 Hz), 5.10 (2H, s), 6.02 (1H, d, J=3.4 Hz), 6.14 (1H, d, J=3.4 Hz), 6.78–7.00 (4H, m), 7.05 (2H, d, J=8.0 Hz), 7.20 (2H, d, J=8.6 Hz).

IR (KBr) cm$^{-1}$; 2928, 1633, 1512, 1269, 1020, 839, 760.

(5) Ethyl (2R)-2-{4-[5-methyl-1-(4-[heptylyl(pentyl) aminophenylmethyl]-1H-pyrrol-2-yl)phenoxy]-3-phenylpropanoate The object compound was obtained from 4-[5-methyl-1-(4-[heptylyl(pentyl)aminophenylmethyl]-1H-pyrrol-2-yl) phenol as an oily substance, according to the similar manner to that of Example 109(7). yield: 59%

$^1$H-NMR (CDCl$_3$) δ; 0.88 (6H, m), 1.26 (11H, m), 1.60 (2H, m), 1.87 (4H, m), 2.14 (3H, s), 3.21 (2H, m), 3.57–3.78 (4H, m), 4.20 (2H, q, J=7.2 Hz), 4.76 (1H, t, J=7.2 Hz), 5.07 (2H, s), 6.00 (1H, d, J=3.4 Hz), 6.13 (1H, d, J=3.4 Hz), 6.75–7.28 (13H, m).

IR (KBr) cm$^{-1}$; 2928, 1738, 1658, 1512, 1398, 1240, 1097, 837, 700.

Example 112

Sodium (2R)-2-{4-[5-methyl-1-(4-[heptylyl(pentyl) aminophenylmethyl]-1H-pyrrol-2-yl)phenoxy]-3-phenylpropanoate (1) (2R)-2-{4-[5-Methyl-1-(4-[heptylyl(pentyl) aminophenylmethyl]-1H-pyrrol-2-yl)phenoxy]-3-phenylpropanoic acid The object compound was obtained from ethyl (2R)-2-{4-[5-methyl-1-(4-[heptylyl(pentyl) aminophenylmethyl]-1H-pyrrol-2-yl)phenoxy]-3-phenylpropanoate as an oily substance, according to the similar manner to that of Example 110(1). yield: 98%

$^1$H-NMR (CDCl$_3$) δ; 0.88 (6H, m), 1.26 (8H, m), 1.60 (2H, m), 1.87 (4H, m), 2.14 (3H, s), 3.21 (2H, m), 3.57–3.78 (4H, m), 4.76 (1H, t, J=7.2 Hz), 5.07 (2H, s), 6.00 (1H, d, J=3.4 Hz), 6.13 (1H, d, J=3.4 Hz), 6.75–7.28 (13H, m).

IR (KBr) cm$^{-1}$; 2930, 1732, 1616, 1523, 1240, 1082, 835, 700.

(2) Sodium (2R)-2-{4-[5-methyl-1-(4-[heptylyl(pentyl) aminophenylmethyl]-1H-pyrrol-2-yl)phenoxy]-3-phenylpropanoate The object compound was obtained from (2R)-2-{4-[5-methyl-1-(4-[heptylyl(pentyl) aminophenylmethyl]-1H-pyrrol-2-yl)phenoxy]-3-phenylpropanoic acid as a solid, according to the similar manner to that of Example 110(2). yield: 72%

¹H-NMR (DMSO) δ; 0.78 (6H, m), 1.08 (10H, m), 1.33 (2H, m), 1.88 (2H, m), 2.04 (3H, s), 2.85–3.14 (4H, m), 3.51 (2H, t, J=6.6 Hz), 4.24 (1H, t, J=7.2 Hz), 5.10 (2H, s), 5.89 (1H, d, J=3.4 Hz), 5.97 (1H, d, J=3.4 Hz), 6.67 (2H, d, J=8.8 Hz), 6.86 (2H, d, J=8.8 Hz), 7.02 (2H, d, J=8.8 Hz), 7.14–7.23 (7H, m).

Example 113

Ethyl (2R)-2-{4-[5-methyl-1-(4-[heptylylaminophenylmethyl]-1H-pyrrol-2-yl)phenoxy]-3-phenylpropanoate (1) 4-[Heptylylamino]benzylamine To a solution of 4-[heptanoylamide]benzylamino-t-butylcarbamate (3.5 g, 10.5 mmol) in ethyl acetate (100 ml) was added 4N hydrogen chloride-ethyl acetate solution (20 ml, 80 mmol) and the mixture was stirred at room temperature for 1 hour. 8N aqueous sodium hydroxide was poured into the solution to adjust the pH to 14 and the mixture was extracted with ethyl acetate. The organic layer was washed with saturated aqueous sodium chloride and dried over magnesium sulfate anhydride, and the solvent was removed under reduced pressure to give the object compound as an oily substance. 2.47 g, (yield 100%)

¹H-NMR (CDCl₃) δ; 0.89 (3H, m), 1.35 (6H, m), 1.67 (2H, t, J=7.0 Hz), 2.32 (2H, t, J=7.6 Hz), 3.82 (2H, s), 7.22 (2H, d, J=8.4 Hz), 7.46 (2H, d, J=8.4 Hz).

(2) 2-(4-Benzyloxyphenyl)-5-methyl-1-(4-[heptylylaminophenylmethyl]-1H-pyrrole

The object compound was obtained from 4-[heptylylamino]benzylamine as an oily substance, according to the similar manner to that of Example 109(5). yield: 50%

Oily substance 1.75 g, (50%)

¹H-NMR (CDCl₃) δ; 0.89 (3H, m), 1.23–1.49 (4H, m), 1.73 (4H, s), 2.00 (2H, t, J=7.4 Hz), 2.16 (3H, s), 3.61 (2H, m), 5.05 (2H, s), 6.03 (1H, d, J=3.2 Hz), 6.15 (1H, d, J=3.2 Hz), 6.89–7.40 (13H, m).

(3) 4-[5-Methyl-1-(4-[heptylylaminophenylmethyl]-1H-pyrrol-2-yl)phenol

The object compound was obtained from 2-(4-benzyloxyphenyl)-5-methyl-1-(4-[heptylylaminophenylmethyl]-1H-pyrrole as an oily substance, according to the similar manner to that of Example 109(6). yield: 100%

¹H-NMR (CDCl₃) δ; 0.88 (3H, m), 1.26 (6H, m), 1.98 (2H, t, J=8.0 Hz), 2.12 (3H, s), 2.37 (2H, t, J=7.4 Hz), 5.02 (2H, s), 6.02 (1H, d, J=3.4 Hz), 6.14 (1H, d, J=3.4 Hz), 6.72–6.88 (4H, m), 7.12 (2H, d, J=8.0 Hz), 7.49 (2H, d, J=8.6 Hz).

(4) Ethyl (2R)-2-{4-[5-methyl-1-(4-[heptylylaminophenylmethyl]-1H-pyrrol-2-yl)phenoxy]-3-phenylpropanoate The object compound was obtained from 4-[5-methyl-1-(4-[heptylylaminophenylmethyl]-1H-pyrrol-2-yl)phenol as an oily substance, according to the similar manner to that of Example 109(7). yield: 33%

¹H-NMR (CDCl₃) δ; 0.88 (3H, m), 1.26 (9H, m), 1.51 (2H, m), 2.01 (3H, s), 3.14 (2H, m), 3.61–3.78 (4H, m), 4.08 (2H, q, J=7.2 Hz), 4.65 (1H, t, J=7.2 Hz), 4.91 (2H, s), 5.91 (1H, d, J=3.4 Hz), 6.02 (1H, d, J=3.4 Hz), 6.64–7.35 (13H, m).

IR (KBr) cm⁻¹; 2928, 1738, 1621, 1522, 1238, 1082, 835, 758.

Example 114

Sodium (2R)-2-{4-[5-methyl-1-(4-[heptylylaminophenylmethyl]-1H-pyrrol-2-yl)phenoxy]-3-phenylpropanoate (1) (2R)-2-{4-[5-Methyl-1-(4-[heptylylaminophenylmethyl]-1H-pyrrol-2-yl)phenoxy]-3-phenylpropanoic acid The object compound was obtained from 4-[5-methyl-1-(4-[heptylylaminophenylmethyl]-1H-pyrrol-2-yl)phenol as an oily substance, according to the similar manner to that of Example 110(1). yield: 93%

¹H-NMR (CDCl₃) δ; 0.88 (6H, m), 1.26 (4H, m), 1.60 (2H, m), 1.87 (4H, m), 2.14 (3H, s), 3.21 (2H, m), 3.57–3.78 (4H, m), 4.76 (1H, t, J=7.2 Hz), 5.07 (2H, s), 6.00 (1H, d, J=3.4 Hz), 6.13 (1H, d, J=3.4 Hz), 6.75–7.28 (13H, m).

IR (KBr) cm⁻¹; 2930, 1732, 1616, 1523, 1240, 1082, 835, 700.

(2) Sodium (2R)-2-{4-[5-methyl-1-(4-[heptylylaminophenylmethyl]-1H-pyrrol-2-yl)phenoxy]-3-phenylpropanoate The object compound was obtained from (2R)-2-{4-[5-methyl-1-(4-[heptylylaminophenylmethyl]-1H-pyrrol-2-yl)phenoxy]-3-phenylpropanoic acid as a solid, according to the similar manner to that of Example 110(2). yield: 95%

¹H-NMR (DMSO) δ; 0.78 (3H, m), 1.08 (4H, m), 1.33 (2H, m), 1.88 (2H, m), 2.04 (3H, s), 2.85–3.14 (4H, m), 4.24 (1H, t, J=7.2 Hz), 5.10 (2H, s), 5.89 (1H, d, J=3.4 Hz), 5.97 (1H, d, J=3.4 Hz), 6.67 (2H, d, J=8.8 Hz), 6.86 (2H, d, J=8.8 Hz), 7.02 (2H, d, J=8.8 Hz), 7.14–7.23 (7H, m), 9.95 (1H, s).

Example 115

Ethyl (2R)-2-(4-{[2-(4-bromophenyl)-1H-indol-1-yl]methyl}phenoxy)-3-phenylpropanoate (1) 1-(4-Bromophenyl)-1-ethanone N-phenylhydrazone A solution of p-bromoacetophenone (5.00 g, 25.1 mmol), phenylhydrazone (2.71 g, 25.1 mmol) and p-toluenesulfonic acid monohydrate (358 mg, 1.88 mmol) in toluene (100 ml) was refluxed for 12 hours under heating, and the mixture was poured into water and extracted with ethyl acetate. The extract was washed with water and dried over magnesium sulfate anhydride. The solvent was removed under reduced pressure. To the residue was added hexane and the mixture was filtered to give the object compound as a solid. 6.68 g (yield: 92.0%)

¹H-NMR (CDCl₃) δ; 2.21 (3H, s), 5.27 (2H, s), 6.86–6.93 (1H, m), 7.15–7.36 (5H, m), 7.49 (2H, d, J=8.4 Hz), 7.66 (2H, d, J=8.4 Hz).

IR (KBr) cm⁻¹; 1603, 1485, 1252, 1152, 1080, 1007, 829, 812, 754, 694.

(2) 2-(4-Bromophenyl)-1H-indole

A mixture of 1-(4-bromophenyl)-1-ethanone N-phenylhydrazone (6.50 g, 22.5 mmol) and polyphosphoric acid (40 g) was stirred at 190° C. for 10 minutes. The mixture was poured into 1 N aqueous sodium hydroxide (400 ml) and extracted with ethyl acetate. The extract was washed with water and dried over magnesium sulfate anhydride, and the solvent was removed under reduced pressure. To the residue was added hexane and the mixture was filtered to give the object compound as a solid. 5.76 g (yield: 94.1%)

¹H-NMR (CDCl₃) δ; 6.82 (1H, s), 7.09–7.65 (8H, m), 8.30 (1H, bs).

IR (KBr) cm⁻¹; 3432, 1432, 1348, 1300, 1007, 829, 793, 748.

(3) 2-(4-Bromophenyl)-1-(4-methoxybenzyl)-1H-indole

To a solution of 2-(4-bromophenyl)-1H-indole (2.00 g, 7.35 mmol) in toluene (16 ml) were added 50% aqueous sodium hydroxide (8 ml), tetra n-butylammonium hydrogensulfate (126 mg, 0.372 mmol) and p-methoxybenzylchloride (1.49 ml, 11.0 mmol) and the mixture was stirred at room temperature for 3 hours. The mixture was poured into water and extracted with ethyl acetate. The extract was washed with water, dried over magnesium sulfate anhydride, and the solvent was removed under reduced pressure. The residue was purified by silica gel column chromatography (hexane:ethyl acetate=30:1) to give the object compound as a solid. 670 mg (yield: 23.3%)

$^1$H-NMR (CDCl$_3$) δ; 3.77 (3H, s), 5.28 (2H, s), 6.63 (1H, s), 6.80 (2H, d, J=8.8 Hz), 6.93 (2H, d, J=8.8 Hz), 7.11–7.69 (8H, m).

IR (KBr) cm$^{-1}$; 1613, 1512, 1460, 1346, 1248, 1175, 1011, 831, 789, 752, 737.

(4) 4-{[2-(4-Bromophenyl)-1H-indol-1-yl]methyl}phenol

To a solution of 2-(4-bromophenyl)-1-(4-methoxybenzyl)-1H-indole (640 mg, 1.63 mmol) in methylene chloride (40 ml) was added boron tribromide (0.617 ml, 6.53 mmol) at 0° C. and the mixture was stirred at 0° C. for 1 hour. The mixture was poured into ice water and extracted with ethyl acetate. The extract was washed with saturated aqueous sodium bicarbonate and dried over magnesium sulfate anhydride. The solvent was removed under reduced pressure to give the object compound as an oily substance. 610 mg (yield: 98.9%)

$^1$H-NMR (CDCl$_3$) δ; 4.90 (1H, s), 5.27 (2H, s), 6.63 (1H, s), 6.72 (2H, d, J=8.8 Hz), 6.88 (2H, d, J=8.8 Hz), 7.13–7.69 (8H, m).

IR (KBr) cm$^{-1}$; 3299, 1615, 1514, 1346, 1240, 1173, 1011, 829, 789, 748, 735.

(5) Ethyl (2R)-2-(4-{[2-(4-bromophenyl)-1H-indol-1-yl]methyl}phenoxy)-3-phenylpropanoate To a solution of 4-{[2-(4-bromophenyl)-1H-indol-1-yl]methyl}phenol (600 mg, 1.59 mmol), ethyl (S)-2-hydroxy-3-phenylpropanoate (617 mg, 3.17 mmol) and triphenylphosphine (831 mg, 3.17 mmol) in toluene (6 ml) was added 1,1'-(azodicarbonyl)dipiperidine (799 m g, 3.17 mmol), and the mixture was stirred at 80° C. for 12 hours and poured into water. The mixture was extracted with ethyl acetate and dried over magnesium sulfate anhydride, and the solvent was removed under reduced pressure. The residue was purified by silica gel column chromatography (hexane:ethyl acetate=30:1) to give the object compound as an oily substance. 650 mg (yield: 73.7%)

$^1$H-NMR (CDCl$_3$) δ; 1.16 (3H, t, J=7.0 Hz), 3.19–3.23 (2H, m), 4.15 (2H, q, J=7.4 Hz), 4.68–4.75 (1H, m), 5.24 (2H, s), 6.61 (1H, s), 6.72 (2H, d, J=8.8 Hz), 6.86 (2H, d, J=8.8 Hz), 7.11–7.73 (13H, m).

IR (KBr) cm$^{-1}$; 1753, 1510, 1460, 1346, 1240, 1178, 1073, 1011, 831, 748, 700.

$[\alpha]_D^{26}$ 10.2° (c 0.700, chloroform)

Example 116

(2R)-2-(4-{[2-(4-Bromophenyl)-1H-indol-1-yl]methyl}phenoxy)-3-phenylpropanoic acid To a mixed solution of ethyl (2R)-2-(4-{[2-(4-bromophenyl)-1H-indol-1-yl]methyl}phenoxy)-3-phenylpropanoate (630 mg, 1.14 mmol) in THF (8 ml) and methanol (4 ml) was added 1N aqueous potassium hydroxide (3.41 ml, 3.41 mmol) and the mixture was stirred for 1 hour at room temperature. The reaction solution was neutralized with 1N hydrochloric acid and extracted with ethyl acetate. The extract was washed with water and dried over magnesium sulfate anhydride. The solvent was removed under reduced pressure to give the object compound as an oily substance. 550 mg (yield: 91.7%)

$^1$H-NMR (CDCl$_3$) δ; 3.25 (2H, m), 4.75–4.81 (1H, m), 5.24 (2H, s), 6.62 (1H, s), 6.72 (2H, d, J=8.8 Hz), 6.87 (2H, d, J=8.8 Hz), 7.08–7.67 (13H, m).

IR (KBr) cm$^{-1}$; 3031, 1732, 1508, 1456, 1238, 1177, 831, 789, 735, 700.

$[\alpha]_D^{27}$ 7.87° (c 1.20, chloroform)

Example 117

Ethyl (2R)-2-{4-[1-(4-bromophenethyl)-4-(decylaminocarbonyl)-5-methyl-1H-pyrrol-2-yl]phenoxy}-3-phenylpropanoate (1) Ethyl 2-acetyl-4-(4-methoxyphenyl)-4-oxobutanoate To a solution of ethyl acetoacetate (14.2 g, 109 mmol) and sodium ethoxide (7.43 g, 109 mmol) in ethanol (200 ml) was added portionwise 4-methoxyphenacylbromide (25.0 g, 109 mmol) under ice-cooling. The mixture was stirred at room temperature for 4 hours. The insoluble matter was filtered out and the solvent was removed under reduced pressure to give the object compound as an oily substance. 29.4 g (yield: 97.0%)

$^1$H-NMR (CDCl$_3$) δ; 1.29 (3H, t, J=7.0 Hz), 2.44 (3H, s), 3.47 (1H, dd, J=6.0, 18.2 Hz), 3.68 (1H, dd, J=8.0, 18.2 Hz), 3.85–4.00 (4H, m), 4.22 (2H, q, J=7.0 Hz), 6.94 (2H, d, J=8.8 Hz), 7.95 (2H, d, J=8.8 Hz).

IR (KBr) cm$^{-1}$; 1740, 1717, 1674, 1601, 1262, 1171, 1028, 835.

(2) Ethyl 1-(4-bromophenethyl)-5-(4-methoxyphenyl)-2-methyl-1H-pyrrole-3-carboxylate A solution of ethyl 2-acetyl-4-(4-methoxyphenyl)-4-oxobutanoate (13.9 g, 50.0 mmol), 2-(4-bromophenyl)ethylamine (10.0 g, 50.0 mmol) and p-toluenesulfonic acid monohydrate (714 mg, 3.75 mmol) in toluene (100 ml) was refluxed for 12 hours under heating and the solvent was removed under reduced pressure. The residue was purified by silica gel column chromatography (hexane:ethyl acetate=7:1) to give the object compound as a solid. 15.0 g (yield: 67.9%)

$^1$H-NMR (CDCl$_3$) δ; 1.34 (3H, t, J=7.2 Hz), 2.52 (3H, s), 2.67 (2H, t, J=7.0 Hz), 3.86 (3H, s), 4.05 (2H, t, J=7.0 Hz), 4.27 (2H, q, J=7.2 Hz), 6.47 (1H, s), 6.68 (2H, d, J=8.4 Hz), 6.91 (2H, d, J=8.8 Hz), 7.15 (2H, d, J=8.8 Hz), 7.29 (2H, d, J=8.4 Hz).

IR (KBr) cm$^{-1}$; 1696, 1493, 1211, 1177, 1069, 837, 812, 775.

(3) 1-(4-Bromophenethyl)-5-(4-methoxyphenyl)-2-methyl-1H-pyrrole-3-carboxylic acid To a mixed solution of ethyl 1-(4-bromophenethyl)-5-(4-methoxyphenyl)-2-methyl-1H-pyrrole-3-carboxylate (11.2 g, 25.3 mmol) in THF (40 ml) and methanol (80 ml) was added 4N aqueous sodium hydroxide (25.7 ml, 101 mmol) and the mixture was stirred at 90° C. for 4 hours. To the reaction solution was added 8 N aqueous sodium hydroxide (38.1 ml, 305 mmol) and the mixture was stirred at 90° C. for 8 hours. The mixture was cooled with ice, neutralized with concentrated hydrochloric acid and extracted with ethyl acetate. The extract was washed with water, dried over magnesium sulfate anhydride and the solvent was removed under reduced pressure to give the object compound as a solid. 10.3 g (yield: 98.1%)

$^1$H-NMR (CDCl$_3$) δ; 2.52 (3H, s), 2.68 (2H, t, J=7.8 Hz), 3.86 (3H, s), 4.07 (2H, t, J=7.8 Hz), 6.54 (1H, s), 6.69 (2H, d, J=8.0 Hz), 6.92 (2H, d, J=8.8 Hz), 7.17 (2H, d, J=8.8 Hz), 7.31 (2H, d, J=8.0 Hz).

IR (KBr) cm$^{-1}$; 3007, 1653, 1568, 1497, 1456, 1252, 1179, 810.

(4) 1-(4-Bromophenethyl)-N-decyl-5-(4-methoxyphenyl)-2-methyl-1H-pyrrole-3-carboxamide To a solution of 1-(4-bromophenethyl)-5-(4-methoxyphenyl)-2-methyl-1H-pyrrole-3-carboxylic acid (2.00 g, 4.83 mmol) in DMF (10 ml) were added n-decylamine (838 mg, 5.33 mmol), diethyl cyanophosphate (946 mg, 5.80 mmol) and triethylamine (0.673 ml, 4.83 mmol), and the mixture was stirred for 1 hour at room temperature. To the reaction solution were added n-decylamine (838 mg, 5.33 mmol), diethyl cyanophosphate (946 mg, 5.80 mmol) and triethylamine (0.673 ml, 4.83 mmol) and the mixture was stirred room temperature for 2 hours. The mixture was poured into water and extracted with ethyl acetate. The extract was washed successively with 1N hydrochloric acid, water and saturated aqueous sodium bicarbonate and dried over magnesium sulfate anhydride, and solvent was removed under reduced pressure. The residue was purified by silica gel column chromatography (hexane:ethyl acetate=4:1) to give the object compound as a solid. 2.16 g (80.9%)

$^1$H-NMR (CDCl$_3$) δ; 0.87 (3H, t, J=6.6 Hz), 1.23–1.67 (16H, m), 2.60 (3H, s), 2.68 (2H, t, J=7.6 Hz), 3.33–3.43 (2H, m), 3.86 (3H, s), 4.02 (2H, t, J=7.6 Hz), 5.73 (1H, t, J=5.6 Hz), 6.11 (1H, s), 6.69 (2H, d, J=8.4 Hz), 6.90 (2H, d, J=8.8 Hz), 7.11 (2H, d, J=8.8 Hz), 7.29 (2H, d, J=8.4 Hz).

IR (KBr) cm$^{-1}$; 3335, 1626, 1570, 1537, 1491, 1275, 1248, 1175, 835, 810, 772.

(5) 1-(4-Bromophenethyl)-N-butyl-5-(4-hydroxyphenyl)-2-methyl-1H-pyrrole-3-carboxamide To a solution of 1-(4-bromophenethyl)-N-decyl-5-(4-methoxyphenyl)-2-methyl-1H-pyrrole-3-carboxamide (2.10 g, 3.79 mmol) in methylene chloride (40 ml) was added boron tribromide (1.51 ml, 16.0 mmol) at 0° C. and the mixture was stirred at 0° C. for 1 hour. The reaction solution was poured into ice water and extracted with ethyl acetate. The extract was washed with saturated aqueous sodium bicarbonate and dried over magnesium sulfate anhydride. The solvent was removed under reduced pressure to give the object compound as a solid. 1.58 g (yield: 77.0%)

$^1$H-NMR (CDCl$_3$) δ; 0.94 (3H, t, J=7.0 Hz), 1.23–1.64 (4H, m), 2.59 (3H, s), 2.67 (2H, t, J=7.4 Hz), 3.36–3.46 (2H, m), 4.02 (2H, t, J=7.4 Hz), 5.77 (1H, t, J=5.6 Hz), 6.11 (1H, s), 6.47 (1H, s), 6.69 (2H, d, J=8.4 Hz), 6.88 (2H, d, J=8.8 Hz), 7.05 (2H, d, J=8.8 Hz), 7.29 (2H, d, J=8.4 Hz).

IR (KBr) cm$^{-1}$; 3123, 2959, 1615, 1574, 1543, 1489, 1269, 1223, 839, 812, 770, 735.

(6) Ethyl (2R)-2-{4-[1-(4-bromophenethyl)-4-(decylaminocarbonyl)-5-methyl-1H-pyrrol-2-yl]phenoxy}-3-phenylpropanoate To a solution of 1-(4-bromophenethyl)-N-butyl-5-(4-hydroxyphenyl)-2-methyl-1H-pyrrole-3-carboxamide (1.75 g, 3.24 mmol), ethyl (S)-2-hydroxy-3-phenylpropanoate (945 mg, 4.87 mmol) and triphenylphosphine (1.28 g, 4.87 mmol) in toluene (20 ml) was added 1,1'-(azodicarbonyl)dipiperidine (1.23 g, 4.87 mmol) and the mixture was stirred at 80° C. for 12 hours. The reaction solution was poured into water and extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.67 g (yield: 72.0%)

$^1$H-NMR (CDCl$_3$) δ; 0.87 (3H, t, J=6.8 Hz), 1.18–1.60 (19H, m), 2.58 (3H, s), 2.65 (2H, t, J=7.0 Hz), 3.26–3.42 (4H, m), 4.01 (2H, t, J=7.0 Hz), 4.22 (2H, q, J=7.0 Hz), 4.79–4.86 (1H, m), 5.70 (1H, bs), 6.07 (1H, s), 6.64 (2H, d, J=8.4 Hz), 6.83 (2H, d, J=8.8 Hz), 7.04 (2H, d, J=8.8 Hz), 7.22–7.35 (7H, m).

IR (KBr) cm$^{-1}$; 3331, 1750, 1634, 1572, 1539, 1489, 1275, 1240, 1181, 1073, 1011, 837, 808, 700.

$[α]_D^{26}$ 3.04° (c 0.750, chloroform)

Example 118

(2R)-2-{4-[1-(4-Bromophenethyl)-4-(decylaminocarbonyl)-5-methyl-1H-pyrrol-2-yl]phenoxy}-3-phenylpropanoic acid To a mixed solution of ethyl (2R)-2-{4-[1-(4-bromophenethyl)-4-(decylaminocarbonyl)-5-methyl-1H-pyrrol-2-yl]phenoxy}-3-phenylpropanoate (1.60 g, 2.23 mmol) in THF (20 ml) and methanol (10 ml) was added 1N aqueous potassium hydroxide (6.69 ml, 6.69 mmol) and the mixture was stirred for 1 hour at room temperature. The reaction solution was neutralized with 1N hydrochloric acid and extracted with ethyl acetate. The extract was washed with water, dried over magnesium sulfate anhydride, and the solvent was removed under reduced pressure. The residue was recrystallized from ethyl acetate and diisopropylether to give the object compound. 663 mg (yield: 43.3%)
Melting point 132–133° C.

$^1$H-NMR (CDCl$_3$) δ; 0.87 (3H, t, J=6.8 Hz), 1.25–1.56 (16H, m), 2.54–2.63 (5H, m), 3.31–3.42 (4H, m), 3.96 (2H, t, J=7.4 Hz), 4.83–4.89 (1H, m), 5.73 (1H, bs), 6.03 (1H, s), 6.59 (2H, d, J=8.4 Hz), 6.81 (2H, d, J=8.8 Hz), 6.99 (2H, d, J=8.8 Hz), 7.20–7.35 (7H, m).

IR (KBr) cm$^{-1}$; 3031, 2926, 1742, 1572, 1543, 1489, 1277, 1242, 1178, 1073, 1011, 835, 812, 700.

$[α]_D^{26}$ −2.32° (c 1.12, chloroform)

Elementary analysis for $C_{39}H_{47}N_2O_4Br$; Calculated: C, 68.11; H, 6.89; N, 4.07. Found: C, 67.92; H, 6.86; N, 4.03.

Example 119

Ethyl (2R)-2-(4-{2-[2-(2-[1,1'-biphenyl]-2-ylethyl)-5-methyl-1H-pyrrol-1-yl]ethyl}phenoxy)-3-phenylpropanoate (1) Ethyl (2E)-3-[1,1'-biphenyl]propenoate To a solution of [1,1'-biphenyl]-2-carbaldehyde (18.5 g, 102 mmol) and ethyl diethylphosphonoacetate (27.5 g, 123 mmol) in THF (200 ml) was added sodium hydride (60%, 4.90 g, 123 mmol) and the mixture was stirred at room temperature for 12 hours. The reaction solution was poured into ice water, acidified with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=30:1) to give the object compound as an oily substance. 17.8 g (yield: 69.2%)

$^1$H-NMR (CDCl$_3$) δ; 1.28 (3H, t, J=7.4 Hz), 4.20 (2H, q, J=7.4 Hz), 6.40 (1H, d, J=15.8 Hz), 7.26–7.48 (9H, m), 7.73 (1H, d, J=15.8 Hz).

IR (KBr) cm$^{-1}$; 1715, 1634, 1476, 1314, 1269, 1196, 1177, 1036, 768, 745, 702.

(2) Ethyl 3-[1,1'-biphenyl]-2-ylpropanoate

To a solution of ethyl (E)-3-[1,1'-biphenyl]-2-ylpropenoate (17.8 g, 70.6 mmol) in ethanol (400 ml) was added 10% palladium carbon (4 g) and the mixture was stirred under hydrogen atmosphere (0.48 MPa) for 16 hours. The insoluble matter was removed and the filtrate was concentrated to give the object compound as an oily substance. 14.3 g (yield: 79.9%)

$^1$H-NMR (CDCl$_3$) δ; 1.18 (3H, t, J=7.0 Hz), 2.41 (2H, t, J=7.4 Hz), 2.94 (2H, t, J=7.4 Hz), 4.04 (2H, q, J=7.0 Hz), 7.22–7.45 (9H, m).

IR (KBr) cm$^{-1}$; 1732, 1480, 1179, 1159, 750, 704.

(3) 3-[1,1'-Biphenyl]-2-ylpropanol

To a suspension of lithium aluminium hydride (4.27 g, 112 mmol) in tetrahydrofuran (200 ml) was added dropwise a solution of ethyl 3-[1,1'-biphenyl]-2-ylpropanoate (14.3 g, 56.2 mmol) in tetrahydrofuran (50 ml) and the mixture was refluxed for 2 hours under heating. To the residue were added water (5 ml) and 1 N aqueous sodium hydroxide (15 ml) under ice-cooling and the mixture was stirred at room temperature for 1 hour. The insoluble matter was removed and the filtrate was concentrated to give the object compound as an oily substance. 11.7 g (yield: 98.3%)

$^1$H-NMR (CDCl$_3$) δ; 1.04 (1H, t, J=5.4 Hz), 1.64–1.78 (2H, m), 2.69 (2H, t, J=7.6 Hz), 3.45–3.51 (2H, m), 7.20–7.47 (9H, m).

IR (KBr) cm$^{-1}$; 3300, 1480, 1451, 1057, 1039, 1009, 750, 702.

(4) 3-[1,1'-Biphenyl]-2-ylpropanal

To a solution of oxalyl chloride (9.60 ml, 110 mmol) in methylene chloride (200 ml) was added dropwise a solution of dimethylsulfoxide (11.6 ml, 146 mmol) in methylene chloride (30 ml) at −78° C. and the mixture was stirred at −78° C. for 10 minutes. To the mixture was added dropwise a solution of 3-[1,1'-biphenyl]-2-ylpropanol (11.7 g, 55.2 mmol) in methylene chloride (30 ml) at −78° C., and the mixture was stirred at −78 to −45° C. for 2 hours. To the obtained mixed solution was added triethylamine (55.7 ml, 400 mmol) at −45° C. and the mixture was stirred at 0° C. for 2 hours. To the obtained mixed solution was added saturated aqueous ammonium chloride (200 ml) and the mixture was stirred at room temperature for 1 hour. The organic layer was separated, washed with water and dried over magnesium sulfate anhydride. The solvent was removed under reduced pressure to give the object compound as an oily substance. 11.1 g (yield: 95.7%)

$^1$H-NMR (CDCl$_3$) δ; 2.54 (2H, t, J=8.4 Hz), 2.95 (2H, t, J=8.4 Hz), 7.23–7.46 (9H, m), 9.63 (1H, s).

IR (KBr) cm$^{-1}$; 1723, 1480, 750, 704.

(5) 7-[1,1'-Biphenyl]-2-yl-2,5-heptanedione

A mixture of 3-[1,1'-biphenyl]-2-ylpropanal (11.1 g, 52.9 mmol), methyl vinyl ketone (3.70 g, 52.9 mmol), triethylamine (14.7 ml, 106 mmol), 3-ethyl-5-(2-hydroxyethyl-4-methyl thiazolium bromide (2.09 g, 8.28 ml) and ethanol (12 ml) was stirred at 77° C. for 48 hours, and the solvent was removed under reduced pressure. The residue was purified by silica gel column chromatography (hexane:ethyl acetate= 4:1) to give the object compound as an oily substance. 6.20 g (yield: 41.9%)

$^1$H-NMR (CDCl$_3$) δ; 2.15 (3H, s), 2.48–2.93 (8H, m), 7.19–7.45 (9H, m).

IR (KBr) cm$^{-1}$; 1713, 1480, 1364, 1171, 1092, 754, 704.

(6) 2-(2-[1,1'-Biphenyl]-2-ylethyl)-1-(4-phenoxyphenethyl)-5-methyl-1H-pyrrole

A solution of 7-[1,1'-biphenyl]-2-yl-2,5-heptanedione (3.00 g, 10.7 mmol), 2-(4-methoxyphenyl)ethylamine (1.62 g, 10.7 mmol) and p-toluenesulfonic acid monohydrate (153 mg, 0.803 mmol) in toluene (100 ml) was refluxed for 12 hours under heating and the solvent was removed under reduced pressure. The residue was purified by silica gel column chromatography (hexane:ethyl acetate=30:1) to give the object compound as an oily substance. 2.53 g (yield: 59.8%)

$^1$H-NMR (CDCl$_3$) δ; 2.07 (3H, s), 2.51–2.69 (4H, m), 2.86–2.95 (2H, m), 3.68 (2H, t, J=7.6 Hz), 3.79 (3H, s), 5.68 (1H, d, J=3.6 Hz), 5.74 (1H, d, J=3.6 Hz), 6.80 (2H, d, J=8.8 Hz), 6.90 (2H, d, J=8.8 Hz), 7.20–7.37 (9H, m).

IR (KBr) cm$^{-1}$; 1512, 1480, 1418, 1300, 1248, 1036, 750, 704.

(7) 4-{2-[2-(2-[1,1'-Biphenyl]-2-ylethyl)-5-methyl-1H-pyrrol-1-yl]ethyl}phenol

To a solution of 2-(2-[1,1'-biphenyl]-2-ylethyl)-1-(4-phenoxyphenethyl)-5-methyl-1H-pyrrole (2.50 g, 6.32 mmol) in methylene chloride (100 ml) was added boron tribromide (2.39 ml, 25.3 mmol) at 0° C. and the mixture was stirred at 0° C. for 1 hour. To the reaction solution was poured ice water and the mixture was extracted with ethyl acetate. The extract was washed with saturated aqueous sodium bicarbonate and dried over magnesium sulfate anhydride. The solvent was removed under reduced pressure to give the object compound as an oily substance. 2.40 g (yield: 99.6%)

$^1$H-NMR (CDCl$_3$) δ; 2.06 (3H, s), 2.51–2.95 (6H, m), 3.66 (2H, t, J=7.6 Hz), 4.74 (1H, bs), 5.68 (1H, d, J=3.2 Hz), 5.72 (1H, d, J=3.2 Hz), 6.73 (2H, d, J=8.6 Hz), 6.84 (2H, d, J=8.6 Hz), 7.21–7.38 (9H, m).

IR (KBr) cm$^{-1}$; 3393, 1615, 1514, 1480, 1437, 1223, 828, 750, 704.

(8) Ethyl (2R)-2-(4-{2-[2-(2-[1,1'-biphenyl]-2-ylethyl)-5-methyl-1H-pyrrol-1-yl]ethyl}phenoxy)-3-phenylpropanoate To a solution of 4-{2-[2-(2-[1,1'-biphenyl]-2-ylethyl)-5-methyl-1H-pyrrol-1-yl]ethyl}phenol (2.40 g, 6.30 mmol), ethyl (S)-2-hydroxy-3-phenylpropanoate (1.84 g, 9.45 mmol) and triphenylphosphine (2.48 g, 9.45 mmol) in toluene (10 ml) was added 1,1'-(azodicarbonyl)dipiperidine (2.38 g, 9.45 mmol) and the mixture was stirred at 80° C. for 12 hours. The reaction solution was poured into water, extracted with ethyl acetate and dried over magnesium sulfate anhydride. The solvent was removed under reduced pressure. The residue was purified by silica gel column chromatography (hexane:ethyl acetate=30:1) to give the object compound as an oily substance. 1.40 g (yield: 39.9%)

$^1$H-NMR (CDCl$_3$) δ; 1.17 (3H, t, J=7.0 Hz), 2.04 (3H, s), 2.51–2.64 (4H, m), 2.85–2.94 (2H, m), 3.21–3.29 (2H, m), 3.63 (2H, t, J=7.4 Hz), 4.15 (2H, q, J=7.0 Hz), 4.72–4.79 (1H, m), 5.67 (1H, d, J=3.2 Hz), 5.71 (1H, d, J=3.2 Hz), 6.74 (2H, d, J=8.8 Hz), 6.85 (2H, d, J=8.8 Hz), 6.92–7.29 (14H, m).

IR (KBr) cm$^{-1}$; 1852, 1732, 1510, 1298, 1240, 1182, 1113, 1084, 1030, 750, 702.

Example 120

Sodium (2R)-2-(4-{2-[2-(2-[1,1'-biphenyl]-2-ylethyl)-5-methyl-1H-pyrrol-1-yl]ethyl}phenoxy)-3-phenylpropanoate (1) (2R)-2-(4-{2-[2-(2-[1,1'-Biphenyl]-2-ylethyl)-5-methyl-1H-pyrrol-1-yl]ethyl}phenoxy)-3-phenylpropanoic acid To a mixed solution of ethyl (2R)-2-(4-{2-[2-(2-[1,1'-biphenyl]-2-ylethyl)-5-methyl-1H-pyrrol-1-yl]ethyl}phenoxy)-3-phenylpropanoate (1.40 g, 2.51 mmol) in THF (30 ml) and methanol (15 ml) was added 1N aqueous potassium hydroxide solution (7.53 ml, 7.53 mmol) and the mixture was stirred for 1 hour at room temperature. The reaction solution was neutralized with 1N hydrochloric acid and extracted with ethyl acetate. The extract was washed with water, dried over magnesium sulfate anhydride, and the solvent was removed under reduced pressure. The residue was purified by silica gel column chromatography (hexane:ethyl acetate=3:1) to give the object compound as an oily substance. 994 mg (yield: 74.7%)

$^1$H-NMR (CDCl$_3$) δ; 2.04 (3H, s), 2.49–2.93 (6H, m), 3.26 (2H, d, J=7.0 Hz), 3.63 (2H, t, J=7.6 Hz), 4.83 (1H, t, J=7.0 Hz), 5.67 (1H, d, J=3.6 Hz), 5.72 (1H, d, J=3.6 Hz), 6.74 (2H, d, J=8.8 Hz), 6.86 (2H, d, J=8.8 Hz), 7.19–7.29 (14H, m).

IR (KBr) cm$^{-1}$; 3063, 1728, 1510, 1236, 750, 702.

(2) Sodium (2R)-2-(4-{2-[2-(2-[1,1'-biphenyl]-2-ylethyl)-5-methyl-1H-pyrrol-1-yl]ethyl}phenoxy)-3-phenylpropanoate Ethanol (15 ml) and a solution of 1N sodium hydroxide in ethanol (1.69 ml) were added to (2R)-2-(4-{2-[2-(2-[1,1'-biphenyl]-2-ylethyl)-5-methyl-1H-pyrrol-1-yl]ethyl}phenoxy)-3-phenylpropanoic acid (994 mg, 1.88 mmol) and the mixture was concentrated. To the residue was added ether to give the object compound as a solid. 940 mg (yield: 68.1%)

$^1$H-NMR (DMSO-d$_6$) δ; 2.02 (3H, s), 2.48–2.58 (4H, m), 2.75–3.15 (4H, m), 3.62 (2H, t, J=8.0 Hz), 4.23–4.29 (1H, m), 5.44 (1H, d, J=3.2 Hz), 5.54 (1H, d, J=3.2 Hz), 6.65 (2H, d, J=8.4 Hz), 6.84 (2H, d, J=8.4 Hz),7.13–7.42 (14H, m).

IR (KBr) cm$^{-1}$; 3027, 1609, 1508, 1416, 1233, 1053, 910, 750, 733, 702.

[α]$_D^{26}$ 14.1° (c 1.16,chloroform)

Example 121

Ethyl (2R)-2-(4-{2-[2-(2-fluoro-6-trifluoromethylphenethyl)-5-methyl-1H-pyrrol-1-yl]ethyl}phenoxy)-3-phenylpropanoate (1) Ethyl (2E)-3-(2-fluoro-6-trifluoromethylphenyl)propenoate To a solution of 2-fluoro-6-trifluoromethyl benzaldehyde (10.0 g, 52.0 mmol) and ethyl diethylphosphonoacetate (14.0 g, 62.4 mmol) in THF (100 ml) was added sodium hydride (60%, 2.50 g, 62.4 mmol) and the mixture was stirred at room temperature for 12 hours. The reaction solution was poured into ice water, acidified with 1N hydrochloric acid and extracted with ethyl acetate. The extract was washed with water, dried over magnesium sulfate anhydride, and the solvent was removed under reduced pressure. The residue was purified by silica gel column chromatography (hexane:ethyl acetate=9:1) to give the object compound as an oily substance. 12.1 g (yield: 89.0%)

$^1$H-NMR (CDCl$_3$) δ; 1.35 (3H, t, J=7.4 Hz), 4.29 (2H, q, J=7.4 Hz), 6.62 (1H, d, J=16.2 Hz), 7.27–7.56 (3H, m), 7.79 (1H, d, J=16.2 Hz).

IR (KBr) cm$^{-1}$; 1723, 1466, 1321, 1254, 1190, 1169, 1132, 1038, 984, 912, 804, 758.

(2) Ethyl 3-(2-fluoro-6-trifluoromethylphenyl)propanoate

To a solution of ethyl (2E)-3-(2-fluoro-6-trifluoromethyl biphenyl)propenoate (12.0 g, 45.8 mmol) in ethanol (200 ml) was added 10% palladium carbon (1.2 g) and the mixture was stirred under hydrogen atmosphere for 4 hours. The insoluble matter was filtered out and the filtrate was concentrated to give the object compound as an oily substance. 11.8 g (yield: 97.5%)

$^1$H-NMR (CDCl$_3$) δ; 1.27 (3H, t, J=7.0 Hz), 2.57 (2H, t, J=8.0 Hz), 3.14 (2H, t, J=8.0 Hz), 4.17 (2H, q, J=7.0 Hz), 7.20–7.48 (3H, m).

IR (KBr) cm$^{-1}$; 1738, 1470, 1319, 1252, 1169, 1127, 889, 802.

(3) 3-(2-Fluoro-6-trifluoromethylphenyl)-1-propanol

To a suspension of lithium aluminium hydride (3.39 g, 89.3 mmol) in tetrahydrofuran (100 ml) was added dropwise a solution of ethyl 3-(2-fluoro-6-trifluoromethylphenyl)propanoate (11.8 g, 44.7 mmol) in tetrahydrofuran (50 ml) and the solution was refluxed for 2 hours under heating. To the residue was added water (3.5 ml) and 1 N aqueous sodium hydroxide solution (10.5 ml) under ice-cooling and the mixture was stirred at room temperature for 1 hour. The insoluble matter was filtered out and the filtrate was concentrated to give the object compound as an oily substance. 9.51 g (yield: 95.9%)

$^1$H-NMR (CDCl$_3$) δ; 1.79–1.93 (2H, m), 2.84–2.95 (2H, m), 3.66–3.77 (2H, m), 7.12–7.46 (3H, m).

IR (KBr) cm$^{-1}$; 3328, 1470, 1319, 1250, 1169, 1125, 1059, 1036, 798.

(4) 3-(2-Fluoro-6-trifluoromethylphenyl)-1-propanal

To a solution of oxalyl chloride (7.47 ml, 85.6 mmol) in methylene chloride (100 ml) was added dropwise a solution of dimethylsulfoxide (9.00 ml, 114 mmol) in methylene chloride (10 ml) at −78° C. and the mixture was stirred at −78° C. for 10 minutes. To the mixed solution was added dropwise a solution of 3-(2-fluoro-6-trifluoromethylphenyl)-1-propanol (9.51 g, 42.8 mmol) in methylene chloride (20 ml) at −78° C. and the mixture was stirred at from −78 to −45° C. for 2 hours. To the obtained mixed solution was added triethylamine (43.3 ml, 311 mmol) at −45° C. and the mixture was stirred at 0° C. for 2 hours. To the obtained mixed solution was added saturated aqueous ammonium chloride solution (200 ml) and the mixture was stirred at room temperature for 1 hour. The organic layer was separated, washed with water and dried over magnesium sulfate anhydride. The solvent was removed under reduced pressure to give the object compound as an oily substance. 9.10 g (yield: 96.6%)

$^1$H-NMR (CDCl$_3$) δ; 2.74 (2H, t, J=8.4 Hz), 3.13 (2H, t, J=8.4 Hz), 7.14–7.48 (3H, m), 9.84 (1H, s).

IR (KBr) cm$^{-1}$; 1725, 1470, 1319, 1250, 1169, 1123, 1032, 801.

(5) 7-(2-Fluoro-6-trifluoromethylphenyl)-2,5-heptanedione

A mixture of 3-(2-fluoro-6-trifluoromethylphenyl)-1-propanal (9.10 g, 41.4 mmol), methyl vinyl ketone (2.90 g, 41.4 mmol), triethylamine (11.5 ml, 82.8 mmol), 3-ethyl-5-(2-hydroxyethyl-4-methylthiazolium bromide (1.63 g, 6.47 ml) and ethanol (9 ml) was stirred at 77° C. for 48 hours and the solvent was removed under reduced pressure. The residue was purified by silica gel column chromatography (hexane:ethyl acetate=9:1) to give the object compound as an oily substance. 2.60 g (yield: 25.0%)

$^1$H-NMR (CDCl$_3$) δ; 2.21 (3H, s), 2.66–3.11 (8H, m), 7.19–7.46 (3H, m).

IR (KBr) cm$^{-1}$; 1715, 1470, 1319, 1252, 1167, 1125, 802, 743, 727.

(6) 2-(2-Fluoro-6-trifluoromethylphenethyl)-1-(4-methoxyphenethyl)-5-methyl-1H-pyrrole A solution of 7-(2-fluoro-6-trifluoromethylphenyl)-2,5-heptanedione (2.50 g, 9.92 mmol), 2-(4-methoxyphenyl)-ethylamine (1.50 g, 9.92 mmol) and p-toluenesulfonic acid monohydrate (142 mg, 0.745 mmol) in toluene (100 ml) was refluxed for 12 hours under heating and the solvent was removed under reduced pressure. The residue was purified by silica gel column chromatography (hexane:ethyl acetate=30:1) to give the object compound as an oily substance. 2.43 g (yield: 60.4%)

$^1$H-NMR (CDCl$_3$) δ; 2.17 (3H, s), 2.67–3.13 (6H, m), 3.78 (3H, s), 3.96 (3H, s), 5.84 (1H, d, J=3.6 Hz), 5.93 (1H, d, J=3.6 Hz), 6.82 (2H, d, J=8.8 Hz), 7.02 (2H, d, J=8.8 Hz), 7.25–7.48 (3H, m).

IR (KBr) cm$^{-1}$; 1613, 1514, 1464, 1420, 1318, 1302, 1250, 1167, 1146, 1125, 1036, 885, 826, 801, 752, 727.

(7) 4-{2-[2-(2-Fluoro-6-trifluoromethylphenethyl)-5-methyl-1H-pyrrol-1-yl]ethyl}phenol To a solution of 2-(2-fluoro-6-trifluoromethylphenethyl)-1-(4-phenoxyphenethyl)-5-methyl-1H-pyrrole (2.33 g, 5.77 mmol) in methylene chloride (100 ml) was added boron tribromide (2.17 ml, 23.0 mmol) at 0° C. and the mixture was stirred at 0° C. for 1 hour. The reaction solution was poured into ice water and extracted with ethyl acetate. The extract was washed with saturated aqueous sodium bicarbonate and dried over magnesium sulfate anhydride. The solvent was removed under reduced pressure to give the object compound as an oily substance. 2.20 g (yield: 97.3%)

¹H-NMR (CDCl₃) δ; 2.16 (3H, s), 2.67–3.13 (6H, m), 3.96 (2H, t, J=8.0 Hz), 4.75 (1H, bs), 5.84 (1H, d, J=2.8 Hz), 5.93 (1H, d, J=2.8 Hz), 6.75 (2H, d, J=8.4 Hz), 6.96 (2H, d, J=8.4 Hz), 7.26–7.49 (3H, m).

IR (KBr) cm⁻¹; 3453, 1514, 1464, 1318, 1250, 1167, 1125, 801, 748.

(8) Ethyl (2R)-2-(4-{2-[2-(2-fluoro-6-trifluoromethylphenethyl)-5-methyl-1H-pyrrol-1-yl]ethyl}phenoxy)-3-phenylpropanoate To a solution of 2-(2-fluoro-6-trifluoromethylphenethyl)-1-(4-phenoxyphenethyl)-5-methyl-1H-pyrrole (2.20 g, 5.62 mmol), ethyl (S)-2-hydroxy-3-phenylpropanoate (1.64 g, 8.43 mmol) and triphenylphosphine (2.21 g, 8.43 mmol) in toluene (40 ml) was added 1,1'-(azodicarbonyl)dipiperidine (2.12 g, 8.43 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.02 g (yield: 31.9%)

¹H-NMR (CDCl₃) δ; 1.33 (3H, t, J=7.4 Hz), 2.14 (3H, s), 2.68–2.84 (4H, m), 3.04–3.12 (2H, m), 3.21–3.29 (2H, m), 3.89–3.93 (2H, m), 4.26 (2H, q, J=7.4 Hz), 4.72–4.79 (1H, m), 5.83 (1H, d, J=3.0 Hz), 5.92 (1H, d, J=3.0 Hz), 6.76 (2H, d, J=8.8 Hz), 6.96 (2H, d, J=8.8 Hz),7.21–7.48 (8H, m).

IR (KBr) cm⁻¹; 1753, 1736, 1510, 1318, 1250, 1184, 1167, 1125, 1030, 885, 802, 748, 700.

Example 122

Sodium (2R)-2-(4-{2-[2-(2-fluoro-6-trifluoromethylphenethyl)-5-methyl-1H-pyrrol-1-yl]ethyl}phenoxy)-3-phenylpropanoate (1) (2R)-2-(4-{2-[2-(2-Fluoro-6-trifluoromethylphenethyl)-5-methyl-1H-pyrrol-1-yl]ethyl}phenoxy)-3-phenylpropanoic acid To a mixed solution of ethyl (2R)-2-(4-{2-[2-(2-fluoro-6-trifluoromethylphenethyl)-5-methyl-1H-pyrrol-1-yl]ethyl}phenoxy)-3-phenylpropanoate (1.02 g, 18.0 mmol) in THF (20 ml) and methanol (10 ml) was added 1N aqueous potassium hydroxide solution (5.39 ml, 5.39 mmol) and the mixture was stirred for 1 hour at room temperature. The reaction solution was neutralized with 1N hydrochloric acid and extracted with ethyl acetate. The extract was washed with water and dried over magnesium sulfate anhydride,and the solvent was removed under reduced pressure. The residue was purified by silica gel column chromatography (hexane:ethyl acetate=3:1) to give the object compound as an oily substance. 533 mg (yield: 54.9%)

¹H-NMR (CDCl₃) δ; 2.14 (3H, s), 2.66–3.11 (6H, m), 3.27 (2H, d, J=6.2 Hz), 3.93 (2H,t, J=8.4 Hz), 4.82 (1H, t, J=6.2 Hz), 5.83 (1H, d, J=3.0 Hz), 5.92 (1H, d, J=3.0 Hz), 6.76 (2H, d, J=8.8 Hz), 6.98 (2H, d, J=8.8 Hz),7.19–7.48 (8H, m).

IR (KBr) cm⁻¹; 3034, 1725, 1510, 1318, 1238, 1167, 1127, 801, 756, 700.

(2) Sodium (2R)-2-(4-{2-[2-(2-fluoro-6-trifluoromethylphenethyl)-5-methyl-1H-pyrrol-1-yl]ethyl}phenoxy)-3-phenylpropanoate Ethanol (5 ml) and a solution of 1N sodium hydroxide in ethanol (0.889 ml) were added to (2R)-2-(4-{2-[2-(2-fluoro-6-trifluoromethylphenethyl)-5-methyl-1H-pyrrol-1-yl]ethyl}phenoxy)-3-phenylpropanoic acid (533 mg, 0.988 mmol) and the mixture was concentrated. Diisopropylether was added to the residue to give the object compound as a solid. 165 mg (yield: 33.1%)

¹H-NMR (DMSO-d₆) δ; 2.12 (3H, s), 2.69–3.14 (6H, m), 3.37–3.64 (2H, m), 3.78–3.93 (2H, m), 4.25–4.29 (1H, m), 5.68 (1H, d, J=2.4 Hz), 5.72 (1H, d, J=2.4 Hz), 6.66 (2H, d, J=8.4 Hz), 6.94 (2H, d, J=8.4 Hz),7.15–7.58 (8H, m).

IR (KBr) cm⁻¹; 2971, 1609, 1508, 1464, 1418, 1318, 1235, 1167, 1125, 1069, 885, 801, 750, 700.

$[\alpha]_D^{24}$ 9.86° (c 0.221 chloroform)

Example 123

Ethyl (2R)-2-[4-(2-{2-methyl-5-[3-(1,1,2,2-tetrafluoroethoxy)phenethyl]-1H-pyrrol-1-yl]ethyl)phenoxy]-3-phenylpropanoate (1) Ethyl (2E)-3-[3-(1,1,2,2-trifluoroethoxy)phenyl]propenoate To a solution of 3-(1,1,2,2-trifluoroethoxy)benzaldehyde (21.4 g, 116 mmol) and ethyl diethylphosphonoacetate (25.9 g, 116 mmol) in THF (200 ml) was added sodium hydride (60%, 4.64 g, 116 mmol) and the mixture was stirred at room temperature for 12 hours. The reaction solution was poured into ice water, acidified with 1N hydrochloric acid and extracted with ethyl acetate. The extract was washed with water, dried over magnesium sulfate anhydride, and the solvent was removed under reduced pressure. The residue was purified by silica gel column chromatography (hexane:ethyl acetate=9:1) to give the object compound as an oily substance. 19.7 g (yield: 69.9%)

¹H-NMR (CDCl₃) δ; 1.34 (3H, t, J=7.0 Hz), 4.27 (2H, q, J=7.0 Hz), 5.65–6.21 (1H, m), 6.45 (1H, d, J=16.2 Hz), 7.27–7.45 (4H, m), 7.65 (1H, d, J=16.2 Hz).

IR (KBr) cm⁻¹; 1715, 1644, 1582, 1487, 1447, 1370, 1304, 1277, 1196, 1119, 1036, 982, 851, 802, 762, 679.

(2) Ethyl 3-[3-(1,1,2,2-trifluoroethoxy)phenyl]propanoate

To a solution of ethyl (2E)-3-[3-(1,1,2,2-trifluoroethoxy)phenyl]propenoate (19.6 g, 67.1 mmol) in ethanol (500 ml) was added 10% palladium carbon (1.2 g) and the mixture was stirred under hydrogen atmosphere for 4 hours. The insoluble matter was filtered out and the filtrate was concentrated to give the object compound as an oily substance. 17.7 g (yield: 89.8%)

¹H-NMR (CDCl₃) δ; 1.23 (3H, t, J=7.0 Hz), 2.62 (2H, t, J=7.4 Hz), 2.97 (2H, t, J=7.4 Hz), 4.13 (2H, q, J=7.0 Hz), 5.62–6.18 (1H, m), 7.06–7.34 (4H, m).

IR (KBr) cm⁻¹; 1732, 1615, 1588, 1489, 1449, 1375, 1304, 1281, 1198, 1121, 801, 760, 693.

(3) 3-[3-(1,1,2,2-Trifluoroethoxy)phenyl]-1-propanol

To a suspension of lithium aluminium hydride (4.54 g, 120 mmol) in tetrahydrofuran (200 ml) was added dropwise a solution of ethyl 3-[3-(1,1,2,2-trifluoroethoxy)phenyl]propanoate (17.6 g, 59.8 mmol) in tetrahydrofuran (100 ml) and the mixture was refluxed for 2 hours under heating. To the residue were added water (5 ml) and 1 N aqueous sodium hydroxide solution (15 ml) under ice-cooling and the mixture was stirred at room temperature for 1 hour. The insoluble matter was filtered out and the filtrate was concentrated to give the object compound as an oily substance. 15.0 g (yield: 99.3%)

¹H-NMR (CDCl₃) δ; 1.32 (1H, t, J=5.2 Hz), 1.83–1.97 (2H, m), 2.74 (2H, t, J=8.4 Hz), 3.64–3.75 (2H, m), 5.62–6.18 (1H, m), 7.03–7.34 (4H, m).

IR (KBr) cm⁻¹; 3310, 1613, 1588, 1489, 1449, 1304, 1281, 1198, 1121, 802, 758, 694.

(4) 3-[3-(1,1,2,2-Trifluoroethoxy)phenyl]propanal

To a solution of oxalyl chloride (10.3 ml, 118 mmol) in methylene chloride (100 ml) was added dropwise a solution of dimethylsulfoxide (12.4 ml, 157 mmol) in methylene chloride (10 ml) at −78° C. and the mixture was stirred at −78° C. for 10 minutes. To the mixed solution was added dropwise a solution of 3-[3-(1,1,2,2-trifluoroethoxy)phenyl]-1-propanol (14.9 g, 59.1 mmol) in methylene chloride (20 ml) at −78° C. and the mixture was stirred at from −78 to −45° C. for 2 hours. To the obtained mixed solution was added triethylamine (59.7 ml, 429 mmol) at −45° C. and the mixture was stirred at 0° C. for 2 hours. To the obtained mixed solution was added saturated aqueous ammonium chloride solution (200 ml) and the mixture was stirred at room temperature for 1 hour. The organic layer was separated, washed with water and dried over magnesium sulfate anhydride. The solvent was removed under reduced pressure to give the object compound as an oily substance. 14.5 g (yield: 98.0%)

$^1$H-NMR (CDCl$_3$) δ; 2.80 (2H, t, J=7.4 Hz), 2.98 (2H, t, J=7.4 Hz), 5.62–6.18 (1H, m), 7.05–7.35 (4H, m), 9.83 (1H, s).

IR (KBr) cm$^{-1}$; 1726, 1304, 1280, 1199, 1123, 802, 758, 693.

(5) 7-[3-(1,1,2,2-Trifluoroethoxy)phenyl]-2,5-heptanedione

A mixture of 3-[3-(1,1,2,2-trifluoroethoxy)phenyl]propanal (14.5 g, 70.7 mmol), methyl vinyl ketone (4.96 g, 70.7 mmol), triethylamine (19.7 ml, 141 mmol), 3-ethyl-5-(2-hydroxyethyl-4-methyl thiazolium bromide (2.79 g, 11.0 ml) and ethanol (15 ml) was stirred at 77° C. for 12 hours and the solvent was removed under reduced pressure. The residue was purified by silica gel column chromatography (hexane:ethyl acetate=7:1) to give the object compound as an oily substance. 10.7 g (yield: 47.3%)

$^1$H-NMR (CDCl$_3$) δ; 2.19 (3H, s), 2.61–2.97 (8H, m), 5.62–6.19 (1H, m), 7.03–7.33 (4H, m).

IR (KBr) cm$^{-1}$; 1715, 1613, 1588, 1489, 1448, 1304, 1281, 1196, 1119, 802, 760, 694.

(6) 4-(2-{2-Methyl-5-[3-(1,1,2,2-tetrafluoroethoxy)phenethyl]-1H-pyrrol-1-yl}ethyl)phenol A solution of 7-[3-(1,1,2,2-trifluoroethoxy)phenyl]-2,5-heptanedione (3.00 g, 9.38 mmol), tyramine (1.28 g, 9.38 mmol) and p-toluenesulfonic acid monohydrate (133 mg, 0.701 mmol) in toluene (100 ml) was refluxed for 12 hours under heating and the solvent was removed under reduced pressure. The residue was purified by silica gel column chromatography (hexane:ethyl acetate=9:1) to give the object compound as an oily substance. 2.77 g (yield: 70.1%)

$^1$H-NMR (CDCl$_3$) δ; 2.16 (3H, s), 2.59–2.95 (6H, m), 3.88 (2H, t, J=7.4 Hz), 4.78 (1H, bs), 5.64–6.19 (3H, m), 6.73 (2H, d, J=8.8 Hz), 6.88 (2H, d, J=8.8 Hz), 7.02–7.34 (4H, m).

IR (KBr) cm$^{-1}$; 3345, 1514, 1300, 1198, 1123, 829, 758.

(7) Ethyl (2R)-2-[4-(2-{2-methyl-5-[3-(1,1,2,2-tetrafluoroethoxy)phenethyl]-1H-pyrrol-1-yl}ethyl)phenoxy]-3-phenylpropanoate To a solution of 4-(2-{2-methyl-5-[3-(1,1,2,2-tetrafluoroethoxy)phenethyl]-1H-pyrrol-1-yl}ethyl)phenol (2.70 g, 6.41 mmol), ethyl (S)-2-hydroxy-3-phenylpropanoate (1.87 g, 9.62 mmol) and triphenylphosphine (2.52 g, 9.62 mmol) in toluene (100 ml) was added 1,1'-(azodicarbonyl)dipiperidine (2.43 g, 9.62 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 1.00 g (yield: 26.1%)

$^1$H-NMR (CDCl$_3$) δ; 1.17 (3H, t, J=7.2 Hz), 2.12 (3H, s), 2.64–2.95 (6H, m), 3.21–3.25 (2H, m), 3.85 (2H, t, J=7.6 Hz), 4.15 (2H, q, J=7.2 Hz), 4.71–4.78 (1H, m), 5.63–6.19 (3H, m), 6.74 (2H, d, J=8.4 Hz), 6.90 (2H, d, J=8.4 Hz), 7.03–7.32 (9H, m).

IR (KBr) cm$^{-1}$; 1752, 1613, 1586, 1510, 1300, 1279, 1236, 1196, 1119, 1030, 754, 700.

Example 124

Sodium (2R)-2-[4-(2-{2-methyl-5-[3-(1,1,2,2-tetrafluoroethoxy)phenethyl]-1H-pyrrol-1-yl}ethyl)phenoxy]-3-phenylpropanoate (1) (2R)-2-[4-(2-{2-methyl-5-[3-(1,1,2,2-tetrafluoroethoxy)phenethyl]-1H-pyrrol-1-yl}ethyl)phenoxy]-3-phenylpropanoic acid To a mixed solution of ethyl (2R)-2-[4-(2-{2-methyl-5-[3-(1,1,2,2-tetrafluoroethoxy)phenethyl]-1H-pyrrol-1-yl}ethyl}phenoxy}-3-phenylpropanoate (980 mg, 1.64 mmol) in THF (20 ml) and methanol (10 ml) was added 1N aqueous potassium hydroxide solution (4.92 ml, 4.92 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=3:1) to give the object compound as an oily substance. 920 mg (yield: 98.5%)

$^1$H-NMR (CDCl$_3$) δ; 2.12 (3H, s), 2.62–2.94 (6H, m), 3.26 (2H, d, J=6.6 Hz), 3.85 (2H, t, J=8.0 Hz), 4.82 (1H, t, J=6.6 Hz), 5.62–6.18 (3H, m), 6.75 (2H, d, J=8.4 Hz), 6.91 (2H, d, J=8.4 Hz), 7.02–7.32 (9H, m).

IR (KBr) cm$^{-1}$; 3034, 1732, 1510, 1300, 1233, 1198, 1121, 758, 700.

(2) Sodium (2R)-2-[4-(2-{2-methyl-5-[3-(1,1,2,2-tetrafluoroethoxy)phenethyl]-1H-pyrrol-1-yl}ethyl)phenoxy]-3-phenylpropanoate To a solution of (2R)-2-[4-(2-{2-methyl-5-[3-(1,1,2,2-tetrafluoroethoxy)phenethyl]-1H-pyrrol-1-yl}ethyl}phenoxy}-3-phenylpropanoic acid (920 mg, 1.62 mmol) were added ethanol (10 ml) and a solution of 1N sodium hydroxide in ethanol (1.45 ml), and the mixture was concentrated. Diisopropylether was added to the residue to give the object compound as a solid. 852 mg (yield: 88.9%)

$^1$H-NMR (DMSO-d$_6$) δ; 2.09 (3H, s), 2.61–3.15 (8H, m), 3.81 (2H, t, J=8.0 Hz), 4.24–4.31 (1H, m), 5.62–5.68 (2H, m), 6.57–7.40 (14H, m).

IR (KBr) cm$^{-1}$; 2924, 1611, 1508, 1416, 1302, 1233, 1198, 1121, 756, 700.

$[α]_D^{25}$ 13.7° (c 0.540, chloroform)

Example 125

Ethyl (2R)-2-[4-(2-{2-methyl-5-[2-(1-naphthyl)ethyl]-1H-pyrrol-1-yl}ethyl}phenoxy)-3-phenylpropanoate (1) Ethyl (2E)-3-(1-naphthyl)propenoate To a solution of 1-naphtaldehyde (30.0 g, 192 mmol) and ethyl diethylphosphonoacetate (51.6 g, 230 mmol) in THF (400 ml) was added sodium hydride (60%, 9.20 g, 230 mmol) and the mixture was stirred at room temperature for 12 hours. The reaction solution was poured into ice water, acidified with 1N hydrochloric acid and extracted with ethyl acetate. The extract was washed with water, dried over magnesium sulfate anhydride, and the solvent was removed under reduced pressure. The residue was purified by silica gel column chromatography (hexane:ethyl acetate=10:1) to give the object compound as an oily substance. 37.7 g (yield: 86.9%)

1H-NMR (CDCl$_3$) δ; 1.38 (3H, t, J=7.0 Hz), 4.32 (2H, q, J=7.0 Hz), 6.53 (1H, d, J=15.8 Hz), 7.45–7.92 (9H, m), 8.20 (1H, d, J=7.4 Hz), 8.53 (1H, d, J=15.8 Hz).

IR (KBr) cm$^{-1}$; 1713, 1634, 1306, 1265, 1254, 1179, 1042, 978, 799, 775.

(2) Ethyl 3-(1-naphthyl)propanoate

To a solution of ethyl (2E)-3-(1-naphthyl)propenoate (37.6 g, 166 mmol) in ethanol (500 ml) was added 10% palladium carbon (4 g) and the mixture was stirred under hydrogen atmosphere for 5 hours. The insoluble matter was filtered out and the filtrate was concentrated to give the object compound as an oily substance. 37.7 g (yield: 99.7%)

$^1$H-NMR (CDCl$_3$) δ; 1.24 (3H, t, J=8.2 Hz), 2.75 (2H, t, J=7.6 Hz), 3.42 (2H, t, J=7.6 Hz), 4.15 (2H, q, J=8.2 Hz), 7.36–8.05 (7H, m).

IR (KBr) cm$^{-1}$; 1732, 1464, 1372, 1177, 1036, 799, 777.

(3) 3-(1-Naphthyl)-1-propanol

To a suspension of lithium aluminium hydride (12.5 g, 329 mmol) in tetrahydrofuran (500 ml) was added dropwise a solution of ethyl 3-(1-naphthyl)propanoate (37.6 g, 165 mmol) in tetrahydrofuran (100 ml) and the mixture was refluxed for 4 hours under heating. To the residue were added water (13 ml) and 1 N aqueous sodium hydroxide solution (39 ml) under ice-cooling and the mixture was stirred at room temperature for 1 hour. The insoluble matter was filtered out and the filtrate was concentrated to give the object compound as an oily substance. 29.6 g (yield: 96.4%)

$^1$H-NMR (CDCl$_3$) δ; 1.95–2.10 (2H, m), 3.18 (2H, t, J=8.0 Hz), 3.71–3.79 (2H, m), 7.15–8.09 (7H, m).

IR (KBr) cm$^{-1}$; 3297, 1597, 1508, 1460, 1397, 1057, 1009, 777.

(4) 3-(1-Naphthyl)-1-propanal

To a solution of oxalyl chloride (27.0 ml, 312 mmol) in methylene chloride (500 ml) was added dropwise a solution of dimethylsulfoxide (32.9 ml, 415 mmol) in methylene chloride (50 ml) at −78° C. and the mixture was stirred at −78° C. for 10 minutes. To the mixed solution was added dropwise a solution of 3-(1-naphthyl)-1-propanol (29.0 g, 156 mmol) in methylene chloride (100 ml) at −78° C., and the mixture was stirred at −78° C. for 15 minutes and at −45° C. for 1 hour. To the obtained mixed solution was added triethylamine (158 ml, 1133 mmol) at −45° C. and the mixture was stirred at 0° C. for 20 minutes. To the obtained mixed solution was added saturated aqueous ammonium chloride solution (500 ml) and the mixture was stirred room temperature for 1 hour. The organic layer was separated, washed with water and dried over magnesium sulfate anhydride. The solvent was removed under reduced pressure to give the object compound as an oily substance. 28.0 g (yield: 97.6%)

$^1$H-NMR (CDCl$_3$) δ; 2.92 (2H, t, J=8.4 Hz), 3.42 (2H, t, J=8.4 Hz), 7.32–8.01 (7H, m), 9.89 (1H, s).

IR (KBr) cm$^{-1}$; 1725, 1395, 791, 777.

(5) 7-(1-Naphthyl)-2,5-heptanedione

A mixture of 3-(1-naphthyl)-1-propanal (28.0 g, 152 mmol), methyl vinyl ketone (10.7 g, 152 mmol), triethylamine (42.3 ml, 304 mmol), 3-ethyl-5-(2-hydroxyethyl-4-methyl thiazolium bromide (5.96 g, 23.6 ml) and ethanol (28 ml) was stirred at 77° C. for 2 days, and the solvent was removed under reduced pressure. The residue was purified by silica gel column chromatography (hexane:ethyl acetate=9:1) to give the object compound as an oily substance. 12.6 g (yield: 32.6%)

$^1$H-NMR (CDCl$_3$) δ; 2.20 (3H, s), 2.64–2.76 (4H, m), 2.92 (2H, t, J=7.2 Hz), 3.37 (2H, t, J=7.2 Hz), 7.26–8.01 (7H, m)

IR (KBr) cm$^{-1}$; 1713, 1397, 1362, 1168, 1098, 799, 779.

(6) 4-(2-{2-Methyl-5-[2-(1-naphthyl)ethyl]-1H-pyrrol-1-yl}ethyl)phenol

A solution of 7-(1-naphthyl)-2,5-heptanedione (3.00 g, 11.8 mmol), tyramine (1.62 g, 11.8 mmol) and p-toluenesulfonic acid monohydrate (168 mg, 0.882 mmol) in toluene (100 ml) was refluxed for 12 hours under heating and the solvent was removed under reduced pressure. The residue was purified by silica gel column chromatography (hexane:ethyl acetate=9:1) to give the object compound as an oily substance. 2.18 g (yield: 52.2%)

$^1$H-NMR (CDCl$_3$) δ; 2.17 (3H, s), 2.75–2.89 (4H, m), 3.41 (2H, t, J=8.0 Hz), 3.85 (2H, t, J=8.0 Hz), 4.95 (1H, s), 5.88 (1H, d, J=3.2 Hz), 6.01 (1H, d, J=3.2 Hz), 6.70 (2H, d, J=8.4 Hz), 6.84 (2H, d, J=8.4 Hz), 7.32–8.06 (7H, m).

IR (KBr) cm$^{-1}$; 3362, 1613, 1595, 1514, 1441, 1418, 1395, 1360, 1298, 1260, 1219, 1173, 828, 781, 756, 733.

(7) Ethyl (2R)-2-[4-(2-{2-methyl-5-[2-(1-naphthyl)ethyl]-1H-pyrrol-1-yl}ethyl)phenoxy]-3-phenylpropanoate To a solution of 4-(2-{2-methyl-5-[2-(1-naphthyl)ethyl]-1H-pyrrol-1-yl}ethyl)phenol (2.10 g, 5.92 mmol), ethyl (S)-2-hydroxy-3-phenylpropanoate (1.73 g, 8.89 mmol) and triphenylphosphine (2.33 g, 8.89 mmol) in toluene (20 ml) was added 1,1'-(azodicarbonyl)dipiperidine (2.24 g, 8.89 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 960 mg (yield: 30.5%)

$^1$H-NMR (CDCl$_3$) δ; 1.16 (3H, t, J=7.4 Hz), 2.14 (3H, s), 2.72 (2H, t, J=7.6 Hz), 2.86 (2H, t, J=7.6 Hz), 3.20–3.29 (2H, m), 3.40 (2H, t, J=7.6 Hz), 3.82 (2H, t, J=7.6 Hz), 4.07 (2H, q, J=7.4 Hz), 4.70–4.76 (1H, m), 5.86 (1H, d, J=3.4 Hz), 6.00 (1H, d, J=3.4 Hz), 6.71 (2H, d, J=8.8 Hz), 6.85 (2H, d, J=8.8 Hz), 7.21–8.06 (12H, m).

IR (KBr) cm$^{-1}$; 1752, 1510, 1298, 1238, 1188, 1084, 1028, 781, 748, 700.

Example 126

Sodium (2R)-2-[4-(2-{2-methyl-5-[2-(1-naphthyl)ethyl]-1H-pyrrol-1-yl}ethyl)phenoxy]-3-phenylpropanoate (1) (2R)-2-[4-(2-{2-Methyl-5-[2-(1-naphthyl)ethyl]-1H-pyrrol-1-yl}ethyl)phenoxy]-3-phenylpropanoic acid To a mixed solution of ethyl (2R)-2-[4-(2-{2-methyl-5-[2-(1-naphthyl)ethyl]-1H-pyrrol-1-yl}ethyl}phenoxy}-3-phenylpropanoate (960 mg, 1.81 mmol) in THF (20 ml) and methanol (10 ml) was added 1N aqueous potassium hydroxide solution (5.42 ml, 5.42 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=3:1) to give the object compound as an oily substance. 880 mg (yield: 96.5%)

$^1$H-NMR (CDCl$_3$) δ; 2.14 (3H, s), 2.71 (2H, t, J=7.0 Hz), 2.84 (2H, t, J=9.2 Hz), 3.25 (2H, d, J=6.2 Hz), 3.39 (2H, t, J=9.2 Hz), 3.82 (2H, t, J=7.0 Hz), 4.79 (1H, t, J=6.2 Hz), 5.86 (1H, d, J=3.4 Hz), 6.00 (1H, d, J=3.4 Hz), 6.72 (2H, d, J=8.6 Hz), 6.85 (2H, d, J=8.6 Hz), 7.18–8.05 (12H, m).

IR (KBr) cm$^{-1}$; 3032, 1728, 1510, 1236, 1181, 1084, 781, 733, 700.

(2) Sodium (2R)-2-[4-(2-{2-methyl-5-[2-(1-naphthyl)ethyl]-1H-pyrrol-1-yl}ethyl)phenoxy]-3-phenylpropanoate Ethanol (8 ml) and a solution of 1N sodium hydroxide in ethanol (1.49 ml) were added to (2R)-2-[4-(2-{2-methyl-5-[2-(1-naphthyl)ethyl]-1H-pyrrol-1-yl}ethyl)phenoxy}-3-phenylpropanoic acid (835 mg, 1.66 mmol) and the mixture was concentrated. To the residue was added diisopropylether to give the object compound as a solid. 711 mg (yield: 90.8%)

$^1$H-NMR (DMSO-d$_6$) δ; 2.11 (3H, s), 2.61 (2H, t, J=7.8 Hz), 2.83 (2H, t, J=7.0 Hz), 2.95–3.17 (2H, m), 3.31 (2H, t, J=7.0 Hz),3.79 (2H, t, J=7.8 Hz), 4.24–4.30 (1H, m), 5.68 (1H, d, J=3.4 Hz), 5.82 (1H, d, J=3.4 Hz),6.65 (2H, d, J=8.4 Hz), 6.83 (2H, d, J=8.4 Hz), 7.08–8.08 (12H, m).

IR (KBr) cm$^{-1}$; 1615, 1510, 1416, 1232, 1059, 1017, 779, 747.

$[α]_D^{26}$ 15.6° (c 0.515, methanol).

Example 127

Ethyl (2R)-2-(4-{2-[2-methyl-5-(2-trifluoromethylphenethyl)-1H-pyrrol-1-yl]ethyl}phenoxy)-3-phenylpropanoate (1) Ethyl (2E)-3-(2-trifluoromethylphenyl)propenoate The object compound was obtained from 2-trifluoromethyl benzaldehyde as an oily substance, according to the similar manner to that of Example 125(1). yield: 96.9%

$^1$H-NMR (CDCl$_3$) δ; 1.35 (3H, t, J=7.4 Hz), 4.29 (2H, q, J=7.4 Hz), 6.41 (1H, d, J=15.8 Hz), 7.48–7.73 (4H, m), 8.02–8.11 (1H, m).

IR (KBr) cm$^{-1}$; 1717, 1642, 1315, 1292, 1277, 1163, 1126, 1038, 980.

(2) Ethyl 3-(2-trifluoromethylphenyl)propanoate

The object compound was obtained from ethyl (2E)-3-(2-trifluoromethylphenyl)propenoate as an oily substance, according to the similar manner to that of Example 125(2). yield: 87.5%

$^1$H-NMR (CDCl$_3$) δ; 1.25 (3H, t, J=7.2 Hz), 2.62 (2H, t, J=7.4 Hz), 3.14 (2H, t, J=7.4 Hz), 4.15 (2H, q, J=7.2 Hz), 7.27–7.65 (4H, m).

IR (KBr) cm$^{-1}$; 1736, 1316, 1177, 1154, 1119, 1061, 1040, 758, 652.

(3) 3-(2-Trifluoromethylphenyl)-1-propanol

The object compound was obtained from ethyl 3-(2-trifluoromethylphenyl)propanoate as an oily substance, according to the similar manner to that of Example 125(3). yield: 96.4%

$^1$H-NMR (CDCl$_3$) δ; 1.40 (1H, t, J=5.6 Hz), 1.82–1.97 (2H, m), 2.89 (2H, t, J=8.4 Hz), 3.68–3.78 (2H, m), 7.18–7.64 (4H, m).

IR (KBr) cm$^{-1}$; 3303, 1314, 1157, 1117, 1061, 1032, 768.

(4) 3-(2-Trifluoromethylphenyl)propanal

The object compound was obtained from 3-(2-trifluoromethylphenyl)-1-propanol as an oily substance, according to the similar manner to that of Example 125(4). yield: 96.6%

$^1$H-NMR (CDCl$_3$) δ; 2.79 (2H, t, J=8.0 Hz), 3.14 (2H, t, J=8.0 Hz), 7.16–7.65 (4H, m), 9.83 (1H, s).

IR (KBr) cm$^{-1}$; 1725, 1608, 1454, 1314, 1161, 1119, 1061, 1038, 770.

(5) 7-(2-Trifluoromethylphenyl)-2,5-heptanedione

The object compound was obtained from 3-(2-trifluoromethylphenyl)propanal as an oily substance, according to the similar manner to that of Example 125(5). yield: 41.3%

$^1$H-NMR (CDCl$_3$) δ; 2.20 (3H, s), 2.63–3.12 (8H, m), 7.27–7.64 (4H, m).

IR (KBr) cm$^{-1}$; 1713, 1314, 1163, 1118, 1061, 1038, 770, 654.

(6) 1-(4-Methoxyphenethyl)-2-methoxy-5-(2-trifluoromethylphenethyl)-1H-pyrrole

The object compound was obtained from 7-(2-trifluoromethylphenyl)-2,5-heptanedione as an oily substance, according to the similar manner to that of Example 125(6). yield: 44.5%

$^1$H-NMR (CDCl$_3$) δ; 2.17 (3H, s), 2.66–3.14 (6H, m), 3.78 (3H, s), 3.90 (2H, t, J=7.4 Hz), 5.84 (1H, d, J=3.2 Hz), 5.90 (1H, d, J=3.2 Hz), 6.81 (2H, d, J=8.4 Hz), 6.96 (2H, d, J=8.4 Hz), 7.25–7.66 (4H, m).

IR (KBr) cm$^{-1}$; 1611, 1512, 1314, 1248, 1119, 1038, 826, 738, 754.

(7) 4-{2-[2-Methyl-5-(2-trifluoromethylphenethyl)-1H-pyrrol-1-yl]ethyl}phenol

The object compound was obtained from 1-(4-methoxyphenethyl)-2-methoxy-5-(2-trifluoromethylphenethyl)-1H-pyrrole as an oily substance, according to the similar manner to that of Example 125(7). yield: 96.6%

$^1$H-NMR (CDCl$_3$) δ; 2.15 (3H, s), 2.66–3.13 (6H, m), 3.88 (2H, t, J=7.8 Hz), 4.95 (1H, bs), 5.83–5.91 (2H, m), 6.74 (2H, d, J=8.8 Hz), 6.89 (2H, d, J=8.8 Hz), 7.26–7.65 (4H, m)

IR (KBr) cm$^{-1}$; 3306, 1611, 1514, 1314, 1121, 1038, 828, 768.

(8) Ethyl (2R)-2-(4-{2-[2-methyl-5-(2-trifluoromethylphenethyl)-1H-pyrrol-1-yl]ethyl}phenoxy)-3-phenylpropanoate The object compound was obtained from 4-{2-[2-methyl-5-(2-trifluoromethylphenethyl)-1H-pyrrol-1-yl]ethyl}phenol as an oily substance, according to the similar manner to that of Example 125(8). yield: 25.2%

$^1$H-NMR (CDCl$_3$) δ; 1.17 (3H, t, J=7.6 Hz), 2.13 (3H, s), 2.67–2.80 (4H, m), 3.04–3.12 (2H, m), 3.21–3.25 (2H, m), 3.86 (2H, t, J=8.0 Hz), 4.15 (2H, q, J=7.6 Hz), 4.71–4.78 (1H, m), 5.82 (1H, d, J=3.2 Hz), 5.89 (1H, d, J=3.2 Hz), 6.74 (2H, d, J=8.4 Hz), 6.92 (2H, d, J=8.4 Hz), 7.15–7.65 (9H, m).

IR (KBr) cm$^{-1}$; 1755, 1732, 1510, 1314, 1238, 1181, 1119, 1038, 768, 748, 700.

$[α]_D^{27}$ 10.9° (c 0.525, chloroform)

Example 128

Sodium (2R)-2-(4-{2-[2-methyl-5-(2-trifluoromethylphenethyl)-1H-pyrrol-1-yl]ethyl}phenoxy)-3-phenylpropanoate (1) (2R)-2-(4-{2-[2-Methyl-5-(2-trifluoromethylphenethyl)-1H-pyrrol-1-yl]ethyl}phenoxy)-3-phenylpropanoic acid The object compound was obtained from ethyl (2R)-2-(4-{2-[2-methyl-5-(2-trifluoromethylphenethyl)-1H-pyrrol-1-yl]ethyl}phenoxy)-3-phenylpropanoate as an oily substance, according to the similar manner to that of Example 126(1). yield: 98.5%

$^1$H-NMR (CDCl$_3$) δ; 2.13 (3H, s), 2.66–2.80 (4H, m), 3.04–3.12 (2H, m), 3.26 (2H, t, J=6.6 Hz), 3.82 (2H, t, J=7.8 Hz), 4.81 (1H, t, J=6.6 Hz), 5.82 (1H, d, J=3.4 Hz), 5.89 (1H, d, J=3.4 Hz), 6.75 (2H, d, J=8.8 Hz), 6.93 (2H, d, J=8.8 Hz), 7.22–7.65 (9H, m).

IR (KBr) cm$^{-1}$; 2928, 1730, 1510, 1314, 1233, 1117, 1038, 766, 754, 700.

$[α]_D^{28}$ 3.65° (c 1.12, chloroform)

(2) Sodium (2R)-2-(4-{2-[2-methyl-5-(2-trifluoromethylphenethyl)-1H-pyrrol-1-yl]ethyl}phenoxy)-3-phenylpropanoate The object compound was obtained from (2R)-2-(4-{2-[2-methyl-5-(2-trifluoromethylphenethyl)-1H-pyrrol-1-yl]ethyl}phenoxy)-3-phenylpropanoic acid as a solid, according to the similar manner to that of Example 126(2). yield: 77.8%

¹H-NMR (DMSO-d₆) δ; 2.11 (3H, s), 2.65–2.73 (4H, m), 2.90–3.16 (4H, m), 3.82 (2H, t, J=7.4 Hz), 4.24–4.31 (1H, m), 5.65 (1H, d, J=3.6 Hz), 5.69 (1H, d, J=3.6 Hz), 6.66 (2H, d, J=8.8 Hz), 6.89 (2H, d, J=8.8 Hz), 7.12–7.68 (9H, m).

IR (KBr) cm⁻¹; 1613, 1508, 1416, 1314, 1233, 1118, 1061, 1038, 767, 700.

Example 129

Ethyl (2R)-2-{4-[1-(4-dodecyloxyphenethyl)-5-methyl-1H-pyrrol-2-yl]phenoxy}-3-phenylpropanoate (1) 4-{2-[2-(4-Benzyloxyphenyl)-5-methyl-1H-pyrrol-1-yl]ethyl}phenol A solution of 1-(4-benzyloxyphenyl)-1,4-pentanedione (3.00 g, 10.6 mmol), tyramine (1.46 g, 10.6 mmol) and p-toluenesulfonic acid monohydrate (151 mg, 0.792 mmol) in toluene (100 ml) was refluxed for 12 hours under heating and the solvent was removed under reduced pressure. The residue was purified by silica gel column chromatography (hexane:ethyl acetate=8:1) to give the object compound as an oily substance. 3.00 g (yield: 73.7%)

¹H-NMR (CDCl₃) δ; 2.22 (3H, s), 2.67 (2H, t, J=7.4 Hz), 4.00 (2H, t, J=7.4 Hz), 4.72 (1H, s), 5.11 (2H, s), 5.91 (1H, d, J=3.4 Hz), 6.03 (1H, d, J=3.4 Hz), 6.65 (2H, d, J=8.8 Hz), 6.76 (2H, d, J=8.8 Hz), 6.99 (2H, d, J=8.8 Hz), 7.24–7.49 (7H, m).

IR (KBr) cm⁻¹; 3389, 1613, 1514, 1242, 1175, 1024, 833, 739, 698.

(2) 2-(4-Benzyloxyphenyl)-1-(4-dodecyloxyphenethyl)-5-methyl-1H-pyrrole

A solution of 4-{2-[2-(4-benzyloxyphenyl)-5-methyl-1H-pyrrol-1-yl]ethyl}phenol (1.50 g, 3.91 mmol), 1-bromododecane (1.41 ml, 5.87 mmol) and potassium carbonate (811 mg, 5.87 mmol) in DMF (15 ml) was stirred at 80° C. for 4 hours. The reaction solution was poured into water and the mixture was extracted with ethyl acetate. The extract was washed with water, dried over magnesium sulfate anhydride and solvent was removed under reduced pressure. The residue was purified by silica gel column chromatography (hexane:ethyl acetate=30:1) to give the object compound as an oily substance. 1.28 g (yield: 59.3%)

¹H-NMR (CDCl₃) δ; 0.88 (3H, t, J=6.6 Hz), 1.22–1.43 (18H, m), 1.69–1.79 (2H, m), 2.23 (3H, s), 2.69 (2H, t, J=7.8 Hz), 3.90 (2H, t, J=6.6 Hz), 3.99 (2H, t, J=7.8 Hz), 5.11 (2H, s), 5.91 (1H, d, J=3.2 Hz), 6.03 (1H, d, J=3.2 Hz), 6.73 (2H, d, J=8.8 Hz), 6.82 (2H, d, J=8.8 Hz), 7.00 (2H, d, J=8.8 Hz), 7.24–7.50 (7H, m).

IR (KBr) cm⁻¹; 1523, 1512, 1175, 1026, 835, 756, 698.

(3) 4-[1-(4-Dodecyloxyphenethyl)-5-methyl-1H-pyrrol-2-yl]phenol

To a solution of 2-(4-benzyloxyphenyl)-1-(4-dodecyloxyphenethyl)-5-methyl-1H-pyrrole (1.23 g, 2.23 mmol) in ethanol (40 ml) and tetrahydrofuran (20 ml) was added 10% palladium carbon (200 mg) and the mixture was stirred under hydrogen atmosphere for 2 hours. The insoluble matter was filtered out and the filtrate was concentrated to give the object compound as an oily substance. 1.02 g (yield: 99.0%)

¹H-NMR (CDCl₃) δ; 0.88 (3H, t, J=6.6 Hz), 1.18–1.42 (18H, m), 1.68–1.79 (2H, m), 2.23 (3H, s), 2.68 (2H, t, J=7.6 Hz), 3.90 (2H, t, J=6.6 Hz), 3.99 (2H, t, J=7.6 Hz), 5.91 (1H, d, J=3.4 Hz), 6.02 (1H, d, J=3.4 Hz), 6.72–6.87 (6H, m), 7.72 (2H, d, J=8.6 Hz).

IR (KBr) cm⁻¹; 3405, 1526, 1512, 1468, 1246, 1177, 837, 821, 756.

(4) Ethyl (2R)-2-{4-[1-(4-dodecyloxyphenethyl)-5-methyl-1H-pyrrol-2-yl]phenoxy}-3-phenylpropanoate To a solution of 4-[1-(4-dodecyloxyphenethyl)-5-methyl-1H-pyrrol-2-yl]phenol (1.00 g, 2.17 mmol), ethyl (S)-2-hydroxy-3-phenylpropanoate (631 mg, 3.25 mmol) and triphenylphosphine (852 mg, 3.25 mmol) in toluene (10 ml) was added 1,1'-(azodicarbonyl)dipiperidine (820 mg, 3.25 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 471 mg (yield: 34.1%)

¹H-NMR (CDCl₃) δ; 0.88 (3H, t, J=7.0 Hz), 1.16–1.38 (21H, m), 1.72–1.79 (2H, m), 2.22 (3H, s), 2.66 (2H, t, J=7.4 Hz), 3.26–3.30 (2H, m), 3.89 (2H, t, J=6.6 Hz), 3.97 (2H, t, J=7.4 Hz), 4.20 (2H, q, J=7.4 Hz), 4.79–4.86 (1H, m), 5.89 (1H, d, J=3.8 Hz), 6.00 (1H, d, J=3.8 Hz), 6.70–6.88 (6H, m), 7.20–7.34 (7H, m).

IR (KBr) cm⁻¹; 1755, 1732, 1512, 1244, 1179, 1032, 837, 756, 700.

Example 130

Sodium (2R)-2-{4-[1-(4-dodecyloxyphenethyl)-5-methyl-1H-pyrrol-2-yl]phenoxy}-3-phenylpropanoate (1) (2R)-2-{4-[5-methyl-1-(4-dodecyloxyphenethyl)-1H-pyrrol-2-yl]phenoxy}-3-phenylpropanoic acid To a mixed solution of ethyl (2R)-2-{4-[5-methyl-1-(4-dodecyloxyphenethyl)-1H-pyrrol-2-yl]phenoxy}-3-phenylpropanoate (461 mg, 0.722 mmol) in THF (10 ml) and methanol (5 ml) was added 1N aqueous potassium hydroxide solution (2.16 ml, 2.16 mmol) and the mixture was stirred for 1 hour at room temperature. The reaction solution was neutralized with 1N hydrochloric acid and extracted with ethyl acetate. The extract was washed with water, dried over magnesium sulfate anhydride, and the solvent was removed under reduced pressure. The residue was purified by silica gel column chromatography (hexane:ethyl acetate=1:1) to give the object compound as an oily substance. 360 mg (yield: 81.6%)

¹H-NMR (CDCl₃) δ; 0.88 (3H, t, J=7.0 Hz), 1.18–1.47 (18H, m), 1.71–1.79 (2H, m), 2.21 (3H, s), 2.64 (2H, t, J=6.2 Hz), 3.31 (2H, d, J=5.8 Hz), 3.85–4.01 (4H, m), 4.90 (1H, t, J=5.8 Hz), 5.89 (1H, d, J=3.2 Hz), 5.99 (1H, d, J=3.2 Hz), 6.69–6.88 (6H, m), 7.19–7.31 (7H, m).

IR (KBr) cm⁻¹; 2926, 1728, 1512, 1244, 1177, 835, 756.

(2) Sodium (2R)-2-{4-[5-methyl-1-(4-dodecyloxyphenethyl)-1H-pyrrol-2-yl]phenoxy}-3-phenylpropanoate Ethanol (3 ml) and a solution of 1N sodium hydroxide in ethanol (0.480 ml) were added to (2R)-2-{4-[5-methyl-1-(4-dodecyloxyphenethyl)-1H-pyrrol-2-yl]phenoxy}-3-phenylpropanoic acid (325 mg, 0.533 mmol) and the mixture was concentrated. To the residue was added ether to give the object compound as a solid. 160 mg (yield: 52.8%)

¹H-NMR (DMSO-d₆) δ; 0.86 (3H, t, J=7.0 Hz), 1.07–1.41 (18H, m), 1.61–1.75 (2H, m), 2.11 (3H, s), 2.50–2.69 (2H, m), 3.24–3.02 (2H, m), 3.80–3.99 (4H, m), 4.31–4.36 (1H, m), 5.73 (1H, d, J=3.2 Hz), 5.80 (1H, d, J=3.2 Hz), 6.70–6.80 (6H, m), 7.10–7.30 (7H, m).

IR (KBr) cm⁻¹; 1614, 1512, 1408, 1244, 1177, 1055, 1030, 829, 758, 700.

$[\alpha]_D^{25}$ 2.96° (c 0.540, methanol)

Example 131

Ethyl (2R)-2-{4-[1-(4-heptyloxyphenethyl)-5-methyl-1H-pyrrol-2-yl]phenoxy}-3-phenylpropanoate (1) 2-(4-Benzyloxyphenyl)-5-methyl-1-(4-heptyloxyphenethyl)-1H-pyrrole The object compound was obtained from 1-bromoheptane as an oily substance, according to the similar manner to that of Example 129(2). yield: 84.6%

$^1$H-NMR (CDCl$_3$) δ; 0.89 (3H, t, J=7.0 Hz), 1.22–1.43 (8H, m), 1.69–1.79 (2H, m), 2.24 (3H, s), 2.69 (2H, t, J=8.0 Hz), 3.90 (2H, t, J=6.6 Hz), 4.00 (2H, t, J=8.0 Hz), 5.11 (2H, s), 5.91 (1H, d, J=3.2 Hz), 6.03 (1H, d, J=3.2 Hz), 6.73 (2H, d, J=8.8 Hz), 6.82 (2H, d, J=8.8 Hz), 6.99 (2H, d, J=8.8 Hz),7.24–7.50 (7H, m).

IR (KBr) cm$^{-1}$; 1613, 1524, 1512, 1244, 1175, 1024, 835, 754, 737, 698.

(2) 4-[1-(4-Heptyloxyphenethyl)-5-methyl-1H-pyrrol-2-yl]phenol

The object compound was obtained from 2-(4-benzyloxyphenyl)-5-methyl-1-(4-heptyloxyphenethyl)-1H-pyrrole as an oily substance, according to the similar manner to that of Example 129(3). yield: 97.6%

$^1$H-NMR (CDCl$_3$) δ; 0.89 (3H, t, J=6.6 Hz), 1.21–1.45 (8H, m), 1.69–1.79 (2H, m), 2.23 (3H, s), 2.68 (2H, t, J=7.6 Hz), 3.90 (2H, t, J=6.6 Hz), 3.99 (2H, t, J=7.6 Hz), 5.91 (1H, d, J=3.2 Hz), 6.03 (1H, d, J=3.2 Hz), 6.72–6.80 (6H, m), 7.22 (2H, d, J=8.6 Hz).

IR (KBr) cm$^{-1}$; 3312, 1613, 1512, 1470, 1400, 1246, 1177, 837, 826, 758.

(3) Ethyl (2R)-2-{4-[1-(4-heptyloxyphenethyl)-5-methyl-1H-pyrrol-2-yl]phenoxy}-3-phenylpropanoate The object compound was obtained from 4-[1-(4-heptyloxyphenethyl)-5-methyl-1H-pyrrol-2-yl]phenol as an oily substance, according to the similar manner to that of Example 129(4). yield: 47.1%

$^1$H-NMR (CDCl$_3$) δ; 0.89 (3H, t, J=6.6 Hz), 1.16–1.39 (11H, m), 1.71–1.79 (2H, m), 2.22 (3H, s), 2.65 (2H, t, J=6.8 Hz), 3.25–3.29 (2H, m), 3.86–4.00 (4H, m), 4.20 (2H, q, J=7.4 Hz), 4.79–4.86 (1H, m), 5.89 (1H, d, J=3.4 Hz), 6.00 (1H, d, J=3.4 Hz), 6.70–6.88 (6H, m), 7.19–7.34 (7H, m).

IR (KBr) cm$^{-1}$; 1755, 1732, 1512, 1479, 1277, 1244, 1179, 1028, 835, 756.

Example 132

Sodium (2R)-2-{4-[1-(4-heptyloxyphenethyl)-5-methyl-1H-pyrrol-2-yl]phenoxy}-3-phenylpropanoate (1) (2R)-2-{4-[1-(4-heptyloxyphenethyl)-5-methyl-1H-pyrrol-2-yl]phenoxy}-3-phenylpropanoic acid The object compound was obtained from ethyl (2R)-2-{4-[1-(4-heptyloxyphenethyl)-5-methyl-1H-pyrrol-2-yl]phenoxy}-3-phenylpropanoate as an oily substance, according to the similar manner to that of Example 130(1). yield: 72.9%

$^1$H-NMR (CDCl$_3$) δ; 0.89 (3H, t, J=7.0 Hz), 1.22–1.43 (8H, m), 1.71–1.79 (2H, m), 2.22 (3H, s), 2.65 (2H, t, J=8.0 Hz), 3.32 (2H, d, J=6.2 Hz), 3.86–4.01 (4H, m), 4.91 (1H, t, J=6.2 Hz), 5.90 (1H, d, J=3.4 Hz), 6.00 (1H, d, J=3.4 Hz), 6.70–6.88 (6H, m), 7.20–7.32 (7H, m).

IR (KBr) cm$^{-1}$; 1728, 1512, 1242, 835, 756, 700.

(2) Sodium (2R)-2-{4-[1-(4-heptyloxyphenethyl)-5-methyl-1H-pyrrol-2-yl]phenoxy}-3-phenylpropanoate The object compound was obtained from (2R)-2-{4-[1-(4-heptyloxyphenethyl)-5-methyl-1H-pyrrol-2-yl]phenoxy}-3-phenylpropanoic acid as a solid, according to the similar manner to that of Example 130(2). yield: 69.8%

$^1$H-NMR (DMSO-d$_6$) δ; 0.87 (3H, t, J=7.0 Hz), 1.08–1.41 (8H, m), 1.58–1.73 (2H, m), 2.11 (3H, s), 2.52–2.65 (2H, m), 2.94–3.21 (2H, m), 3.85–3.91 (4H, m), 4.35–4.40 (1H, m), 5.74 (1H, d, J=3.2 Hz), 5.81 (1H, d, J=3.2 Hz), 6.72–6.85 (6H, m), 7.11–7.34 (7H, m).

IR (KBr) cm$^{-1}$; 1615, 1512, 1406, 1244, 1057, 1030, 829, 758, 700, 563, 532.

$[α]_D^{25}$ 2.85° (c 0.580, methanol)

Example 133

Ethyl (2R)-2-{4-[5-methyl-1-(4-nonyloxyphenethyl)-1H-pyrrol-2-yl]phenoxy}-3-phenylpropanoate (1) 2-(4-Benzyloxyphenyl)-5-methyl-1-(4-nonyloxyphenethyl)-1H-peel The object compound was obtained from 1-bromononane as an oily substance, according to the similar manner to that of Example 129(2). yield: 87.4%

$^1$H-NMR (CDCl$_3$) δ; 0.88 (3H, t, J=6.8 Hz), 1.16–1.53 (12H, m), 1.72–1.79 (2H, m), 2.24 (3H, s), 2.69 (2H, t, J=7.8 Hz), 3.90 (2H, t, J=6.6 Hz), 4.00 (2H, t, J=7.8 Hz), 5.11 (2H, s), 5.91 (1H, d, J=3.2 Hz), 6.04 (1H, d, J=3.2 Hz), 6.74 (2H, d, J=8.8 Hz), 6.82 (2H, d, J=8.8 Hz), 7.00 (2H, d, J=8.8 Hz),7.25–7.49 (7H, m).

IR (KBr) cm$^{-1}$; 1613, 1524, 1512, 1244, 1175, 1026, 835, 754, 737.

(2) 4-[5-Methyl-1-(4-nonyloxyphenethyl)-1H-pyrrol-2-yl]phenol

The object compound was obtained from 2-(4-benzyloxyphenyl)-5-methyl-1-(4-nonyloxyphenethyl)-1H-pyrrole as an oily substance, according to the similar manner to that of Example 129(3). yield: 96.6%

$^1$H-NMR (CDCl$_3$) δ; 0.88 (3H, t, J=6.6 Hz), 1.21–1.42 (12H, m), 1.71–1.79 (2H, m), 2.24 (3H, s), 2.68 (2H, t, J=7.2 Hz), 3.90 (2H, t, J=6.2 Hz), 3.99 (2H, t, J=7.2 Hz), 5.91 (1H, d, J=3.2 Hz), 6.03 (1H, d, J=3.2 Hz), 6.72–6.87 (6H, m), 7.22 (2H, d, J=8.2 Hz)

IR (KBr) cm$^{-1}$; 3385, 1615, 1512, 1470, 1399, 1244, 1177, 837, 824, 758.

(3) Ethyl (2R)-2-{4-[5-methyl-1-(4-nonyloxyphenethyl)-1H-pyrrol-2-yl]phenoxy}-3-phenylpropanoate The object compound was obtained from 4-[5-methyl-1-(4-nonyloxyphenethyl)-1H-pyrrol-2-yl]phenol as an oily substance, according to the similar manner to that of Example 129(4). yield: 54.8%

$^1$H-NMR (CDCl$_3$) δ; 0.88 (3H, t, J=6.6 Hz), 1.16–1.39 (15H, m), 1.72–1.79 (2H, m), 2.22 (3H, s), 2.66 (2H, t, J=8.4 Hz), 3.26–3.29 (2H, m), 3.86–4.00 (4H, m), 4.20 (2H, q, J=7.4 Hz), 4.79–4.86 (1H, m), 5.90 (1H, d, J=3.4 Hz), 6.00 (1H, d, J=3.4 Hz), 6.70–6.88 (6H, m), 7.19–7.34 (7H, m).

IR (KBr) cm$^{-1}$; 1755, 1732, 1512, 1481, 1244, 1179, 1032, 835, 756, 700.

Example 134

Sodium (2R)-2-{4-[5-methyl-1-(4-nonyloxyphenethyl)-1H-pyrrol-2-yl]phenoxy}-3-phenylpropanoate (1) (2R)-2-{4-[5-Methyl-1-(4-nonyloxyphenethyl)-1H-pyrrol-2-yl]phenoxy}-3-phenylpropanoic acid The object compound was obtained from (2R)-2-{4-[5-methyl-1-(4-nonyloxyphenethyl)-1H-pyrrol-2-yl]phenoxy}-3-phenylpropanoic acid as an oily substance, according to the similar manner to that of Example 130(1). yield: 86.8%

$^1$H-NMR (CDCl$_3$) δ; 0.88 (3H, t, J=6.6 Hz), 1.22–1.41 (12H, m), 1.71–1.78 (2H, m), 2.21 (3H, s), 2.64 (2H, t, J=7.0

Hz), 3.31 (2H, d, J=6.2 Hz), 3.85–4.00 (4H, m), 4.89 (1H, t, J=6.2 Hz), 5.89 (1H, d, J=3.8 Hz), 6.00 (1H, d, J=3.8 Hz), 6.69–6.88 (6H, m), 7.19–7.31 (7H, m).

IR (KBr) cm$^{-1}$; 1728, 1512, 1242, 1177, 1086, 1032, 835, 758, 700.

(2) Sodium (2R)-2-{4-[5-methyl-1-(4-nonyloxyphenethyl)-1H-pyrrol-2-yl]phenoxy}-3-phenylpropanoate The object compound was obtained from (2R)-2-{4-[5-methyl-1-(4-nonyloxyphenethyl)-1H-pyrrol-2-yl]phenoxy}-3-phenylpropanoic acid as a solid, according to the similar manner to that of Example 130(2). yield: 82.1%

$^1$H-NMR (DMSO-d$_6$) δ; 0.87 (3H, t, J=6.6 Hz), 1.19–1.33 (12H, m), 1.65–1.71 (2H, m), 2.11 (3H, s), 2.54–2.68 (2H, m), 2.96–3.23 (2H, m), 3.84–3.91 (4H, m), 4.33–4.39 (1H, m), 5.73 (1H, d, J=3.2 Hz), 5.81 (1H, d, J=3.2 Hz), 6.70–6.85 (6H, m), 7.10–7.35 (7H, m).

IR (KBr) cm$^{-1}$; 1615, 1512, 1406, 1244, 1175, 1055, 1032, 839, 758.

$[\alpha]_D^{24}$ 1.88° (c 0.525, methanol)

Example 135

Ethyl (2R)-2-{4-[1-(4-hexyloxyphenethyl)-5-methyl-1H-pyrrol-2-yl]phenoxy}-3-phenylpropanoate (1) 2-(4-Benzyloxyphenyl)-1-(4-hexyloxyphenethyl)-5-methyl-1H-pyrrole The object compound was obtained from 1-bromohexane as an oily substance, according to the similar manner to that of Example 129(2). yield: 70.5%

$^1$H-NMR (CDCl$_3$) δ; 0.90 (3H, t, J=6.6 Hz), 1.27–1.48 (6H, m), 1.69–1.79 (2H, m), 2.24 (3H, s), 2.69 (2H, t, J=7.4 Hz), 3.90 (2H, t, J=6.2 Hz), 4.00 (2H, t, J=7.4 Hz), 5.11 (2H, s), 5.91 (1H, d, J=3.2 Hz), 6.03 (1H, d, J=3.2 Hz), 6.74 (2H, d, J=8.8 Hz), 6.82 (2H, d, J=8.8 Hz), 7.00 (2H, d, J=8.8 Hz),7.03–7.50 (7H, m).

IR (KBr) cm$^{-1}$; 1613, 1524, 1246, 1175, 1026, 835, 756, 737, 698.

(2) 4-[1-(4-Hexyloxyphenethyl)-5-methyl-1H-pyrrol-2-yl]phenol

The object compound was obtained from 2-(4-benzyloxyphenyl)-1-(4-hexyloxyphenethyl)-5-methyl-1H-pyrrole as an oily substance, according to the similar manner to that of Example 129(3). yield: 97.0%

$^1$H-NMR (CDCl$_3$) δ; 0.908 (3H, t, J=6.6 Hz), 1.25–1.47 (6H, m), 1.68–1.79 (2H, m), 2.23 (3H, s), 2.68 (2H, t, J=7.8 Hz), 3.87–4.02 (4H, m), 5.91 (1H, d, J=3.2 Hz), 6.02 (1H, d, J=3.2 Hz), 6.72–6.87 (6H, m), 7.21 (2H, d, J=8.8 Hz)

IR (KBr) cm$^{-1}$; 3407, 1613, 1526, 1512, 1244, 1177, 1030, 837, 822, 758.

(3) Ethyl (2R)-2-{4-[1-(4-hexyloxyphenethyl)-5-methyl-1H-pyrrol-2-yl]phenoxy}-3-phenylpropanoate The object compound was obtained from 4-[1-(4-hexyloxyphenethyl)-5-methyl-1H-pyrrol-2-yl]phenol as an oily substance, according to the similar manner to that of Example 129(4). yield: 53.3%

$^1$H-NMR (CDCl$_3$) δ; 0.90 (3H, t, J=6.0 Hz), 1.16–1.48 (9H, m), 1.69–1.79 (2H, m), 2.22 (3H, s), 2.66 (2H, t, J=7.6 Hz), 3.26–3.30 (2H, m), 3.86–4.00 (4H, m), 4.20 (2H, q, J=7.0 Hz), 4.79–4.86 (1H, m), 5.90 (1H, d, J=3.6 Hz), 6.00 (1H, d, J=3.6 Hz), 6.71–6.92 (6H, m), 7.18–7.32 (7H, m).

IR (KBr) cm$^{-1}$; 1755, 1732, 1512, 1244, 1179, 1086, 1032, 835, 756, 700.

Example 136

Sodium (2R)-2-{4-[1-(4-hexyloxyphenethyl)-5-methyl-1H-pyrrol-2-yl]phenoxy}-3-phenylpropanoate (1) (2R)-2-{4-[1-(4-Hexyloxyphenethyl)-5-methyl-1H-pyrrol-2-yl]phenoxy}-3-phenylpropanoic acid The object compound was obtained from ethyl (2R)-2-{4-[1-(4-hexyloxyphenethyl)-5-methyl-1H-pyrrol-2-yl]phenoxy}-3-phenylpropanoate as an oily substance, according to the similar manner to that of Example 130(1). yield: 78.9%

$^1$H-NMR (CDCl$_3$) δ; 0.90 (3H, t, J=6.2 Hz), 1.26–1.42 (6H, m), 1.68–1.78 (2H, m), 2.21 (3H, s), 2.64 (2H, t, J=8.8 Hz), 3.31 (2H, d, J=6.2 Hz), 3.86–4.00 (4H, m), 4.90 (1H, t, J=6.2 Hz), 5.89 (1H, d, J=3.6 Hz), 5.99 (1H, d, J=3.6 Hz), 6.69–6.88 (6H, m), 7.19–7.33 (7H, m).

IR (KBr) cm$^{-1}$; 2934, 1728, 1512, 1244, 835, 758, 700.

(2) Sodium (2R)-2-{4-[1-(4-hexyloxyphenethyl)-5-methyl-1H-pyrrol-2-yl]phenoxy}-3-phenylpropanoate The object compound was obtained from (2R)-2-{4-[1-(4-hexyloxyphenethyl)-5-methyl-1H-pyrrol-2-yl]phenoxy}-3-phenylpropanoic acid as a solid, according to the similar manner to that of Example 130(2). yield: 96.2%

$^1$H-NMR (DMSO-d$_6$) δ; 0.88 (3H, t, J=6.2 Hz), 1.25–1.39 (6H, m), 1.64–1.72 (2H, m), 2.11 (3H, s), 2.55–2.68 (2H, m), 2.95–3.20 (2H, m), 3.84–3.91 (4H, m), 4.35–4.39 (1H, m), 5.73 (1H, d, J=3.2 Hz), 5.81 (1H, d, J=3.2 Hz), 6.70–6.84 (6H, m), 7.10–7.34 (7H, m).

IR (KBr) cm$^{-1}$; 1615, 1512, 1406, 1308, 1244, 1177, 1057, 1032, 829, 758, 700.

$[\alpha]_D^{25}$ 1.73° (c 0.700, methanol)

Example 137

Ethyl (2R)-2-{4-[5-methyl-1-(4-octyloxyphenethyl)-1H-pyrrol-2-yl]phenoxy}-3-phenylpropanoate (1) 2-(4-Benzyloxyphenethyl)-5-methyl-1-(4-octyloxyphenethyl)-1H-pyrrole A solution of 4-{2-[2-(4-benzyloxyphenethyl)-5-methyl-1H-pyrrol-1-yl]ethyl}phenol (1.00 g, 2.61 mmol), 1-bromooctane (0.541 ml, 3.13 mmol) and potassium carbonate (433 mg, 3.13 mmol) in DMF (10 ml) was stirred at 80° C. for 4 hours. The reaction solution was poured into water and the mixture was extracted with ethyl acetate. The extract was washed with water, dried over magnesium sulfate anhydride and the solvent was removed under reduced pressure. The residue was purified by silica gel column chromatography (hexane:ethyl acetate=30:1) to give the object compound as an oily substance. 1.03 g (yield: 79.8%)

$^1$H-NMR (CDCl$_3$) δ; 0.88 (3H, t, J=6.6 Hz), 1.10–1.56 (10H, m), 1.69–1.79 (2H, m), 2.24 (3H, s), 2.69 (2H, t, J=7.4 Hz), 3.90 (2H, t, J=6.6 Hz),4.00 (2H, t, J=7.4 Hz), 5.11 (2H, s), 5.92 (1H, d, J=3.2 Hz), 6.03 (1H, d, J=3.2 Hz), 6.74 (2H, d, J=8.4 Hz), 6.82 (2H, d, J=8.4 Hz), 7.00 (2H, d, J=8.8 Hz),7.26–7.49 (7H, m).

IR (KBr) cm$^{-1}$; 1610, 1512, 1246, 1180, 1025, 830.

(2) 4-[5-Methyl-1-(4-octyloxyphenethyl)-1H-pyrrol-2-yl]phenol

To a solution of 2-(4-benzyloxyphenethyl)-5-methyl-1-(4-octyloxyphenethyl)-1H-pyrrole (980 mg, 1.98 mmol) in ethanol (20 ml) and tetrahydrofuran (10 ml) was added 10% palladium carbon (100 mg) and the mixture was stirred under hydrogen atmosphere for 2 hours. The insoluble matter was filtered out and the filtrate was concentrated to give the object compound as an oily substance. 800 mg (yield: 99.6%)

$^1$H-NMR (CDCl$_3$) δ; 0.88 (3H, t, J=7.0 Hz), 1.21–1.51 (10H, m), 1.69–1.79 (2H, m), 2.24 (3H, s), 2.68 (2H, t, J=7.6 Hz), 3.87–4.03 (4H, m), 5.91 (1H, d, J=3.2 Hz), 6.03 (1H, d, J=3.2 Hz), 6.72–6.89 (6H, m), 7.72 (2H, d, J=8.8 Hz)

IR (KBr) cm$^{-1}$; 2930, 1512, 1246, 1175, 837, 758.

(3) Ethyl (2R)-2-{4-[5-methyl-1-(4-octyloxyphenethyl)-1H-pyrrol-2-yl]phenoxy}-3-phenylpropanoate To a solution of 4-[5-methyl-1-(4-octyloxyphenethyl)-1H-pyrrol-2-yl]phenol (800 mg, 1.98 mmol), ethyl (S)-2-hydroxy-3-phenylpropanoate (779 mg, 4.00 mmol) and triphenylphosphine (1.05 g, 4.00 mmol) in toluene (10 ml) was added 1,1'-(azodicarbonyl)dipiperidine (1.01 g, 4.00 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 420 mg (yield: 36.5%)

$^1$H-NMR (CDCl$_3$) δ; 0.88 (3H, t, J=6.6 Hz), 1.16–1.51 (13H, m), 1.71–1.79 (2H, m), 2.22 (3H, s), 2.66 (2H, t, J=7.4 Hz), 3.25–3.29 (2H, m), 3.86–4.00 (4H, m), 4.20 (2H, q, J=7.2 Hz), 4.79–4.86 (1H, m), 5.89 (1H, d, J=3.2 Hz), 6.00 (1H, d, J=3.2 Hz), 6.70–6.87 (6H, m), 7.19–7.34 (7H, m).

IR (KBr) cm$^{-1}$; 1755, 1732, 1512, 1244, 1179, 1032, 835, 758, 700.

Example 138

Sodium (2R)-2-{4-[5-methyl-1-(4-octyloxyphenethyl)-1H-pyrrol-2-yl]phenoxy}-3-phenylpropanoate (1) (2R)-2-{4-[5-methyl-1-(4-octyloxyphenethyl)-1H-pyrrol-2-yl]phenoxy}-3-phenylpropanoic acid To a mixed solution of ethyl (2R)-2-{4-[5-methyl-1-(4-octyloxyphenethyl)-1H-pyrrol-2-yl]phenoxy}-3-phenylpropanoate (410 mg, 0.704 mmol) in THF (10 ml) and methanol (5 ml) was added 1N aqueous potassium hydroxide solution (2.11 ml, 2.11 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (ethyl acetate) to give the object compound as an oily substance. 303 mg (yield: 77.5%)

$^1$H-NMR (CDCl$_3$) δ; 0.88 (3H, t, J=6.6 Hz), 1.22–1.52 (10H, m), 1.71–1.79 (2H, m), 2.22 (3H, s), 2.65 (2H, t, J=7.2 Hz), 3.32 (2H, d, J=6.4 Hz), 3.86–4.01 (4H, m), 4.90 (1H, t, J=6.4 Hz), 5.90 (1H, d, J=3.4 Hz), 6.00 (1H, d, J=3.4 Hz), 6.70–6.88 (6H, m), 7.20–7.32 (7H, m).

IR (KBr) cm$^{-1}$; 3032, 1728, 1512, 1242, 1177, 833, 756, 700.

(2) Sodium (2R)-2-{4-[5-methyl-1-(4-octyloxyphenethyl)-1H-pyrrol-2-yl]phenoxy}-3-phenylpropanoate Ethanol (2 ml) and a solution of 1N sodium hydroxide in ethanol (0.451 ml) were added to (2R)-2-{4-[5-methyl-1-(4-octyloxyphenethyl)-1H-pyrrol-2-yl]phenoxy}-3-phenylpropanoic acid (278 mg, 0.501 mmol) and the mixture was concentrated. To the residue was added diisopropylether to give the object compound as a solid. 227 mg (yield: 87.3%)

$^1$H-NMR (DMSO-d$_6$) δ; 0.86 (3H, t, J=6.4 Hz), 1.12–1.51 (10H, m), 1.59–1.66 (2H, m), 2.11 (3H, s), 2.20–2.71 (6H, m), 2.93–3.18 (2H, m), 3.85–3.91 (4H, m), 4.29–4.41 (1H, m), 5.74 (1H, d, J=3.4 Hz), 5.81 (1H, d, J=3.4 Hz), 6.71–6.86 (6H, m), 7.11–7.34 (7H, m).

IR (KBr) cm$^{-1}$; 2928, 1615, 1512, 1242, 1175, 1055, 1030, 839, 758, 700.

Example 139

Ethyl (2R)-2-{4-[1-(4-decyloxyphenethyl)-5-methyl-1H-pyrrol-2-yl]phenoxy}-3-phenylpropanoate (1) 2-(4-Benzyloxyphenethyl)-5-methyl-1-(4-decyloxyphenethyl)-1H-pyrrole The object compound was obtained from 1-bromodecane as an oily substance, according to the similar manner to that of Example 137(1). yield: 85.9%

$^1$H-NMR (CDCl$_3$) δ; 0.88 (3H, t, J=6.6 Hz), 1.10–1.56 (14H, m), 1.69–1.81 (2H, m), 2.24 (3H, s), 2.68 (2H, t, J=6.6 Hz), 3.87–4.03 (4H, m), 5.11 (2H, s), 5.91 (1H, d, J=3.4 Hz), 6.03 (1H, d, J=3.4 Hz), 6.74 (2H, d, J=8.8 Hz), 6.82 (2H, d, J=8.8 Hz), 7.00 (2H, d, J=8.2 Hz), 7.25–7.45 (7H, m).

IR (KBr) cm$^{-1}$; 1512, 1470, 1456, 1246, 1175, 1024, 833, 754, 735, 698.

(2) 4-[1-(4-Decyloxyphenethyl)-5-methyl-1H-pyrrol-2-yl]phenol

The object compound was obtained from 2-(4-benzyloxyphenethyl)-5-methyl-1-(4-decyloxyphenethyl)-1H-pyrrole as an oily substance, according to the similar manner to that of Example 137(2). yield: 95.0%

$^1$H-NMR (CDCl$_3$) δ; 0.88 (3H, t, J=6.4 Hz), 1.06–1.42 (14H, m), 1.68–1.79 (2H, m), 2.23 (3H, s), 2.68 (2H, t, J=8.0 Hz), 3.87–4.02 (4H, m), 5.91 (1H, d, J=3.2 Hz), 6.03 (1H, d, J=3.2 Hz), 6.72–6.88 (6H, m), 7.21 (2H, d, J=8.6 Hz)

IR (KBr) cm$^{-1}$; 3378, 1615, 1512, 1470, 1246, 1177, 837, 822, 758.

(3) Ethyl (2R)-2-{4-[1-(4-decyloxyphenethyl)-5-methyl-1H-pyrrol-2-yl]phenoxy}-3-phenylpropanoate The object compound was obtained from 4-[1-(4-decyloxyphenethyl)-5-methyl-1H-pyrrol-2-yl]phenol as an oily substance, according to the similar manner to that of Example 137(3). yield: 34.4%

$^1$H-NMR (CDCl$_3$) δ; 0.88 (3H, t, J=7.0 Hz), 1.16–1.46 (17H, m), 1.72–1.79 (2H, m), 2.22 (3H, s), 2.656 (2H, t, J=6.8 Hz), 3.25–3.30 (2H, m), 3.86–4.00 (4H, m), 4.20 (2H, q, J=7.0 Hz), 4.79–4.86 (1H, m), 5.89 (1H, d, J=3.4 Hz), 6.00 (1H, d, J=3.4 Hz), 6.70–6.87 (6H, m), 7.19–7.34 (7H, m).

IR (KBr) cm$^{-1}$; 1755, 1732, 1512, 1244, 1179, 1030, 835, 756, 700.

Example 140

Sodium (2R)-2-{4-[1-(4-decyloxyphenethyl)-5-methyl-1H-pyrrol-2-yl]phenoxy}-3-phenylpropanoate (1) (2R)-2-{4-[1-(4-Decyloxyphenethyl)-5-methyl-1H-pyrrol-2-yl]phenoxy}-3-phenylpropanoic acid The object compound was obtained from ethyl (2R)-2-{4-[1-(4-decyloxyphenethyl)-5-methyl-1H-pyrrol-2-yl]phenoxy}-3-phenylpropanoate as an oily substance, according to the similar manner to that of Example 138(1). yield: 88.7%

$^1$H-NMR (CDCl$_3$) δ; 0.88 (3H, t, J=7.0 Hz), 1.21–1.48 (14H, m), 1.71–1.80 (2H, m), 2.21 (3H, s), 2.64 (2H, t, J=6.2 Hz), 3.31 (2H, d, J=6.2 Hz), 3.86–4.01 (4H, m), 4.90 (1H, t, J=6.2 Hz), 5.90 (1H, d, J=3.6 Hz), 6.00 (1H, d, J=3.6 Hz), 6.69–6.89 (6H, m), 7.20–7.31 (7H, m).

IR (KBr) cm$^{-1}$; 2930, 1728, 1512, 1242, 1177, 835, 754.

(2) Sodium (2R)-2-{4-[1-(4-decyloxyphenethyl)-5-methyl-1H-pyrrol-2-yl]phenoxy}-3-phenylpropanoate The object compound was obtained from (2R)-2-{4-[1-(4-decyloxyphenethyl)-5-methyl-1H-pyrrol-2-yl]phenoxy}-3-phenylpropanoic acid as a solid, according to the similar manner to that of Example 138(2). yield: 82.5%

$^1$H-NMR (DMSO-d$_6$) δ; 0.86 (3H, t, J=7.0 Hz), 1.08–1.48 (14H, m), 1.58–1.77 (2H, m), 2.11 (3H, s), 2.51–2.68 (2H, m), 2.93–3.20 (2H, m), 3.79–4.00 (4H, m), 4.32–4.36 (1H, m), 5.73 (1H, d, J=3.6 Hz), 5.81 (1H, d, J=3.6 Hz), 6.71–6.81 (6H, m), 7.10–7.30 (7H, m).

IR (KBr) cm$^{-1}$; 2924, 1615, 1512, 1404, 1244, 1177, 1055, 1030, 839, 829, 756, 700.

$[\alpha]_D^{26}$ 1.81° (c 0.510, methanol)

Example 141

Ethyl (2R)-2-{4-[5-methyl-1-(4-undecyloxyphenethyl)-1H-pyrrol-2-yl]phenoxy}-3-phenylpropanoate (1) 2-(4-Benzyloxyphenyl)-5-methyl-1-(4-undecyloxyphenethyl)-1H-pyrrole A solution of 4-{2-[2-(4-benzyloxyphenyl)-5-methyl-1H-pyrrol-1-yl]ethyl}phenol (1.50 g, 3.91 mmol), 1-bromoundecane (1.31 ml, 5.87 mmol) and potassium carbonate (811 mg, 5.87 mmol) in DMF (15 ml) was stirred at 80° C. for 4 hours. The reaction solution was poured into water and the mixture was extracted with ethyl acetate. The extract was washed with water and dried over magnesium sulfate anhydride, and the solvent was removed under reduced pressure. The residue was purified by silica gel column chromatography (hexane:ethyl acetate=30:1) to give the object compound as an oily substance. 1.80 g (yield: 85.7%)

$^1$H-NMR (CDCl$_3$) δ; 0.88 (3H, t, J=6.6 Hz), 1.26–1.46 (16H, m), 1.68–1.79 (2H, m), 2.23 (3H, s), 2.69 (2H, t, J=7.6 Hz), 3.90 (2H, t, J=6.6 Hz), 4.00 (2H, t, J=7.6 Hz), 5.11 (2H, s), 5.91 (1H, d, J=3.2 Hz), 6.03 (1H, d, J=3.2 Hz), 6.73 (2H, d, J=8.8 Hz), 6.82 (2H, d, J=8.8 Hz), 7.00 (2H, d, J=8.8 Hz), 7.25–7.50 (7H, m).

IR (KBr) cm$^{-1}$; 1611, 1524, 1512, 1468, 1454, 1246, 1175, 1026, 835, 756, 735, 698.

(2) 4-[5-Methyl-1-(4-undecyloxyphenethyl)-1H-pyrrol-2-yl]phenol

To a solution of 2-(4-benzyloxyphenyl)-5-methyl-1-(4-undecyloxyphenethyl)-1H-pyrrole (1.70 g, 3.16 mmol) in ethanol (60 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 1.29 g (yield: 91.5%)

$^1$H-NMR (CDCl$_3$) δ; 0.88 (3H, t, J=6.9 Hz), 1.26–1.43 (16H, m), 1.70–1.78 (2H, m), 2.24 (3H, s), 2.68 (2H, t, J=7.8 Hz), 3.90 (2H, t, J=6.6 Hz), 3.98 (2H, t, J=7.8 Hz), 5.90 (1H, d, J=3.3 Hz), 6.02 (1H, d, J=3.3 Hz), 6.72–6.87 (4H, m), 7.16–7.25 (4H, m).

IR (KBr) cm$^{-1}$; 3408, 1613, 1512, 1468, 1246, 1177, 837, 824, 758.

(3) Ethyl (2R)-2-{4-[5-methyl-1-(4-undecyloxyphenethyl)-1H-pyrrol-2-yl]phenoxy}-3-phenylpropanoate To a solution of 4-[5-methyl-1-(4-undecyloxyphenethyl)-1H-pyrrol-2-yl]phenol (1.29 g, 2.88 mmol), ethyl (S)-2-hydroxy-3-phenylpropanoate (838 mg, 4.32 mmol) and triphenylphosphine (1.13 g, 4.32 mmol) in toluene (1 ml) was added 1,1'-(azodicarbonyl)dipiperidine (1.09 mg, 3.25 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 710 mg (yield: 39.4%)

$^1$H-NMR (CDCl$_3$) δ; 0.88 (3H, t, J=6.6 Hz), 1.16–1.47 (19H, m), 1.68–1.79 (2H, m), 2.22 (3H, s), 2.66 (2H, t, J=7.8 Hz), 3.25–3.29 (2H, m), 3.86–4.00 (4H, m), 4.20 (2H, q, J=7.4 Hz), 4.79–4.86 (1H, m), 5.89 (1H, d, J=3.2 Hz), 6.00 (1H, d, J=3.2 Hz), 6.70–6.89 (6H, m), 7.18–7.34 (7H, m).

IR (KBr) cm$^{-1}$; 1755, 1732, 1613, 1512, 1244, 1179, 1030, 835, 756, 700.

Example 142

Sodium (2R)-2-{4-[5-methyl-1-(4-undecyloxyphenethyl)-1H-pyrrol-2-yl]phenoxy}-3-phenylpropanoate (1) (2R)-2-{4-[5-Methyl-1-(4-undecyloxyphenethyl)-1H-pyrrol-2-yl]phenoxy}-3-phenylpropanoic acid To a mixed solution of ethyl (2R)-2-{4-[5-methyl-1-(4-undecyloxyphenethyl)-1H-pyrrol-2-yl]phenoxy}-3-phenylpropanoate (700 mg, 1.12 mmol) in THF (25 ml) and methanol (12 ml) was added 1N aqueous potassium hydroxide solution (5 ml, 5 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 520 mg (yield: 77.8%)

$^1$H-NMR (CDCl$_3$) δ; 0.88 (3H, t, J=7.0 Hz), 1.23–1.45 (16H, m), 1.71–1.78 (2H, m), 2.22 (3H, s), 2.65 (2H, t, J=7.4 Hz), 3.32 (2H, d, J=5.8 Hz), 3.86–4.01 (4H, m), 4.90 (1H, t, J=5.8 Hz), 5.89 (1H, d, J=3.4 Hz), 6.00 (1H, d, J=3.4 Hz), 6.69–6.88 (6H, m), 7.20–7.33 (7H, m).

IR (KBr) cm$^{-1}$; 2924, 1728, 1512, 1244, 1176, 835, 758, 700.

(2) Sodium (2R)-2-{4-[5-methyl-1-(4-undecyloxyphenethyl)-1H-pyrrol-2-yl]phenoxy}-3-phenylpropanoate Ethanol (5 ml) and a solution of 1N sodium hydroxide in ethanol (0.724 ml) were added to (2R)-2-{4-[5-methyl-1-(4-undecyloxyphenethyl)-1H-pyrrol-2-yl]phenoxy}-3-phenylpropanoic acid (480 mg, 0.804 mmol) and the mixture was concentrated. To the residue was added hexane to give the object compound as a solid. 375 mg (yield: 83.9%)

$^1$H-NMR (DMSO-d$_6$) δ; 0.86 (3H, t, J=7.0 Hz), 1.15–1.39 (16H, m), 1.61–1.73 (2H, m), 2.11 (3H, s), 2.56–2.68 (2H, m), 2.95–3.20 (2H, m), 3.84–3.91 (4H, m), 4.33–4.42 (1H, m), 5.73 (1H, d, J=3.2 Hz), 5.81 (1H, d, J=3.2 Hz), 6.70–6.84 (6H, m), 7.10–7.34 (7H, m).

IR (KBr) cm$^{-1}$; 1613, 1582, 1512, 1468, 1454, 1406, 1310, 1244, 1177, 1055, 1030, 835, 758, 700.

$[\alpha]_D^{25}$ 3.33° (c 0.565, methanol)

Example 143

Ethyl (2R)-2-(4-{5-methyl-1-[4-(3-phenylpropoxy)phenethyl]-1H-pyrrol-2-yl}phenoxy)-3-phenylpropanoate (1) 2-(4-Benzyloxyphenyl)-5-methyl-1-[4-(3-phenylpropoxy)phenethyl]-1H-pyrrole The object compound was obtained from 3-phenylpropylbromide as an oily substance, according to the similar manner to that of Example 141(1). yield: 91.8%

$^1$H-NMR (CDCl$_3$) δ; 1.96–2.15 (2H, m), 2.23 (3H, s), 2.65–2.84 (4H, m), 3.88–4.04 (4H, m), 5.11 (2H, s), 5.91 (1H, d, J=3.4 Hz), 6.03 (1H, d, J=3.4 Hz), 6.73 (2H, d, J=8.8 Hz), 6.82 (2H, d, J=8.8 Hz), 6.99 (2H, d, J=8.8 Hz), 7.15–7.45 (12H, m).

IR (KBr) cm$^{-1}$; 1611, 1524, 1454, 1309, 1279, 1246, 1175, 1026, 835, 750, 698.

(2) 4-{5-Methyl-1-[4-(3-phenylpropoxy)phenethyl]-1H-pyrrol-2-yl}phenol

The object compound was obtained from 2-(4-benzyloxyphenyl)-5-methyl-1-[4-(3-phenylpropoxy)phenethyl]-1H-pyrrole as an oily substance, according to the similar manner to that of Example 141(2). yield: 99.3%

¹H-NMR (CDCl₃) δ; 1.96–2.15 (2H, m), 2.23 (3H, s), 2.64–2.83 (4H, m), 3.88–4.03 (4H, m), 5.91 (1H, d, J=3.2 Hz), 6.02 (1H, d, J=3.2 Hz), 6.71–6.87 (6H, m), 7.15–7.33 (7H, m).

IR (KBr) cm⁻¹; 3314, 1613, 1512, 1246, 1177, 1036, 837, 756, 700.

(3) Ethyl (2R)-2-(4-{5-methyl-1-[4-(3-phenylpropoxy)phenethyl]-1H-pyrrol-2-yl}phenoxy)-3-phenylpropanoate The object compound was obtained from 4-{5-methyl-1-[4-(3-phenylpropoxy)phenethyl]-1H-pyrrol-2-yl}phenol as an oily substance, according to the similar manner to that of Example 141(3). yield: 39.5%

¹H-NMR (CDCl₃) δ; 1.19 (3H, t, J=7.0 Hz), 2.01–2.15 (2H, m), 2.22 (3H, s), 2.66 (2H, t, J=7.6 Hz), 2.80 (2H, t, J=8.0 Hz), 3.25–3.29 (2H, m), 3.88–4.00 (4H, m), 4.19 (2H, q, J=7.0 Hz), 4.79–4.86 (1H, m), 5.89 (1H, d, J=3.4 Hz), 6.00 (1H, d, J=3.4 Hz), 6.70–6.88 (6H, m), 7.15–7.36 (12H, m).

IR (KBr) cm⁻¹; 1755, 1732, 1512, 1481, 1454, 1244, 1179, 1032, 835, 754, 700.

Example 144

Sodium (2R)-2-(4-{5-methyl-1-[4-(3-phenylpropoxy)phenethyl]-1H-pyrrol-2-yl}phenoxy)-3-phenylpropanoate (1) (2R)-2-(4-{5-Methyl-1-[4-(3-phenylpropoxy)phenethyl]-1H-pyrrol-2-yl}phenoxy)-3-phenylpropanoic acid The object compound was obtained from ethyl (2R)-2-(4-{5-methyl-1-[4-(3-phenylpropoxy)phenethyl]-1H-pyrrol-2-yl}phenoxy)-3-phenylpropanoate as an oily substance, according to the similar manner to that of Example 142(1). yield: 99.5%

¹H-NMR (CDCl₃) δ; 2.01–2.14 (2H, m), 2.21 (3H, s), 2.65 (2H, t, J=7.4 Hz), 2.79 (2H, t, J=8.0 Hz), 3.31 (2H, d, J=5.6 Hz), 3.87–4.01 (4H, m), 4.90 (1H, t, J=5.6 Hz), 5.89 (1H, d, J=3.2 Hz), 6.00 (1H, d, J=3.2 Hz), 6.69–6.88 (6H, m), 7.15–7.32 (12H, m).

IR (KBr) cm⁻¹; 3028, 1733, 1512, 1244, 1177, 835, 754, 700.

(2) Sodium (2R)-2-(4-{5-methyl-1-[4-(3-phenylpropoxy)phenethyl]-1H-pyrrol-2-yl}phenoxy)-3-phenylpropanoate The object compound was obtained from (2R)-2-(4-{5-methyl-1-[4-(3-phenylpropoxy)phenethyl]-1H-pyrrol-2-yl}phenoxy)-3-phenylpropanoic acid as a solid, according to the similar manner to that of Example 142(1). yield: 93.2%

¹H-NMR (DMSO-d₆) δ; 1.92–2.06 (2H, m), 2.11 (3H, s), 2.54–2.77 (4H, m), 2.94–3.19 (2H, m), 3.86–3.92 (4H, m), 4.31–4.37 (1H, m), 5.73 (1H, d, J=3.4 Hz), 5.81 (1H, d, J=3.4 Hz), 6.72–6.86 (6H, m), 7.10–7.33 (12H, m).

IR (KBr) cm⁻¹; 1615, 1512, 1410, 1244, 1177, 1036, 839, 754, 700.

$[\alpha]_D^{26}$ 2.40° (c 0.665, methanol).

Example 145

Ethyl (2R)-2-{4-[1-(4-cyclohexylmethoxyphenethyl)-5-methyl-1H-pyrrol-2-yl]phenoxy}-3-phenylpropanoate (1) 2-(4-Benzyloxyphenyl)-1-(4-cyclohexylmethoxyphenethyl)-5-methyl-1H-pyrrole The object compound was obtained from cyclohexylmethyl bromide as an oily substance, according to the similar manner to that of Example 141(1). yield: 67.6%

¹H-NMR (CDCl₃) δ; 0.85–1.88 (11H, m), 2.24 (3H, s), 2.69 (2H, t, J=7.6 Hz), 3.70 (2H, d, J=6.2 Hz), 3.99 (2H, t, J=7.6 Hz), 5.11 (2H, s), 5.91 (1H, d, J=3.2 Hz), 6.03 (1H, d, J=3.2 Hz), 6.73 (2H, d, J=8.8 Hz), 6.82 (2H, d, J=8.8 Hz), 7.00 (2H, d, J=9.2 Hz),7.24–7.50 (7H, m).

IR (KBr) cm⁻¹; 1613, 1524, 1512, 1481, 1468, 1453, 1244, 1174, 1026, 835, 754, 698.

(2) 4-[1-(4-Cyclohexylmethoxyphenethyl)-5-methyl-1H-pyrrol-2-yl]phenol

The object compound was obtained from 2-(4-benzyloxyphenyl)-1-(4-cyclohexylmethoxyphenethyl)-5-methyl-1H-pyrrole as an oily substance, according to the similar manner to that of Example 141(2). yield: 98.6%

¹H-NMR (CDCl₃) δ; 0.98–1.87 (11H, m), 2.24 (3H, s), 2.68 (2H, t, J=7.6 Hz), 3.70 (2H, d, J=6.2 Hz), 3.98 (2H, t, J=7.6 Hz), 5.91 (1H, d, J=3.2 Hz), 6.02 (1H, d, J=3.2 Hz), 6.73–7.30 (8H, m).

IR (KBr) cm⁻¹; 3401, 1613, 1526, 1512, 1244, 1221, 1175, 1026, 837, 758.

(3) Ethyl (2R)-2-{4-[1-(4-cyclohexylmethoxyphenethyl)-5-methyl-1H-pyrrol-2-yl]phenoxy}-3-phenylpropanoate The object compound was obtained from 4-[1-(4-cyclohexylmethoxyphenethyl)-5-methyl-1H-pyrrol-2-yl]phenol as an oily substance, according to the similar manner to that of Example 141(3). yield: 59.0%

¹H-NMR (CDCl₃) δ; 0.95–1.88 (14H, m), 2.22 (3H, s), 2.66 (2H, t, J=7.8 Hz), 3.25–3.29 (2H, m), 3.69 (2H, t, J=6.2 Hz), 3.96 (2H, t, J=7.8 Hz), 4.20 (2H, q, J=7.0 Hz), 4.79–4.86 (1H, m), 5.89 (1H, d, J=3.6 Hz), 6.00 (1H, d, J=3.6 Hz), 6.70–6.92 (6H, m), 7.18–7.36 (7H, m).

IR (KBr) cm⁻¹; 1755, 1732, 1512, 1279, 1244, 1179, 1028, 835, 756, 700.

Example 146

Sodium (2R)-2-{4-[1-(4-cyclohexylmethoxyphenethyl)-5-methyl-1H-pyrrol-2-yl]phenoxy}-3-phenylpropanoate (1) (2R)-2-{4-[1-(4-cyclohexylmethoxyphenethyl)-5-methyl-1H-pyrrol-2-yl]phenoxy}-3-phenylpropanoic acid The object compound was obtained from (2R)-2-{4-[1-(4-cyclohexylmethoxyphenethyl)-5-methyl-1H-pyrrol-2-yl]phenoxy}-3-phenylpropanoic acid as an oily substance, according to the similar manner to that of Example 142(1). yield: 59.4%

¹H-NMR (CDCl₃) δ; 0.88–1.88 (11H, m), 2.22 (3H, s), 2.65 (2H, t, J=7.4 Hz), 3.31 (2H, d, J=6.2 Hz), 3.69 (2H, t, J=6.4 Hz), 3.97 (2H, t, J=7.4 Hz), 4.90 (1H, t, J=6.2 Hz), 5.90 (1H, d, J=3.4 Hz), 6.00 (1H, d, J=3.4 Hz), 6.69–6.88 (6H, m), 7.19–7.34 (7H, m).

IR (KBr) cm⁻¹; 3029, 1728, 1512, 1244, 1177, 1084, 1028, 910, 835, 756, 735, 700.

(2) Sodium (2R)-2-{4-[1-(4-cyclohexylmethoxyphenethyl)-5-methyl-1H-pyrrol-2-yl]phenoxy}-3-phenylpropanoate The object compound was obtained from (2R)-2-{4-[1-(4-cyclohexylmethoxyphenethyl)-5-methyl-1H-pyrrol-2-yl]phenoxy}-3-phenylpropanoic acid as a solid, according to the similar manner to that of Example 142(2). yield: 98.9%

¹H-NMR (DMSO-d₆) δ; 0.96–1.83 (11H, m), 2.11 (3H, s), 2.61 (2H, t, J=7.5 Hz), 3.00–3.22 (2H, m), 3.69 (2H, d, J=6.3 Hz), 3.91 (2H, t, J=7.5 Hz), 4.37–4.41 (1H, m), 5.73 (1H, d, J=3.3 Hz), 5.81 (1H, d, J=3.3 Hz), 6.70–6.83 (6H, m), 7.10–7.34 (7H, m).

IR (KBr) cm⁻¹; 1615, 1512, 1410, 1244, 1028, 829, 758, 700.

$[\alpha]_D^{25}$ −26.3° (c 0.610, methanol)

Example 147

Ethyl (2R)-2-{4-[1-(4-decyloxyphenyl)-5-methyl-1H-pyrrol-2-yl]phenoxy}-3-phenylpropanoate (1) 4-[2-(4-Benzyloxyphenyl)-5-methyl-1H-pyrrol-1-yl]phenol A solution of 1-(4-benzyloxyphenyl)-1,4-pentanedione (10.0 g, 35.4 mmol), p-aminophenol (3.86 g, 35.4 mmol) and p-toluenesulfonic acid monohydrate (504 mg, 2.64 mmol) in toluene (300 ml) was refluxed for 12 hours under heating and the solvent was removed under reduced pressure. The residue was purified by silica gel column chromatography (hexane:ethyl acetate=7:1) to give the object compound as a solid. 6.11 g (yield: 48.5%)

$^1$H-NMR (CDCl$_3$) δ; 2.10 (3H, s), 4.95 (1H, s), 4.98 (2H, s), 6.05 (1H, d, J=3.6 Hz), 6.24 (1H, d, J=3.6 Hz), 6.75–6.83 (4H, m), 6.96–7.04 (4H, m), 7.30–7.42 (5H, m).

IR (KBr) cm$^{-1}$; 3034, 1516, 1240, 1179, 1015, 839, 764, 735, 698.

(2) 2-(4-Benzyloxyphenyl)-1-(4-decyloxyphenyl)-5-methyl-1H-pyrrole

A solution of 4-[2-(4-benzyloxyphenyl)-5-methyl-1H-pyrrol-1-yl]phenol (1.50 g, 4.22 mmol), 1-bromoundecane (1.31 ml, 6.33 mmol) and potassium carbonate (874 mg, 6.33 mmol) in DMF (15 ml) was stirred at 80° C. for 4 hours. The reaction solution was poured into water and the mixture was extracted with ethyl acetate. The extract was washed with water, dried over magnesium sulfate anhydride and solvent was removed under reduced pressure. The residue was purified by silica gel column chromatography (hexane:ethyl acetate=30:1) to give the object compound as an oily substance. 1.78 g (yield: 85.2%)

$^1$H-NMR (CDCl$_3$) δ; 0.88 (3H, t, J=7.0 Hz), 1.19–1.55 (16H, m), 1.72–1.83 (2H, m), 2.11 (3H, s), 3.95 (2H, t, J=6.6 Hz), 4.98 (2H, s), 6.04 (1H, d, J=3.2 Hz), 6.25 (1H, d, J=3.2 Hz), 6.73–7.40 (9H, m).

IR (KBr) cm$^{-1}$; 1609, 1514, 1485, 1470, 1456, 1395, 1289, 1244, 1177, 1040, 1026, 835, 760, 735, 698.

(3) 4-[1-(4-Decyloxyphenethyl)-5-methyl-1H-pyrrol-2-yl]phenol

To a solution of 2-(4-benzyloxyphenyl)-1-(4-decyloxyphenyl)-5-methyl-1H-pyrrole (1.70 g, 3.43 mmol) in ethanol (60 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 1.30 g (yield: 93.5%)

$^1$H-NMR (CDCl$_3$) δ; 0.88 (3H, t, J=6.6 Hz), 1.21–1.48 (14H, m), 1.75–1.82 (2H, m), 2.10 (3H, s), 3.94 (2H, t, J=6.2 Hz), 6.04 (1H, d, J=3.2 Hz), 6.23 (1H, d, J=3.2 Hz), 6.60 (2H, d, J=8.8 Hz), 6.84 (2H, d, J=8.8 Hz), 6.94 (2H, d, J=8.8 Hz), 7.03 (2H, d, J=8.8 Hz).

IR (KBr) cm$^{-1}$; 3358, 1613, 1514, 1470, 1289, 1246, 1169, 1107, 1040, 835, 760.

(4) Ethyl ($^2$R)-2-{4-[1-(4-decyloxyphenyl)-5-methyl-1H-pyrrol-2-yl]phenoxy}-3-phenylpropanoate To a solution of 4-[1-(4-decyloxyphenethyl)-5-methyl-1H-pyrrol-2-yl]phenol (1.30 g, 3.21 mmol), ethyl (S)-2-hydroxy-3-phenylpropanoate (934 mg, 4.81 mmol) and triphenylphosphine (1.26 g, 4.81 mmol) in toluene (2 ml) was added 1,1'-(azodicarbonyl)dipiperidine (1.21 g, 4.81 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 880 mg (yield: 47.0%)

$^1$H-NMR (CDCl$_3$) δ; 0.89 (3H, t, J=6.6 Hz), 1.10–1.46 (17H, m), 1.57–1.83 (2H, m), 2.09 (3H, s), 3.94 (2H, t, J=6.6 Hz), 4.14 (2H, q, J=7.0 Hz), 4.66–4.73 (1H, m), 6.02 (1H, d, J=3.4 Hz), 6.22 (1H, d, J=3.4 Hz), 6.61 (2H, d, J=8.8 Hz), 6.83 (2H, d, J=9.2 Hz), 6.92 (2H, d, J=9.2 Hz), 7.01 (2H, d, J=8.8 Hz), 7.20–7.29 (5H, m).

IR (KBr) cm$^{-1}$; 1755, 1734, 1514, 1287, 1244, 1182, 1084, 1038, 835, 758, 700.

Example 148

Sodium (2R)-2-{4-[1-(4-decyloxyphenyl)-5-methyl-1H-pyrrol-2-yl]phenoxy}-3-phenylpropanoate (1) (2R)-2-{4-[1-(4-Decyloxyphenyl)-5-methyl-1H-pyrrol-2-yl]phenoxy}-3-phenylpropanoic acid To a mixed solution of ethyl (2R)-2-{4-[1-(4-decyloxyphenyl)-5-methyl-1H-pyrrol-2-yl]phenoxy}-3-phenylpropanoate (870 mg, 1.49 mmol) in THF (30 ml) and methanol (15 ml) was added 1N aqueous potassium hydroxide solution(8 ml, 8 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate= 1:1) to give the object compound as an oily substance. 760 mg (yield: 92.0%)

$^1$H-NMR (CDCl$_3$) δ; 0.89 (3H, t, J=6.6 Hz), 1.22–1.44 (14H, m), 1.72–1.82 (2H, m), 2.08 (3H, s), 3.22 (2H, d, J=6.2 Hz), 3.93 (2H, t, J=6.6 Hz), 4.76 (1H, t, J=6.2 Hz), 6.02 (1H, d, J=3.2 Hz), 6.22 (1H, d, J=3.2 Hz), 6.62 (2H, d, J=8.8 Hz), 6.82 (2H, d, J=8.8 Hz), 6.94 (2H, d, J=8.8 Hz), 7.01 (2H, d, J=8.8 Hz), 7.26 (5H, s).

IR (KBr) cm$^{-1}$; 3032, 1730, 1514, 1287, 1244, 1181, 1084, 835, 760, 700.

(2) Sodium (2R)-2-{4-[1-(4-decyloxyphenyl)-5-methyl-1H-pyrrol-2-yl]phenoxy}-3-phenylpropanoate Ethanol (7 ml) and a solution of 1N sodium hydroxide in ethanol (1.14 ml) were added to (2R)-2-{4-[1-(4-decyloxyphenyl)-5-methyl-1H-pyrrol-2-yl]phenoxy}-3-phenylpropanoic acid (700 mg, 1.26 mmol) and the mixture was concentrated. To the residue was added ether to give the object compound as a solid. 441 mg (yield: 67.1%)

$^1$H-NMR (DMSO-d$_6$) δ; 0.87 (3H, t, J=7.0 Hz), 1.14–1.48 (14H, m), 1.65–1.78 (2H, m), 1.99 (3H, s), 2.86–3.12 (2H, m), 3.95 (2H, t, J=6.2 Hz), 4.18–4.28 (1H, m), 5.91 (1H, d, J=3.2 Hz), 6.06 (1H, d, J=3.2 Hz), 6.54 (2H, d, J=8.8 Hz), 6.80 (2H, d, J=8.8 Hz), 6.90 (2H, d, J=8.8 Hz), 7.02 (2H, d, J=8.8 Hz), 7.11–7.28 (5H, m).

IR (KBr) cm$^{-1}$; 1615, 1514, 1397, 1289, 1244, 1181, 1169, 1042, 835, 762, 700.

$[α]_D^{25}$ −1.61° (c 0.730, methanol)

Example 149

Ethyl (2R)-2-{4-[5-methyl-1-{2-[4-(6-phenylhexyloxy)phenyl]ethyl}-1H-pyrrol-2-yl]phenoxy}-3-phenylpropanoate (1) 2-(4-Benzyloxyphenyl)-5-methyl-1-{2-[4-(6-phenylhexyloxy)phenyl]ethyl}-1H-pyrrole A solution of 4-{2-[2-(4-benzyloxyphenyl)-5-methyl-1H-pyrrol-1-yl]ethyl}phenol (1.50 g, 3.91 mmol), 1-bromo-6-phenylhexane (1.42 g, 5.87 mmol) and potassium carbonate (811 mg, 5.87 mmol) in DMF (15 ml) was stirred at 80° C. for 12 hours. The reaction solution was poured into water and the mixture was extracted with ethyl acetate. The extract was washed with water and dried over magnesium sulfate anhydride, and solvent was removed under reduced pressure. The residue was purified by silica gel column chromatography (hexane:ethyl acetate=30:1) to give the object compound as an oily substance. 1.43 g (yield: 67.1%)

$^1$H-NMR (CDCl$_3$) δ; 1.22–1.79 (8H, m), 2.24 (3H, s), 2.57–2.72 (4H, m), 3.86–4.03 (4H, m), 5.11 (2H, s), 5.91 (1H, d, J=3.2 Hz), 6.03 (1H, d, J=3.2 Hz), 6.73 (2H, d, J=8.4 Hz), 6.82 (2H, d, J=8.4 Hz), 7.00 (2H, d, J=8.0 Hz), 7.15–7.49 (12H, m).

IR (KBr) cm$^{-1}$; 1611, 1524, 1512, 1244, 1175, 752, 689.

(2) 4-[5-Methyl-1-{2-[4-(6-phenylhexyloxy)phenyl]ethyl}-1H-pyrrol-2-yl]phenol

To a solution of 2-(4-benzyloxyphenyl)-5-methyl-1-{2-[4-(6-phenylhexyloxy)phenyl]ethyl}-1H-pyrrole (1.35 g, 2.48 mmol) in ethanol (60 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 1.10 g (yield: 98.2%)

$^1$H-NMR (CDCl$_3$) δ; 1.31–1.79 (8H, m), 2.23 (3H, s), 2.57–2.72 (4H, m), 3.86–4.02 (4H, m), 5.91 (1H, d, J=3.6 Hz), 6.02 (1H, d, J=3.6 Hz), 6.71–6.87 (6H, m), 7.15–7.31 (7H, m).

IR (KBr) cm$^{-1}$; 2934, 1613, 1512, 1246, 1177, 837, 752, 700.

(3) Ethyl (2R)-2-{4-[5-methyl-1-{2-[4-(6-phenylhexyloxy)phenyl]ethyl}-1H-pyrrol-2-yl]phenoxy}-3-phenylpropanoate To a solution of 4-[5-methyl-1-{2-[4-(6-phenylhexyloxy)phenyl]ethyl}-1H-pyrrol-2-yl]phenol (1.10 g, 2.42 mmol), ethyl (S)-2-hydroxy-3-phenylpropanoate (706 mg, 3.64 mmol) and triphenylphosphine (954 mg, 3.64 mmol) in toluene (2 ml) was added 1,1'-(azodicarbonyl)dipiperidine (918 mg, 3.64 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=10:1) to give the object compound as an oily substance. 710 mg (yield: 39.4%)

$^1$H-NMR (CDCl$_3$) δ; 1.16–1.79 (11H, m), 2.22 (3H, s), 2.58–2.69 (4H, m), 3.25–3.29 (2H, m), 3.85–3.99 (4H, m), 4.20 (2H, q, J=7.0 Hz), 4.79–4.86 (1H, m), 5.89 (1H, d, J=3.2 Hz), 6.00 (1H, d, J=3.2 Hz), 6.69–6.92 (6H, m), 7.13–7.34 (12H, m).

IR (KBr) cm$^{-1}$; 1753, 1736, 1512, 1480, 1454, 1244, 1179, 1113, 1084, 1030, 835, 754, 700.

Example 150

Sodium (2R)-2-{4-[5-methyl-1-{2-[4-(6-phenylhexyloxy)phenyl]ethyl}-1H-pyrrol-2-yl]phenoxy}-3-phenylpropanoate (1) (2R)-2-{4-[5-Methyl-1-{2-[4-(6-phenylhexyloxy)phenyl]-ethyl}-1H-pyrrol-2-yl]phenoxy}-3-phenylpropanoic acid To a mixed solution of ethyl (2R)-2-{4-[5-methyl-1-{2-[4-(6-phenylhexyloxy)phenyl]ethyl}-1H-pyrrol-2-yl]phenoxy}-3-phenylpropanoate (760 mg, 1.21 mmol) in THF (30 ml) and methanol (15 ml) was added 1N aqueous potassium hydroxide solution (7 ml, 7 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 561 mg (yield: 77.1%)

$^1$H-NMR (CDCl$_3$) δ; 1.42–1.86 (8H, m), 2.21 (3H, s), 2.57–2.69 (4H, m), 3.31 (2H, d, J=6.0 Hz), 3.85–4.00 (4H, m), 4.88 (1H, t, J=6.0 Hz), 5.89 (1H, d, J=3.4 Hz), 6.00 (1H, d, J=3.4 Hz), 6.69–6.88 (6H, m), 7.13–7.34 (12H, m).

IR (KBr) cm$^{-1}$; 2932, 1728, 1512, 1242, 1177, 835, 756, 700.

(2) Sodium (2R)-2-{4-[5-methyl-1-{2-[4-(6-phenylhexyloxy)phenyl]ethyl}-1H-pyrrol-2-yl]phenoxy}-3-phenylpropanoate Ethanol (5 ml) and a solution of 1N sodium hydroxide in ethanol (0.748 ml) were added to (2R)-2-{4-[5-methyl-1-{2-[4-(6-phenylhexyloxy)phenyl]ethyl}-1H-pyrrol-2-yl]phenoxy}-3-phenylpropanoic acid (500 mg, 0.831 mmol) and the mixture was concentrated. To the residue was added hexane to give the object compound as a solid. 436 mg (yield: 93.6%)

$^1$H-NMR (DMSO-d$_6$) δ; 1.34–1.68 (8H, m), 2.11 (3H, s), 2.49–2.62 (4H, m), 2.95–3.25 (2H, m), 3.84–3.95 (4H, m), 4.33–4.39 (1H, m), 5.73 (1H, d, J=3.4 Hz), 5.81 (1H, d, J=3.4 Hz), 6.70–6.85 (6H, m), 7.10–7.35 (12H, m).

IR (KBr) cm$^{-1}$; 1613, 1512, 1408, 1244, 1177, 1053, 1030, 839, 758, 698.

$[\alpha]_D^{28}$ −22.8° (c 1.18, methanol)

Example 151

Ethyl (2R)-2-[4-(5-methyl-1-{2-[4-(4-pentylcyclohexylmethoxy)phenyl]ethyl}-1H-pyrrol-2-yl)phenoxy]-3-phenylpropanoate (1) 4-Pentylcyclohexylmethanol To a suspension of lithium aluminium hydride (9.56 g, 252 mmol) in tetrahydrofuran (400 ml) was added dropwise a solution of 4-n-pentylcyclohexanecarboxylic acid (25.0 g, 126 mmol) in tetrahydrofuran (100 ml) and refluxed for 2 hours under heating. To the residue were added water (10 ml) and 1 N aqueous sodium hydroxide solution (30 ml) under ice-cooling and the mixture was stirred at room temperature for 1 hour. The insoluble matter was filtered out and the filtrate was concentrated to give the object compound as an oily substance. 19.0 g (yield: 81.9%)

$^1$H-NMR (CDCl$_3$) δ; 0.85–1.80 (21H, m), 3.45 (2H, d, J=6.0 Hz).

IR (KBr) cm$^{-1}$; 3277, 1448, 1071, 1038, 986.

(2) 2-(4-Benzyloxyphenyl)-5-methyl-1-{2-[4-(4-pentylcyclohexylmethoxy)phenyl]ethyl}-1H-pyrrole To a solution of 4-{2-[2-(4-benzyloxyphenyl)-5-methyl-1H-pyrrol-1-yl]ethyl}phenol (970 mg, 2.53 mmol), 4-pentylcyclohexylmethanol (699 mg, 3.79 mmol) and triphenylphosphine (994 mg, 3.79 mmol) in toluene (2 ml) was added 1,1'-(azodicarbonyl)dipiperidine (956 mg, 3.79 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as a solid. 1.11 g (yield: 79.9%)

$^1$H-NMR (CDCl$_3$) δ; 0.85–1.91 (21H, m), 2.24 (3H, s), 2.69 (2H, t, J=7.8 Hz), 3.70 (2H, d, J=6.2 Hz), 3.99 (2H, t, J=7.8 Hz), 5.11 (2H, s), 5.92 (1H, d, J=3.2 Hz), 6.03 (1H, d, J=3.2 Hz), 6.73 (2H, d, J=8.8 Hz), 6.82 (2H, d, J=8.8 Hz), 6.99 (2H, d, J=8.8 Hz), 7.24–7.50 (7H, m).

IR (KBr) cm$^{-1}$; 1613, 1524, 1512, 1466, 1454, 1310, 1281, 1244, 1175, 1026, 835, 754, 735, 698.

(3) 4-(5-Methyl-1-{2-[4-(4-pentylcyclohexylmethoxy)phenyl]-ethyl}-1H-pyrrol-2-yl)phenol To a solution of 2-(4-benzyloxyphenyl)-5-methyl-1-{2-[4-(4-pentylcyclohexylmethoxy)phenyl]ethyl}-1H-pyrrole (1.01 g, 1.84 mmol) in ethanol (60 ml) and tetrahydrofuran (30 ml) was added 10% palladium carbon (200 mg) and the mixture was stirred under hydrogen atmosphere for 5 hours. The insoluble matter was filtered out and the filtrate was concentrated to give the object compound as an oily substance. 840 mg (yield: 99.3%)

$^1$H-NMR (CDCl$_3$) δ; 0.86–1.90 (21H, m), 2.24 (3H, s), 2.68 (2H, t, J=7.8 Hz), 3.70 (2H, d, J=6.3 Hz), 3.98 (2H, t, J=7.8 Hz), 5.91 (1H, d, J=3.3 Hz), 6.01 (1H, d, J=3.3 Hz), 6.74 (2H, d, J=8.7 Hz), 6.81–6.87 (4H, m), 7.21 (2H, d, J=9.0 Hz).

IR (KBr) cm$^{-1}$; 3268, 1613, 1512, 1468, 1449, 1246, 1177, 1032, 837, 824, 756.

(4) Ethyl (2R)-2-[4-(5-methyl-1-{2-[4-(4-pentylcyclohexylmethoxy)phenyl]ethyl}-1H-pyrrol-2-yl)phenoxy]-3-phenylpropanoate To a solution of 4-(5-methyl-1-{2-[4-(4-pentylcyclohexylmethoxy)phenyl]ethyl}-1H-pyrrol-2-yl)phenol (830 mg, 1.81 mmol), ethyl (S)-2-hydroxy-3-phenylpropanoate (526 mg, 2.71 mmol) and triphenylphosphine (711 mg, 2.71 mmol) in toluene (1 ml) was added 1,1'-(azodicarbonyl)dipiperidine (684 mg, 2.71 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 560 mg (yield: 48.7%)

$^1$H-NMR (CDCl$_3$) δ; 0.85–1.91 (24H, m), 2.23 (3H, s), 2.66 (2H, t, J=8.0 Hz), 3.25–3.29 (2H, m), 3.69 (2H, d, J=6.2 Hz), 3.96 (2H, t, J=8.0 Hz), 4.20 (2H, q, J=7.0 Hz), 4.79–4.86 (1H, m), 5.89 (1H, d, J=3.2 Hz), 6.00 (1H, d, J=3.2 Hz), 6.69–6.89 (6H, m), 7.19–7.34 (7H, m).

IR (KBr) cm$^{-1}$; 1755, 1732, 1512, 1481, 1468, 1454, 1279, 1244, 1179, 1088, 1032, 835, 758.

Example 152

Sodium (2R)-2-[4-(5-methyl-1-{2-[4-(4-pentylcyclohexylmethoxy)phenyl]ethyl}-1H-pyrrol-2-yl)phenoxy]-3-phenylpropanoate (1) (2R)-2-[4-(5-methyl-1-{2-[4-(4-pentylcyclohexylmethoxy)phenyl]ethyl}-1H-pyrrol-2-yl)phenoxy]-3-phenylpropanoic acid To a mixed solution of ethyl (2R)-2-[4-(5-methyl-1-{2-[4-(4-pentylcyclohexylmethoxy)phenyl]ethyl}-1H-pyrrol-2-yl)phenoxy]-3-phenylpropanoate (550 mg, 0.865 mmol) in THF (20 ml) and methanol (10 ml) was added 1N aqueous potassium hydroxide solution (15 ml, 15 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 342 mg (yield: 65.0%)

$^1$H-NMR (CDCl$_3$) δ; 0.85–1.90 (21H, m), 2.22 (3H, s), 2.64 (2H, t, J=8.2 Hz), 3.31 (2H, d, J=5.6 Hz), 3.69 (2H, d, J=6.6 Hz), 3.96 (2H, t, J=8.2 Hz), 4.89 (1H, t, J=5.6 Hz), 5.89 (1H, d, J=3.2 Hz), 5.99 (1H, d, J=3.2 Hz), 6.68–6.87 (6H, m), 7.19–7.31 (7H, m).

IR (KBr) cm$^{-1}$; 2921, 1728, 1512, 1244, 1177, 1032, 835, 756, 700.

(2) Sodium (2R)-2-[4-(5-methyl-1-{2-[4-(4-pentylcyclohexylmethoxy)phenyl]ethyl}-1H-pyrrol-2-yl)phenoxy]-3-phenylpropanoate Ethanol (5 ml) and a solution of 1N sodium hydroxide in ethanol (0.489 ml) were added to (2R)-2-[4-(5-methyl-1-{2-[4-(4-pentylcyclohexylmethoxy)phenyl]ethyl}-1H-pyrrol-2-yl)phenoxy]-3-phenylpropanoic acid (330 mg, 0.543 mmol) and the mixture was concentrated. To the residue was added diisopropylether to give the object compound as a solid. 256 mg (yield: 83.1%)

$^1$H-NMR (DMSO-d$_6$) δ; 0.83–1.85 (21H, m), 2.11 (3H, s), 2.55–2.69 (2H, m), 2.93–3.18 (2H, m), 3.69 (2H, d, J=6.6 Hz), 3.84–3.97 (2H, m), 4.30–4.36 (1H, m), 5.73 (1H, d, J=3.4 Hz), 5.80 (1H, d, J=3.4 Hz), 6.70–6.85 (6H, m), 7.10–7.33 (7H, m).

IR (KBr) cm$^{-1}$; 1613, 1512, 1408, 1244, 1034, 839, 758, 700.

$[α]_D^{26}$ 2.35° (c 0.580, methanol)

Example 153

Ethyl (2R)-2-(4-{5-methyl-1-[3-(4-octylphenoxy)propyl]-1H-pyrrol-2-yl}phenoxy)-3-phenylpropanoate (1) 3-[2-(4-Benzyloxyphenyl)-5-methyl-1H-pyrrol-1-yl]propan-1-ol A solution of 1-(4-benzyloxyphenyl)pentan-1,4-dione (5.00 g, 17.7 mmol), 3-amino-1-propanol (1.33 g, 17.7 mmol) and p-toluenesulfonic acid monohydrate (253 mg, 1.33 mmol) in toluene (100 ml) was refluxed for 12 hours under heating using Dean-Stark's apparatus, and the solvent was removed under reduced pressure. The residue was purified by silica gel column chromatography (hexane:ethyl acetate=4:1) to give the object compound as a solid. 4.50 g (yield: 79.1%)

$^1$H-NMR (CDCl$_3$) δ; 1.66–1.79 (2H, m), 2.32 (3H, s), 3.39–3.47 (2H, m), 4.03 (2H, d, J=7.4 Hz), 5.09 (2H, s), 5.94 (1H, d, J=3.4 Hz), 6.04 (1H, d, J=3.4 Hz), 7.00 (2H, d, J=8.8 Hz), 7.27–7.49 (7H, m).

IR (KBr) cm$^{-1}$; 2937, 1609, 1524, 1242, 1175, 1024, 835, 756, 698.

(2) 2-(4-Benzyloxyphenyl)-5-methyl-1-[3-(4-octyloxyphenyl)propyl]-1H-pyrrole

To a solution of 3-[2-(4-benzyloxyphenyl)-5-methyl-1H-pyrrol-1-yl]propan-1-ol (1.00 g, 3.11 mmol), 4-octylphenol (642 mg, 3.11 mmol) and triphenylphosphine (1.22 g, 4.67 mmol) in toluene (2 ml) was added 1,1'-(azodicarbonyl)dipiperidine (1.18 g, 4.67 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 1.23 g (yield: 77.4%)

$^1$H-NMR (CDCl$_3$) δ; 0.87 (3H, t, J=6.6 Hz), 1.18–1.61 (12H, m), 1.88–2.00 (2H, m), 2.30 (3H, s), 2.52 (2H, t, J=8.0 Hz), 3.71 (2H, d, J=6.0 Hz), 4.09 (2H, t, J=7.6 Hz), 5.06 (2H, s), 5.92 (1H, d, J=3.4 Hz), 6.03 (1H, d, J=3.4 Hz), 6.66 (2H, d, J=8.4 Hz), 6.92–7.05 (4H, m), 7.24–7.49 (7H, m).

IR (KBr) cm$^{-1}$; 1611, 1524, 1510, 1468, 1454, 1383, 1312, 1281, 1244, 1175, 1024, 833, 756, 698.

(3) 4-{5-Methyl-1-[3-(4-octylphenoxy)propyl]-1H-pyrrol-2-yl}phenol

To a solution of 2-(4-benzyloxyphenyl)-5-methyl-1-[3-(4-octyloxyphenyl)propyl]-1H-pyrrole (1.15 g, 2.26 mmol) in ethanol (60 ml) and tetrahydrofuran (30 ml) was added 10% palladium carbon (200 mg) and the mixture was stirred under hydrogen atmosphere for 6 hours. The insoluble matter was filtered out and the filtrate was concentrated to give the object compound as an oily substance. 930 mg (yield: 98.1%)

$^1$H-NMR (CDCl$_3$) δ; 0.87 (3H, t, J=6.6 Hz), 1.21–1.28 (10H, m), 1.49–1.62 (2H, m), 1.89–1.97 (2H, m), 2.30 (3H, s), 2.52 (2H, t, J=7.4 Hz), 3.72 (2H, t, J=7.4 Hz), 4.07 (2H, t, J=7.4 Hz), 5.91 (1H, d, J=3.4 Hz), 6.02 (1H, d, J=3.4 Hz), 6.67 (2H, d, J=8.8 Hz), 6.80 (2H, d, J=8.8 Hz), 7.04 (2H, d, J=8.8 Hz), 7.22 (2H, d, J=8.8 Hz).

IR (KBr) cm$^{-1}$; 3424, 1613, 1524, 1510, 1242, 1175, 837, 756.

(4) Ethyl (2R)-2-(4-{5-methyl-1-[3-(4-octylphenoxy)propyl]-1H-pyrrol-2-yl}phenoxy)-3-phenylpropanoate To a solution of 4-{5-methyl-1-[3-(4-octylphenoxy)propyl]-1H-pyrrol-2-yl}phenol (930 mg, 2.22 mmol), ethyl (S)-2-hydroxy-3-phenylpropanoate (644 mg, 3.32 mmol) and triphenylphosphine (870 mg, 3.32 mmol) in toluene (2 ml) was added 1,1'-(azodicarbonyl)dipiperidine (839 mg, 3.32 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate= 30:1) to give the object compound as an oily substance. 610 mg (yield: 46.2%)

$^1$H-NMR (CDCl$_3$) δ; 0.88 (3H, t, J=6.4 Hz), 1.15–1.33 (13H, m), 1.47–1.61 (2H, m), 1.88–1.95 (2H, m), 2.28 (3H, s), 2.52 (2H, t, J=8.0 Hz), 3.24–3.29 (2H, m), 3.70 (2H, t, J=5.6 Hz), 4.05 (2H, t, J=7.2 Hz), 4.19 (2H, q, J=7.4 Hz), 4.76–4.79 (1H, m), 5.90 (1H, d, J=3.6 Hz), 6.00 (1H, d, J=3.6 Hz), 6.66 (2H, d, J=8.8 Hz), 6.82 (2H, d, J=8.8 Hz), 7.02 (2H, d, J=8.8 Hz), 7.19–7.33 (7H, m).

IR (KBr) cm$^{-1}$; 1753, 1736, 1524, 1510, 1242, 1179, 1086, 1032, 835, 756, 700.

Example 154

Sodium (2R)-2-(4-{5-methyl-1-[3-(4-octylphenoxy)propyl]-1H-pyrrol-2-yl}phenoxy)-3-phenylpropanoate (1) (2R)-2-(4-{5-Methyl-1-[3-(4-octylphenoxy)propyl]-1H-pyrrol-2-yl}phenoxy)-3-phenylpropanoic acid To a mixed solution of ethyl (2R)-2-(4-{5-methyl-1-[3-(4-octylphenoxy)propyl]-1H-pyrrol-2-yl}phenoxy)-3-phenylpropanoate (600 mg, 1.01 mmol) in THF (20 ml) and methanol (10 ml) was added 1N aqueous potassium hydroxide solution (5 ml, 5 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate= 1:1) to give the object compound as an oily substance. 414 mg (yield: 72.3%)

$^1$H-NMR (CDCl$_3$) δ; 0.87 (3H, t, J=6.6 Hz), 1.22–1.30 (10H, m), 1.49–1.61 (2H, m), 1.89–1.94 (2H, m), 2.29 (3H, s), 2.51 (2H, t, J=7.2 Hz), 3.30 (2H, d, J=5.8 Hz), 3.69 (2H, t, J=5.8 Hz), 4.05 (2H, t, J=7.2 Hz), 4.85 (1H, t, J=5.8 Hz), 5.90 (1H, d, J=3.2 Hz), 6.00 (1H, d, J=3.2 Hz), 6.64 (2H, d, J=8.8 Hz), 6.82 (2H, d, J=8.8 Hz), 7.01 (2H, d, J=8.8 Hz), 7.16–7.33 (7H, m).

IR (KBr) cm$^{-1}$; 3031, 1730, 1510, 1456, 1242, 1177, 1084, 833, 756, 700.

(2) Sodium (2R)-2-(4-{5-methyl-1-[3-(4-octylphenoxy)propyl]-1H-pyrrol-2-yl}phenoxy)-3-phenylpropanoate Ethanol (4 ml) and a solution of 1N sodium hydroxide in ethanol (0.634 ml) were added to (2R)-2-(4-{5-methyl-1-[3-(4-octylphenoxy)propyl]-1H-pyrrol-2-yl}phenoxy)-3-phenylpropanoic acid (400 mg, 0.705 mmol) and the mixture was concentrated. To the residue was added diisopropylether to give the object compound as a solid. 226 mg (yield: 60.4%)

$^1$H-NMR (DMSO-d$_6$) δ; 0.86 (3H, t, J=6.6 Hz), 1.19–1.32 (10H, m), 1.43–1.59 (2H, m), 1.78–1.89 (2H, m), 2.21 (3H, s), 2.47 (2H, t, J=7.2 Hz), 2.96–3.21 (2H, m), 3.69 (2H, t, J=5.8 Hz), 3.99 (2H, t, J=7.8 Hz), 4.33–4.40 (1H, m), 5.75 (1H, d, J=3.8 Hz), 5.81 (1H, d, J=3.8 Hz), 6.66 (2H, d, J=8.4 Hz), 6.78 (2H, d, J=8.4 Hz), 7.00 (2H, d, J=8.4 Hz), 7.10–7.35 (7H, m).

IR (KBr) cm$^{-1}$; 1613, 1512, 1404, 1240, 1177, 1044, 827, 764, 700.

$[\alpha]_D^{25}$ 10.2° (c 0.540, methanol)

Example 155

Ethyl (2R)-2-{4-[1-(3-decyloxyphenyl)-5-methyl-1H-pyrrol-2-yl]phenoxy}-3-phenylpropanoate (1) 3-[2-(4-Benzyloxyphenyl)-5-methyl-1H-pyrrol-1-yl]phenol A solution of 1-(4-benzyloxyphenyl)pentane-1,4-dione (2.00 g, 7.08 mmol), 3-aminophenol (773 mg, 7.08 mmol) and p-toluenesulfonic acid monohydrate (100 mg, 0.528 mmol) in toluene (100 ml) was refluxed for 12 hours under heating and the solvent was removed under reduced pressure. The residue was purified by silica gel column chromatography (hexane:ethyl acetate=4:1) to give the object compound as an oily substance. 1.81 g (yield: 72.1%)

$^1$H-NMR (CDCl$_3$) δ; 2.14 (3H, s), 4.98 (2H, s), 6.05 (1H, d, J=3.2 Hz), 6.25 (1H, d, J=3.2 Hz), 6.60–6.97 (5H, m), 7.01 (2H, d, J=8.8 Hz), 7.18–7.42 (6H, m).

IR (KBr) cm$^{-1}$; 3422, 1599, 1524, 1229, 1179, 1018, 871, 766, 696.

(2) 2-(4-Benzyloxyphenyl)-1-(3-decyloxyphenyl)-5-methyl-1H-pyrrole

A solution of 3-[2-(4-benzyloxyphenyl)-5-methyl-1H-pyrrol-1-yl]phenol (1.80 g, 5.07 mmol), 1-bromoundecane (1.58 ml, 7.60 mmol) and potassium carbonate (1.05 g, 7.06 mmol) in DMF (15 ml) was stirred at 80° C. for 12 hours. The reaction solution was poured into water and the mixture was extracted with ethyl acetate. The extract was washed with water and dried over magnesium sulfate anhydride, and solvent was removed under reduced pressure. The residue was purified by silica gel column chromatography (hexane:ethyl acetate=30:1) to give the object compound as an oily substance. 1.90 g (yield: 75.7%)

$^1$H-NMR (CDCl$_3$) δ; 0.88 (3H, t, J=6.6 Hz), 1.22–1.43 (14H, m), 1.55–1.74 (2H, m), 2.15 (3H, s), 3.84 (2H, t, J=6.6 Hz), 4.98 (2H, s), 6.05 (1H, d, J=3.6 Hz), 6.25 (1H, d, J=3.6 Hz), 6.67–7.42 (13H, m).

IR (KBr) cm$^{-1}$; 1605, 1523, 1489, 1454, 1391, 1283, 1242, 1225, 1196, 1177, 760.

(3) 4-[1-(3-Decyloxyphenyl)-5-methyl-1H-pyrrol-2-yl]phenol

To a solution of 2-(4-benzyloxyphenyl)-1-(3-decyloxyphenyl)-5-methyl-1H-pyrrole (1.80 g, 3.63 mmol) in ethanol (60 ml) and tetrahydrofuran (30 ml) was added 10% palladium carbon (200 mg) and the mixture was stirred for 3 hours under hydrogen atmosphere. The insoluble matter was filtered out and the filtrate was concentrated to give the object compound as an oily substance. 1.40 g (yield: 95.2%)

$^1$H-NMR (CDCl$_3$) δ; 0.88 (3H, t, J=7.4 Hz), 1.21–1.44 (14H, m), 1.64–1.74 (2H, m), 2.14 (3H, s), 3.84 (2H, t, J=6.6

Hz), 6.05 (1H, d, J=3.4 Hz), 6.24 (1H, d, J=3.4 Hz), 6.59–7.26 (8H, m).

IR (KBr) cm$^{-1}$; 3285, 1595, 1526, 1489, 1456, 1265, 1219, 1196, 1171, 835, 762.

(4) Ethyl (2R)-2-{4-[1-(3-decyloxyphenyl)-5-methyl-1H-pyrrole-2-yl]phenoxy}-3-phenylpropanoate To a solution of 4-[1-(3-decyloxyphenyl)-5-methyl-1H-pyrrol-2-yl]phenol (1.40 g, 3.45 mmol), ethyl (S)-2-hydroxy-3-phenylpropanoate (1.00 g, 5.18 mmol) and triphenylphosphine (1.36 g, 5.18 mmol) in toluene (2 ml) was added 1,1'-(azodicarbonyl)dipiperidine (1.31 g, 5.18 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.00 g (yield: 49.8%)

$^1$H-NMR (CDCl$_3$) δ; 0.88 (3H, t, J=6.8 Hz), 1.09–1.42 (17H, m), 1.63–1.78 (2H, m), 2.12 (3H, s), 3.17–3.21 (2H, m), 3.83 (2H, t, J=6.6 Hz), 4.13 (2H, q, J=7.0 Hz), 4.67–4.73 (1H, m), 6.03 (1H, d, J=3.8 Hz), 6.22 (1H, d, J=3.8 Hz), 6.60–7.33 (13H, m).

IR (KBr) cm$^{-1}$; 1757, 1732, 1605, 1601, 1524, 1489, 1283, 1227, 1184, 1084, 1032, 835, 760, 698.

Example 156

Sodium (2R)-2-{4-[1-(3-decyloxyphenyl)-5-methyl-1H-pyrrol-2-yl]phenoxy}-3-phenylpropanoate (1) (2R)-2-{4-[1-(3-Decyloxyphenyl)-5-methyl-1H-pyrrol-2-yl]phenoxy}-3-phenylpropanoic acid To a mixed solution of ethyl (2R)-2-{4-[1-(3-decyloxyphenyl)-5-methyl-1H-pyrrol-2-yl]phenoxy}-3-phenylpropanoate (960 mg, 1.65 mmol) in THF (30 ml) and methanol (15 ml) was added 1N aqueous potassium hydroxide solution (8 ml, 8 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate= 1:1) to give the object compound as an oily substance. 658 mg (yield: 72.0%)

$^1$H-NMR (CDCl$_3$) δ; 0.88 (3H, t, J=7.0 Hz), 1.22–1.42 (14H, m), 1.67–1.74 (2H, m), 2.12 (3H, s), 3.22 (2H, d, J=6.2 Hz), 3.84 (2H, t, J=6.6 Hz), 4.76 (1H, t, J=6.2 Hz), 6.03 (1H, d, J=3.4 Hz), 6.242 (1H, d, J=3.4 Hz), 6.61–7.26 (13H, m).

IR (KBr) cm$^{-1}$; 3065, 1728, 1605, 1522, 1489, 1283, 1229, 1084, 833, 760, 698.

(2) Sodium (2R)-2-{4-[1-(3-decyloxyphenyl)-5-methyl-1H-pyrrol-2-yl]phenoxy}-3-phenylpropanoate Ethanol (6 ml) and a solution of 1N sodium hydroxide in ethanol (1.02 ml) were added to (2R)-2-{4-[1-(3-decyloxyphenyl)-5-methyl-1H-pyrrol-2-yl]phenoxy}-3-phenylpropanoic acid (630 mg, 1.14 mmol) and the mixture was concentrated. To the residue was added ether to give the object compound as a solid. 357 mg (yield: 60.7%)

$^1$H-NMR (DMSO-d$_6$) δ; 0.86 (3H, t, J=6.8 Hz), 1.21–1.41 (14H, m), 1.58–1.69 (2H, m), 2.03 (3H, s), 2.85–3.13 (2H, m), 3.91 (2H, t, J=6.6 Hz), 4.16–4.23 (1H, m), 5.93 (1H, d, J=3.2 Hz), 6.08 (1H, d, J=3.2 Hz), 6.51–7.29 (13H, m).

IR (KBr) cm$^{-1}$; 1613, 1524, 1474, 1406, 1227, 1061, 1030, 829, 764, 700.

[α]$_D^{25}$ 4.55° (c 0.530, methanol)

Example 157

Ethyl (2R)-2-{4-[5-methyl-1-[4-(6-phenylhexyloxy) phenyl]-1H-pyrrol-2-yl]phenoxy}-3-phenylpropanoate (1) 2-(4-Benzyloxyphenyl)-5-methyl-1-[4-(6-phenylhexyloxy)-phenyl]-1H-pyrrole A solution of 4-[2-(4-benzyloxyphenyl)-5-methyl-1H-pyrrol-1-yl]phenol (1.50 g, 4.22 mmol), 1-bromo-6-phenylhexane (1.53 g, 6.33 mmol) and potassium carbonate (874 mg, 6.33 mmol) in DMF (15 ml) was stirred at 80° C. for 12 hours. The reaction solution was poured into water and the mixture was extracted with ethyl acetate. The extract was washed with water, dried over magnesium sulfate anhydride and solvent was removed under reduced pressure. The residue was purified by silica gel column chromatography (hexane:ethyl acetate=20:1) to give the object compound as an oily substance. 1.74 g (yield: 79.4%)

$^1$H-NMR (CDCl$_3$) δ; 1.22–1.83 (8H, m), 2.10 (3H, s), 2.63 (2H, t, J=7.4 Hz), 3.94 (2H, t, J=6.2 Hz), 4.98 (2H, s), 6.04 (1H, d, J=3.2 Hz), 6.25 (1H, d, J=3.2 Hz), 6.74–7.42 (18H, m).

IR (KBr) cm$^{-1}$; 1607, 1514, 1289, 1244, 1177, 1026, 835, 750, 698.

(2) 4-[5-Methyl-1-{2-[4-(6-phenylhexyloxy)phenyl]ethyl}-1H-pyrrol-2-yl]phenol

To a solution of 2-(4-benzyloxyphenyl)-5-methyl-1-{2-[4-(6-phenylhexyloxy)phenyl]ethyl}-1H-pyrrole (1.35 g, 2.48 mmol) in ethanol (60 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 1.10 g (yield: 98.2%)

$^1$H-NMR (CDCl$_3$) δ; 1.31–1.79 (8H, m), 2.23 (3H, s), 2.57–2.72 (4H, m), 3.86–4.02 (4H, m), 5.91 (1H, d, J=3.6 Hz), 6.02 (1H, d, J=3.6 Hz), 6.71–6.87 (6H, m), 7.15–7.31 (7H, m).

IR (KBr) cm$^{-1}$; 2934, 1613, 1512, 1246, 1177, 837, 752, 700.

(3) Ethyl (2R)-2-{4-[5-methyl-1-[4-(6-phenylhexyloxy) phenyl]-1H-pyrrol-2-yl]phenoxy}-3-phenylpropanoate To a solution of 4-[5-methyl-1-{2-[4-(6-phenylhexyloxy) phenyl]ethyl}-1H-pyrrol-2-yl]phenol (1.30 g, 3.05 mmol), ethyl (S)-2-hydroxy-3-phenylpropanoate (890 mg, 4.58 mmol) and triphenylphosphine (1.20 g, 4.58 mmol) in toluene (2 ml) was added 1,1'-(azodicarbonyl)dipiperidine (1.15 g, 4.58 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate= 30:1) to give the object compound as an oily substance. 830 mg (yield: 45.5%)

$^1$H-NMR (CDCl$_3$) δ; 1.14 (3H, t, J=7.4 Hz), 1.22–1.83 (8H, m), 2.08 (3H, s), 2.63 (2H, t, J=8.0 Hz), 3.17–3.21 (2H, m), 3.93 (2H, t, J=7.0 Hz), 4.12 (2H, q, J=7.4 Hz), 4.66–4.73 (1H, m), 6.02 (1H, d, J=3.4 Hz), 6.21 (1H, d, J=3.4 Hz), 6.62 (2H, d, J=9.2 Hz), 6.82 (2H, d, J=8.8 Hz), 6.93 (2H, d, J=9.2 Hz), 7.01 (2H, d, J=8.8 Hz), 7.17–7.30 (10H, m).

IR (KBr) cm$^{-1}$; 1755, 1732, 1514, 1287, 1246, 1184, 1111, 1084, 1032, 835, 760, 700.

Example 158

Sodium (2R)-2-{4-[5-methyl-1-[4-(6-phenylhexyloxy)phenyl]-1H-pyrrol-2-yl]phenoxy}-3-phenylpropanoate (1) (2R)-2-{4-[5-Methyl-1-[4-(6-phenylhexyloxy)phenyl]-1H-pyrrol-2-yl]phenoxy}-3-phenylpropanoic acid To a mixed solution of ethyl (2R)-2-{4-[5-methyl-1-[4-(6-phenylhexyloxy)phenyl]-1H-pyrrol-2-yl]phenoxy}-3-phenylpropanoate (800 mg, 1.33 mmol) in THF (20 ml) and methanol (10 ml) was added 1N aqueous potassium hydroxide solution (7 ml, 7 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 602 mg (yield: 79.0%)

$^1$H-NMR (CDCl$_3$) δ; 1.38–1.83 (8H, m), 2.08 (3H, s), 2.63 (2H, t, J=7.5 Hz), 3.21–3.23 (2H, m), 3.92 (2H, t, J=6.6 Hz), 4.73–4.77 (1H, m), 6.02 (1H, d, J=3.6 Hz), 6.22 (1H, d, J=3.6 Hz), 6.62 (2H, d, J=9.0 Hz), 6.82 (2H, d, J=9.0 Hz), 6.94 (2H, d, J=9.0 Hz), 7.01 (2H, d, J=9.0 Hz), 7.15–7.30 (10H, m).

IR (KBr) cm$^{-1}$; 3027, 1723, 1514, 1244, 835, 758, 698.

(2) Sodium (2R)-2-{4-[5-methyl-1-[4-(6-phenylhexyloxy)phenyl]-1H-pyrrol-2-yl]phenoxy}-3-phenylpropanoate Ethanol (6 ml) and a solution of 1N sodium hydroxide in ethanol (0.900 ml) were added to (2R)-2-{4-[5-methyl-1-[4-(6-phenylhexyloxy)phenyl]-1H-pyrrol-2-yl]phenoxy}-3-phenylpropanoic acid (573 mg, 1.00 mmol) and the mixture was concentrated. To the residue was added hexane to give the object compound as a solid. 449 mg (yield: 83.8%)

$^1$H-NMR (DMSO-d$_6$) δ; 1.31–1.74 (8H, m), 1.99 (3H, s), 2.59 (2H, t, J=7.5 Hz), 2.90–3.12 (2H, m), 3.94 (2H, t, J=6.6 Hz), 4.22–4.26 (1H, m), 5.91 (1H, d, J=3.6 Hz), 6.06 (1H, d, J=3.6 Hz), 6.55 (2H, d, J=8.7 Hz), 6.79 (2H, d, J=8.7 Hz), 6.89 (2H, d, J=8.7 Hz), 7.02 (2H, d, J=8.7 Hz), 7.09–7.30 (10H, m).

IR (KBr) cm$^{-1}$; 1613, 1514, 1404, 1244, 1053, 1028, 833, 764, 698.

Example 159

Ethyl (2R)-2-[4-(5-methyl-1-[4-(4-pentylcyclohexylmethoxy)-phenyl]-1H-pyrrol-2-yl)phenoxy]-3-phenylpropanoate (1) 2-(4-Benzyloxyphenyl)-5-methyl-1-[4-(4-pentylcyclohexylmethoxy)phenyl]-1H-pyrrole To a solution of 4-[2-(4-benzyloxyphenyl)-5-methyl-1H-pyrrol-1-yl]phenol (1.50 g, 4.22 mmol), 4-pentylcyclohexylmethanol (776 mg, 4.22 mmol) and triphenylphosphine (1.66 g, 6.33 mmol) in toluene (2 ml) was added 1,1'-(azodicarbonyl)dipiperidine (1.56 g, 6.33 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=20:1) to give the object compound as an oily substance. 1.53 g (yield: 69.5%)

$^1$H-NMR (CDCl$_3$) δ; 0.85–1.94 (21H, m), 2.10 (3H, s), 3.75 (2H, d, J=6.2 Hz), 4.98 (2H, s), 6.04 (1H, d, J=3.2 Hz), 6.24 (1H, d, J=3.2 Hz), 6.75–7.42 (13H, m).

IR (KBr) cm$^{-1}$; 1609, 1514, 1289, 1244, 1177, 1640, 1026, 833, 758, 735, 696.

(2) 4-(5-Methyl-1-[4-(4-pentylcyclohexylmethoxy)phenyl]-1H-pyrrol-2-yl)phenol

To a solution of 2-(4-benzyloxyphenyl)-5-methyl-1-[4-(4-pentylcyclohexylmethoxy)phenyl]-1H-pyrrole (1.43 g, 2.74 mmol) in ethanol (60 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 1.12 g (yield: 94.9%)

$^1$H-NMR (CDCl$_3$) δ; 0.85–1.93 (21H, m), 2.10 (3H, s), 2.73 (2H, t, J=7.4 Hz), 6.04 (1H, d, J=3.4 Hz), 6.24 (1H, d, J=3.4 Hz), 6.62 (2H, d, J=8.8 Hz), 6.84 (2H, d, J=8.8 Hz), 6.94 (2H, d, J=8.8 Hz), 7.03 (2H, d, J=8.8 Hz).

IR (KBr) cm$^{-1}$; 3291, 1613, 1514, 1466, 1244, 1171, 1040, 833, 760.

(3) Ethyl (2R)-2-[4-(5-methyl-1-[4-(4-pentylcyclohexylmethoxy)phenyl]-1H-pyrrol-2-yl)phenoxy]-3-phenylpropanoate To a solution of 4-(5-methyl-1-[4-(4-pentylcyclohexylmethoxy)phenyl]-1H-pyrrol-2-yl)phenol (1.10 g, 2.55 mmol), ethyl (S)-2-hydroxy-3-phenylpropanoate (742 mg, 3.82 mmol) and triphenylphosphine (1.00 g, 3.82 mmol) in toluene (2 ml) was added 1,1'-(azodicarbonyl)dipiperidine (963 mg, 3.82 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 620 mg (yield: 43.4%)

$^1$H-NMR (CDCl$_3$) δ; 0.86–1.93 (24H, m), 2.08 (3H, s), 3.17–3.21 (2H, m), 3.74 (2H, d, J=6.2 Hz), 4.14 (2H, q, J=7.0 Hz), 4.66–4.73 (1H, m), 6.02 (1H, d, J=3.4 Hz), 6.21 (1H, d, J=3.4 Hz), 6.61 (2H, d, J=8.8 Hz), 6.82 (2H, d, J=8.8 Hz), 6.92 (2H, d, J=8.8 Hz), 7.00 (2H, d, J=8.8 Hz), 7.21–7.29 (5H, m).

IR (KBr) cm$^{-1}$; 1755, 1734, 1514, 1287, 1244, 1182, 1084, 1040, 835, 698.

Example 160

Sodium (2R)-2-[4-(5-methyl-1-[4-(4-pentylcyclohexylmethoxy)phenyl]-1H-pyrrol-2-yl)phenoxy]-3-phenylpropanoate (1) (2R)-2-[4-(5-Methyl-1-[4-(4-pentylcyclohexylmethoxy)-phenyl]-1H-pyrrol-2-yl)phenoxy]-3-phenylpropanoic acid To a mixed solution of ethyl (2R)-2-[4-(5-methyl-1-[4-(4-pentylcyclohexylmethoxy)phenyl]-1H-pyrrol-2-yl)phenoxy]-3-phenylpropanoate (600 mg, 0.987 mmol) in THF (20 ml) and methanol (10 ml) was added 1N aqueous potassium hydroxide solution (5 ml, 5 mmol) and the mixture was stirred for 1 hour at room temperature. The reaction solution was neutralized with 1N hydrochloric acid and extracted with ethyl acetate. The extract was washed with water, dried over magnesium sulfate anhydride, and the solvent was removed under reduced pressure. The residue was purified by silica gel column chromatography (hexane:ethyl acetate=1:1) to give the object compound as an oily substance. 523 mg (yield: 91.4%)

$^1$H-NMR (CDCl$_3$) δ; 0.86–1.92 (21H, m), 2.08 (3H, s), 3.20 (2H, d, J=5.0 Hz), 3.72 (2H, d, J=6.2 Hz), 4.74 (1H, t, J=5.0 Hz), 6.02 (1H, d, J=3.4 Hz), 6.21 (1H, d, J=3.4 Hz), 6.60 (2H, d, J=8.4 Hz), 6.79–7.02 (6H, m), 7.24–7.26 (5H, m).

IR (KBr) cm$^{-1}$; 3031, 1728, 1514, 1287, 1244, 1181, 1082, 1042, 835, 758, 700.

(2) Sodium (2R)-2-[4-(5-methyl-1-[4-(4-pentylcyclohexylmethoxy)phenyl]-1H-pyrrol-2-yl)phenoxy]-3-phenylpropanoate Ethanol (5 ml) and a solution of 1N sodium hydroxide in ethanol (0.786 ml) were added to (2R)-2-[4-(5-methyl-1-[4-

(4-pentylcyclohexylmethoxy)phenyl]-1H-pyrrol-2-yl) phenoxy]-3-phenylpropanoic acid (500 mg, 0.874 mmol) and the mixture was concentrated. To the residue was added hexane to give the object compound as a solid. 445 mg (yield: 94.3%)

$^1$H-NMR (DMSO-d$_6$) δ; 0.83–1.88 (21H, m), 1.99 (3H, s), 2.88–3.13 (2H, m), 3.75 (2H, d, J=5.8 Hz), 4.19–4.25 (1H, m), 5.89 (1H, d, J=3.2 Hz), 6.04 (1H, d, J=3.2 Hz), 6.54 (2H, d, J=8.8 Hz), 6.78 (2H, d, J=8.8 Hz), 6.87 (2H, d, J=8.8 Hz), 7.00 (2H, d, J=8.8 Hz), 7.07–7.28 (5H, m).

IR (KBr) cm$^{-1}$; 1613, 1514, 1399, 1244, 1181, 1042, 1030, 833, 764, 700.

$[α]_D^{25}$ –2.81° (c 0.580, methanol)

Example 161

Ethyl (2R)-2-[4-(1-[4-(4-butylcyclohexylmethoxy) phenyl]-5-methyl-1H-pyrrol-2-yl)phenoxy]-3-phenylpropanoate (1) 4-Butylcyclohexylmethanol To a suspension of lithium aluminum hydride (10.3 g, 272 mmol) in tetrahydrofuran (400 ml) was added dropwise a solution of 4-n-butylcyclohexane carboxylic acid (25.0 g, 136 mmol) in tetrahydrofuran (100 ml) and the mixture was refluxed for 4 hours under heating. To the residue was added water (10 ml) and 1 N aqueous sodium hydroxide solution (30 ml) under ice-cooling and the mixture was stirred at room temperature for 1 hour. The insoluble matter was filtered out and the filtrate was concentrated to give the object compound as an oily substance. 18.9 g (yield: 81.1%)

$^1$H-NMR (CDCl$_3$) δ; 0.89–1.80 (19H, m), 3.42–3.48 (2H, m)

IR (KBr) cm$^{-1}$; 3250, 1449, 1073, 1036.

(2) 2-(4-Benzyloxyphenyl)-5-methyl-1-[4-(4-butylcyclohexylmethoxy)phenyl]-1H-pyrrole The object compound was obtained from 4-butylcyclohexylmethanol as an oily substance, according to the similar manner to that of Example 159(1). yield: 53.1%

$^1$H-NMR (CDCl$_3$) δ; 0.87–1.92 (19H, m), 2.10 (3H, s), 3.74 (2H, d, J=6.3 Hz), 4.98 (2H, s), 6.04 (1H, d, J=3.2 Hz), 6.24 (1H, d, J=3.2 Hz), 6.74–7.06 (8H, m), 7.29–7.42 (5H, m).

IR (KBr) cm$^{-1}$; 1609, 1514, 1466, 1454, 1289, 1244, 1177, 1040, 1026, 835, 758, 735, 696.

(3) 4-(1-[4-(4-Butylcyclohexylmethoxy)phenyl]-5-methyl-1H-pyrrol-2-yl)phenol

The object compound was obtained from 2-(4-benzyloxyphenyl)-5-methyl-1-[4-(4-butylcyclohexylmethoxy)phenyl]-1H-pyrrole as an oily substance, according to the similar manner to that of Example 159(2). yield: 95.1%

$^1$H-NMR (CDCl$_3$) δ; 0.86–1.93 (19H, m), 2.10 (3H, s), 3.74 (2H, d, J=6.2 Hz), 6.03 (1H, d, J=3.4 Hz), 6.23 (1H, d, J=3.4 Hz), 6.61 (2H, d, J=8.8 Hz), 6.85 (2H, d, J=8.8 Hz), 6.94 (2H, d, J=8.8 Hz), 7.03 (2H, d, J=8.8 Hz).

IR (KBr) cm$^{-1}$; 3275, 1613, 1514, 1466, 1246, 1171, 1040, 833, 762.

(4) Ethyl (2R)-2-[4-(1-[4-(4-butylcyclohexylmethoxy) phenyl]-5-methyl-1H-pyrrol-2-yl)phenoxy]-3-phenylpropanoate The object compound was obtained from 4-(1-[4-(4-butylcyclohexylmethoxy)phenyl]-5-methyl-1H-pyrrol-2-yl) phenol as an oily substance, according to the similar manner to that of Example 159(3). yield: 50.5%

$^1$H-NMR (CDCl$_3$) δ; 0.86–1.93 (22H, m), 2.08 (3H, s), 3.17–3.21 (2H, m), 3.73 (2H, d, J=6.3 Hz), 4.14 (2H, q, J=7.2 Hz), 4.68–4.72 (1H, m), 6.01 (1H, d, J=3.3 Hz), 6.21 (1H, d, J=3.3 Hz), 6.62 (2H, d, J=9.0 Hz), 6.83 (2H, d, J=9.0 Hz), 6.93 (2H, d, J=9.0 Hz), 7.00 (2H, d, J=9.0 Hz), 7.20–7.29 (5H, m).

IR (KBr) cm$^{-1}$; 1755, 1734, 1514, 1285, 1244, 1182, 1084, 1040, 835.

Example 162

Sodium (2R)-2-[4-(1-[4-(4-butylcyclohexylmethoxy)phenyl]-5-methyl-1H-pyrrol-2-yl)phenoxy]-3-phenylpropanoate (1) (2R)-2-[4-(1-[4-(4-Butylcyclohexylmethoxy)phenyl]-5-methyl-1H-pyrrol-2-yl)phenoxy]-3-phenylpropanoic acid The object compound was obtained from ethyl (2R)-2-[4-(1-[4-(4-butylcyclohexylmethoxy)phenyl]-5-methyl-1H-pyrrol-2-yl)phenoxy]-3-phenylpropanoate as an oily substance, according to the similar manner to that of Example 160(1). yield: 54.3%

$^1$H-NMR (CDCl$_3$) δ; 0.89–1.93 (19H, m), 2.08 (3H, s), 3.21 (2H, d, J=5.8 Hz), 3.73 (2H, d, J=6.2 Hz), 4.74 (1H, t, J=5.8 Hz), 6.02 (1H, d, J=3.6 Hz), 6.21 (1H, d, J=3.6 Hz), 6.62 (2H, d, J=8.8 Hz), 6.82 (2H, d, J=9.2 Hz), 6.92–7.03 (4H, m), 7.26 (5H, s).

IR (KBr) cm$^{-1}$; 3029, 1732, 1609, 1514, 1287, 1244, 1181, 1042, 835, 760, 700.

(2) Sodium (2R)-2-[4-(1-[4-(4-butylcyclohexylmethoxy) phenyl]-5-methyl-1H-pyrrol-2-yl)phenoxy]-3-phenylpropanoate The object compound was obtained from (2R)-2-[4-(1-[4-(4-butylcyclohexylmethoxy)phenyl]-5-methyl-1H-pyrrol-2-yl)phenoxy]-3-phenylpropanoic acid as a solid, according to the similar manner to that of Example 160(2). yield: 80.0%

$^1$H-NMR (DMSO-d$_6$) δ; 0.88–1.88 (19H, m), 1.99 (3H, s), 2.85–3.11 (2H, m), 3.77 (2H, d, J=6.2 Hz), 4.18–4.23 (1H, m), 5.91 (1H, d, J=3.4 Hz), 6.06 (1H, d, J=3.4 Hz), 6.53 (2H, d, J=8.8 Hz), 6.79 (2H, d, J=8.8 Hz), 6.89 (2H, d, J=8.8 Hz), 7.02 (2H, d, J=8.8 Hz), 7.11–7.27 (5H, m).

IR (KBr) cm$^{-1}$; 1613, 1514, 1399, 1289, 1244, 1044, 835, 764, 700.

$[α]_D^{27}$ –2.80° (c 0.560, methanol)

Example 163

Ethyl (2R)-2-[4-(5-methyl-1-[4-(4-propylcyclohexylmethoxy)phenyl]-1H-pyrrol-2-yl) phenoxy]-3-phenylpropanoate (1) 4-Propylcyclohexylmethanol The object compound was obtained from 4-n-propylcyclohexane carboxylic acid as an oily substance, according to the similar manner to that of Example 161(1). yield: 79.0%

$^1$H-NMR (CDCl$_3$) δ; 0.84–1.80 (17H, m), 3.42–3.48 (2H, m).

IR (KBr) cm$^{-1}$; 3300, 1449, 1071, 1034, 1001, 970.

(2) 2-(4-Benzyloxyphenyl)-5-methyl-1-[4-(4-propylcyclohexylmethoxy)phenyl]-1H-pyrrole The object compound was obtained from 4-propylcyclohexylmethanol as an oily substance, according to the similar manner to that of Example 159(1). yield: 77.0%

$^1$H-NMR (CDCl$_3$) δ; 0.85–1.93 (17H, m), 2.10 (3H, s), 3.75 (2H, d, J=6.2 Hz), 4.98 (2H, s), 6.04 (1H, d, J=3.4 Hz), 6.24 (1H, d, J=3.4 Hz), 6.73–6.87 (4H, m), 6.98–7.07 (4H, m), 7.30–7.39 (5H, m).

IR (KBr) cm$^{-1}$; 1609, 1514, 1466, 1454, 1287, 1244, 1040, 1026, 833, 760, 735, 696.

(3) 4-(5-Methyl-1-[4-(4-propylcyclohexylmethoxy)phenyl]-1H-pyrrol-2-yl)phenol

The object compound was obtained from 2-(4-benzyloxyphenyl)-5-methyl-1-[4-(4-propylcyclohexylmethoxy)phenyl]-1H-pyrrole as an oily substance, according to the similar manner to that of Example 159(2). yield: 97.6%

¹H-NMR (CDCl₃) δ; 0.85–1.93 (17H, m), 2.10 (3H, s), 3.75 (2H, d, J=6.0 Hz), 6.04 (1H, d, J=3.2 Hz), 6.23 (1H, d, J=3.2 Hz), 6.61 (2H, d, J=8.8 Hz), 6.84 (2H, d, J=8.8 Hz), 6.95 (2H, d, J=8.8 Hz), 7.03 (2H, d, J=8.8 Hz).

IR (KBr) cm⁻¹; 3300, 1514, 1466, 1289, 1246, 1171, 835, 762.

(4) Ethyl (2R)-2-[4-(5-methyl-1-[4-(4-propylcyclohexylmethoxy)phenyl]-1H-pyrrol-2-yl)phenoxy]-3-phenylpropanoate The object compound was obtained from 4-(5-methyl-1-[4-(4-propylcyclohexylmethoxy)phenyl]-1H-pyrrol-2-yl)phenol as an oily substance, according to the similar manner to that of Example 159(3). yield: 29.8%

¹H-NMR (CDCl₃) δ; 0.86–1.93 (20H, m), 2.08 (3H, s), 3.17–3.21 (2H, m), 3.74 (2H, d, J=6.2 Hz), 4.14 (2H, q, J=7.4 Hz), 4.66–4.73 (1H, m), 6.02 (1H, d, J=3.8 Hz), 6.21 (1H, d, J=3.8 Hz), 6.61 (2H, d, J=8.8 Hz), 6.82 (2H, d, J=8.8 Hz), 6.91–7.02 (4H, m), 7.26–7.29 (5H, m).

IR (KBr) cm⁻¹; 1753, 1736, 1514, 1287, 1244, 1182, 1084, 1040, 835, 760, 700.

Example 164

Sodium (2R)-2-[4-(5-methyl-1-[4-(4-propylcyclohexylmethoxy)phenyl]-1H-pyrrol-2-yl)phenoxy]-3-phenylpropanoate (1) (2R)-2-[4-(5-Methyl-1-[4-(4-propylcyclohexylmethoxy)phenyl]-1H-pyrrol-2-yl)phenoxy]-3-phenylpropanoic acid The object compound was obtained from ethyl (2R)-2-[4-(5-methyl-1-[4-(4-propylcyclohexylmethoxy)phenyl]-1H-pyrrol-2-yl)phenoxy]-3-phenylpropanoate as an oily substance, according to the similar manner to that of Example 160(1). yield: 93.1%

¹H-NMR (CDCl₃) δ; 0.85–1.92 (17H, m), 2.08 (3H, s), 3.22 (2H, d, J=5.8 Hz), 3.74 (2H, d, J=6.2 Hz), 4.76 (1H, t, J=5.8 Hz), 6.03 (1H, d, J=3.4 Hz), 6.22 (1H, d, J=3.4 Hz), 6.62 (2H, d, J=8.8 Hz), 6.83 (2H, d, J=8.8 Hz), 6.93–7.03 (4H, m), 7.26 (5H, s).

IR (KBr) cm⁻¹; 3031, 1728, 1514, 1287, 1244, 1181, 1084, 1042, 835, 758, 735, 700.

(2) Sodium (2R)-2-[4-(5-methyl-1-[4-(4-propylcyclohexylmethoxy)phenyl]-1H-pyrrol-2-yl)phenoxy]-3-phenylpropanoate The object compound was obtained from (2R)-2-[4-(5-methyl-1-[4-(4-propylcyclohexylmethoxy)phenyl]-1H-pyrrol-2-yl)phenoxy]-3-phenylpropanoic acid as a solid, according to the similar manner to that of Example 160(2). yield: 91.9%

¹H-NMR (DMSO-d₆) δ; 0.83–1.88 (17H, m), 1.99 (3H, s), 2.86–3.11 (2H, m), 3.77 (2H, d, J=6.2 Hz), 4.17–4.22 (1H, m), 5.91 (1H, d, J=3.4 Hz), 6.06 (1H, d, J=3.4 Hz), 6.53 (2H, d, J=8.8 Hz), 6.79 (2H, d, J=8.8 Hz), 6.89 (2H, d, J=8.8 Hz), 7.02 (2H, d, J=8.8 Hz), 7.08–7.24 (5H, m).

IR (KBr) cm⁻¹; 1613, 1514, 1397, 1244, 1044, 1030, 835, 762, 700.

[α]_D²⁷ −5.36° (c 0.645, methanol)

Example 165

Ethyl (2R)-2-(4-{1-[3-(4-benzylphenoxy)propyl]-5-methyl-1H-pyrrol-2-yl}phenoxy)-3-phenylpropanoate (1) 2-(4-Benzyloxyphenyl)-1-[3-(4-benzylphenoxy)propyl]-5-methyl-1H-pyrrole To a solution of 3-[2-(4-benzyloxyphenyl)-5-methyl-1H-pyrrol-1-yl]propan-1-ol (1.00 g, 3.11 mmol), 4-benzylphenol (572 mg, 3.11 mmol) and triphenylphosphine (1.22 g, 4.67 mmol) in toluene (2 ml) was added 1,1'-(azodicarbonyl)dipiperidine (1.18 g, 4.67 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.21 g (yield: 79.6%)

¹H-NMR (CDCl₃) δ; 1.87–2.00 (2H, m), 2.30 (3H, s), 3.70 (2H, t, J=5.6 Hz), 3.90 (2H, s), 4.09 (2H, t, J=7.8 Hz), 5.04 (2H, s), 5.92 (1H, d, J=3.2 Hz), 6.03 (1H, d, J=3.2 Hz), 6.67 (2H, d, J=8.8 Hz), 6.93 (2H, d, J=8.8 Hz), 7.04 (2H, d, J=8.8 Hz), 7.14–7.47 (12H, m).

IR (KBr) cm⁻¹; 1611, 1522, 1510, 1281, 1244, 1175, 1026, 835, 756, 731, 698.

(2) 4-{1-[3-(4-Benzylphenoxy)propyl]-5-methyl-1H-pyrrol-2-yl}phenol

To a solution of 2-(4-benzyloxyphenyl)-1-[3-(4-benzylphenoxy)propyl]-5-methyl-1H-pyrrole (1.15 g, 2.26 mmol) in ethanol (60 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 920 mg (yield: 98.0%)

¹H-NMR (CDCl₃) δ; 1.86–1.99 (2H, m), 2.30 (3H, s), 3.69 (2H, t, J=5.8 Hz), 3.90 (2H, s), 4.08 (2H, t, J=7.0 Hz), 5.91 (1H, d, J=3.2 Hz), 6.00 (1H, d, J=3.2 Hz), 6.61–6.70 (4H, m), 7.03–7.34 (9H, m).

IR (KBr) cm⁻¹; 3399, 1613, 1526, 1510, 1244, 1175, 839, 760, 729, 698.

(3) Ethyl (2R)-2-(4-{1-[3-(4-benzylphenoxy)propyl]-5-methyl-1H-pyrrol-2-yl}phenoxy)-3-phenylpropanoate To a solution of 4-{1-[3-(4-benzylphenoxy)propyl]-5-methyl-1H-pyrrol-2-yl}phenol (910 mg, 2.29 mmol), ethyl (S)-2-hydroxy-3-phenylpropanoate (667 mg, 3.44 mmol) and triphenylphosphine (901 mg, 3.44 mmol) in toluene (2 ml) was added 1,1'-(azodicarbonyl)dipiperidine (867 mg, 3.44 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 680 mg (yield: 51.5%)

¹H-NMR (CDCl₃) δ; 1.18 (3H, t, J=7.2 Hz), 1.87–1.97 (2H, m), 2.28 (3H, s), 3.23–3.27 (2H, m), 3.69 (2H, t, J=6.0 Hz), 3.90 (2H, s), 4.05 (2H, t, J=7.6 Hz), 4.17 (2H, q, J=7.2 Hz), 4.75–4.81 (1H, m), 5.89 (1H, d, J=3.2 Hz), 6.00 (1H, d, J=3.2 Hz), 6.66 (2H, d, J=8.8 Hz), 6.81 (2H, d, J=8.8 Hz), 7.03 (2H, d, J=8.8 Hz), 7.14–7.32 (12H, m).

IR (KBr) cm⁻¹; 1755, 1732, 1611, 1510, 1480, 1454, 1242, 1179, 1084, 1030, 837, 760, 729, 698.

Example 166

Sodium (2R)-2-(4-{1-[3-(4-benzylphenoxy)propyl]-5-methyl-1H-pyrrol-2-yl}phenoxy)-3-phenylpropanoate (1) (2R)-2-(4-{1-[3-(4-Benzylphenoxy)propyl]-5-methyl-1H-pyrrol-2-yl}phenoxy)-3-phenylpropanoic acid To a mixed solution of ethyl (2R)-2-(4-{1-[3-(4-benzylphenoxy)propyl]-5-methyl-1H-pyrrol-2- yl}phenoxy)-3-phenylpropanoate (660 mg, 1.15 mmol) in THF (30 ml) and methanol (15 ml) was added 1N aqueous potassium hydroxide solution (6 ml, 6 mmol) and the mixture was stirred for 1 hour at room temperature. The reaction solution was neutralized with 1N hydrochloric acid and extracted with ethyl acetate. The extract was washed with water and dried over magnesium sulfate anhydride and the solvent was removed under reduced pressure. The residue was purified by silica gel column chromatography (hexane:ethyl acetate=1:1) to give the object compound as an oily substance. 584 mg (yield: 92.8%)

$^1$H-NMR (CDCl$_3$) δ; 1.87–1.97 (2H, m), 2.28 (3H, s), 3.28 (2H, d, J=6.0 Hz), 3.68 (2H, t, J=5.4 Hz), 3.90 (2H, s), 4.05 (2H, t, J=7.6 Hz), 4.83 (1H, t, J=6.0 Hz), 5.90 (1H, d, J=3.8 Hz), 6.00 (1H, d, J=3.8 Hz), 6.64 (2H, d, J=8.8 Hz), 6.80 (2H, d, J=8.8 Hz), 7.02 (2H, d, J=8.8 Hz), 7.14–7.32 (12H, m).

IR (KBr) cm$^{-1}$; 3029, 1726, 1611, 1510, 1242, 1177, 1084, 837, 760, 698.

(2) Sodium (2R)-2-(4-{1-[3-(4-benzylphenoxy)propyl]-5-methyl-1H-pyrrol-2-yl}phenoxy)-3-phenylpropanoate Ethanol (5 ml) and a solution of 1N sodium hydroxide in ethanol (0.900 ml) were added to (2R)-2-(4-{1-[3-(4-benzylphenoxy)propyl]-5-methyl-1H-pyrrol-2-yl}phenoxy)-3-phenylpropanoic acid (546 mg, 1.00 mmol) and the mixture was concentrated. To the residue was added diisopropylether to give the object compound as a solid. 447 mg (yield: 87.3%)

$^1$H-NMR (DMSO-d$_6$) δ; 1.87–1.86 (2H, m), 2.20 (3H, s), 2.93–3.20 (2H, m), 3.69 (2H, t, J=5.6 Hz), 3.90 (2H, s), 3.99 (2H, t, J=7.2 Hz), 4.29–4.35 (1H, m), 5.76 (1H, d, J=3.2 Hz), 5.81 (1H, d, J=3.2 Hz), 6.68–6.79 (4H, m), 7.04–7.34 (14H, m)

IR (KBr) cm$^{-1}$; 1615, 1510, 1404, 1242, 1177, 1055, 1030, 839, 762, 727, 698.

$[α]_D^{29}$ 5.93° (c 0.650, methanol)

Example 167

Ethyl (2R)-2-(4-{1-[3-(4-hexylphenoxy)propyl]-5-methyl-1H-pyrrol-2-yl}phenoxy)-3-phenylpropanoate (1) 2-(4-Benzyloxyphenyl)-1-[3-(4-hexylphenoxy)propyl]-5-methyl-1H-pyrrole The object compound was obtained from 4-hexylphenol as an oily substance, according to the similar manner to that of Example 165(1). yield: 79.3%

$^1$H-NMR (CDCl$_3$) δ; 0.87 (3H, t, J=6.4 Hz), 1.22–1.34 (6H, m), 1.48–1.59 (2H, m), 1.88–1.98 (2H, m), 2.31 (3H, s), 2.52 (2H, t, J=7.2 Hz), 3.71 (2H, t, J=6.0 Hz), 4.09 (2H, t, J=7.8 Hz), 5.06 (2H, s), 5.91 (1H, d, J=3.6 Hz), 6.03 (1H, d, J=3.6 Hz), 6.66 (2H, d, J=8.8 Hz), 6.95 (2H, d, J=8.8 Hz), 7.03 (2H, d, J=8.8 Hz), 7.25–7.49 (7H, m).

IR (KBr) cm$^{-1}$; 1611, 1524, 1510, 1468, 1454, 1242, 1175, 1024, 833, 756, 698.

(2) 4-{1-[3-(4-Hexylphenoxy)propyl]-5-methyl-1H-pyrrol-2-yl}phenol

The object compound was obtained from 2-(4-benzyloxyphenyl)-1-[3-(4-hexylphenoxy)propyl]-5-methyl-1H-pyrrole as an oily substance, according to the similar manner to that of Example 165(2). yield: 99.0% oily substance 99.0%

$^1$H-NMR (CDCl$_3$) δ; 0.88 (3H, t, J=6.6 Hz), 1.22–1.34 (6H, m), 1.49–1.62 (2H, m), 1.87–2.00 (2H, m), 2.30 (3H, s), 2.53 (2H, t, J=7.8 Hz), 3.72 (2H, t, J=6.6 Hz), 4.08 (2H, t, J=7.4 Hz), 5.92 (1H, d, J=3.2 Hz), 6.03 (1H, d, J=3.2 Hz), 6.67 (2H, d, J=8.4 Hz), 6.80 (2H, d, J=8.4 Hz), 7.04 (2H, d, J=8.8 Hz), 7.22 (2H, d, J=8.8 Hz).

IR (KBr) cm$^{-1}$; 3380, 1613, 1510, 1472, 1385, 1242, 1175, 1051, 837, 758.

(3) Ethyl (2R)-2-(4-{1-[3-(4-hexylphenoxy)propyl]-5-methyl-1H-pyrrol-2-yl}phenoxy)-3-phenylpropanoate The object compound was obtained from 4-{1-[3-(4-hexylphenoxy)propyl]-5-methyl-1H-pyrrol-2-yl}phenol as an oily substance, according to the similar manner to that of Example 165(3). yield: 48.8%

$^1$H-NMR (CDCl$_3$) δ; 0.91 (3H, t, J=6.6 Hz), 1.15–1.33 (9H, m), 1.49–1.58 (2H, m), 1.88–1.94 (2H, m), 2.28 (3H, s), 2.52 (2H, t, J=7.8 Hz), 3.24–3.28 (2H, m), 3.70 (2H, t, J=5.8 Hz), 4.05 (2H, t, J=7.6 Hz), 4.19 (2H, q, J=7.2 Hz), 4.76–4.79 (1H, m), 5.90 (1H, d, J=3.8 Hz), 6.00 (1H, d, J=3.8 Hz), 6.66 (2H, d, J=8.8 Hz), 6.82 (2H, d, J=8.8 Hz), 7.02 (2H, d, J=8.8 Hz), 7.19–7.34 (7H, m).

IR (KBr) cm$^{-1}$; 1755, 1738, 1611, 1510, 1480, 1454, 1279, 1179, 1084, 1034, 835, 758, 700.

Example 168

Sodium (2R)-2-(4-{1-[3-(4-hexylphenoxy)propyl]-5-methyl-1H-pyrrol-2-yl}phenoxy)-3-phenylpropanoate (1) (2R)-2-(4-{1-[3-(4-Hexylphenoxy)propyl]-5-methyl-1H-pyrrol-2-yl}phenoxy)-3-phenylpropanoic acid The object compound was obtained from ethyl (2R)-2-(4-{1-[3-(4-hexylphenoxy)propyl]-5-methyl-1H-pyrrol-2-yl}phenoxy)-3-phenylpropanoate as an oily substance, according to the similar manner to that of Example 166(1). yield: 86.0%

$^1$H-NMR (CDCl$_3$) δ; 0.88 (3H, t, J=6.6 Hz), 1.26–1.34 (6H, m), 1.48–1.58 (2H, m), 1.79–1.89 (2H, m), 2.28 (3H, s), 2.52 (2H, t, J=8.0 Hz), 3.29 (2H, d, J=6.2 Hz), 3.69 (2H, t, J=5.8 Hz), 4.05 (2H, t, J=7.4 Hz), 4.83 (1H, t, J=6.2 Hz), 5.89 (1H, d, J=3.4 Hz), 5.99 (1H, d, J=3.4 Hz), 6.65 (2H, d, J=8.8 Hz), 6.82 (2H, d, J=8.8 Hz), 7.01 (2H, d, J=8.8 Hz), 7.21–7.36 (7H, m).

IR (KBr) cm$^{-1}$; 3063, 1728, 1611, 1510, 1480, 1238, 1177, 1084, 833, 758, 700.

(2) Sodium (2R)-2-(4-{1-[3-(4-hexylphenoxy)propyl]-5-methyl-1H-pyrrol-2-yl}phenoxy)-3-phenylpropanoate The object compound was obtained from (2R)-2-(4-{1-[3-(4-hexylphenoxy)propyl]-5-methyl-1H-pyrrol-2-yl}phenoxy)-3-phenylpropanoic acid as a solid, according to the similar manner to that of Example 166(2). yield: 86.4%

$^1$H-NMR (DMSO-d$_6$) δ; 0.86 (3H, t, J=6.6 Hz), 1.19–1.36 (6H, m), 1.43–1.59 (2H, m), 1.78–1.89 (2H, m), 2.22 (3H, s), 2.48 (2H, t, J=7.6 Hz), 2.98–3.23 (2H, m), 3.69 (2H, t, J=5.2 Hz), 4.01 (2H, t, J=7.4 Hz), 4.35–4.39 (1H, m), 5.75 (1H, d, J=3.4 Hz), 5.81 (1H, d, J=3.4 Hz), 6.66 (2H, d, J=8.4 Hz), 6.80 (2H, d, J=8.4 Hz), 6.99 (2H, d, J=8.4 Hz), 7.10–7.35 (7H, m).

IR (KBr) cm$^{-1}$; 1615, 1510, 1410, 1238, 1177, 1053, 828, 760, 700.

$[α]_D^{27}$ 5.55° (c 0.615, methanol)

Example 169

Ethyl (2R)-2-(4-{1-[3-(4-butylphenoxy)propyl]-5-methyl-1H-pyrrol-2-yl}phenoxy)-3-phenylpropanoate (1) 2-(4-Benzyloxyphenyl)-1-[3-(4-butylphenoxy)propyl]-5-methyl-1H-pyrrole The object compound was obtained from 4-butylphenol as an oily substance, according to the similar manner to that of Example 165(1). yield: 86.5%

$^1$H-NMR (CDCl$_3$) δ; 0.91 (3H, t, J=6.8 Hz), 1.22–1.62 (4H, m), 1.88–1.98 (2H, m), 2.31 (3H, s), 2.53 (2H, t, J=7.2

Hz), 3.71 (2H, t, J=5.8 Hz), 4.09 (2H, t, J=7.8 Hz), 5.06 (2H, s), 5.92 (1H, d, J=3.2 Hz), 6.03 (1H, d, J=3.2 Hz), 6.67 (2H, d, J=8.8 Hz), 6.93–7.06 (4H, m), 7.25–7.49 (7H, m).

IR (KBr) cm$^{-1}$; 1611, 1524, 1510, 1480, 1468, 1454, 1381, 1310, 1281, 1242, 1175, 1024, 833, 747, 696.

(2) 4-{1-[3-(4-Butylphenoxy)propyl]-5-methyl-1H-pyrrol-2-yl}phenol

The object compound was obtained from 2-(4-benzyloxyphenyl)-1-[3-(4-butylphenoxy)propyl]-5-methyl-1H-pyrrole as an oily substance, according to the similar manner to that of Example 165(2). yield: 98.5%

$^1$H-NMR (CDCl$_3$) δ; 0.91 (3H, t, J=6.9 Hz), 1.21–1.60 (4H, m), 1.84–1.97 (2H, m), 2.30 (3H, s), 2.53 (2H, t, J=7.5 Hz), 3.72 (2H, t, J=6.6 Hz), 4.07 (2H, t, J=6.3 Hz), 5.91 (1H, d, J=3.3 Hz), 6.02 (1H, d, J=3.3 Hz), 6.67 (2H, d, J=8.4 Hz), 6.82 (2H, d, J=8.4 Hz), 7.03 (2H, d, J=8.4 Hz), 7.22 (2H, d, J=8.4 Hz).

IR (KBr) cm$^{-1}$; 3331, 1613, 1526, 1510, 1470, 1439, 1387, 1240, 1175, 1121, 837, 758, 723, 542.

(3) Ethyl (2R)-2-(4-{1-[3-(4-butylphenoxy)propyl]-5-methyl-1H-pyrrol-2-yl}phenoxy)-3-phenylpropanoate The object compound was obtained from 4-{1-[3-(4-butylphenoxy)propyl]-5-methyl-1H-pyrrol-2-yl}phenol as an oily substance, according to the similar manner to that of Example 165(3). yield: 38.7%

$^1$H-NMR (CDCl$_3$) δ; 0.92 (3H, t, J=6.2 Hz), 1.19 (3H, t, J=7.0 Hz), 1.27–1.59 (4H, m), 1.88–1.95 (2H, m), 2.29 (3H, s), 2.53 (2H, t, J=7.6 Hz), 3.24–3.29 (2H, m), 3.70 (2H, t, J=6.0 Hz), 4.05 (2H, t, J=7.0 Hz), 4.22 (2H, q, J=7.0 Hz), 4.76–4.82 (1H, m), 5.90 (1H, d, J=3.8 Hz), 6.00 (1H, d, J=3.8 Hz), 6.66 (2H, d, J=8.8 Hz), 6.82 (2H, d, J=8.8 Hz), 7.02 (2H, d, J=8.8 Hz), 7.19–7.34 (7H, m).

IR (KBr) cm$^{-1}$; 1755, 1732, 1510, 1480, 1456, 1242, 1179, 1084, 1030, 833, 760.

Example 170

Sodium (2R)-2-(4-{1-[3-(4-butylphenoxy)propyl]-5-methyl-1H-pyrrol-2-yl}phenoxy)-3-phenylpropanoate (1) (2R)-2-(4-{1-[3-(4-butylphenoxy)propyl]-5-methyl-1H-pyrrol-2-yl}phenoxy)-3-phenylpropanoic acid The object compound was obtained from ethyl (2R)-2-(4-{1-[3-(4-butylphenoxy)propyl]-5-methyl-1H-pyrrol-2-yl}phenoxy)-3-phenylpropanoate as an oily substance, according to the similar manner to that of Example 166(1). yield: 68.8%

$^1$H-NMR (CDCl$_3$) δ; 0.91 (3H, t, J=6.6 Hz), 1.29–1.60 (4H, m), 1.87–1.95 (2H, m), 2.29 (3H, s), 2.52 (2H, t, J=8.1 Hz), 3.29–3.31 (2H, m), 3.69 (2H, t, J=5.7 Hz), 4.05 (2H, t, J=7.8 Hz), 4.84–4.88 (1H, m), 5.90 (1H, d, J=3.9 Hz), 5.91 (1H, d, J=3.9 Hz), 6.65 (2H, d, J=8.7 Hz), 6.82 (2H, d, J=8.7 Hz), 7.01 (2H, d, J=8.7 Hz), 7.18–7.33 (7H, m).

IR (KBr) cm$^{-1}$; 3032, 1728, 1512, 1481, 1279, 1240, 1177, 1084, 833, 758, 700.

(2) Sodium (2R)-2-(4-{1-[3-(4-butylphenoxy)propyl]-5-methyl-1H-pyrrol-2-yl}phenoxy)-3-phenylpropanoate The object compound was obtained from (2R)-2-(4-{1-[3-(4-butylphenoxy)propyl]-5-methyl-1H-pyrrol-2-yl}phenoxy)-3-phenylpropanoic acid as a solid, according to the similar manner to that of Example 166(2). yield: 72.9%

$^1$H-NMR (DMSO-d$_6$) δ; 0.89 (3H, t, J=7.2 Hz), 1.23–1.55 (4H, m), 1.78–1.88 (2H, m), 2.21 (3H, s), 2.84 (2H, t, J=7.5 Hz), 2.96–3.19 (2H, m), 3.69 (2H, t, J=6.0 Hz), 4.00 (2H, t, J=6.9 Hz), 4.31–4.35 (1H, m), 5.76 (1H, d, J=3.3 Hz), 5.81 (1H, d, J=3.3 Hz), 6.68 (2H, d, J=8.7 Hz), 6.77 (2H, d, J=8.7 Hz), 7.01 (2H, d, J=8.7 Hz), 7.11–7.33 (7H, m).

IR (KBr) cm$^{-1}$; 1615, 1512, 1410, 1312, 1240, 1177, 1053, 828, 760, 700.

[α]$_D$$^{27}$ 10.7° (c 0.510, methanol)

Example 171

Ethyl (2R)-2-[4-(5-methyl-1-{3-[4-(4-propylcyclohexyl)phenoxy]propyl}-1H-pyrrol-2-yl)phenoxy]-3-phenylpropanoate (1) 2-(4-Benzyloxyphenyl)-5-methyl-1-{3-[4-(4-propylcyclohexyl)phenoxy]propyl}-1H-pyrrole The object compound was obtained from 4-(4-propylcyclohexyl)phenol as an oily substance, according to the similar manner to that of Example 165(1). yield: 80.2%

$^1$H-NMR (CDCl$_3$) δ; 0.86–1.97 (18H, m), 2.30–2.45 (4H, m), 3.71 (2H, t, J=5.6 Hz), 4.09 (2H, t, J=7.8 Hz), 5.06 (2H, s), 5.92 (1H, d, J=3.4 Hz), 6.03 (1H, d, J=3.4 Hz), 6.67 (2H, d, J=8.8 Hz), 6.95 (2H, d, J=8.8 Hz), 7.06 (2H, d, J=8.8 Hz), 7.24–7.49 (7H, m).

IR (KBr) cm$^{-1}$; 1611, 1524, 1468, 1454, 1381, 1312, 1283, 1244, 1177, 1024, 828, 756, 737, 696.

(2) 4-{5-Methyl-1-{3-[4-(4-propylcyclohexyl)phenoxy]propyl}-1H-pyrrol-2-yl}phenol The object compound was obtained from 2-(4-benzyloxyphenyl)-5-methyl-1-{3-[4-(4-propylcyclohexyl)phenoxy]propyl}-1H-pyrrole as an oily substance, according to the similar manner to that of Example 165(2). yield: 98.1%

$^1$H-NMR (CDCl$_3$) δ; 0.86–1.96 (18H, m), 2.29–2.39 (4H, m), 3.72 (2H, t, J=7.0 Hz), 4.07 (2H, t, J=7.8 Hz), 5.91 (1H, d, J=3.4 Hz), 6.02 (1H, d, J=3.4 Hz), 6.68 (2H, d, J=8.8 Hz), 6.80 (2H, d, J=8.8 Hz), 7.07 (2H, d, J=8.8 Hz), 7.21 (2H, d, J=8.8 Hz).

IR (KBr) cm$^{-1}$; 3397, 1613, 1512, 1470, 1447, 1400, 1385, 1244, 1177, 1051, 837, 828, 758, 725, 544.

(3) Ethyl (2R)-2-[4-(5-methyl-1-{3-[4-(4-propylcyclohexyl)phenoxy]propyl}-1H-pyrrol-2-yl)phenoxy]-3-phenylpropanoate The object compound was obtained from 4-{5-methyl-1-{3-[4-(4-propylcyclohexyl)phenoxy]propyl}-1H-pyrrol-2-yl}phenol as an oily substance, according to the similar manner to that of Example 165(3). yield: 42.8%

$^1$H-NMR (CDCl$_3$) δ; 0.86–1.95 (21H, m), 2.29–2.39 (4H, m), 3.24–3.28 (2H, m), 3.70 (2H, t, J=5.8 Hz), 4.04 (2H, t, J=6.8 Hz), 4.19 (2H, q, J=6.6 Hz), 4.76–4.82 (1H, m), 5.90 (1H, d, J=3.4 Hz), 6.00 (1H, d, J=3.4 Hz), 6.67 (2H, d, J=8.8 Hz), 6.82 (2H, d, J=8.8 Hz), 7.05 (2H, d, J=8.8 Hz), 7.20–7.34 (7H, m).

IR (KBr) cm$^{-1}$; 1755, 1732, 1512, 1281, 1244, 1179, 1084, 1032, 829, 756, 700.

Example 172

Sodium (2R)-2-[4-(5-methyl-1-{3-[4-(4-propylcyclohexyl)-phenoxy]propyl}-1H-pyrrol-2-yl)phenoxy]-3-phenylpropanoate (1) (2R)-2-[4-(5-methyl-1-{3-[4-(4-propylcyclohexyl)-phenoxy]propyl}-1H-pyrrol-2-yl)phenoxy]-3-phenylpropanoic acid The object compound was obtained from ethyl (2R)-2-[4-(5-methyl-1-{3-[4-(4-propylcyclohexyl)phenoxy]propyl}-1H-pyrrol-2-yl)phenoxy]-3-phenylpropanoate as an oily substance, according to the similar manner to that of Example 166(1). yield: 71.3%

$^1$H-NMR (CDCl$_3$) δ; 0.87–1.97 (18H, m), 2.29–2.39 (4H, m), 3.30 (2H, d, J=5.8 Hz), 3.69 (2H, t, J=6.0 Hz), 4.04 (2H, t, J=7.0 Hz), 4.85 (1H, t, J=5.8 Hz), 5.90 (1H, d, J=3.2 Hz), 6.00 (1H, d, J=3.2 Hz), 6.66 (2H, d, J=8.8 Hz), 6.81 (2H, d, J=8.8 Hz), 7.05 (2H, d, J=8.8 Hz), 7.21–7.33 (7H, m).

IR (KBr) cm$^{-1}$; 3031, 1728, 1512, 1480, 1281, 1236, 1179, 1084, 829, 758, 700.

(2) Sodium (2R)-2-[4-(5-methyl-1-{3-[4-(4-propylcyclohexyl)phenoxy]propyl}-1H-pyrrol-2-yl)phenoxy]-3-phenylpropanoate The object compound was obtained from (2R)-2-[4-(5-methyl-1-{3-[4-(4-propylcyclohexyl)-phenoxy]propyl}-1H-pyrrole-2-yl)phenoxy]-3-phenylpropanoic acid as a solid, according to the similar manner to that of Example 166(2). yield: 85.7%

$^1$H-NMR (DMSO-d$_6$) δ; 0.84–1.79 (18H, m), 2.21–2.42 (4H, m), 2.92–3.18 (2H, m), 3.69 (2H, t, J=5.8 Hz), 3.99 (2H, t, J=7.0 Hz), 4.28–4.34 (1H, m), 5.76 (1H, d, J=3.2 Hz), 5.81 (1H, d, J=3.2 Hz), 6.66–6.78 (4H, m), 7.03–7.34 (9H, m).

IR (KBr) cm$^{-1}$; 1613, 1512, 1404, 1236, 1179, 1055, 1030, 828, 758, 700.

[α]$_D^{28}$ 8.07° (c 0.665, methanol)

Example 173

Ethyl (2R)-2-(4-{1-[5-methyl-1-[3-(4-pentylcyclohexylmethoxy)propyl]-1H-pyrrol-2-yl]phenoxy}-3-phenylpropanoate (1) (4-Methylcyclohexyl)methyl methanesulfonate To a solution of 4-pentylcyclohexylmethanol (776 mg, 4.22 mmol) and triethylamine (3.77 ml, 27.1 mmol) in ethyl acetate (50 ml) was added dropwise methanesulfonyl chloride (2.08 ml, 27.1 mmol) and the mixture was stirred at room temperature for 1 hour. The reaction solution was poured into water and the mixture was extracted with ethyl acetate. The extract was washed with water and dried over magnesium sulfate anhydride, and the solvent was removed under reduced pressure to give the object compound as a solid. 6.77 g (yield: 95.2%)

$^1$H-NMR (CDCl$_3$) δ; 0.85–1.82 (21H, m), 3.00 (3H, s), 4.02 (2H, d, J=6.2 Hz).

IR (KBr) cm$^{-1}$; 1462, 1449, 1346, 1335, 1171, 980, 955, 864, 849, 530.

(2) 2-(4-Benzyloxyphenyl)-5-methyl-1-[3-(4-pentylcyclohexylmethoxy)propyl]-1H-pyrrole To a suspension of sodium hydride (60%, 137 mg, 3.43 mmol) in THF (5 ml) was added dropwise a solution of 3-[2-(4-benzyloxyphenyl)-5-methyl-1H-pyrrol-1-yl]propan-1-ol (1.00 g, 3.11 mmol) in THF (2 ml) and the mixture was stirred at room temperature for 1 hour under nitrogen atmosphere. To the mixture was added dropwise a solution of (4-methyl cyclohexyl)methyl methanesulfonate (1.06 g, 4.06 mmol) in THF (1 ml), then added tetra n-butylammonium bromide (5.0 mg, 0.0156 mmol), and the mixture was stirred at room temperature for 12 hours. The reaction solution was poured into water and the mixture was extracted with ethyl acetate. The extract was washed with water, dried over magnesium sulfate anhydride, and the solvent was removed under reduced pressure. The residue was purified by silica gel column chromatography (hexane:ethyl acetate=30:1) to give the object compound as an oily substance. 740 mg (yield: 48.7%)

$^1$H-NMR (CDCl$_3$) δ; 0.80–1.82 (23H, m), 2.31 (3H, s), 3.04 (2H, d, J=6.4 Hz), 3.22 (2H, t, J=5.8 Hz), 3.97 (2H, t, J=7.4 Hz), 5.08 (2H, s), 5.92 (1H, d, J=3.8 Hz), 6.03 (1H, d, J=3.8 Hz), 6.99 (2H, d, J=8.8 Hz), 7.03–7.49 (7H, m).

IR (KBr) cm$^{-1}$; 1611, 1524, 1466, 1454, 1377, 1310, 1279, 1242, 1175, 1127, 1111, 1026, 833, 754, 735, 696, 667.

(3) 4-{5-Methyl-1-[3-(4-pentylcyclohexylmethoxy)propyl]-1H-pyrrol-2-yl}phenol

To a solution of 2-(4-benzyloxyphenyl)-5-methyl-1-[3-(4-pentylcyclohexylmethoxy)propyl]-1H-pyrrole (730 mg, 1.50 mmol) in ethanol (20 ml) and tetrahydrofuran (20 ml) was added 10% palladium carbon (200 mg) and the mixture was stirred for 4 hours under hydrogen atmosphere. The insoluble matter was filtered out and the filtrate was concentrated to give the object compound as an oily substance. 585 mg (yield: 98.3%)

$^1$H-NMR (CDCl$_3$) δ; 0.84–1.81 (23H, m), 2.30 (3H, s), 3.06 (2H, d, J=6.2 Hz), 3.22 (2H, t, J=5.8 Hz), 3.95 (2H, t, J=7.8 Hz), 5.91 (1H, d, J=3.4 Hz), 6.01 (1H, d, J=3.4 Hz), 6.83 (2H, d, J=8.8 Hz), 7.24 (2H, d, J=8.8 Hz)

IR (KBr) cm$^{-1}$; 3297, 1615, 1526, 1468, 1449, 1402, 1373, 1265, 1225, 1127, 837, 756.

(4) Ethyl (2R)-2-(4-{1-[5-methyl-1-[3-(4-pentylcyclohexylmethoxy)propyl]-1H-pyrrol-2-yl]phenoxy}-3-phenylpropanoate To a solution of 4-{5-methyl-1-[3-(4-pentylcyclohexylmethoxy)propyl]-1H-pyrrol-2-yl}phenol (575 mg, 1.44 mmol), ethyl (S)-2-hydroxy-3-phenylpropanoate (420 mg, 2.17 mmol) and triphenylphosphine (569 mg, 2.17 mmol) in toluene (1 ml) was added 1,1'-(azodicarbonyl)dipiperidine (547 mg, 2.17 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 310 mg (yield: 37.5%)

$^1$H-NMR (CDCl$_3$) δ; 0.85–1.75 (26H, m), 2.29 (3H, s), 3.07 (2H, d, J=6.6 Hz), 3.16–3.29 (4H, m), 3.92 (2H, t, J=7.2 Hz), 4.19 (2H, q, J=7.0 Hz), 4.77–4.83 (1H, m), 5.89 (1H, d, J=3.4 Hz), 5.99 (1H, d, J=3.4 Hz), 6.83 (2H, d, J=8.4 Hz), 7.20–7.33 (7H, m).

IR (KBr) cm$^{-1}$; 1755, 1736, 1524, 1481, 1454, 1372, 1277, 1238, 1182, 1111, 1084, 1032, 835, 756, 700.

Example 174

Sodium (2R)-2-(4-{1-[5-methyl-1-[3-(4-pentylcyclohexylmethoxy)propyl]-1H-pyrrol-2-yl]phenoxy}-3-phenylpropanoate (1) (2R)-2-(4-{1-[5-Methyl-1-[3-(4-pentylcyclohexylmethoxy)propyl]-1H-pyrrol-2-yl]phenoxy}-3-phenylpropanoic acid To a mixed solution of ethyl (2R)-2-(4-{1-[5-methyl-1-[3-(4-pentylcyclohexylmethoxy)propyl]-1H-pyrrol-2-yl]phenoxy}-3-phenylpropanoate (300 mg, 0.523 mmol) in THF (10 ml) and methanol (10 ml) was added 1N aqueous potassium hydroxide solution (3 ml, 3 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 237 mg (yield: 82.9%)

$^1$H-NMR (CDCl$_3$) δ; 0.85–1.75 (23H, m), 2.29 (3H, s), 3.07 (2H, d, J=5.8 Hz), 3.20 (2H, t, J=6.2 Hz), 3.30 (2H, d, J=5.8 Hz), 4.87 (1H, t, J=5.8 Hz), 4.19 (2H, q, J=7.0 Hz), 4.77–4.83 (1H, m), 5.90 (1H, d, J=3.4 Hz), 6.00 (1H, d, J=3.4 Hz) 6.85 (2H, d, J=8.8 Hz), 7.23–7.33 (7H, m).

IR (KBr) cm$^{-1}$; 2921, 1732, 1524, 1481, 1454, 1233, 1109, 1084, 756, 700.

(2) Sodium (2R)-2-(4-{1-[5-methyl-1-[3-(4-pentylcyclohexylmethoxy)propyl]-1H-pyrrol-2-yl]phenoxy}-3-phenylpropanoate To (2R)-2-(4-{1-[5-methyl-1-[3-(4-pentylcyclohexylmethoxy)propyl]-1H-pyrrol-2-yl]phenoxy}-3-phenylpropanoic acid (210 mg, 0.384 mmol) were added ethanol (5 ml) and a solution of 1N sodium hydroxide in ethanol (0.346 ml) and the mixture was concentrated. Diisopropylether was added to the residue to give the object compound as a solid. 140 mg (yield: 71.4%)

$^1$H-NMR (DMSO-d$_6$) δ; 0.78–1.75 (23H, m), 2.21 (3H, s), 2.93–3.17 (6H, m), 3.88 (2H, t, J=6.6 Hz), 4.30–4.36 (1H, m), 5.75 (1H, d, J=3.4 Hz), 5.80 (1H, d, J=3.4 Hz), 6.76 (2H, d, J=8.8 Hz), 7.09–7.33 (7H, m).

IR (KBr) cm$^{-1}$; 1615, 1522, 1481, 1454, 1410, 1231, 1111, 1065, 1036, 843, 758, 700, 561.

[α]hd D$^{24}$ 9.07° (c 0.590, methanol)

Example 175

Ethyl (2R)-2-{4-[5-methyl-1-(4-pentylcyclohexylmethyl)-1H-pyrrol-2-yl]phenoxy}-3-phenylpropanoate (1) 2-(4-Pentylcyclohexylmethyl)-1H-isoindol-1,3-(2H)-dione To a suspension of potassium phthalimide (3.70 g, 20.0 mmol) in DMF (50 ml) was added (4-methylcyclohexyl) methyl methanesulfonate (5.25 g, 20.0 mmol) and the mixture was stirred at 80° C. for 3 hours. The reaction solution was poured into water and the mixture was extracted with ethyl acetate. The extract was washed with water and dried over magnesium sulfate anhydride. The solvent was removed under reduced pressure to give the object compound as a solid. 5.90 g (yield: 94.2%)

$^1$H-NMR (CDCl$_3$) δ; 0.83–1.74 (21H, m), 3.53 (2H, d, J=6.8 Hz), 7.69–7.87 (4H, m).

IR (KBr) cm$^{-1}$; 1703, 1466, 1433, 1400, 1364, 1063, 1036, 920, 720, 530.

(2) 2-(4-Pentylcyclohexyl)methylamine

To a solution of 2-(4-pentylcyclohexylmethyl)-1H-isoindol-1,3-(2H)-dione (5.70 g, 18.2 mmol) in ethanol (100 ml) was added hydrazine monohydrate (1.31 ml, 27.0 mmol) and the mixture was refluxed for 12 hours under heating. The insoluble matter was filtered out and the filtrate was concentrated. The residue was dissolved into 5 N aqueous sodium hydroxide solution (100 ml) and extracted with ethyl acetate. The extract was washed with water and dried over magnesium sulfate anhydride, and the solvent was removed under reduced pressure to give the object compound as an oily substance. 3.06 g (yield: 91.9%)

$^1$H-NMR (CDCl$_3$) δ; 0.84–1.78 (21H, m), 2.51 (2H, d, J=6.2 Hz).

IR (KBr) cm$^{-1}$; 3368, 1537, 1485, 1426, 1339, 1327.

(3) 2-(4-Benzyloxyphenyl)-5-methyl-1-(4-pentylcyclohexylmethyl)-1H-pyrrole

A solution of 1-(4-benzyloxyphenyl)pentane-1,4-dione (2.00 g, 7.08 mmol), 2-(4-pentylcyclohexyl)ethylamine (1.30 g, 7.08 mmol) and p-toluenesulfonic acid monohydrate (101 mg, 0.523 mmol) in toluene (100 ml) was refluxed for 12 hours under heating using Dean-Stark's apparatus, and the solvent was removed under reduced pressure. The residue was purified by silica gel column chromatography (hexane:ethyl acetate=30:1) to give the object compound as an oily substance. 770 mg (yield: 25.3%)

$^1$H-NMR (CDCl$_3$) δ; 0.65–1.63 (21H, m), 2.28 (3H, s), 3.72 (2H, d, J=6.8 Hz), 5.09 (2H, s), 5.91 (1H, d, J=3.2 Hz), 5.99 (1H, d, J=3.2 Hz), 6.98 (2H, d, J=8.8 Hz), 7.02–7.49 (7H, m).

IR (KBr) cm$^{-1}$; 1611, 1524, 1481, 1454, 1381, 1242, 1175, 1022, 835, 754, 735, 696.

(4) 4-[5-Methyl-1-(4-pentylcyclohexylmethyl)-1H-pyrrol-2-yl]phenol

To a solution of 2-(4-benzyloxyphenyl)-5-methyl-1-(4-pentylcyclohexylmethyl)-1H-pyrrole (770 mg, 1.79 mmol) in ethanol (10 ml) and tetrahydrofuran (10 ml) was added 10% palladium carbon (200 mg) and the mixture was stirred for 4 hours under hydrogen atmosphere. The insoluble matter was filtered out and the filtrate was concentrated to give the object compound as an oily substance. 600 mg (yield: 98.5%)

$^1$H-NMR (CDCl$_3$) δ; 0.65–1.62 (21H, m), 2.28 (3H, s), 3.71 (2H, d, J=7.0 Hz), 5.91 (1H, d, J=3.4 Hz), 5.99 (1H, d, J=3.4 Hz), 6.83 (2H, d, J=8.0 Hz), 7.20 (2H, d, J=8.0 Hz).

IR (KBr) cm$^{-1}$; 3291, 1615, 1526, 1479, 1449, 1400, 1360, 1260, 1217, 1188, 1171, 837, 818, 758.

(5) Ethyl (2R)-2-{4-[5-methyl-1-(4-pentylcyclohexylmethyl)-1H-pyrrol-2-yl]phenoxy}-3-phenylpropanoate To a solution of 4-[5-methyl-1-(4-pentylcyclohexylmethyl)-1H-pyrrol-2-yl]phenol (600 mg, 1.76 mmol), ethyl (S)-2-hydroxy-3-phenylpropanoate (514 mg, 2.65 mmol) and triphenylphosphine (694 mg, 2.65 mmol) in toluene (2 ml) was added 1,1'-(azodicarbonyl) dipiperidine (668 mg, 2.65 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 850 mg (yield: 72.0%)

$^1$H-NMR (CDCl$_3$) δ; 0.63–1.60 (24H, m), 2.26 (3H, s), 3.24–3.29 (2H, m), 3.69 (2H, d, J=7.0 Hz), 4.19 (2H, q, J=7.0 Hz), 4.79–4.86 (1H, m), 5.90 (1H, d, J=3.4 Hz), 5.96 (1H, d, J=3.4 Hz), 6.83 (2H, d, J=8.8 Hz), 7.17–7.33 (7H, m).

IR (KBr) cm$^{-1}$; 1755, 1734, 1524, 1481, 1454, 1281, 1238, 1181, 1086, 1032, 837, 754, 698.

Example 176

Sodium (2R)-2-{4-[5-methyl-1-(4-pentylcyclohexylmethyl)-1H-pyrrol-2-yl]phenoxy}-3-phenylpropanoate (1) (2R)-2-{4-[5-Methyl-1-(4-pentylcyclohexylmethyl)-1H-pyrrol-2-yl]phenoxy}-3-phenylpropanoic acid To a mixed solution of ethyl (2R)-2-{4-[5-methyl-1-(4-pentylcyclohexylmethyl)-1H-pyrrol-2-yl]phenoxy}-3-phenylpropanoate (850 mg, 1.65 mmol) in THF (30 ml) and methanol (15 ml) was added 1N aqueous potassium hydroxide solution (8 ml, 8 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 573 mg (yield: 71.2%)

$^1$H-NMR (CDCl$_3$) δ; 0.63–1.57 (21H, m), 2.27 (3H, s), 3.31 (2H, d, J=5.0 Hz), 3.69 (2H, d, J=7.0 Hz), 4.89 (1H, t, J=5.0 Hz), 5.90 (1H, d, J=3.2 Hz), 5.97 (1H, d, J=3.2 Hz), 6.83 (2H, d, J=8.8 Hz), 7.19–7.34 (7H, m).

IR (KBr) cm$^{-1}$; 3061, 1728, 1524, 1481, 1454, 1308, 1281, 1236, 1084, 835, 756, 700.

(2) Sodium (2R)-2-{4-[5-methyl-1-(4-pentylcyclohexylmethyl)-1H-pyrrol-2-yl]phenoxy}-3-phenylpropanoate Ethanol (5 ml) and a solution of 1N sodium hydroxide in ethanol (1.01 ml) were added to (2R)-2-{4-[5-methyl-1-(4-pentylcyclohexylmethyl)-1H-pyrrol-2-yl]phenoxy}-3-phenylpropanoic acid (550 mg, 1.13 mmol) and the mixture was concentrated. To the residue was added hexane to give the object compound as a solid. 470 mg (yield: 91.4%)

$^1$H-NMR (DMSO-$d_6$) δ; 0.61–1.53 (21H, m), 2.20 (3H, s), 2.93–3.17 (2H, m), 3.71 (2H, d, J=7.0 Hz), 4.29–4.35 (1H, m), 5.75 (2H, s), 6.76 (2H, d, J=8.8 Hz), 7.05–7.33 (7H, m).

IR (KBr) cm$^{-1}$; 1615, 1524, 1414, 1235, 1059, 1030, 837, 756, 698.

$[α]_D^{28}$ 3.97° (c 0.680, methanol)

Example 177

Ethyl (2R)-2-{4-[5-methyl-1-(4-octyloxyphenyl)-1H-pyrrol-2-yl]phenoxy}-3-phenylpropanoate (1) 2-(4-Benzyloxyphenyl)-1-(4-octyloxyphenyl)-5-methyl-1H-pyrrole A solution of 4-[2-(4-benzyloxyphenyl)-5-methyl-1H-pyrrol-1-yl]phenol (1.00 g, 2.82 mmol), 1-bromooctane (0.584 ml, 3.38 mmol) and potassium carbonate (466 mg, 3.38 mmol) in DMF (20 ml) was stirred at 80° C. for 4 hours. The reaction solution was poured into water and the mixture was extracted with ethyl acetate. The extract was washed with water and dried over magnesium sulfate anhydride, and the solvent was removed under reduced pressure. The residue was purified by silica gel column chromatography (hexane:ethyl acetate=30:1) to give the object compound as an oily substance. 1.03 g (yield: 78.0%)

$^1$H-NMR (CDCl$_3$) δ; 0.89 (3H, t, J=6.6 Hz), 1.29–1.55 (10H, m), 1.75–1.83 (2H, m), 2.10 (3H, s), 3.95 (2H, t, J=6.2 Hz), 4.98 (2H, s), 6.04 (1H, d, J=3.2 Hz), 6.25 (1H, d, J=3.2 Hz), 6.77 (2H, d, J=9.2 Hz), 6.85 (2H, d, J=9.2 Hz), 7.33–7.42 (5H, m).

IR (KBr) cm$^{-1}$; 1609, 1514, 1470, 1545, 1395, 1289, 1246, 1177, 1040, 1026, 835, 760, 735, 698.

(2) 4-[5-Methyl-1-(4-octyloxyphenyl)-1H-pyrrol-2-yl]phenol

To a solution of 2-(4-benzyloxyphenyl)-1-(4-octyloxyphenyl)-5-methyl-1H-pyrrole (950 mg, 2.03 mmol) in ethanol (20 ml) and tetrahydrofuran (20 ml) was added 10% palladium carbon (200 mg) and the mixture was stirred for 3 hours under hydrogen atmosphere. The insoluble matter was filtered out and the filtrate was concentrated to give the object compound as an oily substance. 752 mg (yield: 98.0%)

$^1$H-NMR (CDCl$_3$) δ; 0.89 (3H, t, J=7.4 Hz), 1.21–1.96 (12H, m), 2.10 (3H, s), 3.94 (2H, t, J=6.2 Hz), 6.04 (1H, d, J=3.6 Hz), 6.23 (1H, d, J=3.6 Hz), 6.61 (2H, d, J=8.8 Hz), 6.85 (2H, d, J=8.8 Hz), 6.94 (2H, d, J=8.8 Hz), 7.04 (2H, d, J=8.8 Hz).

IR (KBr) cm$^{-1}$; 3339, 1514, 1472, 1246, 1171, 1040, 835, 762.

(3) Ethyl (2R)-2-{4-[5-methyl-1-(4-octyloxyphenyl)-1H-pyrrol-2-yl]phenoxy}-3-phenylpropanoate To a solution of 4-[5-methyl-1-(4-octyloxyphenyl)-1H-pyrrol-2-yl]phenol (740 mg, 1.96 mmol), ethyl (S)-2-hydroxy-3-phenylpropanoate (570 mg, 2.94 mmol) and triphenylphosphine (770 mg, 2.94 mmol) in toluene (2 ml) was added 1,1'-(azodicarbonyl)dipiperidine (741 mg, 2.94 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 420 mg (yield: 39.6%)

$^1$H-NMR (CDCl$_3$) δ; 0.89 (3H, t, J=6.6 Hz), 1.14 (3H, t, J=7.4 Hz), 1.26–1.56 (10H, m), 1.72–1.83 (2H, m), 2.09 (3H, s), 3.17–3.21 (2H, m), 3.94 (2H, t, J=6.6 Hz), 4.14 (2H, q, J=7.4 Hz), 4.66–4.73 (1H, m), 6.02 (1H, d, J=3.6 Hz), 6.21 (1H, d, J=3.6 Hz), 6.61 (2H, d, J=8.8 Hz), 6.83 (2H, d, J=8.8 Hz), 6.93 (2H, d, J=8.8 Hz), 7.01 (2H, d, J=8.8 Hz), 7.21–7.29 (5H, m).

IR (KBr) cm$^{-1}$; 1755, 1734, 1514, 1483, 1456, 1287, 1244, 1182, 1084, 1038, 835, 760, 700.

Example 178

Sodium (2R)-2-{4-[5-methyl-1-(4-octyloxyphenyl)-1H-pyrrol-2-yl]phenoxy}-3-phenylpropanoate (1) (2R)-2-{4-[5-methyl-1-(4-octyloxyphenyl)-1H-pyrrol-2-yl]phenoxy}-3-phenylpropanoic acid To a mixed solution of ethyl (2R)-2-{4-[5-methyl-1-(4-octyloxyphenyl)-1H-pyrrol-2-yl]phenoxy}-3-phenylpropanoate (410 mg, 0.739 mmol) in THF (15 ml) and methanol (8 ml) was added 1N aqueous potassium hydroxide solution (4 ml, 4 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 278 mg (yield: 71.5%)

$^1$H-NMR (CDCl$_3$) δ; 0.89 (3H, t, J=6.9 Hz), 1.24–1.46 (10H, m), 1.74–1.83 (2H, m), 2.09 (3H, s), 3.21–3.24 (2H, m), 3.94 (2H, t, J=6.6 Hz), 4.75–4.79 (1H, m), 6.03 (1H, d, J=3.6 Hz), 6.23 (1H, d, J=3.6 Hz), 6.62 (2H, d, J=9.0 Hz), 6.84 (2H, d, J=9.0 Hz), 6.95 (2H, d, J=9.0 Hz), 7.01 (2H, d, J=9.0 Hz), 7.22–7.30 (5H, m).

IR (KBr) cm$^{-1}$; 2926, 1728, 1514, 1287, 1244, 835, 758, 700.

(2) Sodium (2R)-2-{4-[5-methyl-1-(4-octyloxyphenyl)-1H-pyrrol-2-yl]phenoxy}-3-phenylpropanoate Ethanol (5 ml) and a solution of 1N sodium hydroxide in ethanol (0.444 ml) were added to (2R)-2-{4-[5-methyl-1-(4-octyloxyphenyl)-1H-pyrrol-2-yl]phenoxy}-3-phenylpropanoic acid (260 mg, 0.493 mmol) and the mixture was concentrated. To the residue was added hexane to give the object compound as a solid. 227 mg (yield: 93.0%)

$^1$H-NMR (DMSO-$d_6$) δ; 0.87 (3H, t, J=6.6 Hz), 1.28–1.41 (10H, m), 1.68–1.73 (2H, m), 1.99 (3H, s), 2.87–3.10 (2H, m), 3.95 (2H, t, J=6.3 Hz), 4.19–4.23 (1H, m), 5.92 (1H, d, J=3.3 Hz), 6.07 (1H, d, J=3.3 Hz), 6.53 (2H, d, J=8.7 Hz), 6.79 (2H, d, J=8.7 Hz), 6.91 (2H, d, J=8.7 Hz), 7.03 (2H, d, J=8.7 Hz), 7.10–7.27 (5H, m).

IR (KBr) cm$^{-1}$; 1611, 1514, 1396, 1244, 1181, 1169, 1043, 1030, 835, 764.

$[α]_D^{30}$ −2.52° (c 0.530, methanol)

Example 179

Ethyl (2R)-2-(4-{5-methyl-1-[3-(4-pentylphenoxy)propyl]-1H-pyrrol-2-yl}phenoxy)-3-phenylpropanoate (1) 2-(4-Benzyloxyphenyl)-5-methyl-1-[3-(4-pentylphenoxy)propyl]-1H-pyrrole To a solution of 3-[2-(4-benzyloxyphenyl)-5-methyl-1H-pyrrol-1-yl]propan-1-ol (1.00 g, 3.11 mmol), 4-n-amylphenol (766 mg, 4.67 mmol) and triphenylphosphine (1.22 g, 4.67 mmol) in toluene (2 ml) was added 1,1'-(azodicarbonyl)dipiperidine (1.18 g, 4.67 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.25 g (yield: 86.2%)

$^1$H-NMR (CDCl$_3$) δ; 0.88 (3H, t, J=7.0 Hz), 1.22–1.64 (6H, m), 1.88–1.98 (2H, m), 2.30 (3H, s), 2.52 (2H, t, J=7.8 Hz), 3.71 (2H, d, J=5.8 Hz), 4.09 (2H, t, J=7.4 Hz), 5.06 (2H, s), 5.92 (1H, d, J=3.6 Hz), 6.03 (1H, d, J=3.6 Hz), 6.67 (2H, d, J=8.8 Hz), 6.95 (2H, d, J=8.8 Hz), 7.03 (2H, d, J=8.8 Hz), 7.19–7.49 (7H, m).

IR (KBr) cm$^{-1}$; 1611, 1522, 1510, 1466, 1454, 1309, 1279, 1244, 1175, 1024, 833, 756, 737, 698.

(2) 4-{5-Methyl-1-[3-(4-pentylphenoxy)propyl]-1H-pyrrol-2-yl}phenol

To a solution of 2-(4-benzyloxyphenyl)-5-methyl-1-[3-(4-pentylphenoxy)propyl]-1H-pyrrole (1.17 g, 2.50 mmol) in ethanol (50 ml) and tetrahydrofuran (50 ml) was added 10% palladium carbon (200 mg) and the mixture was stirred for 4 hours under hydrogen atmosphere. The insoluble matter was filtered out and the filtrate was concentrated to give the object compound as an oily substance. 921 mg (yield: 97.7%)

$^1$H-NMR (CDCl$_3$) δ; 0.88 (3H, t, J=6.6 Hz), 1.21–1.33 (4H, m), 1.49–1.60 (2H, m), 1.87–2.00 (2H, m), 2.30 (3H, s), 2.52 (2H, t, J=7.6 Hz), 3.72 (2H, t, J=7.0 Hz), 4.08 (2H, t, J=7.4 Hz), 5.91 (1H, d, J=3.4 Hz), 6.03 (1H, d, J=3.4 Hz), 6.67 (2H, d, J=8.8 Hz), 6.80 (2H, d, J=8.8 Hz), 7.04 (2H, d, J=8.8 Hz), 7.23 (2H, d, J=8.8 Hz).

IR (KBr) cm$^{-1}$; 3380, 1610, 1510, 1470, 1242, 1180, 837, 760.

(3) Ethyl (2R)-2-(4-{5-methyl-1-[3-(4-pentylphenoxy)propyl]-1H-pyrrol-2-yl}phenoxy)-3-phenylpropanoate To a solution of 4-{5-methyl-1-[3-(4-pentylphenoxy)propyl]-1H-pyrrol-2-yl}phenol (910 mg, 2.41 mmol), ethyl (S)-2-hydroxy-3-phenylpropanoate (701 mg, 3.61 mmol) and triphenylphosphine (946 mg, 3.61 mmol) in toluene (5 ml) was added 1,1'-(azodicarbonyl)dipiperidine (910 mg, 3.61 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 770 mg (yield: 57.9%)

$^1$H-NMR (CDCl$_3$) δ; 0.89 (3H, t, J=6.9 Hz), 1.18 (3H, t, J=6.9 Hz), 1.26–1.36 (4H, m), 1.52–1.59 (2H, m), 1.89–2.05 (2H, m), 2.29 (3H, s), 2.52 (2H, t, J=7.8 Hz), 3.24–3.29 (2H, m), 3.70 (2H, t, J=5.7 Hz), 4.05 (2H, t, J=7.5 Hz), 4.18 (2H, q, J=6.9 Hz), 4.77–4.81 (1H, m), 5.90 (1H, d, J=3.3 Hz), 6.00 (1H, d, J=3.3 Hz), 6.65 (2H, d, J=8.4 Hz), 6.82 (2H, d, J=8.4 Hz), 7.01 (2H, d, J=8.4 Hz), 7.20–7.33 (7H, m).

IR (KBr) cm$^{-1}$; 1755, 1734, 1522, 1512, 1480, 1279, 1242, 1179, 1084, 1032, 835, 756, 700.

Example 180

Sodium (2R)-2-(4-{5-methyl-1-[3-(4-pentylphenoxy)propyl]-1H-pyrrol-2-yl}phenoxy)-3-phenylpropanoate (1) (2R)-2-(4-{5-Methyl-1-[3-(4-pentylphenoxy)propyl]-1H-pyrrol-2-yl}phenoxy)-3-phenylpropanoic acid To a mixed solution of ethyl (2R)-2-(4-{5-methyl-1-[3-(4-pentylphenoxy)propyl]-1H-pyrrol-2-yl}phenoxy)-3-phenylpropanoate (750 mg, 1.35 mmol) in THF (20 ml) and methanol (20 ml) was added 1N aqueous potassium hydroxide solution (7 ml, 7 mmol) and the mixture was stirred for 1 hour at room temperature. The reaction solution was neutralized with 1N hydrochloric acid and extracted with ethyl acetate. The extract was washed with water, dried over magnesium sulfate anhydride and the solvent was removed under reduced pressure. The residue was purified by silica gel column chromatography (hexane:ethyl acetate=1:1) to give the object compound as an oily substance. 672 mg (yield: 94.6%)

$^1$H-NMR (CDCl$_3$) δ; 0.88 (3H, t, J=7.0 Hz), 1.26–1.33 (4H, m), 1.53–1.62 (2H, m), 1.87–1.94 (2H, m), 2.29 (3H, s), 2.51 (2H, t, J=7.8 Hz), 3.30 (2H, d, J=6.2 Hz), 3.69 (2H, t, J=5.6 Hz), 4.05 (2H, t, J=8.6 Hz), 4.85 (1H, t, J=6.2Hz), 5.90 (1H, d, J=3.2 Hz), 6.00 (1H, d, J=3.2 Hz), 6.65 (2H, d, J=8.8 Hz), 6.82 (2H, d, J=8.8 Hz), 7.01 (2H, d, J=8.8Hz), 7.20–7.33 (7H, m).

IR (KBr) cm$^{-1}$; 3061, 1728, 1512, 1481, 1242, 1084, 835, 758, 700.

(2) Sodium (2R)-2-(4-{5-methyl-1-[3-(4-pentylphenoxy)propyl]-1H-pyrrol-2-yl}phenoxy)-3-phenylpropanoate Ethanol (6 ml) and a solution of 1N sodium hydroxide in ethanol (1.10 ml) were added to (2R)-2-(4-{5-methyl-1-[3-(4-pentylphenoxy)propyl]-1H-pyrrol-2-yl}phenoxy)-3-phenylpropanoic acid (640 mg, 1.22 mmol) and the mixture was concentrated. To the residue was added diisopropylether to give the object compound as a solid. 499 mg (yield: 82.9%)

$^1$H-NMR (DMSO-d$_6$) δ; 0.87 (3H, t, J=7.0 Hz), 1.22–1.29 (4H, m), 1.453–1.56 (2H, m), 1.77–1.90 (2H, m), 2.21 (3H, s), 2.48 (2H, t, J=8.0 Hz), 2.95–3.22 (2H, m), 3.69 (2H, t, J=6.0 Hz), 4.00 (2H, t, J=7.0 Hz), 4.31–4.37 (1H, m), 5.75 (1H, d, J=3.2 Hz), 5.82 (1H, d, J=3.2 Hz), 6.67 (2H, d, J=8.8 Hz), 6.78 (2H, d, J=8.8 Hz), 7.01 (2H, d, J=8.8Hz), 7.14–7.35 (7H, m).

IR (KBr) cm$^{-1}$; 1615, 1512, 1481, 1410, 1240, 1177, 1035, 835, 758, 700.

$[α]_D^{27}$ 7.45° (c 0.530, methanol)

Example 181

Ethyl (2R)-2-(4-{5-methyl-1-[4-(5-phenylpentyloxy)phenyl]-1H-pyrrol-2-yl}phenoxy)-3-phenylpropanoate (1) 2-(4-Benzyloxyphenyl)-5-methyl-1-[4-(5-phenylpentyloxy)phenyl]-1H-pyrrole To a solution of 4-[2-(4-benzyloxyphenyl)-5-methyl-1H-pyrrol-1-yl]phenol (1.00 g, 2.81 mmol), 5-phenyl-1-pentanol (692 mg, 4.22 mmol), triphenylphosphine (1.11 g, 4.22 mmol) in toluene (2 ml) was added 1,1'-(azodicarbonyl)dipiperidine (1.06 g, 4.22 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as a solid. 1.18 g (yield: 83.7%)

$^1$H-NMR (CDCl$_3$) δ; 1.43–1.86 (6H, m), 2.10 (3H, s), 2.65 (2H, t, J=7.8 Hz), 3.95 (2H, t, J=6.6 Hz), 4.97 (2H, s), 6.04 (1H, d, J=3.6 Hz), 6.24 (1H, d, J=3.6 Hz), 6.73–7.40 (18H, m).

IR (KBr) cm$^{-1}$; 1610, 1514, 1451, 1397, 1290, 1244, 1180, 1040, 1020, 845, 750, 710.

(2) 4-{5-Methyl-1-[4-(5-phenylpentyloxy)phenyl]-1H-pyrrol-2-yl}phenol

To a solution of 2-(4-benzyloxyphenyl)-5-methyl-1-[4-(5-phenylpentyloxy)phenyl]-1H-pyrrole (1.11 g, 2.21 mmol) in ethanol (50 ml) and tetrahydrofuran (50 ml) was added 10% palladium carbon (200 mg) and the mixture was stirred for 4 hours under hydrogen atmosphere. The insoluble matter was filtered out and the filtrate was concentrated to give the object compound as an oily substance. 891 mg (yield: 98.0%)

$^1$H-NMR (CDCl$_3$) δ; 1.49–1.87 (6H, m), 2.10 (3H, s), 2.65 (2H, t, J=7.8 Hz), 3.94 (2H, t, J=6.6 Hz), 6.04 (1H, d, J=3.6 Hz), 6.23 (1H, d, J=3.6 Hz), 6.61 (2H, d, J=8.4 Hz), 6.84 (2H, d, J=8.4 Hz), 6.94 (2H, d, J=8.4 Hz), 7.03 (2H, d, J=8.4 Hz), 7.17–7.28 (5H, m).

IR (KBr) cm$^{-1}$; 3397, 1613, 1512, 1397, 1289, 1246, 1171, 835, 764, 700.

(3) Ethyl (2R)-2-(4-{5-methyl-1-[4-(5-phenylpentyloxy) phenyl]-1H-pyrrol-2-yl}phenoxy)-3-phenylpropanoate To a solution of 4-{5-methyl-1-[4-(5-phenylpentyloxy) phenyl]-1H-pyrrol-2-yl}phenol (880 mg, 2.14 mmol), ethyl (S)-2-hydroxy-3-phenylpropanoate (622 mg, 3.21 mmol) and triphenylphosphine (810 mg, 3.21 mmol) in toluene (3 ml) was added 1,1'-(azodicarbonyl)dipiperidine (809 mg, 3.21 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 530 mg (yield: 42.1%)

$^1$H-NMR (CDCl$_3$) δ; 1.13 (3H, t, J=6.8 Hz), 1.22–1.87 (6H, m), 2.09 (3H, s), 2.66 (2H, t, J=7.6 Hz), 3.17–3.21 (2H, m), 3.94 (2H, t, J=6.2 Hz), 4.13 (2H, q, J=6.8 Hz), 4.66–4.73 (1H, m), 6.02 (1H, d, J=3.2 Hz), 6.22 (1H, d, J=3.2 Hz), 6.61 (2H, d, J=8.8 Hz), 6.82 (2H, d, J=8.8 Hz), 6.93 (2H, d, J=8.8 Hz), 7.01 (2H, d, J=8.8 Hz), 7.18–7.33 (10H, m).

IR (KBr) cm$^{-1}$; 1753, 1734, 1514, 1287, 1244, 1182, 1084, 1032, 837, 760, 700.

Example 182

Sodium (2R)-2-(4-{5-methyl-1-[4-(5-phenylpentyloxy)phenyl]-1H-pyrrol-2-yl}phenoxy)-3-phenylpropanoate (1) (2R)-2-(4-{5-Methyl-1-[4-(5-phenylpentyloxy)phenyl]-1H-pyrrol-2-yl}phenoxy)-3-phenylpropanoic acid To a mixed solution of ethyl (2R)-2-(4-{5-methyl-1-[4-(5-phenylpentyloxy)phenyl]-1H-pyrrol-2-yl}phenoxy)-3-phenylpropanoate (520 mg, 0.884 mmol) in THF (20 ml) and methanol (20 ml) was added 1N aqueous potassium hydroxide solution (5 ml, 5 mmol) and the mixture was stirred for 1 hour at room temperature. The reaction solution was neutralized with 1N hydrochloric acid and extracted with ethyl acetate. The extract was washed with water and dried over magnesium sulfate anhydride, and the solvent was removed under reduced pressure. The residue was purified by silica gel column chromatography (hexane:ethyl acetate=1:1) to give the object compound as an oily substance. 336 mg (yield: 67.9%)

$^1$H-NMR (CDCl$_3$) δ; 1.47–1.86 (6H, m), 2.08 (3H, s), 2.65 (2H, t, J=7.6 Hz), 3.22 (2H, d, J=6.2 Hz), 3.93 (2H, t, J=6.6 Hz), 4.76 (1H, t, J=6.2 Hz), 6.03 (1H, d, J=3.2 Hz), 6.23 (1H, d, J=3.2 Hz), 6.62 (2H, d, J=8.8 Hz), 6.82 (2H, d, J=8.8 Hz), 6.95 (2H, d, J=8.8 Hz), 7.01 (2H, d, J=8.8 Hz), 7.18–7.32 (10H, m).

IR (KBr) cm$^{-1}$; 3029, 1726, 1514, 1287, 1244, 1181, 1169, 1084, 835, 760, 735, 700.

(2) Sodium (2R)-2-(4-{5-methyl-1-[4-(5-phenylpentyloxy)phenyl]-1H-pyrrol-2-yl}phenoxy)-3-phenylpropanoate Ethanol (6 ml) and a solution of 1N sodium hydroxide in ethanol (0.508 ml) were added to (2R)-2-(4-{5-methyl-1-[4-(5-phenylpentyloxy)phenyl]-1H-pyrrol-2-yl}phenoxy)-3-phenylpropanoic acid (316 mg, 0.565 mmol) and the mixture was concentrated. Diisopropylether was added to the residue to give the object compound as a solid. 267 mg (yield: 90.2%)

$^1$H-NMR (DMSO-d$_6$) δ; 1.44–1.79 (6H, m), 1.99 (3H, s), 2.61 (2H, t, J=7.6 Hz), 2.85–3.12 (2H, m), 3.95 (2H, t, J=6.6 Hz), 4.18–4.24 (1H, m), 5.91 (1H, d, J=3.6 Hz), 6.06 (1H, d, J=3.6 Hz), 6.53 (2H, d, J=8.8 Hz), 6.79 (2H, d, J=8.8 Hz), 6.89 (2H, d, J=8.8 Hz), 7.03 (2H, d, J=8.8 Hz), 7.09–7.31 (10H, m).

IR (KBr) cm$^{-1}$; 1613, 1514, 1404, 1244, 1181, 1053, 1028, 833, 766, 748, 700.

Example 183

Ethyl (2R)-2-(4-{5-methyl-1-[4-(4-phenylbutoxy)phenyl]-1H-pyrrol-2-yl}phenoxy)-3-phenylpropanoate (1) 2-(4-Benzyloxyphenyl)-5-methyl-1-[4-(4-phenylbutoxy)-phenyl]-1H-pyrrole The object compound was obtained from 4-phenyl-1-butanol as an oily substance, according to the similar manner to that of Example 181 (1). yield: 86.9%

$^1$H-NMR (CDCl$_3$) δ; 1.81–1.86 (4H, m), 2.10 (3H, s), 2.70 (2H, t, J=7.0 Hz), 3.97 (2H, t, J=5.8 Hz), 4.97 (2H, s), 6.04 (1H, d, J=3.2 Hz), 6.24 (1H, d, J=3.2 Hz), 6.76 (2H, d, J=8.8 Hz), 6.84 (2H, d, J=8.8 Hz), 6.96–7.40 (14H, m).

IR (KBr) cm$^{-1}$; 1609, 1514, 1454, 1395, 1289, 1244, 1175, 1026, 835, 739, 698.

(2) 4-{5-Methyl-1-[4-(4-phenylbutoxy)phenyl]-1H-pyrrol-2-yl}phenol

The object compound was obtained from 2-(4-benzyloxyphenyl)-5-methyl-1-[4-(4-phenylbutoxy)phenyl]-1H-pyrrole as an oily substance, according to the similar manner to that of Example 181 (2). yield: 98.2%

$^1$H-NMR (CDCl$_3$) δ; 1.79–1.86 (4H, m), 2.10 (3H, s), 2.70 (2H, t, J=7.0 Hz), 3.96 (2H, t, J=5.8 Hz), 6.04 (1H, d, J=3.4 Hz), 6.23 (1H, d, J=3.4 Hz), 6.60 (2H, d, J=8.8 Hz), 6.84 (2H, d, J=8.8 Hz), 6.94 (2H, d, J=8.8 Hz), 7.04 (2H, d, J=8.8 Hz), 7.19–7.33 (5H, m)

IR (KBr) cm$^{-1}$; 3300, 1613, 1512, 1454, 1537, 1397, 1289, 1244, 1171, 835, 764, 700.

(3) Ethyl (2R)-2-(4-{5-methyl-1-[4-(4-phenylbutoxy)phenyl]-1H-pyrrol-2-yl}phenoxy)-3-phenylpropanoate The object compound was obtained from 4-{5-methyl-1-[4-(4-phenylbutoxy)phenyl]-1H-pyrrol-2-yl}phenol as an oily substance, according to the similar manner to that of Example 181 (3). yield: 39.8%

$^1$H-NMR (CDCl$_3$) δ; 1.13 (3H, t, J=7.2 Hz), 1.82–1.85 (4H, m), 2.08 (3H, s), 2.70 (2H, t, J=6.9 Hz), 3.17–3.20 (2H, m), 3.96 (2H, t, J=6.0 Hz), 4.13 (2H, q, J=7.2 Hz), 4.67–4.72 (1H, m), 6.01 (1H, d, J=3.3 Hz), 6.22 (1H, d, J=3.3 Hz), 6.61 (2H, d, J=8.7 Hz), 6.82 (2H, d, J=8.7 Hz), 6.92 (2H, d, J=8.7 Hz), 7.01 (2H, d, J=8.7 Hz), 7.17–7.32 (10H, m).

IR (KBr) cm$^{-1}$; 1752, 1734, 1514, 1483, 1287, 1244, 1182, 1084, 1032, 835, 760, 700.

Example 184

Sodium (2R)-2-(4-{5-methyl-1-[4-(4-phenylbutoxy)phenyl]-1H-pyrrol-2-yl}phenoxy)-3-phenylpropanoate (1) (2R)-2-(4-{5-Methyl-1-[4-(4-phenylbutoxy)phenyl]-1H-pyrrol-2-yl}phenoxy)-3-phenylpropanoic acid The object compound was obtained from ethyl (2R)-2-(4-{5-methyl-1-[4-(4-phenylbutoxy)phenyl]-1H-pyrrol-2-yl}phenoxy)-3-phenylpropanoate as an oily substance, according to the similar manner to that of Example 182(1). yield: 74.3%

¹H-NMR (CDCl₃) δ; 1.81–1.85 (4H, m), 2.08 (3H, s), 2.70 (2H, t, J=7.0 Hz), 3.22 (2H, d, J=5.8 Hz), 3.95 (2H, t, J=6.0 Hz), 4.75 (1H, t, J=5.8 Hz), 6.03 (1H, d, J=3.2 Hz), 6.23 (1H, d, J=3.2 Hz), 6.62 (2H, d, J=8.8 Hz), 6.82 (2H, d, J=8.8 Hz), 6.94 (2H, d, J=8.8 Hz), 7.01 (2H, d, J=8.8 Hz), 7.16–7.36 (10H, m).

IR (KBr) cm⁻¹; 3031, 1728, 1514, 1287, 1244, 1181, 1084, 835, 758, 700.

(2) Sodium (2R)-2-(4-{5-methyl-1-[4-(4-phenylbutoxy)phenyl]-1H-pyrrol-2-yl}phenoxy)-3-phenylpropanoate The object compound was obtained from (2R)-2-(4-{5-methyl-1-[4-(4-phenylbutoxy)phenyl]-1H-pyrrol-2-yl}phenoxy)-3-phenylpropanoic acid as a solid, according to the similar manner to that of Example 182(2). yield: 89.3%

¹H-NMR (DMSO-d₆) δ; 1.74 (4H, bs), 1.98 (3H, s), 2.65 (2H, t, J=7.0 Hz), 2.84–3.10 (2H, m), 3.98 (2H, t, J=6.0 Hz), 4.16–4.21 (1H, m), 5.91 (1H, d, J=3.4 Hz), 6.06 (1H, d, J=3.42 Hz), 6.52 (2H, d, J=8.8 Hz), 6.79 (2H, d, J=8.8 Hz), 6.92 (2H, d, J=8.8 Hz), 7.03 (2H, d, J=8.8 Hz), 7.11–7.32 (10H, m).

IR (KBr) cm⁻¹; 1615, 1514, 1399, 1244, 1181, 1169, 1049, 1030, 835, 766, 750, 700.

$[\alpha]_D^{28}$ –5.33° (c 0.545, methanol)

Example 185

Ethyl (2R)-2-(4-{1-[3-(4-heptylphenoxy)propyl]-5-methyl-1H-pyrrol-2-yl}phenoxy)-3-phenylpropanoate (1) 2-(4-Benzyloxyphenyl)-1-[3-(4-heptylphenoxy)propyl]-5-methyl-1H-pyrrole To a solution of 3-[2-(4-benzyloxyphenyl)-5-methyl-1H-pyrrol-1-yl]propan-1-ol (1.00 g, 3.11 mmol), 4-n-heptylphenol (897 mg, 4.67 mmol) and triphenylphosphine (1.22 g, 4.67 mmol) in toluene (2 ml) was added 1,1'-(azodicarbonyl)dipiperidine (1.18 g, 4.67 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.20 g (yield: 80.0%)

¹H-NMR (CDCl₃) δ; 0.87 (3H, t, J=7.0 Hz), 1.22–1.28 (8H, m), 1.49–1.61 (2H, m), 1.91–2.01 (2H, m), 2.30 (3H, s), 2.52 (2H, t, J=8.0 Hz), 3.71 (2H, t, J=5.8 Hz), 4.09 (2H, t, J=7.2 Hz), 5.06 (2H, s), 5.92 (1H, d, J=3.2 Hz), 6.03 (1H, d, J=3.2 Hz), 6.66 (2H, d, J=8.8 Hz), 6.91–7.49 (11H, m).

IR (KBr) cm⁻¹; 1611, 1524, 1510, 1468, 1454, 1383, 1310, 1281, 1244, 1175, 1053, 1024, 833, 756, 735, 698.

(2) 4-{1-[3-(4-Heptylphenoxy)propyl]-5-methyl-1H-pyrrol-2-yl}phenol

To a solution of 2-(4-benzyloxyphenyl)-5-methyl-1-[3-(4-heptylphenoxy)propyl]-1H-pyrrole (1.14 g, 2.37 mmol) in ethanol (30 ml) and tetrahydrofuran (30 ml) was added 10% palladium carbon (200 mg) and the mixture was stirred for 4 hours under hydrogen atmosphere. The insoluble matter was filtered out and the filtrate was concentrated to give the object compound as an oily substance. 911 mg (yield: 94.8%)

¹H-NMR (CDCl₃) δ; 0.87 (3H, t, J=6.6 Hz), 1.21–1.28 (8H, m), 1.51–1.61 (2H, m), 1.87–1.97 (2H, m), 2.30 (3H, s), 2.52 (2H, t, J=7.6 Hz), 3.71 (2H, t, J=7.0 Hz), 4.07 (2H, t, J=7.4 Hz), 5.91 (1H, d, J=3.6 Hz), 6.02 (1H, d, J=3.6 Hz), 6.67 (2H, d, J=8.4 Hz), 6.80 (2H, d, J=8.8 Hz), 7.04 (2H, d, J=8.4 Hz), 7.22 (2H, d, J=8.8 Hz).

IR (KBr) cm⁻¹; 3407, 1613, 1512, 1470, 1385, 1242, 1175, 1051, 837, 758.

(3) Ethyl (2R)-2-(4-{1-[3-(4-heptylphenoxy)propyl]-5-methyl-1H-pyrrol-2-yl}phenoxy)-3-phenylpropanoate To a solution of 4-{1-[3-(4-heptylphenoxy)propyl]-5-methyl-1H-pyrrol-2-yl}phenol (910 mg, 2.22 mmol), ethyl (S)-2-hydroxy-3-phenylpropanoate (673 mg, 3.47 mmol) and triphenylphosphine (910 mg, 3.47 mmol) in toluene (3 ml) was added 1,1'-(azodicarbonyl)dipiperidine (876 mg, 3.47 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate= 30:1) to give the object compound as an oily substance. 490 mg (yield: 30.8%)

¹H-NMR (CDCl₃) δ; 0.88 (3H, t, J=6.6 Hz), 1.15–1.33 (11H, m), 1.51–1.60 (2H, m), 1.88–1.94 (2H, m), 2.29 (3H, s), 2.52 (2H, t, J=8.0Hz), 3.24–3.28 (2H, m), 3.70 (2H, t, J=5.8 Hz), 4.05 (2H, t, J=7.2 Hz), 4.19 (2H, q, J=7.0 Hz), 4.76–4.82 (1H, m), 5.90 (1H, d, J=3.8 Hz), 6.00 (1H, d, J=3.8 Hz), 6.66 (2H, d, J=8.4 Hz), 6.82 (2H, d, J=8.8 Hz), 7.02 (2H, d, J=8.8 Hz), 7.19–7.34 (7H, m).

IR (KBr) cm⁻¹; 1753, 1736, 1611, 1510, 1242, 1179, 1084, 1032, 835, 756, 700.

Example 186

Sodium (2R)-2-(4-{1-[3-(4-heptylphenoxy)propyl]-5-methyl-1H-pyrrol-2-yl}phenoxy)-3-phenylpropanoate (1) (2R)-2-(4-(1-[3-(4-Heptylphenoxy)propyl]-5-methyl-1H-pyrrol-2-yl}phenoxy)-3-phenylpropanoic acid To a mixed solution of ethyl (2R)-2-(4-{1-[3-(4-heptylphenoxy)propyl]-5-methyl-1H-pyrrol-2-yl}phenoxy)-3-phenylpropanoate (480 mg, 0.825 mmol) in THF (15 ml) and methanol (15 ml) was added 1N aqueous potassium hydroxide solution (3 ml, 3 mmol) and the mixture was stirred for 1 hour at room temperature. The reaction solution was neutralized with 1N hydrochloric acid and extracted with ethyl acetate. The extract was washed with water and dried over magnesium sulfate anhydride and the solvent was removed under reduced pressure. The residue was purified by silica gel column chromatography (hexane:ethyl acetate=1:1) to give the object compound as an oily substance. 353 mg (yield: 77.3%)

¹H-NMR (CDCl₃) δ; 0.87 (3H, t, J=6.6 Hz), 1.23–1.30 (8H, m), 1.48–1.62 (2H, m), 1.84–1.95 (2H, m), 2.28 (3H, s), 2.51 (2H, t, J=7.8 Hz), 3.29 (2H, d, J=6.2 Hz), 3.70 (2H, t, J=5.8 Hz), 4.04 (2H, t, J=7.0 Hz), 4.84 (1H, t, J=6.2Hz), 5.89 (1H, d, J=3.6 Hz), 5.99 (1H, d, J=3.6 Hz), 6.64 (2H, d, J=8.8 Hz), 6.81 (2H, d, J=8.8 Hz), 7.01 (2H, d, J=8.8Hz), 7.20–7.30 (7H, m).

IR (KBr) cm⁻¹; 3032, 1728, 1510, 1240, 1177, 1084, 835, 758, 700.

(2) Sodium (2R)-2-(4-{1-[3-(4-heptylphenoxy)propyl]-5-methyl-1H-pyrrol-2-yl}phenoxy)-3-phenylpropanoate Ethanol (6 ml) and a solution of 1N sodium hydroxide in ethanol (0.536 ml) were added to (2R)-2-(4-{1-[3-(4-heptylphenoxy)propyl]-5-methyl-1H-pyrrol-2-yl}phenoxy)-3-phenylpropanoic acid (330 mg, 0.596 mmol) and the mixture was concentrated. To the residue was added diisopropylether to give the object compound as a solid. 212 mg (yield: 68.6%)

¹H-NMR (DMSO-d₆) δ; 0.85 (3H, t, J=7.0 Hz), 1.18–1.35 (8H, m), 1.44–1.58 (2H, m), 1.66–1.91 (2H, m), 2.21 (3H, s), 2.47 (2H, t, J=7.6 Hz), 2.92–3.19 (2H, m), 3.69 (2H, t, J=5.8 Hz), 3.99 (2H, t, J=7.6 Hz), 4.29–4.35 (1H, m), 5.76 (1H, d, J=3.2 Hz), 5.82 (1H, d, J=3.2 Hz), 6.66–6.99 (4H, m), 7.03–7.34 (9H, m).

IR (KBr) cm$^{-1}$; 1613, 1512, 1470, 1404, 1242, 1177, 1042, 829, 764, 700.
$[\alpha]_D^{27}$ 10.3° (c 0.585, methanol)

Example 187

Ethyl (2R)-2-(4-{5-methyl-1-[3-(4-nonylphenoxy)propyl]-1H-pyrrol-2-yl}phenoxy)-3-phenylpropanoate (1) 2-(4-Benzyloxyphenyl)-5-methyl-1-[3-(4-nonylphenoxy)-propyl]-1H-pyrrole The object compound was obtained from 4-n-nonylphenol as an oily substance, according to the similar manner to that of Example 185(1). yield: 95.6%

$^1$H-NMR (CDCl$_3$) δ; 0.88 (3H, t, J=6.6 Hz), 1.23–1.30 (12H, m), 1.51–1.60 (2H, m), 1.88–1.98 (2H, m), 2.31 (3H, s), 2.52 (2H, t, J=8.0 Hz), 3.71 (2H, t, J=5.8 Hz), 4.09 (2H, t, J=7.2 Hz), 5.06 (2H, s), 5.92 (1H, d, J=3.4 Hz), 6.03 (1H, d, J=3.4 Hz), 6.66 (2H, d, J=8.4 Hz), 6.70–7.06 (4H, m), 7.25–7.49 (7H, m).

IR (KBr) cm$^{-1}$; 1611, 1524, 1510, 1468, 1454, 1309, 1279, 1244, 1175, 1026, 833, 696.

(2) 4-{5-Methyl-1-[3-(4-nonylphenoxy)propyl]-1H-pyrrol-2-yl}phenol

The object compound was obtained from 2-(4-benzyloxyphenyl)-5-methyl-1-[3-(4-nonylphenoxy)propyl]-1H-pyrrole as an oily substance, according to the similar manner to that of Example 185(2). yield: 95.3%

$^1$H-NMR (CDCl$_3$) δ; 0.88 (3H, t, J=7.0 Hz), 1.22–1.29 (12H, m), 1.49–1.59 (2H, m), 1.87–1.97 (2H, m), 2.30 (3H, s), 2.52 (2H, t, J=7.6 Hz), 3.72 (2H, t, J=5.8 Hz), 4.07 (2H, t, J=7.42 Hz), 5.91 (1H, d, J=3.4 Hz), 6.02 (1H, d, J=3.4 Hz), 6.67 (2H, d, J=8.8 Hz), 6.81 (2H, d, J=8.4 Hz), 7.04 (2H, d, J=8.4 Hz), 7.22 (2H, d, J=8.8 Hz).

IR (KBr) cm$^{-1}$; 3387, 1613, 1526, 1510, 1468, 1439, 1387, 1310, 1242, 1175, 837, 758.

(3) Ethyl (2R)-2-(4-{5-methyl-1-[3-(4-nonylphenoxy)propyl]-1H-pyrrol-2-yl}phenoxy)-3-phenylpropanoate The object compound was obtained from 4-{5-methyl-1-[3-(4-nonylphenoxy)propyl]-1H-pyrrol-2-yl}phenol as an oily substance, according to the similar manner to that of Example 185 (3). yield: 27.2%

$^1$H-NMR (CDCl$_3$) δ; 0.88 (3H, t, J=6.6 Hz), 1.15–1.37 (15H, m), 1.51–1.61 (2H, m), 1.88–1.95 (2H, m), 2.29 (3H, s), 2.52 (2H, t, J=8.0Hz), 3.24–3.28 (2H, m), 3.70 (2H, t, J=6.2 Hz), 4.05 (2H, t, J=7.8 Hz), 4.19 (2H, q, J=7.0 Hz), 4.76–4.82 (1H, m), 5.90 (1H, d, J=3.4 Hz), 6.00 (1H, d, J=3.4 Hz), 6.66 (2H, d, J=8.4 Hz), 6.82 (2H, d, J=8.8 Hz), 7.02 (2H, d, J=8.4 Hz), 7.21–7.34 (7H, m).

IR (KBr) cm$^{-1}$; 1755, 1736, 1524, 1510, 1279, 1240, 1179, 1084, 1032, 835, 756, 700.

Example 188

Sodium (2R)-2-(4-{5-methyl-1-[3-(4-nonylphenoxy)propyl]-1H-pyrrol-2-yl}phenoxy)-3-phenylpropanoate (1) (2R)-2-(4-{5-Methyl-1-[3-(4-nonylphenoxy)propyl]-1H-pyrrol-2-yl}phenoxy)-3-phenylpropanoic acid The object compound was obtained from ethyl (2R)-2-(4-{5-methyl-1-[3-(4-nonylphenoxy)propyl]-1H-pyrrol-2-yl}phenoxy)-3-phenylpropanoate as an oily substance, according to the similar manner to that of Example 186(1). yield: 70.9%

$^1$H-NMR (CDCl$_3$) δ; 0.88 (3H, t, J=7.0 Hz), 1.23–1.30 (12H, m), 1.49–1.59 (2H, m), 1.86–1.92 (2H, m), 2.28 (3H, s), 2.51 (2H, t, J=8.0Hz), 3.28 (2H, d, J=6.6 Hz), 3.77 (2H, t, J=5.6 Hz), 4.04 (2H, t, J=7.0 Hz), 4.84 (1H, t, J=6.6 Hz), 5.90 (1H, d, J=3.2 Hz), 5.99 (1H, d, J=3.2 Hz), 6.64 (2H, d, J=8.4 Hz), 6.81 (2H, d, J=8.8 Hz), 7.01 (2H, d, J=8.8 Hz), 7.20–7.30 (7H, m).

IR (KBr) cm$^{-1}$; 3031, 1728, 1510, 1242, 1177, 1084, 833, 700.

(2) Sodium (2R)-2-(4-{5-methyl-1-[3-(4-nonylphenoxy)propyl]-1H-pyrrol-2-yl}phenoxy)-3-phenylpropanoate The object compound was obtained from (2R)-2-(4-{5-methyl-1-[3-(4-nonylphenoxy)propyl]-1H-pyrrol-2-yl}phenoxy)-3-phenylpropanoic acid as a solid, according to the similar manner to that of Example 186(2). yield: 67.4%

$^1$H-NMR (DMSO-d$_6$) δ; 0.85 (3H, t, J=6.6 Hz), 1.18–1.31 (12H, m), 1.45–1.57 (2H, m), 1.75–1.89 (2H, m), 2.21 (3H, s), 2.47 (2H, t, J=7.6 Hz), 2.93–3.19 (2H, m), 3.69 (2H, t, J=6.0 Hz), 3.99 (2H, t, J=7.0 Hz), 4.29–4.39 (1H, m), 5.76 (1H, d, J=3.4 Hz), 5.81 (1H, d, J=3.4 Hz), 6.67 (2H, d, J=8.4 Hz), 6.76 (2H, d, J=8.8 Hz), 6.99–7.34 (9H, m).

IR (KBr) cm$^{-1}$; 1615, 1584, 1512, 1472, 1454, 1404, 1309, 1227, 1179, 1053, 829, 762, 700.

$[\alpha]_D^{27}$ 7.97° (c 0.530, methanol)

Example 189

Ethyl (2R)-2-{4-[1-(4-decylphenyl)-5-methyl-1H-pyrrol-2-yl]phenoxy}-3-phenylpropanoate (1) 2-(4-Benzyloxyphenyl)-1-(4-decylphenyl)-5-methyl-1H-pyrrole A solution of 1-(4-benzyloxyphenyl)pentane-1,4-dione (2.00 g, 7.08 mmol), 4-n-decylaniline (1.65 mg, 7.08 mmol) and p-toluenesulfonic acid monohydrate (101 mg, 0.523 mmol) in toluene (100 ml) was refluxed for 12 hours under heating using Dean-Stark's apparatus and the solvent was removed under reduced pressure. The residue was purified by silica gel column chromatography (hexane:ethyl acetate=30:1) to give the object compound as an oily substance. 2.79 g (yield: 82.1%)

$^1$H-NMR (CDCl$_3$) δ; 0.87 (3H, t, J=7.0 Hz), 1.20–1.34 (14H, m), 1.55–1.66 (2H, m), 2.13 (3H, s), 2.62 (2H, t, J=7.8 Hz), 4.97 (2H, s), 6.05 (1H, d, J=3.2 Hz), 6.24 (1H, d, J=3.2 Hz), 6.75 (2H, d, J=8.8 Hz), 6.97 (2H, d, J=8.8 Hz), 7.03 (2H, d, J=8.4 Hz), 7.15 (2H, d, J=8.4 Hz), 7.33–7.41 (5H, m).

IR (KBr) cm$^{-1}$; 1611, 1522, 1454, 1393, 1281, 1240, 1177, 1038, 1026, 833, 760, 735, 696.

(2) 4-[1-(4-Decylphenyl)-5-methyl-1H-pyrrol-2-yl]phenol

To a solution of 2-(4-benzyloxyphenyl)-1-(4-decylphenyl)-5-methyl-1H-pyrrole (2.77 g, 5.77 mmol) in methanol (40 ml) and tetrahydrofuran (40 ml) was added 10% palladium carbon (200 mg) and the mixture was stirred for 4 hours under hydrogen atmosphere. The insoluble matter was filtered out and the filtrate was concentrated to give the object compound as an oily substance. 2.10 g (yield: 93.3%)

$^1$H-NMR (CDCl$_3$) δ; 0.88 (3H, t, J=7.0 Hz), 1.21–1.31 (14H, m), 1.54–1.68 (2H, m), 2.11 (3H, s), 2.61 (2H, t, J=8.0 Hz), 6.05 (1H, d, J=3.2 Hz), 6.24 (1H, d, J=3.2 Hz), 6.59 (2H, d, J=8.8 Hz), 6.92 (2H, d, J=8.8 Hz), 7.02 (2H, d, J=8.2 Hz), 7.14 (2H, d, J=8.2 Hz).

IR (KBr) cm$^{-1}$; 3328, 1615, 1514, 1485, 1437, 1397, 1262, 1171, 835, 760.

(3) Ethyl (2R)-2-{4-[1-(4-decylphenyl)-5-methyl-1H-pyrrol-2-yl]phenoxy}-3-phenylpropanoate To a solution of 4-[1-(4-decylphenyl)-5-methyl-1H-pyrrol-2-yl]phenol (2.08 g, 5.34 mmol), ethyl (S)-2-hydroxy-3-phenylpropanoate (1.56 g, 8.00 mmol) and triphenylphosphine (2.10 g, 8.00 mmol) in toluene (6 ml) was added 1,1'-(azodicarbonyl)dipiperidine (2.02 g, 8.00 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 1.64 g (yield: 54.3%)

$^1$H-NMR (CDCl$_3$) δ; 0.88 (3H, t, J=6.6 Hz), 1.13 (3H, t, J=7.2 Hz), 1.17–1.34 (14H, m), 1.53–1.65 (2H, m), 2.10 (3H, s), 2.60 (2H, t, J=7.8 Hz), 3.17–3.21 (2H, m), 4.13 (2H, q, J=7.2 Hz), 4.66–4.73 (1H, m), 6.03 (1H, d, J=3.4 Hz), 6.22 (1H, d, J=3.4 Hz), 6.60 (2H, d, J=9.2 Hz), 6.91 (2H, d, J=9.2 Hz), 7.00 (2H, d, J=8.6 Hz), 7.13 (2H, d, J=8.6 Hz), 7.21–7.36 (5H, m).

IR (KBr) cm$^{-1}$; 1755, 1736, 1520, 1238, 1182, 1084, 1036, 833, 762, 745, 698.

Example 190

Sodium (2R)-2-{4-[1-(4-decylphenyl)-5-methyl-1H-pyrrol-2-yl]phenoxy}-3-phenylpropanoate (1) (2R)-2-{4-[1-(4-Decylphenyl)-5-methyl-1H-pyrrol-2-yl]phenoxy}-3-phenylpropanoic acid To a mixed solution of ethyl (2R)-2-{4-[1-(4-decylphenyl)-5-methyl-1H-pyrrol-2-yl]phenoxy}-3-phenylpropanoate (1.62g, 2.86 mmol) in THF (60 ml) and methanol (60 ml) was added 1N aqueous potassium hydroxide solution (10 ml, 10 mmol) and the mixture was stirred for 1 hour at room temperature. The reaction solution was neutralized with 1N hydrochloric acid and extracted with ethyl acetate. The extract was washed with water and dried over magnesium sulfate anhydride and the solvent was removed under reduced pressure. The residue was purified by silica gel column chromatography (ethyl acetate) to give the object compound as an oily substance. 1.10 g (yield: 71.4%)

$^1$H-NMR (CDCl$_3$) δ; 0.88 (3H, t, J=6.6 Hz), 1.22–1.29 (14H, m), 1.54–1.66 (2H, m), 2.10 (3H, s), 2.61 (2H, t, J=8.4 Hz), 3.21 (2H, d, J=6.2 Hz), 4.75 (1H, t, J=6.2 Hz), 6.03 (1H, d, J=3.2 Hz), 6.23 (1H, d, J=3.2 Hz), 6.60 (2H, d, J=8.8 Hz), 6.92 (2H, d, J=8.8 Hz), 7.00 (2H, d, J=8.8 Hz), 7.13 (2H, d, J=8.8 Hz), 7.26 (5H, bs).

IR (KBr) cm$^{-1}$; 3393, 1728, 1522, 1236, 1181, 1084, 833, 760, 700.

(2) Sodium (2R)-2-{4-[1-(4-decylphenyl)-5-methyl-1H-pyrrol-2-yl]phenoxy}-3-phenylpropanoate Ethanol (10 ml) and a solution of 1N sodium hydroxide in ethanol (1.76 ml) were added to (2R)-2-{4-[1-(4-decylphenyl)-5-methyl-1H-pyrrol-2-yl]phenoxy}-3-phenylpropanoic acid (1.05 g, 1.95 mmol) and the mixture was concentrated. Diisopropylether was added to the residue to give the object compound as a solid. 802 mg (yield: 81.4%)

$^1$H-NMR (DMSO-d$_6$) δ; 0.86 (3H, t, J=6.6 Hz), 1.18–1.33 (14H, m), 1.52–1.64 (2H, m), 2.01 (3H, s), 2.59 (2H, t, J=7.6 Hz), 2.86–3.16 (2H, m), 4.19–4.24 (1H, m), 5.92 (1H, d, J=3.8 Hz), 6.07 (1H, d, J=3.8 Hz), 6.52 (2H, d, J=8.8 Hz), 6.77 (2H, d, J=8.8 Hz), 7.02 (2H, d, J=8.0 Hz), 7.08–7.27 (7H, m).

IR (KBr) cm$^{-1}$; 1615, 1520, 1395, 1235, 1059, 1032, 831, 762, 700.

Example 191

Ethyl (2R)-2-{4-[1-(4-heptyloxyphenyl)-5-methyl-1H-pyrrol-2-yl]phenoxy}-3-phenylpropanoate (1) 2-(4-Benzyloxyphenyl)-1-(4-heptyloxyphenyl)-5-methyl-1H-pyrrole A solution of 4-[2-(4-benzyloxyphenyl)-5-methyl-1H-pyrrol-1-yl]phenol (1.00 g, 2.82 mmol), 1-bromoheptane (0.543 ml, 3.38 mmol) and potassium carbonate (466 mg, 3.38 mmol) in DMF (20 ml) was stirred at 80° C. for 4 hours. The reaction solution was poured into water and the mixture was extracted with ethyl acetate. The extract was washed with water, dried over magnesium sulfate anhydride and solvent was removed under reduced pressure. The residue was purified by silica gel column chromatography (hexane:ethyl acetate=30:1) to give the object compound as an oily substance. 840 g (yield: 65.6%)

$^1$H-NMR (CDCl$_3$) δ; 0.90 (3H, t, J=7.0 Hz), 1.22–1.46 (8H, m), 1.72–1.83 (2H, m), 2.10 (3H, s), 3.95 (2H, t, J=6.6 Hz), 4.98 (2H, s), 6.04 (1H, d, J=3.2 Hz), 6.24 (1H, d, J=3.2 Hz), 6.76 (2H, d, J=8.8 Hz), 6.85 (2H, d, J=8.8 Hz), 6.96–7.07 (4H, m), 7.33–7.40 (5H, m).

IR (KBr) cm$^{-1}$; 1609, 1514, 1483, 1468, 1454, 1393, 1289, 1244, 1177, 1040, 1026, 83.5, 760, 735, 698.

(2) 4-[1-(4-Heptyloxyphenyl)-5-methyl-1H-pyrrol-2-yl]phenol

To a solution of 2-(4-benzyloxyphenyl)-1-(4-heptyloxyphenyl)-5-methyl-1H-pyrrole (820 mg, 1.81 mmol) in ethanol (30 ml) and tetrahydrofuran (30 ml) was added 10% palladium carbon (200 mg) and the mixture was stirred for 3 hours under hydrogen atmosphere. The insoluble matter was filtered out and the filtrate was concentrated to give the object compound as an oily substance. 650 mg (yield: 98.9%)

$^1$H-NMR (CDCl$_3$) δ; 0.90 (3H, t, J=6.6 Hz), 1.28–1.43 (8H, m), 1.69–1.79 (2H, m), 2.10 (3H, s), 3.95 (2H, t, J=6.6 Hz), 6.04 (1H, d, J=3.6 Hz), 6.23 (1H, d, J=3.6 Hz), 6.61 (2H, d, J=8.4 Hz), 6.85 (2H, d, J=9.2 Hz), 6.94 (2H, d, J=8.4 Hz), 7.04 (2H, d, J=9.2 Hz).

IR (KBr) cm$^{-1}$; 3403, 1613, 1514, 1472, 1437, 1246, 1171, 1040, 835, 762.

(3) Ethyl (2R)-2-{4-[1-(4-heptyloxyphenyl)-5-methyl-1H-pyrrol-2-yl]phenoxy}-3-phenylpropanoate To a solution of 4-[1-(4-heptyloxyphenyl)-5-methyl-1H-pyrrol-2-yl]phenol (640 mg, 1.76 mmol), ethyl (S)-2-hydroxy-3-phenylpropanoate (513 mg, 2.64 mmol) and triphenylphosphine (692 mg, 2.64 mmol) in toluene (2 ml) was added 1,1'-(azodicarbonyl)dipiperidine (666 mg, 2.64 mmol) and the mixture was stirred at 80° C. for 12 hours. The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=30:1) to give the object compound as an oily substance. 240 mg (yield: 25.2%)

$^1$H-NMR (CDCl$_3$) δ; 0.90 (3H, t, J=6.2 Hz), 1.14 (3H, t, J=7.0 Hz), 1.35–1.55 (8H, m), 1.76–1.83 (2H, m), 2.09 (3H, s), 3.17–3.21 (2H, m), 3.94 (2H, t, J=6.6 Hz), 4.14 (2H, q, J=7.0 Hz), 4.66–4.73 (1H, m), 6.02 (1H, d, J=3.6 Hz), 6.21 (1H, d, J=3.6 Hz), 6.61 (2H, d, J=8.8 Hz), 6.83 (2H, d, J=8.4 Hz), 6.93 (2H, d, J=8.4 Hz), 7.01 (2H, d, J=8.8 Hz), 7.25–7.27 (5H, m).

IR (KBr) cm$^{-1}$; 1755, 1734, 1514, 1483, 1287, 1182, 1084, 1038, 835, 760, 700.

Example 192

Sodium (2R)-2-{4-[1-(4-heptyloxyphenyl)-5-methyl-1H-pyrrol-2-yl]phenoxy}-3-phenylpropanoate (1) (2R)-2-{4-[1-(4-Heptyloxyphenyl)-5-methyl-1H-pyrrol-2-yl]phenoxy}-3-phenylpropanoic acid To a mixed solution of ethyl (2R)-2-{4-[1-(4-heptyloxyphenyl)-5-methyl-1H-pyrrol-2-yl]phenoxy}-3-phenylpropanoate (235 mg, 0.435 mmol) in THF (7 ml) and methanol (7 ml) was added 1N aqueous potassium hydroxide solution (2 ml, 2 mmol) and the mixture was stirred for 1 hour at room temperature. The reaction solution was neutralized with 1N hydrochloric acid and extracted with ethyl acetate. The extract was washed with water, dried over magnesium sulfate anhydride and the solvent was removed under reduced pressure. The residue was purified by silica gel column chromatography (hexane:ethyl acetate=1:1) to give the object compound as an oily substance. 210 mg (yield: 94.2%)

$^1$H-NMR (CDCl$_3$) δ; 0.90 (3H, t, J=7.0 Hz), 1.22–1.41 (8H, m), 1.74–1.81 (2H, m), 2.08 (3H, s), 3.20 (2H, d, J=5.4 Hz), 3.92 (2H, t, J=6.2 Hz), 4.74 (1H, t, J=5.4 Hz), 6.02 (1H, d, J=3.6 Hz), 6.21 (1H, d, J=3.6 Hz), 6.60 (2H, d, J=8.4 Hz), 6.82 (2H, d, J=8.8 Hz), 6.93 (2H, d, J=8.4 Hz), 7.00 (2H, d, J=8.8 Hz), 7.25–7.26 (5H, m).

IR (KBr) cm$^{-1}$; 2930, 1728, 1514, 1287, 1244, 1181, 1084, 1042, 835, 760, 700.

(2) Sodium (2R)-2-{4-[1-(4-heptyloxyphenyl)-5-methyl-1H-pyrrol-2-yl]phenoxy}-3-phenylpropanoate Ethanol (5 ml) and a solution of 1N sodium hydroxide in ethanol (0.333 ml) were added to (2R)-2-{4-[1-(4-heptyloxyphenyl)-5-methyl-1H-pyrrol-2-yl]phenoxy}-3-phenylpropanoic acid (190 mg, 0.371 mmol) and the mixture was concentrated. Diisopropylether was added to the residue to give the object compound as a solid. 135 mg (yield: 75.8%)

$^1$H-NMR (DMSO-d$_6$) δ; 0.89 (3H, t, J=6.6 Hz), 1.22–1.48 (8H, m), 1.69–1.79 (2H, m), 1.99 (3H, s), 2.87–3.13 (2H, m), 3.95 (2H, t, J=6.2 Hz), 4.18–4.24 (1H, m), 5.91 (1H, d, J=3.4 Hz), 6.06 (1H, d, J=3.4 Hz), 6.54 (2H, d, J=8.8 Hz), 6.79 (2H, d, J=8.8 Hz), 6.89 (2H, d, J=8.8 Hz), 7.02 (2H, d, J=8.8 Hz), 7.11–7.29 (5H, m).

IR (KBr) cm$^{-1}$; 1611, 1514, 1404, 1289, 1244, 1181, 1169, 1042, 1030, 836, 764, 700.

[α]$_D^{29}$ −2.41° (c 0.595, methanol)

Example 193

Ethyl (2R)-2-{4-[5-methyl-1-(4-nonyloxyphenyl)-1H-pyrrol-2-yl]phenoxy}-3-phenylpropanoate (1) 2-(4-Benzyloxyphenyl)-1-(4-nonyloxyphenyl)-5-methyl-1H-pyrrole The object compound was obtained from 1-bromononane as an oily substance, according to the similar manner to that of Example 191(1). yield: 70.6%

$^1$H-NMR (CDCl$_3$) δ; 0.88 (3H, t, J=7.0 Hz), 1.20–1.46 (12H, m), 1.72–1.83 (2H, m), 2.10 (3H, s), 3.95 (2H, t, J=6.6 Hz), 4.98 (2H, s), 6.04 (1H, d, J=3.6 Hz), 6.24 (1H, d, J=3.6 Hz), 6.76 (2H, d, J=9.0 Hz), 6.85 (2H, d, J=9.0 Hz), 6.96–7.07 (4H, m), 7.30–7.42 (5H, m).

IR (KBr) cm$^{-1}$; 1609, 1514, 1468, 1454, 1289, 1246, 1177, 1040, 1026, 835, 760, 735, 698.

(2) 4-[5-Methyl-1-(4-nonyloxyphenyl)-1H-pyrrol-2-yl]phenol

The object compound was obtained from 2-(4-benzyloxyphenyl)-1-(4-nonyloxyphenyl)-5-methyl-1H-pyrrole as an oily substance, according to the similar manner to that of Example 191(2). yield: 97.7%

$^1$H-NMR (CDCl$_3$) δ; 0.88 (3H, t, J=6.6 Hz), 1.21–1.36 (12H, m), 1.66–1.78 (2H, m), 2.10 (3H, s), 3.94 (2H, t, J=7.6 Hz), 6.04 (1H, d, J=3.2 Hz), 6.23 (1H, d, J=3.2 Hz), 6.61 (2H, d, J=8.6 Hz), 6.85 (2H, d, J=9.2 Hz), 6.96 (2H, d, J=8.6 Hz), 7.04 (2H, d, J=9.2 Hz), 6.96–7.07 (4H, m).

IR (KBr) cm$^{-1}$; 3400, 1610, 1514, 1472, 1244, 1171, 835.

(3) Ethyl (2R)-2-{4-[5-methyl-1-(4-nonyloxyphenyl)-1H-pyrrol-2-yl]phenoxy}-3-phenylpropanoate The object compound was obtained from 4-[5-methyl-1-(4-nonyloxyphenyl)-1H-pyrrol-2-yl]phenol as an oily substance, according to the similar manner to that of Example 191(3). yield: 24.8%

$^1$H-NMR (CDCl$_3$) δ; 0.89 (3H, t, J=7.2 Hz), 1.14 (3H, t, J=7.2 Hz), 1.24–1.46 (12H, m), 1.74–1.84 (2H, m), 2.08 (3H, s), 3.17–3.21 (2H, m), 3.94 (2H, t, J=6.6 Hz), 4.14 (2H, q, J=7.2 Hz), 4.67–4.72 (1H, m), 6.02 (1H, d, J=3.3 Hz), 6.22 (1H, d, J=3.3, Hz), 6.61 (2H, d, J=9.0 Hz), 6.83 (2H, d, J=9.0 Hz), 6.93 (2H, d, J=9.0 Hz), 7.01 (2H, d, J=9.0 Hz), 7.19–7.33 (5H, m).

IR (KBr) cm$^{-1}$; 1755, 1736, 1514, 1483, 1287, 1244, 1182, 1084, 1038, 835, 758, 698.

Example 194

Sodium (2R)-2-{4-[5-methyl-1-(4-nonyloxyphenyl)-1H-pyrrol-2-yl]phenoxy}-3-phenylpropanoate (1) (2R)-2-{4-[5-Methyl-1-(4-nonyloxyphenyl)-1H-pyrrol-2-yl]phenoxy}-3-phenylpropanoic acid The object compound was obtained from ethyl (2R)-2-{4-[5-methyl-1-(4-nonyloxyphenyl)-1H-pyrrol-2-yl]phenoxy}-3-phenylpropanoate as an oily substance, according to the similar manner to that of Example 192(1). yield: 66.9%

$^1$H-NMR (CDCl$_3$) δ; 0.89 (3H, t, J=6.8 Hz), 1.23–1.43 (12H, m), 1.74–1.81 (2H, m), 2.08 (3H, s), 3.13–3.22 (2H, m), 3.91 (2H, t, J=5.8 Hz), 4.69–4.75 (1H, m), 6.02 (1H, d, J=3.2 Hz), 6.20 (1H, d, J=3.2 Hz), 6.58 (2H, d, J=9.2 Hz), 6.80–7.02 (6H, m), 7.23–7.26 (5H, m).

IR (KBr) cm$^{-1}$; 3034, 1728, 1514, 1287, 1244, 1084, 835, 760, 700.

(2) Sodium (2R)-2-{4-[5-methyl-1-(4-nonyloxyphenyl)-1H-pyrrol-2-yl]phenoxy}-3-phenylpropanoate The object compound was obtained from (2R)-2-{4-[5-methyl-1-(4-nonyloxyphenyl)-1H-pyrrol-2-yl]phenoxy}-3-phenylpropanoic acid as a solid, according to the similar manner to that of Example 192(2). yield: 80.4%

$^1$H-NMR (DMSO-d$_6$) δ; 0.87 (3H, t, J=6.6 Hz), 1.21–1.42 (12H, m), 1.65–1.76 (2H, m), 1.99 (3H, s), 2.85–3.11 (2H, m), 3.95 (2H, t, J=6.2 Hz), 4.15–4.20 (1H, m), 5.91 (1H, d, J=3.4 Hz), 6.06 (1H, d, J=3.4 Hz), 6.53 (2H, d, J=8.8 Hz), 6.79 (2H, d, J=8.8 Hz), 6.90 (2H, d, J=8.8 Hz), 7.03 (2H, d, J=8.8 Hz), 7.11–7.27 (5H, m).

IR (KBr) cm$^{-1}$; 1613, 1514, 1397, 1289, 1246, 1171, 1049, 833, 760, 700.

Example 195

Ethyl (2R)-2-[4-(1-{3-[2-(1,3-benzoxazol-2-yl)phenoxy]propyl}-5-methyl-1H-pyrrol-2-yl)phenoxy]-3-phenylpropanoate (1) 2-(2-{3-[2-(4-Benzyloxyphenyl)-5-methyl-1H-pyrrol-1-yl]propoxy}phenyl)-1,3-benzoxazole To a solution of 3-[2-(4-benzyloxyphenyl)-5-methyl-1H-pyrrol-1-yl]propan-1-ol (1.00 g, 3.11 mmol), 2-(2-hydroxyphenyl)benzoxazole (986 mg, 4.67 mmol) and triphenylphosphine (1.22 g, 4.67 mmol) in toluene (2 ml) was added 1,1'-(azodicarbonyl)dipiperidine (1.18 g, 4.67 mmol) and the mixture was stirred at 80° C. for 12 hours.

The reaction solution was poured into water and the mixture was extracted with ethyl acetate. The extract was dried over magnesium sulfate anhydride and the solvent was removed under reduced pressure. The residue was purified by silica gel column chromatography (hexane:ethyl acetate=7:1) to give the object compound as an oily substance. 950 mg (yield: 59.4%)

$^1$H-NMR (CDCl$_3$) δ; 2.05–2.10 (2H, m), 2.30 (3H, s), 3.92 (2H, t, J=5.6 Hz), 4.29 (2H, t, J=7.4 Hz), 4.93 (2H, s), 5.91 (1H, d, J=3.2 Hz), 6.01 (1H, d, J=3.2 Hz), 6.74 (2H, d, J=8.8 Hz), 6.87 (1H, d, J=8.4 Hz), 7.07 (1H, t, J=7.6 Hz), 7.18–7.54 (11H, m), 7.74–7.79 (1H, m), 8.09–8.14 (1H, m).

IR (KBr) cm$^{-1}$; 1615, 1524, 1454, 1385, 1309, 1283, 1267, 1244, 1175, 1026, 835, 750, 698.

(2) 4-(1-{3-[2-(1,3-Benzoxazol-2-yl)phenoxy]propyl}-5-methyl-1H-pyrrol-2-yl)phenol To a solution of 2-(2-{3-[2-(4-benzyloxyphenyl)-5-methyl-1H-pyrrol-1-yl]propoxy}phenyl)-1,3-benzoxazole (930 mg, 1.81 mmol) in methanol (40 ml) and tetrahydrofuran (40 ml) was added 10% palladium carbon (200 mg) and the mixture was stirred for 4 hours under hydrogen atmosphere. The insoluble matter was filtered out and the filtrate was concentrated to give the object compound as a solid. 730 mg (yield: 98.4%)

$^1$H-NMR (CDCl$_3$) δ; 1.93–2.11 (2H, m), 2.28 (3H, s), 3.83 (2H, t, J=6.0 Hz), 4.22 (2H, t, J=6.8 Hz), 5.91 (1H, d, J=3.4 Hz), 5.98 (1H, d, J=3.4 Hz), 6.54 (2H, d, J=8.0 Hz), 6.83 (1H, d, J=8.4 Hz), 7.03–7.56 (7H, m), 7.75–7.80 (1H, m), 8.05–8.10 (1H, m).

IR (KBr) cm$^{-1}$; 3063, 1613, 1584, 1549, 1526, 1493, 1483, 1545, 1387, 1312, 1269, 1244, 1169, 1038, 910, 839, 750.

(3) Ethyl (2R)-2-[4-(1-{3-[2-(1,3-benzoxazol-2-yl)phenoxy]propyl}-5-methyl-1H-pyrrol-2-yl)phenoxy]-3-phenylpropanoate To a solution of 4-(1-{3-[2-(1,3-benzoxazol-2-yl)phenoxy]propyl}-5-methyl-1H-pyrrol-2-yl)phenol (710 mg, 1.73 mmol), ethyl (S)-2-hydroxy-3-phenylpropanoate (504 mg, 2.59 mmol) and triphenylphosphine (679 mg, 2.59 mmol) in toluene (2 ml) was added 1,1'-(azodicarbonyl)dipiperidine (654 mg, 2.59 mmol) and the mixture was stirred at 80° C. for 12 hours. The reaction solution was poured into water and the mixture was extracted with ethyl acetate. The extract was dried over magnesium sulfate anhydride, and the solvent was removed under reduced pressure. The residue was purified by silica gel column chromatography (hexane:ethyl acetate=30:1) to give the object compound as an oily substance. 390 mg (yield: 37.5%)

$^1$H-NMR (CDCl$_3$) δ; 1.20 (3H, t, J=7.4 Hz), 1.98–2.05 (2H, m), 2.27 (3H, s), 3.18–3.26 (2H, m), 3.91 (2H, t, J=5.8 Hz), 4.15 (2H, q, J=7.4 Hz), 4.22 (2H, t, J=7.4 Hz), 4.70–4.77 (1H, m), 5.89 (1H, d, J=3.2 Hz), 5.98 (1H, d, J=3.2 Hz), 6.68 (2H, d, J=8.4 Hz), 6.87 (1H, d, J=8.0 Hz), 7.04 (1H, t, J=7.2 Hz), 7.14–7.55 (11H, m), 7.74–7.79 (1H, m), 8.00–8.05 (1H, m).

IR (KBr) cm$^{-1}$; 1752, 1732, 1613, 1524, 1481, 1454, 1309, 1269, 1240, 1187, 1084, 1033, 750, 700.

Example 196

Sodium (2R)-2-[4-(1-{3-[2-(1,3-benzoxazol-2-yl)phenoxy]propyl}-5-methyl-1H-pyrrol-2-yl)phenoxy]-3-phenylpropanoate (1) (2R)-2-[4-(1-{3-[2-(1,3-Benzoxazol-2-yl)phenoxy]propyl}-5-methyl-1H-pyrrol-2-yl)phenoxy]-3-phenylpropanoic acid To a mixed solution of ethyl (2R)-2-[4-(1-{3-[2-(1,3-benzoxazol-2-yl)phenoxy]propyl}-5-methyl-1H-pyrrol-2-yl)phenoxy]-3-phenylpropanoate (380 mg, 0.633 mmol) in THF (15 ml) and methanol (15 ml) was added 1N aqueous potassium hydroxide solution (3 ml, 3 mmol) and the mixture was stirred for 1 hour at room temperature. The reaction solution was neutralized with 1N hydrochloric acid and extracted with ethyl acetate. The extract was washed with water and dried over magnesium sulfate anhydride and the solvent was removed under reduced pressure. The residue was purified by silica gel column chromatography (ethyl acetate) to give the object compound as an oily substance. 206 mg (yield: 56.9%)

$^1$H-NMR (CDCl$_3$) δ; 2.05–2.10 (2H, m), 2.33 (3H, s), 3.26–3.72 (2H, m), 3.47–3.87 (2H, m), 4.07–4.35 (2H, m), 4.67–4.73 (1H, m), 5.88 (1H, d, J=3.4 Hz), 5.93 (1H, d, J=3.4 Hz), 6.11 (2H, d, J=8.4 Hz), 6.76–6.82 (3H, m), 7.04 (1H, t, J=7.0 Hz), 7.26–7.54 (10H, m), 7.93–7.98 (1H, m).

IR (KBr) cm$^{-1}$; 3032, 1730, 1613, 1524, 1495, 1481, 1454, 1240, 1181, 1084, 1042, 910, 837, 750, 700.

(2) Sodium (2R)-2-[4-(1-{3-[2-(1,3-benzoxazol-2-yl)phenoxy]propyl}-5-methyl-1H-pyrrol-2-yl)phenoxy]-3-phenylpropanoate Ethanol (5 ml) and a solution of 1N sodium hydroxide in ethanol (0.299 ml) were added to (2R)-2-[4-(1-{3-[2-(1,3-benzoxazol-2-yl)phenoxy]propyl}-5-methyl-1H-pyrrol-2-yl)phenoxy]-3-phenylpropanoic acid (190 mg, 0.332 mmol) and the mixture was concentrated. Diisopropylether was added to the residue to give the object compound as a solid. 162 mg (yield: 91.0%)

$^1$H-NMR (DMSO-d$_6$) δ; 1.85–1.94 (2H, m), 2.17 (3H, s), 2.93–3.18 (2H, m), 3.91–3.99 (2H, m), 4.12–4.18 (2H, m), 4.32–4.39 (1H, m), 5.74 (1H, d, J=3.2 Hz), 5.81 (1H, d, J=3.2 Hz), 6.68 (2H, d, J=8.4 Hz), 7.04–7.99 (15H, m).

IR (KBr) cm$^{-1}$; 1613, 1524, 1481, 1454, 1416, 1310, 1269, 1236, 1034, 839, 750, 700.

$[α]_D^{30}$ 13.2° (c 0.580, methanol)

Formulation Example 1

| | |
|---|---|
| (1) Compound of Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethyl cellulose | 20 mg |
| total | 120 mg |

(1) to (6) are mixed and compressed with a tableting machine according to a conventional method to give a tablet.

Formulation Example 2

| | |
|---|---|
| (1) Compound of Example 52 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethyl cellulose | 20 mg |
| total | 120 mg |

Test Example 1

(1) Cloning of PTP1B Gene and Purification of Protein

Based on the sequence of human PTP-1B registered in Genbank (M31724) database, primer 1 and primer 2 were synthesized, and PTP1B cDNA was amplified from human skeletal muscle cDNA library (Clonetech, Inc. HL5002a) according to PCR method using these primers. The cycle of reactions at 98° C. for 10 seconds, at 58° C. for 30 seconds and at 72° C. for 90 seconds was repeated 35 cycles. The PCR reaction product (1322 bp) was cloned to pT7 Blue-T vector (Novagen, Inc.) to identify the base sequence.

Human PTP 1B cDNA (1322 bp) (100 ng) was amplified with primer 3 and primer 4 in order to express 1–321 amino acid region encoding enzyme active domain of PTP1B. The PCR reaction product (976 bp) was cloned to pT7 Blue-T vector (Novagen, Inc.) to identify the base sequence.

The pT7 Blue-T vector-human PTP1B cDNA (976 bp) was cleaved with restriction enzymes NdeI and SalI (Takara Shuzo Co., Ltd.) and subjected to electrophoresis using 0.7% agarose gel, and a 969 bp fragment was excised and purified. The fragment was introduced into pET32a (+) vector (Novagen, Inc.) cleaved with restriction enzymes NdeI and XhoI (Takara Shuzo Co., Ltd.), to constitute a vector pET32a (+)-human PTP1B cDNA (969 bp), which expresses PTP1B (321 amino acid) with 6 histidine residues binded to a C-terminal thereof under a control of T7 lac promotor.

E.coli BL21 DE3 pLysS (Novagen, Inc.) was transformed with the pET32a (+)-human PTP 1B cDNA (969 bp) to give an ampicillin (50 μg/ml) resistant bacterium. This was shake cultured at 37° C. using 5L of 2xYT medium (ampicillin (50 μg/ml)). When $OD_{600nm}$ reached to 0.5, IPTG (Isopropyl b-D-Thiogalactoside) was added to the culture medium so as to be 1 mM in order to induce the expression of protein, and this medium was further cultured at 37° C. overnight. The bacterium was collected by centrifugation (8000 rpm, 10 minutes, 4° C.).

The bacterium was suspended in lysis buffer (50 ml) (20 mM Tris HCl (pH 8.0), 0.5 M NaCl, 1 mM PMSF, 5 mM benzamidine, Lysozyme 5 mg) and crushed by sonication. To the supernatant after centrifuging (12000 rpm, 10 minutes, 4° C.) was added imidazole so as to be 50 mM and the mixture was mixed with His Bind resin (Novagen, Inc.) binded with Ni ion (4° C., overnight). The mixture was washed with 200 ml of (20 mM Tris HCl (pH 8.0), 0.5 M NaCl, 1 mM PMSF, 5 mM benzamidine, 50 mM imidazole), eluted with (20 mM Tris HCl (pH 8.0), 0.5 M NaCl, 1 mM PMSF, 5 mM benzamidine, 400 mM imidazole) and concentrated by centrifugation using Ultrafree-15 Biomax-50 (MILLIPORE Corp.) (11 mg/ml, 4ml). The purified protein (PTP1B) was identified by Western blotting method using SDS-PAGE, coomassie Blue stain and anti-PTP1B antibody (UBI Inc.).

(2) Measurement of PTP1B Inhibitory Activity

The PTP1B inhibitory activity of the test compound was evaluated by measuring the ability of the test compound to dephosphorylate p-nitrophenylphosphate (pNPP) (a change of the absorbance at 405 nm).

To a buffer for measurement of the activity (0.1 M sodium acetate (pH 6.5), 1 mM EDTA, 10 mM DTT) (10 ml) was added PTP1B enzyme solution (2 μl) and the mixture was added to each well of a 96-well microtiter plate (100 μl each). A solution of the test compound in DMSO (10 μl) and 2 mM pNPP/the buffer for measurement of the activity (90 μl) were then added to each well, and the absorbance at 405 nm was measured. After keeping at 37° C. for 1 hour, the absorbance was measured again to evaluate a change of the absorbance. Regarding the change of the absorbance in the absence of the test compound as 100%, the concentration of the compound necessary for 50% inhibition ($IC_{50}$ value) was calculated.

The results are as follows.

| Test compound | $IC_{50}$ value (μM) |
| --- | --- |
| Compound of Example 2 | 0.89 |
| Compound of Example 4 | 6.48 |
| Compound of Example 6 | 0.5 |
| Compound of Example 8 | 0.38 |
| Compound of Example 10 | 0.34 |
| Compound of Example 12 | 3.1 |
| Compound of Example 14 | 5.87 |
| Compound of Example 16 | 0.41 |
| Compound of Example 18 | 1.01 |
| Compound of Example 20 | 0.53 |
| Compound of Example 22 | 0.71 |
| Compound of Example 24 | 0.32 |
| Compound of Example 26 | 0.42 |
| Compound of Example 28 | 0.48 |
| Compound of Example 30 | 0.72 |
| Compound of Example 32 | 2.1 |
| Compound of Example 34 | 1.1 |
| Compound of Example 36 | 1.43 |
| Compound of Example 38 | 1.6 |
| Compound of Example 40 | 1.2 |
| Compound of Example 42 | 4.9 |
| Compound of Example 44 | 0.33 |
| Compound of Example 46 | 0.40 |
| Compound of Example 48 | 0.36 |
| Compound of Example 50 | 0.94 |
| Compound of Example 52 | 0.31 |
| Compound of Example 54 | 0.31 |
| Compound of Example 56 | 0.13 |
| Compound of Example 58 | 0.34 |
| Compound of Example 60 | 0.36 |
| Compound of Example 62 | 0.21 |
| Compound of Example 64 | 0.23 |
| Compound of Example 66 | 0.17 |
| Compound of Example 94 | 0.09 |

INDUSTRIAL APPLICABILITY

The compound (I), (II) and a salt thereof have a superior protein phosphatase inhibitory action and are useful as a prophylactic or therapeutic agent for diabetes and the like.

What is claimed is:

1. A compound of the formula:

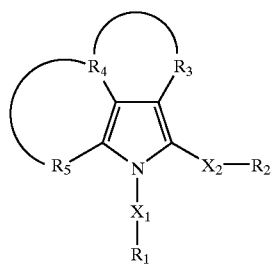

(I)

wherein $X_1$ and $X_2$ are;
one of $R_1$ and $R_2$ is a $C_{6-14}$ aryl group having substituent(s) selected from 1) an optionally substituted carboxy-$C_{1-6}$ alkoxy group and 2) an optionally substituted carboxy-$C_{1-6}$ aliphatic hydrocarbon group, wherein the $C_{6-14}$ aryl group optionally has additional substituent(s), and the other is an optionally substituted $C_{6-14}$ group or a hydrogen atom; and
$R_3$, $R_4$ and $R_5$ are the same or different and each is a hydrogen atom or a substituent, or $R_4$ may link together with $R_3$ or $R_5$ to form an optionally substituted ring;
provided that when $R_3$ is a hydrogen atom, $R_4$ is a hydrogen atom and $R_5$ is methyl, $X_2$—$R_2$ is not 4-cyclohexylphenyl; when $R_3$ is 4-metboxyphenyl, $R_4$ is a hydrogen atom and $R_5$ is methyl, $X_2$—$R_2$ is not 4-methoxyphenyl;
or a salt thereof.

2. The compound according to claim 1, wherein one of $R_1$ and $R_2$ is a $C_{6-14}$ aryl group having substituent(s) selected from 1) an optionally substituted carboxy-$C_{1-6}$ alkoxy group and 2) an optionally substituted carboxy-$C_{1-6}$ aliphatic hydrocarbon group, wherein the $C_{6-14}$ aryl group optionally has additional substituent(s), and the other is an optionally substituted $C_{6-14}$ group.

3. The compound according to claim 1, wherein $R_1$ or $R_2$ is a $C_{6-14}$ aryl substituted with a carboxy-($C_{6-14}$ aryl-substituted)$C_{1-6}$ alkoxy group or a $C_{1-6}$ alkoxy-carbonyl-($C_{6-14}$ aryl-substituted)$C_{1-6}$ alkoxy group.

4. The compound according to claim 1, wherein one of $R_1$ and $R_2$ is a $C_{6-14}$ aryl substituted with a carboxy-($C_{6-14}$ aryl-substituted) $C_{1-6}$ alkoxy group or a $C_{1-6}$ alkoxy-carbonyl-($C_{6-14}$ alyl-substituted)$C_{1-6}$ alkoxy group, and the other is an optionally substituted $C_{6-14}$ aryl.

5. The compound according to claim 1, wherein $R_3$, $R_4$ and $R_5$ are the same or different and each is a hydrogen atom or a hydrocarbon group.

6. The compound according to claim 1, wherein each $R_3$ and R.4 is a hydrogen atom.

7. The compound according to claim 1, wherein $R_5$ is a $C_{1-6}$ alkyl.

8. A prodrug of the compound according to claim 1.

9. A pharmaceutical composition comprising the compound according to claim 1 or a prodrug thereof.

10. A method for preparing a compound of the formula:

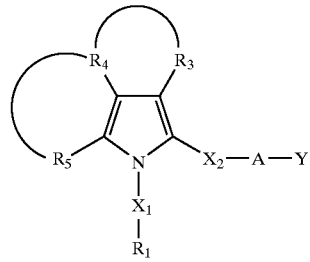

wherein A is a cycle group and the other symbols in the formula have the same meanings as claim 1 or a salt thereof, which comprises reacting a compound of the formula:

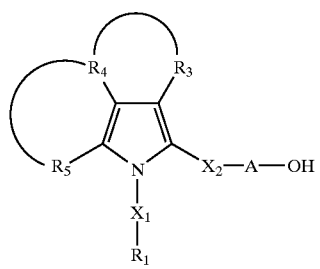
wherein the symbols in the formula have the same meanings as above or a salt thereof with a compound of the formula:
H—Y
wherein Y is an optionally substituted carboxy-$C_{1p\text{-}6}$ alkoxy group.
* * * * *

UNITED STATES PATENT AND TRADEMARK OFFICE
CERTIFICATE OF CORRECTION

PATENT NO. : 6,911,468 B2
DATED : June 28, 2005
INVENTOR(S) : Takahiro Matsumoto, Nozomi Katayama and Hiroshi Mabuchi It is certified that error appears in the above-identified patent and that said Letters Patent is hereby corrected as shown below:

Column 191,
Lines 30-40, please replace the chemical structure

"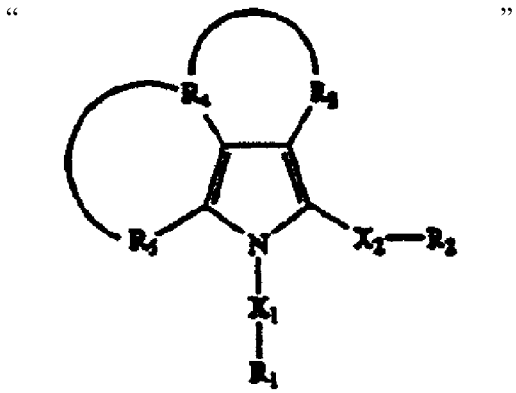"

with the following:

-- 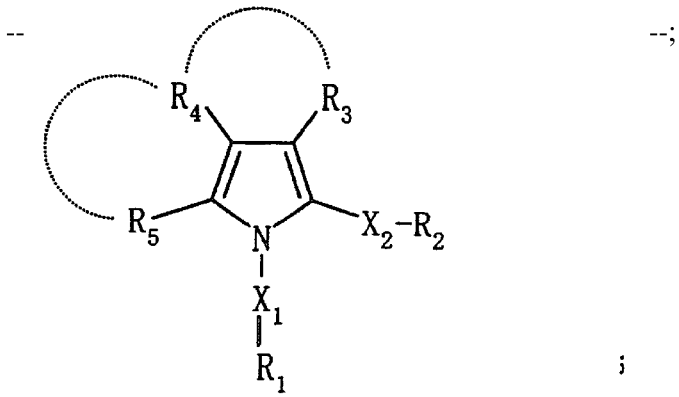 --;

Line 43, please delete "wherein $X_1$ and $X_2$ are" and insert -- wherein $X_1$ and $X_2$ are a bond --;
Line 56, please delete "when $R_3$ is 4-metboxyphenyl, $R_4$" and insert -- when $R_3$ is 4-methoxyphenyl, $R_4$ --;

UNITED STATES PATENT AND TRADEMARK OFFICE
CERTIFICATE OF CORRECTION

PATENT NO. : 6,911,468 B2
DATED : June 28, 2005
INVENTOR(S) : Takahiro Matsumoto, Nozomi Katayama and Hiroshi Mabuchi It is certified that error appears in the above-identified patent and that said Letters Patent is hereby corrected as shown below:

Column 192,
Line 41, please delete "The compound according to Claim 1, wherein each $R_3$ and R.4 is a hydrogen atom" and insert -- The compound according to Claim 1, wherein each $R_3$ and $R_4$ is a hydrogen atom --.
Lines 51-61, please replace the chemical structure "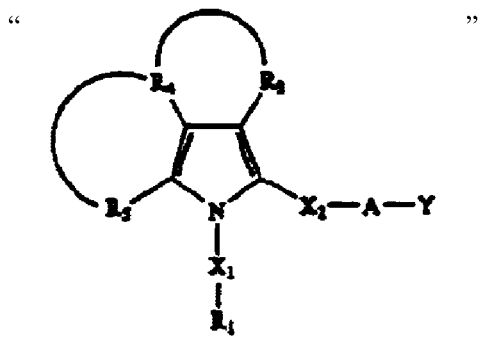"

with the following: --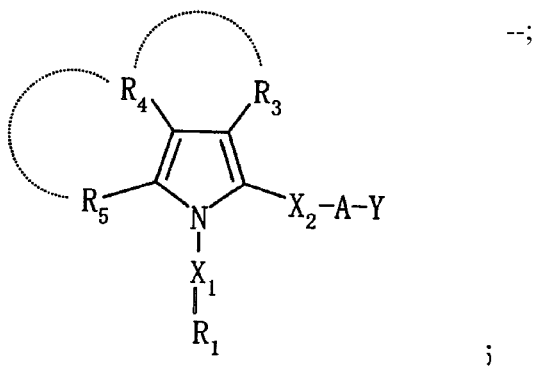--;

Column 193
Lines 1-10, please replace the chemical structure

"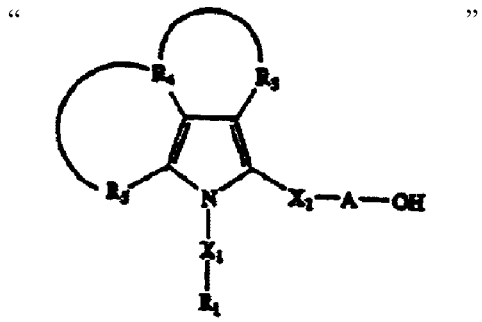"

UNITED STATES PATENT AND TRADEMARK OFFICE
CERTIFICATE OF CORRECTION

PATENT NO. : 6,911,468 B2
DATED : June 28, 2005
INVENTOR(S) : Takahiro Matsumoto, Nozomi Katayama and Hiroshi Mabuchi It is certified that error appears in the above-identified patent and that said Letters Patent is hereby corrected as shown below:

Column 193 (cont'd),
with the following:

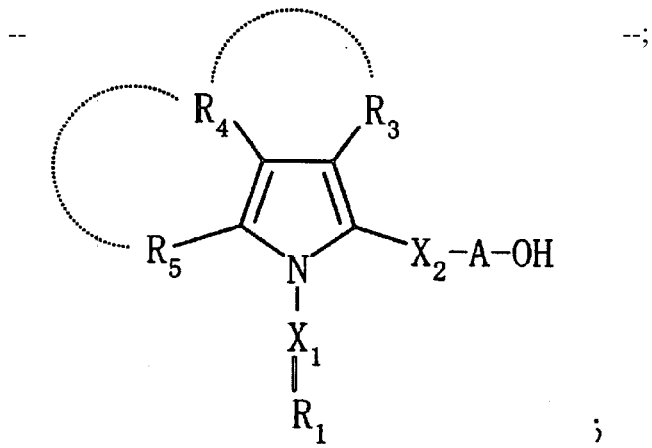

Column 194,
Line 10, please delete "wherein Y is an optionally substituted carboxy-$C_{1p-6}$ alkoxy group" and insert -- wherein Y is an optionally substituted carboxy-$C_{1-6}$ alkoxy group --.

Signed and Sealed this

Eighth Day of November, 2005

JON W. DUDAS
*Director of the United States Patent and Trademark Office*